(12) United States Patent
Ruiz-Opazo et al.

(10) Patent No.: US 11,584,792 B2
(45) Date of Patent: Feb. 21, 2023

(54) ANTIBODY THERAPIES AND METHODS FOR TREATING CORONAVIRUS INFECTION

(71) Applicant: TRUSTEES OF BOSTON UNIVERSITY, Boston, MA (US)

(72) Inventors: Nelson Ruiz-Opazo, Westwood, MA (US); Victoria Herrera, Westwood, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 17/501,050

(22) Filed: Oct. 14, 2021

(65) Prior Publication Data
US 2022/0144939 A1 May 12, 2022

Related U.S. Application Data

(60) Provisional application No. 63/092,176, filed on Oct. 15, 2020.

(51) Int. Cl.
| | | |
|---|---|---|
| *C07K 16/24* | (2006.01) | |
| *C07K 16/30* | (2006.01) | |
| *A61K 39/395* | (2006.01) | |
| *A61K 45/06* | (2006.01) | |
| *A61P 31/14* | (2006.01) | |

(52) U.S. Cl.
CPC ...... *C07K 16/249* (2013.01); *A61K 39/39558* (2013.01); *A61K 45/06* (2013.01); *A61P 31/14* (2018.01); *C07K 16/30* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 4,867,973 A | 9/1989 | Goers | |
| 5,969,098 A | 10/1999 | Brittain | |
| 7,504,490 B1 | 3/2009 | Weinstock | |
| 8,956,609 B2 | 2/2015 | Herrera et al. | |
| 10,202,457 B2 * | 2/2019 | Ruiz-Opazo | A61P 35/00 |
| 2009/0028852 A1 | 1/2009 | Herrera | |
| 2009/0215680 A1 | 8/2009 | Caboche et al. | |
| 2009/0317836 A1 | 12/2009 | Kuhn | |
| 2011/0313229 A1 | 12/2011 | Sugaya | |
| 2013/0022551 A1 | 1/2013 | Ruiz-Opazo et al. | |
| 2013/0177500 A1 | 7/2013 | Ruiz-Opaz | |
| 2016/0108124 A1 | 4/2016 | Ruiz-Opazo et al. | |
| 2017/0058036 A1 | 3/2017 | Ruiz-Opazo et al. | |
| 2017/0253657 A1 | 9/2017 | Constantin | |

FOREIGN PATENT DOCUMENTS

| | | | |
|---|---|---|---|
| WO | 2003002144 A1 | 1/2003 | |
| WO | 2006055665 A2 | 5/2006 | |
| WO | 2007102354 A2 | 9/2007 | |
| WO | 2010114801 A1 | 10/2010 | |
| WO | 2012012750 A1 | 1/2012 | |
| WO | 2013112467 A1 | 8/2013 | |
| WO | 2016127255 A1 | 8/2016 | |
| WO | 2017035249 A1 | 3/2017 | |
| WO | 2019055958 A1 | 3/2019 | |

OTHER PUBLICATIONS

MacCallum et al. Journal of Molecular Biology, 262:732-745, 1996.*
Casset et al. Biochemical and Biophysical Research Communications, 307:198-205, 2003.*
Rudikoff, et al. Proc. Natl. Acad. Sci. USA, 79(6):1979-1983.*
Herrera et al, Sci Reports 12: 5583, 2022.*
Mustafa et al, (Hindawi Mediators of Inflammation vol. 2020, Article ID 8198963, https://doi.org/10.1155/2020/8198963.*
Druml et al. Endothelin-1 in adult respiratory distress syndrome. Am. Rev. Respir. Dis. 148(5), 1169-1173 (1993).
Filep et al. "Neutrophil apoptosis: a target for enhancing the resolution of inflammation." J. Cell Biochem. 108(5), 1039-1046 (2009).
Gregoire et al. "Impaired efferocytosis and neutrophil extracellular trap clearance by macrophages in ARDS." Eur. Respir. J. 52(2), 1702590 (2018).
Moulding et al. "Mcl-1 expression in human neutrophils: regulation by cytokines and correlation with cell survival." Blood 92(7), 2495-2502 (1998).
Templeton et al. "Prognostic Role of Neutrophil-to-Lymphocyte Ratio in Solid Tumors: A Systematic Review and Meta-Analysis." JNCI: Journal of the National Cancer Institute 106(6): 1-11 (2014).
Thalin et al., "NETosis promotes cancer-associated arterial microthrombosis presenting as ischemic stroke with troponin elevation." Thrombosis Research 139:56-64 (2016).
UniProt Submission BOL3A2_Human [Retrieved from Internet Feb. 7, 2017; <http://www.uniprot.org/uniprot/B0L3A2.txt?version=11>] (2008).
Vajdos et al., "Comprehensive functional maps of the antigen-binding site of an anti-ErbB2 antibody obtained with shotgun scanning mutagenesis", J Mol Biol 320(2) 415-428 (2002).

(Continued)

*Primary Examiner* — Bridget E Bunner
*Assistant Examiner* — Fozia M Hamud
(74) *Attorney, Agent, or Firm* — Nixon Peabody LLP; Ronald I. Eisenstein; Nicole D. Kling

(57) ABSTRACT

Described herein are methods of treating COVID19 from a coronavirus infection, methods of treating a subject having a coronavirus infection, methods of improving a survival rate of a subject having a coronavirus infection, methods of determining prognosis of a subject having a coronavirus infection, methods of preventing or treating organ-dysfunction or multi-organ dysfunction or failure associated with a coronavirus infection, methods of combinational therapy for a subject having a coronavirus infection, methods of reducing microthrombi formation or low flow organ-ischemia associated with a coronavirus infection by administering a DEspR inhibitor.

28 Claims, 168 Drawing Sheets

Specification includes a Sequence Listing.

(56) References Cited

OTHER PUBLICATIONS

Vassallo et al. "E.R. The counter-intuitive role of the neutrophil in the acute respiratory distress syndrome." Br. Med. Bull. 131(1), 43-55 (2019).
Wong et al., "Diabetes primes neutrophils to undergo NETosis, which impairs wound healing." Nature Medicine 21 (7):815-819 (2015).
Yang et al., "Identification of local and circulating cancer stem cells in human liver cancer", Hepatolofy 47(3) 919-928 (2008).
Yipp et al. "NETosis: how vital is it?." Blood 122(16): 2784-2794 (2013).
Zouki et al. "Endothelin-1 enhances neutrophil adhesion to human coronary artery endothelial cells: role of ET(A) receptors and platelet-activating factor." Br. J. Pharmacol. 127(4), 969-979 (1999).
Abdollahi et al., "Evading tumor evasion: current concepts and perspectives of anti-angiogenic cancer therapy", Drug Resist Updat 13(1-2) 16-28 (2010).
Bergers et al., "Modes of resistance to anti-angiogenic therapy", Nat Rev Cancer 8(8) 592-603 (2008).
Brown et al., "Tolerance of single, but not multiple, amino acid replacements in antibody VH CDR 2: a means of minimizing B cell wastage from somatic hypermutation?", J Immunol 156(9) 3285-3291 (1996).
Carmeliet et al., "Abnormal blood vessel development and lethality in embryos lacking a single VEGF allele", Nature 380(6573) 435-439 (1996).
Carmeliet et ai., "Angiogenesis in life, disease and medicine", Nature 438(7070) 932-936 (2005).
Casset et al., "A peptide mimetic of an anti-CD4 monoclonal antibody by rational design", Biochem Biophys Res Commun 307(1) 198-205 (2003).
Clouthier et al., "Cranial and cardiac neural crest defects in endothelin-A receptor-deficient mice", Development 125(5) 813-824 (1998).
Colman et al., "Effects of amino acid sequence changes on antibody-antigen interactions", Res Immunol 145(1) 33-36 (1994).
Cools-Lartigue et al., "Neutrophil extracellular traps in cancer progression." Cellular and Molecular Life Sciences 71(21):4179-4194 (2014).
Crawford et al., "Chapter 6. Mouse models to investigate anti-cancer effects of VEGF inhibitors", Methods Enzymol 445:125-139 (2008).
Decano et al., "Dual enothelin-1/VEGFsp receptor (DEspR) roles in adult angiogenesis in despr+/− knockout micr and carotid artery disease rat model", Manuscript submitted to Circulation. (2010).
Decano et al., "Early-life sodium exposure unmasks susceptibility to stroke in hyperlipidemic, hypertensive heterozygous Tg25 rats transgenic for human cholesteryl ester transfer protein", Circulation 119(11) 1501-1509 (2009).
Decano et al., "Molecular imaging of vasa vasorum neovascularization via DEspR-targeted contrast-enhanced ultrasound micro-imaging in transgenic atherosclerosis rat model", Mol Imaging Biol 13(6) 1096-1106 (2011).
Desai et al. "Matters of life and death. How neutrophils die or survive along NET release and is "NETosis"=necroptosis?." Cellular and Molecular Life Sciences 73(11): 2211-2219 (2016).
Ebos et al., "Accelerated metastasis after short-term treatment with a potent inhibitor of tumor angiogenesis", Cancer Cell 15(3) 232-239 (2009).
Edwards et al., "Regulation of neutrophil apoptosis by Mcl-1." Biochemical Society Transactions 32:489-492 (2004).
Edwards et al. "The remarkable flexibility of the human antibody repertoire; isolation of over one thousand different antibodies to a single protein, BLyS." Journal of molecular biology 334(1): 103-118 (2003).
El Kebir et al., "Modulation of neutrophil apoptosis and the resolution of inflammation through β2 integrins." Frontiers in Immunology 4(6) (2013).
El Kebir et al., "Targeting neutrophil apoptosis for enhancing the resolution of inflammation." Cells 2(2):330-348 (2013).

Fadini et al., "A perspective on NETosis in diabetes and cardiometabolic disorders." Nutrition, Metabolism and Cardiovascular Diseases 26(1):1-8 (2016).
Ferrara et al., "Heterozygous embryonic lethality induced by targeted inactivation of the VEGF gene", Nature 380 (6573) 439-442 (1996).
Ferrara et al., "Pathways mediating VEGF-independent tumor angiogenesis", Cytokine Growth Factor Rev 21(1) 21-26 (2010).
Ferrara et al. "Recombinant renewable polyclonal antibodies." MAbs. 7(1): 32-41 (2015).
Fridlender et al. "Transcriptomic Analysis Comparing Tumor-Associated Neutrophils with Granulocytic Myeloid-Derived Suppressor Cells and Normal Neutrophils." PLoS One 7(2): e31524 (2012).
Gamicia et al., "Neutrophil extracellular traps in sepsis." Shock 42(4):286-294 (2014).
Gattinoni et al., "Ventilator-induced lung injury: the anatomical and physiological framework." Critical Care Medicine 38(10):S539-S548 (2010).
Genbank, dual endothelial-1 (VEGRsp)/angiotension II receptor [*Homo sapiens*], NCBI LOCUS ABP04239, AC ABP04236 GI:144954326 (2008).
Gloriosso et al., "Association of ATP1A1 and dear single-nucleotide polymorphism haplotypes with essential hypertension: sex-specific and haplotype-specific effects", Circ Res 100(10) 1522-1529 (2007).
Goel et al. "Plasticity within the antigen-combining site may manifest as molecular mimicry in the humoral immune response." The Journal of Immunology 173(12): 7358-7367 (2004).
Hanahan et al., "Hallmarks of cancer: the next generation", Cell 144(5) 646-674 (2011).
Herrera et al., "Analysis of gender-specific atherosclerosis susceptibility in transgenic[hCETP]25DS rat model", Atherosclerosis 17791) 9-18 (2004).
Herrera et al., "Confirmation of translatability and functionality certifies the dual endothelin1/VEGFsp receptor (DEspR) protein." BMC Molecular Biology 17(1):15 (2016).
Herrera et al., "DEspR roles in tumor vasculo-angiogenesis, invasiveness, CSC-survival and anoikis resistance: a 'common receptor coordinator' paradigm." PloS One 9(1):e85821 (2014).
Herrera et ai., "Embryonic lethality in Dear gene-deficient mice: new player in angiogenesis", Physiol Genomics 23(3) 257-268 (2005).
Herrera et al., "Sex-specific hippocampus-dependent cognitive deficits and increased neuronal autophagy in DEspR haploinsufficiency in mice", Physiol Genomics 35(3) 316-329 (2008).
Lescar et al. "Crystal structure of a cross-reaction complex between Fab F9. 13.7 and guinea fowl lysozyme." Journal of Biological Chemistry 270(30): 18067-18076 (1995).
Lin et al., "Origins of circuiating endothelial cells and endothelial outgrowth from blood", J Clin Invest 105(1) 71-77 (2000).
Lloyd et ai. "Modelling the human immune response: performance of a 1011 human antibody repertoire against a broad panel of therapeutically relevant antigens." Protein Engineering, Design & Selection 22(3): 159-168 (2009).
Loges et al., "Mechanisms of resistance to anti-angiogenic therapy and development of third-generation anti-angiogenic drug candidates", Genes Cancer 1(1) 12-25 (2010),.
MacCallum et al., "Antibody-antigen interactions: contact analysis and binding site topography", J Moi Biol 262(5) 732-745 (1996).
McCarthy. "Antiangiogenesis drug promising for metastatic colorectal cancer." The Lancet 361 (9373): 1959 (2003).
Michaud et al., "Mechanisms of ventilator-induced lung injury: the clinician's perspective." Critical Care 7(3):209-2010 (2003).
Narasaraju et al., "Neutrophils as Possible Therapeutic Targets in Severe Influenza Pneumonia." Journal of Infectious Pulmonary Diseases 2(2):1-3 (2016).
Paez-Ribes et al., "Antiangiogenic therapy elicits malignant progression of tumors to increased local invasion and distant metastasis", Cancer Cell 15(3) 220-231 (2009).
Paul, "Fundamental Immunology", Third Edition, Raven Press, New York, Chapter 8, 292-295 (1993).

(56) References Cited

OTHER PUBLICATIONS

Rudikoff et al., "Single amino acid substitution altering antigen-binding specificity", Proc Natl Acad Sci USA 79(6) 1979-1983 (1982), Ruiz-Opazo et al., "Molecular characterization of a dual endothelin-1/Angiotensin II receptor", Mol Med 4(2) 96-108 (1998).

Sela-Culang et al. "The structural basis of antibody-antigen recognition." Frontiers in Immunology 4(302): 1-13 (2013).

Swami et al., "Multipotent tumour endothelial cells", Nature Reviews Cancer 8(11) 2008.

Zuo et al. "Neutrophil extracellular traps and thrombosis in COVID-19." Journal of thrombosis and thrombolysis 51.2 (2021): 446-453.

Badraoui et al. "Acute respiratory distress syndrome: a life threatening associated complication of SARS-CoV-2 infection inducing COVID-19." Journal of Biomolecular Structure and Dynamics 39.17 (2021): 6842-6851.

Baseler et al. "An acute immune response to Middle East respiratory syndrome coronavirus replication contributes to viral pathogenicity." The American journal of pathology 186.3 (2016): 630-638.

Chollet-Martin et al. "Interactions between neutrophils and cytokines in blood and alveolar spaces during ARDS." American journal of respiratory and critical care medicine 154.3 (1996): 594-601.

Cockrell et al. "A mouse model for MERS coronavirus-induced acute respiratory distress syndrome." Nature microbiology 2.2 (2016): 1-11.

Grommes et al. "Contribution of neutrophils to acute lung injury." Molecular medicine 17.3 (2011): 293-307.

Williams et al. "Evidence for chemokine synergy during neutrophil migration in ARDS." Thorax 72.1 (2017): 66-73.

Zemans et al. "What drives neutrophils to the alveoli in ARDS?." Thorax 72.1 (2017): 1-3.

\* cited by examiner

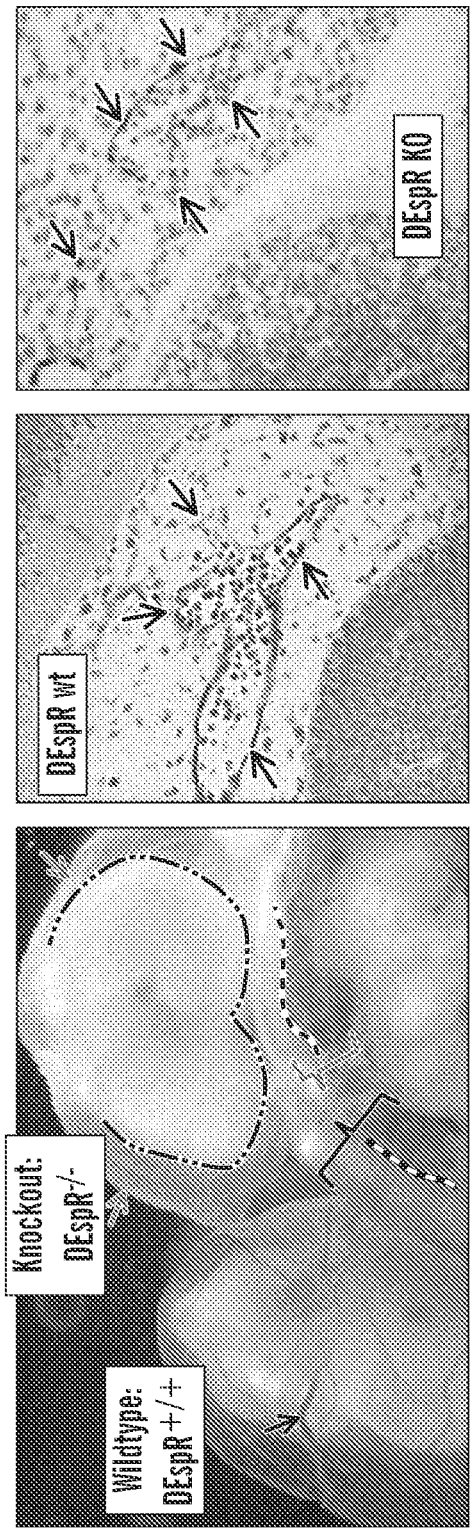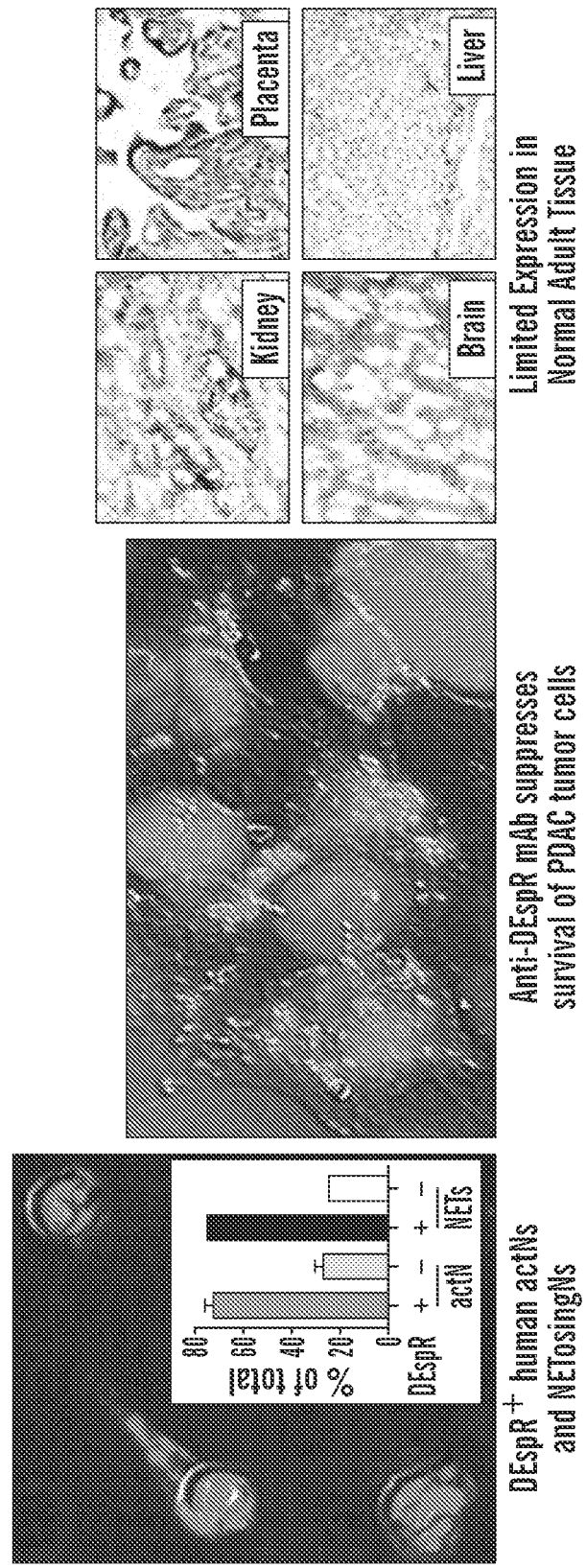
FIG. 2

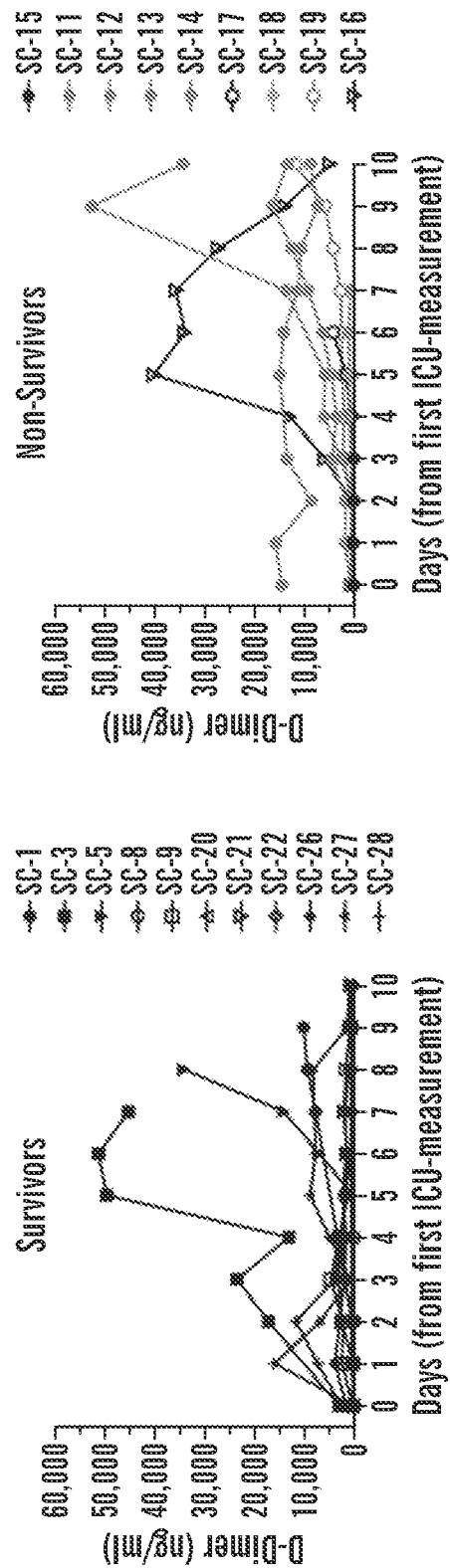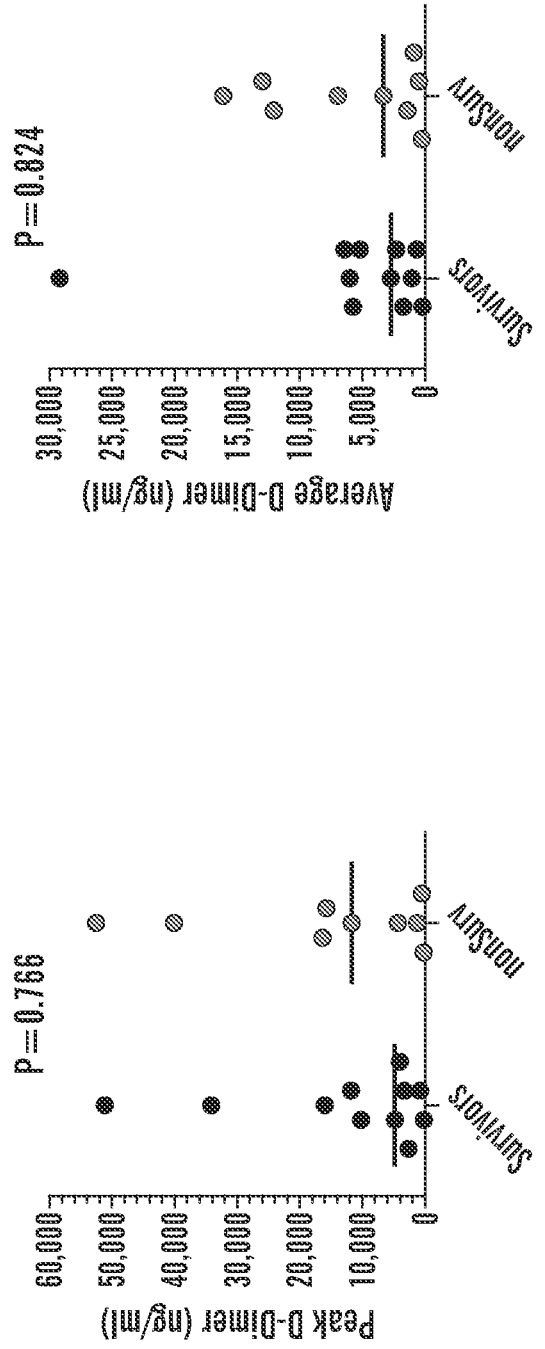
FIG. 19

Total Rogue Ns + Ms: sum of % CD11b+DEspR+ neutrophils (Ns) and monocytes (Ms)

$R_S$: Spearman Rank Correlation

Severity of ARDS-COVID: defined by #days in the ICU, with ICU-death imputed as > longest length of stay 0:     <7 days in ICU 0.5:    >30 days in ICU & discharge with 1.0     ICU death ARDS dx: Berlin Definition criteria Comparative analysis:
Spearman rank order correlation analysis of SF ratio, NLR, DEspR+CD11B+ Ns & Ms vs Severity of Disease in AC4-AC11 patients

| Group | $R_s$ | P |
|---|---|---|
| | Severity of Disease | |
| DEspR+CD11B+ Ns | 0.717 | 0.037 |
| DEspR+CD11B+ Ms | 0.544 | 0.139 |
| DEspR+CD11B+ [Ns+Ms] | 0.861 | 0.0018 |
| Neutrophil Lymphocyte Ratio [NLR] | 0.548 | 0.139 |
| PsO2/FiO2 [SF] ratio - hypoxemia | -0.274 | 0.460 | n = 8 subjects (AC4-AC11). NLR, neutrophil/lymphocyte ratio; statistical analysis = Spearman Rank Order Correlation. ICU days, # days patient spent in ICU (ranged 6-63 days).

Severity of Disease: 0 = 1-28 days in ICU, 0.5 = 29-xx days in ICU and/or sequela, 1 = Deceased.

FIG. 23

| Group | R | P nominal | P Bonferroni |
|---|---|---|---|
| FACS based biomarkers | | | |
| % DEspR+CD11b+ 'rogue' Ns [total] | 0.915 | 0.000001 | 0.000008 |
| % DEspR+CD11b+ 'rogue' Ls | 0.714 | 0.0091 | 0.073 |
| % DEspR+CD11b+ 'rogue' Ms | 0.804 | 0.0028 | 0.022 |

FIG. 38 n = 13 subjects; NLR, neutrophil/lymphocyte ratio; [total], neutrophils + early apoptosis neutrophils combined; Ls, lymphocytes, Ms, monocytes
Statistical analysis = Linear regression; outcomes: 0 = survived, 0.5 = survived with sequelae, 1 = deceased.
-R: negative correlation, inverse relation of dependent variable (outcome) and explanatory variable (biomarkers).

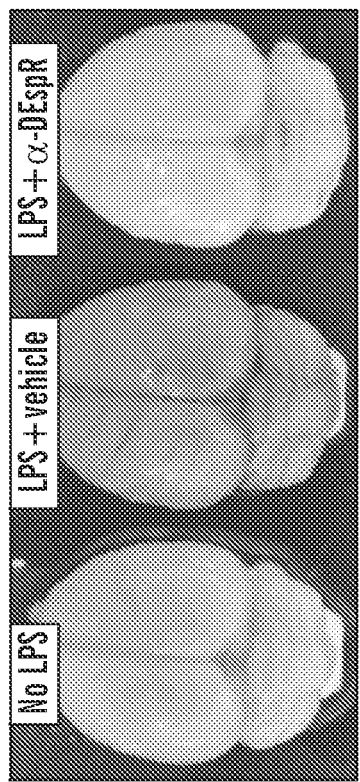
FIG. 41A
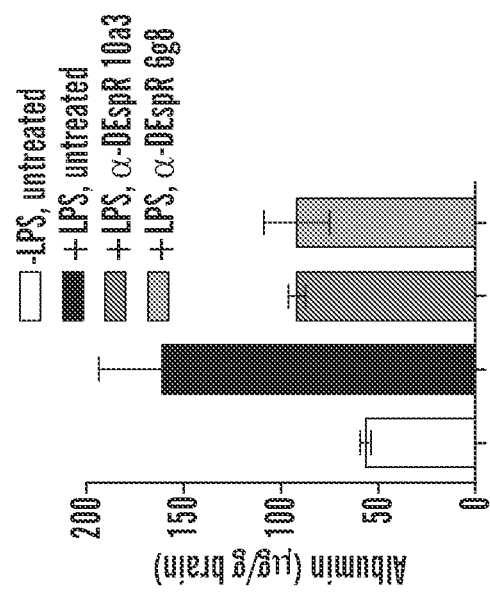
FIG. 41B
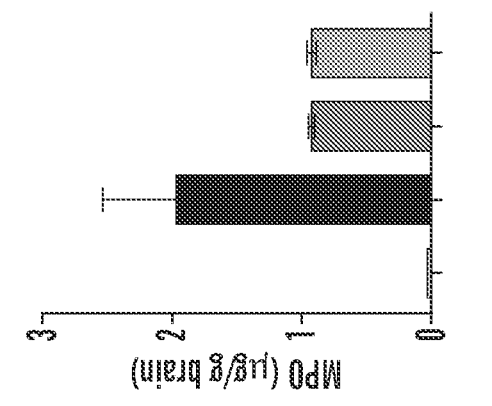
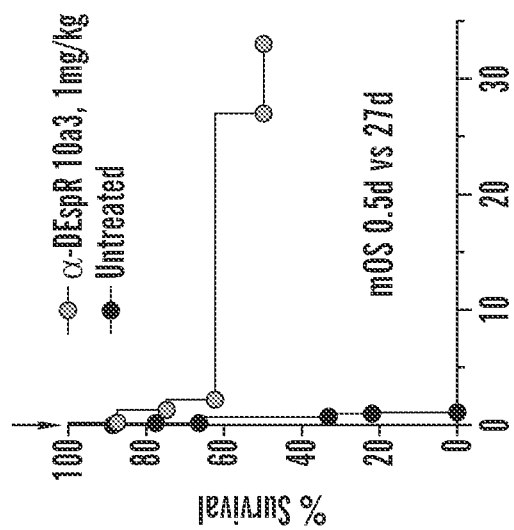

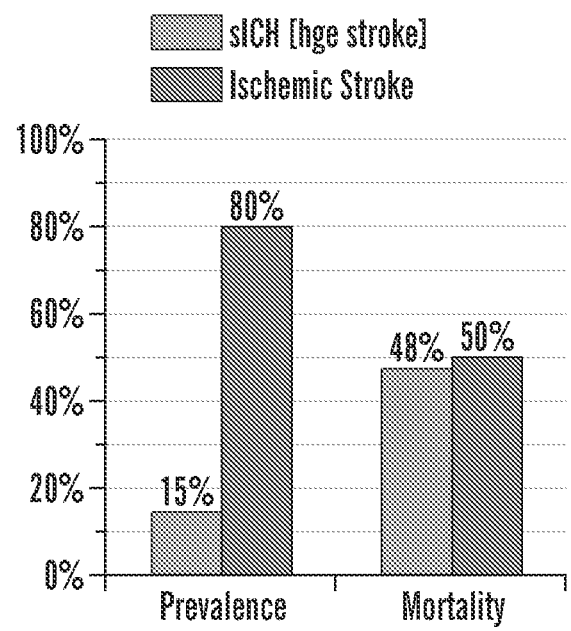
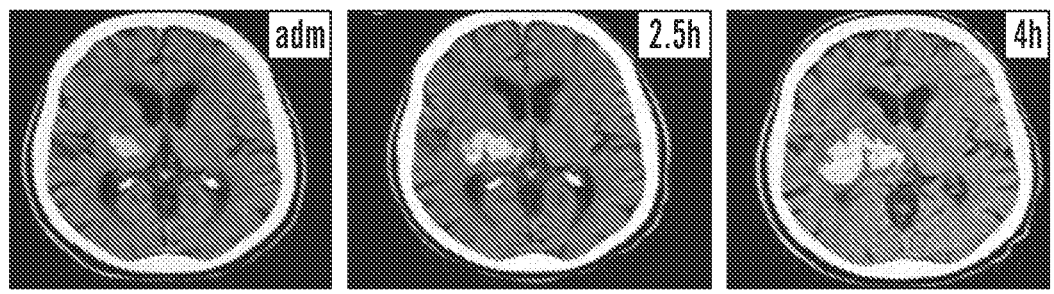
*FIG. 42*

- Core hematoma (⇨)
- Multiple micro-bleeds (⇢)
- Large zone of perihematomal edema (○)

▇ DEspR  ▇ DAPI (DNA)  ▇ DEspR/DAPI costain  ▇ SMA (microvessels)

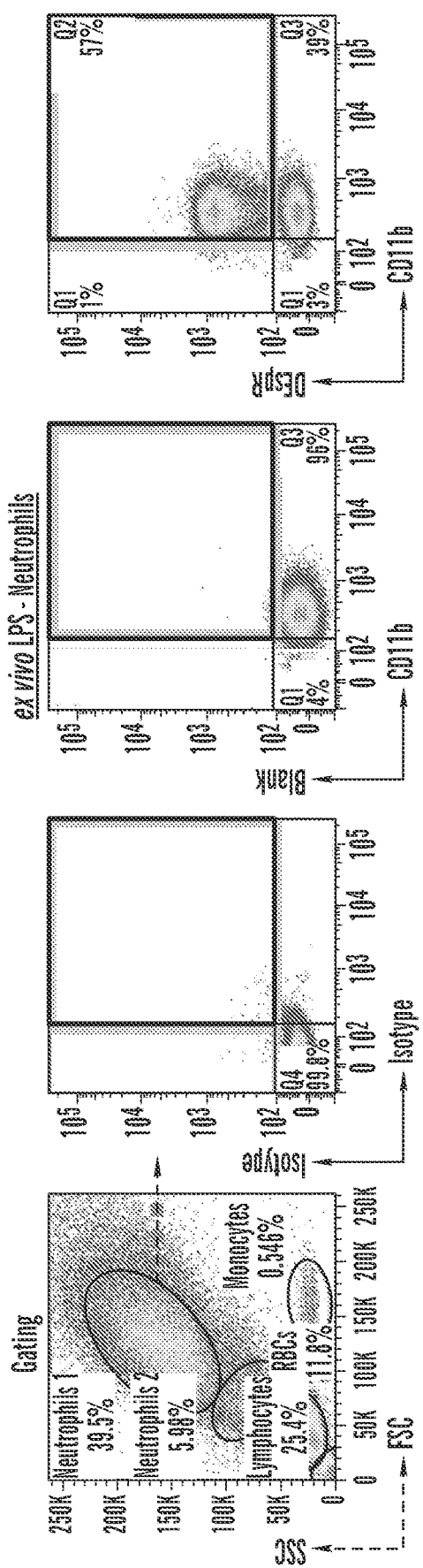
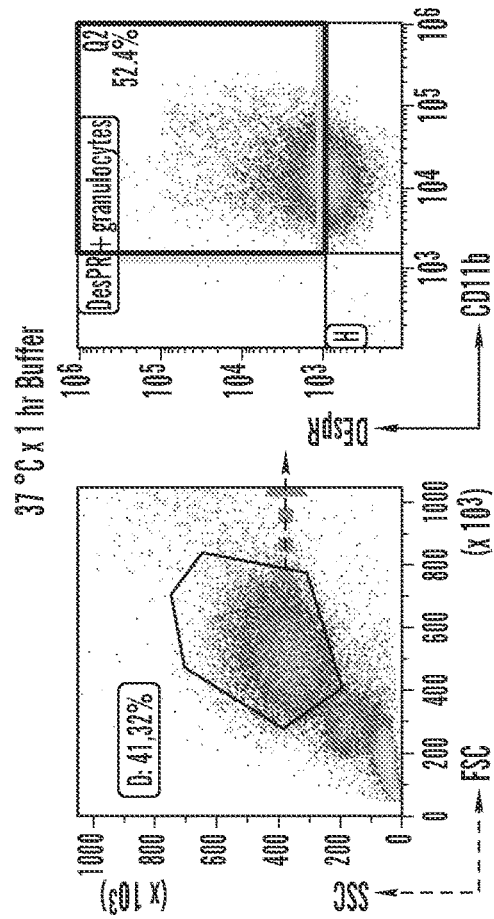
FIG. 50E
FIG. 50F

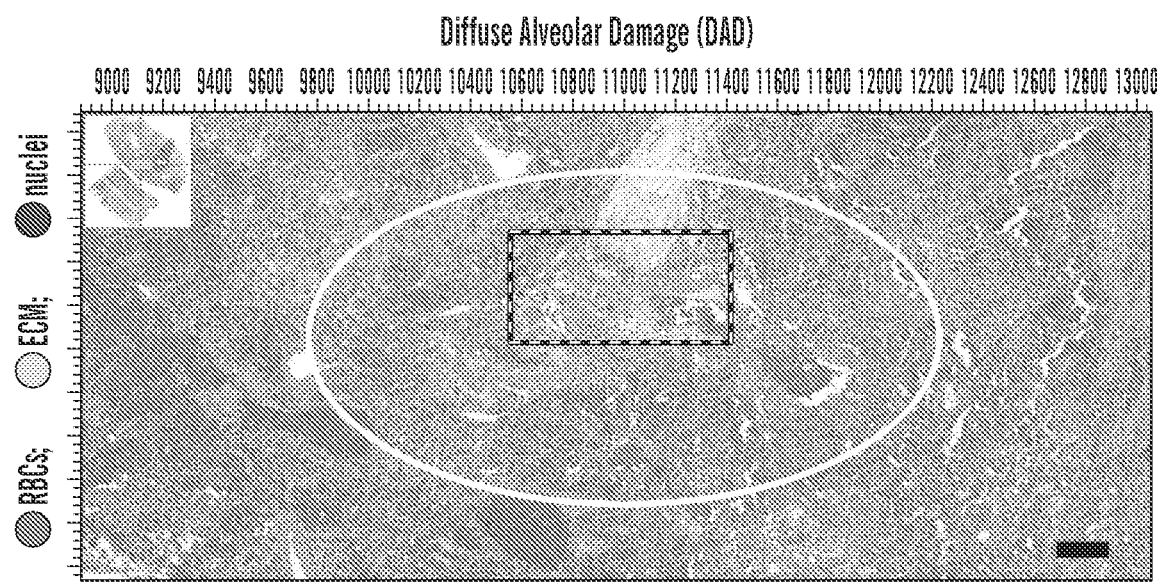
FIG. 51A
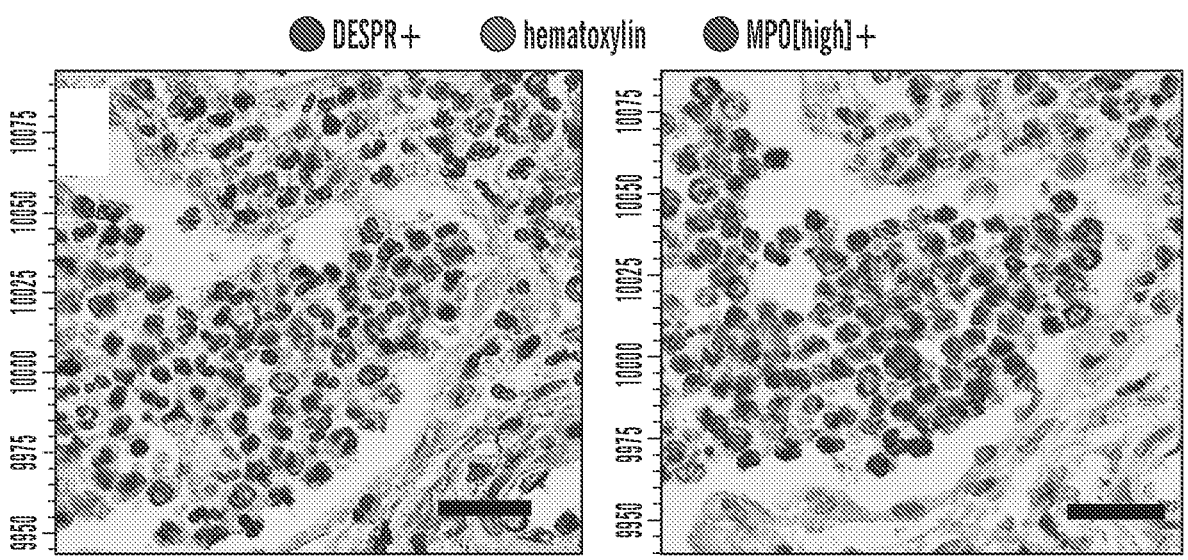
FIG. 51B
FIG. 51C

DEspR-network genes: ▢ Modulators  ▢ Bioeffect  ▢ DEspR-ligands  ▢ TLR4-ligands
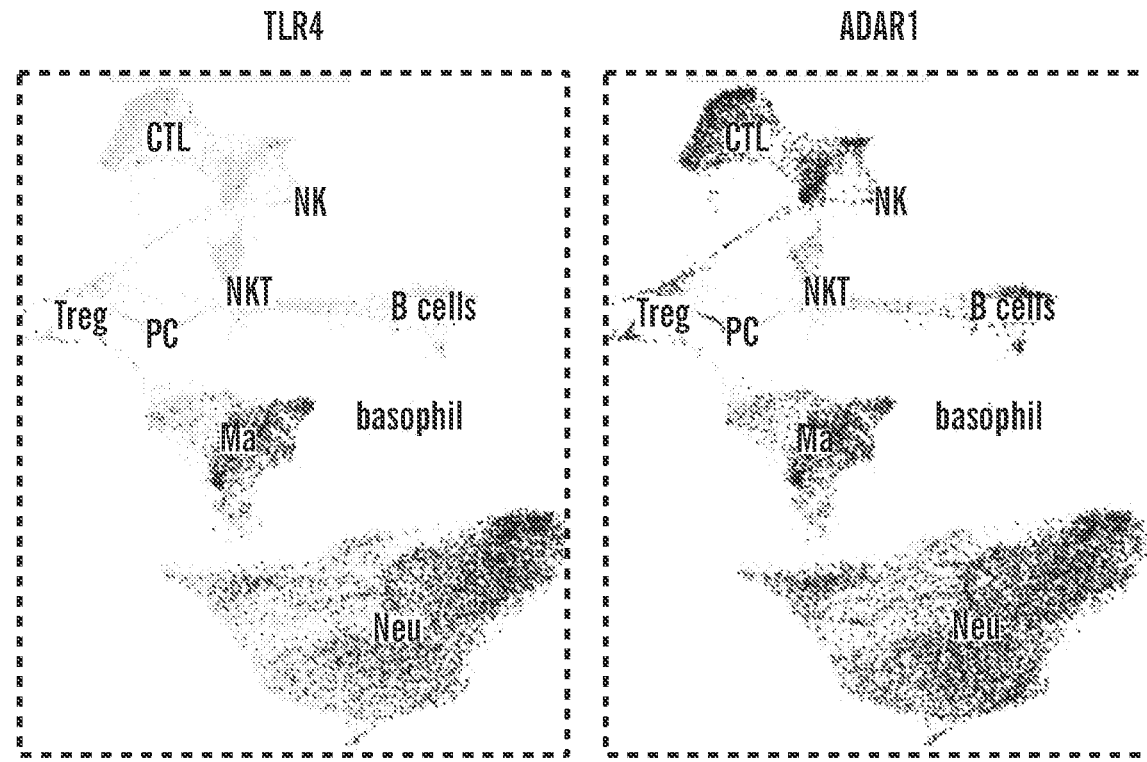
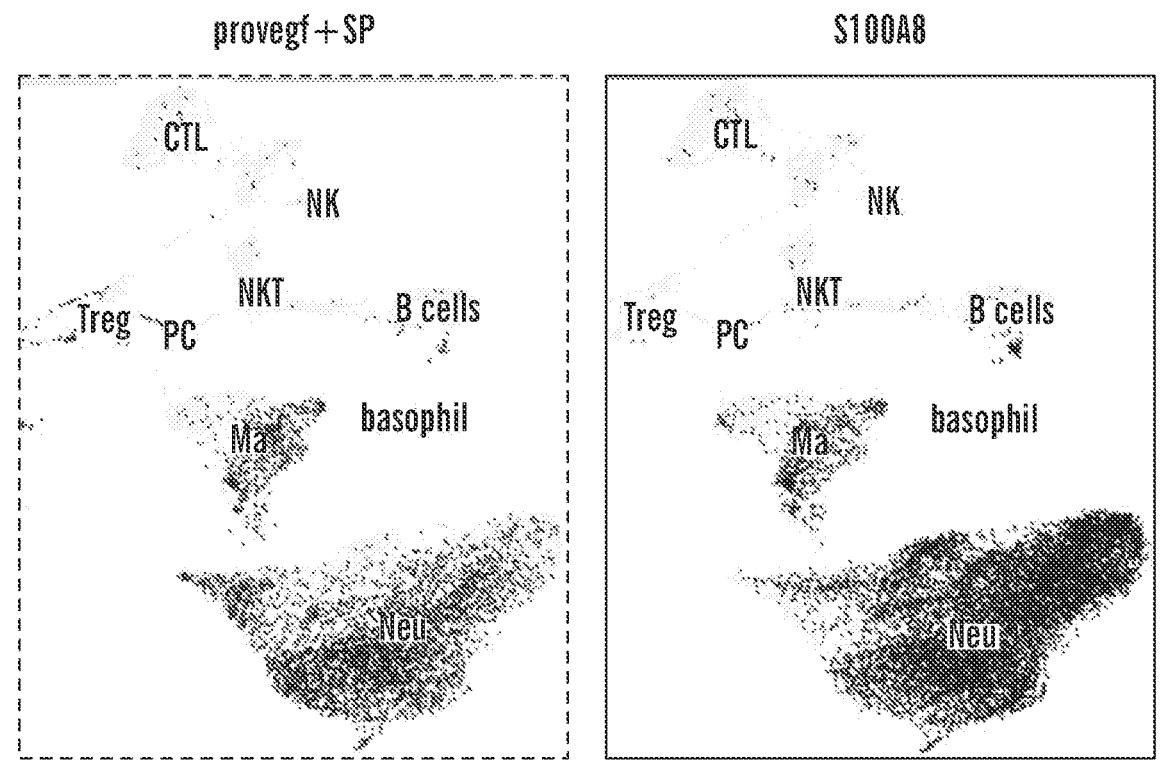
FIG. 52B DEspR-network genes:  ⬚ Modulators   ☐ Bioeffect   ⬚ DEspR-ligands   ☐ TLR4-ligands
Mcl1
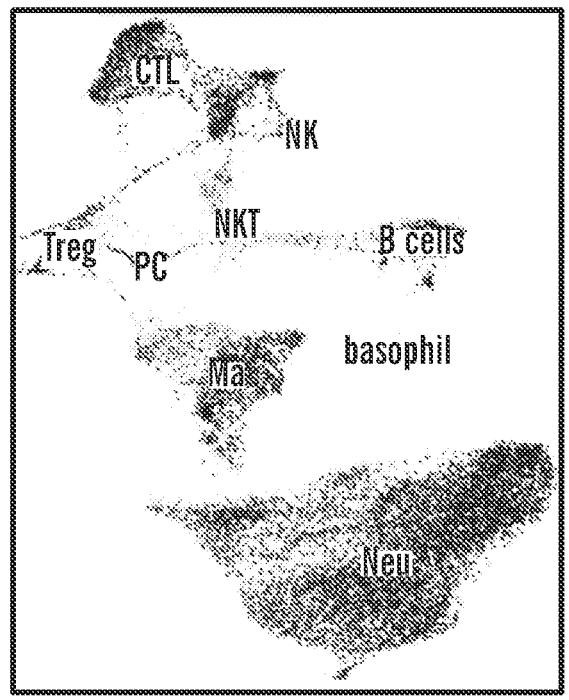
S100A9
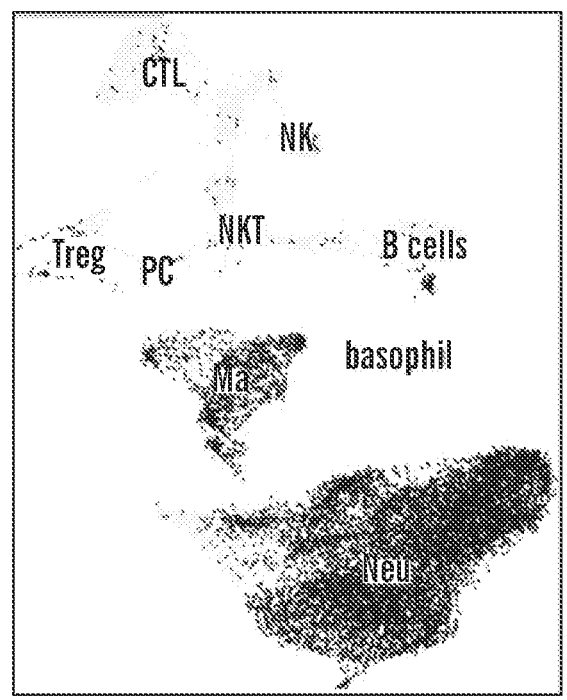
FIG. 52C

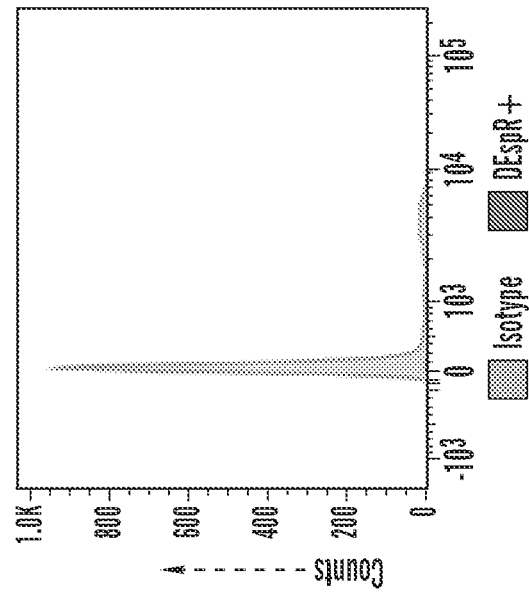
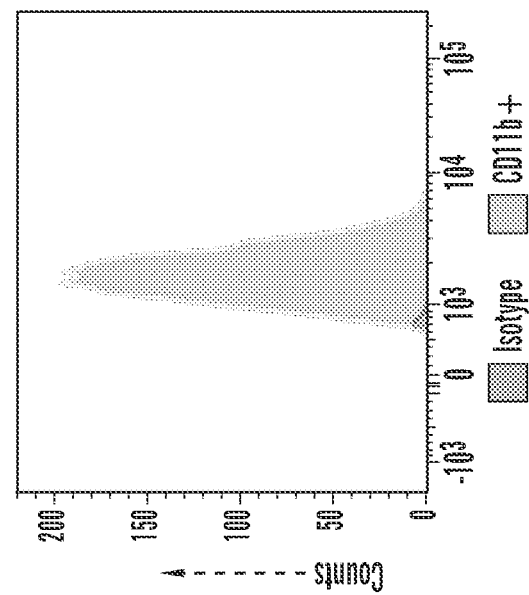
FIG. 53J

| Spearman Rank Correlation matrix analysis in ARDS (non-COVID) n = 19 subjects. | | | | | | | | |
|---|---|---|---|---|---|---|---|---|
| | Clinical measures of severity | | | | | | | |
| | ICU-free days | | S/F ratio | | t1-SOFA | | t2-SOFA | |
| Biomarkers | $r_S$ | P-value | $r_S$ | P-value | $r_S$ | P-value | $r_S$ | P-value |
| CBC-differential | | | | | | | | |
| NLR | -0.2675 | 0.2964 | -0.2399 | 0.3681 | -0.1222 | 0.6382 | 0.0764 | 0.7776 |
| Flow cytometry analyses | | | | | | | | |
| #D+actNs | -0.8000 | 0.0002 | -0.3753 | 0.1520 | 0.4185 | 0.0954 | 0.7057 | 0.0031 |
| %D+actNs | -0.7768 | 0.0001 | -0.4062 | 0.1190 | 0.5572 | 0.0163 | 0.7897 | 0.0003 |
| %D+act[Ns+Ms] | -0.8055 | 0.0003 | -0.5147 | 0.0517 | 0.4392 | 0.0899 | 0.5366 | 0.0420 |
| %D+actMs | -0.6438 | 0.0088 | -0.4754 | 0.0749 | 0.1232 | 0.6474 | 0.1935 | 0.4879 |
| %D+actLs | -0.7899 | 0.0003 | -0.3591 | 0.1714 | 0.2383 | 0.3544 | 0.5244 | 0.0392 |
| Cytoplast$^{Hi}$ | -0.2911 | 0.2540 | 0.0144 | 0.9598 | -0.2428 | 0.3441 | 0.2652 | 0.3165 |
| Cytoplast$^{LOW}$ | -0.3929 | 0.1195 | -0.4448 | 0.0978 | 0.1319 | 0.6103 | 0.4719 | 0.0666 |
| ELISA - plasma levels | | | | | | | | |
| IL-6 | 0.0232 | 0.9273 | -0.0486 | 0.8587 | 0.3484 | 0.1565 | -0.0050 | 0.9864 |
| ET-1 | -0.0682 | 0.8011 | 0.0769 | 0.7966 | 0.3546 | 0.1938 | 0.0277 | 0.9232 |
| MPO | 0.2840 | 0.2533 | 0.3932 | 0.1319 | -0.2310 | 0.3564 | -0.2521 | 0.3252 |
| sC5b9 | -0.2904 | 0.2425 | 0.1016 | 0.7061 | 0.0785 | 0.7629 | 0.0578 | 0.8239 |
| PCR analysis | | | | | | | | |
| mt/nucl DNA | -0.0359 | 0.8978 | 0.1473 | 0.6158 | -0.0647 | 0.8104 | 0.4435 | 0.0990 |

FIG. 56A

Legend: n = 19 subjects ARDS, all cause [pre-COVID19 pandemic].

, total number K/αL whole blood; %, % from total Ns, Ms, or Ls; actNs, CD11b+ activated neutrophils; cytoplast^Hi, high granularity (SSC) cytoplast, cytoplast^LOW, low granularity cytoplast; D+, cell surface DEspR+ expression; ET-1, endothelin-1 plasma levels; IL-6, interleukin-6 plasma levels; Ls, lymphocytes; Ms, monocytes; MPO, plasma myeloperoxidase levels; mt/nucl DNA, mitochondrial to nuclear DNA ratio; Ns, neutrophils. NLR, neutrophil to lymphocyte ratio; sC5b9, plasma levels of soluble complement terminal C5b9-complex.

Clinical measures of severity: ICU-free days at day 28 = [28 – number of [ICU days] with NonSurvivors = -1 and Survivors > 28 ICU days = 0. S/F ratio, SpO2/FiO2 ratio as a measure of hypoxemia severity. t1-SOFA, sequential organ failure assessment (SOFA) score on day of flow cytometry analysis; t2-SOFA, SOFA score at end of ICU stay (day before ICU-discharge or ICU-death).

Statistical analysis: Spearman Rank Order Correlation coefficient rho (r_s) effect size: strong r_s 0.6 – 0.79; very strong r_s 0.8 – 1.0 monotonic relationship between paired data. Data points used are peak values for subjects with multiple FCM analyses. Spearman Correlation Coefficient r_s > 0.605, alpha < 0.05, Power > 0.8 *(grey italics)*.

FIG. 56B

| Spearman Rank Correlation matrix analysis: COVID19-ARDS subjects requiring ventilator support. | | | | | | | | |
|---|---|---|---|---|---|---|---|---|
| | Clinical Measures of ARDS severity | | | | | | | |
| Biomarkers | ICU-free days | | S/F ratio | | t1-SOFA | | t2-SOFA | |
| CBC-differential | $r_S$ | P-value | $r_S$ | P-value | $r_S$ | P-value | $r_S$ | P-value |
| Neutrophil-lymphocyte ratio | -0.6201 | 0.0470 | -0.3364 | 0.3132 | 0.6514 | 0.0340 | 0.7936 | 0.0051 |
| Flow cytometry (FCM) | | | | | | | | |
| #D+actNs | -0.8033 | 0.0044 | -0.6273 | 0.0440 | 0.6052 | 0.0527 | 0.5367 | 0.0920 |
| %D+actNs | -0.7657 | 0.0084 | -0.6091 | 0.0519 | 0.5174 | 0.1061 | 0.4220 | 0.1961 |
| %D+act[Ns+Ms] | -0.8737 | 0.0009 | -0.7545 | 0.0098 | 0.4250 | 0.1928 | 0.5367 | 0.0920 |
| %D+actMs | -0.7298 | 0.0142 | -0.7973 | 0.0048 | 0.4491 | 0.1658 | 0.7379 | 0.0120 |
| Immunofluorescence Cytology | | | | | | | | |
| #D+actNETosing Ns | -0.8880 | 0.001 | -0.8050 | 0.0039 | 0.5960 | 0.057 | 0.7750 | 0.007 |
| Circularity index | 0.7140 | 0.0174 | 0.7091 | 0.0182 | -0.2284 | 0.5006 | -0.5230 | 0.1020 |

Legend: n = 11 subjects. #, number (K/μL) whole blood; %, % positive among all neutrophils (Ns) or monocytes (Ms); D+, total (cell surface + intracellular) DEspR+ expression; #D+actNs, DEspR+CD11b+ neutrophil (K/μL); %D+actMs, %DEspR+CD11b+ monocytes among all monocytes; NLR, neutrophil to lymphocyte ratio = absolute neutrophil/absolute lymphocyte, #D+actNETosing Ns (K/μL): number of DEspR+CD11b+ NETosing Ns, calculated as follows: (#D+Ns × %NETosing Ns)/100.

Clinical measures of severity: ICU-free days at day 28 = [28 – number of ICU days] with NonSurvivors = -1 and Survivors > 28 ICU days = 0. S/F ratio, SpO2/FiO2 ratio as a measure of hypoxemia severity. t1-SOFA, sequential organ failure assessment (SOFA) score on day of flow cytometry analysis; t2-SOFA, SOFA score at end of ICU stay (day before ICU-discharge or ICU-death).

Statistical analysis: Spearman Rank Order Correlation coefficient rho ($r_S$) effect size: strong $r_S$ 0.6 – 0.79; very strong $r_S$ 0.8 – 1.0 monotonic relation between paired data, (- $r_S$) negative monotonic relation between paired data. Data points are peak values for subjects with multiple FCM analyses. Spearman Correlation Coefficient $r_S$ > 0.758, alpha < 0.05, Power > 0.8 (grey italics); $r_S$ > 0.6, alpha < 0.05, power 0.7 to 0.8 (bold).

*FIG. 57*

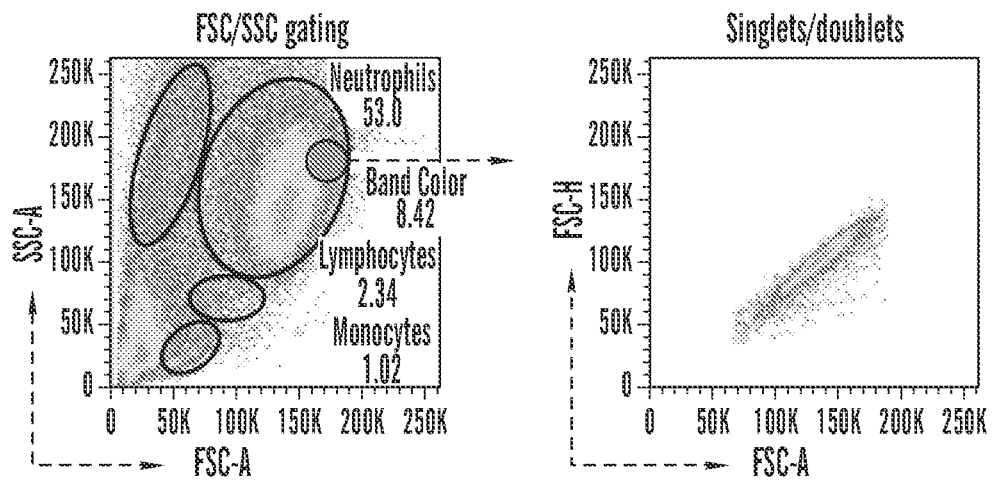
FIG. 60A  FIG. 60B
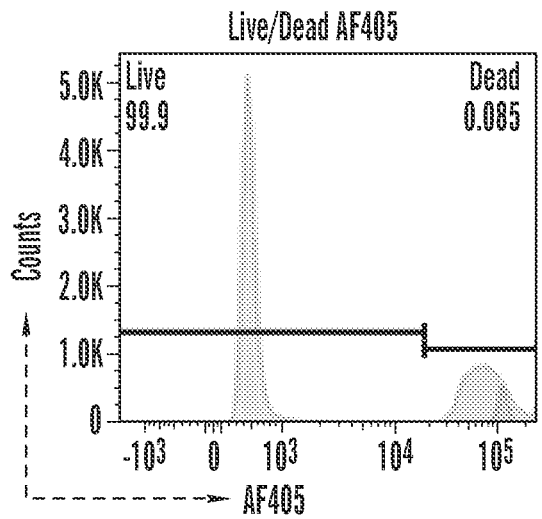
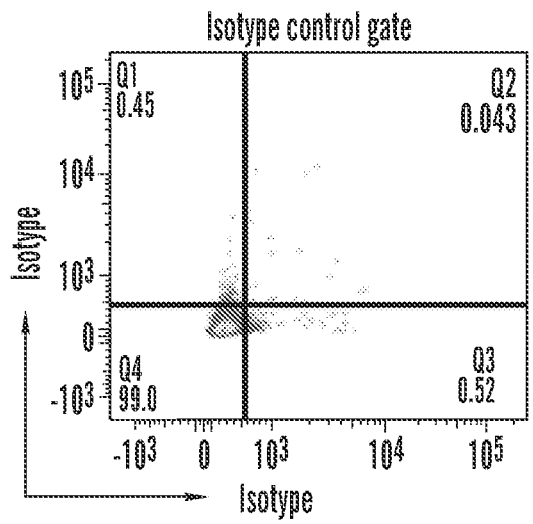
FIG. 60C  FIG. 60D
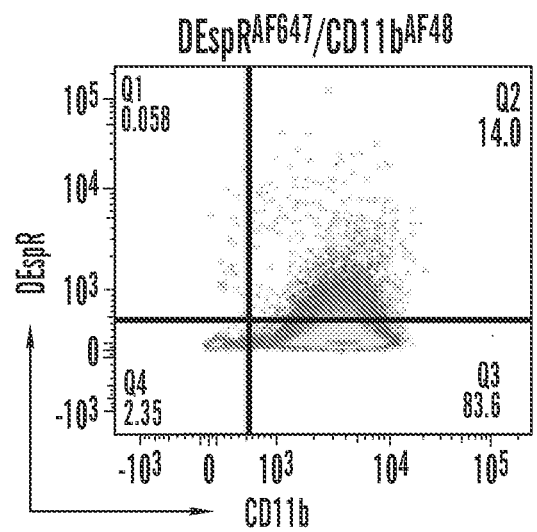
FIG. 60E

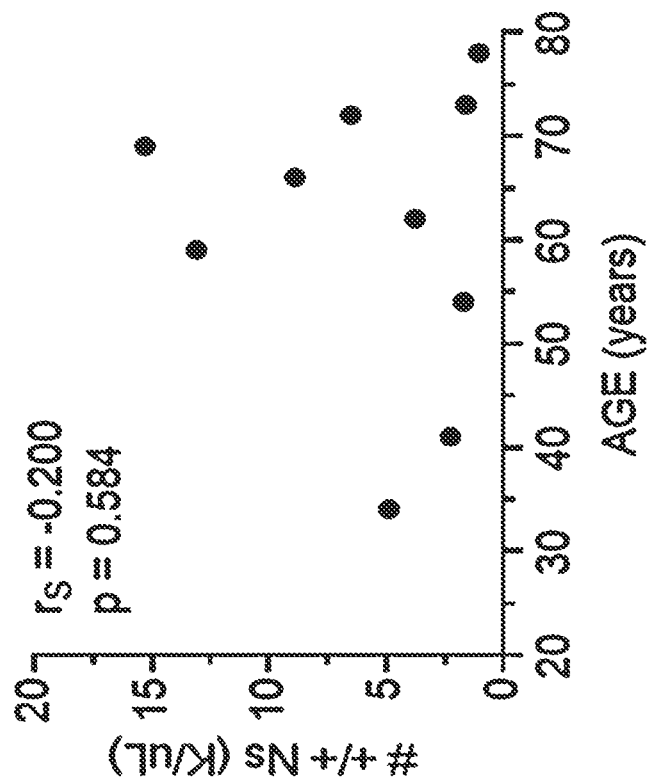
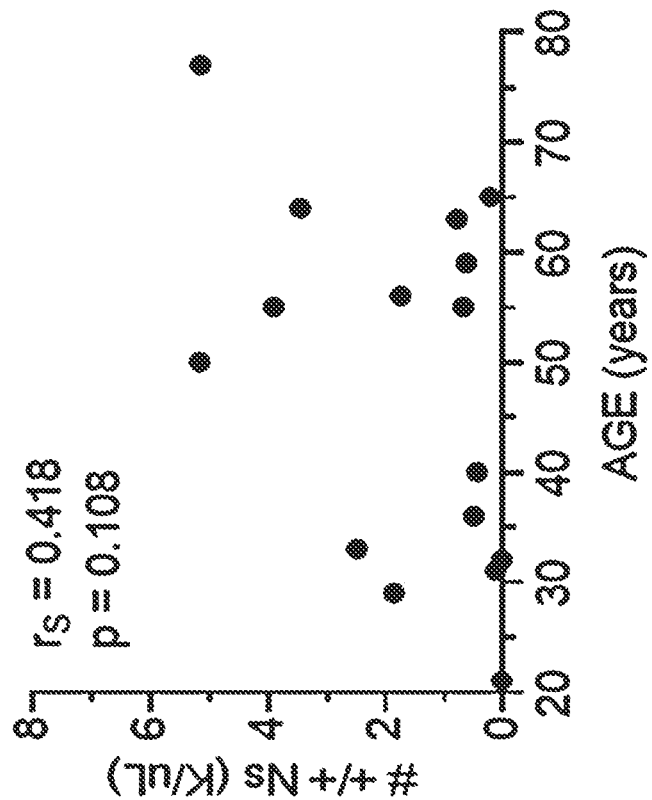
FIG. 60N
FIG. 60M ized and well tolerated, even at high doses. There is, in addition, extensive experience with administering mAbs to patients by either the IV route or by subcutaneous injection. Unlike small molecule drugs, mAbs are highly specific for their targets, which generally leads to fewer off-target side effects.

ANTIBODY THERAPIES AND METHODS FOR TREATING CORONAVIRUS INFECTION

CROSS-REFERENCE TO RELATED APPLICATIONS

This application claims benefit under 35 U.S.C. § 119(e) of U.S. Provisional Application No. 63/092,176 filed Oct. 15, 2020, the contents of which are incorporated herein by reference in their entirety.

GOVERNMENT SUPPORT

This invention was made with government support under NIH Grant No. U54HL 119145 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Nov. 3, 2021, is named 701586-098910US-PT_SL.txt and is 18,496 bytes in size.

TECHNICAL FIELD

The technology described herein relates to methods of treating a coronavirus infection and pathologies associated with a coronavirus infection.

BACKGROUND

Secondary organ-dysfunction or multi-organ dysfunction or failure is driven by a state of hyperinflammation wherein one's own immune system cells attacks self indiscriminately—killing one's own normal cells rather than only eliminating infectious pathogens, causing morbidity and mortality in many major indications, including respiratory pathologies such COVID19 infection and acute respiratory distress syndrome (ARDS). However, not all COVID19 patients develop hyperinflammation and ARDS, some have mild disease, some remain asymptomatic. It has also been observed that viral load is not the driver of COVID19 ARDS and multi-organ dysfunction syndrome (MODS) or multi-organ failure (MOF) but rather a hyperinflammation response. DEspR+ neutrophils and monocytes are significantly increased in human clinical samples taken from patients with ARDS progressing to death or with poor outcomes; initial findings show similar associations in spontaneous intracerebral hemorrhage (sICH) and COVID19-ARDS or SARS CoV2-driven ARDS. Although 20-50% of COVID19-ARDS patients progress to death, to date, there is little therapeutic intervention available and remains great need unmet. Inhibitors of IL-6 receptor, the receptor for the hallmark of COVID19 hyperinflammation or cytokine storm interleukin-6 or IL-6, have failed in Phase III clinical trials further emphasizing the major therapeutic challenges amplified by the high unmet need.

SUMMARY

As described herein, the disclosure related to an antibody therapy for Acute Respiratory Distress Syndrome (ARDS) associated with a coronavirus infection (e.g., COVID19 infection).

In some aspects, provided herein is a method of treating a coronavirus infection in a subject, the subject determined to have an elevated level of DEspR+CD11b+ cells as compared to a non-infected subject, the method comprising administering a DEspR inhibitor to the subject, wherein the administering is effective to treat the coronavirus infection in the subject.

In some embodiments, the administering is effective to treat COVID19 disease manifestations and complications beyond the coronavirus infectivity status in the subject. For example, the administration is effect to treat pneumonia, fever, dry cough, headache, dyspnea, microthrombosis, cytokine levels, and DEspR+ neutrophil levels.

In some embodiments, the coronavirus is SARS CoV2 causing COVID-19.

In some embodiments, the DEspR+CD11b+ cells are DEspR+CD11b+ neutrophils, DEspR+CD11b+ monocytes, DEspR+CD11b+ lymphocytes, DEspR+CD11b+ cytoplasts or a combination, an aggregate, or DEspR+ DNA strands. In some embodiments, the DEspR+CD11b+ cells are at least 20, 30, 40, 50, 60, 70, 80, 90, or 100% of the whole corresponding cell population. In some embodiments, the subject is further determined to have an elevated DEspR+ neutrophil to lymphocyte ratio (d+NLR); elevated ratio of DEspR+ neutrophils to COVID19-associated (a) hyperinflammation cytokines or cytokine storm biomarkers, (b) oxidative stress biomarkers, (c) endothelial dysfunction biomarkers, or (d) a combination thereof, or a combination thereof. In some embodiments, the hyperinflammation cytokines or cytokine storm biomarkers comprise IL-6. In some embodiments, the oxidative stress biomarkers comprise myeloperoxidase (MPO). In some embodiments, the endothelial dysfunction biomarkers comprise endothelin-1 (ET1). In some embodiments, the non-infected (i.e., control) subject does not have a coronavirus infection. In some embodiments, the DEspR inhibitor is an anti-DEspR antibody, antibody reagent, or fragment (e.g., antigen-binding fragment) thereof. In some embodiments, the anti-DEspR antibody, antibody reagent, or fragment thereof comprises complementary determining regions selected from SEQ ID NOs: 1-3, 9-11, 17-19, 5-7, 13-15, 21-23, 25-27, 29-31, and 33-35.

In some aspects, provided herein is a method of treating a subject having a coronavirus infection, the method comprising (i) determining whether the subject has a high risk of poor outcome or morbidity by detecting a level or rising level of DEspR+CD11b+ cells, a level of (1) non-resolving neutrophil-monocyte inflammatory amplification that blocks initiation of next step anti-viral adaptive immunity, anti-viral cellular immunity, resolution, or a combination, measured as: DEspR+CD11b+ cells, (2) a level of hyperinflammation-response marked by elevated ratio DEspR+CD11b+ neutrophils to plasma cytokine storm biomarkers, or to plasma oxidative stress biomarkers or to endothelial dysfunction biomarkers, or (3) a combination thereof, as individual or combinatorial measures in a sample obtained from the subject, wherein an elevated level of DEspR+CD11b+ cells, high ratios of DEspR+ neutrophils to COVID-19 associated elevated cytokines, elevated oxidative stress biomarkers, elevated endothelial activation biomarker levels, or a combination thereof in the sample obtained from the subject compared with a sample obtained from a control subject is an indicative that the subject has a high risk of poor outcome or morbidity, wherein the control subject does not have a coronavirus infection, and (ii) administering to the subject a DEspR inhibitor.

In some aspects, provided herein is a method of improving a survival rate of a subject having a coronavirus infection, the method comprising (i) determining whether the subject has a high risk of poor outcome or morbidity by detecting a level or rising level of DEspR+CD11b+ cells, a level of (1) non-resolving neutrophil-monocyte inflammatory amplification that blocks initiation of next step anti-viral adaptive immunity, anti-viral cellular immunity, resolution, or a combination, measured as: DEspR+CD11b+ cells, (2) a level of hyperinflammation-response marked by elevated ratio DEspR+CD11b+ neutrophils to plasma cytokine storm biomarkers, or to plasma oxidative stress biomarkers or to endothelial dysfunction biomarker, or (3) a combination thereof, as individual or combinatorial measures in a sample obtained from the subject, wherein an elevated or rising level of DEspR+CD11b+ cells or hyperinflammation ratio-markers in the sample obtained from the subject compared with a level of DEspR+CD11b+ cells in a sample obtained from a control subject is indicative that the subject has a high risk of poor outcome or morbidity, wherein the control subject does not have a coronavirus infection, and (ii) administering to the subject a DEspR inhibitor.

In some aspects, provided herein is a method of determining prognosis of a subject having a coronavirus infection, the method comprising: detecting in a sample obtained from the subject a level of, or rising DEspR+CD11b+ cells, or DEspR-bound DNA, or a level of (1) non-resolving neutrophil-monocyte inflammatory amplification that blocks initiation of next step anti-viral adaptive immunity, anti-viral cellular immunity, resolution, or a combination, measured as: DEspR+CD11b+ neutrophils and monocytes, (2) a level of hyperinflammation-response marked by elevated ratio DEspR+CD11b+ neutrophils to plasma cytokine storm biomarkers, or to plasma oxidative stress biomarkers or to endothelial dysfunction biomarker, or (3) a combination thereof, as individual or combinatorial measures in a sample obtained from the subject, wherein an elevated or rising levels of DEspR+CD11b+ cells, plasma DEspR-bound DNA, high ratios of DEspR+ neutrophils to COVID-19 associated elevated cytokines, elevated oxidative stress biomarker, elevated endothelial activation biomarker level or a combination thereof in the sample obtained from the subject compared with a level of DEspR+CD11b+ neutrophils in a sample obtained from a control subject is an indicative that the subject has a high risk of poor outcome or morbidity, wherein the control subject does not have a coronavirus infection.

In some embodiments, the DEspR+CD11b+ cells are DEspR+CD11b+ neutrophils, DEspR+CD11b+ monocytes, DEspR+CD11b+ lymphocytes, DEspR+CD11b+ cytoplasts or a combination, an aggregate, or DEspR+ DNA strands. In some embodiments, the plasma cytokine storm biomarkers comprise IL-6, IL-8, IL-11, IL-18, or a combination thereof. In some embodiments, the plasma oxidative stress biomarkers comprise myeloperoxidase. In some embodiments, the endothelial dysfunction biomarkers comprise endothelin-1. In some embodiments, the COVID-19 associated elevated cytokines comprises IL-6, IL-8, IL-11 or IL-18, or a combination thereof. In some embodiments, the elevated oxidative stress biomarkers comprise myeloperoxidase. In some embodiments, the elevated endothelial activation biomarkers comprise endothelin-1. In some embodiments, the level of DEspR+CD11b+ cells is detected by measuring a level of DEspR+CD11b+ aggregates or DEspR+ DNA strands in the blood sample. In some embodiments, the level of DEspR+CD11b+ cells in the subject determines whether the subject will require intensive care.

In some aspects, provided herein is a method of preventing or treating organ-dysfunction or multi-organ dysfunction or failure associated with a coronavirus infection in a subject in need thereof, wherein subject is determined to have elevated or rising levels of DEspR+CD11b+ cells, elevated hyperinflammation DEspR+ neutrophil-IL6/MPO/ET1 ratios, or a combination thereof, as compared to a control subject, the method comprising administering a DEspR inhibitor.

In some embodiments, the DEspR+CD11b+ cells are DEspR+CD11b+ neutrophils, DEspR+CD11b+ monocytes, DEspR+CD11b+ lymphocytes, DEspR+CD11b+ cytoplasts or a combination, an aggregate, or DEspR+ DNA strands. In some embodiments, the organ-dysfunction or multi-organ dysfunction or failure associated with the coronavirus infection arises from microcirculatory dysfunction, microvascular inclusion, low flow ischemia, thromboses, systemic microthromboses, microcirculatory vascular aggregation, or a combination thereof. In some embodiments, the organ-dysfunction or multi-organ dysfunction or failure associated with the coronavirus infection is derived from COVID19-induced cytokine storm, low flow organ ischemia from DEspR+CD11b+ aggregates leading to characteristic COVID19-hypoxemia, renal dysfunction, cardiac ischemia, neurological dysfunction from low flow ischemia or delayed cerebral ischemia or neuroinflammation, liver dysfunction/failure, hematological coagulopathy or microthromboses, or a combination thereof. In some embodiments, the neurological dysfunction is characterized by loss of consciousness, seizures, confusion or a combination thereof. In some embodiments, the organ-dysfunction or multi-organ dysfunction or failure associated with the coronavirus infection is selected from the group consisting of systemic inflammatory response syndrome (SIRS); acute lung injury (ALI); acute respiratory distress syndrome (ARDS); multi-organ failure or multi-organ dysfunction syndrome (MODS); acute kidney injury (AKI); liver failure, ischemic stroke; delayed cerebral ischemia, and/or encephalopathy. In some embodiments, the organ-dysfunction or multi-organ dysfunction or failure associated with the coronavirus infection is ARDS.

In some aspects, provided herein is a method of combinational therapy for a subject having a coronavirus infection, the method comprising: administering to the subject a therapeutic agent or a therapy in combination with a DEspR inhibitor, wherein the therapeutic agent or the therapy prevents or alleviates a sign or a symptom associated with the coronavirus infection in the subject.

In some embodiments, the therapy is an application of a respiratory ventilation, or an alternative delivery system for supplemental oxygen.

In some aspects, provided herein is a method of reducing microthrombi formation associated with a coronavirus infection in a subject in need thereof, the method comprising: administering to the subject a DEspR inhibitor, thereby reducing systemic microthrombi formation associated with the coronavirus infection in the subject.

In some embodiments, the method further comprises administering antithrombotics in combination. In some embodiments, the DEspR inhibitor is an anti-DEspR antibody or fragment thereof. In some embodiments, the anti-DEspR antibody or fragment thereof comprises complementary determining regions selected from SEQ ID Nos: 1-3, 9-11, 17-19, 5-7, 13-15, 21-23, 25-27, 29-31, and 33-35.

BRIEF DESCRIPTION OF THE DRAWINGS

FIG. 2 shows that DEspR functions as an anti-apoptotic receptor and is involved in branched angiogenesis.

FIG. 6A shows representative images of fluorescence-activated cell sorting (FACS) gating of forward versus side scatter (FSC)/side-scattered light (SSC) neutrophils, single-cells compared with isotype controls. FIG. 6B shows graphs of DEspR+ rogueNs compared with Neutrophil Lymphocyte Ratio (NLR) at t−1 same ICU-day. Serum diagnostic marker: % RogueN levels stratifies patients for mortality risk in both ARDS and COVID19: informs patient management and identify cohort for clinical trials.

FIG. 7A depicts a graph of % Rogue neutrophils vs. outcome in ARDS patients (Rs=0.864, p=2×10$^{-7}$). FIG. 7B depicts a graph of % Rogue monocytes vs. outcome in ARDS patients (Rs=0.713, p=0.0023). FIG. 7C depicts graphs of peak Rogue neutrophils vs outcome in ARDS patients and peak Rogue monocytes vs outcome in ARDS patients. Analysis of 12 (PILOT), 16 DRIVE, 12 (COVID19—DRIVE) patient samples (10 excluded post-hoc: DNR (do-not-resuscitate), technical issues, EPIC file closure, LIPS>4.5 but nonARDS).

FIG. 8A depicts a graph of % DEspR+CD11+ neutrophils vs. outcome in ARDS patients. FIG. 8B depicts a graph of plasma myeloperoxidase vs. outcome in ARDS patients. FIG. 8C depicts a graph of neutrophil elastase vs. outcome in ARDS patients. FIG. 8D depicts a graph of terminal complement complex vs. outcome in ARDS patients.

FIG. 11A shows representative results of CD11b+DEspR+ neutrophils of AC4.1 (over 61 days in intensive care unit (ICU)). FIG. 11B shows representative results of CD11b+DEspR+ neutrophils of AC6.1 (7 days in ICU).

FIG. 12A shows % DEspR+N levels vs ICU-LOS (length of stay in ICU). Total DEspR=intracellular+ cell surface. FIG. 12B shows relative timeline of % Rogue N testing (i) ARDS Dx; (ii) t−1 Rogue N % levels; and (iii) ICU-LOS. COVID19+ ARDS: ICU, on ventilator (N=8, 1 non-survivor, AC10, imputed max LOS).

FIG. 13A depicts Neutrophil-Lymphocyte Ratio vs. the number of Days in ICU at t−1.

FIG. 13B depicts PsO2/FiO2 Ratio (SF ratio) vs the number of Days in ICU on ventilator. COVID19+, ARDS: ICU, on ventilator (N=8, all survivors). COVID19+ ARDS: ICU, on ventilator (N=8, all survivors). Patient record data was use and shown NRL and SF Ratio did not correlate with ICU days in contrast to % DEspR+cd11b+.

FIG. 16A shows representative results of CD11b+DEspR+ neutrophils of AC4.1 (61 days in intensive care unit (ICU)). FIG. 16B shows representative results of CD11b+DEspR+ neutrophils of AC6.1 (7 days in ICU).

FIG. 17A shows a graph of % DEspR+CD11b+ (Ns+Ms) vs # of ICU Days. Total DEspR=intracellular DEspR+ cell surface DEspR. FIG. 17B shows a graph of relative timeline of % rogue N+M testing (i) ARDS Dx; (ii) t−1 Rogue N % levels; and (iii) ICU-length of stay (LOS) in days.

FIG. 19 shows that increased D-Dimer levels did not differentiate high-mortality risk patients in a COVID19+, ARDS pilot study.

FIG. 22A, % DEspR+CD11b+ Ns. FIG. 22B, % DEspR+ CD11b+ Ms. FIG. 22C, NLR. FIG. 22D, SF ratio: PsO2/FiO2.

FIG. 23 depicts a table showing that % Rogue Ns+Ms exhibits the highest correlation with outcomes in ARDS-COVID19 patients, better than NLR, SF ratio ARDS severity indicator, and with respective individual Spearman R.

FIG. 24A, shows nasopharyngeal sample from healthy controls with minimal to no white blood cells, in contrast to COVID19 patient samples with both respiratory epithelial cells and abundant white blood cells representing neutrophils, monocyte macrophages and non-resident monocyte macrophages, cytotoxic T cells, Tregs, B-cells, monocyte-dendritic cells, natural killer T-cells. FIG. 24B shows COVID19 patient samples with subtype distinction between moderately ill COVID19 patients (not in the ICU) compared to critically ill COVID19 patients in the ICU. FIG. 24C shows bronchial lavage samples from 2 critically ill patients showing that majority of cells in the sample are neutrophils. FIG. 24D shows differential distribution of leukocyte subsets between COVID19 critically ill patients—one who died with minimal macrophages, and one who survived with more monocyte/macrophages. FIGS. 24E-24G show Nasopharynx, Bronchial lavage, and Protected Bronchial Brush samples with white blood cells dominating the population of cells obtained from COVID19 patient nasopharyngeal and bronchial lavage cells with neutrophils as the largest subgroup. In contrast, protected bronchial brush samples are comprised of mostly respiratory epithelial cells. Abbreviations use: neutrophils (neu), non-resident macrophages (nrMa), MoDC, monocyte dendritic cells; NK, natural killer cells, B-cells, CTL, cytotoxic T-cells, Treg, regulatory T-cells; NKT, natural killer T-cells.

FIGS. 25A-25D show scRNA-seq profiles of ADAR1 and HIF1a in bronchial lavage samples and nasopharyngeal samples, and FIGS. 25E-25H show scRNA-seq profiles of Mcl1 and FBXW7 in bronchial lavage samples and nasopharyngeal samples.

FIGS. 28A-28B depict IL6-R+ monocytes and neutrophils, effectors of IL-6 mediated hyperinflammation. FIGS. 28C-28F show that through released IL-8, respiratory epithelia can directly activate recruited neutrophils (Ns) and monocytes (Ms), but that neutrophils and monocytes can sustain their reciprocal activation via an IL-8/IL-8R autocrine loop (monocyte-neutrophil crosstalk).

FIGS. 29A-29D depict minimal IL-6 expression in COVID19 patient samples in both moderately ill and critically ill patient samples from the nasopharynx and bronchial lavage. Only Mo/macrophages express IL-6 but only sparsely as 99% of all cells are negative for IL-6 expression in this set of COVID19 patient samples. IL-6 Receptor (IL-6R) expression is detected in neutrophils and monocytes indicating Ns and Ms as effectors of elevated IL-6 mediated hyperinflammation in COVID19. FIGS. 29E-29H depict IL-1β/IL-IP receptor autocrine loop in nasopharynx and bronchial lavage, proposing key roles of monocyte-neutrophil crosstalk in COVID19 patients.

FIGS. 30A-30H show IL8+ and IL-18+ respiratory epithelia, and IL-8 and IL-18 ligand+/receptor+ on Ns and Ms. FIGS. 30A-30D depict IL-8 cytokine and IL-8 receptor in COVID19 moderately and critically ill patient samples from the nasopharynx and bronchial lavage. FIGS. 30E-30H depict IL-18 cytokine and IL-18 receptor-1.

FIGS. 31A-31B depict PDL-1+neutrophils and monocytes expression in COVID19 ICU patients, showing a potential pro-lymphopenia mechanism. PDL-1+ Ns+Ms may contribute to the lack of development of anti-viral T-cell mediated immunity. FIGS. 31C-31D depict neutrophils of COVID19 ICU-patients do not express 1L-10, showing no coordinated turnoff switch to turn-off inflammation pathways, since IL-10 is needed for pro-resolution pathways.

FIGS. 33A-33B depict IL-18 cytokine expression in samples from the nasopharynx and bronchial lavage. FIGS. 33C-33D depict IL-18 Receptor-1 expression in samples from the nasopharynx and bronchial lavage.

FIGS. 34A-34B depict IL-1β cytokine expression in samples from the nasopharynx and bronchial lavage. FIGS. 34C-34D depict IL-1β Receptor expression in samples from the nasopharynx and bronchial lavage.

FIG. 37A depicts a graph of Neutrophil-Lymphocyte ratio vs. outcomes in COVID19+, ARDS patients. FIG. 37B depicts a graph of C-reactive protein vs. outcomes in COVID19+, ARDS patients. FIG. 37C depicts a graph of D-Dimer vs. outcomes in COVID19+, ARDS patients.

FIG. 38 depicts a table showing linear relationship of DEspR+ cells, neutrophils Ns, monocytes Ms, and lymphocytes Ls with outcome of ARDS. Linear regression analysis of poor outcome vs biomarkers in ARDS patients (with various underlying causes) show significant linear relationship of DEspR+ Ns, Ms, Ls with outcome of ARDS (survival vs non-survival). n=13 subjects; NLR, neutrophil/lymphocyte ratio; [total], neutrophils+early apoptosis neutrophils combined; Ls, lymphocytes; Ms, monocytes. Statistical analysis=Linear regression: outcomes: 0=survived; 0.5=survived with sequelae; 1=deceased. R: negative correlation, inverse relation of dependent variable (outcome) and explanatory variable (biomarkers).

FIGS. 41A and 41B show that anti-DEspR mAb blocks neutrophil-mediated encephalopathy when DEspR+ neutrophils and monocytes are experimentally increased by LPS, a PAMP, or by LPS-induced DAMPs, all of which activate TLR4 as a model of SARS CoV2 spike protein docking on TLR4 receptors on neutrophils and monocytes. FIG. 41A shows that LPS administration to rats with brain microvascular dysfunction modeled in pre-stroke sICH rats, as would be present in COVID19 infected patients, produces encephalopathy and multi organ failure. FIG. 41B shows that anti-DEspR (1 mg/kg) reverses DEspR+ actN/actM-mediated encephalopathy and mortality.

FIG. 42 shows that secondary brain injury mediated by the innate immune system drives mortality and morbidity, in spontaneous ICH.

FIG. 46A depicts a graph using anti-DEspR 10a3. FIG. 46B depicts a graph using NCTX-01.

FIGS. 50A-50H depict DEspR expression on normal human volunteer (NHV) neutrophils. (FIG. 50A) Immunofluorescence of 24-hour old NHV neutrophils: DEspR (hu6g8), DAPI, merged. DEspR+ NETosing neutrophils are indicated with arrows, DEspR(−) neutrophils are encircled. Bar=20 µm. (FIG. 50B) Bar graph showing semi-quantitation of % DEspR+ neutrophils and NETosing neutrophils in 6 high power fields per slide in 3 slides prepared from NHV polled neutrophils. (FIG. 50C) Western blot analysis showing DEspR expressed in normal human kidney (HK), neutrophils (HN1) and LPS-stimulated neutrophils (HN2), MW, molecular weight markers. LB, Laemli buffer as negative control. (FIG. 50D) Flow cytometry (FCM) analysis of EDTA-anticoagulated NHV whole blood, non-stimulated. Gating of white blood cells for neutrophils, monocytes, lymphocytes and red blood cells (RBC) by their respective clouds determined by differential forward scatter (FSC, x-axis), side scatter (SSC, Y-axis). features, and fluorescence markers: anti-CD11b-FITC, anti-DEspR (hu6g8)-AF568. (FIG. 50E) FCM analysis ofNHV (EDTA-anticoagulated) whole blood stimulated with LPS (75 µg/ml, 1-hr at 37° C.), Panels left-to-right: FSC/SSC gating for neutrophils; isotype controls hIgG4-AF568, mIgG2-AF488; FMO-CD11b+); CD11b (X-axis) vs DEspR (Y=axis). (FIGS. 50F-50H) FCM analysis of NHV (Li-heparin anticoagulated) showing increased DEspR+CD11b+ neutrophils in 3 different conditions: (FIG. 50F) after 1-hr incubation at 37° C., (FIG. 50G) after 1 hr LPS-stimulation (75 ng/ml) at 37° C.; and (FIG. 50H) after paraformaldehyde permeabilization done after 1 hr LPS-incubation at 37° C. PFA-permeabilization detects increased DEspR with high (intracellular and cell-surface DEspR) and low (cell-surface) DEspR+ expression.

FIGS. 51A-51K depict DEspR+ neutrophils and monocytes in ARDS post-mortem lung sections. (FIG. 51A). H&E section showing area of diffuse alveolar damage (DAD) in post-mortem lung section from ARDS patient. Dashed box=region of Interest (ROI) analyzed in higher magnification in FIGS. 51D-51I). (FIG. 51B) Immunohistochemical-diaminobenzidene (IHC-DAB)-staining of bronchiolar exudate and transmural infiltrates showing DEspR+ expression, and (FIG. 51C) myeloperoxidase (MPO)+ expression, hematoxylin as counterstain. (FIGS. 51D-51E) Higher magnification of Region of Interest (ROI) #1 (FIG. 51D) and #2 (FIG. 51E.) with diffuse alveolar damage (DAD) shown in (FIG. 51A). (FIGS. 51F-51G) IHC-DAB staining of adjacent serial sections showing DEspR+ expression in inflammatory cells in DAD-ROI#1 (FIG. 51F) and ROI#2 (FIG. 51G). (FIGS. 51H-51I) MPO+[high-expression] IHC-DAB staining in ROI#1 and #2 show high levels typically seen in neutrophils. The 5× lower levels of MPO+ expression in macrophages were not detected in conditions used; hematoxylin counterstain. (FIG. 51J) Representative H&E image of area with acute alveolar injury with intra-alveolar hemorrhages in lung sections also exhibiting diffuse alveolar damage. Box depicts ROI shown in (FIG. 51K). (FIG. 51K) Representative IHC-DAB staining for DEspR+ expression in area of acute alveolar injury. DEspR+ neutrophils and monocytes in the intravascular lumen, parenchyma, alveolar walls and intra-alveolar spaces. Bar=20 microns.

FIGS. 52A-52E depict single cell RNA-seq profiles of genes that modulate DEspR expression: DEspR-expression network. (FIGS. 52A-52C) Profiles of scRNA-seq analysis showing UMAP cluster depicting neutrophils (Ns), monocytes (Ms) and lymphocytes ([) identified by scRNA-sequence profiles of broncholavage fluid samples from critically ill COVID19 patients (n=2), and corresponding scRNA-seq levels of DEspR-modulators: HIF1α, modulator of DEspR transcription, at RNA level (Hif1α stabilized in normoxia by activated TLR4), at protein level (ADAR1 RNA-editase), mobilization to cell surface upon activation (TLR4), DEspR-bioeffect marker for pro-survival role (Mcl1), DEspR-ligands endothelin-1 (EDN1, ECE1), and signal peptide (propeptide VEGF), and TLR4-activators during cell injury—alarmins: S100A8 and S100A9. No expression (light grey), >2× expression (black). (FIG. 52D) Quantitative scRNA-seq database analysis of DEspR-expression network genes measured as % of cells in sample with >2×-fold increase in RNA levels in nasopharyngeal samples comparing non-COVID19 control patients (n=5, mean sd: 3.1±1.9), mild COVID19 patients (n=8: 42.6±10.2), and critically ill COVID19 patients (n=11: 54.1 10.6). Non-parametric one-way ANOVA with Tukey's multiple comparisons testing: *, p=0.0226, **p<0.0001. (FIG. 52E) Quantitative scRNA-seq database analysis of DEspR-expression network genes comparing %>2× expression for each gene among neutrophils (Ns) and monocytes-macrophages (Ms) in nasopharyngeal (np) and broncholavage fluid (blf) samples, (n=9 genes in DEspR-expNetwork per cell type) in COVID19-patient samples. Average % expression of all 9 genes in Ns-np: (mean±sd: 46.78%±19.9); Ms-np: (12.7%±10.7); Ns-blf: (55.3% 25.1), and Ms-blf (4.2% 2.8). Non-parametric one-way ANOVA with Sidak's multiple comparisons testing: *, p=0.0006; ****, p<0.0001.

FIGS. 53A-53L depict analysis of DEspR+ neutrophils in ARDS and COVID-19-ARDS patients. (FIGS. 53A-53F) Representative FCM analysis, done in triplicates, of neutrophils (Ns), monocytes (Ms) and lymphocytes (Ls) in non-survivor vs survivor patient with ARDS. Corresponding isotype controls vs double immunotyping with anti-DEspR (hu6g8) and anti-CD11b. Quadrant 2 (Q2) for DEspR+ CD11b+ neutrophils, monocytes and/or lymphocytes. (FIGS. 53G-53J) Representative FCM-analysis of PFA-fixed samples from patient with COVID-19-ARDS, mechanically ventilated, 61 days in the ICU (FIGS. 53G-53H) compared to (FIG. 53I-53J) COVID19-ARDS patient discharged after 6 days in the ICU. CD11b+DEspR+ neutrophils (Ns) (contour plot and histogram of fluorescence intensities), and monocytes (Ms). (FIG. 53K) Graph of duration of ICU-stay (days) from day of FCM-analysis of DEspR+CD11b+Ns (1st symbol) until discharge or death (2nd symbol), stratified by level of number (#) of cell surface DEspR+CD11b+ neutrophils (K/µL) detected. Time zero marks day of ARDS diagnosis in non-COVID19 ARDS, and in (FIG. 53L) COVID19-ARDS. d/c, discharge; wk, week. No FCM-analysis on day of discharge or death.

(FIG. 54A) Correlation matrix ARDS: Spearman Rank Correlation, n=19 patients with ARDS diagnosis (Berlin definition) of cell surface DEspR+ expression levels (% or number #) in CD11b+ activated neutrophils (actNs), monocytes (actMs), and lymphocytes (actLs) and corresponding correlation with 1] clinical parameters of severity [ICU-free days at 28-days, defined as (28-# of ICU-days) with ICU-death=−1, and >28-days in the ICU=0; PsO2/FiO2 or S/F ratio, Sequential Organ Failure Assessment (SOFA) scores on day of FCM-analysis (t1-SOFA), SOFA on day of ICU-discharge or ICU-death (t2- SOFA)]; 2] plasma biomarkers reported to be elevated in ARDS by others [interleukin-6 (IL-6), endothelin-1 (ET1), myeloperoxidase (MPO), terminal complex of complement (sC5b9), and mitochondrial/nuclear DNA ratio (mt/nucl DNA), and 3] NETosis parameters: DEspR+ cytoplast levels with high or low granularity (SSC) on flow cytometry. See FIG. 56 for specific values: rho, P-values with power>0.8. (FIG. 54B) ARDS: neutrophil-to-lymphocyte ratio (NLR) between survivors (S) n=12, (mean sd: 10.96±5.4) and non-survivors (non-S) n=6 (18.03±11.21), Mann Whitney p=0.33 (n.s). (FIG. 54C) ARDS: number (#) of cell-surface DEspR+CD11b+ neutrophils (Ns) detected in ARDS-survivors: n=12, (mean±sd: 0.8035±0.8) vs non-survivors: n=6 (8.1±6.0); two-tailed Mann Whitney p=0.0001 (*), effect size Hedges' g with 4% correction: 2.03). (FIG. 54D) ARDS: Comparison of % of DEspR+CD11b+ neutrophils in ARDS: survivors: n=13, (10.3±10.0) vs non-survivors: n=6, (48.2±6.3); two-tailed Mann Whitney p<0.0001 (**), effect size Hedge's g with 4% correction: 4.03. (FIG. 54E) ARDS: Kaplan-Meir Survival curve analysis with threshold for DEspR+CD11b+ neutrophil-counts set at 3 K/µL whole blood as determined from FIG. 54C. Log rank (Mantel-Cox) test Chi square 20.56, P<0.0001, Hazard Ratio (Mantel-Haenszel) 90.5, 95% CI of ratio: 12.91 to 634.7. (FIG. 54F) Correlation matrix COVID19-ARDS: n=11 (severe COVID19 requiring mechanical ventilation). Parameters as defined in FIG. 54A, with addition of # of DEspR+CD11b+ NETosing neutrophils (D+actNETosing Ns), and circularity index of neutrophils (<0.8 indicative of NETosing neutrophil, see Example 11 Methods). (FIG. 54G) COVID19-ARDS: comparison of neutrophil-to-lymphocyte ratio (NLR) between survivors: n=7 (mean±sd: 10.7±7.7) and non-survivors: n=4 (55.3±41.4). two-tailed Mann Whitney p=0.0242 (*), effect size Hedge's g with 4% correction: 1.73. (FIG. 54H) COVID19-ARDS: comparison of DEspR+CD11b+ neutrophil-counts (K/µL) in whole blood between survivors: n=7 (mean±sd: 3.8±2.99) and non-Survivors: n=4 (13.8±7.9), two-tailed Mann Whitney p=0.04 (*), effect size Hedge's g with 4% correction: 1.82. (FIG. 54I) COVID19- ARDS: #DEspR+ NETosing neutrophil-counts (K/μL) whole blood, survivors: n=7 (mean±sd: 1.3±1.29) and non-Survivors: n=4 (10.0±5.7). Two-tailed Mann Whitney p=0.0121 (*), effect size Hedge's g with 4% correction: 2.4.

(FIGS. 55A-55D) Analysis of DEspR[−] and DEspR+ neutrophils obtained from patients with ARDS at baseline (<1 hr from sampling), and after incubation with/without hu6g8 treatment (100 μg/ml) at 37° C. with simulated shear for 17 hrs (patient #1), or 20 hrs (patient#2). Flow cytometry assessed number of (FIG. 55A) DEspR[−] vs (FIG. 55B) DEspR+ surviving neutrophils compared to baseline. ELISA analyses of (FIG. 55C) MPO and (FIG. 55D) soluble terminal complex of complement (sC5b9) after ex vivo hu6g8 treatment. Normal MPO and sC5b9 levels notated. (FIG. 55E) Representative image at t−12 hrs from video-recorded live cell imaging of NHP-white blood cells (WBCs) documented to have >90% DEspR+CD11b+ neutrophils among all neutrophils, and exposed to 10 μg/ml hu6g8 AF568 antibody at 4° C.×30 minutes to eliminate non-specific cell uptake by macropinocytosis or endocytosis. DEspR+ NHP-neutrophils, apoptotic cell budding (encircled), and Sytox Green (SytoxG)-positive membrane permeable. (FIG. 55F) Representative t−12 hr image of isotype hu-IgG4 AF568 shows minimal to no isotype-AF568 uptake; constitutive apoptosis cell budding (encircled), SytoxGreen-positive staining in cells with loss of cell membrane integrity. (FIG. 55G) Quantitation of cells exhibiting apoptotic-typical cell budding per high power field (n=18 HPFs/group, 15-56 cells/HPF), % mean, 95% CI of means: mockTx (16%, 13-19%), TxDEspR+ (44%, 40-47%), TxDEspR[−] (12%, 8.6-16%). One way ANOVA with Tukey's multiple comparisons test: p<0.0001 (**). (FIG. 55H) Quantitation of SytoxG+ non-viable cells per high power field (n=18 HPFs/group, >16-50 cells/HPF), mean, 95% CI of mean for mockTx isotype control (22.2, 18.6-25.7), for hu6g8Tx (35.2, 27.3-43.2); two tailed t-test p=0.0033 ().

FIGS. 56A-56B depict a table of Spearman Rank Correlation matrix analysis.

FIG. 57 depicts a table of Spearman Rank Correlation matrix analysis.

(FIG. 58A) Western blot analysis of human kidney (HK), and NHV neutrophils that have survived 24-hrs in cold storage (N1), and LPS-stimulated NHV-neutrophils (N2). (FIGS. 58B-58C) Representative flow cytometry (FCM) analysis of NHV neutrophils (EDTA-anticoagulated) shows effects of RBC-lysis procedure before or after binding of antibody for double immunophenotyping: anti-DEspR and anti-CD11b mAbs. (FIG. 58D) Representative FCM analysis of NHV neutrophils (Li-heparin anticoagulated) shows time- and temperature-dependent effects on NHV DEspR+ expression in ex vivo experimental system.

(FIG. 59A) UMAP showing no expression of ETAR in neutrophils (Ns) and monocyte/macrophages (Ms); (FIG. 59B) UMAP showing no ETBR in neutrophils, few in monocytes; (FIG. 59C) UMAP of VEGF-R2 or KDR showing no expression; (FIG. 59D) minimal expression of AGER in neutrorphils and monocytes; (FIG. 59E), low expression of PADI4 in neutrophils, (FIG. 59F) minimal expression of CD47 'don't eat me' signal in neutrophils. (FIGS. 59G-59H) scRNA-seq results show high levels of TLR4 in monocytes (Ms) and neutrophils (Ns), and presence of receptors for cytokines found to be elevated in ARDS and severe COVID19 in both Ns and Ms. Greater expression in neutrophils is observed for IL-18 receptor. Diagram depicts direct activation of TLR4 on neutrophils and monocyte/macrophages via SARS-CoV2 (CoV2) spike protein docking on TLR4 as a pathogen-associated molecular pattern (PAMP), and/or from damage associated molecular patterns (DAMPs) such as alarmins S100A8, S100A9 released predominantly from high-expressing neutrophils.

FIGS. 60A-60N depict Flow cytometry analysis of DEspR+ neutrophils. (FIG. 60A) Gating strategy for optical homogeneity or granularity (side scatter area SSC-A) and size (forward scatter area FSC-A), selection of neutrophil cloud (dashed); (FIG. 60B) gating for singlets (FSC-A vs FSC-H); (FIG. 60C) affirmation of non-dead cells, (FIG. 60D) gating for isotype controls matched for isotype and fluorophore to both anti-DEspR and anti-CD11b antibodies; (FIG. 60E) representative scatter plot of DEspR+CD11b+ activated neutrophils in quadrant 2 (Q2), CD11b+DEspR[−] in Q3, DEspR, —CD11b–DEspR– in Q1. Corresponding histograms of counts (# of cells) and Fluorescence intensity (x-axis) of antibody binding with matched respective isotype-fluorophores: (FIGS. 60M-60N) Scatter plot of number of DEspR+ CD11b+ neutrophils (#+/+Ns) vs age of patients showing no significant correlation (Spearman Rank Correlation coefficient (rS) in patients with ARDS (n=19) and in patients with COVID-19 ARDS (n=9) requiring mechanical ventilation.

(FIG. 61A) Comparative FCM analysis of DEspR+ cytoplasts in healthy donors (sample #1, #2), compared with (FIG. 61B) patients in the ICU with sepsis-ARDS and died (#3, #4), and with (FIG. 61C) patients with sepsis-ARDS (#5) or sepsis alone (#6) and survived. (FIGS. 61D-61F) Using another marker of neutrophil activation representing degranulated neutrophils, CD66b, comparative FCM analysis of DEspR+CD11b+ neutrophils in (FIG. 61D) healthy donors (sample #1, #2), compared with (61EE) sepsis-ARDS non-survivors (#3, #4), and with (FIG. 61F) patients with sepsis-ARDS (#5) or sepsis alone (#6) and survived.

(FIGS. 62A-

62D) Representative flow cytometry (FCM) analysis of NHP blood sample validating (FIG. 62A) gating of neutrophil cloud by FSC/SSC, (FIG. 62B) selection of singlets (FSC-A×FSC-H), (FIG. 62C-62D) validation of DEspR binding to live cells with live/dead AF450 stain dot plot (FIG. 62C) and histogram of mean fluorescence intensity (FIG. 62D). (FIGS. 62E-62H) Representative FCM analysis of NHP neutrophils. (FIG. 62E) Fluorescence gating based on matched isotype-fluorophore (hu-IgG4 AF647, mu-IgG2 AF488) controls, (FIG. 62F) DEspR+CD11b+ activated neutrophils are detected in 94.5% of all neutrophils in quadrant 2 (Q2), and confirmed on histograms of fluorescence intensities for (FIG. 62G) hu6g8-AF647, and (FIG. 62H) CD11b-AF488. (FIG. 62I) Representative confocal image at t−45 minutes after addition of hu6g8-AF568 10 µg/ml in PBS to NHP white blood cells, and incubated at 4° C.×20 minutes, followed by washing off of excess unbound hu6g8-AF568 antibody, then placed into microfluidic chip. Live cell imaging begun at t−30 minutes documenting adhesion; image taken at t−45 minutes. Long arrows: hu6g8-AF568 bound to cell membrane, Short arrows: cells with internalized hu6g8-AF568.

DETAILED DESCRIPTION

Figure 1:
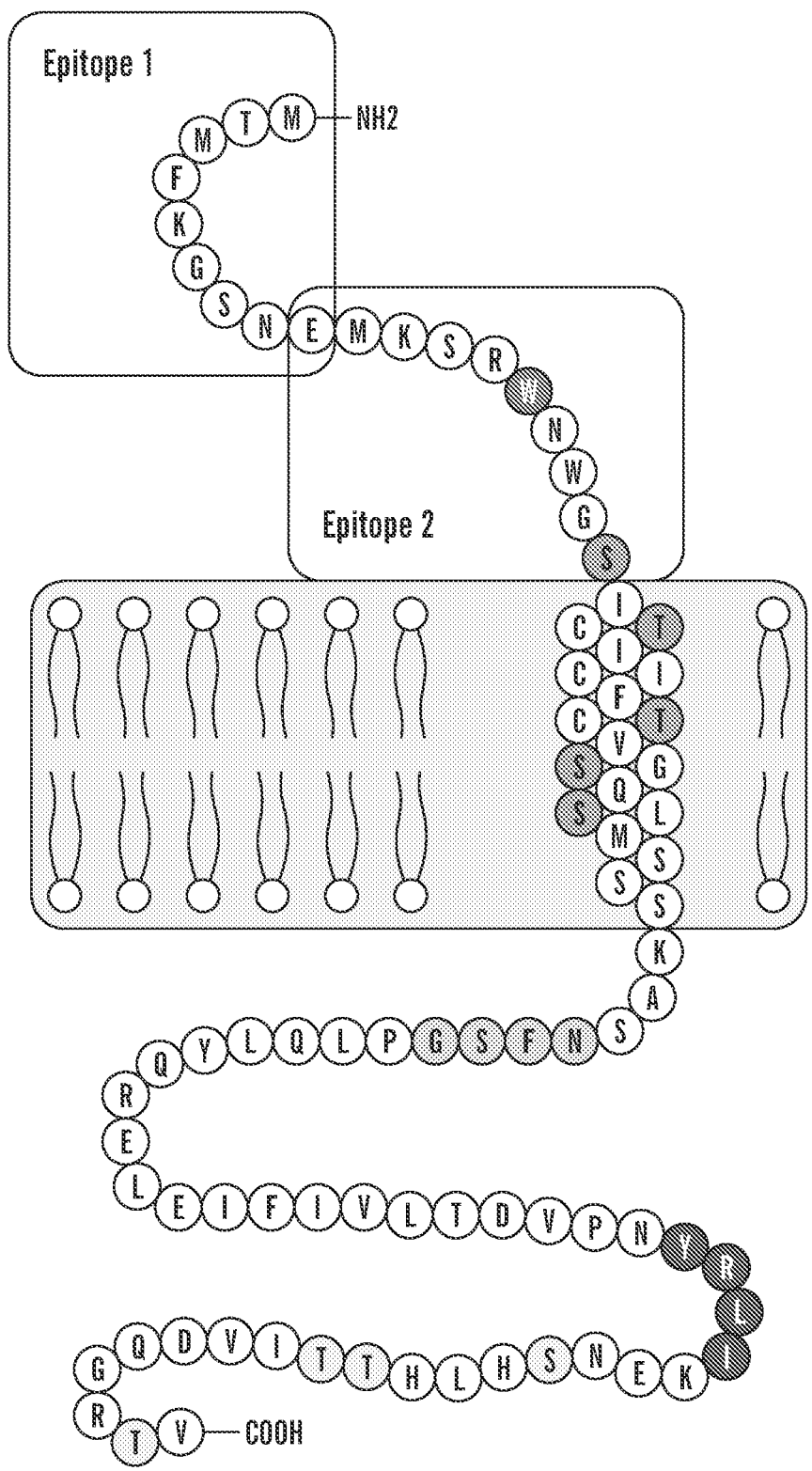
FIG. 1 depicts the schematic representation of DEspR (Dual Endothelin-1/signal peptide VEGF Receptor (SEQ ID NO: 37).

As described herein, it has been found that anti-DEspR reagents functionally shut down DEspR+ actPMNs that are dysregulated. This dysregulation can lead to organ-dysfunction or multi-organ dysfunction or failure associated with a coronavirus infection rather than resolution of that infection. Accordingly, the DEspR inhibitors, e.g., anti-DEspR reagents, described herein can inhibit the excessive injurious functions of DEspR+ "rogue" or hyper-activated PMNs (actPMNs) that drive neutrophil-mediated secondary organ-dysfunction or multi-organ dysfunction or failure associated with a coronavirus infection, e.g., by inhibiting the extended lifespan of such actPMNs. This inhibition reduces the excessive injurious level of actPMNs activity and/or the time during which rogue DEspR+ actPMNs activity of a given level is present in a subject. Accordingly, such DEspR inhibitors, e.g, anti-DEspR reagents, can be used to treat a number of conditions characterized by and/or caused by DEspR+ actPMNs. Without wishing to be bound by theory, it is contemplated herein that the anti-DEspR reagent may act by binding DEspR present on the surface of actPMNs. Alternatively, the anti-DEspR reagents may act through another mechanism, e.g., by binding to a molecule that shares one or more epitopes with DEspR.

In some aspects, described herein is a method of decreasing the survival and/or activity of an activated neutrophil, the method comprising contacting the neutrophil with a DEspR inhibitor. In some aspects, described herein is a method of preventing or decreasing neutrophil extracellular trap (NET) release or actPMN NETosis in a subject in need thereof, the method comprising administering a therapeutically effective amount of a DEspR inhibitor to the subject.

As used herein "actPMN", "activated PMN", or "activated neutrophil" refers to a neutrophil (e.g. polymorphic nuclear cell) which has been activated, e.g., by chemotactic signals, cytokines, complement, and/or the presence of LPS. Activated neutrophils can exhibit, e.g., NET production/release, increased levels of cell-surface integrins (e.g., CD11b/CD18), ROS production and release, and degranulation. Levels of these markers and activities are readily measured by assays known in the art and described in the Examples herein. ActPMNs are further characterized by increased survival, e.g., beyond the normal lifespan (e.g., hours, or 1-2 days in some reports) of unactivated neutrophils. In some embodiments of any of the aspects, an actPMN can be a DEspR+ neutrophil. In some embodiments of any of the aspects, an actPMN can be a CD11b+ neutrophil.

As used herein, the term "NET" or "neutrophil extracellular trap" refers to an extracellular complex of nucleosomes and proteins, e.g. proteins having anti-microbial activity. Upon activation, neutrophils and other cells undergo a cell death program termed "NETosis" and release portions of nuclear DNA in the form of nucleosomes in complex with various proteins having antimicrobial activity (i.e. NETs). Release of NETs from neutrophils has been associated with inflammation and microthrombosis during sepsis and non-infectious diseases and demonstrated to contribute to the pathology of various diseases described herein. Vital NETosis refers to the release of NETs without concomitant cell death of the neutrophil. As used herein, the term "NETosis" refers to neutrophil extracellular trap (NET) formation.

As used herein, "DEspR" or "dual endothelin/VEGF signal peptide receptor" refers to a receptor expressed in tumor cells, microvessels, and anchorage-independent cancer stem cells (CSCs), with differential expression in cell- and nuclear-membranes, as well as in the cytoplasm. DEspR is differentially increased in both human pancreatic cancer and glioblastoma in contrast to adjacent normal tissue. However, despite these data, DEspR is still annotated as a non-coding RNA or ncRNA FBXW7 antisense RNA1 in the NCBI database. Sequences for DEspR polypeptides and nucleic acids are known in the art, e.g., human DEspR (NCBI Gene ID: 102191832). For example, a DEspR polypeptide can be: MTMFKGSNEMKSRWNWGSITCI-ICFTCVGSQLSMSSSKASNFSGPLQLYQRELEI-FIVLTDVPNYR LIKENSHLHTTIVDQGRTV (SEQ ID NO: 37), as described by, e.g., Accession Number EF212178.1, Gene ID 102191832, or Glorioso et al. 2007, together with naturally occurring allelic, splice variants, and processed forms thereof. Typically, as used herein, DEspR refers to human DEspR of SEQ ID NO: 37.

As used herein, the term "inhibitor" refers to an agent which can decrease the expression and/or activity of a target, e.g. by at least 10% or more, e.g. by 10% or more, 50% or more, 70% or more, 80% or more, 90% or more, 95% or more, or 98% or more. The efficacy of an inhibitor of one or more targets, e.g., its ability to decrease the level and/or activity of the target can be determined, e.g. by measuring the level of an expression product of the target and/or the activity of the target. Methods for measuring the level of a given mRNA and/or polypeptide are known to one of skill in the art, e.g. RT-PCR with primers can be used to determine the level of RNA and Western blotting with an antibody can be used to determine the level of a polypeptide. The activity of, e.g. DEspR can be determined using methods known in the art. In some embodiments, the inhibitor can be an inhibitory nucleic acid; an aptamer; an antibody reagent; an antibody; or a small molecule.

In some embodiments of any of the aspects, a DEspR inhibitor can be an anti-DEspR antibody reagent, antibody, or an antigen-binding fragment thereof. As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments, an antibody reagent can comprise a monoclonal antibody or a polypeptide comprising an antigen-binding domain of a monoclonal antibody. For example, an antibody can include a heavy (H)

chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments as well as complete antibodies.

As used herein, the term "antibody" refers to immunoglobulin molecules and immunologically active portions of immunoglobulin molecules, i.e., molecules that contain an antigen binding site that immunospecifically binds an antigen. The term also refers to antibodies comprised of two immunoglobulin heavy chains and two immunoglobulin light chains as well as a variety of forms including full length antibodies and antigen-binding portions thereof; including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding portion thereof, and/or bifunctional hybrid antibodies.

Each heavy chain is composed of a variable region of said heavy chain (abbreviated here as HCVR or VH) and a constant region of said heavy chain. The heavy chain constant region consists of three domains CH1, CH2 and CH3. Each light chain is composed of a variable region of said light chain (abbreviated here as LCVR or VL) and a constant region of said light chain. The light chain constant region consists of a CL domain. The VH and VL regions may be further divided into hypervariable regions referred to as complementarity-determining regions (CDRs) and interspersed with conserved regions referred to as framework regions (FR). Each VH and VL region thus consists of three CDRs and four FRs which are arranged from the N terminus to the C terminus in the following order: FR1, CDR1, FR2, CDR2, FR3, CDR3, FR4. This structure is well known to those skilled in the art.

As used herein, the term "CDR" refers to the complementarity determining regions within antibody variable sequences. There are three CDRs in each of the variable regions of the heavy chain and of the light chain, which are designated CDR1, CDR2 and CDR3, for each of the variable regions. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Other boundaries defining CDRs overlapping with the Kabat CDRs have been described by Padlan (FASEB J. 9:133-139 (1995)) and MacCallum (J Mol Biol 262(5):732-45 (1996)) and Chothia (J. Mol. Biol. 196:901-917 (1987) and Nature 342:877-883 (1989)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems.

The term "antigen-binding portion" of an antibody refers to one or more portions of an antibody as described herein, said portions) still having the binding affinities as defined above herein. Portions of a complete antibody have been shown to be able to carry out the antigen-binding function of an antibody. In accordance with the term "antigen-binding portion" of an antibody, examples of binding portions include (i) an Fab portion, i.e., a monovalent portion composed of the VL, VH, CL and CHI domains; (ii) an F(ab')2 portion, i.e., a bivalent portion comprising two Fab portions linked to one another in the hinge region via a disulfide bridge; (iii) an Fd portion composed of the VH and CH1 domains; (iv) an Fv portion composed of the FL and VH domains of a single arm of an antibody; and (v) a dAb portion consisting of a VH domain or of VH, CH1, CH2, DH3, or VH, CH2, CH3 (dAbs, or single domain antibodies, comprising only VL domains have also been shown to specifically bind to target epitopes). Although the two domains of the Fv portion, namely VL and VH, are encoded by separate genes, they may further be linked to one another using a synthetic linker, e.g., a poly-G4S amino acid sequence ('G4S' disclosed as SEQ ID NO: 38), and recombinant methods, making it possible to prepare them as a single protein chain in which the VL and VH regions combine in order to form monovalent molecules (known as single chain Fv (ScFv)). The term "antigen-binding portion" of an antibody is also intended to comprise such single chain antibodies. Other forms of single chain antibodies such as "diabodies" are likewise included here. Diabodies are bivalent, bispecific antibodies in which VH and VL domains are expressed on a single polypeptide chain, but using a linker which is too short for the two domains being able to combine on the same chain, thereby forcing said domains to pair with complementary domains of a different chain and to form two antigen-binding sites. An immunoglobulin constant domain refers to a heavy or light chain constant domain. Human IgG heavy chain and light chain constant domain amino acid sequences are known in the art.

An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

Furthermore, an antibody or antibody reagent as described herein may be part of a larger immunoadhesion molecule formed by covalent or noncovalent association of said antibody or antibody portion with one or more further proteins or peptides. Relevant to such immunoadhesion molecules are the use of the streptavidin core region in order to prepare a tetrameric scFv molecule and the use of a cysteine residue, a marker peptide and a C-terminal polyhistidinyl, e.g., hexahistidinyl tag ('hexahistidinyl tag' disclosed as SEQ ID NO: 39) in order to produce bivalent and biotinylated scFv molecules.

In some embodiments, the antibody or antibody reagent described herein can be an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, and a functionally active epitope-binding portion thereof.

In some embodiments, the antibody or antigen-binding portion thereof is a fully human antibody. In some embodiments, the antibody, antigen-binding portion thereof, is a humanized antibody or antibody reagent. In some embodiments, the antibody, antigen-binding portion thereof, is a fully humanized antibody or antibody reagent. In some embodiments, the antibody or antigen-binding portion thereof, is a chimeric antibody or antibody reagent. In some embodiments, the antibody, antigen-binding portion thereof, is a recombinant polypeptide.

The term "human antibody" refers to antibodies whose variable and constant regions correspond to or are derived from immunoglobulin sequences of the human germ line, as described, for example, by Kabat et al. (see Kabat, et al. (1991) Sequences of Proteins of Immunological Interest, Fift Edition, U.S. Department of Health and Human Services, NIH Publication No. 91-3242). However, the human antibodies can contain amino acid residues not encoded by human germ line immunoglobulin sequences (for example mutations which have been introduced by random or site-specific mutagenesis in vitro or by somatic mutation in vivo), for example in the CDRs, and in particular in CDR3. Recombinant human antibodies as described herein have variable regions and may also contain constant regions derived from immunoglobulin sequences of the human germ line (see Kabat, E. A., et al. (1991) Sequences of Proteins of Immunological Interest, Fifth Edition, U.S. Department of Health and Human Services, NIH Publication No. 91-3242). According to particular embodiments, however, such recombinant human antibodies are subjected to in-vitro mutagenesis (or to a somatic in-vivo mutagenesis, if an animal is used which is transgenic due to human Ig sequences) so that the amino acid sequences of the VH and VL regions of the recombinant antibodies are sequences which although related to or derived from VH and VL sequences of the human germ line, do not naturally exist in vivo within the human antibody germ line repertoire. According to particular embodiments, recombinant antibodies of this kind are the result of selective mutagenesis or back mutation or of both. Preferably, mutagenesis leads to an affinity to the target which is greater, and/or an affinity to non-target structures which is smaller than that of the parent antibody. Generating a humanized antibody from the sequences and information provided herein can be practiced by those of ordinary skill in the art without undue experimentation. In one approach, there are four general steps employed to humanize a monoclonal antibody, see, e.g., U.S. Pat. Nos. 5,585,089; 6,835,823; 6,824,989. These are: (1) determining the nucleotide and predicted amino acid sequence of the starting antibody light and heavy variable domains; (2) designing the humanized antibody, i.e., deciding which antibody framework region to use during the humanizing process; (3) the actual humanizing methodologies/techniques; and (4) the transfection and expression of the humanized antibody.

Usually the CDR regions in humanized antibodies and human antibody variants are substantially identical, and more usually, identical to the corresponding CDR regions in the mouse or human antibody from which they were derived. In some embodiments, it is possible to make one or more conservative amino acid substitutions of CDR residues without appreciably affecting the binding affinity of the resulting humanized immunoglobulin or human antibody variant. In some embodiments, substitutions of CDR regions can enhance binding affinity.

The term "chimeric antibody" refers to antibodies which contain sequences for the variable region of the heavy and light chains from one species and constant region sequences from another species, such as antibodies having murine heavy and light chain variable regions linked to human constant regions. Humanized antibodies have variable region framework residues substantially from a human antibody (termed an acceptor antibody) and complementarity determining regions substantially from a non-human antibody, e.g., a mouse-antibody, (referred to as the donor immunoglobulin). The constant region(s), if present, are also substantially or entirely from a human immunoglobulin. The human variable domains are usually chosen from human antibodies whose framework sequences exhibit a high degree of sequence identity with the (murine) variable region domains from which the CDRs were derived. The heavy and light chain variable region framework residues can be substantially similar to a region of the same or different human antibody sequences. The human antibody sequences can be the sequences of naturally occurring human antibodies or can be consensus sequences of several human antibodies.

In addition, techniques developed for the production of "chimeric antibodies" by splicing genes from a mouse, or other species, antibody molecule of appropriate antigen specificity together with genes from a human antibody molecule of appropriate biological activity can be used. The variable segments of chimeric antibodies are typically linked to at least a portion of an immunoglobulin constant region (Fc), typically that of a human immunoglobulin. Human constant region DNA sequences can be isolated in accordance with well-known procedures from a variety of human cells, such as immortalized B-cells. The antibody can contain both light chain and heavy chain constant regions. The heavy chain constant region can include CH1, hinge, CH2, CH3, and, sometimes, CH4 regions. For therapeutic purposes, the CH2 domain can be deleted or omitted.

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant antibody or antibody reagent as described herein. Such functional activities include binding to cells and/or anti-cellular activity. Additionally, a polypeptide having functional activity means the polypeptide exhibits activity similar, but not necessarily identical to, an activity of a reference antibody or antibody reagent as described herein, including mature forms, as measured in a particular assay, such as, for example, a biological assay, with or without dose dependency. In the case where dose dependency does exist, it need not be identical to that of the reference antibody or antibody reagent, but rather substantially similar to the dose-dependence in a given activity as compared to the reference antibody or antibody reagent as described herein (i.e., the candidate polypeptide will exhibit greater activity, or not more than about 25-fold less, about 10-fold less, or about 3-fold less activity relative to the antibodies or antibody reagents described herein).

In some embodiments, the antibody reagents described herein are not naturally-occurring biomolecules. For example, a murine antibody raised against an antigen of human origin would not occur in nature absent human intervention and manipulation, e.g., manufacturing steps carried out by a human. Chimeric antibodies are also not naturally-occurring biomolecules, e.g., in that they comprise sequences obtained from multiple species and assembled into a recombinant molecule. In certain particular embodiments, the human antibody reagents described herein are not naturally-occurring biomolecules, e.g., fully human antibodies directed against a human antigen would be subject to negative selection in nature and are not naturally found in the human body.

In some embodiments, the antibody or antibody reagent is an isolated polypeptide. In some embodiments, the antibody or antibody reagent is a purified polypeptide. In some embodiments, the antibody or antibody reagent is an engineered polypeptide.

In some aspects, described herein is an antibody, antigen reagent, or antigen-binding fragment thereof that specifically binds a DEspR polypeptide. In some embodiments of any of the aspects, the antibody, antigen reagent, or antigen-binding fragment thereof comprises at least one heavy or light chain complementarity determining region (CDR) selected from the group consisting of:
  (a) a light chain CDR1 having the amino acid sequence of SEQ ID NO: 9;
  (b) a light chain CDR2 having the amino acid sequence of SEQ ID NO: 10;
  (c) a light chain CDR3 having the amino acid sequence of SEQ ID NO: 11;
  (d) a heavy chain CDR1 having the amino acid sequence of SEQ ID NO: 1;
  (e) a heavy chain CDR2 having the amino acid sequence of SEQ ID NO: 2; and
  (f) a heavy chain CDR3 having the amino acid sequence of SEQ ID NO: 3; or
a conservative substitution variant of one or more of (a)-(f). In some embodiments of any of the aspects, the antibody, antibody reagent, or antigen-binding fragment thereof comprises at least one heavy or light chain complementarity determining region (CDR) selected from the group consisting of:
  (a) a light chain CDR1 having the amino acid sequence of SEQ ID NO: 9;
  (b) a light chain CDR2 having the amino acid sequence of SEQ ID NO: 10;
  (c) a light chain CDR3 having the amino acid sequence of SEQ ID NO: 11;
  (d) a heavy chain CDR1 having the amino acid sequence of SEQ ID NO: 1;
  (e) a heavy chain CDR2 having the amino acid sequence of SEQ ID NO: 2; and
  (f) a heavy chain CDR3 having the amino acid sequence of SEQ ID NO: 3.

In some embodiments of any of the aspects, the antibody, antibody reagent, or antigen-binding portion thereof specifically binds to DEspR and competes for binding with an antibody comprising:
  (a) a light chain CDR1 having the amino acid sequence of SEQ ID NO: 9;
  (b) a light chain CDR2 having the amino acid sequence of SEQ ID NO: 10;
  (c) a light chain CDR3 having the amino acid sequence of SEQ ID NO: 11;
  (d) a heavy chain CDR1 having the amino acid sequence of SEQ ID NO: 1;
  (e) a heavy chain CDR2 having the amino acid sequence of SEQ ID NO: 2; and
  (f) a heavy chain CDR3 having the amino acid sequence of SEQ ID NO: 3.

In some embodiments of any of the aspects, the antibody, antibody reagent, or antigen-binding fragment thereof, comprises heavy chain CDRs having the amino acid sequences of SEQ ID NOs: 1-3. In some embodiments of any of the aspects, the antibody, antibody reagent, or antigen-binding fragment thereof, comprises heavy chain CDRs having the amino acid sequences of SEQ ID NOs: 1-3 or a conservative substitution variant of such amino acid sequence. In some embodiments of any of the aspects, the antibody, antibody reagent, or antigen-binding fragment thereof, comprises light chain CDRs having the amino acid sequences of SEQ ID NOs: 9-11. In some embodiments of any of the aspects, the antibody, antibody reagent, or antigen-binding fragment thereof, comprises light chain CDRs having the amino acid sequences of SEQ ID NOs: 9-11 or a conservative substitution variant of such amino acid sequence.

In some embodiments of any of the aspects, the antibody, antibody reagent, or antigen-binding fragment thereof comprises the heavy or light chain complementarity determining region (CDR)s as follows:
  (a) a light chain CDR1 having the amino acid sequence of SEQ ID NO: 9;
  (b) a light chain CDR2 having the amino acid sequence of SEQ ID NO: 10;
  (c) a light chain CDR3 having the amino acid sequence of SEQ ID NO: 11;
  (d) a heavy chain CDR1 having the amino acid sequence of SEQ ID NO: 1;
  (e) a heavy chain CDR2 having the amino acid sequence of SEQ ID NO: 2; and
  (f) a heavy chain CDR3 having the amino acid sequence of SEQ ID NO: 3.

In some embodiments of any of the aspects, the antibody, antibody reagent, or antigen-binding fragment thereof comprises the heavy or light chain complementarity determining region (CDR)s as follows:
  (a) a light chain CDR1 having the amino acid sequence of SEQ ID NO: 9;
  (b) a light chain CDR2 having the amino acid sequence of SEQ ID NO: 10;
  (c) a light chain CDR3 having the amino acid sequence of SEQ ID NO: 11;
  (d) a heavy chain CDR1 having the amino acid sequence of SEQ ID NO: 1;
  (e) a heavy chain CDR2 having the amino acid sequence of SEQ ID NO: 2; and
  (f) a heavy chain CDR3 having the amino acid sequence of SEQ ID NO: 3; or a conservative substitution variant of the amino acid sequence of any of (a)-(f).

In some embodiments, the antibody, antibody reagent, or antigen-binding portion thereof can comprise one or more CDRs (e.g., one CDR, two CDRs, three CDRs, four CDRs, five CDRs, or six CDRs) having the sequence of a CDR selected from SEQ ID NOs: 1-3 and 9-11. In some embodiments, the antibody, antibody reagent, antigen-binding portion thereof, or CAR can comprise CDRs having the sequence of the CDRs of SEQ ID NOs: 1-3 and 9-11.

In some aspects, described herein is an antibody, antigen reagent, or antigen-binding fragment thereof that specifically binds a DEspR polypeptide. In some embodiments of any of the aspects, the antibody, antigen reagent, or antigen-binding fragment thereof comprises at least one heavy or light chain complementarity determining region (CDR) selected from the group consisting of:
  (a) a light chain CDR1 having the amino acid sequence of SEQ ID NO: 17;
  (b) a light chain CDR2 having the amino acid sequence of SEQ ID NO: 18;
  (c) a light chain CDR3 having the amino acid sequence of SEQ ID NO: 19;
  (d) a heavy chain CDR1 having the amino acid sequence of SEQ ID NO: 1;

(e) a heavy chain CDR2 having the amino acid sequence of SEQ ID NO: 2; and (f) a heavy chain CDR3 having the amino acid sequence of SEQ ID NO: 3; or a conservative substitution variant of one or more of (a)-(f). In some embodiments of any of the aspects, the antibody, antibody reagent, or antigen-binding fragment thereof comprises at least one heavy or light chain complementarity determining region (CDR) selected from the group consisting of:

(a) a light chain CDR1 having the amino acid sequence of SEQ ID NO: 17;

(b) a light chain CDR2 having the amino acid sequence of SEQ ID NO: 18;

(c) a light chain CDR3 having the amino acid sequence of SEQ ID NO: 19;

(d) a heavy chain CDR1 having the amino acid sequence of SEQ ID NO: 1;

(e) a heavy chain CDR2 having the amino acid sequence of SEQ ID NO: 2; and (f) a heavy chain CDR3 having the amino acid sequence of SEQ ID NO: 3.

In some embodiments of any of the aspects, the antibody, antibody reagent, or antigen-binding portion thereof specifically binds to DEspR and competes for binding with an antibody comprising:

(a) a light chain CDR1 having the amino acid sequence of SEQ ID NO: 17;

(b) a light chain CDR2 having the amino acid sequence of SEQ ID NO: 18;

(c) a light chain CDR3 having the amino acid sequence of SEQ ID NO: 19;

(d) a heavy chain CDR1 having the amino acid sequence of SEQ ID NO: 1;

(e) a heavy chain CDR2 having the amino acid sequence of SEQ ID NO: 2; and (f) a heavy chain CDR3 having the amino acid sequence of SEQ ID NO: 3.

In some embodiments of any of the aspects, the antibody, antibody reagent, or antigen-binding fragment thereof, comprises heavy chain CDRs having the amino acid sequences of SEQ ID NOs: 1-3. In some embodiments of any of the aspects, the antibody, antibody reagent, or antigen-binding fragment thereof, comprises heavy chain CDRs having the amino acid sequences of SEQ ID NOs: 1-3 or a conservative substitution variant of such amino acid sequence. In some embodiments of any of the aspects, the antibody, antibody reagent, or antigen-binding fragment thereof, comprises light chain CDRs having the amino acid sequences of SEQ ID NOs: 17-19. In some embodiments of any of the aspects, the antibody, antibody reagent, or antigen-binding fragment thereof, comprises light chain CDRs having the amino acid sequences of SEQ ID NOs: 17-19 or a conservative substitution variant of such amino acid sequence.

In some embodiments of any of the aspects, the antibody, antibody reagent, or antigen-binding fragment thereof comprises the heavy or light chain complementarity determining region (CDR)s as follows:

(a) a light chain CDR1 having the amino acid sequence of SEQ ID NO: 17;

(b) a light chain CDR2 having the amino acid sequence of SEQ ID NO: 18;

(c) a light chain CDR3 having the amino acid sequence of SEQ ID NO: 19;

(d) a heavy chain CDR1 having the amino acid sequence of SEQ ID NO: 1;

(e) a heavy chain CDR2 having the amino acid sequence of SEQ ID NO: 2; and (f) a heavy chain CDR3 having the amino acid sequence of SEQ ID NO: 3.

In some embodiments of any of the aspects, the antibody, antibody reagent, or antigen-binding fragment thereof comprises the heavy or light chain complementarity determining region (CDR)s as follows:

(a) a light chain CDR1 having the amino acid sequence of SEQ ID NO: 17;

(b) a light chain CDR2 having the amino acid sequence of SEQ ID NO: 18;

(c) a light chain CDR3 having the amino acid sequence of SEQ ID NO: 19;

(d) a heavy chain CDR1 having the amino acid sequence of SEQ ID NO: 1;

(e) a heavy chain CDR2 having the amino acid sequence of SEQ ID NO: 2; and (f) a heavy chain CDR3 having the amino acid sequence of SEQ ID NO: 3; or a conservative substitution variant of the amino acid sequence of any of (a)-(f).

In some embodiments, the antibody, antibody reagent, or antigen-binding portion thereof can comprise one or more CDRs (e.g., one CDR, two CDRs, three CDRs, four CDRs, five CDRs, or six CDRs) having the sequence of a CDR selected from SEQ ID NOs: 1-3 and 17-19. In some embodiments, the antibody, antibody reagent, antigen-binding portion thereof, or CAR can comprise CDRs having the sequence of the CDRs of SEQ ID NOs: 1-3 and 17-19.

In some aspects, described herein is an antibody, antigen reagent, or antigen-binding fragment thereof that specifically binds a DEspR polypeptide. In some embodiments of any of the aspects, the antibody, antigen reagent, or antigen-binding fragment thereof comprises at least one heavy or light chain complementarity determining region (CDR) selected from the group consisting of:

(a) a light chain CDR1 having the amino acid sequence of SEQ ID NO: 13;

(b) a light chain CDR2 having the amino acid sequence of SEQ ID NO: 14;

(c) a light chain CDR3 having the amino acid sequence of SEQ ID NO: 15;

(d) a heavy chain CDR1 having the amino acid sequence of SEQ ID NO: 5;

(e) a heavy chain CDR2 having the amino acid sequence of SEQ ID NO: 6; and (f) a heavy chain CDR3 having the amino acid sequence of SEQ ID NO: 7; or a conservative substitution variant of one or more of (a)-(f). In some embodiments of any of the aspects, the antibody, antibody reagent, or antigen-binding fragment thereof comprises at least one heavy or light chain complementarity determining region (CDR) selected from the group consisting of:

(a) a light chain CDR1 having the amino acid sequence of SEQ ID NO: 13;

(b) a light chain CDR2 having the amino acid sequence of SEQ ID NO: 14;

(c) a light chain CDR3 having the amino acid sequence of SEQ ID NO: 15;

(d) a heavy chain CDR1 having the amino acid sequence of SEQ ID NO: 5;

(e) a heavy chain CDR2 having the amino acid sequence of SEQ ID NO: 6; and (f) a heavy chain CDR3 having the amino acid sequence of SEQ ID NO: 7.

In some embodiments of any of the aspects, the antibody, antibody reagent, or antigen-binding portion thereof specifically binds to DEspR and competes for binding with an antibody comprising:

(a) a light chain CDR1 having the amino acid sequence of SEQ ID NO: 13;
(b) a light chain CDR2 having the amino acid sequence of SEQ ID NO: 14;
(c) a light chain CDR3 having the amino acid sequence of SEQ ID NO: 15;
(d) a heavy chain CDR1 having the amino acid sequence of SEQ ID NO: 5;
(e) a heavy chain CDR2 having the amino acid sequence of SEQ ID NO: 6; and
(f) a heavy chain CDR3 having the amino acid sequence of SEQ ID NO: 7.

In some embodiments of any of the aspects, the antibody, antibody reagent, or antigen-binding fragment thereof, comprises heavy chain CDRs having the amino acid sequences of SEQ ID NOs: 5-7. In some embodiments of any of the aspects, the antibody, antibody reagent, or antigen-binding fragment thereof, comprises heavy chain CDRs having the amino acid sequences of SEQ ID NOs: 5-7 or a conservative substitution variant of such amino acid sequence. In some embodiments of any of the aspects, the antibody, antibody reagent, or antigen-binding fragment thereof, comprises light chain CDRs having the amino acid sequences of SEQ ID NOs: 13-15. In some embodiments of any of the aspects, the antibody, antibody reagent, or antigen-binding fragment thereof, comprises light chain CDRs having the amino acid sequences of SEQ ID NOs: 13-15 or a conservative substitution variant of such amino acid sequence.

In some embodiments of any of the aspects, the antibody, antibody reagent, or antigen-binding fragment thereof comprises the heavy or light chain complementarity determining region (CDR)s as follows:
(a) a light chain CDR1 having the amino acid sequence of SEQ ID NO: 13;
(b) a light chain CDR2 having the amino acid sequence of SEQ ID NO: 14;
(c) a light chain CDR3 having the amino acid sequence of SEQ ID NO: 15;
(d) a heavy chain CDR1 having the amino acid sequence of SEQ ID NO: 5;
(e) a heavy chain CDR2 having the amino acid sequence of SEQ ID NO: 6; and
(f) a heavy chain CDR3 having the amino acid sequence of SEQ ID NO: 7.

In some embodiments of any of the aspects, the antibody, antibody reagent, or antigen-binding fragment thereof comprises the heavy or light chain complementarity determining region (CDR)s as follows:
(a) a light chain CDR1 having the amino acid sequence of SEQ ID NO: 13;
(b) a light chain CDR2 having the amino acid sequence of SEQ ID NO: 14;
(c) a light chain CDR3 having the amino acid sequence of SEQ ID NO: 15;
(d) a heavy chain CDR1 having the amino acid sequence of SEQ ID NO: 5;
(e) a heavy chain CDR2 having the amino acid sequence of SEQ ID NO: 6; and
(f) a heavy chain CDR3 having the amino acid sequence of SEQ ID NO: 7; or a conservative substitution variant of the amino acid sequence of any of (a)-(f).

In some embodiments, the antibody, antibody reagent, or antigen-binding portion thereof can comprise one or more CDRs (e.g., one CDR, two CDRs, three CDRs, four CDRs, five CDRs, or six CDRs) having the sequence of a CDR selected from SEQ ID NOs: 5-7 and 13-15. In some embodiments, the antibody, antibody reagent, antigen-binding portion thereof, or CAR can comprise CDRs having the sequence of the CDRs of SEQ ID NOs: 5-7 and 13-15.

In some aspects, described herein is an antibody, antigen reagent, or antigen-binding fragment thereof that specifically binds a DEspR polypeptide. In some embodiments of any of the aspects, the antibody, antigen reagent, or antigen-binding fragment thereof comprises at least one heavy or light chain complementarity determining region (CDR) selected from the group consisting of:
(a) a light chain CDR1 having the amino acid sequence of SEQ ID NO: 25;
(b) a light chain CDR2 having the amino acid sequence of SEQ ID NO: 26;
(c) a light chain CDR3 having the amino acid sequence of SEQ ID NO: 27;
(d) a heavy chain CDR1 having the amino acid sequence of SEQ ID NO: 21;
(e) a heavy chain CDR2 having the amino acid sequence of SEQ ID NO: 22; and
(f) a heavy chain CDR3 having the amino acid sequence of SEQ ID NO: 23; or a conservative substitution variant of one or more of (a)-(f). In some embodiments of any of the aspects, the antibody, antibody reagent, or antigen-binding fragment thereof comprises at least one heavy or light chain complementarity determining region (CDR) selected from the group consisting of:
(a) a light chain CDR1 having the amino acid sequence of SEQ ID NO: 25;
(b) a light chain CDR2 having the amino acid sequence of SEQ ID NO: 26;
(c) a light chain CDR3 having the amino acid sequence of SEQ ID NO: 27;
(d) a heavy chain CDR1 having the amino acid sequence of SEQ ID NO: 21;
(e) a heavy chain CDR2 having the amino acid sequence of SEQ ID NO: 22; and
(f) a heavy chain CDR3 having the amino acid sequence of SEQ ID NO: 23.

In some embodiments of any of the aspects, the antibody, antibody reagent, or antigen-binding portion thereof specifically binds to DEspR and competes for binding with an antibody comprising:
(a) a light chain CDR1 having the amino acid sequence of SEQ ID NO: 25;
(b) a light chain CDR2 having the amino acid sequence of SEQ ID NO: 26;
(c) a light chain CDR3 having the amino acid sequence of SEQ ID NO: 27;
(d) a heavy chain CDR1 having the amino acid sequence of SEQ ID NO: 21;
(e) a heavy chain CDR2 having the amino acid sequence of SEQ ID NO: 22; and
(f) a heavy chain CDR3 having the amino acid sequence of SEQ ID NO: 23.

In some embodiments of any of the aspects, the antibody, antibody reagent, or antigen-binding fragment thereof, comprises heavy chain CDRs having the amino acid sequences of SEQ ID NOs: 21-23. In some embodiments of any of the aspects, the antibody, antibody reagent, or antigen-binding fragment thereof, comprises heavy chain CDRs having the amino acid sequences of SEQ ID NOs: 21-23 or a conservative substitution variant of such amino acid sequence. In some embodiments of any of the aspects, the antibody, antibody reagent, or antigen-binding fragment thereof, comprises light chain CDRs having the amino acid sequences of SEQ ID NOs: 25-27. In some embodiments of any of the aspects, the antibody, antibody reagent, or antigen-binding fragment thereof, comprises light chain CDRs having the amino acid sequences of SEQ ID NOs: 25-27 or a conservative substitution variant of such amino acid sequence.

In some embodiments of any of the aspects, the antibody, antibody reagent, or antigen-binding fragment thereof comprises the heavy or light chain complementarity determining region (CDR)s as follows:
(a) a light chain CDR1 having the amino acid sequence of SEQ ID NO: 25;
(b) a light chain CDR2 having the amino acid sequence of SEQ ID NO: 26;
(c) a light chain CDR3 having the amino acid sequence of SEQ ID NO: 27;
(d) a heavy chain CDR1 having the amino acid sequence of SEQ ID NO: 21;
(e) a heavy chain CDR2 having the amino acid sequence of SEQ ID NO: 22; and
(f) a heavy chain CDR3 having the amino acid sequence of SEQ ID NO: 23.

In some embodiments of any of the aspects, the antibody, antibody reagent, or antigen-binding fragment thereof comprises the heavy or light chain complementarity determining region (CDR)s as follows:
(a) a light chain CDR1 having the amino acid sequence of SEQ ID NO: 25;
(b) a light chain CDR2 having the amino acid sequence of SEQ ID NO: 26;
(c) a light chain CDR3 having the amino acid sequence of SEQ ID NO: 27;
(d) a heavy chain CDR1 having the amino acid sequence of SEQ ID NO: 21;
(e) a heavy chain CDR2 having the amino acid sequence of SEQ ID NO: 22; and
(f) a heavy chain CDR3 having the amino acid sequence of SEQ ID NO: 23; or a conservative substitution variant of the amino acid sequence of any of (a)-(f).

In some embodiments, the antibody, antibody reagent, or antigen-binding portion thereof can comprise one or more CDRs (e.g., one CDR, two CDRs, three CDRs, four CDRs, five CDRs, or six CDRs) having the sequence of a CDR selected from SEQ ID NOs: 21-23 and 25-27. In some embodiments, the antibody, antibody reagent, antigen-binding portion thereof, or CAR can comprise CDRs having the sequence of the CDRs of SEQ ID NOs: 21-23 and 25-27.

In some aspects, described herein is an antibody, antigen reagent, or antigen-binding fragment thereof that specifically binds a DEspR polypeptide. In some embodiments of any of the aspects, the antibody, antigen reagent, or antigen-binding fragment thereof comprises at least one heavy or light chain complementarity determining region (CDR) selected from the group consisting of:
(a) a light chain CDR1 having the amino acid sequence of SEQ ID NO: 33;
(b) a light chain CDR2 having the amino acid sequence of SEQ ID NO: 34;
(c) a light chain CDR3 having the amino acid sequence of SEQ ID NO: 35;
(d) a heavy chain CDR1 having the amino acid sequence of SEQ ID NO: 29;
(e) a heavy chain CDR2 having the amino acid sequence of SEQ ID NO: 30; and
(f) a heavy chain CDR3 having the amino acid sequence of SEQ ID NO: 31; or a conservative substitution variant of one or more of (a)-(f). In some embodiments of any of the aspects, the antibody, antibody reagent, or antigen-binding fragment thereof comprises at least one heavy or light chain complementarity determining region (CDR) selected from the group consisting of:
(a) a light chain CDR1 having the amino acid sequence of SEQ ID NO: 33;
(b) a light chain CDR2 having the amino acid sequence of SEQ ID NO: 34;
(c) a light chain CDR3 having the amino acid sequence of SEQ ID NO: 35;
(d) a heavy chain CDR1 having the amino acid sequence of SEQ ID NO: 29;
(e) a heavy chain CDR2 having the amino acid sequence of SEQ ID NO: 30; and
(f) a heavy chain CDR3 having the amino acid sequence of SEQ ID NO: 31.

In some embodiments of any of the aspects, the antibody, antibody reagent, or antigen-binding portion thereof specifically binds to DEspR and competes for binding with an antibody comprising:
(a) a light chain CDR1 having the amino acid sequence of SEQ ID NO: 33;
(b) a light chain CDR2 having the amino acid sequence of SEQ ID NO: 34;
(c) a light chain CDR3 having the amino acid sequence of SEQ ID NO: 35;
(d) a heavy chain CDR1 having the amino acid sequence of SEQ ID NO: 29;
(e) a heavy chain CDR2 having the amino acid sequence of SEQ ID NO: 30; and
(f) a heavy chain CDR3 having the amino acid sequence of SEQ ID NO: 31.

In some embodiments of any of the aspects, the antibody, antibody reagent, or antigen-binding fragment thereof, comprises heavy chain CDRs having the amino acid sequences of SEQ ID NOs: 29-31. In some embodiments of any of the aspects, the antibody, antibody reagent, or antigen-binding fragment thereof, comprises heavy chain CDRs having the amino acid sequences of SEQ ID NOs: 29-31 or a conservative substitution variant of such amino acid sequence. In some embodiments of any of the aspects, the antibody, antibody reagent, or antigen-binding fragment thereof, comprises light chain CDRs having the amino acid sequences of SEQ ID NOs: 33-35. In some embodiments of any of the aspects, the antibody, antibody reagent, or antigen-binding fragment thereof, comprises light chain CDRs having the amino acid sequences of SEQ ID NOs: 33-35 or a conservative substitution variant of such amino acid sequence.

In some embodiments of any of the aspects, the antibody, antibody reagent, or antigen-binding fragment thereof comprises the heavy or light chain complementarity determining region (CDR)s as follows: (a) a light chain CDR1 having the amino acid sequence of SEQ ID NO: 33;
(b) a light chain CDR2 having the amino acid sequence of SEQ ID NO: 34;
(c) a light chain CDR3 having the amino acid sequence of SEQ ID NO: 35;
(d) a heavy chain CDR1 having the amino acid sequence of SEQ ID NO: 29;
(e) a heavy chain CDR2 having the amino acid sequence of SEQ ID NO: 30; and
(f) a heavy chain CDR3 having the amino acid sequence of SEQ ID NO: 31.

In some embodiments of any of the aspects, the antibody, antibody reagent, or antigen-binding fragment thereof comprises the heavy or light chain complementarity determining region (CDR)s as follows:

(a) a light chain CDR1 having the amino acid sequence of SEQ ID NO: 33;
(b) a light chain CDR2 having the amino acid sequence of SEQ ID NO: 34;
(c) a light chain CDR3 having the amino acid sequence of SEQ ID NO: 35;
(d) a heavy chain CDR1 having the amino acid sequence of SEQ ID NO: 29;
(e) a heavy chain CDR2 having the amino acid sequence of SEQ ID NO: 30; and
(f) a heavy chain CDR3 having the amino acid sequence of SEQ ID NO: 31; or a conservative substitution variant of the amino acid sequence of any of (a)-(f).

In some embodiments, the antibody, antibody reagent, or antigen-binding portion thereof can comprise one or more CDRs (e.g., one CDR, two CDRs, three CDRs, four CDRs, five CDRs, or six CDRs) having the sequence of a CDR selected from SEQ ID NOs: 29-31 and 33-35. In some embodiments, the antibody, antibody reagent, antigen-binding portion thereof, or CAR can comprise CDRs having the sequence of the CDRs of SEQ ID NOs: 29-31 and 33-35.

In some embodiments, the antibody, antibody reagent, or antigen-binding portion thereof can comprise CDRs having at least 90% homology, at least 95% homology, at least 97% homology, at least 98% homology, or more with the CDRs of an antibody of Table 1. As will be understood by those skilled in the art, a variety of algorithms are available that permit comparison of sequences in order to determine their degree of homology, including by permitting gaps of designated length in one sequence relative to another when considering which residues "correspond" to one another in different sequences. One procedure for obtaining antibody mutants, such as CDR mutants, is "alanine scanning mutagenesis" (Cunningham & Wells, Science 244:1081-1085 (1989); and Cunningham & Wells, Proc Nat Acad Sci USA 84:6434-6437 (1991)). One or more of the hypervariable region residue(s) are replaced by alanine or polyalanine residue(s). Those hypervariable region residue(s) demonstrating functional sensitivity to the substitutions then are refined by introducing further or other mutations at or for the sites of substitution. Thus, while the site for introducing an amino acid sequence variation is predetermined, the nature of the mutation per se need not be predetermined. Similar substitutions can be attempted with other amino acids, depending on the desired property of the scanned residues. A more systematic method for identifying amino acid residues to modify comprises identifying hypervariable region residues involved in binding DEspR and those hypervariable region residues with little or no involvement with DEspR binding. An alanine scan of the non-binding hypervariable region residues is performed, with each ala mutant tested for enhancing binding to DEspR. In another embodiment, those residue(s) significantly involved in binding DEspR are selected to be modified. Modification can involve deletion of a residue or insertion of one or more residues adjacent to a residue of interest. However, normally the modification involves substitution of the residue by another amino acid. A conservative substitution can be a first substitution. If such a substitution results in a change in biological activity (e.g., binding affinity), then another conservative substitution can be made to determine if more substantial changes are obtained. Even more substantial modification in an antibody range and presentation of biological properties can be accomplished by selecting an amino acid that differs more substantially in properties from that normally resident at a site. Thus, such a substitution can be made while maintaining: (a) the structure of the polypeptide backbone in the area of the substitution, for example, as a sheet or helical conformation; (b) the charge or hydrophobicity of the molecule at the target site, or (c) the bulk of the side chain.

Exemplary antibodies and antibody reagents which bind DEspR are described in US Patent Publications 2017/0058036 and 2016/0108124, each of which are incorporated by reference herein in their entireties.

TABLE 1

Exemplary anti-DEspR antibody reagent sequences, per the Kabat system

| | Sequence | SEQ ID NO |
|---|---|---|
| 6G8G7 HV1 | | |
| Heavy chain CDR1 | GYGVN | 1 |
| Heavy Chain CDR2 | MIWDDGSTDYNSALKS | 2 |
| Heavy Chain CDR3 | DPVVHFYAMDY | 3 |
| VH Domain | GSQVQLQESGPGLVAPSQSLSITCTVSGFSLTGYGVNWVRQPPGKGLEWLGMIWDDGSTDYNSALKSRLIITKDNSRSQVFLKMNSLQTDDTARYYCARDPVVHFYAMDYWGQGTSVTVSSAKTTPPSVYGGGGS | 4 |
| HV2 | | |
| Heavy chain CDR1 | RYWMS | 5 |
| Heavy Chain CDR2 | EINPDSSTINYTPSLKD | 6 |
| Heavy Chain CDR3 | HGRGMDY | 7 |
| VH Domain | GSEVQLQESGGGLVQPGGSLKLSCAASGFDFSRYWMSWVRQAPGKGLEWIGEINPDSSTINYTPSLKDKFIISRDTAKKTLYLQMSKVRSEDTALYYCARHGRGMDYWSQGTSVTVSSAKTTPPSVYGGGGS | 8 |

TABLE 1-continued Exemplary anti-DEspR antibody reagent sequences, per the Kabat system

| | Sequence | SEQ ID NO |
|---|---|---|
| KV1 | | |
| Light Chain CDR1 | KASQNVDSNVA | 9 |
| Light Chain CDR2 | SASYRYS | 10 |
| Light Chain CDR3 | QQYHSYP | 11 |
| VL Domain | GGGGSDIVLTQTNQIMSASVGDRVSVTCKASQNVDSNVAWYQQK PGHSPKALIYSASYRYSRVPDRITGSGSGTDFTLTITNVQSKDL ADYFCQQYHSYPLLAFGAGTKLELKRADAAPTVSLE | 12 |
| KV2 | | |
| Light Chain CDR1 | KASQSVSNDVA | 13 |
| Light Chain CDR2 | YASNRYT | 14 |
| Light Chain CDR3 | QQDYSSPFT | 15 |
| VL Domain | GGGSDIVLTQTHKFLLVSAGDRITITCKASQSVSNDVAWYQQKP GQSPKLLIYYASNRYTGVPDRFTGSGYGTDFTFTISTVQADDLA VYFCQQDYSSPFTFGGGTKLEIKRADAAPTVSLE | 16 |
| KV8 | | |
| Light Chain CDR1 | SASSSVSFMH | 17 |
| Light Chain CDR2 | STSNLAS | 18 |
| Light Chain CDR3 | QQRSSYP | 19 |
| VL Domain | GGGGSDIVITQSNAIMSASPGEKVTITCSASSSVSFMHWFQQKP GTSPKLWIYSTSNLASGVPARFSGSGSGTSYSLTISRMEAEDAA TYYCQQRSSYPLTFGAGTKLELKRADAAPTVSLE | 20 |
| 7C5B2 HV2 | | |
| Heavy chain CDR1 | SYAVS | 21 |
| Heavy Chain CDR2 | VIWGDGSTDYHSALIS | 22 |
| Heavy Chain CDR3 | GTGTGFAY | 23 |
| VH Domain | QVQLKESGPGLVAPSQSLSITCTVSGFSLKSYAVSWVRQPPGKG LEWLGVIWGDGSTDYHSALISRLSISKDNSKSQFFLRLNSLQTD DTATYYCARGTGTGFAYWGQGTLVTVSA | 24 |
| KV2 | | |
| Light chain CDR1 | RSSQSLVHSNGNTYLH | 25 |
| Light Chain CDR2 | KVSNRFS | 26 |
| Light Chain CDR3 | SQCTHIPWT | 27 |
| VL Domain | DVVMTQTPLSLPVSLGDQASISCRSSQSLVHSNGNTYLHWYLQK PGQSPKWYKVSNRFSGVPDRFSGSGSGTDFTLKISRVEAEDLGI YFCSQCTHIPWTFGGGTNLEIK | 28 |
| 7C5B2 | | |
| Heavy chain CDR1 | GFSLTSYDIS | 29 |
| Heavy Chain CDR2 | VIWTGGGTNYNSAFMS | 30 |
| Heavy Chain CDR3 | DRDYDGWYFDV | 31 |
| VH Domain | QVQLKESGPGLVAPSQSLSITCTVSGFSLTSYDISWIRQPPGKG LEWLGVIWTGGGTNYNSAFMSRLSISKDNSKSQVFLKMNSLQTD DTAIYYCVRDRDYDGWYFDVWGAGTTVTVSS | 32 |

TABLE 1-continued

Exemplary anti-DEspR antibody reagent sequences, per the Kabat system

| | Sequence | SEQ ID NO |
|---|---|---|
| Light chain CDR1 | RSSQSIVHSNGNTYLE | 33 |
| Light Chain CDR2 | KVSNRFS | 34 |
| Light Chain CDR3 | FQGSHVPYT | 35 |
| VL Domain | DVLMTQTPLSLPVSLGDQASISCRSSQSIVHSNGNTYLEWYLQK PGQSPKLLIYKVSNRFSGVPDRFSGSGSGTDFTLKISRVEAEDL GVYYCFQGSHVPYTFGGGTKLEIK | 36 |

In some embodiments, the antibody or antibody reagent as described herein can be a variant of a sequence described herein, e.g., a conservative substitution variant of an antibody polypeptide. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or portion thereof that retains activity, e.g., antigen-specific binding activity for the relevant target polypeptide, e.g., DEspR. A wide variety of PCR-based site-specific mutagenesis approaches are also known in the art and can be applied by the ordinarily skilled artisan.

One of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retain the ability to specifically bind the target antigen (e.g., DEspR). Such conservatively modified variants are in addition to and do not exclude polymorphic variants, interspecies homologs, and alleles consistent with the disclosure.

Examples of substitution variants include conservative substitution of amino acids, e.g., in a VH or VL, domain, that do not alter the sequence of a CDR. A conservative substitution in a sequence not comprised by a CDR can be a substitution relative to a wild-type or naturally-occurring sequence, e.g., human or murine framework and/or constant regions of an antibody sequence. In some embodiments, a conservatively modified variant of an antibody reagent can comprise alterations other than in the CDRs, e.g., a conservatively modified variant of an antibody, antibody reagent, or antigen-binding portion thereof, can comprise CDRs having the sequence of one or more of SEQ ID NOs: 1-3, 9-11, 17-19, 5-7, 13-15, 21-23, 25-27, 29-31, and 33-35. In some embodiments, a conservatively modified variant of an antibody, antibody reagent, or antigen-binding portion thereof, can comprise CDRs having the sequences of SEQ ID NOs: 1-3, 9-11, 17-19, 5-7, 13-15, 21-23, 25-27, 29-31, and 33-35.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g., antigen-binding activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

A variant amino acid or DNA sequence preferably is at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g., BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required.

Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

In particular embodiments wherein an antibody or antibody reagent as described herein comprises at least one CDR which is not identical to the sequence of SEQ ID Nos: 1-3, 9-11, 17-19, 5-7, 13-15, 21-23, 25-27, 29-31, and 33-35, the amino acid sequence of that at least one CDR can be selected by methods well known to one of skill in the art. For example, Fujii, 2004, "Antibody affinity maturation by random mutagenesis" in Methods in Molecular Biology: Antibody Engineering 248: 345-349 (incorporated by reference herein in its entirety), particularly at FIG. 2 and Section 3.3, describes methods of generating a library for any CDR of interest. This allows one of ordinary skill in the art to identify alternative CDRs, including conservative substitution variants of the specific CDR sequences described herein, which, when present in an antibody or antigen-binding portion thereof as described herein, will result in an antigen or antigen-binding portion thereof which will bind a cell surface antigen. The method described in Fujii et al. also permits one of ordinary skill in the art to screen for a light chain sequence which will give the desired binding behavior when combined with a known heavy chain fragment and vice versa.

In some embodiments of any of the aspects, the DEspR inhibitor described herein can be a bi-specific reagent, e.g., a bi-specific antibody or antibody reagent. Bispecific agents comprise a molecule which is able to physically contact and inhibit two different molecules simultaneously. In some embodiments of any of the aspects, the bispecific agent is a bispecific monoclonal antibody reagent, e.g., a bsAb. In some embodiments of any of the aspects, bispecific agents comprise a molecule which is able to physically contact and inhibit i) DEspR and ii) PD1 or PD-L1 simultaneously. As used herein, the term "bispecific" antibody or antibody reagent refers to an antibody or antibody reagent that comprises a first domain which has a binding site that has binding specificity for a first target, and a second domain which has a binding site that has binding specificity for a second target, i.e., the agent has specificity for two targets, e.g., i) DEspR and ii) PD1 or PD-L1. The first target and the second target are not the same (i.e., are different targets (e.g., proteins)). In some embodiments, the different targets can be co-expressed on the same cell. In some embodiments, a bispecific reagent can bind targets present on a single cell (heterophilic binding in cis), and/or bind one target on one cell and the other on another cell (heterophilic binding in trans). Accordingly, a bispecific reagent as described herein can selectively and specifically bind to a cell that expresses the first target and the second target. A non-limiting example of a bispecific reagent is a bispecific antibody construct. Bispecific antibody constructs comprising antigen-binding portions of antibodies specific for two different antigens can be readily constructed by one of skill in the art. Generally, sequences encoding the antigen-binding domain of a first antibody characterized and known to bind a desired epitope on one antigen can be joined, either directly, or through any of a variety of linkers as known to the ordinarily skilled artisan, to sequences encoding the antigen-binding domain of a second antibody characterized and known to bind a desired epitope on a second antigen. Such sequences can be inserted into an appropriate vector and introduced to a cell to produce the bispecific antibody polypeptide by methods known to those of ordinary skill in the art. PD-1 and/or PD-L1 inhibitors (e.g., anti-PD1 and/or anti-PD-L1 antibodies) are known in the art.

In some embodiments of any of the aspects, the bi-specific antibody reagent can bind specifically to and inhibit i) DEspR and ii) a target that modulates (e.g., inhibits) immune cell activity and/or survival. The purpose of binding to the target that modulates immune cell activity can include to simulate or inhibit immune cell activity, e.g., to enhance T-cell activity for tumor-surveillance, or to bind to an immune cell to approximate (bring together) two cells, e.g., the DEspR+ neutrophil and CD14+ macrophage. The target can be, e.g., a cell surface receptor, ligand or extracellular protein, or an intracellular protein. It has previously been demonstrated that anti-DEspR antibodies are internalized after binding to DEspR (see, e.g., Herrera et al. PLoS One 2014 9:e112335; which is incorporated by reference herein in its entirety), permitting the use of bispecific antibodies that bind to both DEspR and an intracellular target. Non-limiting examples of suitable cell surface receptors are PD1; CTLA-4 (e.g., NCBI Gene ID: 1493); TLR-2 (e.g., NCBI Gene ID: 7097); TLR-4 (e.g., NCBI Gene ID: 7099); CD14 (e.g., NCBI Gene ID: 929); or CD168 (e.g., NCBI Gene ID: 3161). Non-limiting examples of suitable ligands or extracellular protein are PD-Li; CD80 (e.g., NCBI Gene ID: 941): CD86 (e.g., NCBI Gene ID: 942); myeloperoxidase (MPO) (e.g., NCBI Gene ID 4353); cathepsin-G (e.g., NCBI Gene ID: 1511); neutrophil elastase (NE) (e.g., NCBI Gene ID: 1991), arginase-1 (e.g., NCBI Gene ID: 383), G-CSF (e.g., CSF3 or NCBI Gene ID: 1441), and GM-CSF (e.g., CSF2 or NCBI Gene ID: 1439). Non-limiting examples of suitable intracellular proteins include Mcl-1 (e.g., NCBI Gene ID: 4170); cIAP2 (e.g., NCBI Gene ID: 330); STAT3 (e.g., NCBI Gene ID: 6774); ERK1/2 (e.g. NCBI Gene ID: 5595 and 5594) petptidylarginine deaminase (PAD4) (e.g., NCBI Gene ID: 23569); galectin 1 (e.g., NCBI Gene ID: 3956), galectin 3 (e.g., NCBI Gene ID: 3958), or adenosine deaminase of RNA-1 (ADAR-1) (e.g., NCBI Gene ID: 103). Antibodies specific for such targets are known in the art.

Bi-specific antibody reagents against DEspR and any of the targets described herein are readily prepared using the CDRs of any of the target-specific antibodies described herein or known in the art.

The antibody reagents described herein can be further modified to improve, e.g., immunogenicity or half-life. For example, an antibody reagent as described herein can be an IgG4 antibody reagent and/or a hinge-stabilized IgG4 antibody reagent. In some embodiments of any of the aspects, hinge-stabilization can comprise a S228P mutation relative to the wildtype IgG4 sequence.

Antibody reagents described herein can be administered to a subject by administering a cell comprising and/or expressing the antibody reagent. For example, the cell can be a T cell, CAR-T cell, or adoptively transferred T cell. In some embodiments of any of the aspects, the antibody reagent is a chimeric antigen receptor (CAR). In some embodiments of any of the aspects, the antibody reagent described herein is not a CAR, and the cell comprises the presently described antibody reagent in addition to a CAR.

CAR-T cell and related therapies relate to adoptive cell transfer of immune cells (e.g., T cells) expressing a CAR that binds specifically to a targeted cell type to treat a subject. In some embodiments of any of the aspects, the cells administered as part of the therapy can be autologous to the subject. In some embodiments of any of the aspects, the cells administered as part of the therapy are not autologous to the subject. In some embodiments of any of the aspects, the cells are engineered and/or genetically modified to express the CAR and/or the antibody reagent described herein. CAR, CAR-T, and other adoptive cell transfer technologies are well known in the art. Further discussion of CAR-T therapies can be found, e.g., in Maus et al. Blood 2014 123:2624-35; Reardon et al. Neuro-Oncology 2014 16:1441-1458; Hoyos et al. Haematologica 2012 97:1622; Byrd et al. J Clin Oncol 2014 32:3039-47; Maher et al. Cancer Res 2009 69:4559-4562; and Tamada et al. Clin Cancer Res 2012 18:6436-6445; each of which is incorporated by reference herein in its entirety.

In some embodiments of any of the aspects, the DEspR inhibitor, or anti-DEspR antibody reagent, or bi-specific antibody reagent described herein is an antibody-drug conjugate. The antibody-drug conjugate can comprise at least one anti-DEspR antibody reagent and at least one drug conjugated to the antibody reagent.

In particular embodiments, an antibody-drug conjugate comprises an antibody, antibody reagent, or antigen-binding portion thereof as described herein. The drug can be, e.g., a thrombolytic or chemotherapeutic molecule as described elsewhere herein. In some embodiments of any of the aspects, the antibody-drug conjugate comprises a thrombolytic agent directly conjugated and/or bound to an antibody or antigen-binding portion thereof. In some embodiments of any of the aspects, the antibody-drug conjugate comprises a drug, e.g., a thrombolytic or chemotherapeutic agent directly conjugated and/or bound to an antibody or antigen-binding portion thereof. In some embodiments of any of the aspects, binding can be non-covalent, e.g., by hydrogen bonding, electrostatic, or van der Waals interactions; however, binding may also be covalent. By "conjugated" is meant the covalent linkage of at least two molecules. In some embodiments of any of the aspects, the composition can be an antibody-drug conjugate.

In some embodiments of any of the aspects, an antibody, antibody reagent, or antigen-binding portion thereof can be bound to and/or conjugated to multiple drug molecules, e.g., chemotherapeutic molecules. In some embodiments of any of the aspects, an antibody-drug conjugate can be bound to and/or conjugated to multiple drug molecules, e.g, chemotherapeutic molecules. In some embodiments of any of the aspects, the ratio of a given drug molecule, e.g., chemotherapeutic molecule to an antibody or antigen-binding portion thereof can be from about 1:1 to about 1,000:1, e.g., a single antibody reagent molecule can be linked to, conjugated to, etc. from about 1 to about 1,000 individual drug molecules, e.g., chemotherapeutic molecules.

In some embodiments of any of the aspects, an antibody, or antigen-binding portion thereof, and additional drug or reagents, e.g, the chemotherapeutic agent, can be present in a scaffold material. Scaffold materials suitable for use in therapeutic compositions are known in the art and can include, but are not limited to, a nanoparticle; a matrix; a hydrogel; and a biomaterial, biocompatible, and/or biodegradable scaffold material. As used herein, the term "nanoparticle" refers to particles that are on the order of about 10-9 or one to several billionths of a meter. The term "nanoparticle" includes nanospheres; nanorods; nanoshells; and nanoprisms; these nanoparticles may be part of a nanonetwork.

The term "nanoparticles" also encompasses liposomes and lipid particles having the size of a nanoparticle. As used herein, the term "matrix" refers to a 3-dimensional structure comprising the components of a composition described herein (e.g., an antibody or antigen-binding portion thereof). Non-limiting examples of matrix structures include foams; hydrogels; electrospun fibers; gels; fiber mats; sponges; 3-dimensional scaffolds; non-woven mats; woven materials; knit materials; fiber bundles; and fibers and other material formats (See, e.g., Rockwood et al. Nature Protocols 2011 6:1612-1631 and US Patent Publications 2011/0167602; 2011/0009960; 2012/0296352; and U.S. Pat. No. 8,172,901; each of which is incorporated by reference herein in its entirety). The structure of the matrix can be selected by one of skill in the art depending upon the intended application of the composition, e.g., electrospun matrices can have greater surface area than foams.

In some embodiments of any of the aspects, the scaffold is a hydrogel. As used herein, the term "hydrogel" refers to a three-dimensional polymeric structure that is insoluble in water but which is capable of absorbing and retaining large quantities of water to form a stable, often soft and pliable, structure. In some embodiments of any of the aspects, water can penetrate in between the polymer chains of the polymer network, subsequently causing swelling and the formation of a hydrogel. In general, hydrogels are superabsorbent. Hydrogels have many desirable properties for biomedical applications. For example, they can be made nontoxic and compatible with tissue, and they are highly permeable to water, ions, and small molecules. Hydrogels are superabsorbent (they can contain over 99% water) and can be comprised of natural (e.g., silk) or synthetic polymers, e.g., PEG.

As used herein, "biomaterial" refers to a material that is biocompatible and biodegradable. As used herein, the term "biocompatible" refers to substances that are not toxic to cells. In some embodiments of any of the aspects, a substance is considered to be "biocompatible" if its addition to cells in vitro results in less than or equal to approximately 20% cell death. In some embodiments of any of the aspects, a substance is considered to be "biocompatible" if its addition to cells in vivo does not induce inflammation and/or other adverse effects in vivo. As used herein, the term "biodegradable" refers to substances that are degraded under physiological conditions. In some embodiments of any of the aspects, a biodegradable substance is a substance that is broken down by cellular machinery. In some embodiments of any of the aspects, a biodegradable substance is a substance that is broken down by chemical processes.

Exemplary drugs for use in antibody-drug conjugates can comprise a thrombolytic, a chemotherapeutic, a nanoparticle, a polypeptide, an imaging agent, a fluorophore, a small molecule, an enzyme, a nucleic acid molecule, or a chemical. Non-limiting examples of chemotherapeutics include mertansine, emtansine, gemcitabine, temozolomide, paclitaxel, or cis/oxali-platin. Non-limiting examples of nanoparticles include iron oxide-nanoparticle (IONP), polymeric nanoparticle, or gold nanoparticle, or chimeric nanoparticle. Non-limiting examples of an enzyme include DNaseI, e.g., human DNaseI, DNase I, matrix metalloproteinase 1 (MMP1) matrix metalloproteinase 2 (MMP2), matrix metalloproteinase 3 (MMP3), a tissue inhibitor of metalloproteinases (TIMP), a protease, a recombinase, or a plasminogen activator. Non-limiting examples of polypeptides include chymostatin, angiopoietin 1/2, and SDF-1. Non-limiting examples of chemicals include 4-aminobenzoichydrazide or NX-059 nitrone. In some embodiments of the methods described herein, the subject can be a subject who is further administered a PD1 and/or PD-L 1 inhibitor therapy, e.g., sequentially or concurrently, e.g., in the same composition or in separate compositions. Non-limiting examples of nucleic acid molecules can include RNA-inhibitors (siRNA, miRNA) or RNA modulator (miRNA) or transcription factor decoys (DNA-decoy).

In some embodiments of the methods described herein, the subject can be a subject who was In some aspects, described herein is a DEspR inhibitor, anti-DEspR antibody reagent, antibody-drug conjugate, and/or bispecific reagent as described in any of the aspects or embodiments herein.

In some aspects, provided herein is a method of treating a coronavirus infection in a subject, the subject determined to have an elevated level of DEspR+CD11b+ cells as compared to a non-infected subject, the method comprising administering a DEspR inhibitor to the subject, wherein said administering is effective to treat or prevent the coronavirus infection lethality or pathological sequelae in the subject.

In some embodiments, the coronavirus is SARS CoV2, the virus causing COVID-19.

In some embodiments, the DEspR+CD11b+ cells are DEspR+CD11b+ neutrophils, DEspR+CD11b+ monocytes, DEspR+CD11b+ lymphocytes, DEspR+CD11b+ cytoplasts, or a combination or an aggregate. In some embodiments, the DEspR+CD11b+ cells are at least 20, 30, 40, 50, 60, 70, 80, 90, or 100% of the whole corresponding cell population. In some embodiments, the DEspR+CD11b+ cells are at least 1, 2, 3, 4, 5, 6, 7, 8, 9, 10, 15, 20, 25, 30, 35, 40, 45, 50, 55, 60, 65, 70, 75, 80, 85, 90, 95, or 100% of the whole corresponding cell population.

In some embodiments, the subject is further determined to have an elevated DEspR+ neutrophil to lymphocyte ratio (d+NLR); elevated ratio of DEspR+ neutrophils to COVID19-associated (a) hyperinflammation cytokines or cytokine storm biomarkers, (b) oxidative stress biomarkers, (c) endothelial dysfunction biomarkers, or (d) a combination thereof; or a combination thereof. In some embodiments, hyperinflammation cytokines or cytokine storm biomarkers comprise IL-6. In some embodiments, the oxidative stress biomarkers comprise myeloperoxidase (MPO). In some embodiments, the endothelial dysfunction biomarkers comprise endothelin-1 (ET1). In some embodiments, the control subject does not have a coronavirus infection.

In some embodiments, the DEspR inhibitor is an anti-DEspR antibody or fragment thereof. In some embodiments, the anti-DEspR antibody or fragment thereof comprises complementary determining regions selected from SEQ ID Nos: 1-3, 9-11, 17-19, 5-7, 13-15, 21-23, 25-27, 29-31, and 33-35.

In some aspects, provided herein is a method of treating a subject having a coronavirus infection, the method comprising: (i) determining whether the subject has a high risk of poor outcome or morbidity by detecting a level or rising level of DEspR+CD11b+ cells, a level of (1) non-resolving neutrophil-monocyte inflammatory amplification that blocks initiation of next step anti-viral adaptive immunity, anti-viral cellular immunity, hyperinflammation-resolution, or a combination, measured as: DEspR+CD11b+ cells, (2) a level of hyperinflammation-response marked by elevated ratio DEspR+CD11b+ neutrophils to plasma cytokine storm biomarkers, or to plasma oxidative stress biomarkers, or to endothelial dysfunction biomarker, or (3) a combination thereof, as individual or combinatorial measures in a sample obtained from the subject, wherein an elevated level of DEspR+CD11b+ cells, high ratios of DEspR+ neutrophils to COVID-19 associated elevated cytokines, elevated oxidative stress biomarkers, elevated endothelial activation biomarker levels, or lymphopenia, or elevated DAMPs levels such as circulating mitochondrial DNA, nuclear DNA or a combination thereof, or a combination thereof in the sample obtained from the subject compared with a sample obtained from a control subject is an indicative that the subject has a high risk of poor outcome or morbidity, wherein the control subject does not have a coronavirus infection, and (ii) administering to the subject a DEspR inhibitor.

In some aspects, provided herein is a method of improving a survival rate of a subject having a coronavirus infection, the method comprising: (i) determining whether the subject has a high risk of poor outcome or morbidity by detecting a level or rising level of DEspR+CD11 b+ cells, a level of (1) high neutrophil-monocyte inflammatory amplification that blocks initiation of next step anti-viral adaptive immunity, anti-viral cellular immunity, hyperinflammation-resolution, or a combination, measured as: DEspR+CD11b+ cells, (2) a level of hyperinflammation-response marked by elevated ratio DEspR+CD11b+ neutrophils to plasma cytokine storm biomarkers, or to plasma oxidative stress biomarkers or to endothelial dysfunction biomarker, or (3) a combination thereof, as individual or combinatorial measures in a sample obtained from the subject, wherein an elevated or rising level of DEspR+CD11b+ cells or hyperinflammation ratio-markers in the sample obtained from the subject compared with a level of DEspR+CD11b+ cells in a sample obtained from a control subject is indicative that the subject has a high risk of poor outcome or morbidity, wherein the control subject does not have a coronavirus infection, and (ii) administering to the subject a DEspR inhibitor.

In some aspects, provided herein is a method of determining prognosis of a subject having a coronavirus infection, the method comprising: detecting in a sample obtained from the subject a level of, or rising DEspR+CD11b+ cells, or DEspR-bound DNA, or a level of (1) non-resolving neutrophil-monocyte inflammatory amplification that blocks initiation of next step anti-viral adaptive immunity, anti-viral cellular immunity, hyperinflammation-resolution, or a combination, measured as: DEspR+CD11b+ neutrophils and monocytes, (2) a level of hyperinflammation-response marked by elevated ratio DEspR+CD11b+ neutrophils to plasma cytokine storm biomarkers, or to plasma oxidative stress biomarkers or to endothelial dysfunction biomarker, or (3) a combination thereof, as individual or combinatorial measures in a sample obtained from the subject, wherein an elevated or rising levels of DEspR+CD11b+ cells, plasma DEspR-bound DNA, high ratios of DEspR+ neutrophils to COVID-19 associated elevated cytokines, elevated oxidative stress biomarker, elevated endothelial activation biomarker level or a combination thereof in the sample obtained from the subject compared with a level of DEspR+CD11b+ neutrophils in a sample obtained from a control subject is an indicative that the subject has a high risk of poor outcome or morbidity, wherein the control subject does not have a coronavirus infection.

In some embodiments, the DEspR+CD11b+ cells are DEspR+CD11b+ neutrophils, DEspR+CD11b+ monocytes, DEspR+CD11b+ lymphocytes, DEspR+CD11b+ cytoplasts, or a combination or an aggregate. In some embodiments, the plasma cytokine storm biomarkers comprise IL-6, IL-8, IL-1beta or IL-18, or a combination thereof. In some embodiments, the plasma oxidative stress biomarkers comprise myeloperoxidase. In some embodiments, the endothelial dysfunction biomarkers comprise endothelin-1. In some embodiments, the COVID-19 associated elevated cytokines comprises IL-6, IL-8, IL-1beta or IL-18, or a combination thereof. In some embodiments, the elevated oxidative stress biomarkers comprise myeloperoxidase. In some embodiments, the elevated endothelial activation biomarkers comprise endothelin-1. In some embodiments, the level of DEspR+CD11b+ cells is detected by measuring a level of DEspR+CD11b+ aggregates in the blood sample. In some embodiments, the level of DEspR+CD11b+ cells in the subject determines whether the subject will require intensive care.

In some aspects, provided herein is a method of preventing or treating organ-dysfunction or multi-organ dysfunction or failure associated with coronavirus infection in a subject in need thereof, wherein subject is determined to have elevated or rising levels of DEspR+CD11b+ cells, elevated hyperinflammation DEspR+ neutrophil-IL6/MPO/ET1 ratios, or a combination thereof, as compared to a control subject, the method comprising administering a DEspR inhibitor.

In some embodiments, the DEspR+CD11b+ cells are DEspR+CD11b+ neutrophils, DEspR+CD11b+ monocytes, DEspR+CD11b+ lymphocytes, DEspR+CD11b+ cytoplasts, or a combination or an aggregate. In some embodiments, the organ-dysfunction or multi-organ dysfunction or failure associated with the coronavirus infection arises from microcirculatory dysfunction, microvascular inclusion, low flow ischemia, thromboses, systemic microthromboses, microcirculatory vascular aggregation, or a combination thereof. In some embodiments, the organ-dysfunction or multi-organ dysfunction or failure associated with the coronavirus infection is derived from COVID19-induced cytokine storm, low flow organ ischemia from DEspR+ aggregates or DEspR+ DNA strands leading to characteristic COVID19-severe hypoxemia, renal dysfunction, cardiac ischemia, neurological dysfunction, liver dysfunction/failure, hematological coagulopathy or microthromboses, or a combination thereof. In some embodiments, the neurological dysfunction is characterized by loss of consciousness, seizures, confusion or a combination thereof. In some embodiments, the organ-dysfunction or multi-organ dysfunction or failure associated with the coronavirus infection is selected from the group consisting of systemic inflammatory response syndrome (SIRS); acute lung injury (ALI); acute respiratory distress syndrome (ARDS); multi-organ failure or multi-organ dysfunction syndrome (MODS); acute kidney injury (AKI); liver failure, ischemic stroke; delayed cerebral ischemia, and/or encephalopathy. In some embodiments, the organ-dysfunction or multi-organ dysfunction or failure associated with the coronavirus infection is ARDS.

In some aspects, provided herein is a method of combinational therapy for a subject having a coronavirus infection, the method comprising; administering to the subject a therapeutic agent or a therapy in combination with a DEspR inhibitor, wherein the therapeutic agent or the therapy prevents or alleviates a sign or a symptom associated with the coronavirus infection in the subject.

In some embodiments, the therapy is an application of a respiratory ventilation or an alternative oxygen delivery support.

In some aspects, provided herein is a method of reducing microthrombi formation associated with a coronavirus infection in a subject in need thereof, the method comprising: administering to the subject a DEspR inhibitor in combination with an anti-thrombotic agent, thereby reducing systemic microthrombi formation associated with the coronavirus infection in the subject.

As used herein, "anti-thrombotic" refers to an agent that reduces the level and/or formation of thrombi (blood clots). Anti-thrombotics can include but are not limited to anti-platelet agents (e.g., cyclooxygenase inhibitors (e.g., aspirin or triflusal), ADP/P2Y inhibitors (e.g, clopidogrel, pasugrel, tacigrelor, cangrelor, ticlopidine), phosphodiesterase inhibitors such as cilostazol, PAR-1 antagonists such as vorapaxar, Glycoprotein IIb/IIIA inhibitors (e.g, abciximab, eptifibatide, and tirofiban), Adeonsine reuptake inhibitors such as dipyridamole, and thromboxane inhibitors (e.g., terutroban); anticoagulants (e.g., courmarins (e.g, warfarin, acenocoumarol, phenprocoumon, atromentin, and phenindione), heparin and derivatives thereof, Factor Xa inhibitors (e.g, darexaban, letaxaban, eribaxaban, fondaparinux, idraparinux, and idrabiotaparinux), DOACs (e.g., dabigatran, rivaroxaban, apixaban, edoxaban, and betrixaban), thrombin inhibitors (e.g., hirudin, lepirudin, bivalirudin, argatroban, dabigatran, ximelagatran), antithrombin protein, batroxobin, and hementin), and thrombolytic agents.

In some aspects, provided herein is a method of reducing microthrombi formation associated with a coronavirus infection in a subject in need thereof, the method comprising: administering to the subject a DEspR inhibitor, thereby reducing systemic microthrombi formation associated with the coronavirus infection in the subject.

In some embodiments, the DEspR inhibitor is an anti-DEspR antibody or fragment thereof. In some embodiments, the anti-DEspR antibody or fragment thereof comprises complementary determining regions selected from SEQ ID Nos: 1-3, 9-11, 17-19, 5-7, 13-15, 21-23, 25-27, 29-31, and 33-35.

In some aspects, provided herein is a method of treating a coronavirus infection in a subject, the subject determined to have an elevated level of DEspR+CD11b+ cells as compared to a non-infected subject, the method comprising administering a DEspR inhibitor to the subject, wherein said administering is effective to treat the coronavirus infection in the subject.

In some embodiments, the coronavirus is COVID-19. In some embodiments, the DEspR+CD11b+ cells are DEspR+CD11b+ neutrophils, DEspR+CD11b+ monocytes, DEspR+CD11b+ lymphocytes, DEspR+CD11b+ cytoplasts, or a combination or an aggregate.

In some aspects, provided herein is a method of treating a coronavirus infection in a subject, the subject determined to have an elevated level of DEspR+ cells as compared to a non-infected subject, the method comprising administering a DEspR inhibitor to the subject, wherein said administering is effective to treat the coronavirus infection in the subject. In some embodiments, the coronavirus is COVID-19. In some embodiments, the DEspR+ cells are DEspR+ neutrophils, DEspR+ monocytes, DEspR+ lymphocytes, DEspR+ cytoplasts, or a combination or an aggregate. In some embodiments, the DEspR+ cells further express CD11b.

"CD11b," also known as Integrin alpha M, ITGAM, CD11B, CR3A, MAC-1, MAC1A, MO1A, SLEB6, and integrin subunit alpha M, as referred to herein, includes any of the recombinant or naturally-occurring forms of CD11b protein or variants or homologs thereof that maintain CD11b (e.g., within at least 50%, 80%, 90%, 95%, 96%, 97%, 98%, 99% or 100% activity compared to CD11b). In some aspects, the variants or homologs have at least 80%, 85%, 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring CD11b protein. In some embodiments, the CD11b protein is substantially identical to the protein identified by the UniProt reference number P11215 or a variant or homolog having substantial identity thereto. In some embodiments, CD11b is a human CD11b protein.

In some aspects, provided herein is a method of treating a coronavirus infection in a subject, the subject determined to have an elevated level of DEspR+ cells as compared to a non-infected subject, the method comprising administering a DEspR inhibitor to the subject, wherein said administering is effective to treat the coronavirus infection in the subject. In some embodiments, the DEspR+CD11b+ cells are at least 20, 30, 40, 50, 60, 70, 80, 90, 100, or higher % of the whole corresponding cell population. In some embodiments, the DEspR+CD11b+ cells are at least 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900, 2000, 2500, 3000, 3500, 4000, 4500, 5000, 5500, 6000, 6500, 7000, 7500, 8000, 8500, 9000, 10000 or higher % of the whole corresponding cell population.

In some embodiments, the subject is further determined to have an elevated DEspR+ neutrophil to lymphocyte ratio (d+NLR); elevated ratio of DEspR+ neutrophils to COVID19-associated (a) hyperinflammation cytokines or cytokine storm biomarkers, (b) oxidative stress biomarkers, (c) endothelial dysfunction biomarkers, or (d) a combination thereof, or a combination thereof. In some embodiments, hyperinflammation cytokines or cytokine storm biomarkers comprise IL-6. In some embodiments, the oxidative stress biomarkers comprise myeloperoxidase (MPO). In some embodiments, the endothelial dysfunction biomarkers comprise endothelin-1 (ET1). In some embodiments, the control subject does not have a coronavirus infection.

"IL-6," also known as Interleukin 6, IL6, BSF2, HGF, HSF, IFNB2, IL-6, BSF-2, CDF, and IFN-beta-2, as referred to herein, includes any of the recombinant or naturally-occurring forms of IL-6 protein or variants or homologs thereof that maintain IL-6 (e.g., within at least 50%, 80%, 90%, 95%, 96%, 97%, 98%, 99% or 100% activity compared to IL-6). In some aspects, the variants or homologs have at least 80%, 85%, 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring IL-6 protein. In some embodiments, the IL-6 protein is substantially identical to the protein identified by the UniProt reference number P05231 or a variant or homolog having substantial identity thereto. In some embodiments, IL-6 is a human IL-6 protein.

"IL-8," also known as Interleukin 8, IL8, chemokine (C-X-C motif) ligand 8, CXCL8, GCP-1, GCP1, LECT, LUCT, LYNAP, MDNCF, MONAP, NAF, NAP-1, NAP1, IL8, C-X-C motif chemokine ligand 8, Interleukin-8, and SCYB8, as referred to herein, includes any of the recombinant or naturally-occurring forms of IL-8 protein or variants or homologs thereof that maintain IL-8 (e.g., within at least 50%, 80%, 90%, 95%, 96%, 97%, 98%, 99% or 100% activity compared to IL-8). In some aspects, the variants or homologs have at least 80%, 85%, 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring IL-8 protein. In some embodiments, the IL-8 protein is substantially identical to the protein identified by the UniProt reference number P10145 or a variant or homolog having substantial identity thereto. In some embodiments, IL-8 is a human IL-8 protein.

"IL-1β," also known as Interleukin 1 beta, leukocytic pyrogen, leukocytic endogenous mediator, mononuclear cell factor, lymphocyte activating factor, ILIB, IL-1, IL1-BETA, IL1F2, interleukin 1 beta, and IL1beta, as referred to herein, includes any of the recombinant or naturally-occurring forms of IL-1β protein or variants or homologs thereof that maintain IL-1β (e.g., within at least 50%, 80%, 90%, 95%, 96%, 97%, 98%, 99% or 100% activity compared to IL-1β). In some aspects, the variants or homologs have at least 80%, 85%, 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring IL-1β protein. In some embodiments, the IL-1β protein is substantially identical to the protein identified by the UniProt reference number P01584 or a variant or homolog having substantial identity thereto. In some embodiments, IL-1β is a human IL-1β protein.

"IL-18," also known as Interleukin-18, interferon-gamma inducing factor, IL18, IGIF, IL-1g, IL1F4, and interleukin 18, as referred to herein, includes any of the recombinant or naturally-occurring forms of IL-18 protein or variants or homologs thereof that maintain IL-18 (e.g., within at least 50%, 80%, 90%, 95%, 96%, 97%, 98%, 99% or 100% activity compared to IL-18). In some aspects, the variants or homologs have at least 80%, 85%, 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring IL-18 protein. In some embodiments, the IL-18 protein is substantially identical to the protein identified by the UniProt reference number Q14116 or a variant or homolog having substantial identity thereto. In some embodiments, IL-18 is a human IL-18 protein.

"Myeloperoxidase," also known as MPO, as referred to herein, includes any of the recombinant or naturally-occurring forms of myeloperoxidase protein or variants or homologs thereof that maintain myeloperoxidase (e.g., within at least 50%, 80%, 90%, 95%, 96%, 97%, 98%, 99% or 100% activity compared to myeloperoxidase). In some aspects, the variants or homologs have at least 80%, 85%, 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring myeloperoxidase protein. In some embodiments, the myeloperoxidase protein is substantially identical to the protein identified by the UniProt reference number P05164 or a variant or homolog having substantial identity thereto. In some embodiments, myeloperoxidase is a human myeloperoxidase protein.

"Endothelin-1," also known as EDN1 and ET1, as referred to herein, includes any of the recombinant or naturally-occurring forms of endothelin-1 protein or variants or homologs thereof that maintain endothelin-1 (e.g., within at least 50%, 80%, 90%, 95%, 96%, 97%, 98%, 99% or 100% activity compared to endothelin-1). In some aspects, the variants or homologs have at least 80%, 85%, 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring endothelin-1 protein. In some embodiments, the endothelin-1 protein is substantially identical to the protein identified by the UniProt reference number P05305 or a variant or homolog having substantial identity thereto. In some embodiments, endothelin-1 is a human endothelin-1 protein.

In some aspects, provided herein is a method of treating a subject having a coronavirus infection, the method comprising: (i) determining whether the subject has a high risk of poor outcome or morbidity by detecting a level or rising level of DEspR+CD11b+ cells, a level of (1) non-resolving neutrophil-monocyte inflammatory amplification that blocks initiation of next step anti-viral adaptive immunity, anti-viral cellular immunity, hyperinflammation-resolution, or a combination, measured as: DEspR+CD11b+ cells, (2) a level of hyperinflammation-response marked by elevated ratio DEspR+CD11b+ neutrophils to plasma cytokine storm biomarkers, or to plasma oxidative stress biomarkers or to endothelial dysfunction biomarker, or (3) a combination thereof, as individual or combinatorial measures in a sample obtained from the subject, wherein an elevated level of DEspR+CD11b+ cells, high ratios of DEspR+ neutrophils to COVID-19 associated elevated cytokines, elevated oxidative stress biomarkers, elevated endothelial activation biomarker levels, or a combination thereof in the sample obtained from the subject compared with a sample obtained from a control subject is an indicative that the subject has a high risk of poor outcome or morbidity, wherein the control subject does not have a coronavirus infection, and (ii) administering to the subject a DEspR inhibitor (e.g., administering the DEspR inhibitor when the subject is determined to have a high risk).

In some aspects, provided herein is a method of improving a survival rate of a subject having a coronavirus infection, the method comprising: (i) determining whether the subject has a high risk of poor outcome or morbidity by detecting a level or rising level of DEspR+CD11 b+ cells, a level of (1) non-resolving neutrophil-monocyte inflammatory amplification that blocks initiation of next step antiviral adaptive immunity, anti-viral cellular immunity, hyperinflammation-resolution, or a combination, measured as: DEspR+CD11b+ cells, (2) a level of hyperinflammation-response marked by elevated ratio DEspR+CD11b+ neutrophils to plasma cytokine storm biomarkers, or to plasma oxidative stress biomarkers or to endothelial dysfunction biomarker, or (3) a combination thereof, as individual or combinatorial measures in a sample obtained from the subject, wherein an elevated or rising level of DEspR+CD11b+ cells or hyperinflammation ratio-markers in the sample obtained from the subject compared with a level of DEspR+CD11b+ cells in a sample obtained from a control subject is indicative that the subject has a high risk of poor outcome or morbidity, wherein the control subject does not have a coronavirus infection, and (ii) administering to the subject a DEspR inhibitor (e.g., administering the DEspR inhibitor when the subject is determined to have a high risk).

In some aspects, provided herein is a method of determining prognosis of a subject having a coronavirus infection, the method comprising: detecting in a sample obtained from the subject a level of, or rising DEspR+CD11b+ cells, or DEspR-bound DNA, or a level of (1) non-resolving neutrophil-monocyte inflammatory amplification that blocks initiation of next step anti-viral adaptive immunity, anti-viral cellular immunity, hyperinflammation-resolution, or a combination, measured as: DEspR+CD11b+ neutrophils and monocytes, (2) a level of hyperinflammation-response marked by elevated ratio DEspR+CD11b+ neutrophils to plasma cytokine storm biomarkers, or to plasma oxidative stress biomarkers or to endothelial dysfunction biomarker, or (3) a combination thereof, as individual or combinatorial measures in a sample obtained from the subject, wherein an elevated or rising levels of DEspR+CD11b+ cells, plasma DEspR-bound DNA, high ratios of DEspR+ neutrophils to COVID-19 associated elevated cytokines, elevated oxidative stress biomarker, elevated endothelial activation biomarker level or a combination thereof in the sample obtained from the subject compared with a level of DEspR+CD11b+ neutrophils in a sample obtained from a control subject is an indicative that the subject has a high risk of poor outcome or morbidity, wherein the control subject does not have a coronavirus infection.

In some embodiments, the DEspR+CD11b+ cells are DEspR+CD11b+ neutrophils, DEspR+CD11b+ monocytes, DEspR+CD11b+ lymphocytes, DEspR+CD11b+ cytoplasts, or a combination or an aggregate. In some embodiments, the plasma cytokine storm biomarkers comprise IL-6, IL-8, IL-1beta or IL-18, or a combination thereof. In some embodiments, the plasma oxidative stress biomarkers comprise myeloperoxidase. In some embodiments, the endothelial dysfunction biomarkers comprise endothelin-1. In some embodiments, the COVID-19 associated elevated cytokines comprises IL-6, IL-8, IL-1beta or IL-18, or a combination thereof. In some embodiments, the elevated oxidative stress biomarkers comprise myeloperoxidase. In some embodiments, the elevated endothelial activation biomarkers comprise endothelin-1. In some embodiments, the level of DEspR+CD11b+ cells is detected by measuring a level of DEspR+CD11b+ aggregates in the blood sample. In some embodiments, the level of DEspR+CD11b+ cells in the subject determines whether the subject will require intensive care.

In some aspects, provided herein is a method of preventing or treating organ-dysfunction or multi-organ dysfunction or failure associated with a coronavirus infection in a subject in need thereof, wherein subject is determined to have elevated or rising levels of DEspR+CD11b+ cells, elevated hyperinflammation DEspR+ neutrophil-IL6/MPO/ET1 ratios, or a combination thereof, as compared to a control subject, the method comprising administering a DEspR inhibitor.

In some embodiments, the DEspR+CD11b+ cells are DEspR+CD11b+ neutrophils, DEspR+CD11b+ monocytes, DEspR+CD11b+ lymphocytes, DEspR+CD11b+ cytoplasts, or a combination or an aggregate.

In some aspects, provided herein is a method of treating a subject having a coronavirus infection, the method comprising: (i) determining whether the subject has a high risk of poor outcome or morbidity by detecting a level or rising level of DEspR+ cells, a level of (1) non-resolving neutrophil-monocyte inflammatory amplification that blocks initiation of next step anti-viral adaptive immunity, anti-viral cellular immunity, hyperinflammation-resolution, or a combination, measured as: DEspR+ cells, (2) a level of hyperinflammation-response marked by elevated ratio DEspR+ neutrophils to plasma cytokine storm biomarkers, or to plasma oxidative stress biomarkers or to endothelial dysfunction biomarker, or (3) a combination thereof, as individual or combinatorial measures in a sample obtained from the subject, wherein an elevated level of DEspR+ cells, high ratios of DEspR+ neutrophils to COVID-19 associated elevated cytokines, elevated oxidative stress biomarkers, elevated endothelial activation biomarker levels, or a combination thereof in the sample obtained from the subject compared with a sample obtained from a control subject is an indicative that the subject has a high risk of poor outcome or morbidity, wherein the control subject does not have a coronavirus infection, and (ii) administering to the subject a DEspR inhibitor (e.g., administering the DEspR inhibitor when the subject is determined to have a high risk).

In some aspects, provided herein is a method of improving a survival rate of a subject having a coronavirus infection, the method comprising: (i) determining whether the subject has a high risk of poor outcome or morbidity by detecting a level or rising level of DEspR+CD11 b+ cells, a level of (1) non-resolving neutrophil-monocyte inflammatory amplification that blocks initiation of next step antiviral adaptive immunity, anti-viral cellular immunity, hyperinflammation-resolution, or a combination, measured as: DEspR+CD11b+ cells, (2) a level of hyperinflammation-response marked by elevated ratio DEspR+ neutrophils to plasma cytokine storm biomarkers, or to plasma oxidative stress biomarkers or to endothelial dysfunction biomarker, or (3) a combination thereof, as individual or combinatorial measures in a sample obtained from the subject, wherein an elevated or rising level of DEspR+ cells or hyperinflammation ratio-markers in the sample obtained from the subject compared with a level of DEspR+ cells in a sample obtained from a control subject is indicative that the subject has a high risk of poor outcome or morbidity, wherein the control subject does not have a coronavirus infection, and (ii) administering to the subject a DEspR inhibitor (e.g., administering the DEspR inhibitor when the subject is determined to have a high risk).

In some aspects, provided herein is a method of determining prognosis of a subject having a coronavirus infection, the method comprising: detecting in a sample obtained from the subject a level of, or rising DEspR+ cells, or DEspR-bound DNA, or a level of (1) non-resolving neutrophil-monocyte inflammatory amplification that blocks initiation of next step anti-viral adaptive immunity, anti-viral cellular immunity, hyperinflammation-resolution, or a combination, measured as: DEspR+ neutrophils and monocytes, (2) a level of hyperinflammation-response marked by elevated ratio DEspR+ neutrophils to plasma cytokine storm biomarkers, or to plasma oxidative stress biomarkers or to endothelial dysfunction biomarker, or (3) a combination thereof, as individual or combinatorial measures in a sample obtained from the subject, wherein an elevated or rising levels of DEspR+ cells, plasma DEspR-bound DNA, high ratios of DEspR+ neutrophils to COVID-19 associated elevated cytokines, elevated oxidative stress biomarker, elevated endothelial activation biomarker level or a combination thereof in the sample obtained from the subject compared with a level of DEspR+ neutrophils in a sample obtained from a control subject is an indicative that the subject has a high risk of poor outcome or morbidity, wherein the control subject does not have a coronavirus infection.

In some embodiments, the DEspR+ cells are DEspR+ neutrophils, DEspR+ monocytes, DEspR+ lymphocytes, DEspR+ cytoplasts, or a combination or an aggregate. In some embodiments, the DEspR+ cells further express CD11b. In some embodiments, DEspR+ neutrophils are DEspR+CD11b+ neutrophils. In some embodiments, the level of DEspR+ cells in the subject determines whether the subject will require intensive care.

In some aspects, provided herein is a method of preventing or treating organ-dysfunction or multi-organ dysfunction or failure associated with a coronavirus infection in a subject in need thereof, wherein subject is determined to have elevated or rising levels of DEspR+ cells, elevated hyperinflammation DEspR+ neutrophil-IL6/MPO/ET1 ratios, or a combination thereof, as compared to a control subject, the method comprising administering a DEspR inhibitor. In some embodiments, the DEspR+ cells are DEspR+ neutrophils, DEspR+ monocytes, DEspR+ lymphocytes, DEspR+ cytoplasts, or a combination or an aggregate. In some embodiments, the DEspR+ cells further express CD11b.

In some embodiments, the organ-dysfunction or multi-organ dysfunction or failure associated with the coronavirus infection arises from microcirculatory dysfunction, microvascular inclusion, low flow ischemia, thromboses, systemic microthromboses, microcirculatory vascular aggregation, or a combination thereof. In some embodiments, the organ-dysfunction or multi-organ dysfunction or failure associated with the coronavirus infection is derived from COVID19-induced cytokine storm, low flow organ ischemia from DEspR+CD11b+ aggregates leading to characteristic COVID19-severe hypoxemia, renal dysfunction, cardiac ischemia, neurological dysfunction, liver dysfunction/failure, hematological coagulopathy or microthromboses, or a combination thereof. In some embodiments, the neurological dysfunction is characterized by loss of consciousness, seizures, confusion or a combination thereof. In some embodiments, the organ-dysfunction or multi-organ dysfunction or failure associated with the coronavirus infection is selected from the group consisting of systemic inflammatory response syndrome (SIRS); acute lung injury (ALI); acute respiratory distress syndrome (ARDS); multi-organ failure or multi-organ dysfunction syndrome (MODS); acute kidney injury (AKI); and liver failure. In some embodiments, the organ-dysfunction or multi-organ dysfunction or failure associated with the coronavirus infection is ARDS.

In some embodiments, the organ-dysfunction or multi-organ dysfunction or failure associated with the coronavirus infection is associated with red blood cell aggregates, DNA debris aggregates, or microcirculatory vascular aggregates. In some embodiments, the DNA debris aggregates are aggregates containing cell free DNA (cfDNA).

In some aspects, the subject described herein can further have a condition or disease wherein neutrophils contribute to pathogenesis or worsening of the disease in a subject in need thereof, and/or a condition or disease wherein neutrophils, NETs, or NETosing or NETting neutrophils contribute to pathogenesis, chronicity, or worsening of the disease in a subject in need thereof. In some embodiments, the method can further comprise administering a therapeutically effective amount of an anti-DEspR antibody reagent conjugated to another anti-neutrophil or anti-NET reagent, e.g., to a second anti-neutrophil or anti-NET reagent.

A condition or disease wherein neutrophils contribute to pathogenesis or worsening of the disease is any disease in which the activity and/or level of neutrophils, e.g., activated neutrophils, contributes to the pathology of the condition, e.g., contribute to the development or cause of the disease, as opposed to being a symptom of or reaction to the disease itself. Such conditions are known in the art and can include, by way of non-limiting example, systemic inflammatory response syndrome (SIRS); acute lung injury (ALI); acute respiratory distress syndrome (ARDS); multi-organ failure or multi-organ dysfunction syndrome (MOS) from, e.g., ARDS, hemorrhagic shock, surgery, burns, or sepsis; sepsis; sepsis-induced coagulopathy; trauma; multiple sclerosis; acute kidney injury (AKI); AKI-associated tubular necrosis and distant organ injury; post-trauma surgery; hemorrhagic shock; infections, or cytokine storms induced by drugs or any agent; ischemic or hemorrhagic stroke; secondary brain injury in stroke; myocardial ischemia/infarction; atherosclerotic vulnerable plaques; atherosclerotic thrombosis; coronary artery disease; acute coronary syndrome; heart failure; reperfusion injury; comorbidities (e.g., thrombosis and endotheilial dysfunction) in kidney dialysis patients; ischemic or drug-induced hemorrhagic transformation in the brain, hemorrhagic encephalopathy, traumatic brain injury; anoxic brain injury, chronic kidney disease; cancer; an actPMN-dependent cancer; diabetes; type 1 diabetes; type 2 diabetes; angiopathies; vasculopathies; end-organ complications (e.g., retinopathy or diabetic kidney disease); poor wound healing of diabetic ulcers; deep vein thrombosis; cancer; cancer metastasis; systemic microthrombosis; chemotherapy-induced microthrombosis; atherosclerotic thrombosis; systemic lupus erythematosus (SLE); lupus nephritis; SLE-accelerated atherosclerosis; rheumatoid arthritis; COPD; cystic fibrosis; pulmonary disease; Alzheimer's Disease; sickle cell disease; inflammatory bowel disease (IBD); Crohn's disease; ulcerative colitis; and indeterminate colitis. Such conditions are known in the art and can include, by way of non-limiting example, are coronavirus infection, or organ-dysfunction or multi-organ dysfunction or failure associated with a coronavirus infection.

In some embodiments of any of the aspects, a subject treated according to the methods described herein can be a subject having or diagnosed as having systemic inflammatory response syndrome (SIRS); acute lung injury (ALI); acute respiratory distress syndrome (ARDS); multi-organ failure or multi-organ dysfunction syndrome (MOS) from, e.g., ARDS, hemorrhagic shock, surgery, burns, or sepsis; sepsis; sepsis-induced coagulopathy; trauma; multiple sclerosis; acute kidney injury (AKI); AKI-associated tubular necrosis and distant organ injury; post-trauma surgery; hemorrhagic shock; infections, or cytokine storms induced by drugs or any agent; ischemic or hemorrhagic stroke; secondary brain injury in stroke; myocardial ischemia/infarction; atherosclerotic vulnerable plaques; atherosclerotic thrombosis; coronary artery disease; acute coronary syndrome; heart failure; reperfusion injury; comorbidities (e.g., thrombosis and endotheilial dysfunction) in kidney dialysis patients; ischemic or drug-induced hemorrhagic transformation in the brain, hemorrhagic encephalopathy, traumatic brain injury; anoxic brain injury, chronic kidney disease; cancer; an actPMN-dependent cancer; diabetes; type 1 diabetes; type 2 diabetes; angiopathies; vasculopathies; end-organ complications (e.g., retinopathy or diabetic kidney disease); poor wound healing of diabetic ulcers; deep vein thrombosis; cancer; cancer metastasis; systemic microthrombosis; chemotherapy-induced microthrombosis; atherosclerotic thrombosis; systemic lupus erythematosus (SLE); lupus nephritis; SLE-accelerated atherosclerosis; rheumatoid arthritis; COPD; cystic fibrosis; pulmonary disease; Alzheimer's Disease; sickle cell disease; inflammatory bowel disease (IBD); Crohn's disease; ulcerative colitis; indeterminate colitis, corona-virus infection, or organ-dysfunction or multi-organ dysfunction or failure associated with a coronavirus infection.

Neutrophils have been implicated in the exacerbation bouts in multiple sclerosis. Accordingly, the methods described herein can relate to treatment of multiple sclerosis. Neutrophils have been implicated in acute kidney injury, which has no treatment to date. Accordingly, the methods described herein can relate to treatment of acute kidney injury. Immune evasion is implicated in the progression of precancerous lesions to malignant lesions, or micrometastatic lesions to macro-metastases. Neutrophils contribute to immune evasion by releasing substances that inhibit T-cells in their roles in immune-surveillance, thus increased DEspR-mediated survival in DEspR+ neutrophils contribute to the precancer-to-malignancy switch. Accordingly, the methods described herein can relate to treatment of precancerous lesions. Notably, several cancers are associated with prior infections and/or neutrophilia: pancreatitis is a risk factor for pancreatic cancer, and neutrophilia is induced by smoking which is linked to lung cancer.

In some embodiments, the subject treated according to the methods described herein can be a subject who has, or is determined to have increased levels of circulating DEspR+ neutrophils; increased levels of DEspR+ activated neutrophils; increased levels of NETs; increased plasma levels of neutrophil elastase (NE); increased plasma levels of neutrophil myeloperoxidase (MPO); or a tumor comprising one or more of: DEspR+ neutrophils; DEspR+ NETosing neutrophils; NETs; an increased level of a neutrophil released immune-suppressor; an increased level of citrullinated-histone-3; and increased level of a neutrophil stimulator. Non-limiting neutrophil-released immune suppressors include arginase-1; PD-Li; myeloperoxidase (MPO); neutrophil-elastase (NE); or cathepsin G. Non-limiting neutrophil stimulators include G-CSF, ET1, Hif1a, or a DAMP. In some embodiments of any of the aspects, a level can be increased relative to a reference level, e.g., to the subject at an earlier time point, to a subject without cancer, or a subject with a cancer not involving NETs, NETosis, or activated neutrophils.

As used herein, "anti-NET" compound or reagent refers to any compound or reagent that degrades or targets for degradation any component of a NET for clearance and/or prevents the formation of NETs. Also included are compounds that otherwise inhibit the activity of a NET component. An anti-NET compound can be a nucleic acid (DNA or RNA), small molecule, lipid, carbohydrate, protein, peptide, antibody, or antibody fragment. In some embodiments, an anti-NET compound can be an enzyme, e.g. an enzyme which cleaves and/or degrades, e.g. a nucleic acid, protein, polypeptide, or carbohydrate. Examples of anti-NET compounds are described in US Patent Publication US 20140199329; which is incorporated by reference herein in its entirety. Non-limiting examples of anti-NET reagents can include DNase; RNase; a histone-degrading enzyme; an inhibitor of chromatin decondensation; an antibody against a component of a NET; an elastase inhibitor; a PAD inhibitor; and a PAD4 inhibitor.

As used herein, "anti-neutrophil" compound or reagent refers to any compound or reagent that is toxic to a neutrophil, promotes apoptosis, and/or inhibits one or more activities of an actPMN, such as inhibition of neutrophil adhesion or transmigration (e.g., anti-ICAM1), inhibition of neutrophil activation (e.g., anti-CD11b), or depletion of neutrophil precursors in the bone marrow (e.g., chemotherapies).

The compositions and methods described herein can be administered to a subject having or diagnosed as having a disease or condition as described herein. In some embodiments, the methods described herein comprise administering an effective amount of compositions described herein, e.g. an agent, e.g., a DEspR inhibitor, to a subject in order to alleviate a symptom of a disease or condition. As used herein, "alleviating a symptom" is ameliorating any condition or symptom associated with the disease or condition. As compared with an equivalent untreated control, such reduction is by at least 5%, 10%, 20%, 40%, 50%, 60%, 80%, 90%, 95%, 99% or more as measured by any standard technique. In one embodiments, the method described herein comprises administering an effective amount of a human or humanized antibody referred to herein as an anti-DEspR antibody. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, or intratumoral administration. Administration can be local or systemic.

The term "effective amount" as used herein refers to the amount of an agent, e.g., a DEspR inhibitor needed to alleviate at least one or more symptom of the disease or disorder, and relates to a sufficient amount of pharmacological composition to provide the desired effect. The term "therapeutically effective amount" therefore refers to an amount of an agent, e.g., a DEspR inhibitor that is sufficient to provide a particular effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the active ingredient, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for actPMNs and/or NETs, among others. The dosage can be determined by a physician and adjusted, as necessary, to suit observed effects of the treatment.

In some embodiments, the technology described herein relates to a pharmaceutical composition comprising an agent, e.g., a DEspR inhibitor, as described herein, and optionally a pharmaceutically acceptable carrier. In some embodiments, the active ingredients of the pharmaceutical composition comprise an agent, e.g., a DEspR inhibitor, as described herein. In some embodiments, the active ingredients of the pharmaceutical composition consist essentially of an agent, e.g., a DEspR inhibitor, as described herein. In some embodiments, the active ingredients of the pharmaceutical composition consist of an agent, e.g., a DEspR inhibitor, as described herein. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. an agent, e.g., a DEspR inhibitor, as described herein.

In some embodiments, the pharmaceutical composition comprising an agent, e.g., a DEspR inhibitor, as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of an agent, e.g., a DEspR inhibitor, as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt as disclosed herein can also be incorporated into the parenteral dosage forms of the disclosure, including conventional and controlled-release parenteral dosage forms.

Pharmaceutical compositions comprising an agent, e.g., a DEspR inhibitor, as described herein can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the composition can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In some embodiments of any of the aspects, the agent, e.g., a DEspR inhibitor, described herein is administered as a monotherapy, e.g., another treatment for the disease or condition is not administered to the subject.

In some embodiments of any of the aspects, the methods described herein can further comprise administering a second agent and/or treatment to the subject, e.g. as part of a combinatorial therapy. Non-limiting examples of a second agent (including exemplary chemotherapies) and/or treatment can include anti-thrombotics, radiation therapy, surgery, chemotherapeutics, and other treatments described elsewhere herein.

Further, the methods of treatment can further include the use of surgical treatments. In certain embodiments, an effective dose of a composition comprising an agent, e.g., a DEspR inhibitor, as described herein can be administered to a patient once. In certain embodiments, an effective dose of a composition comprising an agent, e.g., a DEspR inhibitor, as described herein can be administered to a patient repeatedly. For systemic administration, subjects can be administered a therapeutic amount of a composition comprising an agent, e.g., a DEspR inhibitor, as described herein, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the active ingredient. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising an agent, e.g., a DEspR inhibitor, as described herein can be administered over a period of time, such as over a 5 minute, 10 minute, 15 minute, 20 minute, or 25 minute period.

The dosage ranges for the administration of an agent, e.g., a DEspR inhibitor, as described herein, according to the methods described herein depend upon, for example, the form of the agent, e.g., a DEspR inhibitor, as described herein, its potency, and the extent to which symptoms, markers, or indicators of a condition described herein are desired to be reduced, for example the percentage reduction desired for actPMNs and/or NETs. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of an agent, e.g., a DEspR inhibitor, as described herein in, e.g. the treatment of a condition described herein, or to induce a response as described herein (e.g. increased PMN cell death) can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. level of actPMNs and/or NETs, or the level of DEspR+CD11b+ cells, or the ratio of DEsprR+CD11b+ neutrophils to other markers described elsewhere herein. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein, for example treatment of cancer or NETosis, coronavirus infection, or organ-dysfunction or multi-organ dysfunction or failure associated with a coronavirus infection.

When using an experimental animal model, efficacy of treatment is evidenced when a statistically significant change in a marker is observed, e.g. actPMN and/or NET levels, or the level of DEspR+CD11b+ cells, or the ratio of DEsprR+CD11b+ neutrophils to other markers described elsewhere herein.

In vitro and animal model assays are provided herein which allow the assessment of a given dose of an agent, e.g., a DEspR inhibitor, as described herein. By way of non-limiting example, the effects of a dose of an agent, e.g., a DEspR inhibitor, as described herein can be assessed by measuring actPMN levels, actPMN survival, actPMN activity (e.g., myeloperoxidase levels, neutrophil elastase levels), neutrophil-lymphocyte ratio, levels of NETs, and/or the level of DEspR+CD11b+ cells, or the ratio of DEsprR+CD11b+ neutrophils to other markers described elsewhere herein.

In some embodiments of any of the aspects, the subject administered a treatment as described herein can be a subject determined to have DEspR+ neutrophils and/or an increased or elevated level of DEspR+ neutrophils.

In some aspects, described herein is a method of identifying a subject at risk of neutrophil extracellular trap (NET) release, vital NETosis or actPMN NETosis, the method comprising detecting the level of DEspR+ neutrophils in a sample obtained from the subject, wherein an increased level of DEspR+ neutrophils relative to a reference indicates the subject is at increased risk of neutrophil extracellular trap (NET) release, vital NETosis or actPMN NETosis. In some aspects, described herein is a method of identifying a subject at risk of neutrophil extracellular trap (NET) release, vital NETosis or actPMN NETosis, the method comprising detecting the level of DEspR in neutrophils obtained from the subject, wherein an increased level of DEspR+ in the neutrophils relative to a reference indicates the subject is at increased risk of neutrophil extracellular trap (NET) release, vital NETosis or actPMN NETosis.

In some embodiments of any of the aspects, a subject determined not to have an elevated level of DEspR+CD11b+ cells; an elevated DEspR+ neutrophil to lymphocyte ratio (d+NLR); or elevated ratio of DEspR+ neutrophils to COVID19-associated (a) hyperinflammation cytokines or cytokine storm biomarkers, (b) oxidative stress biomarkers, (c) endothelial dysfunction biomarkers, or (d) a combination thereof, is administered.

In some embodiments of any of the aspects, the method comprises administering a DEspR inhibitor to a subject previously determined to have an elevated level of DEspR+CD11b+ cells; an elevated DEspR+ neutrophil to lymphocyte ratio (d+NLR); or elevated ratio of DEspR+ neutrophils to COVID19-associated (a) hyperinflammation cytokines or cytokine storm biomarkers, (b) oxidative stress biomarkers, (c) endothelial dysfunction biomarkers, or (d) a combination thereof. In some embodiments of any of the aspects, described herein is a method comprising: a) first determining the level of DEspR+CD11b+ cells; DEspR+ neutrophil to lymphocyte ratio (d+NLR); or ratio of DEspR+ neutrophils to COVID19-associated (a) hyperinflammation cytokines or cytokine storm biomarkers, (b) oxidative stress biomarkers, (c) endothelial dysfunction biomarkers, or (d) a combination thereof in a sample obtained from a subject; and b) then administering a DEspR inhibitor to the subject if the level is elevated relative to a reference.

In some embodiments of any of the aspects, the step of determining if the subject has an elevated level of DEspR+CD11b+ cells; an elevated DEspR+ neutrophil to lymphocyte ratio (d+NLR); or elevated ratio of DEspR+ neutrophils to COVID19-associated (a) hyperinflammation cytokines or cytokine storm biomarkers, (b) oxidative stress biomarkers, (c) endothelial dysfunction biomarkers, or (d) a combination thereof can comprise i) obtaining or having obtained a sample from the subject and ii) performing or having performed an assay on the sample obtained from the subject to determine/measure the level of DEspR+CD11b+ cells; DEspR+ neutrophil to lymphocyte ratio (d+NLR); or ratio of DEspR+ neutrophils to COVID19-associated (a) hyperinflammation cytokines or cytokine storm biomarkers, (b) oxidative stress biomarkers, (c) endothelial dysfunction biomarkers, or (d) a combination thereof in the subject. In some embodiments of any of the aspects, the step of determining if the subject has an elevated level of DEspR+CD11b+ cells;

an elevated DEspR+ neutrophil to lymphocyte ratio (d+NLR); or elevated ratio of DEspR+ neutrophils to COVID19-associated (a) hyperinflammation cytokines or cytokine storm biomarkers, (b) oxidative stress biomarkers, (c) endothelial dysfunction biomarkers, or (d) a combination thereof can comprise performing or having performed an assay on a sample obtained from the subject to determine/measure the level of DEspR+CD11b+ cells; DEspR+ neutrophil to lymphocyte ratio (d+NLR); or ratio of DEspR+ neutrophils to COVID19-associated (a) hyperinflammation cytokines or cytokine storm biomarkers, (b) oxidative stress biomarkers, (c) endothelial dysfunction biomarkers, or (d) a combination thereof in the subject. In some embodiments of any of the aspects, the step of determining if the subject has an elevated level of DEspR+CD11b+ cells; an elevated DEspR+ neutrophil to lymphocyte ratio (d+NLR); or elevated ratio of DEspR+ neutrophils to COVID19-associated (a) hyperinflammation cytokines or cytokine storm biomarkers, (b) oxidative stress biomarkers, (c) endothelial dysfunction biomarkers, or (d) a combination thereof can comprise ordering or requesting an assay on a sample obtained from the subject to determine/measure the level of DEspR+CD11b+ cells; DEspR+ neutrophil to lymphocyte ratio (d+NLR); or ratio of DEspR+ neutrophils to COVID19-associated (a) hyperinflammation cytokines or cytokine storm biomarkers, (b) oxidative stress biomarkers, (c) endothelial dysfunction biomarkers, or (d) a combination thereof in the subject. In some embodiments of any of the aspects, the step of determining if the subject has an elevated level of DEspR+CD11b+ cells; an elevated DEspR+ neutrophil to lymphocyte ratio (d+NLR); or elevated ratio of DEspR+ neutrophils to COVID19-associated (a) hyperinflammation cytokines or cytokine storm biomarkers, (b) oxidative stress biomarkers, (c) endothelial dysfunction biomarkers, or (d) a combination thereof can comprise receiving the results of an assay on a sample obtained from the subject to determine/measure the level of DEspR+CD11b+ cells; DEspR+ neutrophil to lymphocyte ratio (d+NLR); or ratio of DEspR+ neutrophils to COVID19-associated (a) hyperinflammation cytokines or cytokine storm biomarkers, (b) oxidative stress biomarkers, (c) endothelial dysfunction biomarkers, or (d) a combination thereof in the subject. In some embodiments of any of the aspects, the step of determining if the subject has an elevated level of DEspR+CD11b+ cells; an elevated DEspR+ neutrophil to lymphocyte ratio (d+NLR); or elevated ratio of DEspR+ neutrophils to COVID19-associated (a) hyperinflammation cytokines or cytokine storm biomarkers, (b) oxidative stress biomarkers, (c) endothelial dysfunction biomarkers, or (d) a combination thereof can comprise receiving a report, results, or other means of identifying the subject as a subject with an elevated level of DEspR+CD11b+ cells; an elevated DEspR+ neutrophil to lymphocyte ratio (d+NLR); or elevated ratio of DEspR+ neutrophils to COVID19-associated (a) hyperinflammation cytokines or cytokine storm biomarkers, (b) oxidative stress biomarkers, (c) endothelial dysfunction biomarkers, or (d) a combination thereof.

In one aspect of any of the embodiments, described herein is a method comprising: a) determining if the subject has an elevated level of DEspR+CD11b+ cells; an elevated DEspR+ neutrophil to lymphocyte ratio (d+NLR); or elevated ratio of DEspR+ neutrophils to COVID19-associated (a) hyperinflammation cytokines or cytokine storm biomarkers, (b) oxidative stress biomarkers, (c) endothelial dysfunction biomarkers, or (d) a combination thereof; and b) instructing or directing that the subject be administered a DEspR inhibitor if the subject has an elevated level of DEspR+CD11b+ cells; an elevated DEspR+ neutrophil to lymphocyte ratio (d+NLR); or elevated ratio of DEspR+ neutrophils to COVID19-associated (a) hyperinflammation cytokines or cytokine storm biomarkers, (b) oxidative stress biomarkers, (c) endothelial dysfunction biomarkers, or (d) a combination thereof.

In some embodiments of any of the aspects, the step of instructing or directing that the subject be administered a particular treatment can comprise providing a report of the assay results. In some embodiments of any of the aspects, the step of instructing or directing that the subject be administered a particular treatment can comprise providing a report of the assay results and/or treatment recommendations in view of the assay results.

In some embodiments of any of the aspects, the expression level of e.g., DEspR, can be measured by determining the level of an expression product of the DEspR, gene, e.g., a DEspR RNA transcript or a DEspR polypeptide. Such molecules can be isolated, derived, or amplified from a biological sample, such as a biofluid. In some embodiments of any of the aspects, a detectable signal is generated by the antibody or antigen-binding portion thereof when a DEspR molecule is present. In some embodiments of any of the aspects, the antibody or antigen-binding portion thereof is detectably labeled or capable of generating a detectable signal. In some embodiments of any of the aspects, the level of the, e.g., DEspR molecule, is determined using a method selected from the group consisting of: Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy; FACS; and immunoelectrophoresis assay. In some embodiments of any of the aspects, the antibody or antigen-binding portion thereof is detectably labeled or generates a detectable signal. In some embodiments of any of the aspects, the expression level of, e.g., DEspR, is normalized relative to the expression level of one or more reference genes or reference proteins. In some embodiments of any of the aspects, the reference level DEspR is the expression level of DEspR in a prior sample obtained from the subject.

In some embodiments of any of the aspects, the level of, e.g., DEspR, can be the level of DEspR polypeptide. Detection of polypeptides can be according to any method known in the art. Immunological methods to detect particular polypeptides in accordance with the present technology include, but are not limited to antibody techniques such as immunohistochemistry, immunocytochemistry, flow cytometry, fluorescence-activated cell sorting (FACS), immunoblotting, radioimmunoassays, western blotting, immunoprecipitation, enzyme-linked immunosorbant assays (ELISA), and derivative techniques that make use of antibody reagents as described herein.

Immunochemical methods require the use of an antibody reagent specific for the target molecule (e.g., the antigen or in the embodiments described herein, an e.g., DEspR polypeptide. In some embodiments of any of the aspects, the assays, methods, and/or systems described herein can comprise: an anti-DEspR antibody reagent. In some embodiments of any of the aspects, the antibody reagent can be detectably labeled. In some embodiments of any of the aspects, the antibody reagent can be attached to a solid support (e.g., bound to a solid support). In some embodiments of any of the aspects, the solid support can comprise a particle (including, but not limited to an agarose or latex bead or particle or a magnetic particle), a bead, a nanoparticle, a polymer, a substrate, a slide, a coverslip, a plate, a dish, a well, a membrane, and/or a grating. The solid support can include many different materials including, but not limited to, polymers, plastics, resins, polysaccharides, silicon or silica based materials, carbon, metals, inorganic glasses, and membranes.

In one embodiment, an assay, method, and/or system as described herein can comprise an ELISA. In an exemplary embodiment, a first antibody reagent can be immobilized on a solid support (usually a polystyrene micro titer plate). The solid support can be contacted with a sample obtained from a subject, and the antibody reagent will bind ("capture") antigens for which it is specific (e.g., DEspR). The solid support can then be contacted with a second labeled antibody reagent (e.g., a detection antibody reagent). The detection antibody reagent can, e.g., comprise a detectable signal, be covalently linked to an enzyme, or can itself be detected by a secondary antibody which is linked to an enzyme through bio-conjugation. The presence of a signal indicates that both the first antibody reagent immobilized on the support and the second "detection" antibody reagent have bound to an antigen, i.e., the presence of a signal indicated the presence of a target molecule. Between each step the plate is typically washed with a mild detergent solution to remove any proteins or antibodies that are not specifically bound. After the final wash step the plate is developed by adding an enzymatic substrate to produce a visible signal, which indicates the quantity of the target polypeptides in the sample. Older ELISAs utilize chromogenic substrates, though newer assays employ fluorogenic substrates with much higher sensitivity. There are other different forms of ELISA, which are well known to those skilled in the art.

In one embodiment, the assays, systems, and methods described herein can comprise a lateral flow immunoassay test (LFIA), also known as the immunochromatographic assay, or strip test to measure or determine the level of, e.g., DEspR polypeptide in a sample. LFIAs are a simple device intended to detect the presence (or absence) of a target in a sample. There are currently many LFIA tests used for medical diagnostics either for home testing, point of care testing, or laboratory use. LFIA tests are a form of immunoassay in which the test sample flows along a solid substrate via capillary action. After the sample is applied to the test strip it encounters a colored antibody reagent which mixes with the sample, and if bound to a portion of the sample, transits the substrate encountering lines or zones which have been pretreated with a second antibody reagent. Depending upon the level of the target present in the sample the colored antibody reagent can become bound at the test line or zone. LFIAs are essentially immunoassays adapted to operate along a single axis to suit the test strip format or a dipstick format. Strip tests are extremely versatile and can be easily modified by one skilled in the art for detecting an enormous range of antigens from fluid samples such as urine, blood, water samples etc. Strip tests are also known as dip stick test, the name bearing from the literal action of "dipping" the test strip into a fluid sample to be tested. LFIA strip test are easy to use, require minimum training and can easily be included as components of point-of-care test (POCT) diagnostics to be used on site in the field. LFIA tests can be operated as either competitive or sandwich assays. Sandwich LFIAs are similar to sandwich ELISA. The sample first encounters colored particles which are labeled with antibody reagents specific for a target (e.g., a DEspR-specific antibody reagent). The test line will also contain antibody reagents (e.g., a DEspR-specific antibody reagent). The test line will show as a colored band in positive samples.

In some embodiments of any of the aspects, the lateral flow immunoassay can be a double antibody sandwich assay, a competitive assay, a quantitative assay or variations thereof. There are a number of variations on lateral flow technology. It is also possible to apply multiple capture zones to create a multiplex test.

A typical test strip consists of the following components: (1) sample application area comprising an absorbent pad (i.e. the matrix or material) onto which the test sample is applied; (2) conjugate or reagent pad—this contains antibody reagent(s) specific to the target which can be conjugated to colored particles (usually colloidal gold particles, or latex microspheres); (3) test results area comprising a reaction membrane—typically a hydrophobic nitrocellulose or cellulose acetate membrane onto which antibody reagents are immobilized in a line across the membrane as a capture zone or test line (a control zone may also be present, containing antibodies specific for the antibody reagents conjugated to the particles or microspheres); and (4) optional wick or waste reservoir—a further absorbent pad designed to draw the sample across the reaction membrane by capillary action and collect it. The components of the strip are usually fixed to an inert backing material and may be presented in a simple dipstick format or within a plastic casing with a sample port and reaction window showing the capture and control zones. While not strictly necessary, most tests will incorporate a second line which contains an antibody that picks up free latex/gold in order to confirm the test has operated correctly.

The use of "dip sticks" or LFIA test strips and other solid supports has been described in the art in the context of an immunoassay for a number of antigen biomarkers. U.S. Pat. Nos. 4,943,522; 6,485,982; 6,187,598; 5,770,460; 5,622,871; 6,565,808, U.S. patent application Ser. No. 10/278,676; U.S. Ser. No. 09/579,673 and U.S. Ser. No. 10/717,082, which are incorporated herein by reference in their entirety, are non-limiting examples of such lateral flow test devices. Three U.S. patents (U.S. Pat. No. 4,444,880, issued to H. Tom; U.S. Pat. No. 4,305,924, issued to R. N. Piasio; and U.S. Pat. No. 4,135,884, issued to J. T. Shen) describe the use of "dip stick" technology to detect soluble antigens via immunochemical assays. The apparatuses and methods of these three patents broadly describe a first component fixed to a solid surface on a "dip stick" which is exposed to a solution containing a soluble antigen that binds to the component fixed upon the "dip stick," prior to detection of the component-antigen complex upon the stick. It is within the skill of one in the art to modify the teaching of these "dip stick" technologies as necessary for the detection of, e.g., DEspR polypeptides. In some embodiments of any of the aspects, the dip stick (or LFIA) can be suitable for use with urine samples. In some embodiments of any of the aspects, a dip stick can be suitable for use with blood samples.

Immunochemistry is a family of techniques based on the use of a specific antibody, wherein antibodies are used to specifically target molecules inside or on the surface of cells. In some embodiments of any of the aspects, immunohistochemistry ("IHC") and immunocytochemistry ("ICC") techniques can be used to detect or measure the levels of, e.g., DEspR polypeptide. IHC is the application of immunochemistry to tissue sections, whereas ICC is the application of immunochemistry to cells or tissue imprints after they have undergone specific cytological preparations such as, for example, liquid-based preparations. In some instances, signal amplification may be integrated into the particular protocol, wherein a secondary antibody, that includes a label, follows the application of an antibody reagent specific for platelets or leukocytes. Typically, for immunohistochemistry, tissue obtained from a subject and fixed by a suitable fixing agent such as alcohol, acetone, and paraformaldehyde, is sectioned and reacted with an antibody. Conventional methods for immunohistochemistry are described in Buchwalow and Bocker (Eds) "Immunohistochemistry: Basics and Methods" Springer (2010): Lin and Prichard "Handbook of Practical Immunohistochemistry" Springer (2011); which are incorporated by reference herein in their entireties. In some embodiments of any of the aspects, immunocytochemistry may be utilized where, in general, tissue or cells obtained from a subject are fixed by a suitable fixing agent such as alcohol, acetone, and paraformaldehyde, to which is reacted an antibody. Methods of immunocytological staining of human samples is known to those of skill in the art and described, for example, in Burry "Immunocytochemistry: A Practical Guide for Biomedical Research" Springer (2009); which is incorporated by reference herein in its entirety.

In some embodiments of any of the aspects, one or more of the antibody reagents described herein can comprise a detectable label and/or comprise the ability to generate a detectable signal (e.g., by catalyzing a reaction converting a compound to a detectable product). Detectable labels can comprise, for example, a light-absorbing dye, a fluorescent dye, or a radioactive label. Detectable labels, methods of detecting them, and methods of incorporating them into an antibody reagent are well known in the art.

In some embodiments of any of the aspects, detectable labels can include labels that can be detected by spectroscopic, photochemical, biochemical, immunochemical, electromagnetic, radiochemical, or chemical means, such as fluorescence, chemifluoresence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or non-covalent means to the antibody reagent. Alternatively, a detectable label can be linked such as by directly labeling a molecule that achieves binding to the antibody reagent via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, the detection antibody is labeled with a fluorescent compound. When the fluorescently labeled antibody is exposed to light of the proper wavelength, its presence can then be detected due to fluorescence. In some embodiments of any of the aspects, a detectable label can be a fluorescent dye molecule, or fluorophore including, but not limited to fluorescein, phycoerythrin, phycocyanin, o-phthaldehyde, fluorescamine, Cy3™, Cy5™, allophycocyanine, Texas Red, peridenin chlorophyll, cyanine, tandem conjugates such as phycoerythrin-Cy5™, green fluorescent protein, rhodamine, fluorescein isothiocyanate (FITC) and Oregon Green™, rhodamine and derivatives (e.g., Texas red and tetrarhodimine isothiocynate (TRITC)), biotin, phycoerythrin, AMCA, CyDyes™, 6-carboxyfhiorescein (commonly known by the abbreviations FAM and F), 6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g., Cy3, Cy5 and Cy7 dyes; coumarins, e.g umbelliferone; benzimide dyes, e.g., Hoechst 33258; phenanthridine dyes, e.g., Texas Red; ethidium dyes; acridine dyes; carbazole dyes; phenoxazine dyes; porphyrin dyes; polymethine dyes, e.g., cyanine dyes such as Cy3, Cy5, etc; BODIPY dyes and quinoline dyes.

In some embodiments of any of the aspects, a detectable label can be a radiolabel including, but not limited to $^{3}$H, $^{125}$I, $^{35}$S, $^{4}$C, $^{32}$P, and $^{33}$P.

In some embodiments of any of the aspects, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use to detectably label an antibody reagent include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase.

In some embodiments of any of the aspects, a detectable label is a chemiluminescent label, including, but not limited to lucigenin, luminol, luciferin, isoluminol, theromatic acridinium ester, imidazole, acridinium salt and oxalate ester.

In some embodiments of any of the aspects, a detectable label can be a spectral colorimetric label including, but not limited to colloidal gold or colored glass or plastic (e.g., polystyrene, polypropylene, and latex) beads.

In some embodiments of any of the aspects, antibodies can also be labeled with a detectable tag, such as c-Myc, HA, VSV-G, HSV, FLAG, V5, HIS, or biotin. Other detection systems can also be used, for example, a biotin-streptavidin system. In this system, the antibodies immunoreactive (i. e. specific for) with the biomarkers of interest is biotinylated. Quantity of biotinylated antibody bound to the biomarkers is determined using a streptavidin-peroxidase conjugate and a chromagenic substrate. Such streptavidin peroxidase detection kits are commercially available, e. g. from DAKO; Carpinteria, Calif.

An antibody reagent can also be detectably labeled using fluorescence emitting metals such as $^{152}$Eu, or others of the lanthanide series. These metals can be attached to the antibody reagent using such metal chelating groups as diethylenetriaminepentaacetic acid (DTPA) or ethylenediaminetetraacetic acid (EDTA).

The methods as described herein can relate to determining if a subject has an increased level of, e.g., DEspR relative to a reference level. In some embodiments of any of the aspects, the reference level of the marker (e.g., DEspR) can be the level of the marker in a healthy subject not having, or not diagnosed as having, e.g., coronavirus infection, or organ-dysfunction or multi-organ dysfunction or failure associated with a coronavirus infection. In some embodiments of any of the aspects, the reference level can be the level in a sample of similar cell type, sample type, sample processing, and/or obtained from a subject of similar age, sex and other demographic parameters as the sample/subject for which the level of the target is to be determined. In some embodiments of any of the aspects, the test sample and control reference sample are of the same type, that is, obtained from the same biological source, and comprising the same composition, e.g., the same number and type of cells and/or type of sample material. Accordingly, in some embodiments of any of the aspects, the level of the target which is increased can vary as demographic factors such as age, gender, genotype, environmental factors, and individual medical histories vary. In some embodiments of any of the aspects, the reference level can comprise the level of the target, (e.g., DEspR or DEspR+ neutrophils) in a sample of the same type taken from a subject not exhibiting any signs or symptoms of, e.g., coronavirus infection, or organ-dysfunction or multi-organ dysfunction or failure associated with a coronavirus infection. In some embodiments of any of the aspects, the reference expression level of the marker can be the expression level of the marker in a prior sample obtained from the subject. This permits a direct analysis of any change in levels in that individual.

In some embodiments of any of the aspects, a level of a marker can be increased relative to a reference level if the level of the marker is at least 1.25× the reference level, e.g., at least 1.25×, at least 1.5×, at least 2×, at least 3×, at least 4×, at least 5×, at least 6×, or greater of the reference level. In some embodiments of any of the aspects, the expression level of the marker can be normalized relative to the expression level of one or more reference genes or reference proteins. In some embodiments of any of the aspects, the expression level of the marker can be normalized relative to a reference value.

In some embodiments of any of the aspects, the expression level of no more than 20 other genes is determined. In some embodiments of any of the aspects, the expression level of no more than 10 other genes is determined.

The term "sample" or "test sample" as used herein denotes a sample taken or isolated from an organism, e.g., a urine sample from a subject. Exemplary biological samples include, but are not limited to, a biofluid sample; serum; plasma; urine; saliva; and/or tumor sample, etc. The term also includes a mixture of the above-mentioned samples. The term "test sample" also includes untreated or pretreated (or pre-processed) biological samples. In some embodiments of any of the aspects, a test sample can comprise cells from a subject. As used herein, the term "biofluid" refers to any fluid obtained from a biological source and includes, but is not limited to, blood, urine, and bodily secretions.

The test sample can be obtained by removing a sample from a subject, but can also be accomplished by using a previously isolated sample (e.g., isolated at a prior timepoint and isolated by the same or another person). In addition, the test sample can be freshly collected or a previously collected sample.

In some embodiments of any of the aspects, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments of any of the aspects, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments of any of the aspects, the test sample is a clarified test sample, for example, prepared by centrifugation and collection of a supernatant comprising the clarified test sample. In some embodiments of any of the aspects, a test sample can be a pre-processed test sample, for example, supernatant or filtrate resulting from a treatment selected from the group consisting of centrifugation, filtration, thawing, purification, and any combinations thereof. In some embodiments of any of the aspects, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of a marker as described herein.

In some embodiments of any of the aspects, the methods, assays, and systems described herein can further comprise a step of obtaining a test sample from a subject. In some embodiments of any of the aspects, the subject can be a human subject.

In some embodiments of any of the aspects, the methods, assays, and systems described herein can comprise creating a report based on the level of the marker. In some embodiments of any of the aspects, the report denotes raw values for the marker, in the test sample (plus, optionally, the level of the marker in a reference sample) or it indicates a percentage or fold increase in the marker as compared to a reference level, and/or provides a signal that the subject is at risk of having, or not having coronavirus infection, or organ-dysfunction or multi-organ dysfunction or failure associated with a coronavirus infection.

As used herein "at risk of having" refers to at least a 2-fold greater likelihood of having a particular condition as compared to a subject that did not have an elevated and/or increased level of the marker, e.g., a 2-fold, or 2.5-fold, or 3-fold, or 4-fold, or greater risk.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed disclosure, because the scope of the claims is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

"Coronaviruses" consist of a large and diverse family of enveloped, positive-sense, single-stranded RNA viruses. Every coronavirus contains four structural proteins, for example spike (S), envelope (E), membrane (M), and nucleocapsid (N) proteins. Coronavirus diversity is reflected in the variable S proteins, which have evolved into forms differing in their receptor interactions and their response to various environmental triggers of virus-cell membrane fusion. In particular, the RBD of the S protein is the most variable genomic part in the betacoronavirus group.

Four serologically distinct groups of coronaviruses have been described, i.e., alpha, beta (previously referred to as group 2), delta, and gamma. Within each group, viruses are characterized by their host range and genome sequence. The alphacoronaviruses and betacoronaviruses infect only mammals, while the gammacoronaviruses and deltacoronaviruses primarily infect birds, although some of them can also infect mammals. Novel mammalian coronaviruses are now regularly identified. (see e.g., Su et al., Trends Microbiol. 2016; 24: 490-502). Betacoronaviruses (Beta-CoV) of known clinical important to humans includes viruses of the A, B and C lineage and more particularly, the A lineage: OC43 (which can cause the common cold) and HKU1; the B lineage: SARS-CoV and SARS-CoV-2 (which causes the disease COVID-19); and the C lineage: MERS-CoV.

In one embodiment, the coronavirus infection described herein is a betacoronavirus infection and more particularly, an A-lineage, B-lineage, or C lineage coronavirus infection. In another particular embodiment, the coronavirus infection described herein is an infection of severe acute respiratory syndrome coronavirus 2 (SARS-CoV-2) infections. SARS-CoV-2 (also referred to as 2019-nCoV) was identified in January 2020 as the causative agent of Severe Acute Respiratory Syndrome 2, also referred to as Covid-19.

Clinical signs associated with SARS-CoV-2 include pneumonia, fever, dry cough, headache, and dyspnea, which may progress to respiratory failure and death. The incubation period for SARS-CoV-2 of 2 to 14 days can be longer than for SARS-CoV and MERS-CoV, which have a mean incubation time of 5 to 7 days.

SARS-CoV-2 was sequenced and isolated by January 2020 (see e.g., e.g., Zhou N. N Engl J Med., 382 (2020), pp. 727-733). Several sequences of SARS-CoV-2 have since been released (see e.g., complete genome, SARS-CoV-2 Jan. 2020/NC_045512.2 Assembly (wuhCorl)).

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of a disease or condition described herein, e.g., coronavirus infection, or organ-dysfunction or multi-organ dysfunction or failure associated with a coronavirus infection. A subject can be male or female.

In some embodiments of any of the aspects, the subject or patient can be a human. In some embodiments of any of the aspects, the subject or patient can be a mammal. Thus, in one embodiment, mammals can include cats, dogs, pigs, horses, cows, sheep, and goats, as well as humans. The methods described herein are applicable to veterinary methods and treatments. For example, where laminitis in horses is caused by actPMNs, in some embodiments the subject is a non-human mammal.

A subject can be one who has been previously diagnosed with or identified as suffering from or having a condition in need of treatment or one or more complications related to such a condition, and optionally, have already undergone treatment for a disease or condition or the one or more complications related to the disease or condition. Alternatively, a subject can also be one who has not been previously diagnosed as having the disease or condition or one or more complications related to the disease or condition. For example, a subject can be one who exhibits one or more risk factors for the disease or condition or one or more complications related to the disease or condition or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

In some embodiments, the polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to the assays described below herein. A functional fragment can comprise conservative substitutions of the sequences disclosed herein.

In some embodiments, the polypeptide described herein can be a variant of a sequence described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA. Suitable RNA can include, e.g., mRNA.

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

In some embodiments, a nucleic acid encoding a polypeptide as described herein (e.g. an antibody or antibody reagent) is comprised by a vector. In some of the aspects described herein, a nucleic acid sequence encoding a given polypeptide as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of nonessential viral genes. The vector and/or particle may be utilized for the purpose of transferring any nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder. The term "treating" includes reducing or alleviating at least one adverse effect or symptom of a condition, disease or disorder described herein. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight more than about 50, but less than about 5000 Daltons (5 kD). Preferably the small molecule has a molecular weight of less than 3 kD, still more preferably less than 2 kD, and most preferably less than 1 kD. In some cases it is preferred that a small molecule have a molecular mass equal to or less than 700 Daltons.

As used herein, the term "thrombolytic" refers to any agent capable of inducing reperfusion by dissolving, dislodging or otherwise breaking up a clot, e.g., by either dissolving a fibrin-platelet clot, or inhibiting the formation of such a clot. Reperfusion occurs when the clot is dissolved and blood flow is restored. Exemplary thrombolytic agents include, but are not limited to, tissue-type plasminogen activator (t-PA), streptokinase (SK), prourokinase, urokinase (uPA), alteplase (also known as Activase®, Genentech, Inc.), reteplase (also known as r-PA or Retavase®, Centocor, Inc.), tenecteplase (also known as TNK™, Genentech, Inc.), Streptase® (AstraZeneca, LP), lanoteplase (Bristol-Myers Squibb Company), monteplase (Eisai Company, Ltd.), saruplase (also known as r-scu-PA and Rescupase™, Grunenthal GmbH, Corp.), staphylokinase, and anisoylated plasminogen-streptokinase activator complex (also known as APSAC, Anistreplase and Eminase®, SmithKline Beecham Corp.). Thrombolytic agents also include other genetically engineered plasminogen activators. The invention can additionally employ hybrids, physiologically active fragments or mutant forms of the above thrombolytic agents. The term "tissue-type plasminogen activator" as used herein is intended to include such hybrids, fragments and mutants, as well as both naturally derived and recombinantly derived tissue-type plasminogen activator.

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in in nature.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein, an "epitope" can be formed on a polypeptide both from contiguous amino acids, or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, about 9, or about 8-10 amino acids in a unique spatial conformation. An "epitope" includes the unit of structure conventionally bound by an immunoglobulin VH/VL pair. Epitopes define the minimum binding site for an antibody, and thus represent the target of specificity of an antibody. In the case of a single domain antibody, an epitope represents the unit of structure bound by a variable domain in isolation. The terms "antigenic determinant" and "epitope" can also be used interchangeably herein. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics.

"Avidity" is the measure of the strength of binding between an antigen-binding molecule (such as an antibody or antigen-binding portion thereof described herein) and the pertinent antigen. Avidity is related to both the affinity between an antigenic determinant and its antigen binding site on the antigen-binding molecule, and the number of pertinent binding sites present on the antigen-binding molecule. Typically, antigen-binding proteins (such as an antibody or portion of an antibody as described herein) will bind to their cognate or specific antigen with a dissociation constant (KD of $10^{-5}$ to $10^{-12}$ moles/liter or less, such as $10^{-7}$ to $10^{-12}$ moles/liter or less, or $10^{-8}$ to $10^{-12}$ moles/liter (i.e., with an association constant (KA) of $10^{-5}$ to $10^{-12}$ liter/moles or more, such as $10^7$ to $10^{12}$ liter/moles or $10^8$ to $10^{12}$ liter/moles). Any KD value greater than $10^{-4}$ mol/liter (or any KA value lower than $10^4$ $M^{-1}$) is generally considered to indicate non-specific binding. The KD for biological interactions which are considered meaningful (e.g., specific) are typically in the range of $10^{-12}$ M (0.1 nM) to $10^{-5}$ M (10,000 nM). The stronger an interaction, the lower is its KD. For example, a binding site on an antibody or portion thereof described herein will bind to the desired antigen with an affinity less than 500 nM, such as less than 200 nM, or less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as other techniques as mentioned herein.

Accordingly, as used herein, "selectively binds" or "specifically binds" refers to the ability of an peptide (e.g., an antibody, or portion thereof) described herein to bind to a target, such as DEspR, with a KD $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. Specific binding can be influenced by, for example, the affinity and avidity of the polypeptide agent and the concentration of polypeptide agent. The person of ordinary skill in the art can determine appropriate conditions under which the polypeptide agents described herein selectively bind the targets using any suitable methods, such as titration of a polypeptide agent in a suitable cell binding assay. A polypeptide specifically bound to a target is not displaced by a non-similar competitor. In certain embodiments, an antibody reagent is said to specifically bind an antigen when it preferentially recognizes its target antigen in a complex mixture of proteins and/or macromolecules.

In some embodiments, an antibody reagent as described herein binds to DEspR with a dissociation constant ($K_D$) of $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. In some embodiments, an antibody reagent as described herein binds to DEspR with a dissociation constant ($K_D$) of from about $10^{-5}$ M to $10^{-6}$ M. In some embodiments, an antibody reagent as described herein binds to DEspR with a dissociation constant ($K_D$) of from about $10^{-6}$ M to $10^{-7}$ M. In some embodiments, an antibody reagent as described herein binds to DEspR with a dissociation constant ($K_D$) of from about $10^{-7}$ M to $10^{-8}$ M. In some embodiments, an antibody reagent as described herein binds to DEspR with a dissociation constant ($K_D$) of from about $10^{-8}$ M to $10^{-9}$ M. In some embodiments, an antibody reagent as described herein binds to DEspR with a dissociation constant ($K_D$) of from about $10^{-9}$ M to $10^{-10}$ M. In some embodiments, an antibody reagent as described herein binds to DEspR with a dissociation constant ($K_D$) of from about $10^{-10}$ M to $10^{-11}$ M. In some embodiments, an antibody reagent as described herein binds to DEspR with a dissociation constant ($K_D$) of from about $10^{-11}$ M to $10^{-12}$ M. In some embodiments, an antibody reagent as described herein binds to DEspR with a dissociation constant ($K_D$) of less than $10^{-12}$ M.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

In some embodiments of any of the aspects, the agent that inhibits DEspR is an inhibitory nucleic acid. In some embodiments of any of the aspects, inhibitors of the expression of a given gene can be an inhibitory nucleic acid. As used herein, "inhibitory nucleic acid" refers to a nucleic acid molecule which can inhibit the expression of a target, e.g., double-stranded RNAs (dsRNAs), inhibitory RNAs (iRNAs), and the like.

Double-stranded RNA molecules (dsRNA) have been shown to block gene expression in a highly conserved regulatory mechanism known as RNA interference (RNAi). The inhibitory nucleic acids described herein can include an RNA strand (the antisense strand) having a region which is 30 nucleotides or less in length, i.e., 15-30 nucleotides in length, generally 19-24 nucleotides in length, which region is substantially complementary to at least part the targeted mRNA transcript. The use of these iRNAs enables the targeted degradation of mRNA transcripts, resulting in decreased expression and/or activity of the target As used herein, the term "iRNA" refers to an agent that contains RNA (or modified nucleic acids as described below herein) and which mediates the targeted cleavage of an RNA transcript via an RNA-induced silencing complex (RISC) pathway. In some embodiments of any of the aspects, an iRNA as described herein effects inhibition of the expression and/or translation and/or activity of a target, e.g. DEspR. In some embodiments of any of the aspects, contacting a cell with the inhibitor (e.g. an iRNA) results in a decrease in the target mRNA level in a cell by at least about 5%, about 10%, about 20%, about 30%, about 40%, about 50%, about 60%, about 70%, about 80%, about 90%, about 95%, about 99%, up to and including 100% of the target mRNA level found in the cell without the presence of the iRNA. In some embodiments of any of the aspects, administering an inhibitor (e.g. an iRNA) to a subject results in a decrease in the target mRNA level in the subject by at least about 5%, about 10%, about 20%, about 30%, about 40%, about 50%, about 60%, about 70%, about 80%, about 90%, about 95%, about 99%, up to and including 100% of the target mRNA level found in the subject without the presence of the iRNA.

In some embodiments of any of the aspects, the iRNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of the target, e.g., it can span one or more intron boundaries. The other strand (the sense strand) includes a region that is complementary to the antisense strand, such that the two strands hybridize and form a duplex structure when combined under suitable conditions. Generally, the duplex structure is between 15 and 30 base pairs in length inclusive, more generally between 18 and 25 base pairs in length inclusive, yet more generally between 19 and 24 base pairs in length inclusive, and most generally between 19 and 21 base pairs in length, inclusive. Similarly, the region of complementarity to the target sequence is between 15 and 30 base pairs in length inclusive, more generally between 18 and 25 base pairs in length inclusive, yet more generally between 19 and 24 base pairs in length inclusive, and most generally between 19 and 21 base pairs in length nucleotides in length, inclusive. In some embodiments of any of the aspects, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway). dsRNAs having duplexes as short as 9 base pairs can, under some circumstances, mediate RNAi-directed RNA cleavage. Most often a target will be at least 15 nucleotides in length, preferably 15-30 nucleotides in length.

Exemplary embodiments of types of inhibitory nucleic acids can include, e.g, siRNA, shRNA, miRNA, and/or amiRNA, which are well known in the art.

In some embodiments of any of the aspects, the RNA of an iRNA, e.g., a dsRNA, is chemically modified to enhance stability or other beneficial characteristics. The nucleic acids described herein may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments of any of the aspects, the modified RNA will have a phosphorus atom in its internucleoside backbone.

Modified RNA backbones can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2-5' linked analogs of these, and those) having inverted polarity wherein the adjacent pairs of nucleoside units are linked 3'-5' to 5'-3' or 2'-5' to 5'-2'. Various salts, mixed salts and free acid forms are also included. Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; others having mixed N, O, S and CH2 component parts, and oligonucleosides with heteroatom backbones, and in particular —CH2-NH—CH2-, —CH2-N(CH3)-O—CH2-[known as a methylene (methylimino) or MMI backbone], —CH2-O—N(CH3)-CH2-, —CH2-N(CH3)-N(CH3)-CH2- and —N(CH3)-CH2— [wherein the native phosphodiester backbone is represented as —O—P—O—CH2-].

In other RNA mimetics suitable or contemplated for use in iRNAs, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) Nucleic Acids Research 33(1):439-447; Mook, OR. Et al., (2007) Mol Canc Ther 6(3):833-843; Grunweller, A. et al., (2003) Nucleic Acids Research 31(12): 3185-3193).

Modified RNAs can also contain one or more substituted sugar moieties. The iRNAs, e.g., dsRNAs, described herein can include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Exemplary suitable modifications include O[(CH2)nO] mCH3, O(CH2).nOCH3, O(CH2)nNH2, O(CH2) nCH3, O(CH2)nONH2, and O(CH2)nON[(CH2)nCH3)]2, where n and m are from 1 to about 10. In some embodiments of any of the aspects, dsRNAs include one of the following at the 2' position: C1 to C10 lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments of any of the aspects, the modification includes a 2' methoxyethoxy (2'-O—CH2CH2OCH3, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O(CH2)2ON(CH3)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH2-O—CH2-N(CH2)2, also described in examples herein below.

Other modifications include 2'-methoxy (2'-OCH3), 2'-aminopropoxy (2'-OCH2CH2CH2NH2) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs may also have sugar mimetics such as cyclobutyl moieties in place of the pentofuranosyl sugar.

An inhibitory nucleic acid can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Certain of these nucleobases are particularly useful for increasing the binding affinity of the inhibitory nucleic acids featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

The preparation of the modified nucleic acids, backbones, and nucleobases described above are well known in the art.

Another modification of an inhibitory nucleic acid featured in the invention involves chemically linking to the inhibitory nucleic acid to one or more ligands, moieties or conjugates that enhance the activity, cellular distribution, pharmacokinetic properties, or cellular uptake of the iRNA. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylaminocarbonyloxycholesterol moiety (Crooke et al., J. Pharmacol. Exp. Ther., 1996, 277:923-937).

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, $4^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff's Clinical Oncology, 2013 Elsevier; and Fischer D S (ed): The Cancer Chemotherapy Handbook, 4th ed. St. Louis, Mosby-Year Book, 2003).

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Some embodiments of the technology described herein can be defined according to any of the following numbered paragraphs:

1. A method of treating a coronavirus infection in a subject, the subject determined to have an elevated level of DEspR+CD11b+ cells as compared to a non-infected subject, the method comprising administering a DEspR inhibitor to the subject, wherein the administering is effective to treat the coronavirus infection in the subject.
2. The method of paragraph 1, wherein the administering is effective to treat COVID19 disease manifestations and complications beyond the coronavirus infectivity status in the subject.
3. The method of any one of paragraphs 1-2, wherein the coronavirus is SARS CoV2 causing COVID-19.
4. The method of any one of paragraphs 1-3, wherein the DEspR+CD11b+ cells are DEspR+CD11b+ neutrophils, DEspR+CD11b+ monocytes, DEspR+CD11b+ lymphocytes, DEspR+CD11b+ cytoplasts or a combination, an aggregate, or DEspR+ DNA strand s.
5. The method of any one of paragraphs 1-4, wherein the DEspR+CD11b+ cells are at least 20, 30, 40, 50, 60, 70, 80, 90, 100% of the whole corresponding cell population.
6. The method of any one of paragraphs 1-5, wherein the subject is further determined to have an elevated DEspR+ neutrophil to lymphocyte ratio (d+NLR); elevated ratio of DEspR+ neutrophils to COVID19- associated (a) hyperinflammation cytokines or cytokine storm biomarkers, (b) oxidative stress biomarkers, (c) endothelial dysfunction biomarkers, or (d) a combination thereof; or a combination thereof.

7. The method of any one of paragraphs 1-6, wherein the hyperinflammation cytokines or cytokine storm biomarkers comprise IL-6.
8. The method of any one of paragraphs 1-7, wherein the oxidative stress biomarkers comprise myeloperoxidase (MPO).
9. The method of any one of paragraphs 1-8, wherein the endothelial dysfunction biomarkers comprise endothelin-1 (ET1).
10. The method of any one of paragraphs 1-9, wherein the control subject does not have a coronavirus infection.
11. The method of any one of paragraphs 1-10, wherein the DEspR inhibitor is an anti-DEspR anti-body or fragment thereof.
12. The method of paragraph 11, wherein the anti-DEspR antibody or fragment thereof comprises complementary determining regions selected from SEQ ID Nos: 1-3, 9-11, 17-19, 5-7, 13-15, 21-23, 25-27, 29-31, and 33-35.
13. A method of treating a subject having a coronavirus infection, the method comprising
    (i) determining whether the subject has a high risk of poor outcome or morbidity by detecting a level or rising level of DEspR+CD11b+ cells, a level of (1) non-resolving neutrophil-monocyte inflammatory amplification that blocks initiation of next step anti-viral adaptive immuni-ty, anti-viral cellular immunity, resolution, or a combination, measured as: DEspR+CD11b+ cells, (2) a level of hyperinflammation-response marked by elevated ratio DEspR+CD11b+ neutrophils to plasma cytokine storm biomarkers, or to plasma oxidative stress biomarkers or to endothelial dys-function biomarkers, or (3) a combination thereof, as individual or combinatorial measures in a sample obtained from the subject,
    wherein an elevated level of DEspR+CD11b+ cells, high ratios of DEspR+ neutrophils to COVID-19 associated elevated cytokines, elevated oxidative stress biomarkers, elevated endothelial activation biomarker levels, or a combination thereof in the sample obtained from the subject com-pared with a sample obtained from a control subject is an indicative that the subject has a high risk of poor outcome or morbidity, wherein the control subject does not have a coronavirus infection, and
    ( ) administering to the subject a DEspR inhibitor.
14. A method of improving a survival rate of a subject having a coronavirus infection, the method comprising
    (i) determining whether the subject has a high risk of poor outcome or morbidity by detect-ing a level or rising level of DEspR+CD11b+ cells, a level of (1) non-resolving neutrophil-monocyte inflammatory amplification that blocks initiation of next step anti-viral adaptive immuni-ty, anti-viral cellular immunity, resolution, or a combination, measured as: DEspR+CD11b+ cells, (2) a level of hyperinflammation-response marked by elevated ratio DEspR+CD11b+ neutrophils to plasma cytokine storm biomarkers, or to endothelial dys-function biomarker, or (3) a combination thereof, as individual or combinatorial measures in a sample obtained from the subject,
    wherein an elevated or rising level of DEspR+CD11b+ cells or hyperinflammation ratio-markers in the sample obtained from the subject compared with a level of DEspR+CD11b+ cells in a sample obtained from a control subject is indicative that the subject has a high risk of poor out-come or morbidity, wherein the control subject does not have a coronavirus infection, and
    (ii) administering to the subject a DEspR inhibitor.
15. A method of determining prognosis of a subject having a coronavirus infection, the method comprising:
    detecting in a sample obtained from the subject a level of, or rising DEspR+CD11b+ cells, or DEspR-bound DNA, or a level of (1) non-resolving neutrophil-monocyte inflammatory amplifi-cation that blocks initiation of next step anti-viral adaptive immunity, anti-viral cellular immunity, resolution, or a combi-nation, measured as: DEspR+CD11b+ neutrophils and monocytes, (2) a level of hyperinflammation-response marked by elevated ratio DEspR+CD11b+ neutrophils to plasma cytokine storm biomarkers, or to plasma oxidative stress biomarkers or to endothe-lial dysfunction biomarker, or (3) a combination thereof, as individual or combinatorial measures in a sample ob-tained from the subject,
    wherein an elevated or rising levels of DEspR+CD11b+ cells, plasma DEspR-bound DNA, high ratios of DEspR+ neutrophils to COVID-19 associ-ated elevated cytokines, elevated oxidative stress biomarker, elevated endothelial activation biomarker level or a combination thereof in the sample obtained from the subject compared with a level of DEspR+CD11b+ neutrophils in a sam-ple obtained from a control subject is an indicative that the subject has a high risk of poor outcome or morbidity, wherein the control subject does not have a coronavirus infec-tion.
16. The method of any one of paragraphs 13-15, wherein the DEspR+CD11b+ cells are DEspR+CD11b+ neutro-phils, DEspR+CD11b+ monocytes, DEspR+CD11b+ lymphocytes, DEspR+CD11b+ cytoplasts or a combi-nation, an aggregate, or DEspR+ DNA strands.
17. The method of any one of paragraphs 13-16, wherein the plasma cytokine storm biomarkers com-prise IL-6, IL-8, IL-1β, IL-18, or a combination thereof.
18. The method of any one of paragraphs 13-17, wherein the plasma oxidative stress biomarkers com-prise myeloperoxidase.
19. The method of any one of paragraphs 13-18, wherein the endothelial dysfunction biomarkers comprise endothelin-1.
20. The method of any one of paragraphs 13-19, wherein the COVID-19 associated elevated cytokines com-prises IL-6, IL-8, IL-1β or IL-18, or a combination thereof.
21. The method of any one of paragraphs 13-20, wherein the elevated oxidative stress biomarkers comprise myeloperoxidase.
22. The method of any one of paragraphs 13-21, wherein the elevated endothelial activation bi-omarkers com-prise endothelin-1.
23. The method of any one of paragraphs 13-22, wherein the level of DEspR+CD11b+ cells is detect-ed by measuring a level of DEspR+CD11b+ aggregates or DEspR+ DNA strands in the blood sam-ple.

24. The method of any one of paragraphs 13-23, wherein the level of DEspR+CD11b+ cells in the subject determines whether the subject will require intensive care.
25. A method of preventing or treating organ-dysfunction or multi-organ dysfunction or failure associated with a coronavirus infection in a subject in need thereof, wherein subject is determined to have elevated or rising levels of DEspR+CD11b+ cells, elevated hyperinflammation DEspR+ neutrophil-IL6/MPO/ET1 ratios, or a combination thereof, as compared to a control subject, the method comprising administering a DEspR inhibitor.
26. The method of paragraph 25, wherein the DEspR+CD11b+ cells are DEspR+CD11b+ neutrophils, DEspR+CD11b+ monocytes, DEspR+CD11b+ lymphocytes, DEspR+CD11b+ cytoplasts or a combination, an aggregate, or DEspR+ DNA strands.
27. The method of any one of paragraphs 25-26, wherein the organ-dysfunction or multi-organ dysfunction or failure associated with the coronavirus infection arises from microcirculatory dysfunction, microvascular inclusion, low flow ischemia, thromboses, systemic microthromboses, micro-circulatory vascular aggregation, or a combination thereof.
28. The method of any one of paragraphs 25-27, wherein the organ-dysfunction or multi-organ dys-function or failure associated with the coronavirus infection is derived from COVID19-induced cytokine storm, low flow organ ischemia from DEspR+CD11b+ aggregates leading to characteristic COVID19-hypoxemia, renal dysfunction, cardiac ischemia, neurological dysfunction from low flow ischemia or delayed cerebral ischemia or neuroinflammation, liver dysfunction/failure, hema-tological coagulopathy or microthromboses, or a combination thereof.
29. The method of paragraph 28, wherein the neurological dysfunction is characterized by loss of con-sciousness, seizures, confusion or a combination thereof.
30. The method of any one of paragraphs 25-29, wherein the organ-dysfunction or multi-organ dysfunction or failure associated with the coronavirus infection is selected from the group consisting of systemic inflammatory response syndrome (SIRS); acute lung injury (ALI); acute respiratory dis-tress syndrome (ARDS); multi-organ failure or multi-organ dysfunction syndrome (MODS); acute kidney injury (AKI); liver failure, ischemic stroke; delayed cerebral ischemia, and/or encephalopathy.
31. The method of any one of paragraphs 25-30, wherein the organ-dysfunction or multi-organ dys-function or failure associated with the coronavirus infection is ARDS.
32. A method of combinational therapy for a subject having a coronavirus infection, the method comprising; administering to the subject a therapeutic agent or a therapy in combination with a DEspR inhibitor, wherein the therapeutic agent or the therapy prevents or alleviates a sign or a symptom associated with the coronavirus infection in the subject.
33. The method of paragraph 32, wherein the therapy is an application of a respiratory ventilation, or an alternative delivery system for supplemental oxygen.
34. A method of reducing microthrombi formation associated with a coronavirus infection in a subject in need thereof, the method comprising: administering to the subject a DEspR inhibitor, thereby reducing systemic microthrombi formation associated with the coronavirus infection in the subject.
35. The method of paragraph 34, further comprising administering anti-thrombotics in combination.
36. The method of any one of paragraphs 13, 14, and 16-35, wherein the DEspR inhibitor is an anti-DEspR antibody or fragment thereof.
37. The method of paragraph 36, wherein the anti-DEspR antibody or fragment thereof comprises complementary determining regions selected from SEQ ID Nos: 1-3, 9-11, 17-19, 5-7, 13-15, 21-23, 25-27, 29-31, and 33-35.

Some embodiments of the technology described herein can be defined according to any of the following numbered paragraphs:

1. A method of treating a coronavirus infection in a subject, the subject determined to have an elevated level of DEspR+CD11b+ cells as compared to a non-infected subject, the method comprising administering a DEspR inhibitor to the subject, wherein said administering is effective to treat the coronavirus infection in the subject.
2. The method of paragraph 1, wherein the coronavirus is COVID-19.
3. The method of any one of paragraphs 1-2, wherein the DEspR+CD11b+ cells are DEspR+CD11b+ neutrophils, DEspR+CD11b+ monocytes, DEspR+CD11b+ lymphocytes, DEspR+CD11b+ cytoplasts, or a combination or an aggregate.
4. The method of any one of paragraphs 1-3, wherein the DEspR+CD11b+ cells are at least 20, 30, 40, 50, 60, 70, 80, 90, 100% of the whole corresponding cell population.
5. The method of any one of paragraphs 1-4, wherein the subject is further determined to have an elevated DEspR+ neutrophil to lymphocyte ratio (d+NLR); elevated ratio of DEspR+ neutrophils to COVID19-associated (a) hyperinflammation cytokines or cytokine storm biomarkers, (b) oxidative stress biomarkers, (c) endothelial dysfunction biomarkers, or (d) a combination thereof, or a combination thereof.
6. The method of any one of paragraphs 1-5, wherein the hyperinflammation cytokines or cytokine storm biomarkers comprise IL-6.
7. The method of any one of paragraphs 1-6, wherein the oxidative stress biomarkers comprise myeloperoxidase (MPO).
8. The method of any one of paragraphs 1-7, wherein the endothelial dysfunction biomarkers comprise endothelin-1 (ET1).
9. The method of any one of paragraphs 1-8, wherein the control subject does not have a coronavirus infection.
10. The method of any one of paragraphs 1-9, wherein the DEspR inhibitor is an anti-DEspR antibody or fragment thereof.
11. The method of paragraph 10, wherein the anti-DEspR antibody or fragment thereof comprises complementary determining regions selected from SEQ ID Nos: 1-3, 9-11, 17-19, 5-7, 13-15, 21-23, 25-27, 29-31, and 33-35.
12. A method of treating a subject having a coronavirus infection, the method comprising
    (i) determining whether the subject has a high risk of poor outcome or morbidity by detecting a level or rising level of DEspR+CD11b+ cells, a level of (1) non-resolving neutrophil-monocyte inflammatory amplification that blocks initiation of next step antiviral adaptive immunity, anti-viral cellular immunity, hyperinflammation-resolution, or a combination, measured as: DEspR+CD11b+ cells, (2) a level of hyperinflammation-response marked by elevated ratio DEspR+CD11b+ neutrophils to plasma cytokine storm biomarkers, or to plasma oxidative stress biomarkers or to endothelial dysfunction biomarker, or (3) a combination thereof, as individual or combinatorial measures in a sample obtained from the subject, wherein an elevated level of DEspR+CD11b+ cells, high ratios of DEspR+ neutrophils to COVID-19 associated elevated cytokines, elevated oxidative stress biomarkers, elevated endothelial activation biomarker levels, or a combination thereof in the sample obtained from the subject compared with a sample obtained from a control subject is an indicative that the subject has a high risk of poor outcome or morbidity, wherein the control subject does not have a coronavirus infection, and (ii) administering to the subject a DEspR inhibitor.

13. A method of improving a survival rate of a subject having a coronavirus infection, the method comprising
   (i) determining whether the subject has a high risk of poor outcome or morbidity by detecting a level or rising level of DEspR+CD11b+ cells, a level of (1) non-resolving neutrophil-monocyte inflammatory amplification that blocks initiation of next step anti-viral adaptive immunity, anti-viral cellular immunity, hyperinflammation-resolution, or a combination, measured as: DEspR+CD11b+ cells, (2) a level of hyperinflammation-response marked by elevated ratio DEspR+CD11b+ neutrophils to plasma cytokine storm biomarkers, or to plasma oxidative stress biomarkers or to endothelial dysfunction biomarker, or (3) a combination thereof, as individual or combinatorial measures in a sample obtained from the subject,
   wherein an elevated or rising level of DEspR+CD11b+ cells or hyperinflammation ratio-markers in the sample obtained from the subject compared with a level of DEspR+CD11b+ cells in a sample obtained from a control subject is indicative that the subject has a high risk of poor outcome or morbidity, wherein the control subject does not have a coronavirus infection, and
   (i) administering to the subject a DEspR inhibitor.

14. A method of determining prognosis of a subject having a coronavirus infection, the method comprising:
   detecting in a sample obtained from the subject a level of, or rising DEspR+CD11b+ cells, or DEspR-bound DNA, or a level of (1) non-resolving neutrophil-monocyte inflammatory amplification that blocks initiation of next step anti-viral adaptive immunity, anti-viral cellular immunity, hyperinflammation-resolution, or a combination, measured as: DEspR+CD11b+ neutrophils and monocytes, (2) a level of hyperinflammation-response marked by elevated ratio DEspR+CD11b+ neutrophils to plasma cytokine storm biomarkers, or to plasma oxidative stress biomarkers or to endothelial dysfunction biomarker, or (3) a combination thereof, as individual or combinatorial measures in a sample obtained from the subject,
   wherein an elevated or rising levels of DEspR+CD11b+ cells, plasma DEspR-bound DNA, high ratios of DEspR+ neutrophils to COVID-19 associated elevated cytokines, elevated oxidative stress biomarker, elevated endothelial activation biomarker level or a combination thereof in the sample obtained from the subject compared with a level of DEspR+CD11b+ neutrophils in a sample obtained from a control subject is an indicative that the subject has a high risk of poor outcome or morbidity, wherein the control subject does not have a coronavirus infection or is a coronavirus infection survivor.

15. The method of any one of paragraphs 12-14, wherein the DEspR+CD11b+ cells are DEspR+CD11b+ neutrophils, DEspR+CD11b+ monocytes, DEspR+CD11b+ lymphocytes, DEspR+CD11b+ cytoplasts, or a combination or an aggregate.

16. The method of any one of paragraphs 12-15, wherein the plasma cytokine storm biomarkers comprise IL-6, IL-8, IL-1β or IL-18, or a combination thereof.

17. The method of any one of paragraphs 12-16, wherein the plasma oxidative stress biomarkers comprise myeloperoxidase.

18. The method of any one of paragraphs 12-17, wherein the endothelial dysfunction biomarkers comprise endothelin-1.

19. The method of any one of paragraphs 12-18, wherein the COVID-19 associated elevated cytokines comprises IL-6, IL-8, IL-1β or IL-18, or a combination thereof.

20. The method of any one of paragraphs 12-19, wherein the elevated oxidative stress biomarkers comprise myeloperoxidase.

21. The method of any one of paragraphs 12-20, wherein the elevated endothelial activation biomarkers comprise endothelin-1.

22. The method of any one of paragraphs 12-21, wherein the level of DEspR+CD11b+ cells is detected by measuring a level of DEspR+CD11b+ aggregates in the blood sample.

23. The method of any one of paragraphs 12-22, wherein the level of DEspR+CD11b+ cells in the subject determines whether the subject will require intensive care.

24. A method of preventing or treating organ-dysfunction or multi-organ dysfunction or failure associated with a coronavirus infection in a subject in need thereof, wherein subject is determined to have elevated or rising levels of DEspR+CD11b+ cells, elevated hyperinflammation DEspR+ neutrophil-IL6/MPO/ET1 ratios, or a combination thereof, as compared to a control subject, the method comprising administering a DEspR inhibitor.

25. The method of paragraph 24, wherein the DEspR+CD11b+ cells are DEspR+CD11b+ neutrophils, DEspR+CD11b+ monocytes, DEspR+CD11b+ lymphocytes, DEspR+CD11b+ cytoplasts, or a combination or an aggregate.

26. The method of any one of paragraphs 24-25, wherein the organ-dysfunction or multi-organ dysfunction or failure associated with the coronavirus infection arises from microcirculatory dysfunction, microvascular inclusion, low flow ischemia, thromboses, systemic microthromboses, microcirculatory vascular aggregation, or a combination thereof.

27. The method of any one of paragraphs 24-26, wherein the organ-dysfunction or multi-organ dysfunction or failure associated with the coronavirus infection is derived from COVID19-induced cytokine storm, low flow organ ischemia from DEspR+CD11b+ aggregates leading to characteristic COVID19-severe hypoxemia, renal dysfunction, cardiac ischemia, neurological dysfunction, liver dysfunction/failure, hematological coagulopathy or microthromboses, or a combination thereof.
28. The method of paragraph 27, wherein the neurological dysfunction is characterized by loss of consciousness, seizures, confusion or a combination thereof.
29. The method of any one of paragraphs 24-28, wherein the organ-dysfunction or multi-organ dysfunction or failure associated with the coronavirus infection is selected from the group consisting of systemic inflammatory response syndrome (SIRS); acute lung injury (ALI); acute respiratory distress syndrome (ARDS); multi-organ failure or multi-organ dysfunction syndrome (MODS); acute kidney injury (AKI); and liver failure.
30. The method of any one of paragraphs 24-29, wherein the organ-dysfunction or multi-organ dysfunction or failure associated with the coronavirus infection is ARDS.
31. A method of combinational therapy for a subject having a coronavirus infection, the method comprising; administering to the subject a therapeutic agent or a therapy in combination with a DEspR inhibitor, wherein the therapeutic agent or the therapy prevents or alleviates a sign or a symptom associated with the coronavirus infection in the subject.
32. The method of paragraph 31, wherein the therapy is an application of a respiratory ventilation.
33. A method of reducing microthrombi formation associated with a coronavirus infection in a subject in need thereof, the method comprising:
administering to the subject a DEspR inhibitor, thereby reducing systemic microthrombi formation associated with the coronavirus infection in the subject.
34. The method of any one of paragraphs 12, 13, and 15-33, wherein the DEspR inhibitor is an anti-DEspR antibody or fragment thereof.
35. The method of paragraph 34, wherein the anti-DEspR antibody or fragment thereof comprises complementary determining regions selected from SEQ ID Nos: 1-3, 9-11, 17-19, 5-7, 13-15, 21-23, 25-27, 29-31, and 33-35.

Some embodiments of the technology described herein can be defined according to any of the following numbered paragraphs:
1. A method of treating a coronavirus infection in a subject, the subject determined to have elevated levels of DEspR+CD11b+ neutrophils as compared to a control subject, the method comprising administering a DEspR inhibitor to the subject.
2. The method of paragraph 1, wherein the coronavirus is COVID-19.
3. The method of paragraph 1, wherein the DEspR+CD11b+ neutrophils are at least 20, 30, 40, 50% of the whole neutrophil population.
4. The method of paragraph 1, wherein the subject is further determined to have an elevated neutrophil to lymphocyte ratio (NLR).
5. The method of paragraph 1, wherein the control subject control subject does not have a coronavirus infection.
6. The method of paragraph 1, wherein the DEspR inhibitor is an anti-DespR antibody or fragment thereof.
7. The method of paragraph 6, wherein the anti-DEspR antibody or fragment thereof comprises complementary determining regions selected from SEQ ID Nos: 1-3, 9-11, 17-19, 5-7, 13-15, 21-23, 25-27, 29-31, and 33-35.
8. A method of treating a subject having a coronavirus infection, the method comprising
    (i) determining whether the subject has a high risk of poor outcome or morbidity by detecting a level of DEspR+CD11b+ neutrophils in a sample obtained from the subject,
    wherein an elevated level of DEspR+CD11b+ neutrophils in the sample obtained from the subject compared with a level of DEspR+CD11b+ neutrophils in a sample obtained from a control subject is an indicative that the subject has a high risk of poor outcome or morbidity, wherein the control subject does not have a coronavirus infection, and
    (ii) administering to the subject a DEspR inhibitor.
9. A method of improving a survival rate of a subject having a coronavirus infection, the method comprising
    (i) determining whether the subject has a high risk of poor outcome or morbidity by detecting a level of DEspR+CD11b+ neutrophils in a sample obtained from the subject,
    wherein an elevated level of DEspR+CD11b+ neutrophils in the sample obtained from the subject compared with a level of DEspR+CD11b+ neutrophils in a sample obtained from a control subject is an indicative that the subject has a high risk of poor outcome or morbidity, wherein the control subject does not have a coronavirus infection, and
    (iii) administering to the subject a DEspR inhibitor.
10. A method of determining prognosis of a subject having a coronavirus infection, the method comprising:
    detecting a level of DEspR+CD11b+ neutrophils in a sample obtained from the subject,
    wherein an elevated level of DEspR+CD11b+ neutrophils in the sample obtained from the subject compared with a level of DEspR+CD11b+ neutrophils in a sample obtained from a control subject is an indicative that the subject has a high risk of poor outcome or morbidity, wherein the control subject does not have a coronavirus infection.
11. The method of any of paragraphs 8-10, wherein the level of DEspR+CD11b+ neutrophils is detected by measuring a level of DEspR+CD11b+ aggregates in the blood sample.
12. The method of paragraph 10, wherein the level of DEspR+CD11b+ neutrophils in the subject determines whether the subject will require intensive care.
13. A method of treating an organ-dysfunction or multi-organ dysfunction or failure associated with a coronavirus infection in a subject in need thereof, wherein subject is determined to have elevated levels of DEspR+CD11b+ neutrophils as compared to a control subject, the method comprising administering a DEspR inhibitor.
14. The method of paragraph 13, wherein the organ-dysfunction or multi-organ dysfunction or failure associated with the coronavirus infection comprises microthrombus formation.
15. The method of paragraph 13, wherein the organ-dysfunction or multi-organ dysfunction or failure associated with the coronavirus infection comprises organ-specific or multi-organ dysfunction or failure.
16. The method of paragraph 13, wherein the organ-dysfunction or multi-organ dysfunction or failure associated with the coronavirus infection is selected from the group consisting of systemic inflammatory response syndrome (SIRS); acute lung injury (ALI); acute respiratory distress syndrome (ARDS); multi-organ failure or multi-organ dysfunction syndrome (MODS); acute kidney injury (AKI); and liver failure.
17. The method of paragraph 13, wherein the organ-dysfunction or multi-organ dysfunction or failure associated with the coronavirus infection is ARDS.
18. A method of combinational therapy for a subject having a coronavirus infection, the method comprising; administering to the subject a therapeutic agent or a therapy in combination with a DEspR inhibitor, wherein the therapeutic agent or the therapy prevents or alleviates a sign or a symptom associated with the coronavirus infection in the subject.
19. The method of paragraph 18, wherein the therapy is an application of a respiratory ventilation.
20. A method of reducing microthrombus formation associated with a coronavirus infection in a subject in need thereof, the method comprising:
administering to the subject a DEspR inhibitor, thereby reducing the microthrombus formation associated with the coronavirus infection in the subject.

Some embodiments of the technology described herein can be defined according to any of the following numbered paragraphs:
1. A method of treating a coronavirus infection in a subject, the method comprising administering a therapeutically effective amount of a DEspR inhibitor to the subject.
2. The method of paragraph 1, wherein the subject is determined to have an elevated level of DEspR+ CD11b+ cells as compared to a non-infected subject.
3. The method of any one of paragraphs 1-2, wherein the administering is effective to treat COVID19 disease manifestations and complications beyond the coronavirus infectivity status in the subject.
4. The method of any one of paragraphs 1-3, wherein the coronavirus is SARS CoV2 causing COVID-19.
5. The method of any one of paragraphs 2-4, wherein the DEspR+CD11b+ cells are DEspR+CD11b+ neutrophils, DEspR+CD11b+ monocytes, DEspR+CD11b+ lymphocytes, DEspR+CD11 b+ cytoplasts, or DEspR+ DNA strands, or a combination or aggregate of any of the foregoing.
6. The method of any one of paragraphs 1-5, wherein the DEspR+CD11b+ cells are at least 20, 30, 40, 50, 60, 70, 80, 90, or 100% of the whole corresponding cell population.
7. The method of any one of paragraphs 1-6, wherein the subject is further determined to have an elevated DEspR+ neutrophil to lymphocyte ratio (d+NLR); elevated ratio of DEspR+ neutrophils to COVID19-associated (a) hyperinflammation cytokines or cytokine storm biomarkers, (b) oxidative stress biomarkers, (c) endothelial dysfunction biomarkers, or (d) a combination thereof, or a combination thereof.
8. The method of any one of paragraphs 1-7, wherein the hyperinflammation cytokines or cytokine storm biomarkers comprise IL-6, IL-8, IL-1β, or IL-18, or a combination thereof.
9. The method of any one of paragraphs 1-8, wherein the oxidative stress biomarkers comprise myeloperoxidase (MPO).
10. The method of any one of paragraphs 1-9, wherein the endothelial dysfunction biomarkers comprise endothelin-1 (ET1).
11. The method of any one of paragraphs 1-10, wherein the non-infected subject does not have a coronavirus infection.
12. The method of any one of paragraphs 1-11, wherein the DEspR inhibitor is an anti-DEspR antibody reagent or fragment thereof.
13. The method of paragraph 12, wherein the anti-DEspR antibody reagent or fragment thereof comprises complementary determining regions selected from SEQ ID Nos: 1-3, 9-11, 17-19, 5-7, 13-15, 21-23, 25-27, 29-31, and 33-35.
14. The method of paragraph 12, wherein the anti-DEspR antibody reagent or fragment thereof comprises 6 complementary determining regions selected from SEQ ID Nos: 1-3, 9-11, 17-19, 5-7, 13-15, 21-23, 25-27, 29-31, and 33-35.
15. The method of paragraph 12, wherein the anti-DEspR antibody reagent or fragment thereof comprises 6 complementary determining regions selected from:
SEQ ID Nos: 1-3 and 9-11; SEQ ID Nos: 1-3 and 17-19; SEQ ID Nos: 5-7 and 13-15; SEQ ID Nos: 21-23 and 25-27; and SEQ ID Nos: 29-31 and 33-35.
16. A method of treating a subject having a coronavirus infection, the method comprising
(i) determining whether the subject has a high risk of poor outcome or morbidity by detecting a level or rising level of DEspR+CD11b+ cells, a level of (1) non-resolving neutrophil-monocyte inflammatory amplification that blocks initiation of next step anti-viral adaptive immunity, anti-viral cellular immunity, resolution, or a combination, measured as: DEspR+CD11b+ cells, (2) a level of hyperinflammation-response marked by elevated ratio DEspR+ CD11b+ neutrophils to plasma cytokine storm biomarkers, or to plasma oxidative stress biomarkers or to endothelial dysfunction biomarkers, or (3) a combination thereof, as individual or combinatorial measures in a sample obtained from the subject,
wherein an elevated level of DEspR+CD11b+ cells, high ratios of DEspR+ neutrophils to COVID-19 associated elevated cytokines, elevated oxidative stress biomarkers, elevated endothelial activation biomarker levels, or a combination thereof in the sample obtained from the subject compared with a sample obtained from a control subject is an indicative that the subject has a high risk of poor outcome or morbidity, wherein the control subject does not have a coronavirus infection, and
(ii) administering to the subject a DEspR inhibitor.
17. A method of treating a subject having a coronavirus infection in a subject in need thereof, the method comprising administering a DEspR inhibitor to a subject determined to have:
i) an elevated level or rising level of DEspR+CD11b+ cells, or
ii) an elevated level of (1) non-resolving neutrophil-monocyte inflammatory amplification that blocks initiation of next step anti-viral adaptive immunity, anti-viral cellular immunity, resolution, or a combination, measured as: DEspR+CD11b+ cells, (2) a level of hyperinflammation-response marked by elevated ratio DEspR+CD11b+ neutrophils to plasma cytokine storm biomarkers, or to plasma oxidative stress biomarkers or to endothelial dysfunction biomarkers, or (3) a combination thereof, as individual or combinatorial measures in a sample obtained from the subject, and as compared to the level in a control subject not having a coronavirus infection.

18. A method of determining whether a subject with coronavirus infection has a high risk of poor outcome or morbidity and/or is likely to respond to treatment with a DEspR inhibitor, the method comprising:
    detecting:
    i) a level or rising level of DEspR+CD11b+ cells; or
    ii) a level of (1) non-resolving neutrophil-monocyte inflammatory amplification that blocks initiation of next step anti-viral adaptive immunity, anti-viral cellular immunity, resolution, or a combination, measured as: DEspR+CD11b+ cells, (2) a level of hyperinflammation-response marked by elevated ratio DEspR+CD11b+ neutrophils to plasma cytokine storm biomarkers, or to plasma oxidative stress biomarkers or to endothelial dysfunction biomarkers, or (3) a combination thereof,
    as individual or combinatorial measures in a sample obtained from the subject;
    wherein an elevated level of DEspR+CD11b+ cells, high ratios of DEspR+ neutrophils to COVID-19 associated elevated cytokines, elevated oxidative stress biomarkers, elevated endothelial activation biomarker levels, or a combination thereof in the sample obtained from the subject compared with a sample obtained from a control subject is an indicative that the subject has a high risk of poor outcome or morbidity and/or that the subject is likely to respond to treatment with a DEspR inhibitor; wherein the control subject does not have a coronavirus infection.

19. A method of improving a survival rate of a subject having a coronavirus infection, the method comprising
    (i) determining whether the subject has a high risk of poor outcome or morbidity by detecting a level or rising level of DEspR+CD11b+ cells, a level of (1) non-resolving neutrophil-monocyte inflammatory amplification that blocks initiation of next step anti-viral adaptive immunity, anti-viral cellular immunity, resolution, or a combination, measured as: DEspR+CD11b+ cells, (2) a level of hyperinflammation-response marked by elevated ratio DEspR+CD11b+ neutrophils to plasma cytokine storm biomarkers, or to plasma oxidative stress biomarkers or to endothelial dysfunction biomarker, or (3) a combination thereof, as individual or combinatorial measures in a sample obtained from the subject,
    wherein an elevated or rising level of DEspR+CD11b+ cells or hyperinflammation ratio-markers in the sample obtained from the subject compared with a level of DEspR+CD11b+ cells in a sample obtained from a control subject is indicative that the subject has a high risk of poor outcome or morbidity, wherein the control subject does not have a coronavirus infection, and
    (iii) administering to the subject a DEspR inhibitor.

20. A method of determining prognosis of a subject having a coronavirus infection, the method comprising:
    detecting in a sample obtained from the subject a level of, or rising DEspR+CD11b+ cells, or DEspR-bound DNA, or a level of (1) non-resolving neutrophil-monocyte inflammatory amplification that blocks initiation of next step anti-viral adaptive immunity, anti-viral cellular immunity, resolution, or a combination, measured as: DEspR+CD11b+ neutrophils and monocytes, (2) a level of hyperinflammation-response marked by elevated ratio DEspR+CD11 b+ neutrophils to plasma cytokine storm biomarkers, or to plasma oxidative stress biomarkers or to endothelial dysfunction biomarker, or (3) a combination thereof, as individual or combinatorial measures in a sample obtained from the subject,
    wherein an elevated or rising levels of DEspR+CD11b+ cells, plasma DEspR-bound DNA, high ratios of DEspR+ neutrophils to COVID-19 associated elevated cytokines, elevated oxidative stress biomarker, elevated endothelial activation biomarker level or a combination thereof in the sample obtained from the subject compared with a level of DEspR+CD11b+ neutrophils in a sample obtained from a control subject is an indicative that the subject has a high risk of poor outcome or morbidity, wherein the control subject does not have a coronavirus infection.

21. The method of any one of paragraphs 16-20, wherein the DEspR+CD11b+ cells are DEspR+CD11b+ neutrophils, DEspR+CD11b+ monocytes, DEspR+CD11b+ lymphocytes, DEspR+CD11b+ cytoplasts or a combination, an aggregate, or DEspR+ DNA strands.

22. The method of any one of paragraphs 16-21, wherein the plasma cytokine storm biomarkers comprise IL-6, IL-8, IL-1β, IL-18, or a combination thereof.

23. The method of any one of paragraphs 16-22, wherein the plasma oxidative stress biomarkers comprise myeloperoxidase.

24. The method of any one of paragraphs 16-23, wherein the endothelial dysfunction biomarkers comprise endothelin-1.

25. The method of any one of paragraphs 16-24, wherein the COVID-19 associated elevated cytokines comprises IL-6, IL-8, IL-1β, or IL-18, or a combination thereof.

26. The method of any one of paragraphs 16-25, wherein the elevated oxidative stress biomarkers comprise myeloperoxidase.

27. The method of any one of paragraphs 16-26, wherein the elevated endothelial activation biomarkers comprise endothelin-1.

28. The method of any one of paragraphs 16-27, wherein the level of DEspR+CD11b+ cells is detected by measuring a level of DEspR+CD11b+ aggregates or DEspR+ DNA strands in a blood sample.

29. The method of any one of paragraphs 16-28, wherein an elevated or rising level of DEspR+CD11b+ cells in the subject indicates the subject will require intensive care.

30. A method of preventing or treating organ-dysfunction or multi-organ dysfunction or failure associated with a coronavirus infection in a subject in need thereof, the method comprising administering a therapeutically effective amount of a DEspR inhibitor to the subject.

31. The method of paragraph 30, subject is a subject determined to have elevated or rising levels of DEspR+CD11b+ cells, elevated hyperinflammation DEspR+ neutrophil-IL6/MPO/ET1 ratios, or a combination thereof, as compared to a control subject.

32. The method of any one of paragraphs 30-31, wherein the DEspR+CD11b+ cells are DEspR+CD11b+ neutrophils, DEspR+CD11b+ monocytes, DEspR+CD11b+ lymphocytes, DEspR+CD11b+ cytoplasts or a combination, an aggregate, or DEspR+ DNA strands.

33. The method of any one of paragraphs 30-32, wherein the organ-dysfunction or multi-organ dysfunction or failure associated with the coronavirus infection arises from microcirculatory dysfunction, microvascular inclusion, low flow ischemia, thromboses, systemic microthromboses, microcirculatory vascular aggregation, or a combination thereof.

34. The method of any one of paragraphs 30-33, wherein the organ-dysfunction or multi-organ dysfunction or failure associated with the coronavirus infection is derived from COVID19-induced cytokine storm, low flow organ ischemia from DEspR+CD11b+ aggregates leading to characteristic COVID19-hypoxemia, renal dysfunction, cardiac ischemia, neurological dysfunction from low flow ischemia or delayed cerebral ischemia or neuroinflammation, liver dysfunction/failure, hematological coagulopathy or microthromboses, or a combination thereof.

35. The method of paragraph 34, wherein the neurological dysfunction is characterized by loss of consciousness, seizures, confusion, or a combination thereof.

36. The method of any one of paragraphs 30-35, wherein the organ-dysfunction or multi-organ dysfunction or failure associated with the coronavirus infection is selected from the group consisting of systemic inflammatory response syndrome (SIRS); acute lung injury (ALI); acute respiratory distress syndrome (ARDS); multi-organ failure or multi-organ dysfunction syndrome (MODS); acute kidney injury (AKI); liver failure, ischemic stroke; delayed cerebral ischemia, and/or encephalopathy.

37. The method of any one of paragraphs 30-36, wherein the organ-dysfunction or multi-organ dysfunction or failure associated with the coronavirus infection is ARDS.

38. A method of combinational therapy for a subject having a coronavirus infection, the method comprising; administering to the subject a therapeutic agent or a therapy in combination with a DEspR inhibitor, wherein the therapeutic agent or the therapy prevents or alleviates a sign or a symptom associated with the coronavirus infection in the subject.

39. The method of paragraph 38, wherein the therapy is an application of a respiratory ventilation, or an alternative delivery system for supplemental oxygen.

40. A method of reducing microthrombi formation associated with a coronavirus infection in a subject in need thereof, the method comprising:
administering to the subject a DEspR inhibitor, thereby reducing systemic microthrombi formation associated with the coronavirus infection in the subject.

41. The method of paragraph 40, further comprising administering one or more anti-thrombotic-.

42. The method of any one of paragraphs 16-41, wherein the DEspR inhibitor is an anti-DEspR antibody reagent or fragment thereof.

43. The method of paragraph 42, wherein the anti-DEspR antibody reagent or fragment thereof comprises complementary determining regions selected from SEQ ID Nos: 1-3, 9-11, 17-19, 5-7, 13-15, 21-23, 2527, 29-31, and 33-35.

44. The method of paragraph 42, wherein the anti-DEspR antibody reagent or fragment thereof comprises 6 complementary determining regions selected from SEQ ID Nos: 1-3, 9-11, 17-19, 5-7, 13-15, 21-23, 25-27, 29-31, and 33-35.

45. The method of paragraph 42, wherein the anti-DEspR antibody reagent or fragment thereof comprises 6 complementary deteriminig regions selected from:

SEQ ID Nos: 1-3 and 9-11; SEQ ID Nos: 1-3 and 17-19; SEQ ID Nos: 5-7 and 13-15; SEQ ID Nos: 21-23 and 25-27; and SEQ ID Nos: 29-31 and 33-35.

46. A DEspR inhibitor for use in a method of: treating a coronavirus infection in a subject, or preventing or treating organ-dysfunction or multi-organ dysfunction or failure associated with a coronavirus infection in a subject, the method comprising administering a therapeutically effective amount of the DEspR inhibitor to the subject.

47. A combination of a DEspR inhibitor and an anti-thrombotic for use in a method of: treating a coronavirus infection in a subject, or preventing or treating organ-dysfunction or multi-organ dysfunction or failure associated with a coronavirus infection in a subject, or reducing systemic microthrombi formation associated with a coronavirus infection is a subject, the method comprising administering a therapeutically effective amount of the DEspR inhibitor and the anti-thrombotic to the subject.

48. The DEspR inhibitor or combination of any of paragraphs paragraph 46-47, wherein the coronavirus is SARS CoV2 causing COVID-19.

49. The DEspR inhibitor or combination of any one of paragraphs 46-48, wherein the subject is determined to have an elevated or rising level of DEspR+CD11b+ cells as compared to a non-infected subject and/or the method comprises a first step of determining if the subject has an elevated level of DEspR+CD11b+ cells as compared to a non-infected subject.

50. The DEspR inhibitor or combination of paragraph 49, wherein the DEspR+CD11b+ cells are DEspR+CD11b+ neutrophils, DEspR+CD11b+ monocytes, DEspR+CD11b+ lymphocytes, DEspR+CD11 b+ cytoplasts, or DEspR+ DNA strands, or a combination or aggregate of any of the foregoing.

51. The DEspR inhibitor or combination of any one of paragraphs 49-50, wherein the level of DEspR+CD11b+ cells is determined by measuring a level of DEspR+CD11b+ aggregates or DEspR+ DNA strands in a blood sample.

52. The DEspR inhibitor or combination of any one of paragraphs 49-51, wherein the DEspR+CD11b+ cells are at least 20, 30, 40, 50, 60, 70, 80, 90, or 100% of the whole corresponding cell population.

53. The DEspR inhibitor or combination of any one of paragraphs 46-52, wherein the subject is determined to have and/or the method comprises a first step of determining if the subject has an elevated DEspR+ neutrophil to lymphocyte ratio (d+NLR); elevated ratio of DEspR+ neutrophils to COVID19-associated (a) hyperinflammation cytokines or cytokine storm biomarkers, (b) oxidative stress biomarkers, (c) endothelial dysfunction biomarkers, or (d) a combination thereof, or a combination thereof.

54. The DEspR inhibitor or combination of paragraph 53, wherein the hyperinflammation cytokines or cytokine storm biomarkers comprise IL-6, IL-8, IL-1β, or IL-18, or a combination thereof.

55. The DEspR inhibitor or combination of any one of paragraphs 53-54, wherein the oxidative stress biomarkers comprise myeloperoxidase (MPO).

56. The DEspR inhibitor or combination of any one of paragraphs 53-55, wherein the endothelial dysfunction biomarkers comprise endothelin-1 (ET1).

57. The DEspR inhibitor or combination of any one of paragraphs 53-56, wherein the non-infected subject does not have a coronavirus infection.
58. The DEspR inhibitor or combination of any one of paragraphs 53-57, wherein the DEspR inhibitor is an anti-DEspR antibody reagent or fragment thereof.
59. The DEspR inhibitor or combination of paragraph 58, wherein the anti-DEspR antibody reagent or fragment thereof comprises complementary determining regions selected from SEQ ID Nos: 1-3, 9-11, 17-19, 5-7, 13-15, 21-23, 25-27, 29-31, and 33-35.
60. The DEspR inhibitor or combination of paragraph 58, wherein the anti-DEspR antibody reagent or fragment thereof comprises 6 complementary deterimining regions selected from SEQ ID Nos: 1-3, 9-11, 17-19, 5-7, 13-15, 21-23, 25-27, 29-31, and 33-35.
61. The DEspR inhibitor or combination of paragraph 58, wherein the anti-DEspR antibody reagent or fragment thereof comprises 6 complementary deterimining regions selected from:
    SEQ ID Nos: 1-3 and 9-11; SEQ ID Nos: 1-3 and 17-19; SEQ ID Nos: 5-7 and 13-15; SEQ ID Nos: 21-23 and 25-27; and SEQ ID Nos: 29-31 and 33-35.
62. The DEspR inhibitor or combination of any of paragraphs 46-61, wherein the method further comprises administering to the subject a therapeutic agent or a therapy that prevents or alleviates a sign or a symptom associated with the coronavirus infection in the subject.

Some embodiments of the technology described herein can be defined according to any of the following numbered paragraphs:

1. A method of treating a coronavirus infection in a subject, the method comprising administering a therapeutically effective amount of a DEspR inhibitor to the subject.
2. The method of paragraph 1, wherein the subject is determined to have an elevated level of DEspR+CD11b+ cells as compared to a non-infected subject.
3. The method of paragraph 1, wherein the administering is effective to treat COVID19 disease manifestations and complications beyond the coronavirus infectivity status in the subject.
4. The method of paragraph 1, wherein the coronavirus is SARS CoV2 causing COVID-19.
5. The method of paragraph 2, wherein the DEspR+CD11b+ cells are DEspR+CD11b+ neutrophils, DEspR+CD11b+ monocytes, DEspR+CD11b+ lymphocytes, DEspR+CD11b+ cytoplasts, or DEspR+ DNA strands, or a combination or aggregate of any of the foregoing.
6. The method of paragraph 1, wherein the subject is further determined to have an elevated DEspR+ neutrophil to lymphocyte ratio (d+NLR); elevated ratio of DEspR+ neutrophils to COVID19-associated (a) hyperinflammation cytokines or cytokine storm biomarkers, (b) oxidative stress biomarkers, (c) endothelial dysfunction biomarkers, or (d) a combination thereof, or a combination thereof.
7. The method of paragraph 6, wherein the hyperinflammation cytokines or cytokine storm biomarkers comprise IL-6, IL-8, IL-1β, or IL-18, or a combination thereof.
8. The method of paragraph 6, wherein the oxidative stress biomarkers comprise myeloperoxidase (MPO).
9. The method of paragraph 6, wherein the endothelial dysfunction biomarkers comprise endothelin-1 (ET1).
10. The method of paragraph 1, wherein the DEspR inhibitor is an anti-DEspR antibody reagent or fragment thereof.
11. The method of paragraph 10, wherein the anti-DEspR antibody reagent or fragment thereof comprises complementary determining regions selected from SEQ ID Nos: 1-3, 9-11, 17-19, 5-7, 13-15, 21-23, 25-27, 29-31, and 33-35.
12. The method of paragraph 10, wherein the anti-DEspR antibody reagent or fragment thereof comprises 6 complementary determining regions selected from SEQ ID Nos: 1-3, 9-11, 17-19, 5-7, 13-15, 21-23, 25-27, 29-31, and 33-35.
13. The method of paragraph 10, wherein the anti-DEspR antibody reagent or fragment thereof comprises 6 complementary determining regions selected from:
    SEQ ID Nos: 1-3 and 9-11; SEQ ID Nos: 1-3 and 17-19; SEQ ID Nos: 5-7 and 13-15; SEQ ID Nos: 21-23 and 25-27; and SEQ ID Nos: 29-31 and 33-35.
14. A method of treating a subject having a coronavirus infection in a subject in need thereof, the method comprising administering a DEspR inhibitor to a subject determined to have:
    ii) an elevated level or rising level of DEspR+CD11b+ cells, or
    ii) an elevated level of (1) non-resolving neutrophil-monocyte inflammatory amplification that blocks initiation of next step anti-viral adaptive immunity, anti-viral cellular immunity, resolution, or a combination, measured as: DEspR+CD11b+ cells, (2) a level of hyperinflammation-response marked by elevated ratio DEspR+CD11b+ neutrophils to plasma cytokine storm biomarkers, or to plasma oxidative stress biomarkers or to endothelial dysfunction biomarkers, or (3) a combination thereof,
    as individual or combinatorial measures in a sample obtained from the subject, and as compared to the level in a control subject not having a coronavirus infection.
15. The method of paragraph 14, wherein the DEspR+CD11b+ cells are DEspR+CD11b+ neutrophils, DEspR+CD11b+ monocytes, DEspR+CD11b+ lymphocytes, DEspR+CD11b+ cytoplasts or a combination, an aggregate, or DEspR+ DNA strands.
16. The method of paragraph 14, wherein the level of DEspR+CD11b+ cells is detected by measuring a level of DEspR+CD11b+ aggregates or DEspR+ DNA strands in a blood sample.
17. The method of paragraph 14, wherein an elevated or rising level of DEspR+CD11b+ cells in the subject indicates the subject will require intensive care.
18. A method of preventing or treating organ-dysfunction or multi-organ dysfunction or failure associated with a coronavirus infection in a subject in need thereof, the method comprising administering a therapeutically effective amount of a DEspR inhibitor to the subject.
19. The method of paragraph 18, subject is a subject determined to have elevated or rising levels of DEspR+CD11b+ cells, elevated hyperinflammation DEspR+ neutrophil-IL6/MPO/ET1 ratios, or a combination thereof, as compared to a control subject.
20. The method of paragraph 18, wherein the DEspR+CD11b+ cells are DEspR+CD11b+ neutrophils, DEspR+CD11b+ monocytes, DEspR+CD11b+ lymphocytes, DEspR+CD11b+ cytoplasts or a combination, an aggregate, or DEspR+ DNA strands.
21. The method of paragraph 18, wherein the organ-dysfunction or multi-organ dysfunction or failure associated with the coronavirus infection arises from microcirculatory dysfunction, microvascular inclusion, low flow ischemia, thromboses, systemic microthromboses, microcirculatory vascular aggregation, or a combination thereof.

22. The method of paragraph 18, wherein the organ-dysfunction or multi-organ dysfunction or failure associated with the coronavirus infection is derived from COVID19-induced cytokine storm, low flow organ ischemia from DEspR+CD11 b+ aggregates leading to characteristic COVID19-hypoxemia, renal dysfunction, cardiac ischemia, neurological dysfunction from low flow ischemia or delayed cerebral ischemia or neuroinflammation, liver dysfunction/failure, hematological coagulopathy or microthromboses, or a combination thereof.

23. The method of paragraph 22, wherein the neurological dysfunction is characterized by loss of consciousness, seizures, confusion, or a combination thereof.

24. The method of paragraph 18, wherein the organ-dysfunction or multi-organ dysfunction or failure associated with the coronavirus infection is selected from the group consisting of systemic inflammatory response syndrome (SIRS); acute lung injury (ALI); acute respiratory distress syndrome (ARDS); multi-organ failure or multi-organ dysfunction syndrome (MODS); acute kidney injury (AKI); liver failure, ischemic stroke; delayed cerebral ischemia, and/or encephalopathy.

25. The method of paragraph 18, wherein the organ-dysfunction or multi-organ dysfunction or failure associated with the coronavirus infection is ARDS.

26. A method of combinational therapy for a subject having a coronavirus infection, the method comprising; administering to the subject a therapeutic agent or a therapy in combination with a DEspR inhibitor, wherein the therapeutic agent or the therapy prevents or alleviates a sign or a symptom associated with the coronavirus infection in the subject.

27. The method of paragraph 26, wherein the therapy is an application of a respiratory ventilation, or an alternative delivery system for supplemental oxygen.

The technology described herein is further illustrated by the following examples which in no way should be construed as being further limiting.

EXAMPLES

Example 1: Anti-DEspR Therapy

This invention relates to anti-DEspR technologies to treat coronavirus infection or signs or symptoms associated with a coronavirus infection or pathologies associated with coronavirus infection. The anti-DEspR technologies inhibit or abrogate the extended survival mechanisms in activated neutrophils ($IC_{50}$<8 nM) thus inhibiting all activated neutrophil activity that drives and reciprocally interacts with other cell players towards a maladaptive pathogenic cascade. The actPMN-driven pathogenic cascade results in a rapid feed-forward reciprocal interaction toward disease progression, and subsequent debilitating sequelae or death.

This invention further relates to compositions comprising DEspR-inhibiting compounds and methods of using these DEspR-inhibiting compounds for the treatment of conditions or diseases that involve pathogenic cascades associated with coronavirus infection.

Neutrophils are polymorphic nuclear cells (PMCs) with 2-5 lobes in their nucleus, and are the most abundant type of white blood cells in humans. Under physiologic conditions, neutrophils are constitutively apoptotic with short circulating half-life of 6-8 hrs. Upon activation as occurs in inflammation, neutrophils have extended survival or delayed apoptosis (beyond 1-2 days) in order to fulfill their vital roles in defending the host against invading pathogens. Neutrophils are first-responders in innate immunity and within minutes localize to sites of injury or infection. They are the hallmark of inflammation capable of 1) killing bacteria upon release of radical oxygen species, protease, myeloperoxidase, elastase; as well as capable of 2) trapping bacteria physically and killing them in neutrophil extracellular traps (NETs)—"web-like structures made up of decondensed chromatin fibers 15-17 nm diameters, histones and DNA containing antimicrobial enzymes."

However, the very same bacterial killing mechanisms can result in maladaptive pathogenic cascades that cause organ-dysfunction or multi-organ dysfunction or failure associated with a coronavirus infection directly (much like killing bacteria), the neutrophil paradox. Moreover, the activated neutrophil's maladaptive effects are expanded by crosstalk between activated neutrophils and other cells (lymphocytes, antigen-presenting cells, endothelial cells, cancer cells) through mediators such as cytokines, setting up feed-forward reciprocal interactions. The very same NETs can cause thrombosis—as seen in deep vein thrombosis and in microthrombosis as well as in atherosclerotic thrombosis.

Activated neutrophil-mediated mechanisms underlying organ-dysfunction or multi-organ dysfunction or failure associated with a coronavirus infection can drive pathogenic cascades in different organ system diseases associated with coronavirus infection, such as the following examples (not all inclusive): the lungs in acute lung injury (ALI) and acute respiratory distress syndrome (ARDS), in hemorrhagic transformation in stroke, in chronic kidney disease, in aggressive cancer and metastasis (e.g., high neutrophil counts (high neutrophil-to-lymphocyte ratios, NLR) are associated with poor clinical outcome in multiple human cancer types: pancreatic ductal adenocarcinoma, hepatocellular, colorectal, renal, non-small cell lung cancer melanoma, gastric, glioblastoma, and head and neck cancers. Neutrophils are active players in tumor progression and promote aggressive tumor growth with epithelial to mesenchymal transition and increased metastatic potential, seen in pancreatic ductal adenocarcinoma, breast and colorectal cancers), thrombosis through NETosis (e.g., NETS promote thrombosis by providing a scaffold for platelet and RBC adhesion and aggregation and enhancing coagulation. NETosis associated thrombi and NETosis markers correlate with thrombotic diseases activity as reported in thrombotic microangiopathies in cancer, deep vein thrombosis, and in atherothrombosis), in diabetes poor wound healing, in several pulmonary diseases (e.g., the detrimental effect of excessive NET release is particularly important to lung diseases, because NETs can expand more easily in the pulmonary alveoli, causing lung injury. Moreover, NETs and its associated molecules are able to directly induce epithelial and endothelial cell death. In this regard, massive NET formation has been reported in several pulmonary diseases, including asthma, chronic obstructive pulmonary disease, cystic fibrosis, respiratory syncytial virus bronchiolitis, influenza, bacterial pneumonia, and tuberculosis, among others. Thus, NET formation must be tightly regulated in order to avoid NET-mediated tissue damage), and in Alzheimer's Disease.

Because of the rapid pace of activated neutrophil-driven pathogenic cascade associated with coronavirus infection, a quick-response therapy is needed as provided, e.g., by anti-DEspR humab therapy as described herein. Just as anti-DEspR decreases survival of CSCs, anti-DEspR abrogates the extended survival in activated neutrophils, hence preventing maladaptive excessive neutrophil-mediated organ-dysfunction or multi-organ dysfunction or failure associated with a coronavirus infection and NET-mediated pathogenic cascades associated with coronavirus infection.

Figure 3:
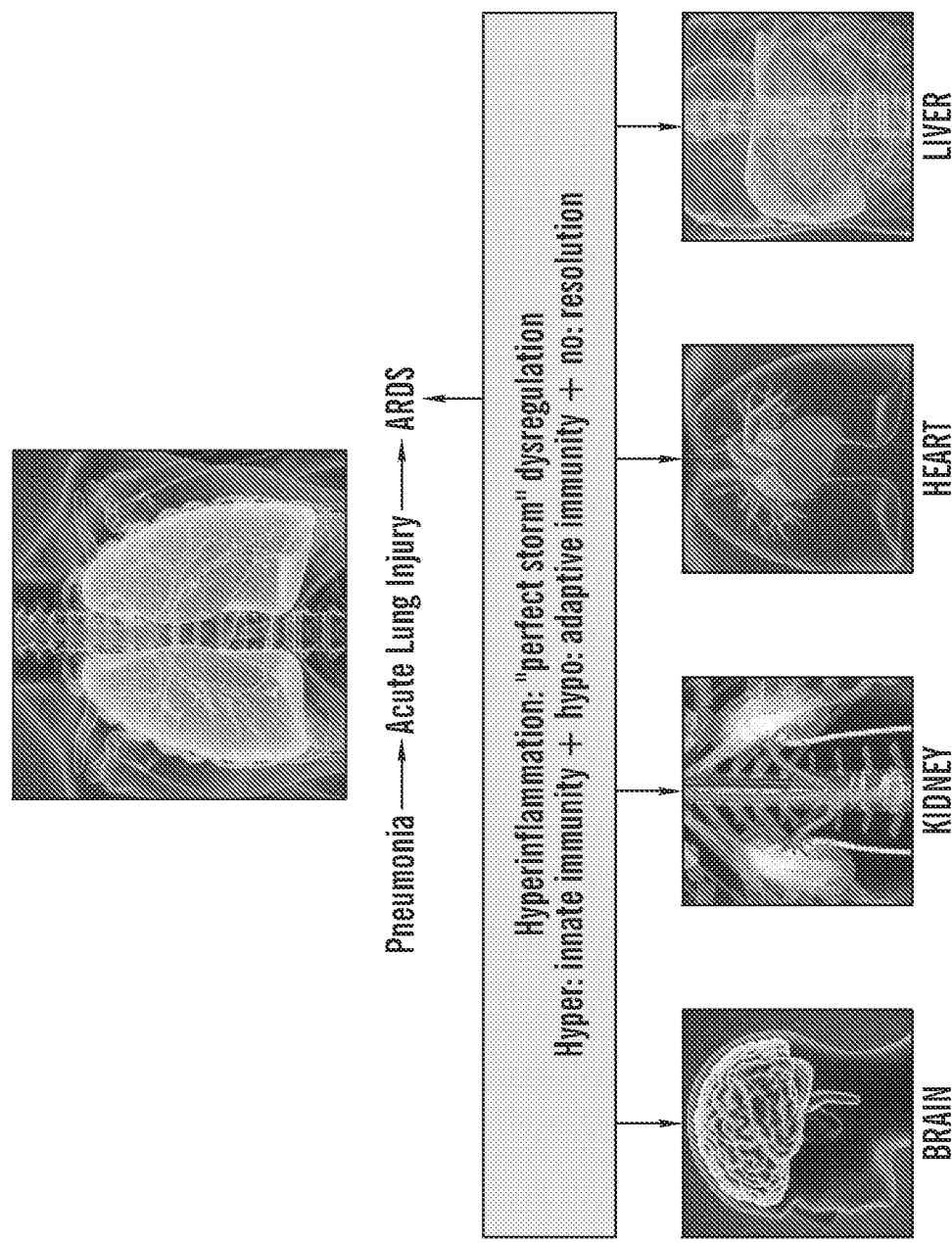
FIG. 3 depicts acute respiratory distress syndrome (ARDS)-multi organ failure associated with coronavirus infection.

ARDS-multi-organ failure associated with coronavirus infection, for example, organ-dysfunction or multi-organ dysfunction or failure associated with a coronavirus infection (FIG. 3), is characterized by low survival, yet no therapy is available. A common feature in each of the indications is that an insult, injury, or "reaction" in a chronic condition initiates an inflammatory cascade which recruits neutrophils to the target organ and leads to increased unchecked activated neutrophils. Modern medicine can often control and alleviate the underlying trigger of the pathology but cannot control the damage causing inflammatory cascade once initiated. Exemplary organ-dysfunction or multi-organ dysfunction or failure associated with a coronavirus infection in CNS includes, but is not limited to, spontaneous ICH, traumatic brain injury, hemorrhagic transformation. Exemplary organ-dysfunction or multi-organ dysfunction or failure associated with a coronavirus infection in lung includes, but is not limited to, ARDS, COPD, and neutrophilic asthma. Exemplary organ-dysfunction or multi-organ dysfunction or failure associated with a coronavirus infection in heart includes, but is not limited to, non-reflow AMI (acute myocardial infarction) and MACE (major adverse cardiovascular events). Exemplary organ-dysfunction or multi-organ dysfunction or failure associated with a coronavirus infection in kidney includes, but is not limited to, CKD (chronic kidney disease) proteinuria, AKI (acute kidney injury) (sepsis), and AKI (acute kidney injury) (trauma).

In US, EU, and UK, patient cohort is increasing. Patients with coronavirus, e.g., COVID19, infection require longer ICU days, and exhibit approximately 33-40% mortality. The survivors also show long-term disability, hence. Hence, increased health care challenges have been raised.

Secondary organ-dysfunction or multi-organ dysfunction or failure is driven by a subset of activated neutrophils causing morbidity and mortality in many major indications, including respiratory pathologies such COVID19 infection, ARDS, and pathologies characterized by decline associated with elevated neutrophil to lymphocyte ratio, such as intracerebral hemorrhage (sICH), Sepsis, TBI, CKD, AKI and MACE. Secondary (2°) organ-dysfunction or multi-organ dysfunction or failure associated with a coronavirus infection mediated by act-$N^{DEspR+/CD11b+}$ neutrophils drives morbidity and mortality in multiple major indications that have little to no therapeutic intervention. DEspR+ actN are significantly increased in human clinical samples taken from patients with ARDS progressing to death or with poor outcomes; initial findings show similar associations in sICH and COVID19 driven ARDS.

Exemplary secondary organ-dysfunction or multi-organ dysfunction or failure associated with a coronavirus infection after primary infection includes, but is not limited to, lung damage, heart damage, and organ failure, and needs for ventilation. In some embodiments, ventilators use in COVID19 may be up to 14 days. In some embodiments, additional target tissues affected by ARDS-COVID includes liver function as well. Overall survival and rates of progression COVID19-ARDS patients indicate that 2050% of COVID19-ARDS patients progress to death. Clinical deterioration/recovery quantifiable by a variety of organ measurements such as lung function. Exemplary serum markers for rapid, quantitative assessment include, but is not limited to, myeloperoxidase (MPO), neutrophil elastase (NE), and neutrophil/lymphocyte ratio (NLR).

In some embodiments, disclosed herein is a novel receptor, DEspR, which drives a population of activated neutrophils to become apoptotic resistant, often NETosing, going from repair and resolution to producing secondary organ-dysfunction or multi-organ dysfunction or failure associated with a coronavirus infection.

Anti-DEspR re-engages the neutrophil's apoptosis mechanisms by blocking STAT3-mediated upregulation of Mcl1, as well as causes decreased Mell. Mcl1 is implicated in the extended survival of activated neutrophils, which in the quiescent state are constitutively apoptotic. By inducing apoptosis of activated neutrophils (which are phagocytosed by macrophages), anti-DEspR prevents the pathogenic cascade of neutrophil-mediated organ-dysfunction or multi-organ dysfunction or failure associated with a coronavirus infection (via proteases, cathepsin G, proteinase 3, myeloperoxidase). Prevention of activated neutrophil progression to NETosis, thus prevents NET-mediated pathogenic cascades associated with coronavirus infection. Anti-DEspR can also be used as a targeting moiety for nanoconjugates/drug conjugates targeting activated neutrophil infiltrates, circulating neutrophils, and NETs in the circulation or in tissues (e.g., lungs, joints, muscle, heart, etc) or in pathologies (e.g., thrombus, tumors, ulcers, wounds).

DEspR (Dual EndothelinI-signal peptide Receptor) is a stress survival receptor in activated neutrophils (survival extension=dysregulation or "rogue") (FIG. 1). DEspR is a novel cell surface receptor conferring cell survival through MCL1 and CIAP2. DEspR, also known as "FBXW7-AS1 non-coding RNA" remains mostly unstudied due to the annotation in public databases. DEspR transcript is a target of ADAR1 RNA editing. DEspR is expressed by cells under stress (anoikis), DAMPS-activated TLR-4, or stabilized Hif1a (e.g., subset of activated neutrophils, angiogenic endothelial cells, invasive solid tumor cells and CSCs, including pancreatic, breast, colorectal, NSCLC, bladder, ovarian, prostate and gastric cancers, glioblastoma, and tumor associated neutrophils. Ligand binding of DEspR significantly increases survival of human cells expressing it by increasing expression of survival proteins MCL1 and CIAP2 (BIRC3) and/or decreasing degradations of proteins such as MCL1 through downregulating FBXW7. mAb binding to DEspR reduces survival of human cells expressing it by decreasing expression of survival proteins Mcl1 and CIAP2 (BIRC3) and/or increasing expression of pro-apoptotic genes Apaf1. Histology and cDNA representation of DEspR shows limited expression on adult tissues (FIG. 2). DEspR functions as an anti-apoptotic receptor and is involved in branched angiogenesis.

Figure 4:
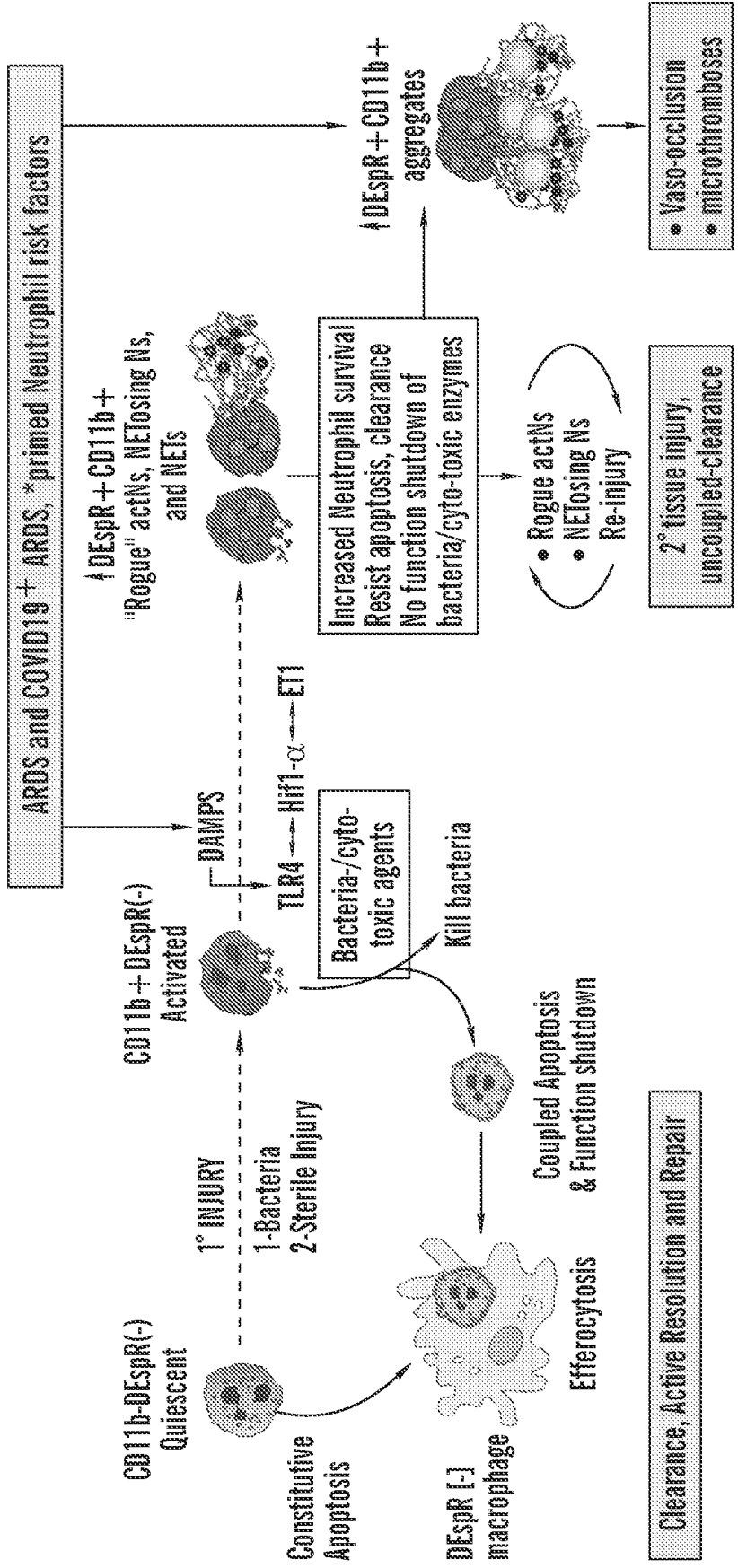
FIG. 4 shows that DEspR is a stress survival receptor in activated neutrophils. Survival extension decouples function shutdown leading to dysregulated "rogues" (survival extension=dysregulation or "rogue").

DEspR expressed on "rogue" neutrophils and NETosing neutrophils provides a therapeutic target for preventing or treating coronavirus infection, alleviating or reducing signs or symptoms associated with coronavirus infection, improving the progression of signs or symptoms associated with coronavirus, or reducing or treating pathologies associated with coronavirus (FIG. 4).

Figure 5:
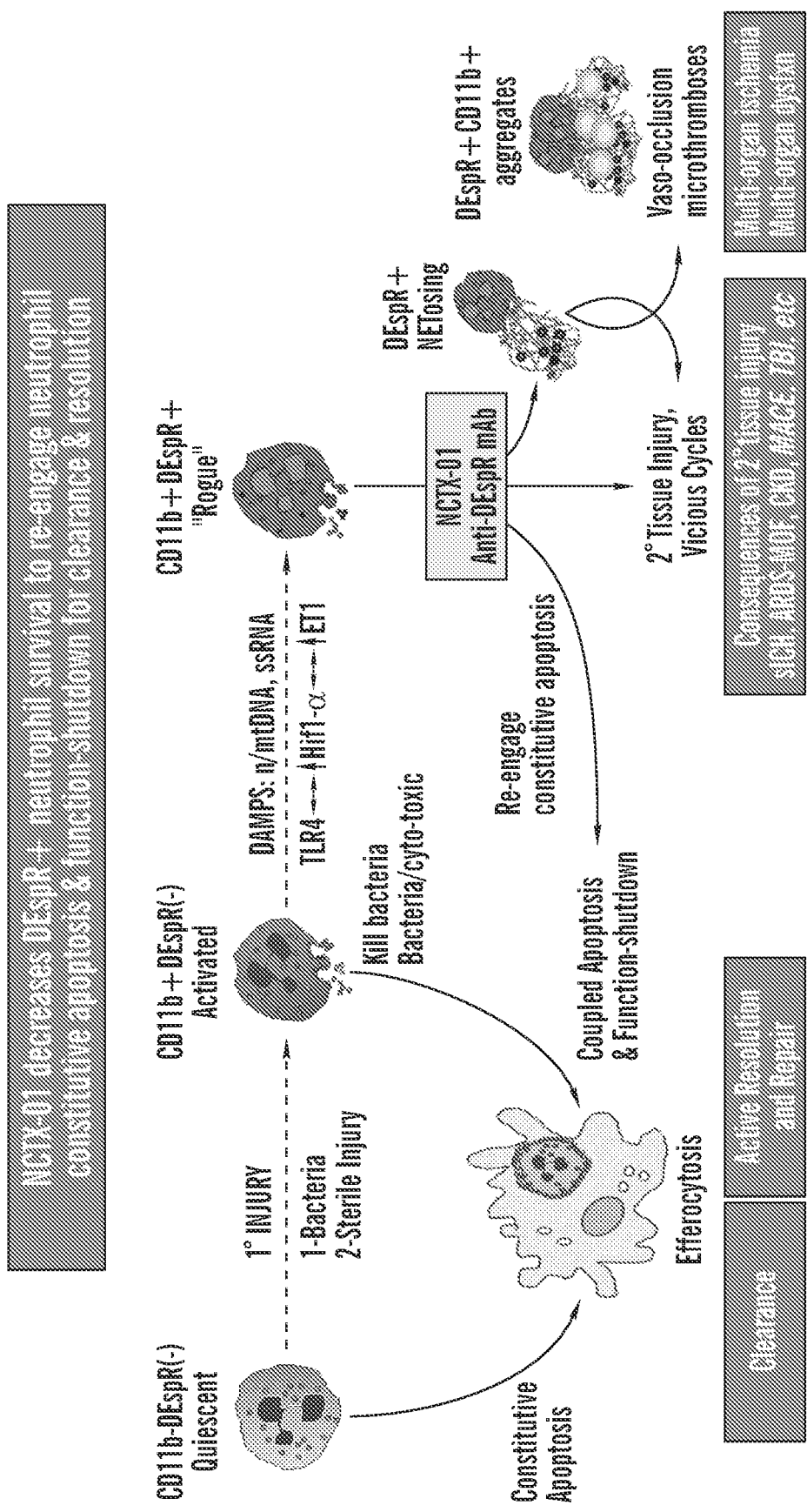
FIG. 5 depicts the mode of action of anti-DEspR mAb. An exemplary anti-DEspR mAb, NCTX-01, decreases DEspR+ neutrophil survival to re-engage neutrophil constitutive apoptosis & function-shutdown for clearance & resolution.

Anti-DEspR mAb detects DEspR expression on rat LPS-activated neutrophils (FIG. 5). For example, an exemplary anti-DEspR mAb, NCTX-01, decreases DEspR+ neutrophil survival to re-engage neutrophil constitutive apoptosis & function-shutdown for clearance & resolution.

In some embodiments, anti-DEspR mAb is designed based on epitope (e.g., in binding domain; rat, human, non-human primates (NHP)-reactive), backbone (hinge-stabilized S228P-IgG4), and biophysical properties (e.g., minimized T-cell epitopes, minimized instability motifs). In some embodiment, anti-DEspR mAb comprises functionality, such as target-engagement (e.g., best target affinity among candidates, and improved over precursor mAb), target-bioeffects (e.g., blocking effects of ET-1, decreased neutrophil survival, anti-DEspR decreased Mcl1 levels (required for neutrophil survival), anti-DEspR mAb (e.g., NCTX-01)/DEspR internalization, translocation to nucleus, and apoptosis), target-safety (e.g., no observed lysis/release of neutrophil granule contents, no complement activation), and developability (e.g., fulfilling 5 in silico-developability criteria). In some embodiments, anti-DEspR mAb is produced by CHO-transients, for example, as a mixed pool. In some embodiments, anti-DEspR mAb is produced using CHO-stable by selecting 4 high producers and ready for GMP production for IND-enabling verification and manufacturing.

In some embodiments, anti-DEspR mAb is NCTX-01, which is a humanized anti-DEspR IgG4$^{S228P}$ recombinant mAb, selected based on multiple parameters tested in independent experimental evaluation systems. In some embodiment, NCTX-01 is developed as a potential novel ARDS therapy for patients having a coronavirus, e.g., COVID19, infection. In some embodiment, the therapeutic window is determined by serial analysis of pre-ARDS to ARDS, analysis of NETosing neutrophils, analysis of COVID19+ ARDS in subjects, or a combination thereof. In some embodiments, biomarker(s) for ARDS patient responders to NCTX-01 are identified, such as % DEspR+ rogue Ns±Ms, neutrophil-lymphocyte ratio, and stratifier ratios. In some embodiments, the bronchial lavage fluid (BLF) in ARDS patients a coronavirus, e.g., COVID19, infection is analyzed. For example, in some embodiments, % DEspR+ rogue neutrophils in the BLF compared with the blood from non-human primates (NHPS). For another example, in some embodiments, single cell RNA-seq database analysis is performed using BL fluid cells from COVID19 patients.

In some embodiments, a lead mAb, NCTX-01, binds to DEspR and allows apoptosis to resolve these actN without affecting other neutrophils or immune cells needed for injury repair and healing to initiate/progress. NCTX-01 restores physiological control and eliminating secondary organ-dysfunction or multi-organ dysfunction or failure associated with a coronavirus infection. Lead indication: respiratory indications marked by high NLR and NETosing neutrophils. In some embodiments, NCTX-01, provides breakthrough efficacy, in which mortality and morbidity are the end points, such as an aggressive sICH, an infection- or antigen-induced multiple organ failure (MOF).

Notably, low-dose (1-2 mg/kg/dose instead of usual 15-20 mg/kg/dose) lipopolysaccharide activated neutrophils as marked by CD11b (Mac1) induction compared to non-activated or quiescent neutrophils (Q4). Majority of CD11b activated neutrophils are DEspR+ in contrast to CD11b+ but DEspR(−) activated neutrophils. Ex vivo, anti-DEspR mabs (e.g., anti-ratDEspR 10a3, and pan-species reactive anti-Human/Rat/Monkey DEspR mAb, 6g8) treatment of activated neutrophils decreased their survival in contrast to control non-treated activated neutrophils (1-way ANOVA, Tukey's post-hoc multiple comparisons P<0.0001).

Anti-DEspR re-engages the neutrophil's apoptosis mechanisms by blocking STAT3-mediated upregulation of Mcl1, as well as causes decreased Mell. Mcl1 is implicated in the extended survival of activated neutrophils, which in the quiescent state are constitutively apoptotic. By inducing apoptosis of activated neutrophils (which are phagocytosed by macrophages), anti-DEspR prevents the pathogenic cascade of neutrophil-mediated organ-dysfunction or multi-organ dysfunction or failure associated with a coronavirus infection (via proteases, cathepsin G, proteinase 3, myeloperoxidase). Prevention of activated neutrophil progression to NETosis, thus prevents NET-mediated pathogenic cascades associated with coronavirus infection. Anti-DEspR can also be used as a targeting moiety for nanoconjugates/drug conjugates targeting activated neutrophil infiltrates, circulating neutrophils, and NETs in the circulation or in tissues (e.g., lungs, joints, muscle, heart, etc) or in pathologies (e.g., thrombus, tumors, ulcers, wounds).

In some embodiments, the present disclosure describes developing a first-in-class humanized anti-DEspR IgG4S228P antibody therapy, NCTX-01, with the potential to prevent or reverse neutrophil-driven secondary organ-dysfunction or multi-organ dysfunction or failure in ARDS-MOF patients having a coronavirus (e.g., COVID19) infection, in order to improve outcomes, such as averting death, decreasing ICU-days, decreasing disability in survivors, etc. In some embodiments, the present disclosure describes methods of treating subjects or patients with neutrophil-driven secondary organ-dysfunction or multi-organ dysfunction or failure, for example, ARDS-MOF subjects or patients having a coronavirus (e.g., COVID19) infection. In some embodiments, the organ-dysfunction or multi-organ dysfunction or failure associated with a coronavirus infection is intracerebral hemorrhage (ICH) perihematomal brain edema.

Example 2: Ex Vivo Studies of Patient Blood Samples from Patients with ARDS and COVID19+ ARDS Prospective ex vivo blood sample analysis was performed for ARDS patients (n=16) and COVID19+ ARDS patients (n=8). Prospective clinical biomarker trend analysis (prior to ex vivo blood sample analysis) was also performed for COVID19+ ARDS patients (n=8 for survivors; n=8 for non-survivors).

Figure 6A:
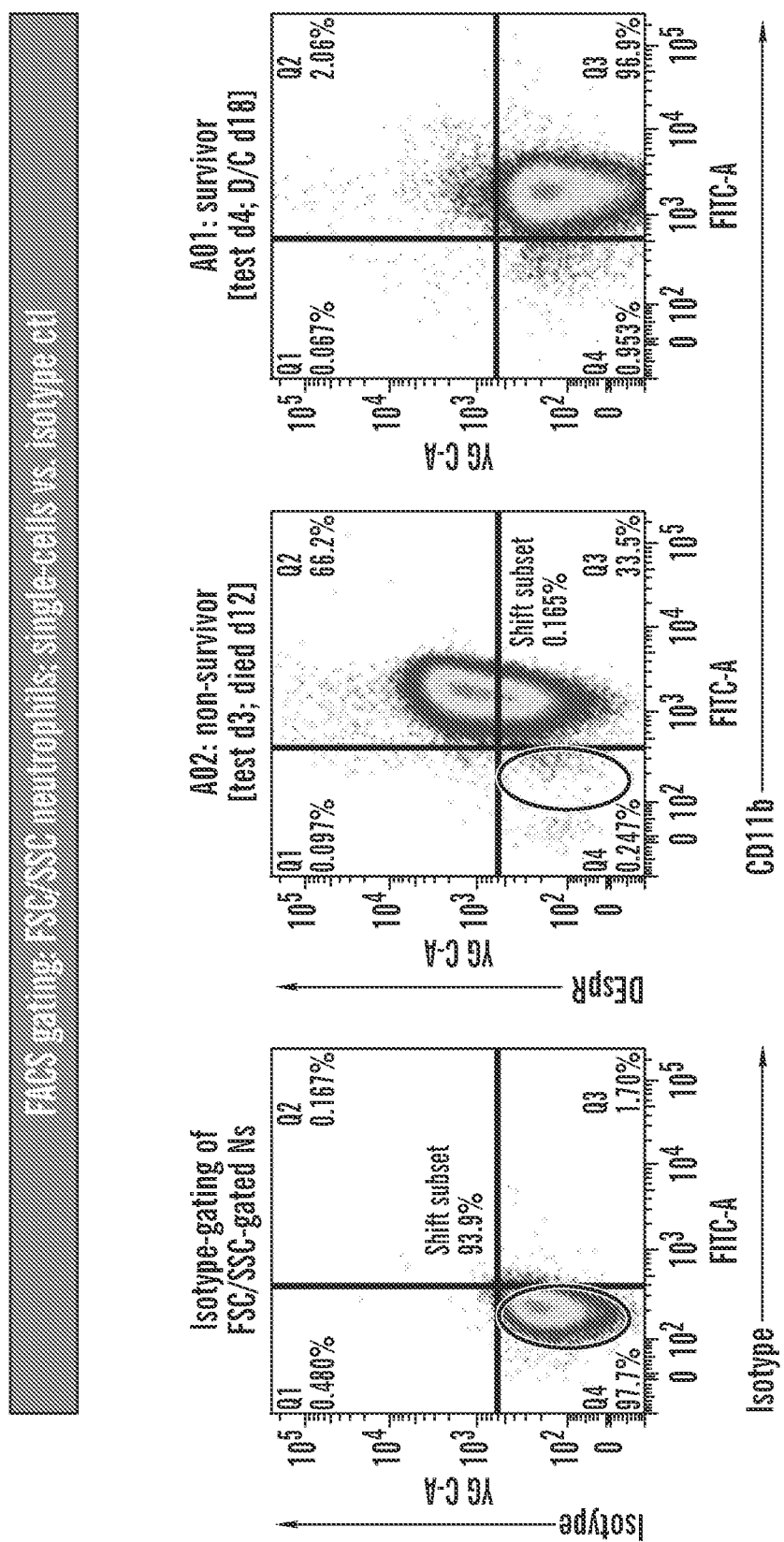
FIGS. 6A-6B depict detecting DEspR+CD11b+ neutrophils (rogueNs or Ns) in acute respiratory distress syndrome (ARDS), nonCOVID Patients.
Figure 6B:
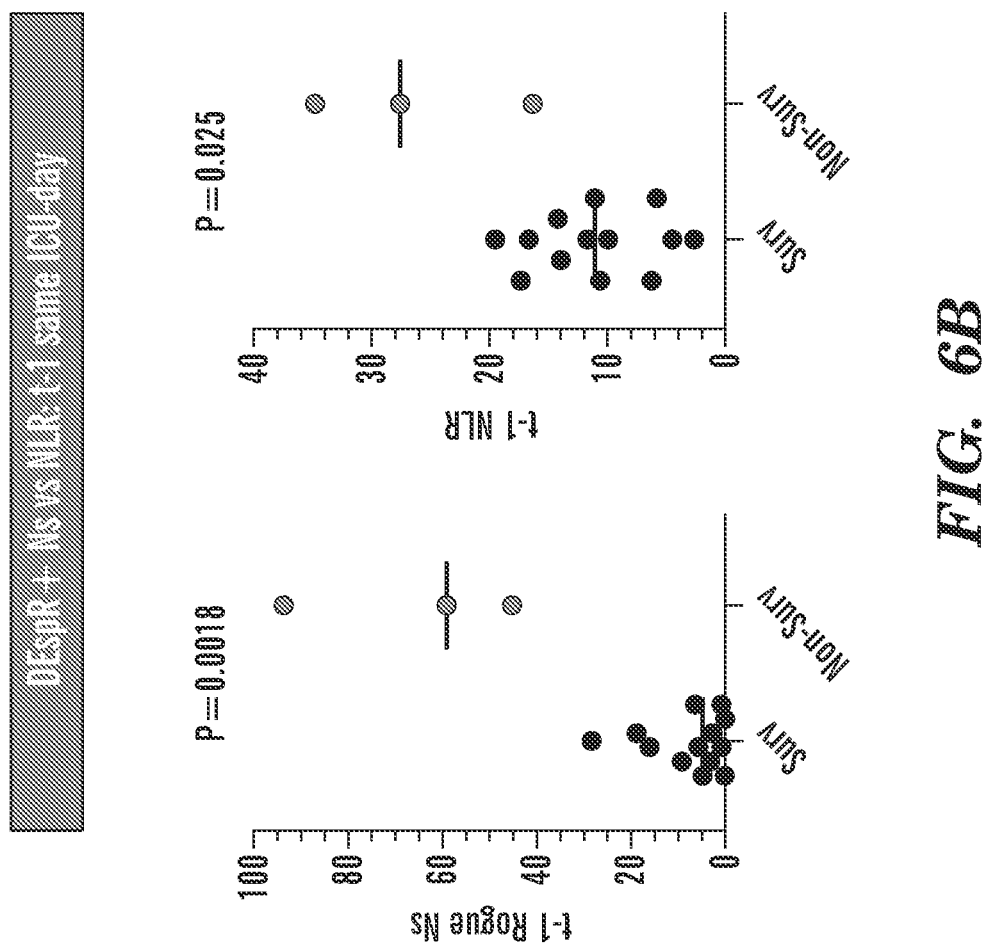

Prospective study of detecting CD11b+DEspR+ neutrophils (rogueNs) in nonCOVID. ARDS patients was performed (FIGS. 6A and 6B). The percentage of the RogueN levels (% RogueN levels) can be used as a blood diagnostic marker to stratify patients for mortality risk in both ARDS and COVID19, as it informs patient management and identifies cohort for clinical trials.

Total neutrophils comprise all neutrophils with high side scatter properties (SSC) or granularity, be it high forwards scatter (FSC) or low FSC corresponding to relatively larger or smaller in size. DEspR+CD11b+ or 'rogue' Ns are gated for high SSC/high FSC, and early apoptotic neutrophils (eaNs) are gated as high(er) SSC/lower FSC on flow cytometry.

Figure 7A:
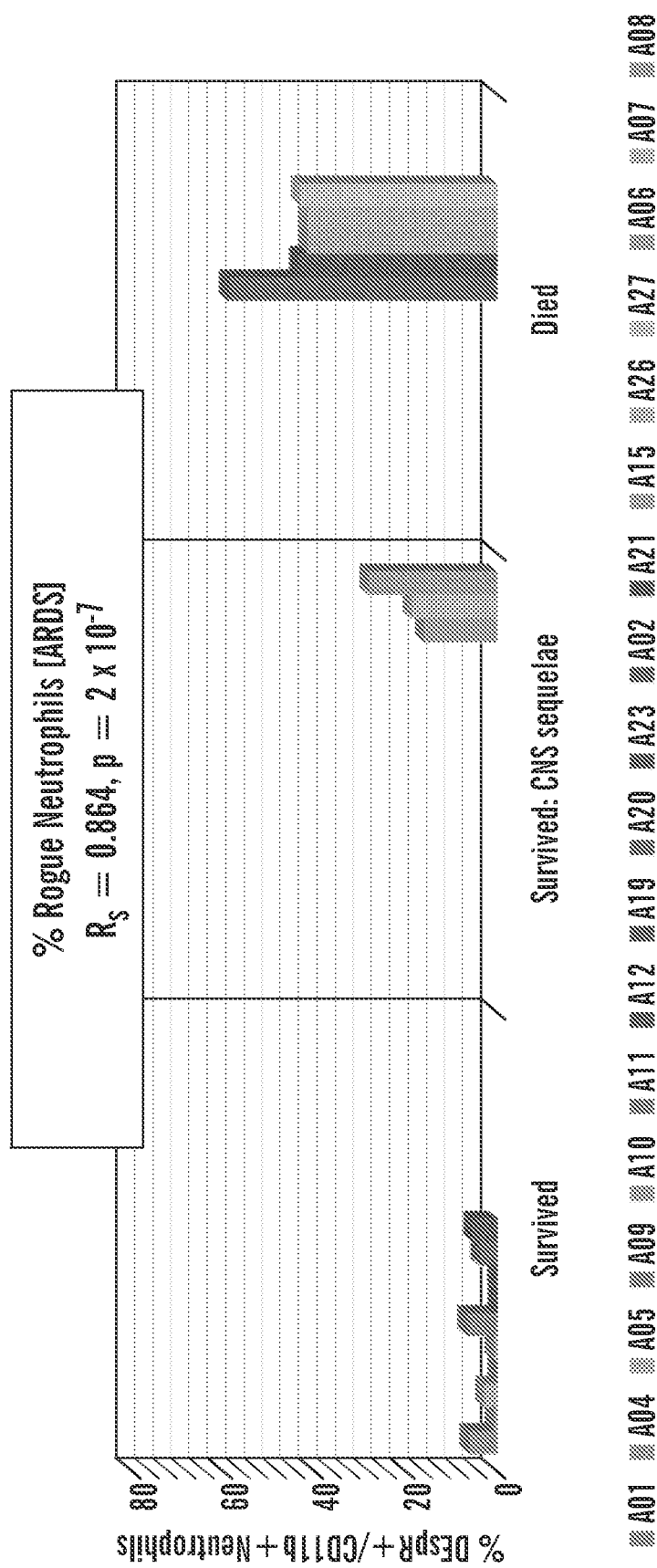
FIGS. 7A-7C show that the percentages of cell-surface DEspR+/CD11b+ neutrophils (rogueNs) and monocytes (% cell-surface DEspR+/CD11b+ neutrophils and monocytes) are associated with increased risk of poor outcome in ARDS patients (n=18), proposed as a stratifier of putative patient responders.
Figure 7B:
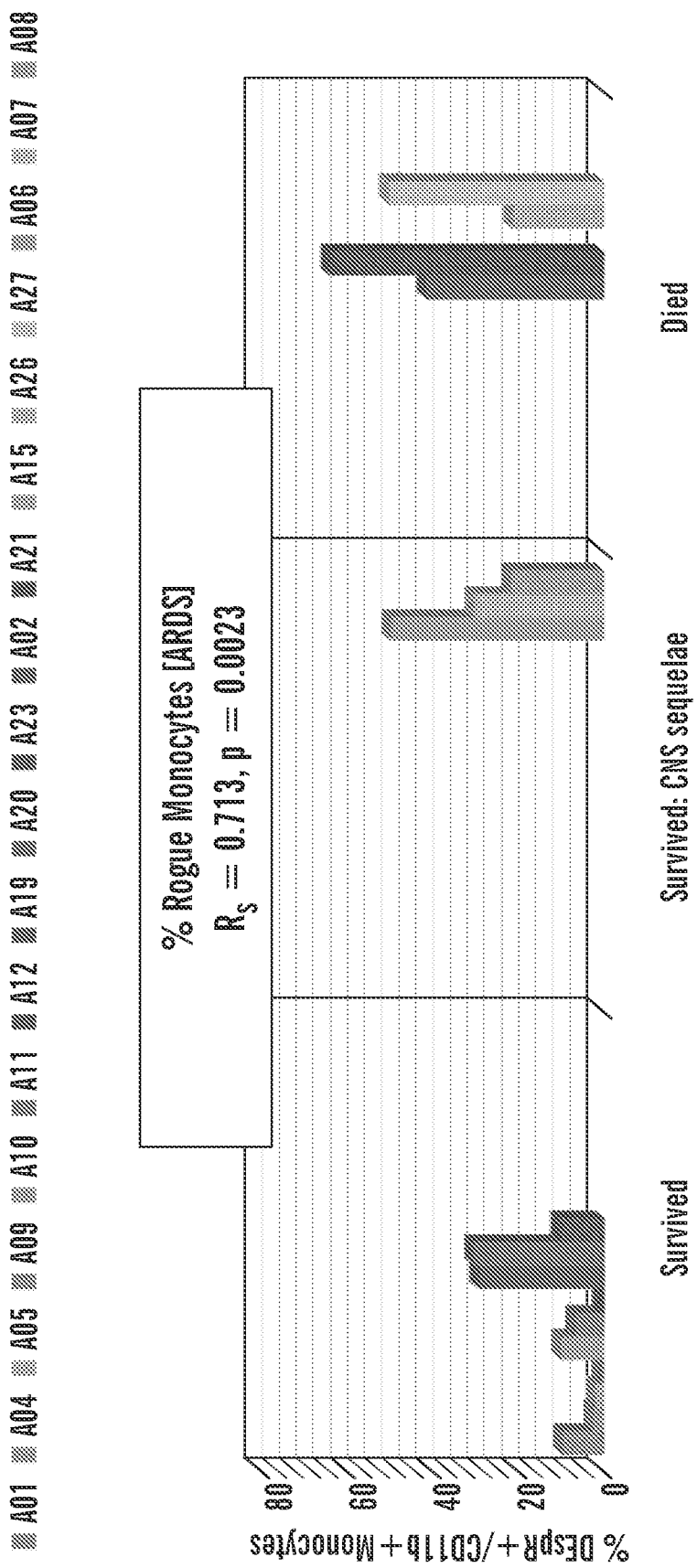
Figure 7C:
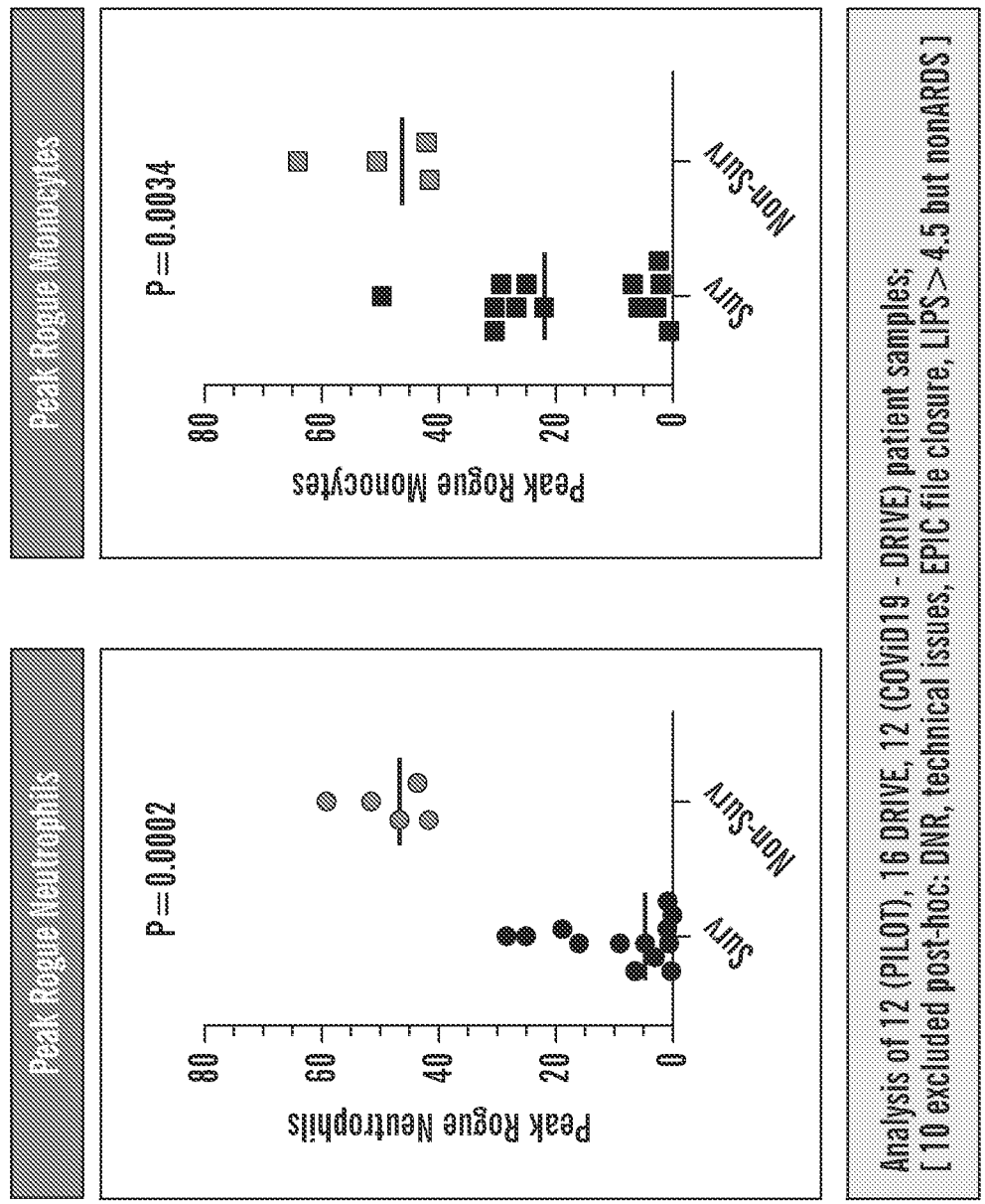
Figure 8A:
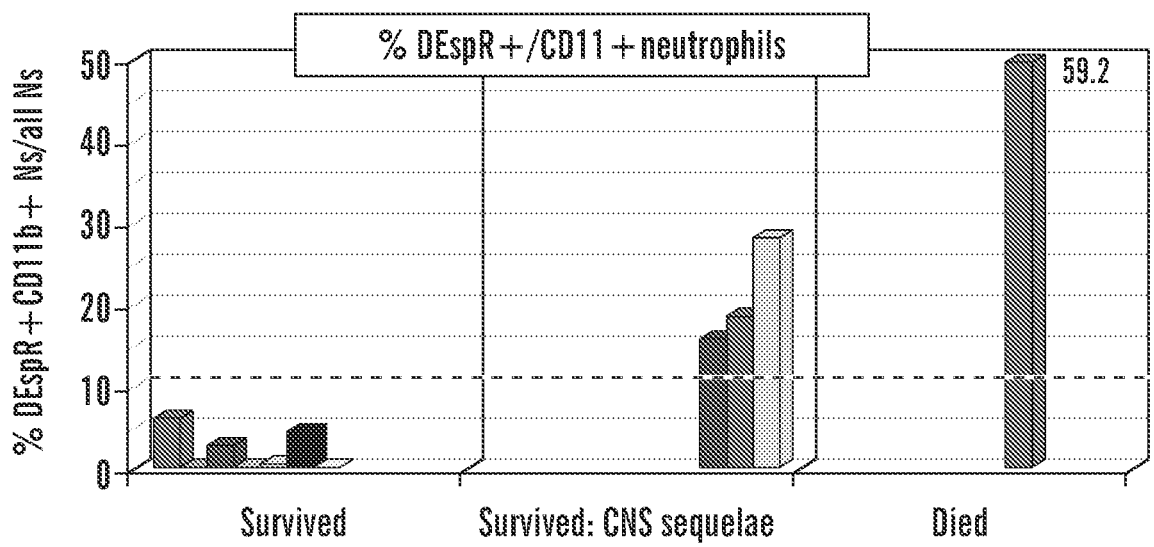
FIGS. 8A-8D shows that no other serum marker is correlated to patient outcome in the Analysis of DEspR in acute lung injury, ARDS and Multiorgan failure (ADAAM)/ARDS Study.
Figure 8B:
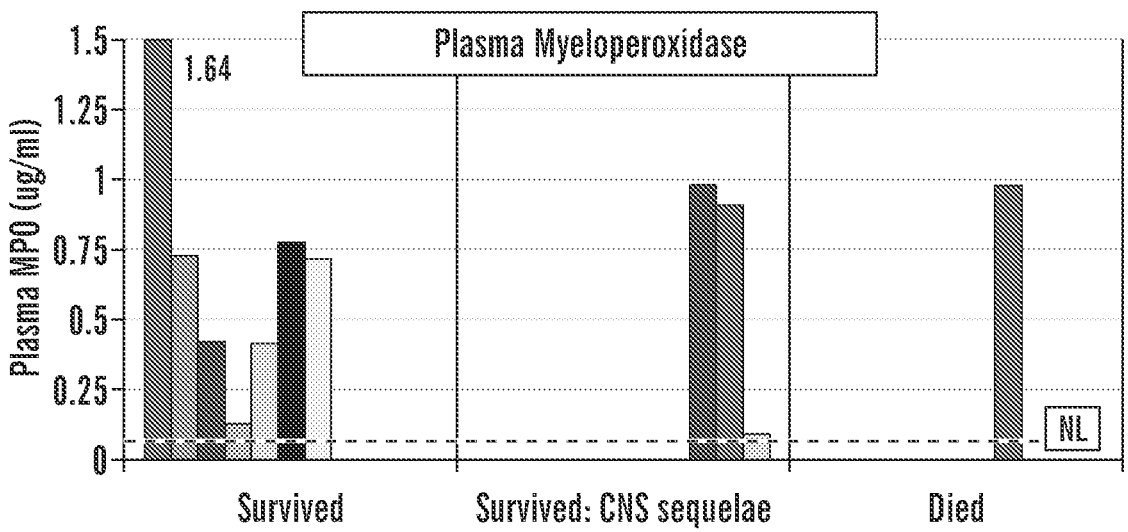
Figure 8C:
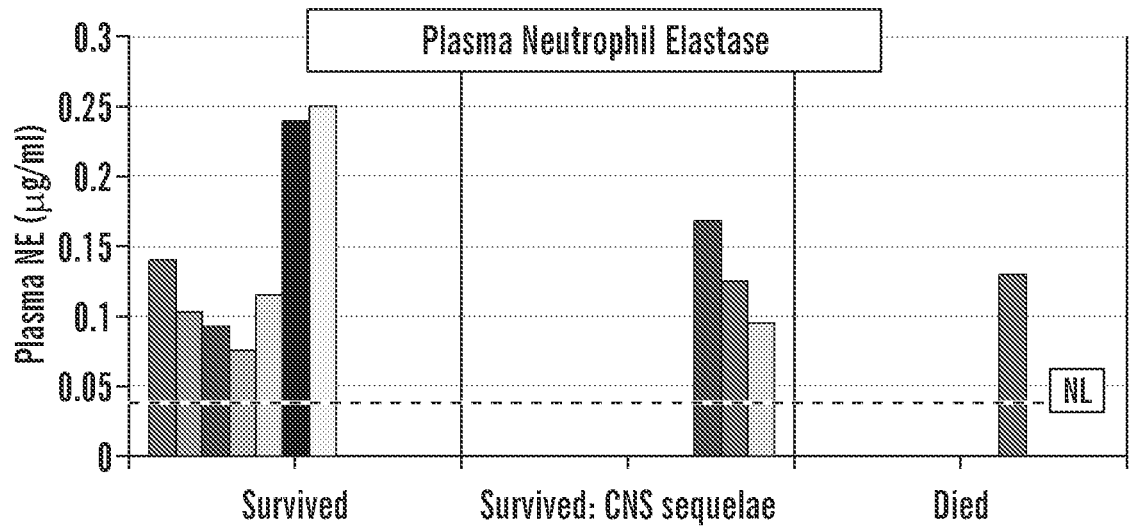
Figure 8D:
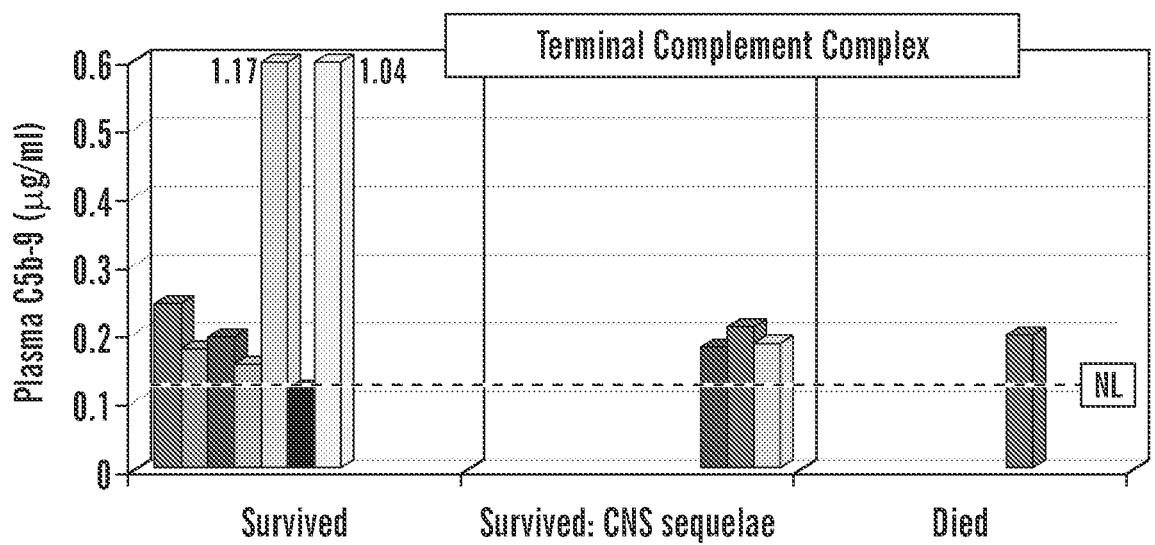

In ARDS patients, the % cell-surface DEspR+/CD11b+ neutrophils (rogueNs) are associated with increased risk of poor outcome in an 18 patient ex vivo study, thus, serving as a stratifier of putative patient responders (FIGS. 7A and 7C). Spearman Rank Correlation. In addition, the % cell-surface DEspR+/CD11b+ monocytes are also associated with increased risk of poor outcome in ARDS patients (n=18)

Figure 9:
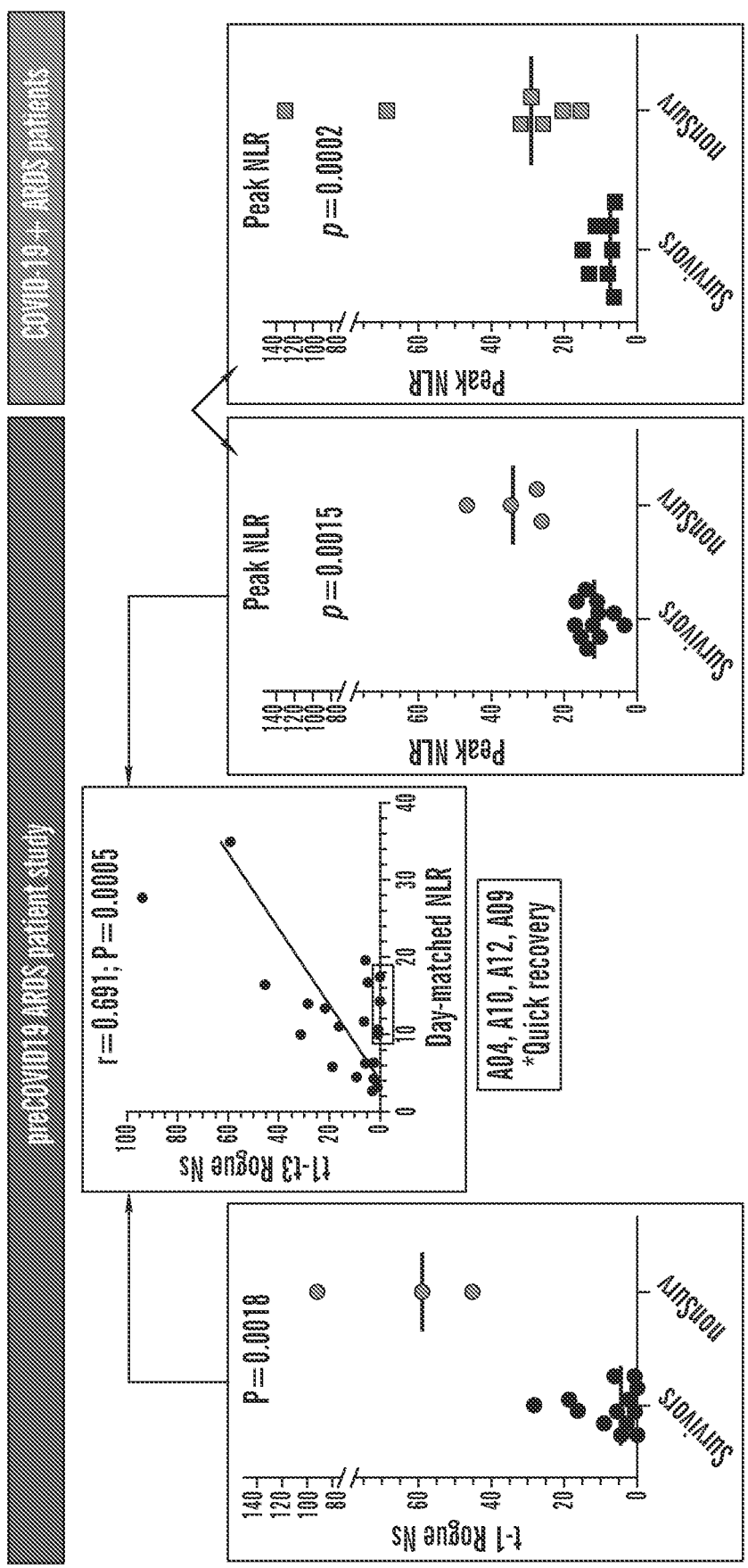
FIG. 9 depicts the exemplified use of NLR and rogue NS as biomarkers for clinical trials and patient management.
Figure 10A:
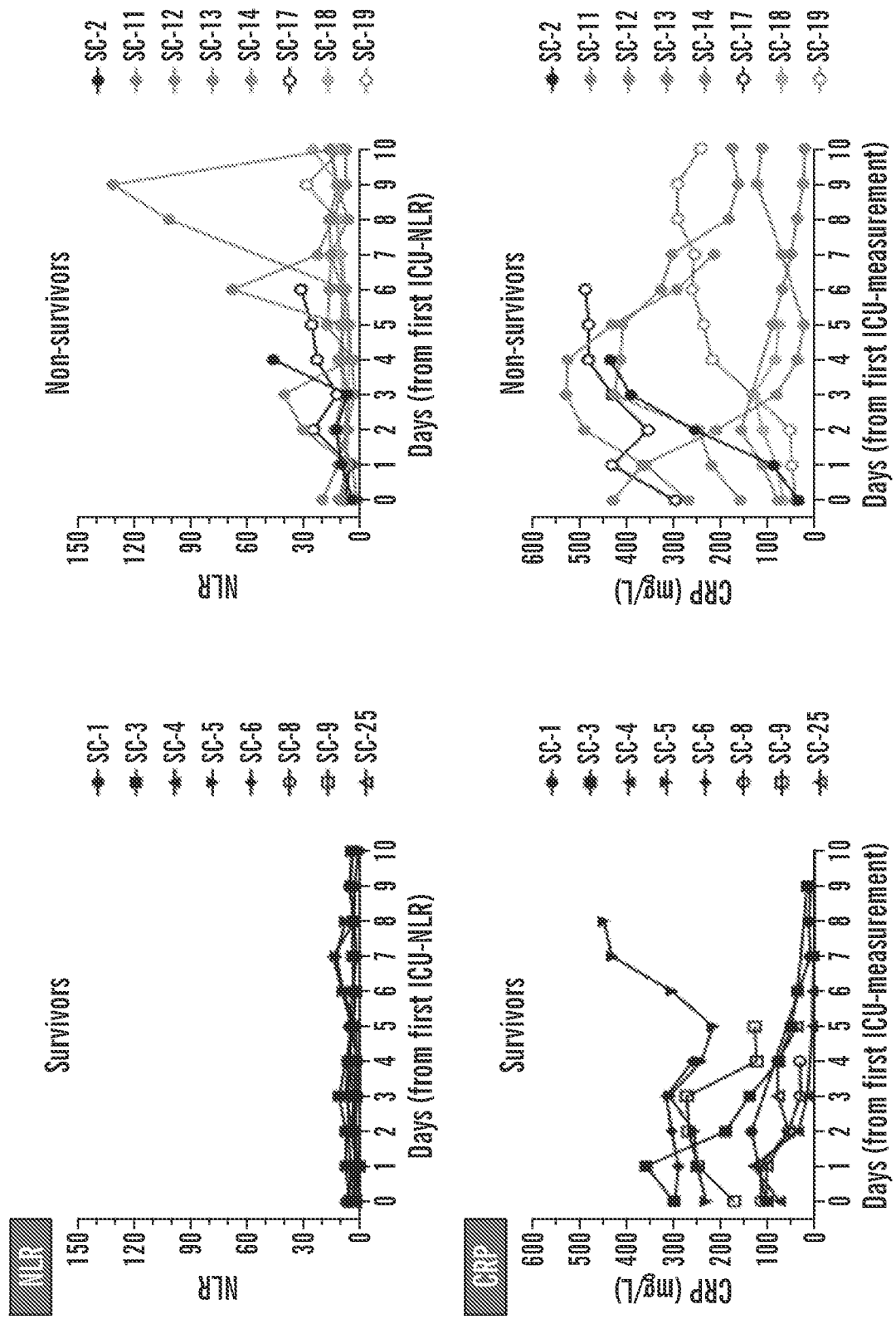
FIGS. 10A-10B depict exemplary inflammation biomarkers. For example, Neutrophil Lymphocyte Ratio (NLR) differentiates COVID19+ ARDS non-survivors (p=0.0002), but C-Reactive Protein (CRP) does not.
Figure 10B:
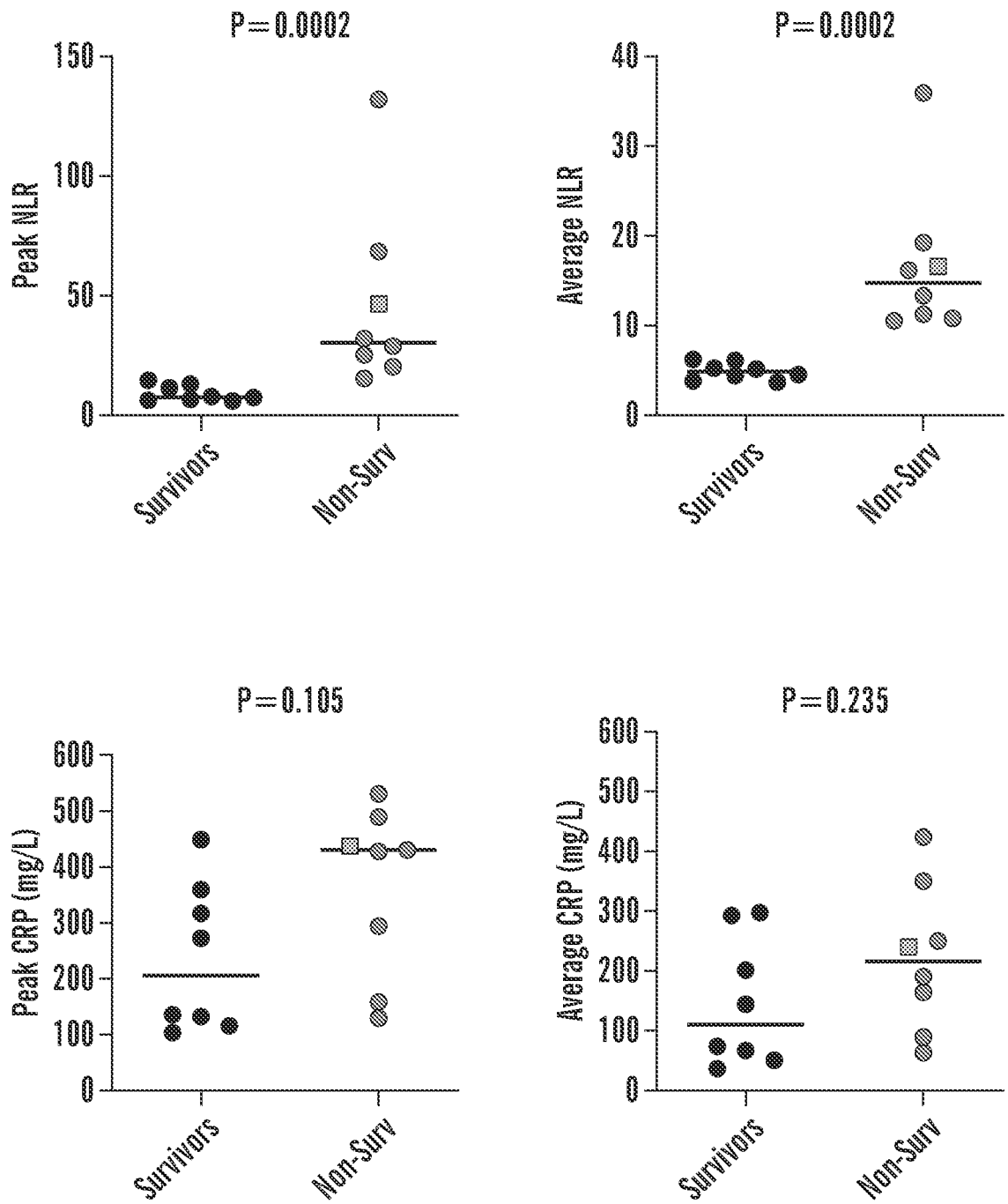

(FIGS. 7B and 7C). In some embodiments, the % DEspR+ Ns is a biomarker for survival and comorbidities. In some embodiments, the % DEspR+ Ns is a biomarker to select potential patient responders to anti-DEspR therapy. Unlike % DEspR+/CD11+ neutrophils (FIG. 8A), no other serum markers, such as myeloperoxidase (FIG. 8B), plasma neutrophil elastase (FIG. 8C), and terminal complement complex (FIG. 8D), are correlated to patient outcome in ARDS study (FIGS. 8A-8D). Therefore, NLR and Rogue Ns may be use as biomarkers for clinical trials and patient management, as shown by FIG. 9. Further, an inflammation biomarker, Neutrophil Lymphocyte Ratio (NLR) differentiates COVID19+, ARDS non-survivors (p=0.0002), but C-Reactive Protein (CRP) does not (FIGS. 10A-10B). The NLR is derived from the ratio of the absolute neutrophil count and absolute lymphocyte count.

Example 3: Development of DEspR Detection Assays for COVID19/ARDS Patients

Complex regulation of DEspR+ provides challenges as well as many points for detection, for example, surface versus combined (e.g., intracellular store+surface) expression levels, protein versus mRNA levels.

PFA-fixed blood samples allows detection of total DEspR (intracellular and cell surface DEspR) under biosafety-level (BL) 1 handling even with infectious agents. Fresh blood samples allows detection of surface specific DEspR but may require elevated BL handling in infection situation.

Patient stratification based on DEspR+ has the potential to: (i) identify patients more at critical risk of progression to multi-organ failure, (ii) identify patient who may have increased risk of morbidities associated with infection and high ICU days, and/or (iii) identify patients for anti-DEspR treatment which may decrease ICU length-of-stay, decrease mortality rate, and/or decrease long term sequelae.

Figure 11A:
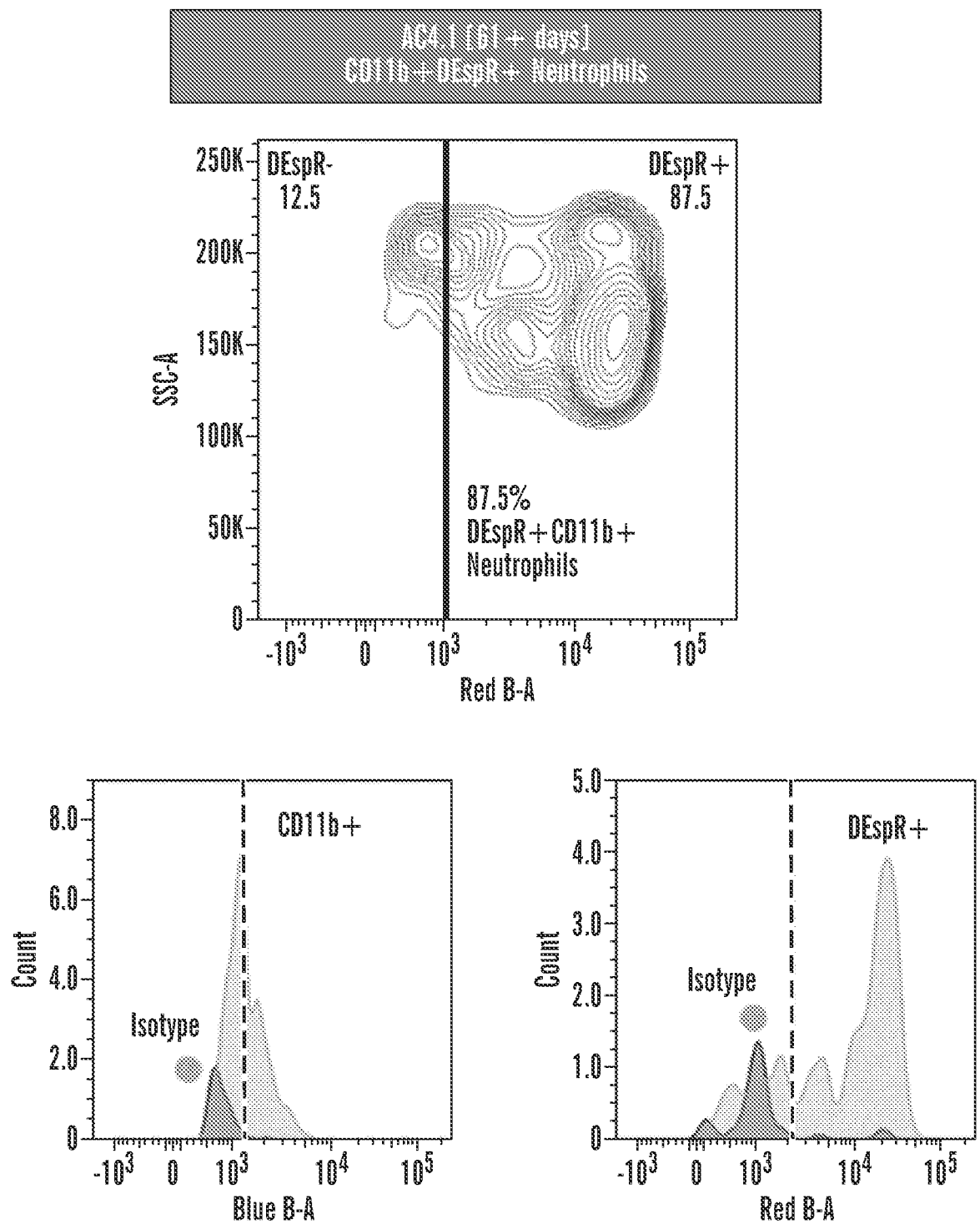
FIGS. 11A-11B depict detection of % CD11b+/DEspR+ neutrophils in COVID19+, ARDS patients by FACS analysis for total DEspR.
Figure 11B:
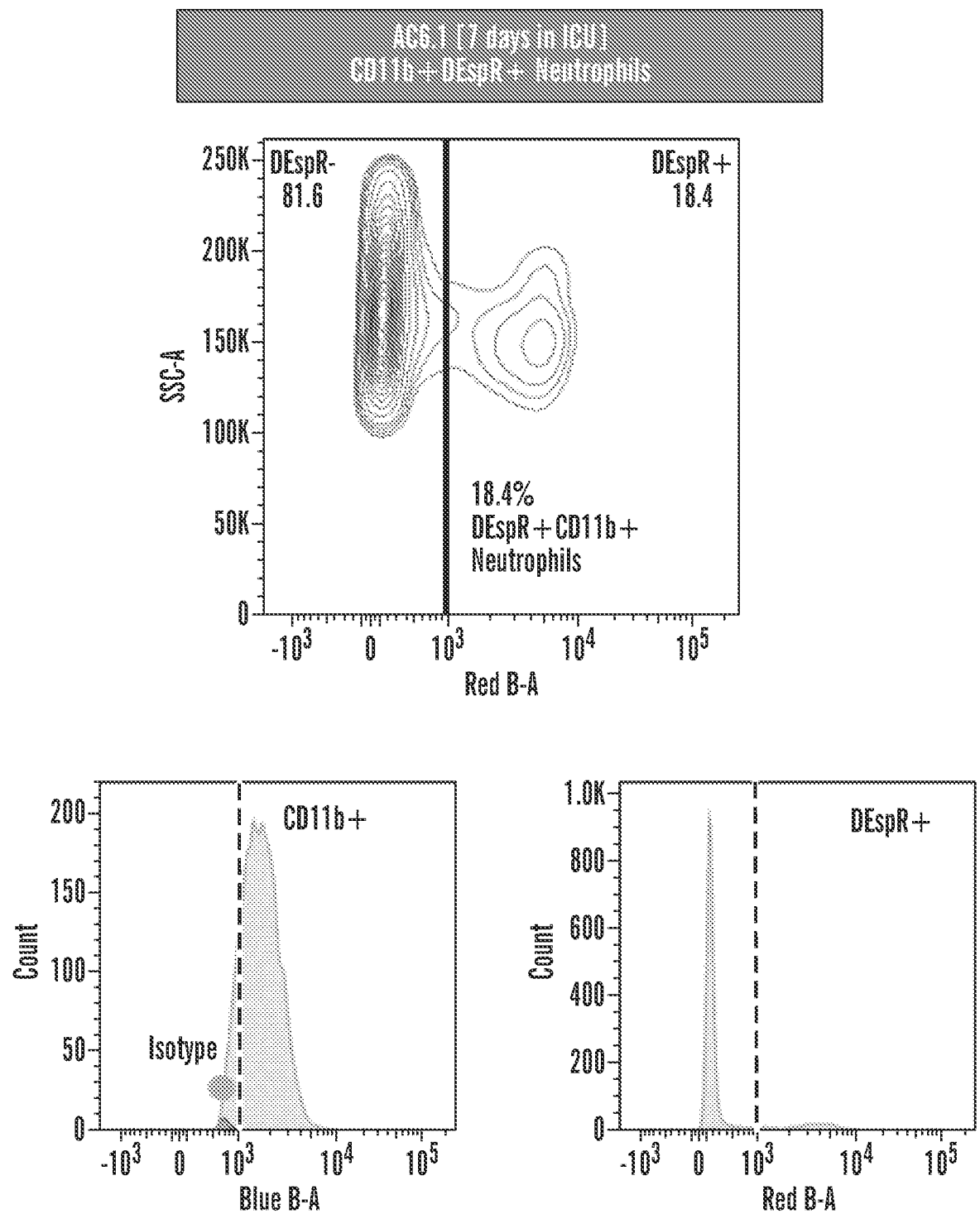
Figure 12A:
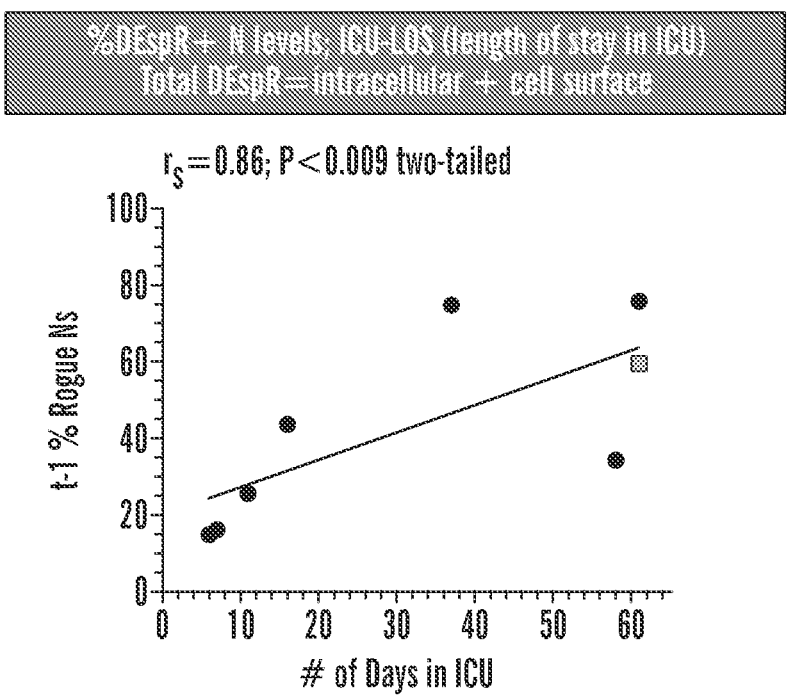
FIGS. 12A-12B show that % total DEspR+/CD11b+ activated neutrophils correlates with number of ICU days. Surface-active and intracellular-reserve DEspR in patients with COVID19+ ARDS correlate with length of stay (LOS) in the ICU (# of ICU-day).
Figure 12B:
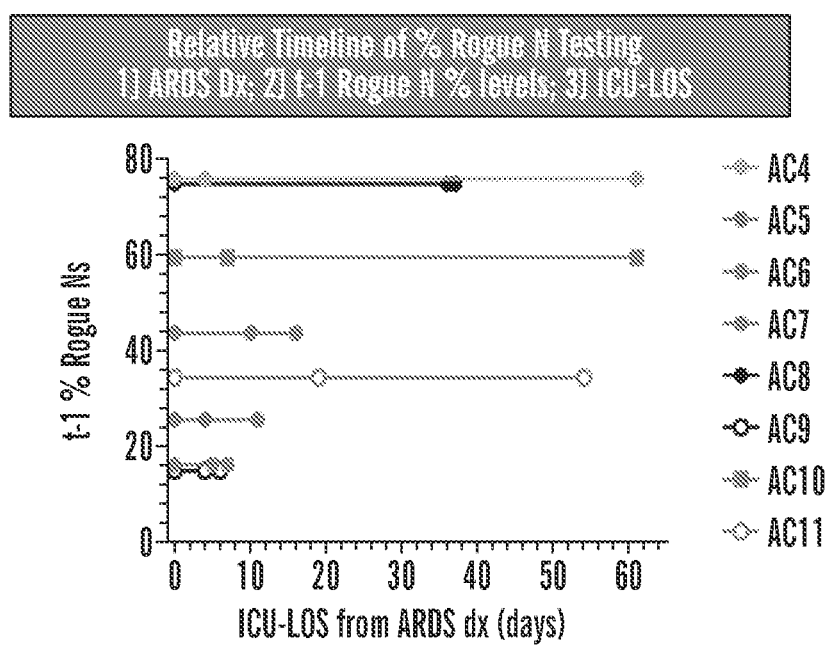
Figure 13A:
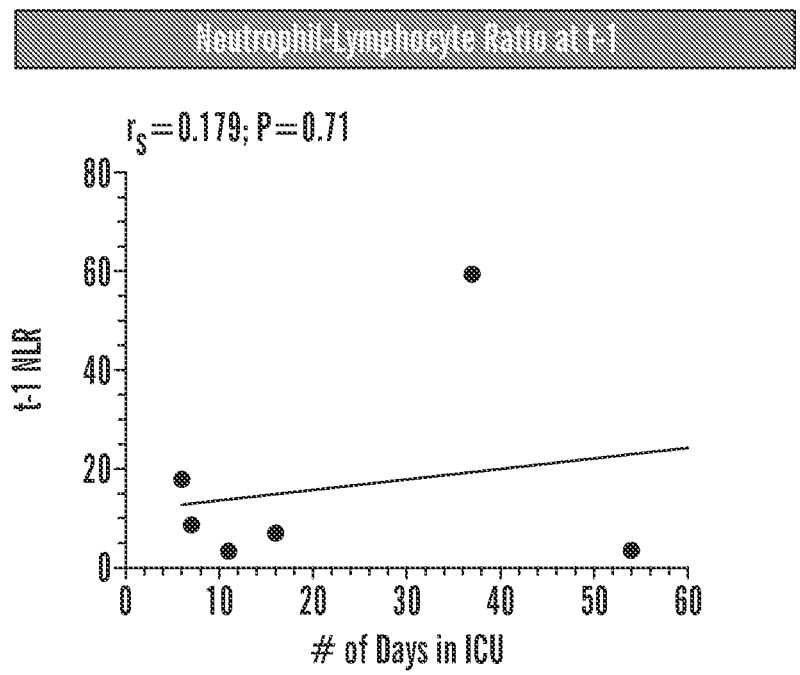
FIGS. 13A-13B show that in contrast to % DEspR+ Ns, NLR and PsO2/FiO2 Ratio (SF Ratio (~hypoxemia)) show no significant correlation with the number of Days in ICU in COVID19+, ARDS patients on ventilator.
Figure 13B:
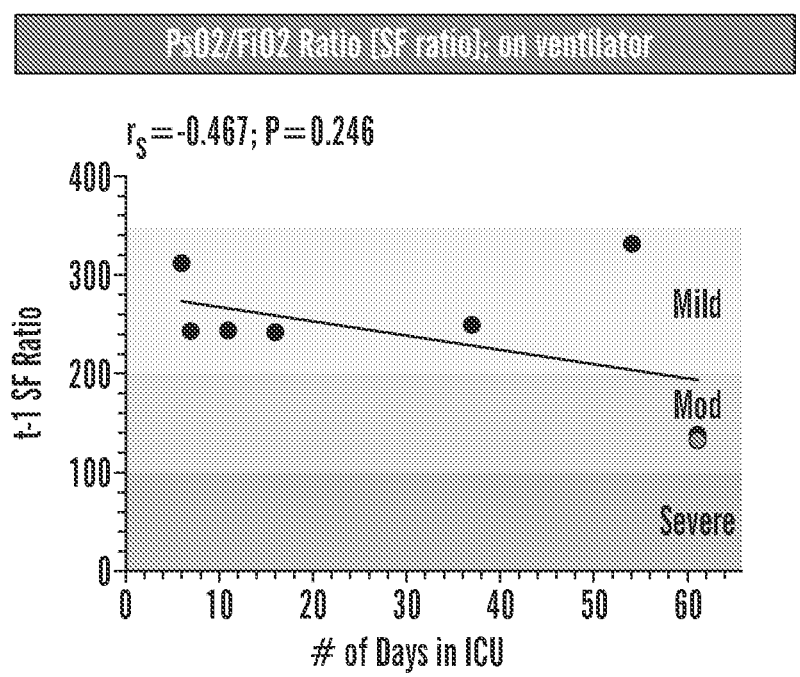

The percentage of CD11b+/DEspR+ neutrophils (% CD11b+/DEspR+ neutrophils) in COVID19+, ARDS Patients was detected by FACS analysis for total DEspR in AC4.1 patients (61+ days in ICU) (FIG. 11A) and in AC6.1 patients (7 days in ICU) (FIG. 11B), respectively. FIGS. 11A and 11B shows differential increase in % CD11b+/DEspR+ neutrophils using PFA-fixed samples in COVID19+ ARDS patients. Intracellular DEspR+/CD11b+ cells+ cell surface DEspR+/CD11b+ cells=total DEspR+/CD11b+ cells. The percentage of total DEspR+/CD11b+ activated neutrophils (% total DEspR+/CD11b+ activated neutrophils) correlates with number of ICU days (FIGS. 12A and 12B). COVID19+ ARDS: ICU, on ventilator (N=8, all survivors). FIG. 12A depicts % DEspR+ N levels; ICU-LOS (length of stay in ICU). Total DEspR=intracellular+ cell surface. FIG. 12B depicts relative timeline of % Rogue N Testing (i) ARDS Dx; (ii) t−1 Rogue N % levels; and (iii) ICU-LOS. That is, the surface-active and intracellular-reserve DEspR level in patients with COVID19+ ARDS correlates with length of stay (LOS) in the ICU (# of ICU-day). The COVID19+ ARDS patients were ICU, on ventilator (N=8, 1 non-survivor, AC10, imputed max LOS). In contrast to % DEspR+ Ns, NLR and SF Ratio (e.g., hypoxemia) showed no significant correlation with # of Days in ICU for COVID19+ARDS patients on ventilator (FIGS. 13A and 13B). The COVID19+ARDS patients were in ICU, on ventilator (N=8, all survivors). Patient record data was use and show NRL and SF Ratio did not correlate with ICU days in contrast to % DEspR+cd11b+. FIG. 13A depicts Neutrophil-Lymphocyte Ratio at t−1. FIG. 13B depicts PsO$_2$/FiO$_2$ Ratio (SF ratio); on ventilator.

The term "PsO$_2$/FiO$_2$ ratio (P/F ratio)," also known as the Horowitz index, the Carrico index, and the P/F ratio, as used herein, refers to the ratio of arterial oxygen partial pressure (PaO$_2$ in mmHg) to fractional inspired oxygen (FiO$_2$ expressed as a fraction, not a percentage). In some embodiments, P/F ratio is a widely used clinical indicator of hypoxaemia. Alternative indices of oxygenation may include, but be not limited to, Oxygen saturations in arterial blood (SpO$_2$ and SaO$_2$), S/F ratio (SpO$_2$ to FiO$_2$ ratio), PaO$_2$ (arterial oxygen tension), A-a gradient (difference between alveolar oxygen tension (PAO$_2$) and PaO$_2$), Oxygenation index (OI) (the reciprocal of P/F times mean airway pressure (MAP): OI=(FiO$_2$×MAP)/PaO$_2$), P/FP Ratio (PaO$_2$/(FiO$_2$× PEEP), a/A ratio (ratio of PaO$_2$ and PAO$_2$), Respiratory index (RI) (RI=pO$_2$(A−a)/pO$_2$(a), normal RI is <0.4).

The term "Hypoxemia" or "hypoxaemia," as used herein, refers to a below-normal level of oxygen in the blood, specifically in the arteries. In some embodiments, hypoxemia is a sign of a problem related to breathing or circulation, and may result in various symptoms, such as shortness of breath.

Example 4: NETosing Neutrophils and NET-N/RBC Aggregates in ARDS Associated with Coronavirus Infection Cellular mechanism contributing to microthrombotic complications in ARDS patients, and in COVID19+ARDS patients and use as a diagnostic and patient stratification tool.

Figure 14:
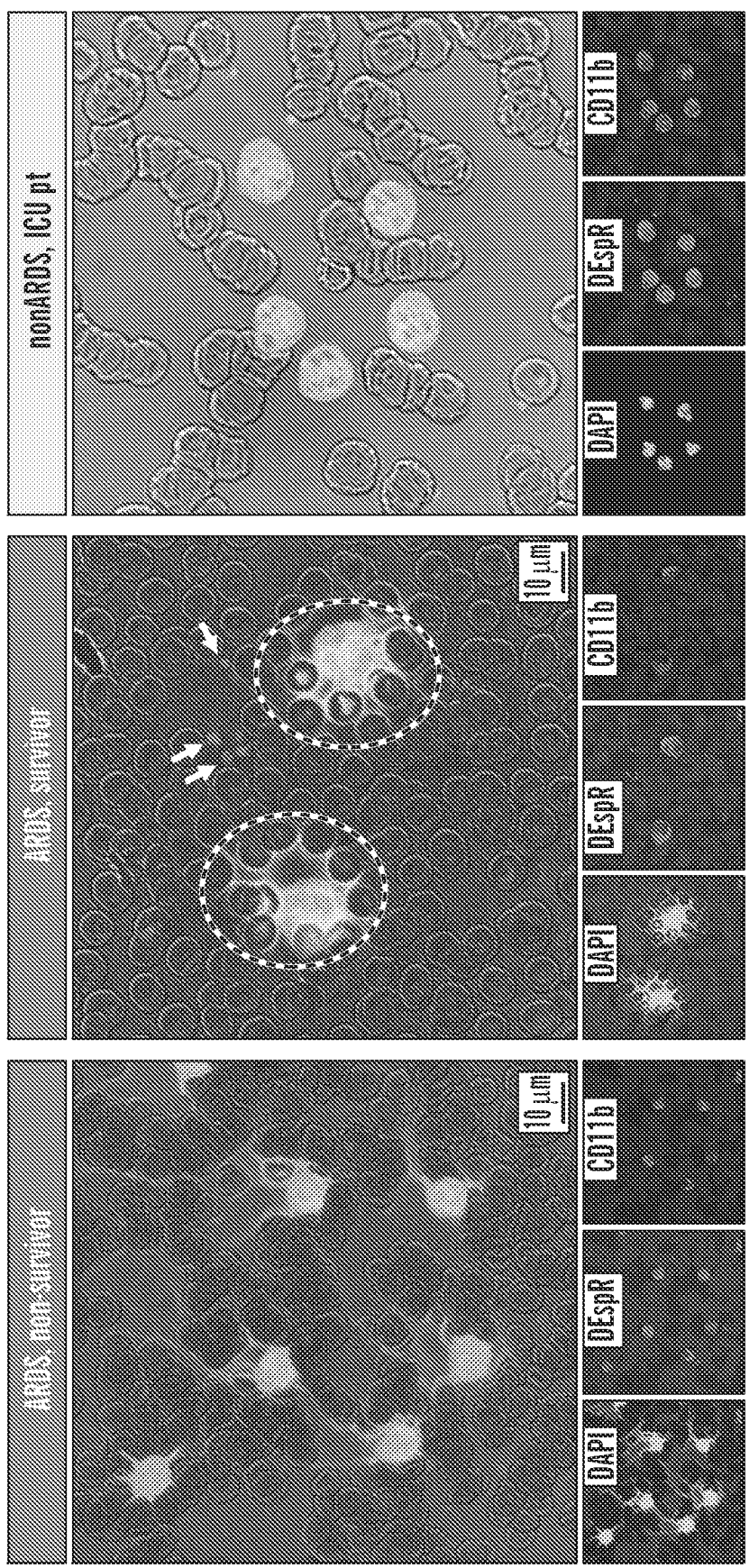
FIG. 14 depicts representative results of the high content image assay developed to assess NETosing neutrophils, which show differential increase of DEspR+/CD11b+ NETosing neutrophils and NETosing N-RBC aggregates in ARDS patients. ARDS, non-survivor vs. ARDS, survivor vs nonARDS, ICU pt (ICU patients).
Figure 15:
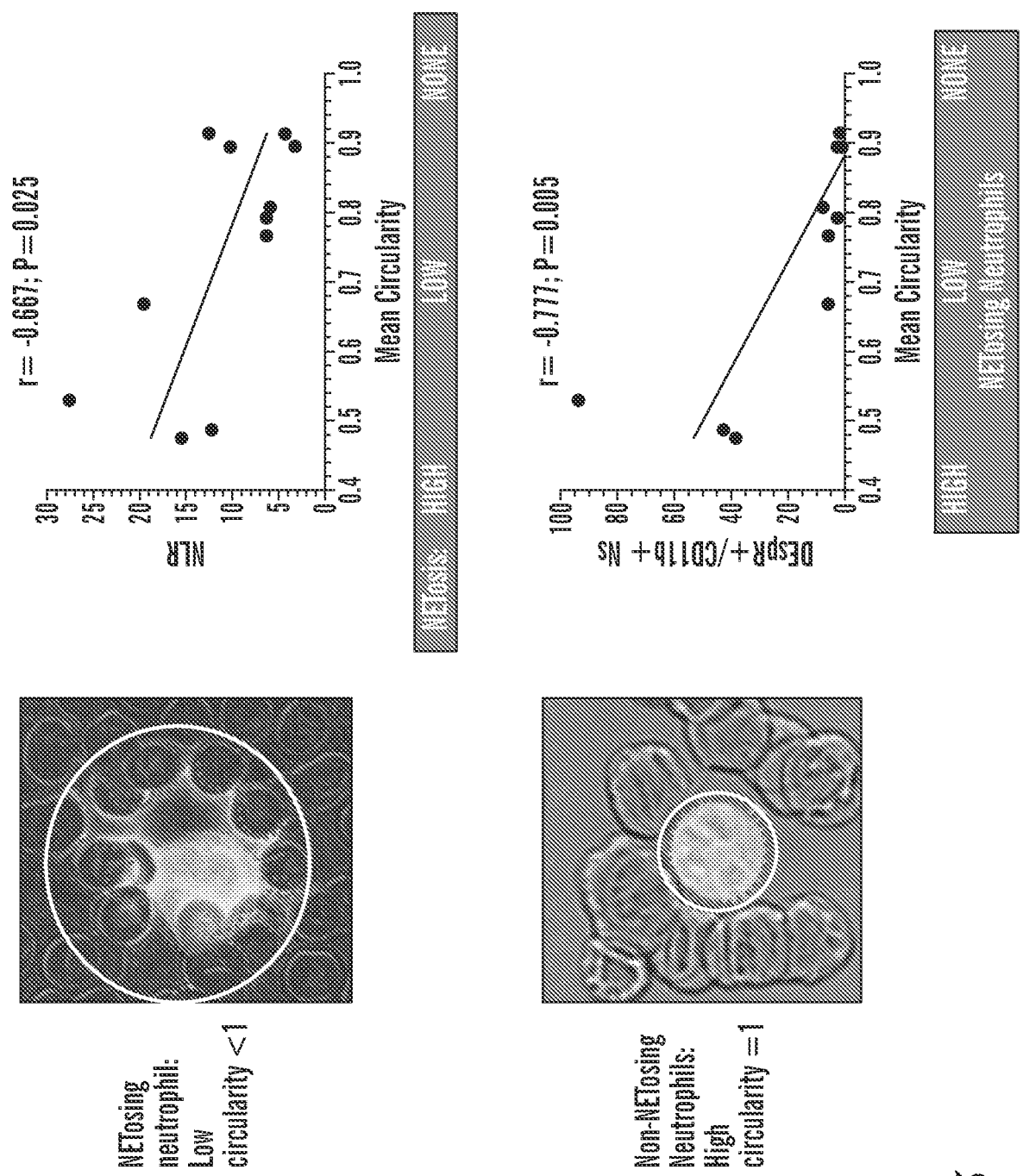
FIG. 15 depicts cell-based quantitation showing that CD11b+DEspR+ "rogue" Ns and NLR correlate with CD11b+/DEspR+ NETosing neutrophils in ARDS patients. NETosing neutrophil: Low circularity<1, Non-NETosing Neutrophils: High circularity=1. Concordance in 5 shape analysis parameters: circularity, convexity, shape factor, contour perimeter, shape area.

The high content image assay was developed to assess NETosing neutrophils. FIG. 14 shows the representative images from the high content image assay showing differential increase of DEspR+/CD11b+ NETosing neutrophils and NETosing N-RBC aggregates in ARDS patients. Cell-based quantitation shows that CD11b+DEspR+ "rogue" Ns and NLR correlate with CD11b+/DEspR+ NETosing neutrophils in ARDS patients (FIG. 15). In some embodiments, concordance in 5 shape analysis parameters includes circularity, convexity, shape factor, contour perimeter, shape area.

Figure 16A:
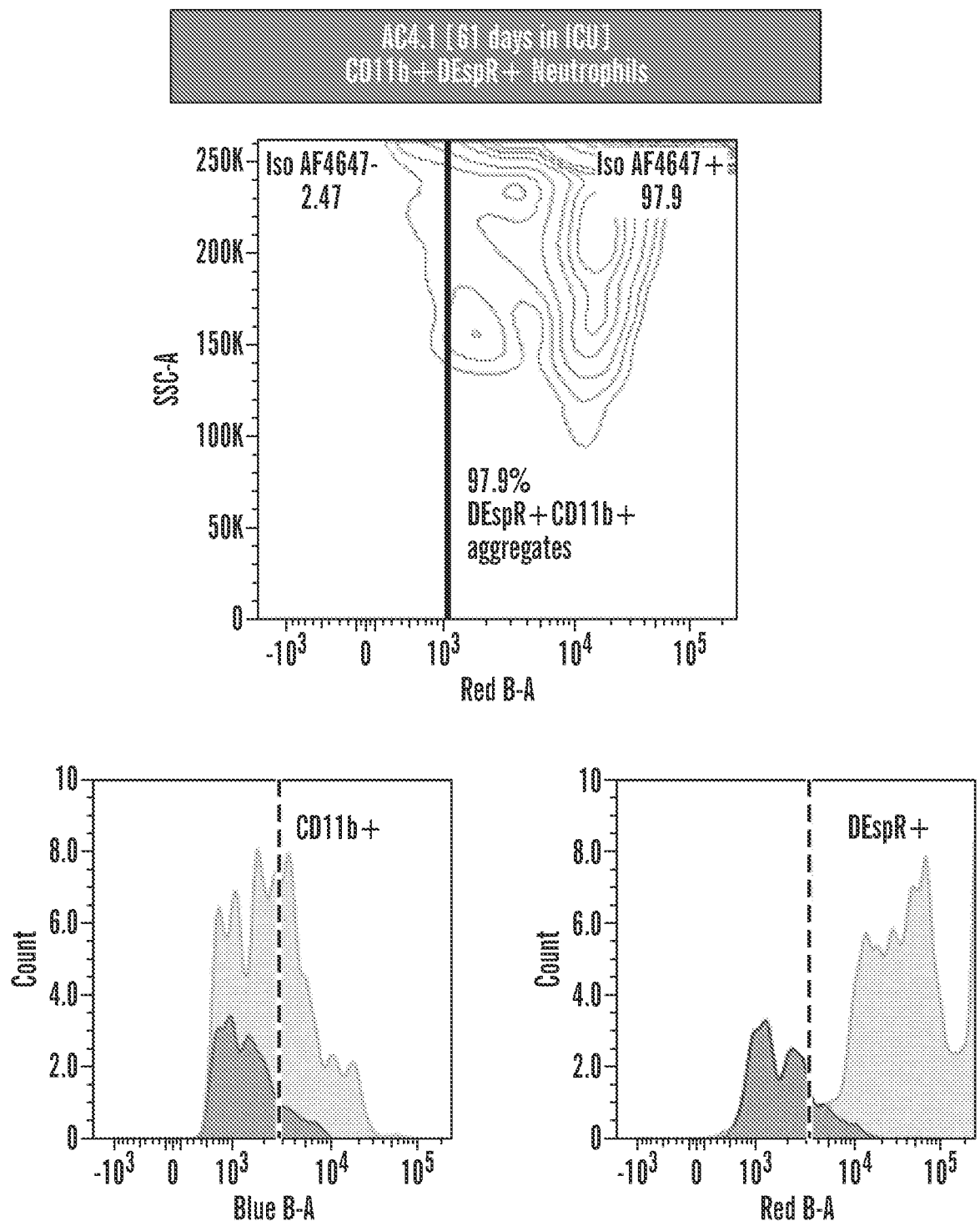
FIGS. 16A-16B depicts differential increase in % CD11b+/DEspR+ aggregates in COVID19+, ARDS patients. PFA-fixed samples: intracellular+ cell surface=total DEspR+/CD11b+.
Figure 16B:
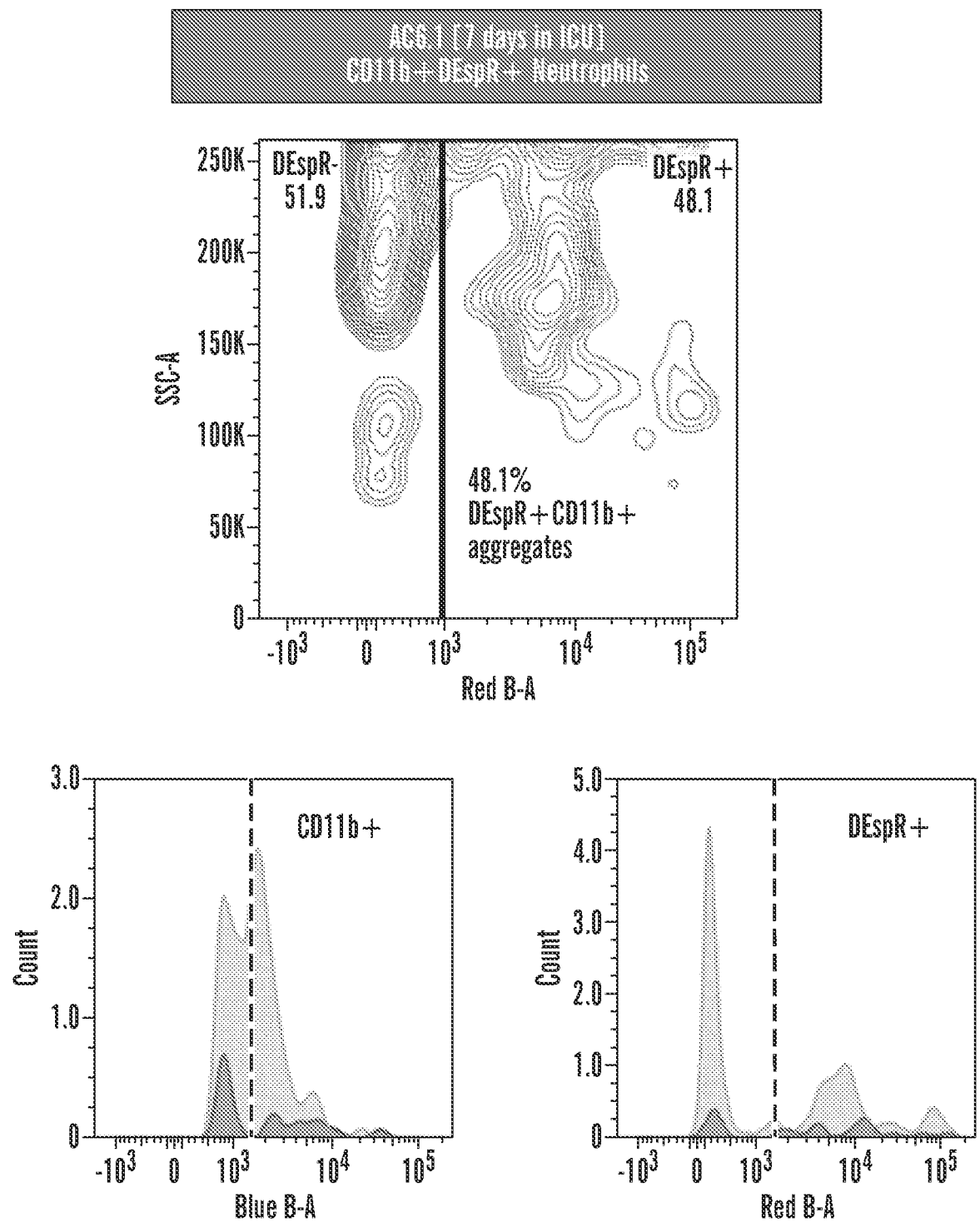
Figure 17A:
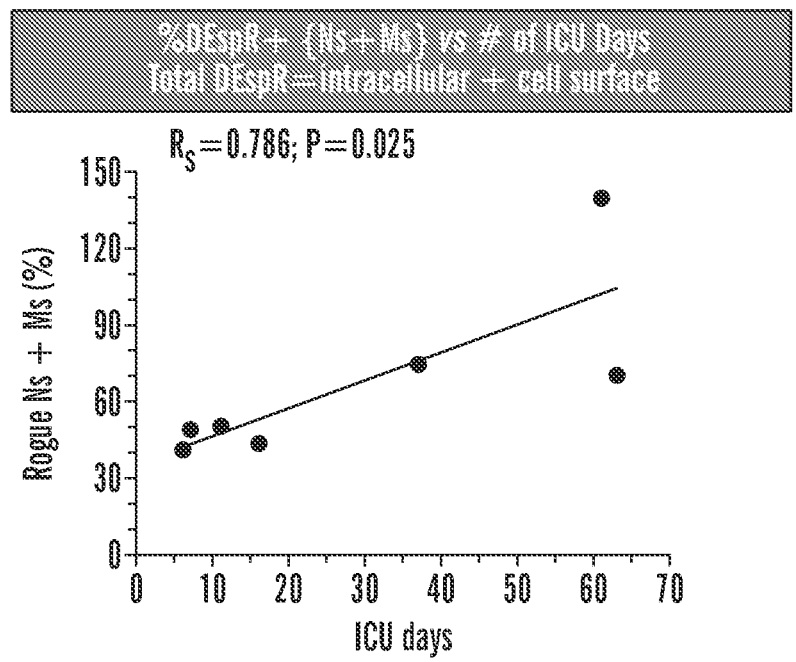
FIGS. 17A-17B depicts the correlation of the % of total DEspR+CD11b+ neutrophils and monocytes with length of stay in the ICU in COVID19+, ARDS patients, proposed as a patient stratifier and response indicator.
Figure 17B:
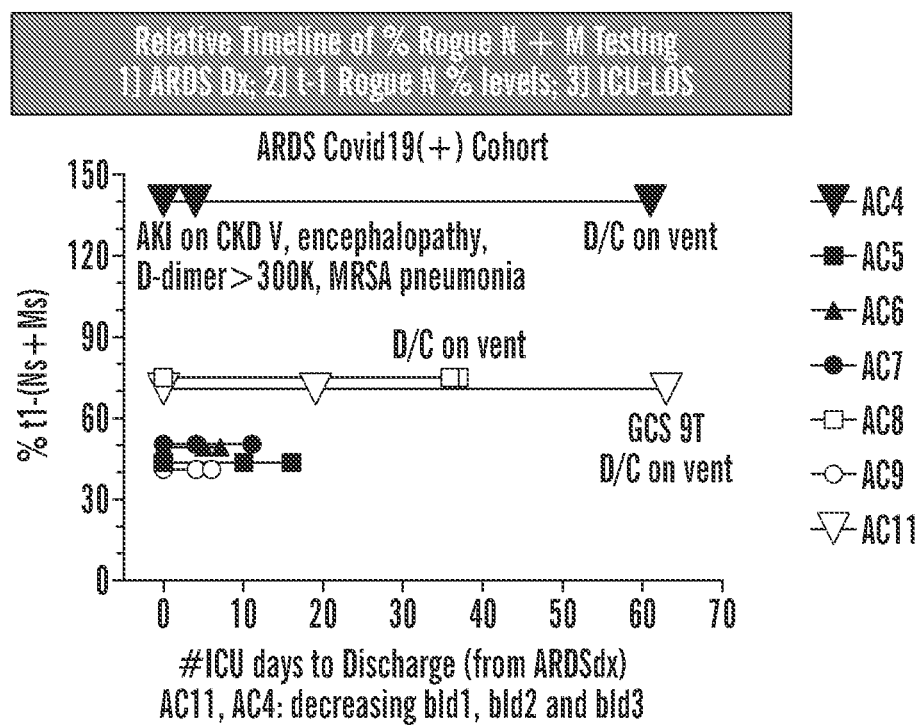
Figure 18:
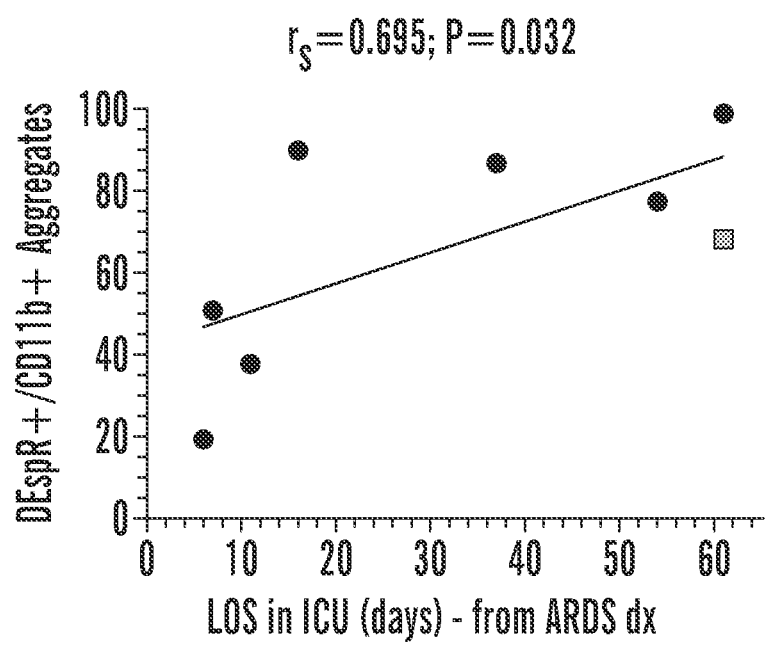
FIG. 18 shows that differential increase in % CD11b+/DEspR+ aggregates (FACS non-singlets) in COVID19+ ARDS patients correlates with the LOS in number of ICU-days. NETosing N-RBC hetero/homotypic aggregates in ARDS—nidus for micro-thromboses complications in ARDS

FIGS. 16A and 16B show differential increase in % CD11b+/DEspR+ aggregates in COVID19+ARDS patients, comparing those in AC4.1 patients (61 days in ICU) with those in AC6.1 patients (7 days in ICU). FIGS. 17A and 17B show the % of total DEspR+ neutrophils & monocytes correlate with length of stay in the ICU of coronavirus, e.g., COVID19, +ARDS patients, hence, provided as a patient stratifier & response indicator. Differential increase in % CD11b+/DEspR+ aggregates (FACS non-singlets) in COVID19+ ARDS patients was observed, as shown by FIG. 18. In some embodiments, NETosing N-RBC hetero/homotypic aggregates in ARDS is nidus for microthromboses complications in ARDS. In COVID19+ ARDS pilot study, increased D-Dimer levels did not differentiate high-mortality risk patients, as shown by FIG. 19.

COVID19 Driven ARDS provides rapid readouts for efficient clinical trials & point-of-care for, e.g., secondary organ dysfunction/failure after primary coronavirus infection, biomarkers for rapid, quantitative assessment, overall survival and rates of progression and/or morbidity. Exemplary secondary organ dysfunction/failure after primary coronavirus infection includes, but is not limited to, acute lung injury, ARDS, heart damage, liver dysfunction, and/or kidney failure. Exemplary biomarkers for rapid, quantitative assessment include, but are not limited to, myeloperoxidase (MPO), neutrophil elastase (NE), and/or neutrophil/lymphocyte ratio (NLR). For overall survival and rates of progression of coronavirus infection patients, for example, 20-50% of COVID19-ARDS patients progress to death. In some instances, the ventilator use in coronavirus, or COVID19, infection patients may be more than 14 days. For morbidity, in some embodiments, clinical deterioration/recovery may be quantifiable by serial organ failure assessment (SOFA) score. In some embodiments, additional target tissues affected by ARDS-COVID are increasingly observed affecting vital organs, such as, for example, heart, liver, and kidney in addition to systemic microthromboses.

Example 5: DEspR+ Neutrophils and Monocytes

Figure 20:
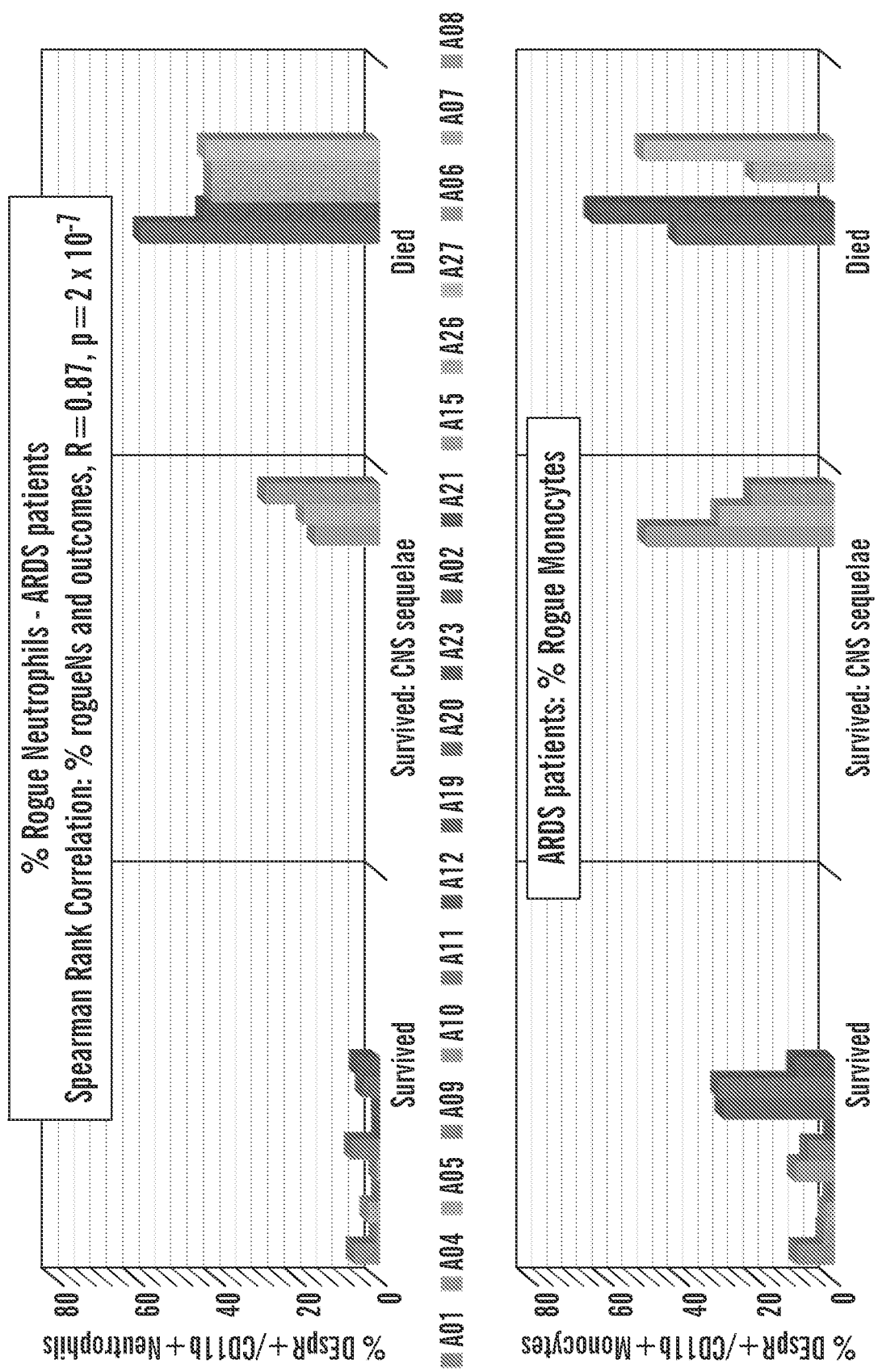
FIG. 20 shows that in ARDS patients, the % DEspR+/CD11b+ neutrophils (rogueNs) and % DEspR+/CD11b+ monocytes (rogue Ms) are associated with increased risk of poor outcome in an 18 patient ex vivo study, proposed as stratifier of putative patient responders.

In ARDS patients, the % DEspR+/CD11b+ neutrophils (rogueNs) as well as the % DEspR+/CD11b+ monocytes (Ms) are associated with increased risk of poor outcome in an 18 patient ex vivo study, thus, proposed as stratifiers of putative patient responders (FIG. 20).

Figure 21:
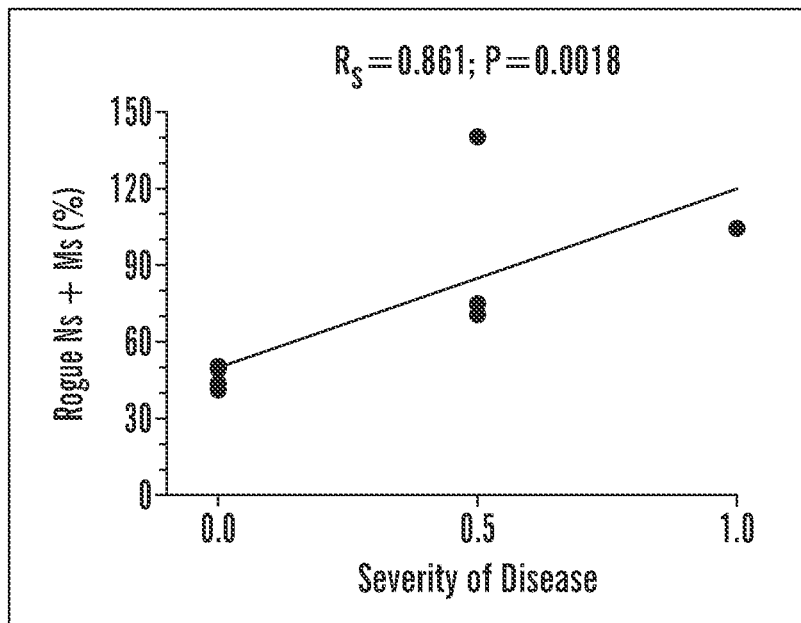
FIG. 21 depicts a mechanism-based patient stratifier, % Rogue Ns+ monocytes (Ms) of which increased correlation with outcomes in ARDS-COVID19 patients supports "rogue N+M" crosstalk towards hyperinflammation. Greater correlation of % total DEspR+ (Ns+Ms) with severity of disease in ARDS-COVID19 patients, supporting nodal role DEspR+ rogue N+M interactions.
Figure 22B:
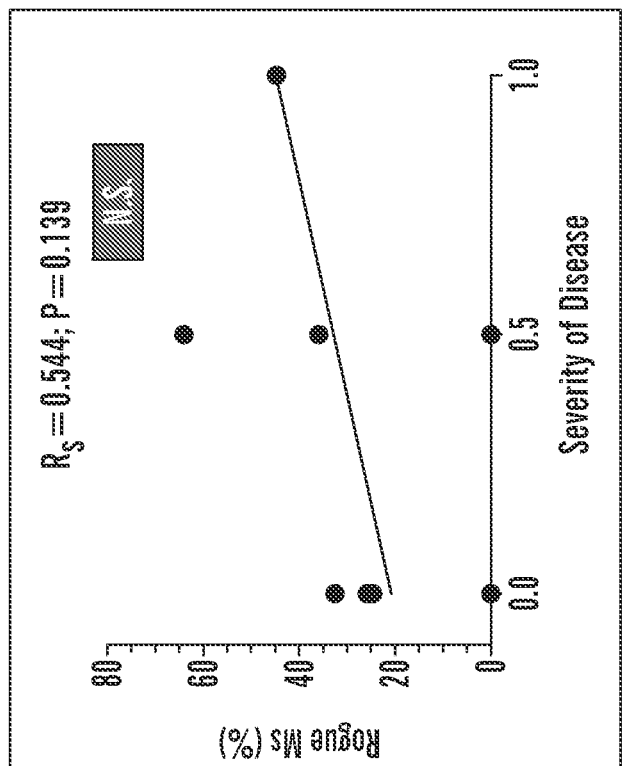
FIGS. 22A-22D depicts a mechanism-based patient stratifier, % Rogue Ns+ monocytes (Ms) of which increased correlation with outcomes in ARDS-COVID19 patients supports "rogue N+M" crosstalk towards hyperinflammation.
Figure 22A:
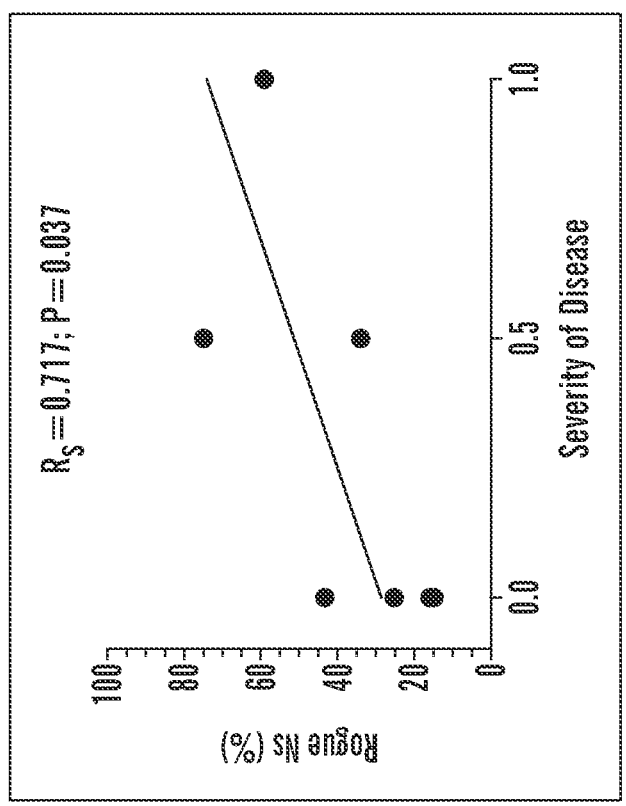
Figures 22C, 22D:
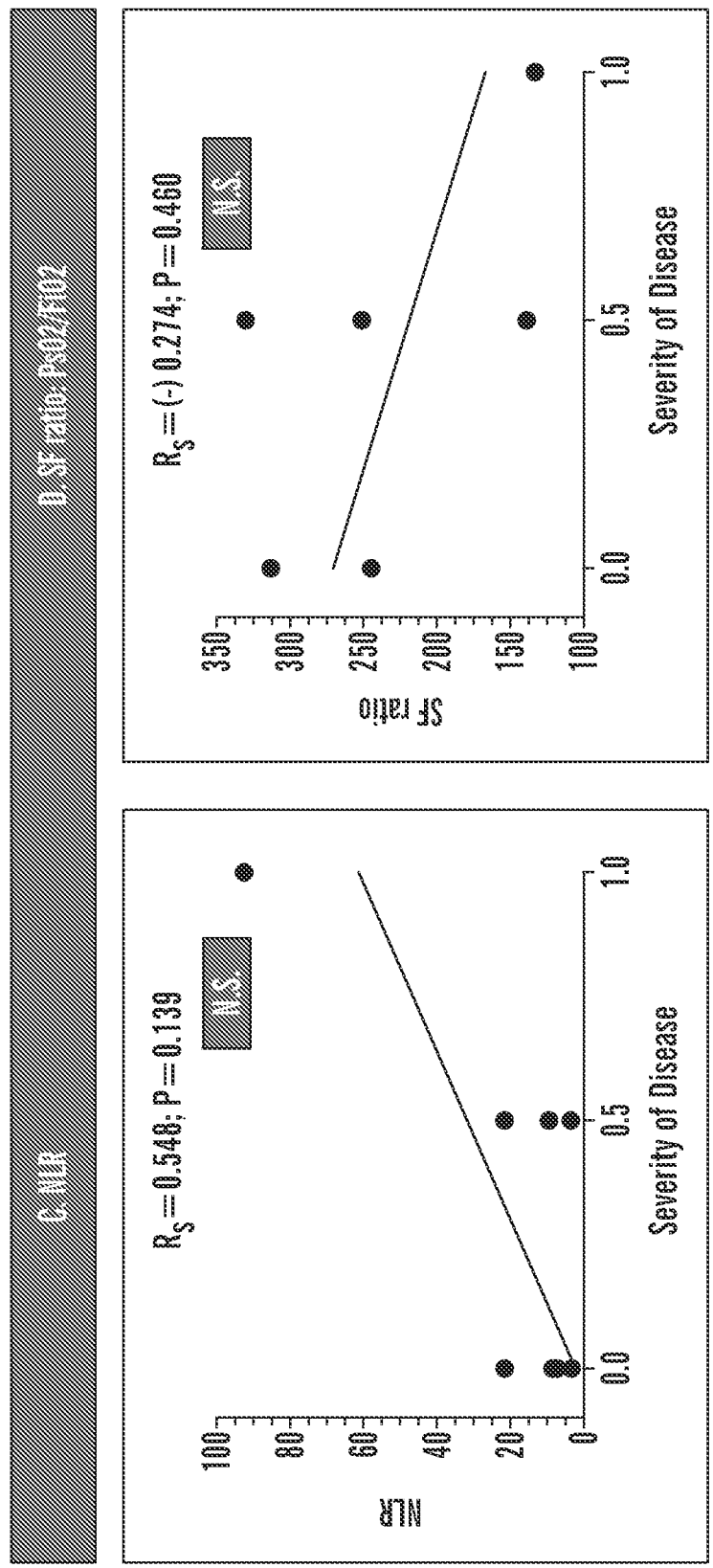

In some embodiments, the percentage of Rogue Ns and Ms (% Rogue Ns+Ms) may be used as a mechanism-based patient stratifier, as the increased correlation with outcomes in ARDS-COVID19 patients supports "rogue N+M" crosstalk towards hyperinflammation. FIG. 21 depicts a graph showing the total Rogue Ns+Ms vs. severity of disease, showing greater correlation of % total DEspR+ (Ns+Ms) with severity of disease, thus, supporting nodal role DEspR+ rogue N M interactions in ARDS-COVID19 patients. In some embodiments, total Rogue Ns+Ms is the sum of % CD11b+DEspR+ neutrophils (Ns) and monocytes (Ms). FIG. 22A depicts a graph showing % DEspR+CD11b+ Ns vs. severity of disease. FIG. 22B depicts a graph showing % DEspR+CD11b+ Ms vs. severity of disease. FIG. 22C depicts a graph showing NLR vs. severity of disease. FIG. 22D depicts a graph showing SF ratio: PsO2/FiO2 vs. severity of disease. In some embodiments, the severity of ARDS-COVID patients is defined by the number of days (# days) in the ICU, with ICU-death imputed as >longest length of stay: for example, 0: <7 days in ICU; 0.5: >30 days in ICU & discharge with; 1.0: ICU death. In some embodiments, ARDS diagnostics (dx) follows Berlin Definition criteria.

FIG. 23 shows comparative analysis of Spearman rank order correlation analysis of SF ratio, NLR, DEspR+ CD11B+Ns & Ms vs severity of disease in ARDS-COVID19 (AC4-AC11) patients. In some embodiments, the percentage of Rogue Ns+Ms (% Rogue Ns+Ms) exhibits the highest correlation with outcomes in ARDS-COVID19 patients (FIG. 23). In some embodiments, % Rogue Ns+Ms is better than NLR, SF ratio ARDS severity indicator with respective individual Spearman R.

Example 6: Neutrophil—Monocyte Early Involvement and Crosstalk

FIGS. 24A-36 depict FACS data showing single cell RNA-seq database.

Figure 24A:
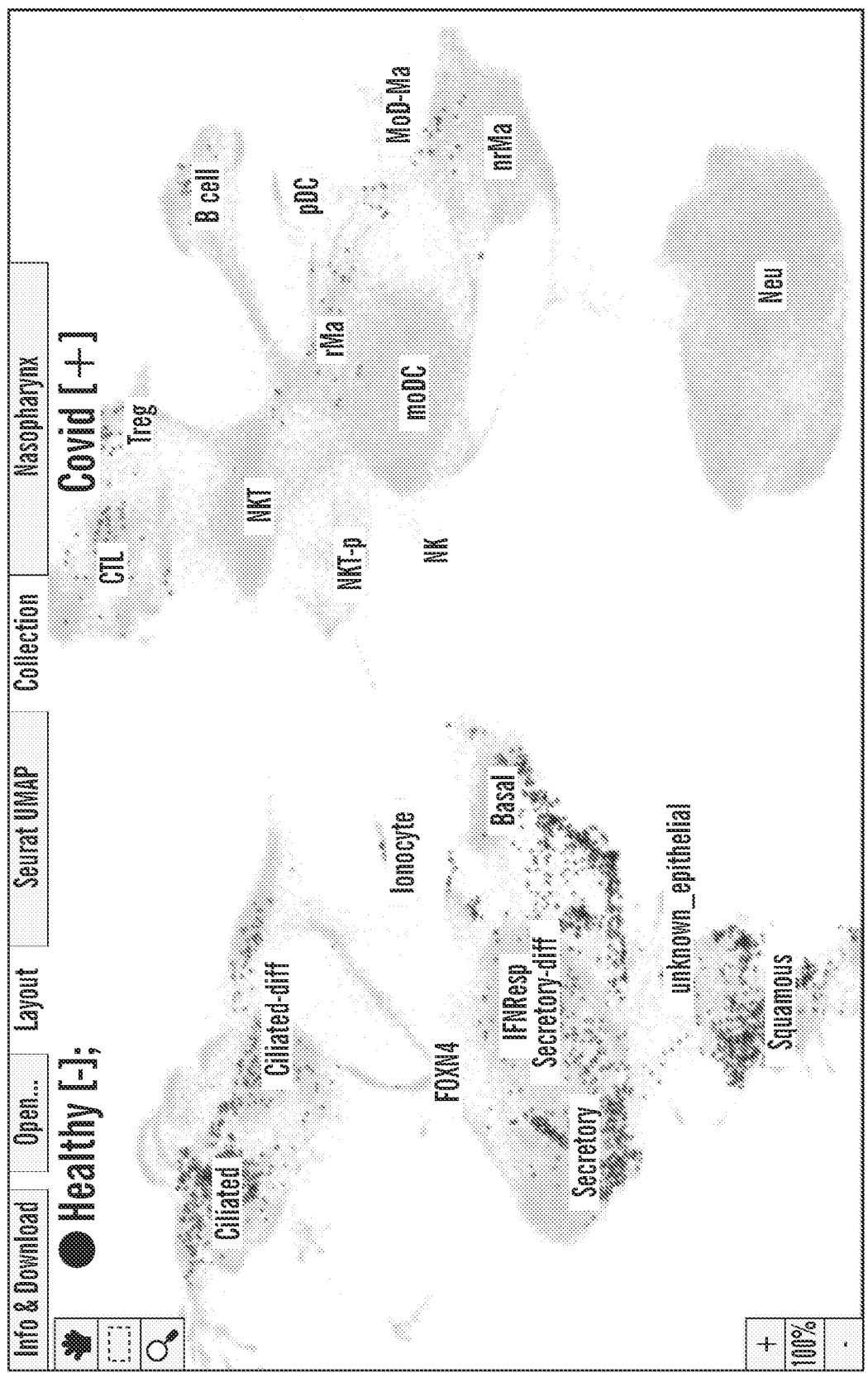
FIGS. 24A-24G depicts subsets of cells in nasopharyngeal and bronchial lavage samples identified based on unique molecular identifiers on single cell RNA-sequencing.
Figure 24B:
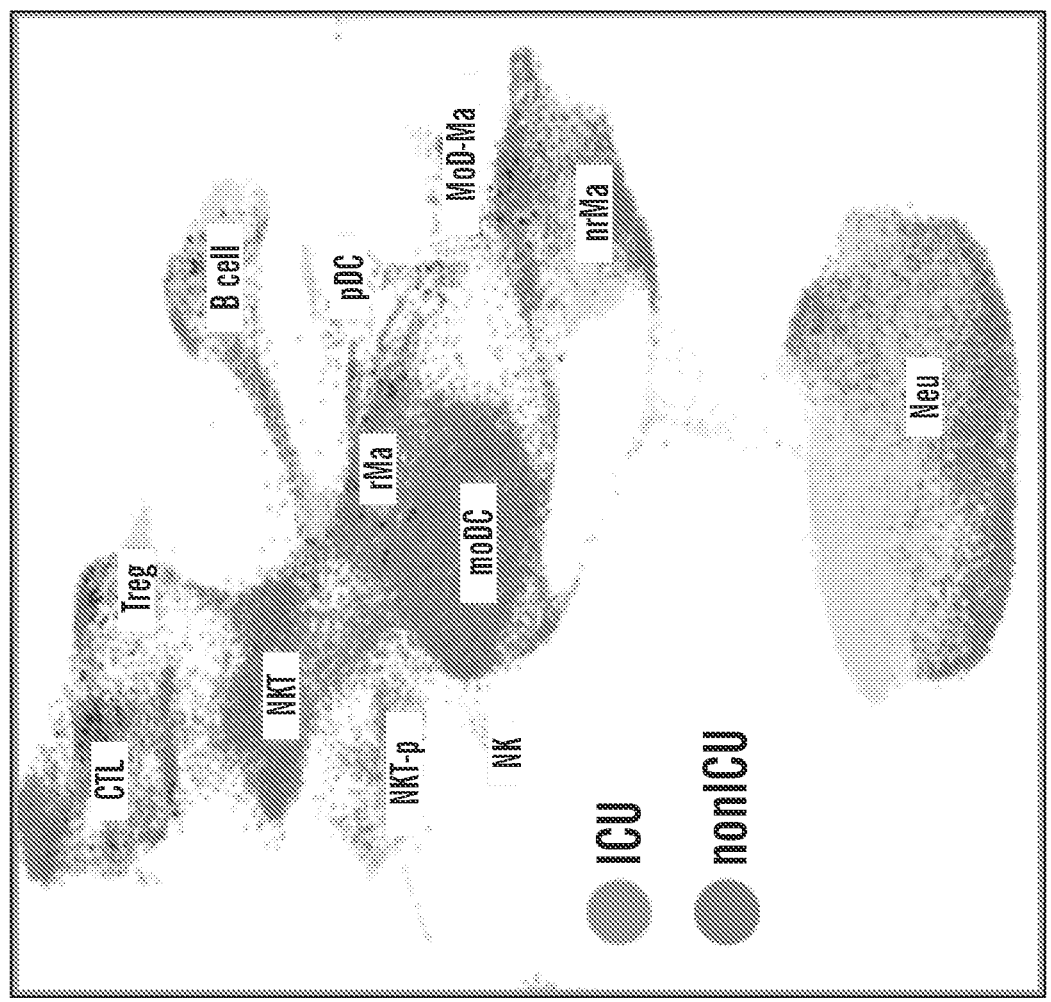
Figure 24C:
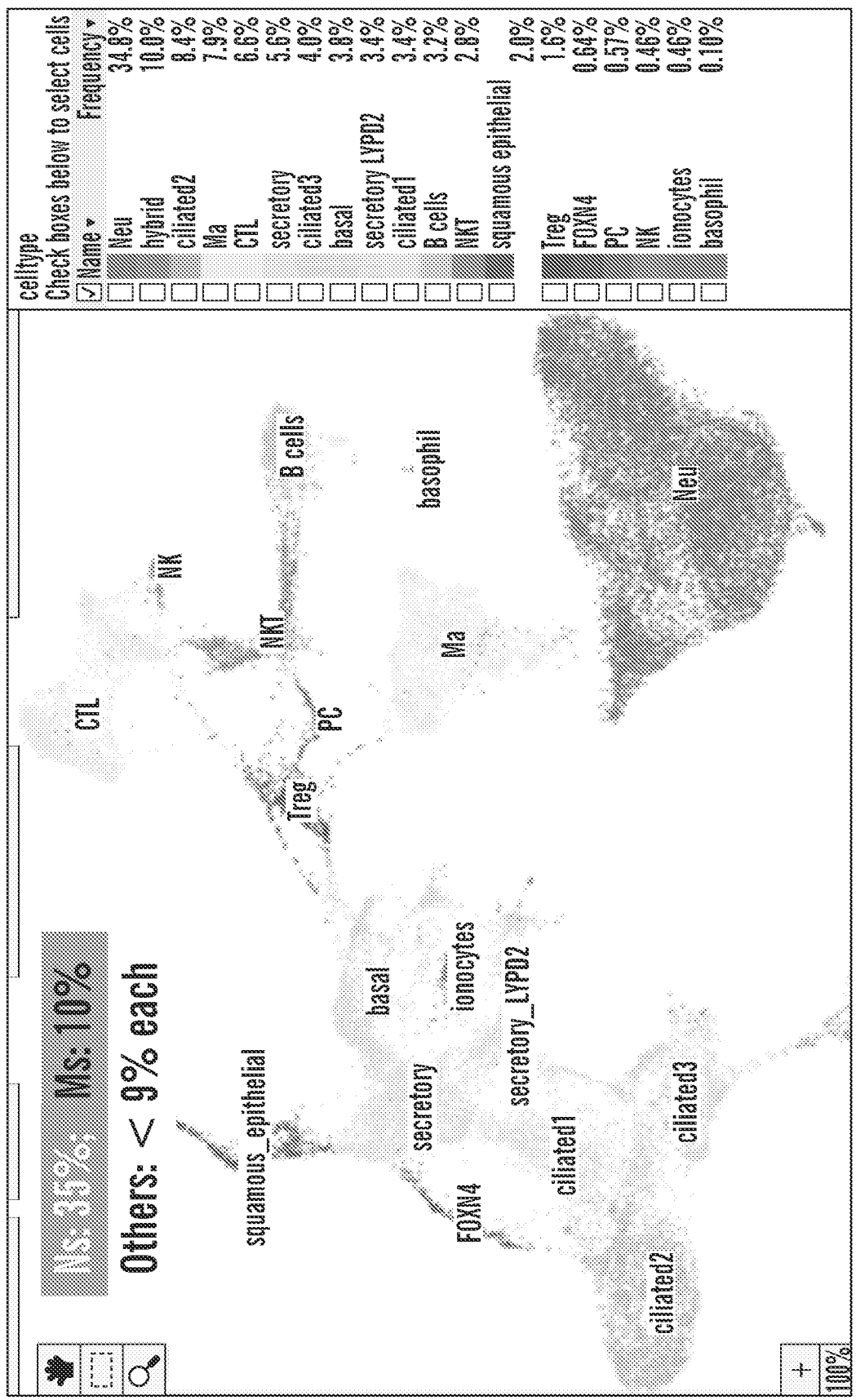
Figure 24D:
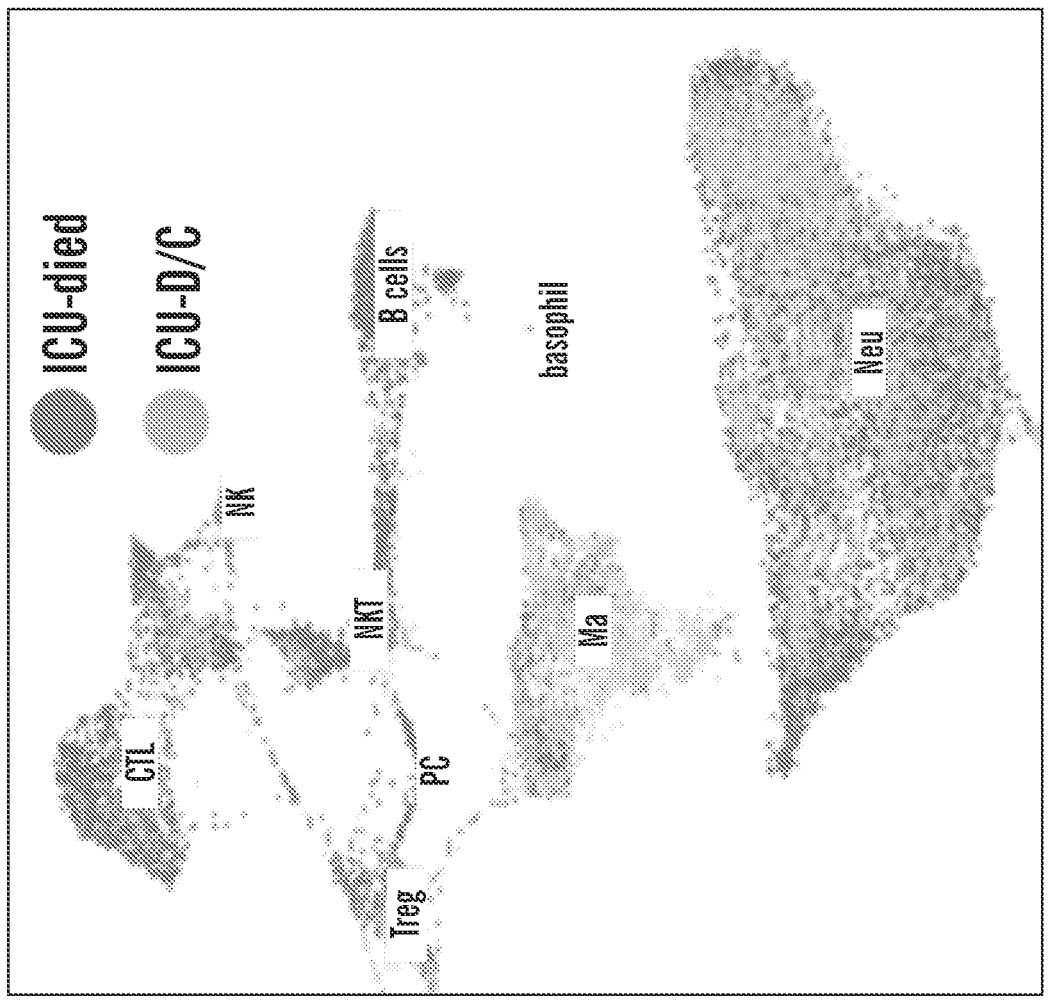
Figure 24E:
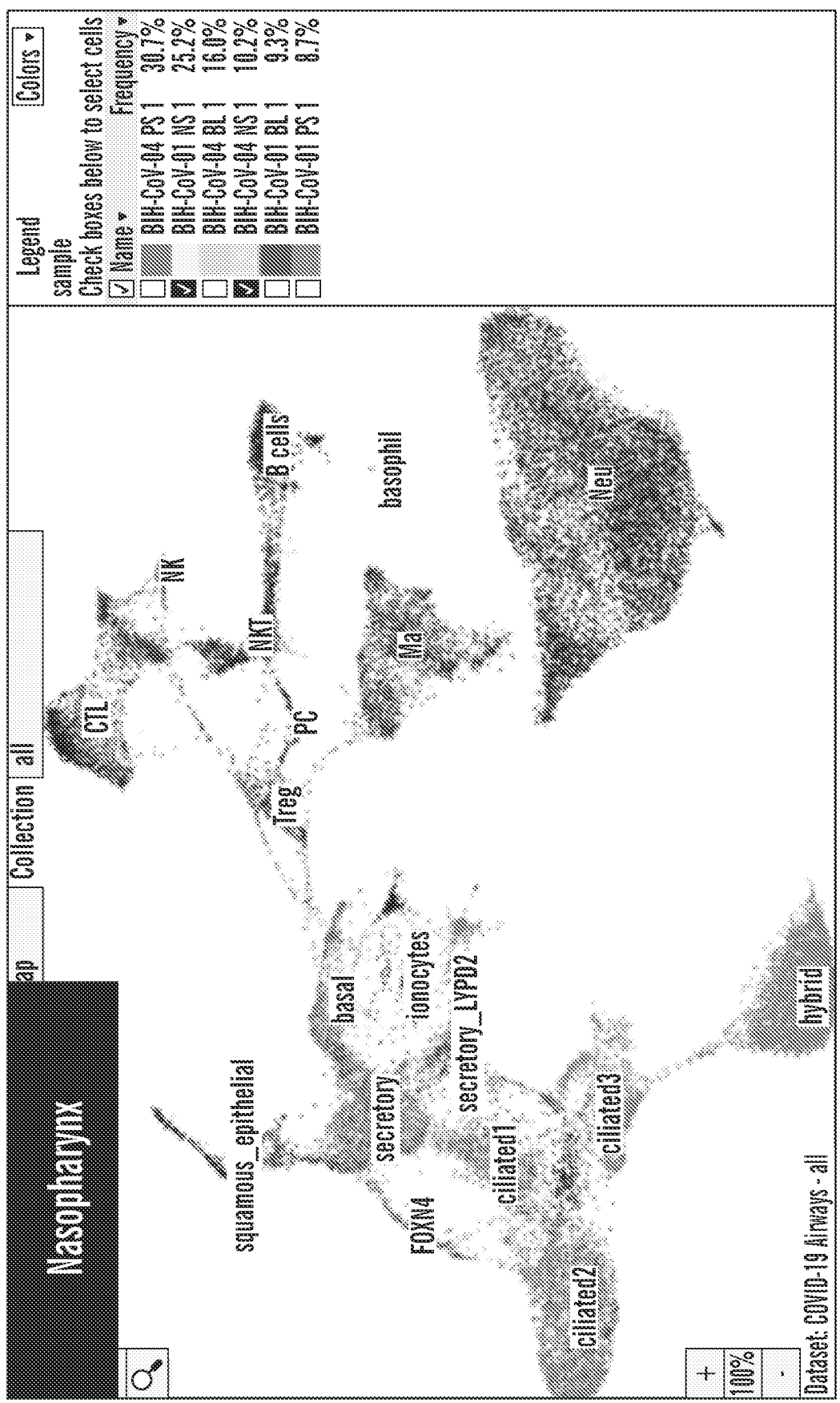
Figure 24F:
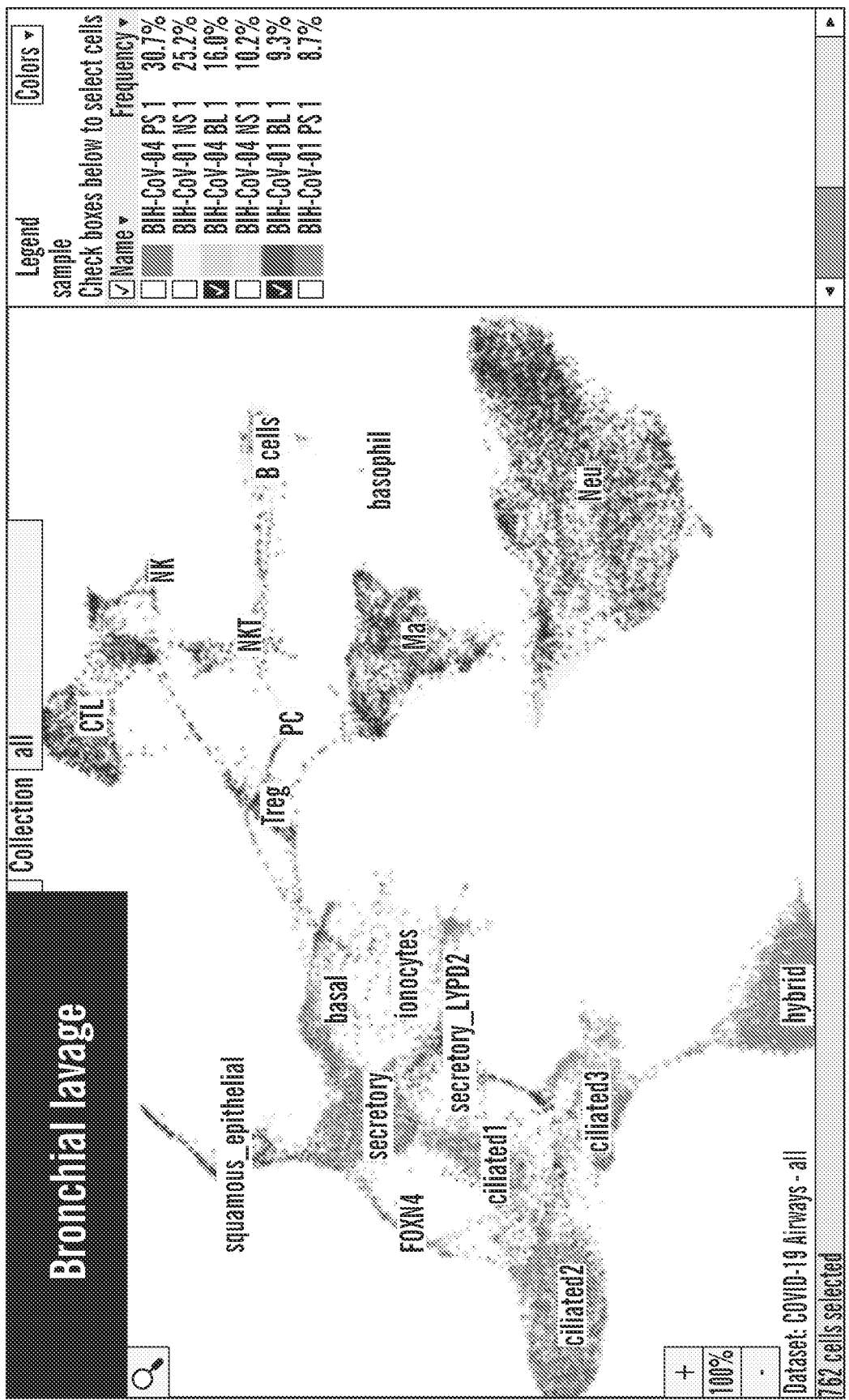
Figure 24G:
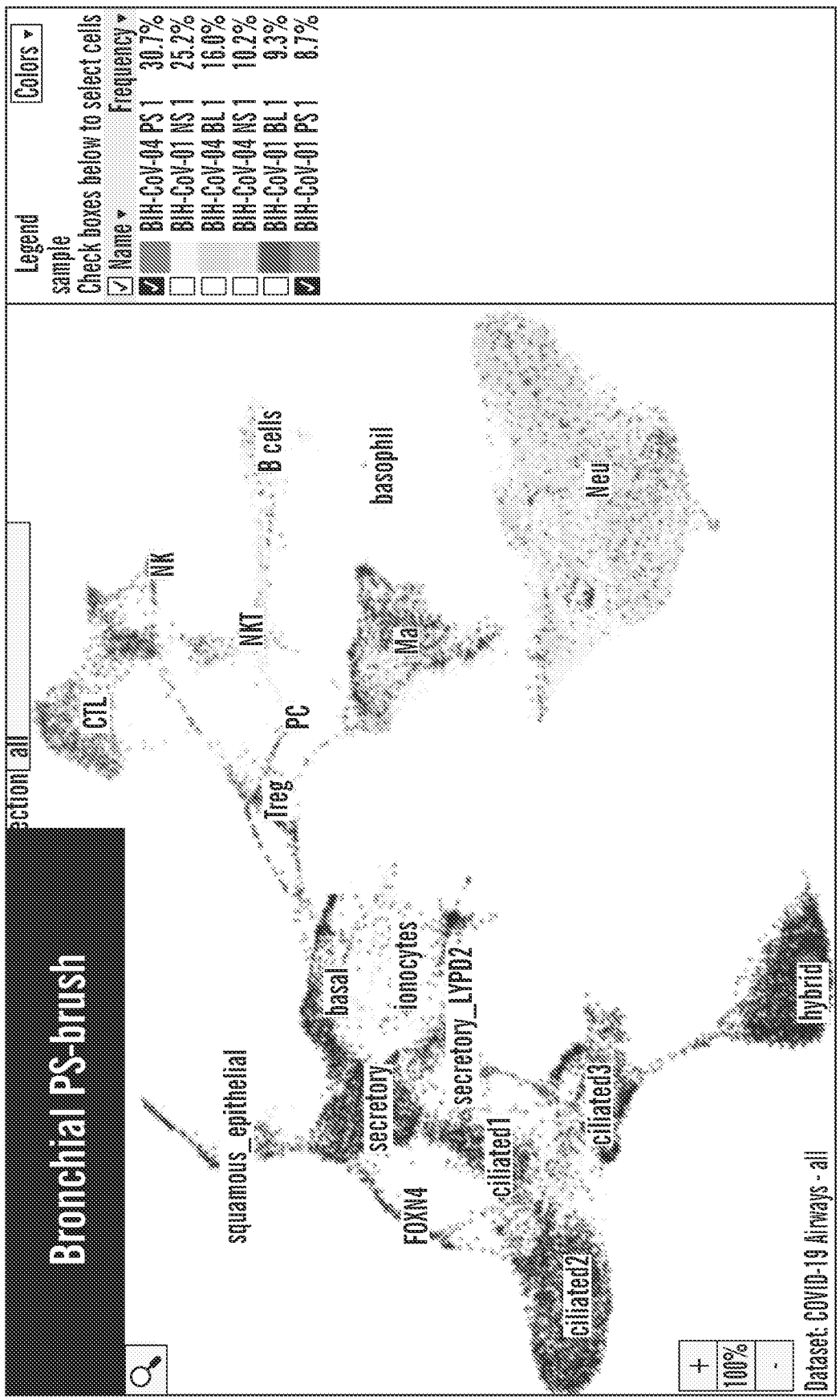
Figure 25A:
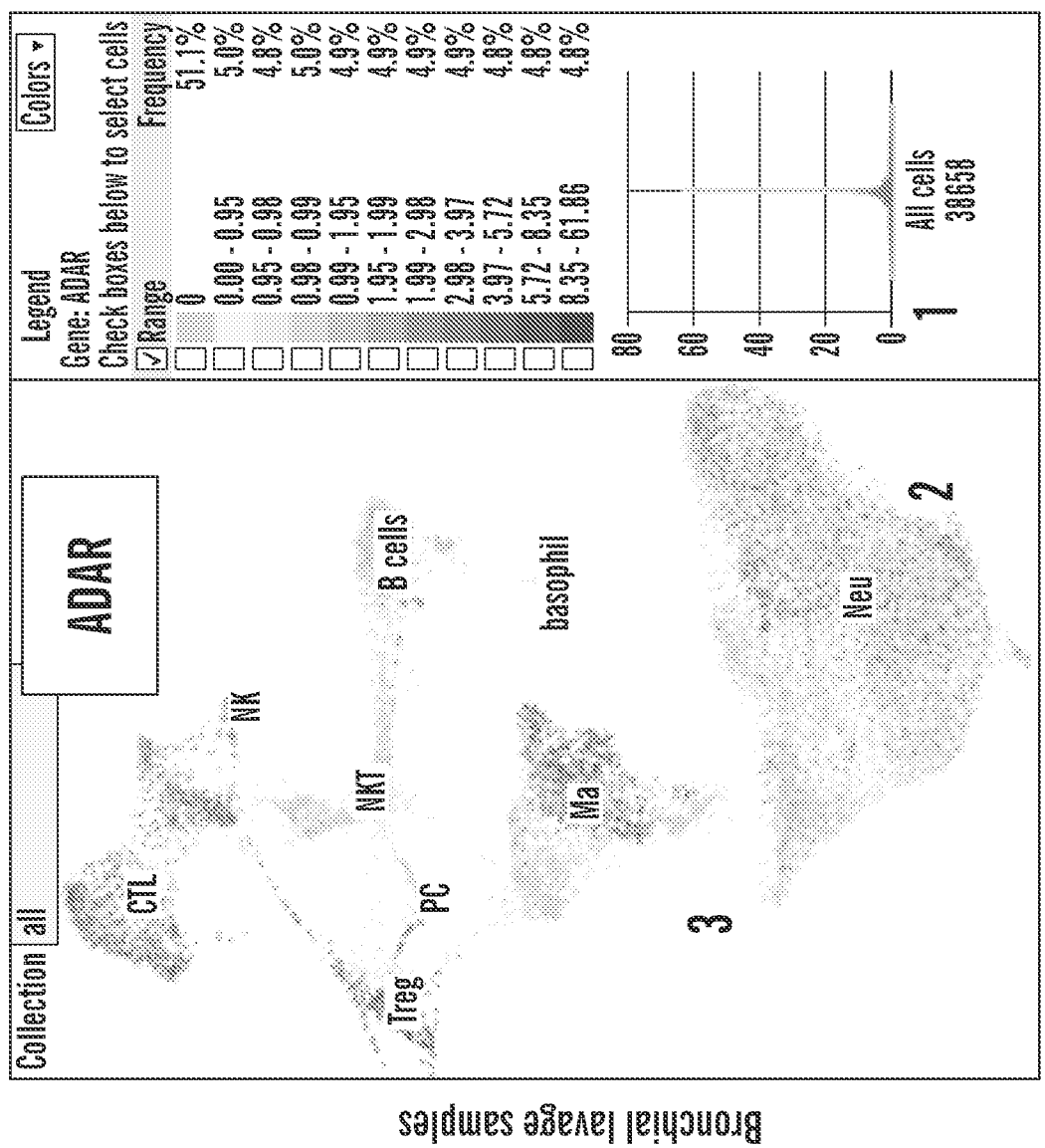
FIGS. 25A-25H depict single cell RNA (scRNA)-seq profiles of ADAR1, HIF1a, Mcl1 and FBXW7 in COVID 19 moderate and critically ill patients samples from the nasopharynx and bronchial lavage fluid. Robust expression of ADAR, Hif1a, and Mcl1, in contrast to low to no FBXW7 expression are concordant with DEspR+ expression in neutrophils and monocytes by FACS.
Figure 25B:
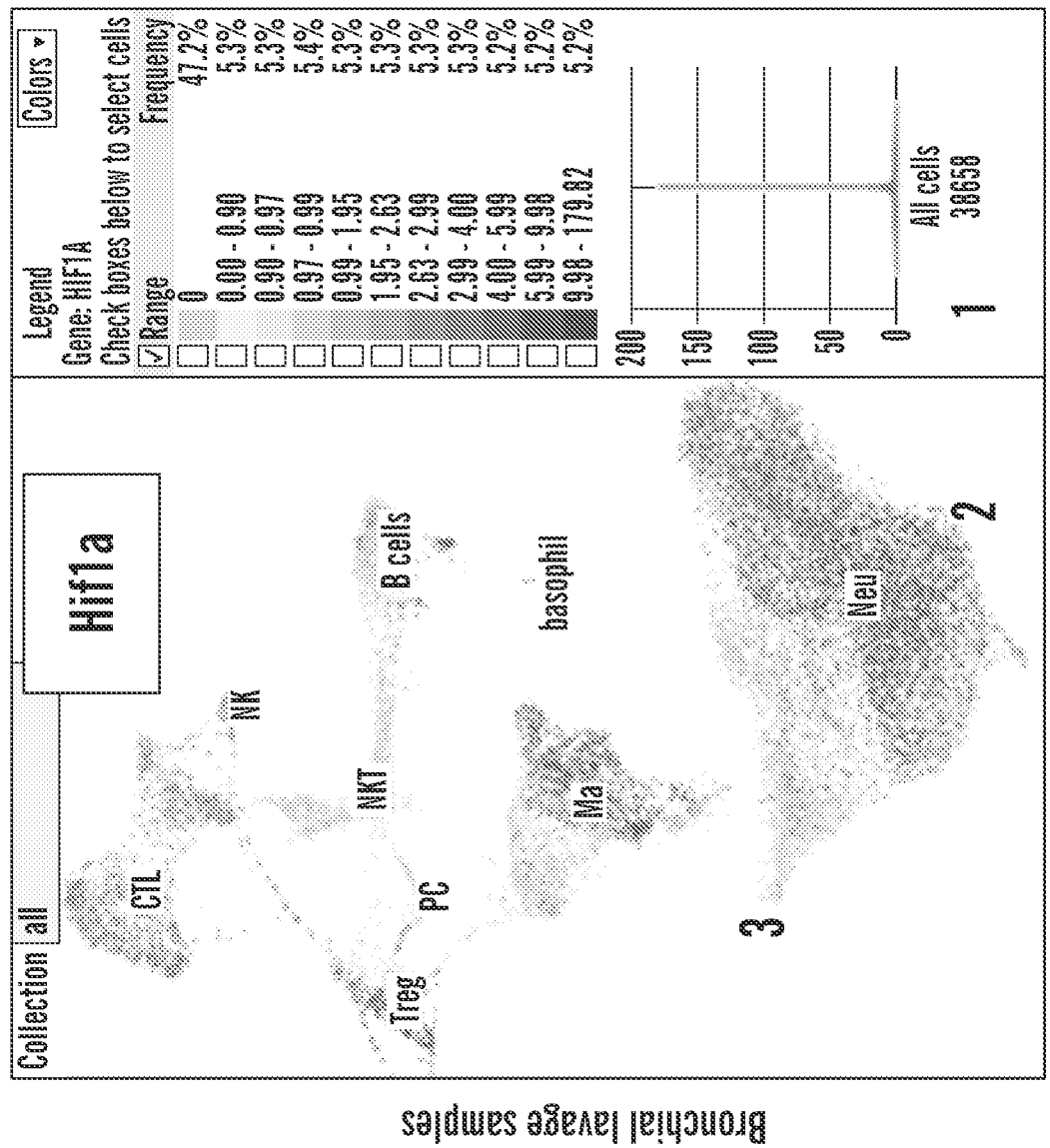
Figure 25C:
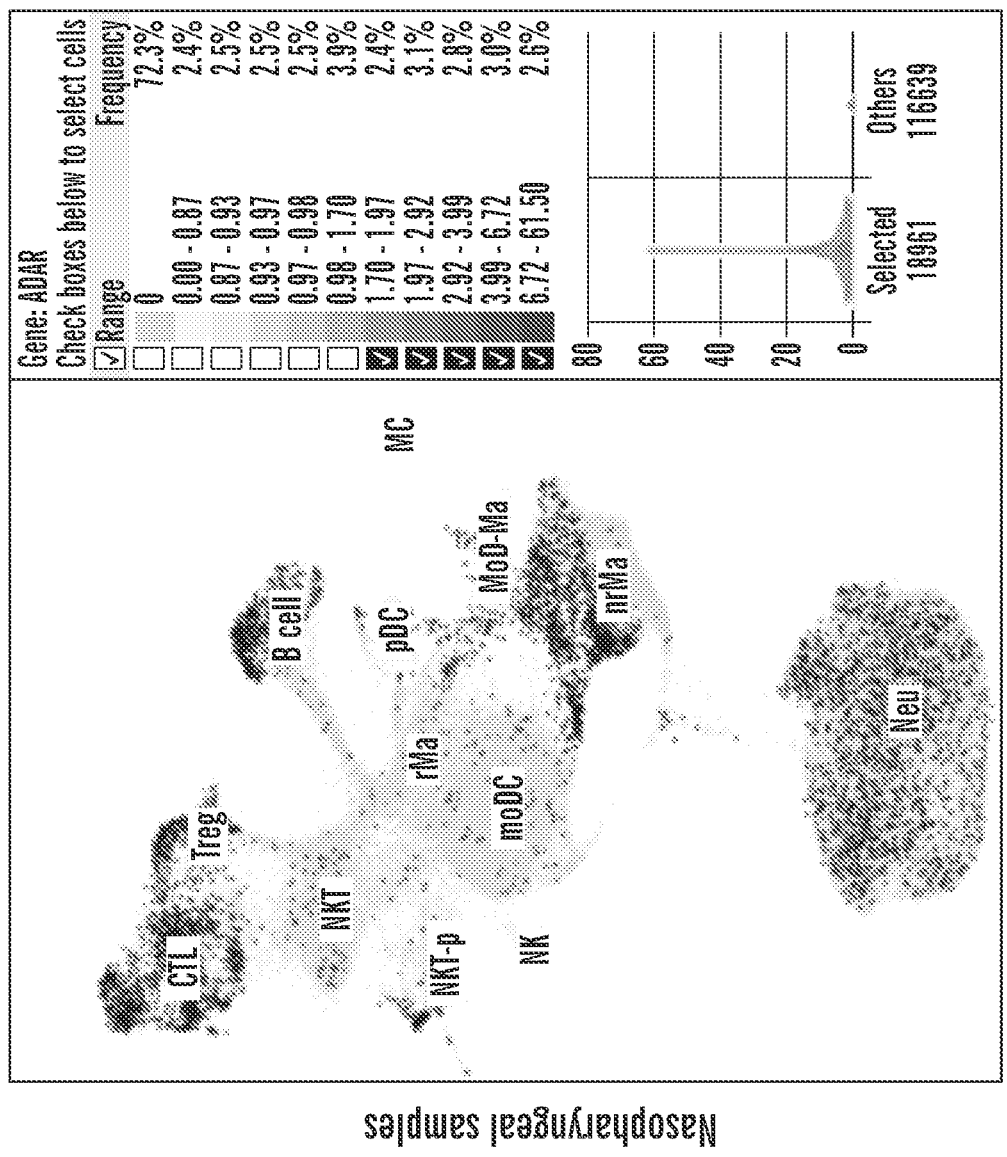
Figure 25D:
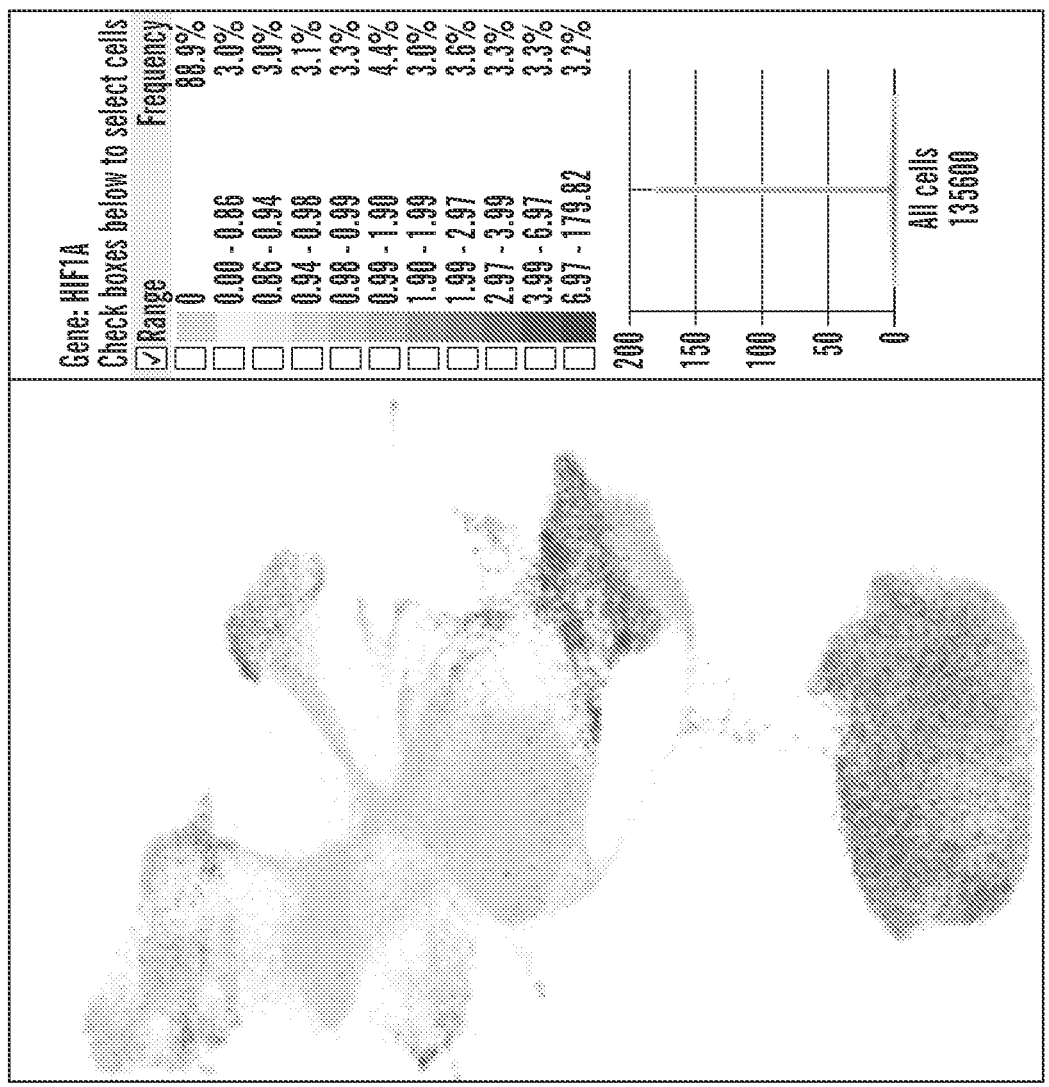
Figure 25E:
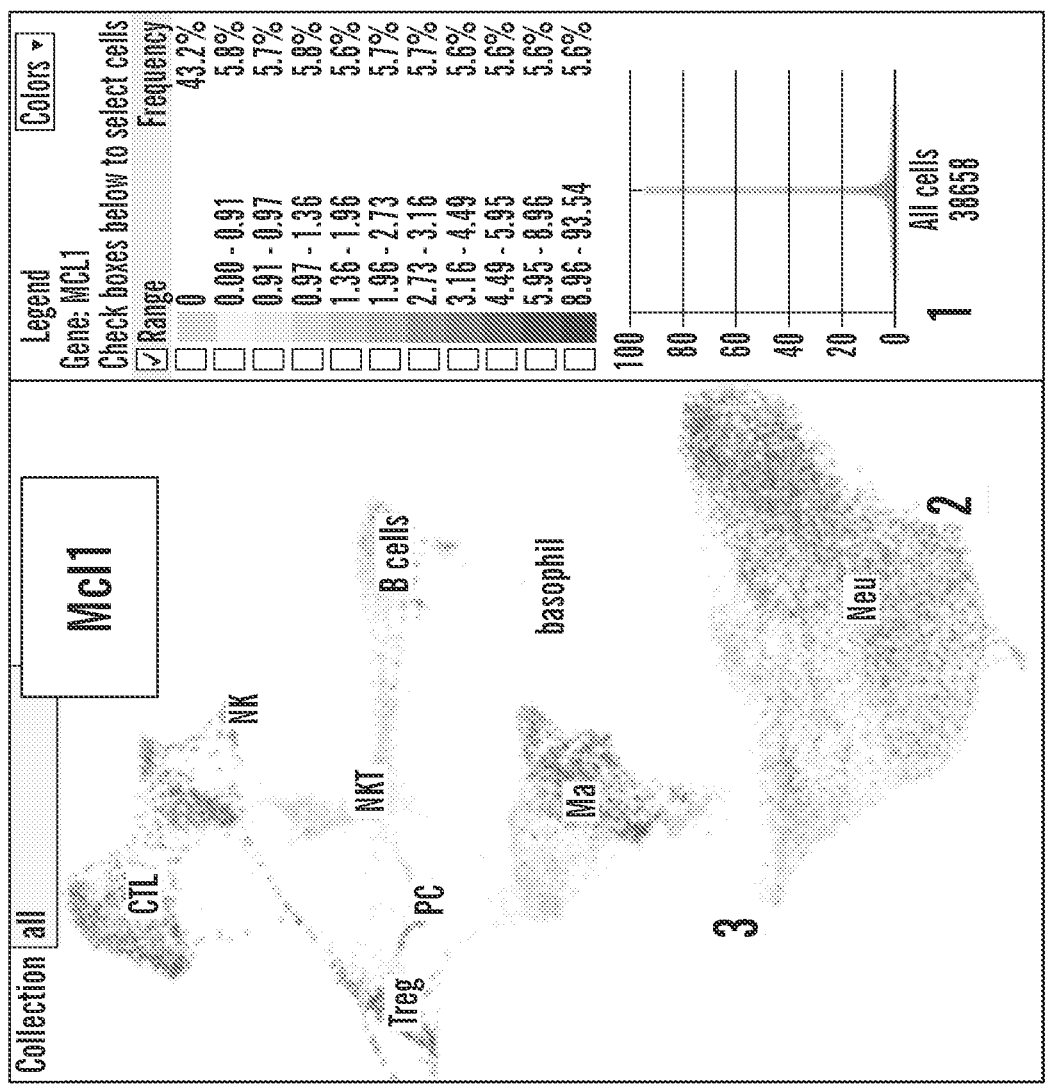
Figure 25F:
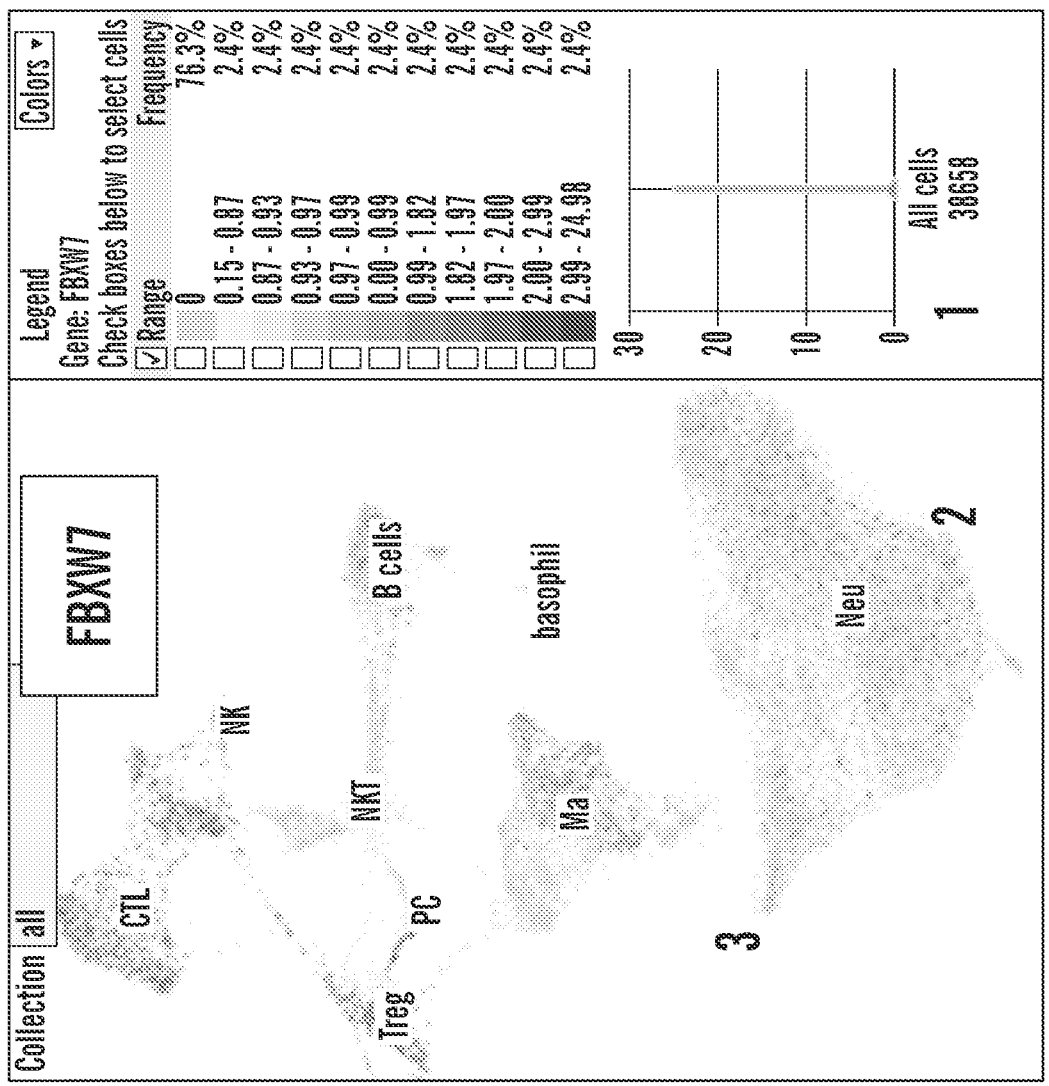
Figure 25G:
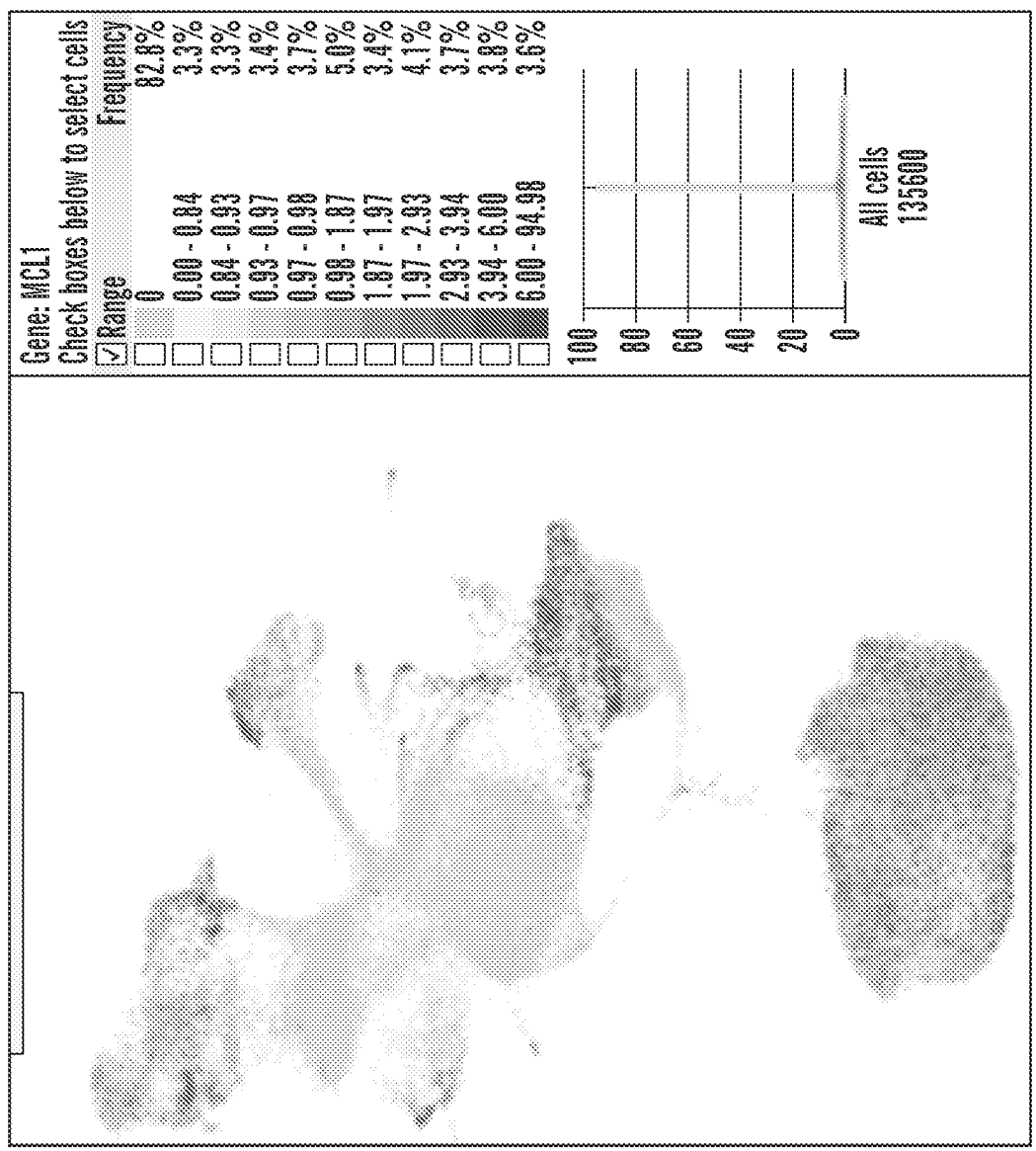
Figure 25H:
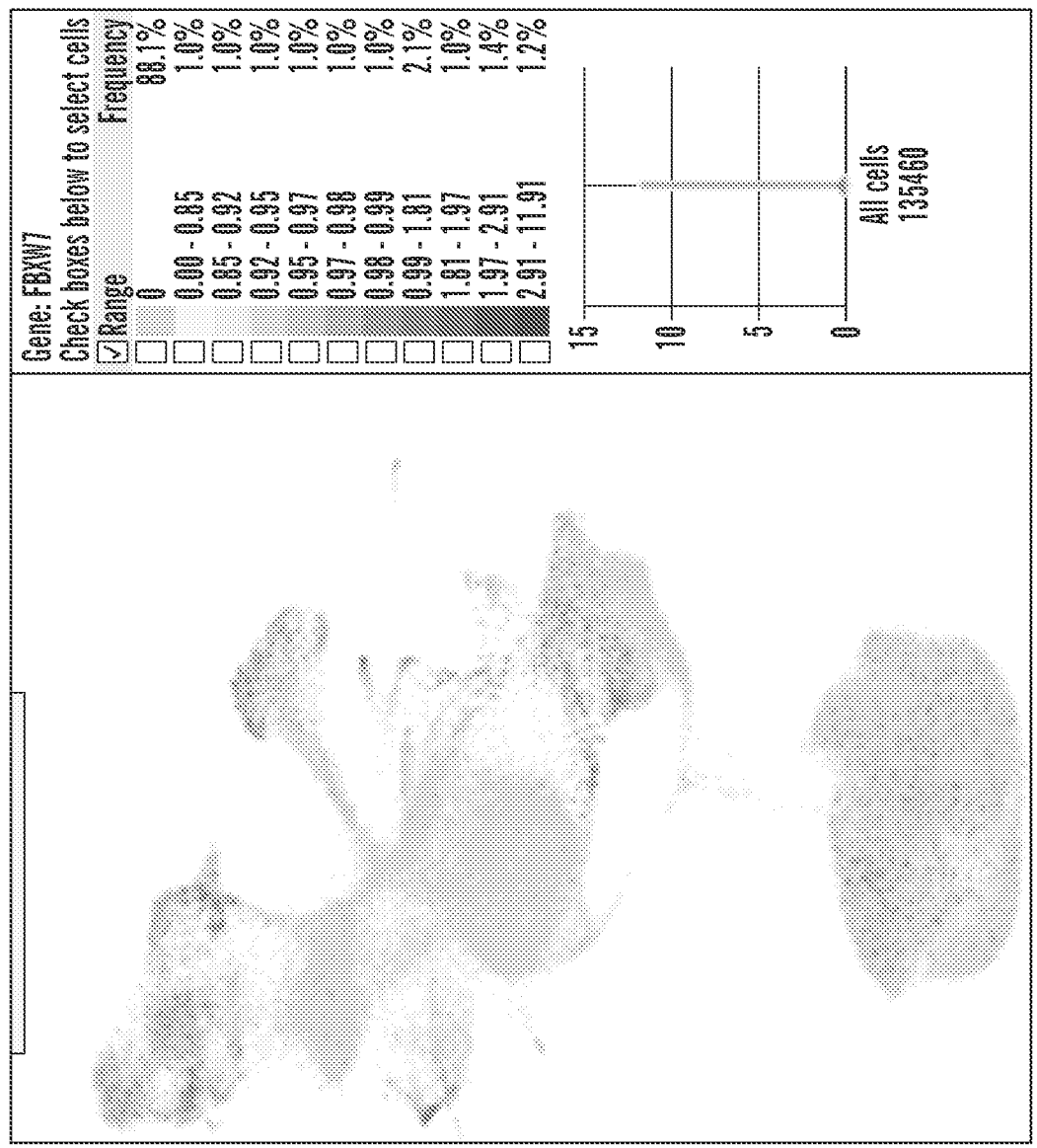

FIGS. 24A-24G depict neutrophils and monocytes as majority cells in nasopharyngeal and bronchial lavage samples. FIGS. 24A-24D shows comparisons of health vs. subject having coronavirus infection, ICU vs. nonICU, Ns vs Ms vs other cells, and ICU-died vs ICU-discharge (D/C). FIGS. 24E-24G show results from nasopharynx, the bronchial lavage, and bronchoscopic bronchial protected specimen (PS)-brush samples.

FIGS. 25A-25H depict scRNA-seq profiles of ADAR1, HIF1a, Mcl1 and FBXW7 in bronchial lavage samples and nasopharyngeal samples from COVID 19 moderate and critically ill patients, which is concordant with DEspR+ neutrophils and monocytes by FACS.

Figure 26A:
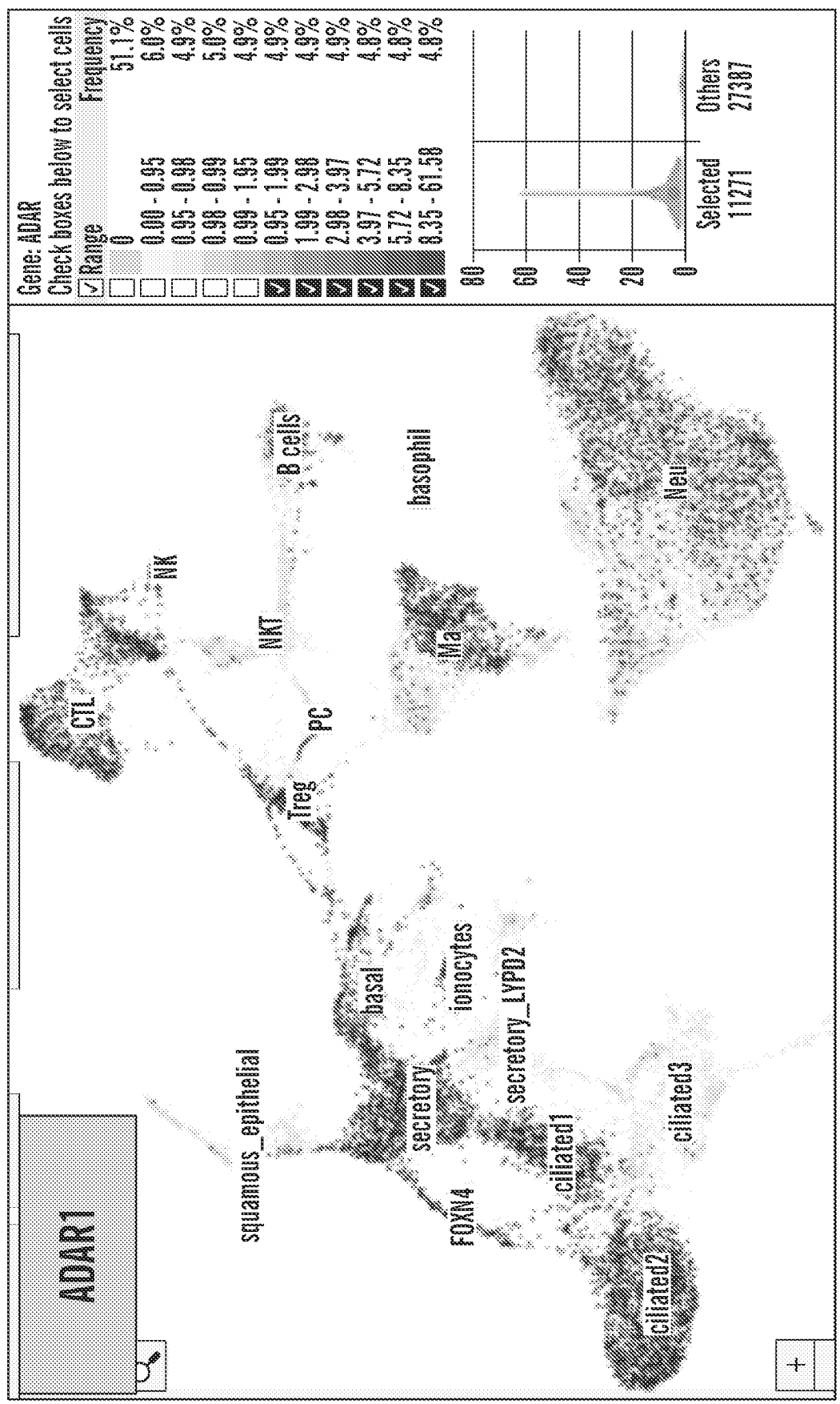
FIGS. 26A-26C depict DEspR+ rogue Ns and Ms autocrine loop in critically ill COVID 19 patients: ADAR1+, HIF1α+, high Mcl1+, and low FBXW7, and ET-1+.
Figure 26B:
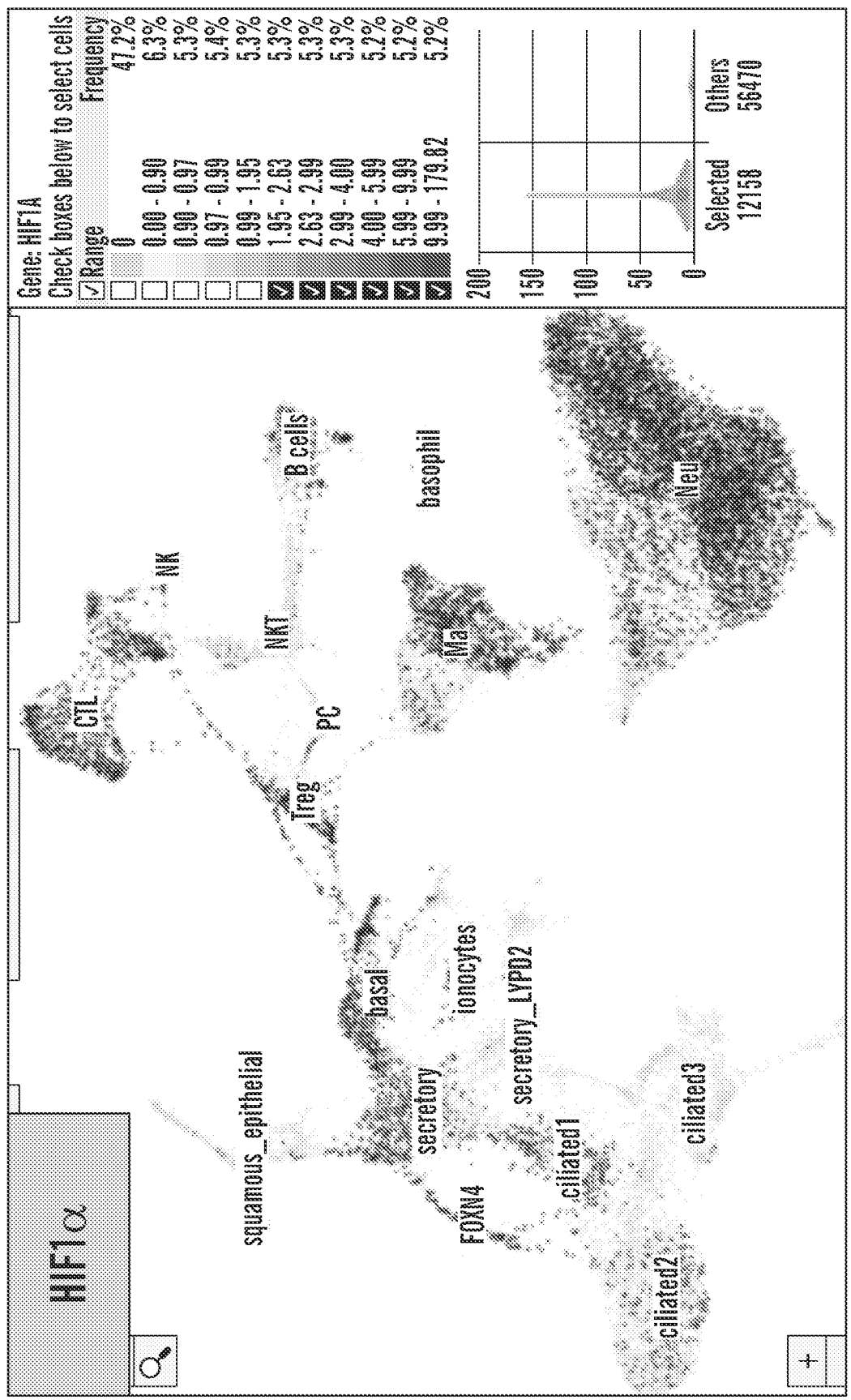
Figure 26C:
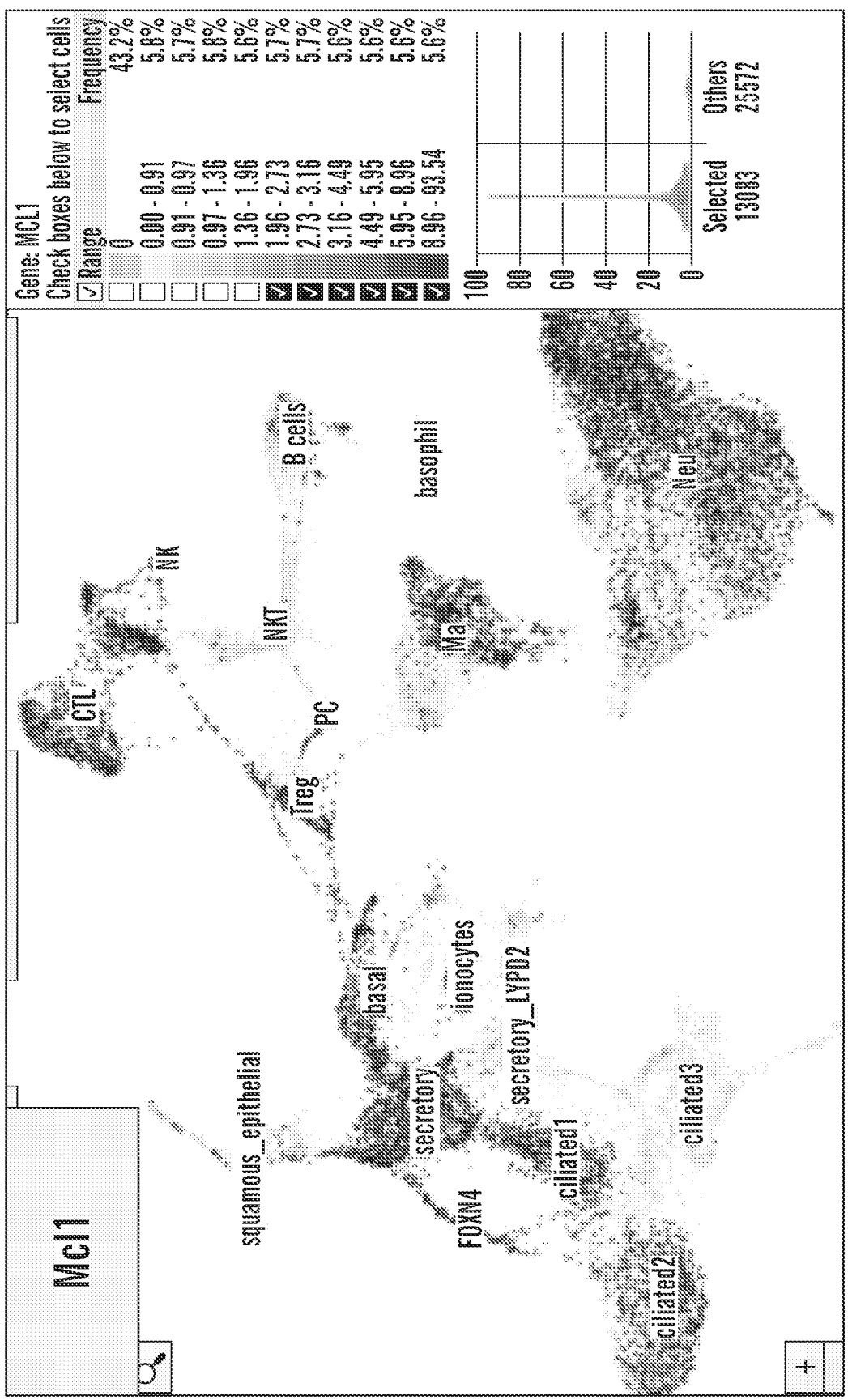
Figure 26D:
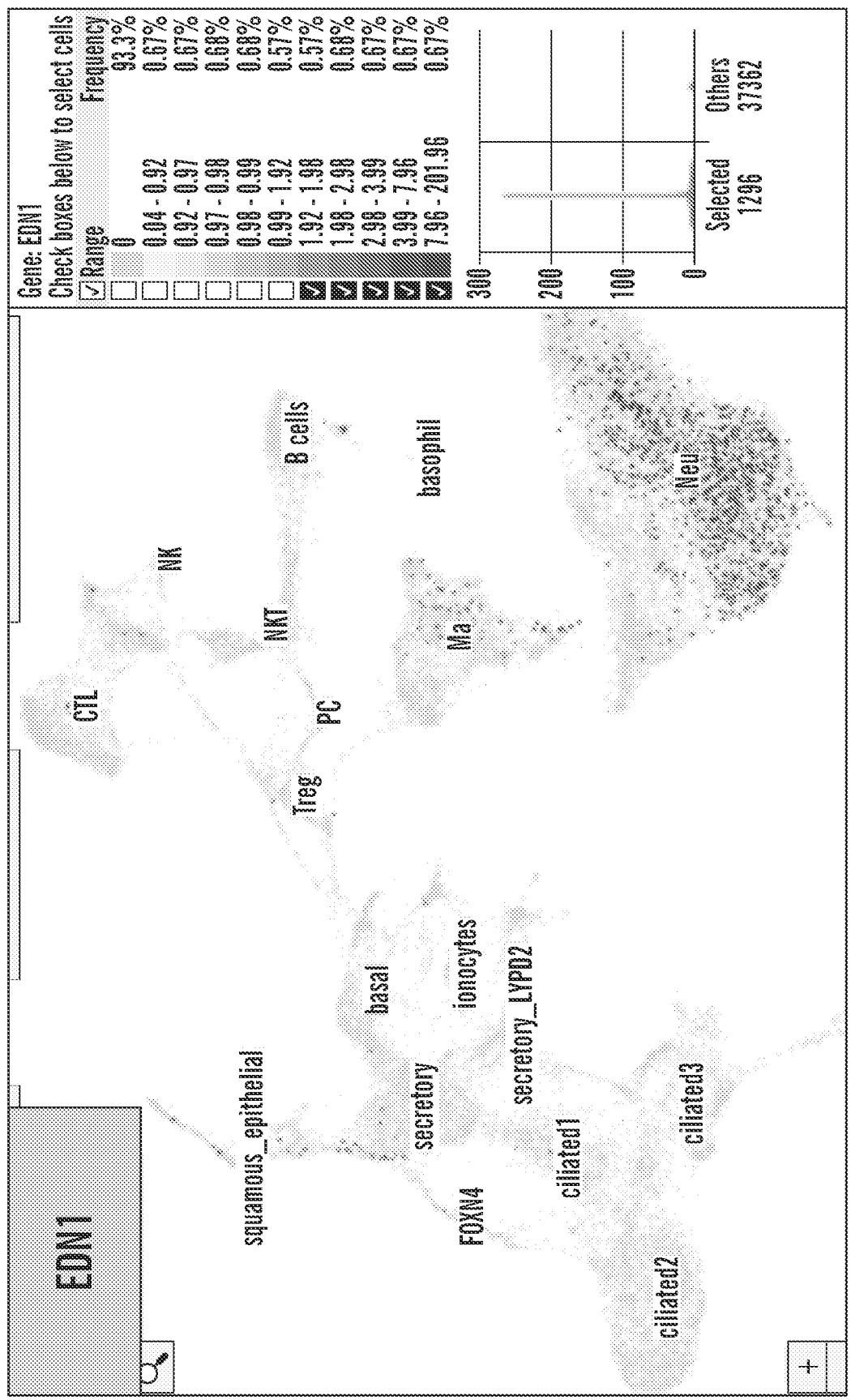
FIGS. 26D-26F depict autocrine loop, in which neutrophils express DEspR ligands: endothelin 1 (EDN1) and endothelin converting enzyme (ECE1); and signal peptide of VEGF (SPVEGF)
Figure 26E:
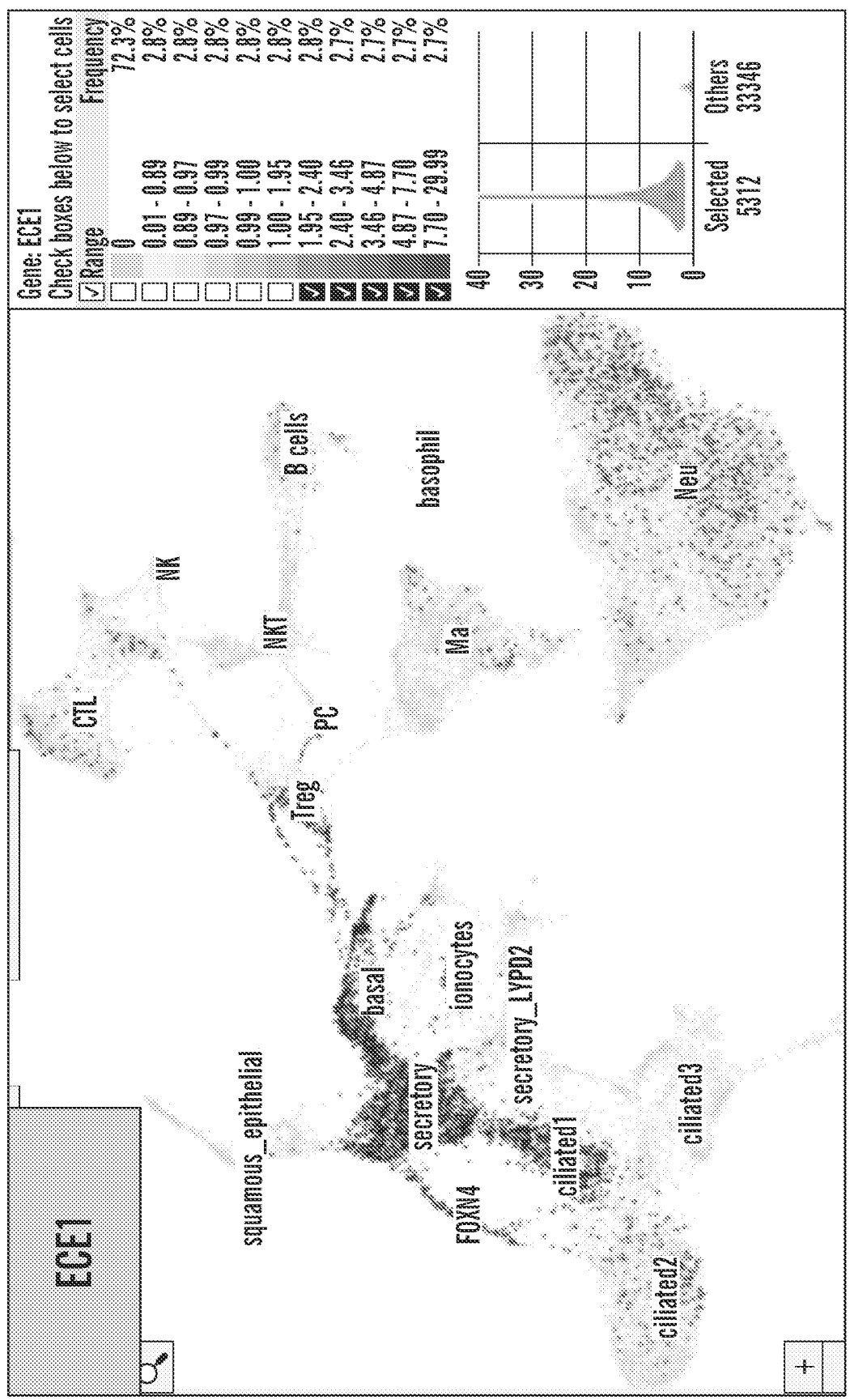
Figure 26F:
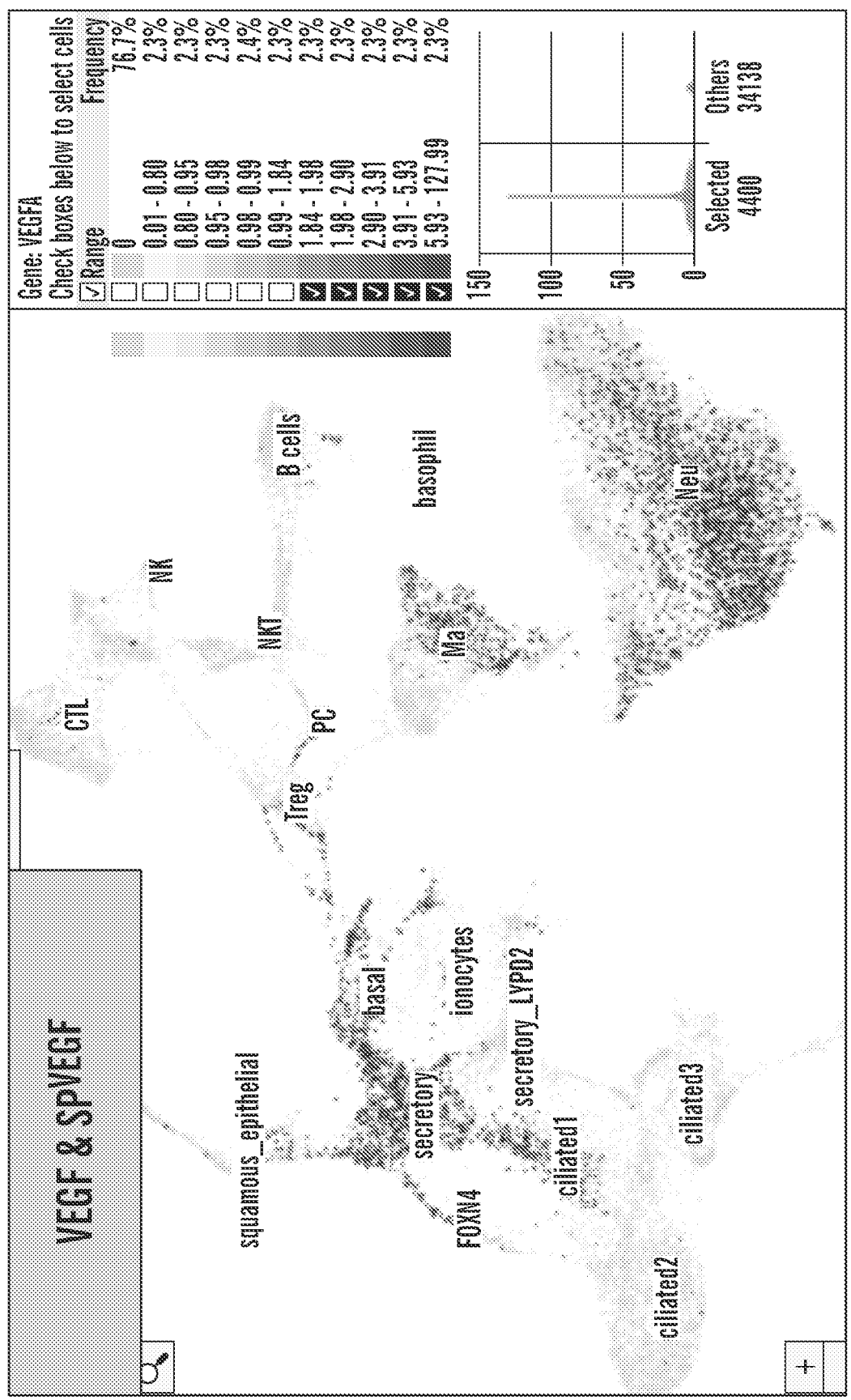

FIGS. 26A-26C depicts DEspR+ rogue Ns and Ms autocrine loop in critically ill COVID 19 patients, showing ADAR1+, HIF1a+, high Mcl1+, and low FBXW7, and ET-1+. FIGS. 26D-26F depicts autocrine loop indicating that neutrophils express DEspR ligands and shows endothelin 1 (EDN1) and endothelin converting enzyme, and signal peptide of VEGF.

Figure 27:
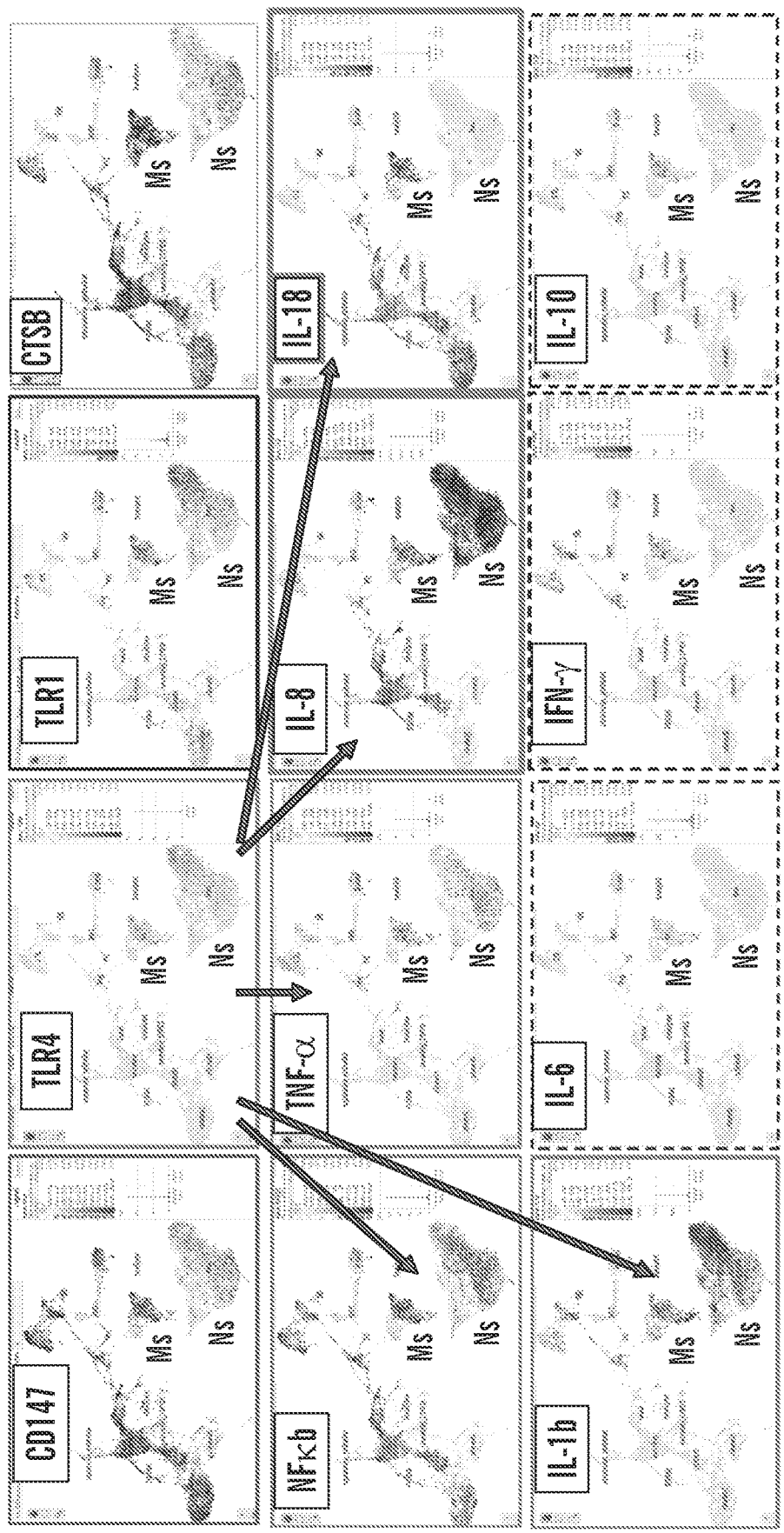
FIG. 27 shows that receptors with which CoV2 spike protein can dock, such as TLR4, TLR1, and CD147, are expressed on neutrophils and monocytes per se, and that a 'cleaver' protein, cathepsin-B (CTSB) is also expressed in monocytes and neutrophil, thus showing direct SARS CoV2 activation of neutrophils and monocytes upon docking with TLR4/1 and CD147, this providing a direct pathway from viral spike protein to a feedforward cytokine network shown to be elevated in COVID19 patients: IL-8, IL-'8, IL1-beta.

FIG. 27 showing that CoV2 spike protein docks (TLR4, TLR1, CD147), and 'cleaver' CTSB (Cathepsin B) in monocytes and neutrophil, indicating that direct activation pathway to feedforward cytokine network.

Figure 28A:
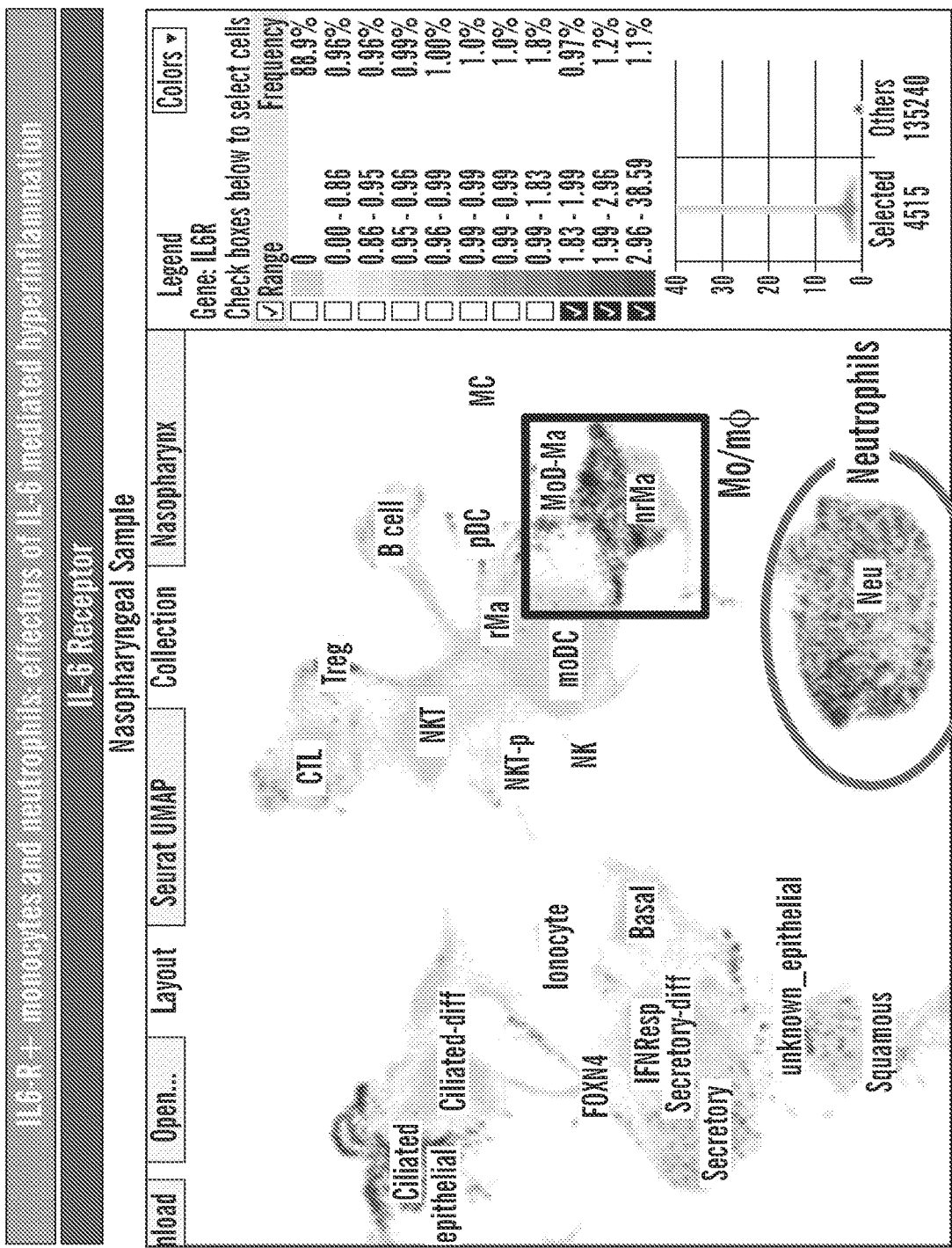
FIGS. 28A-28F depict single-cell RNA-seq database[R. Eils] analysis, showing neutrophil and monocyte crosstalk via IL-8 autocrine loop and as IL-6 effectors in ARDS-COVID19 patients. IL-6: minimal to no expression in ACE2+ respiratory epithelial cells, suggesting that elevated IL-6 in COVID19 patients is likely predominantly from known ACE2+ endothelial cells (ECs), and supports a key role of reciprocal interactions of activated-ECs and primed neutrophils.
Figure 28B:
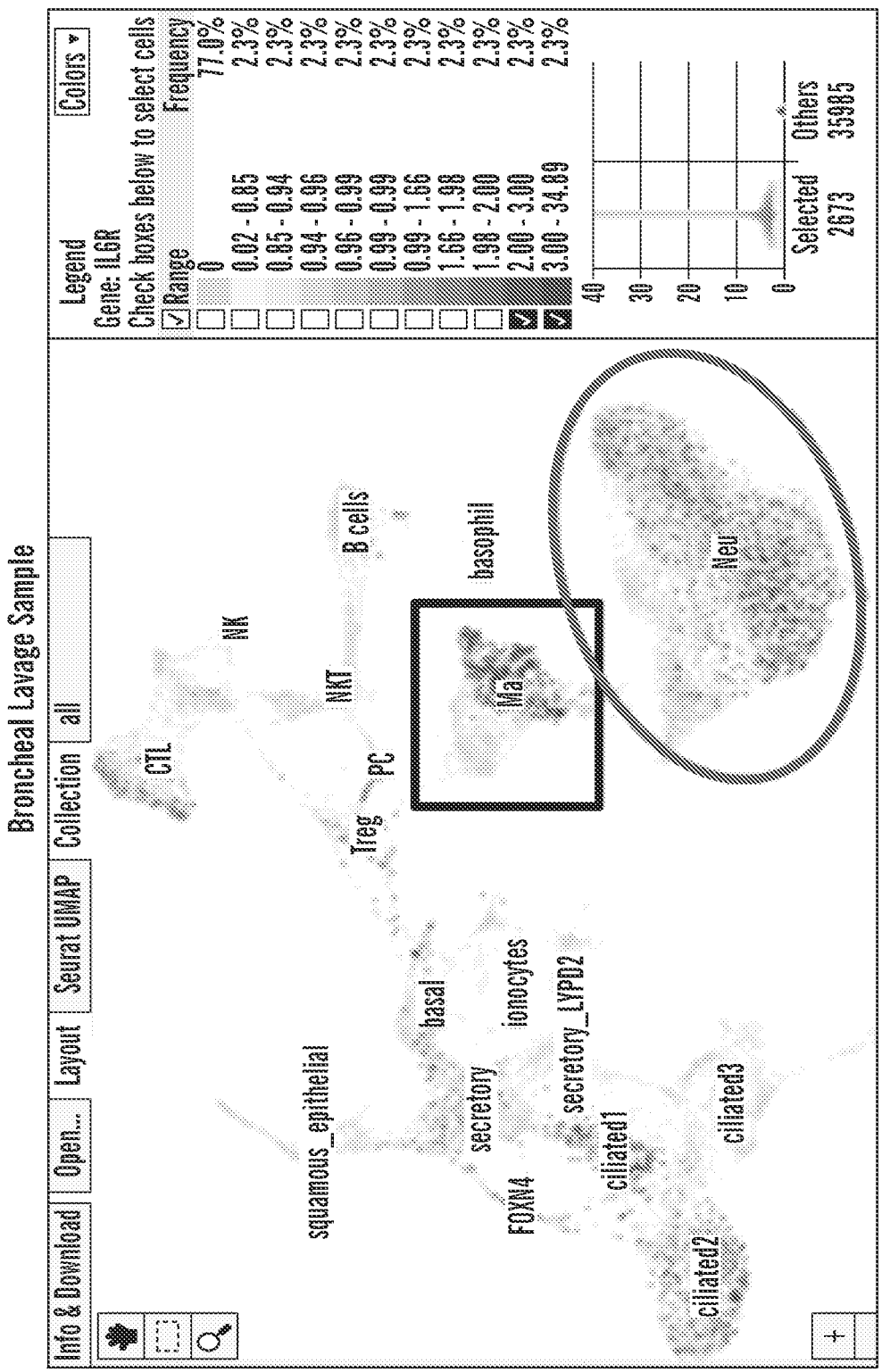
Figure 28C:
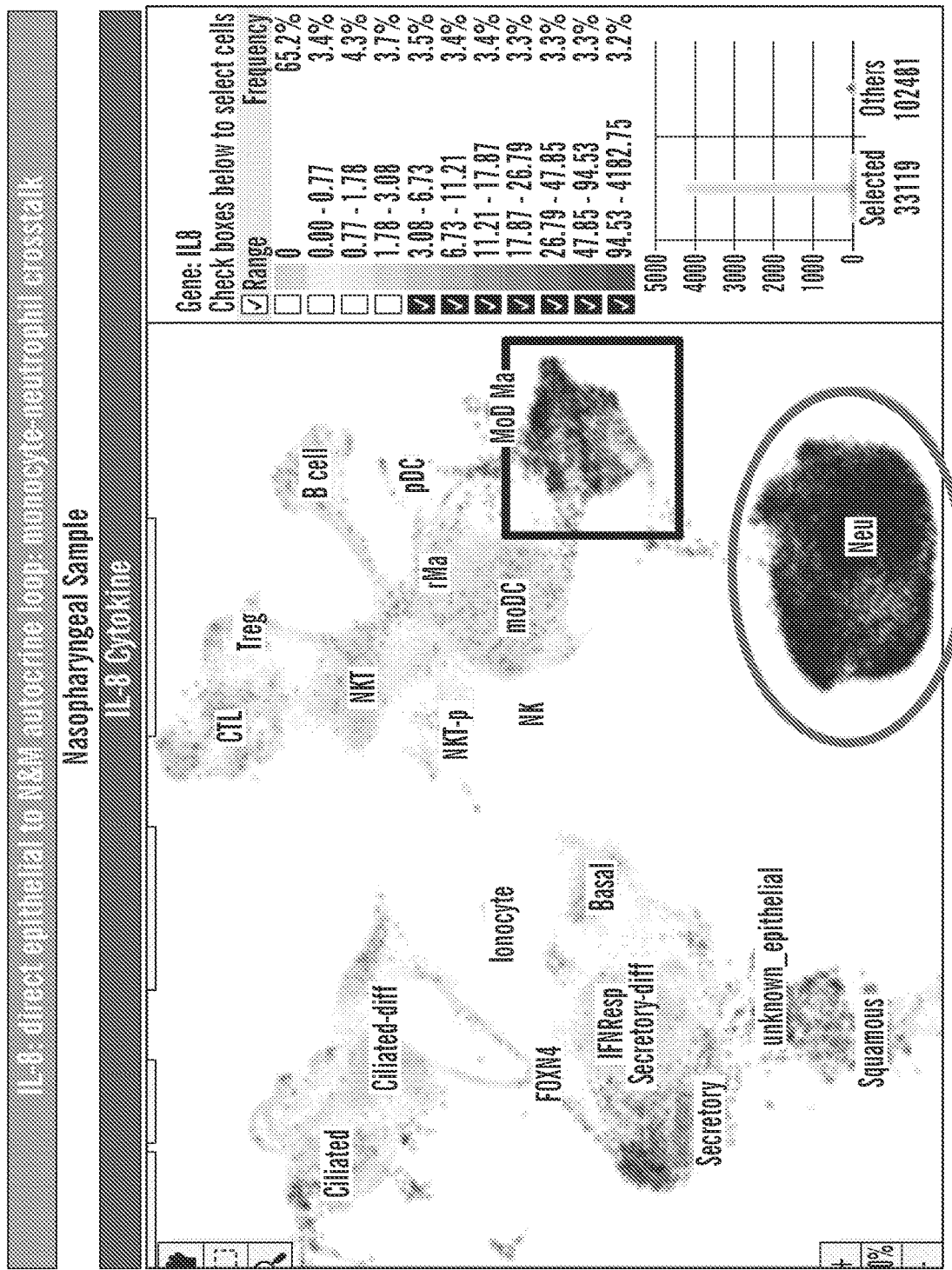
Figure 28D:
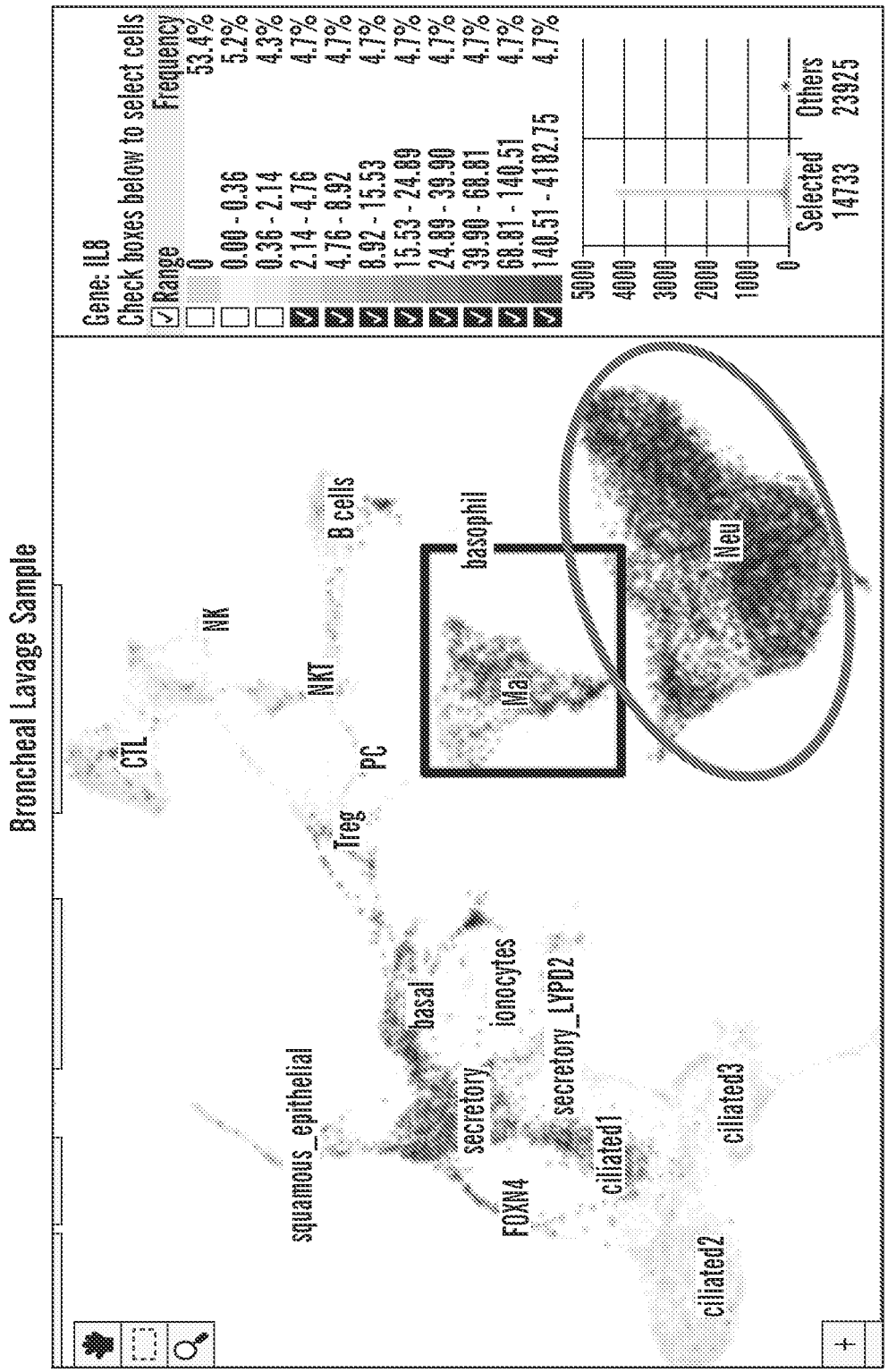
Figure 28E:
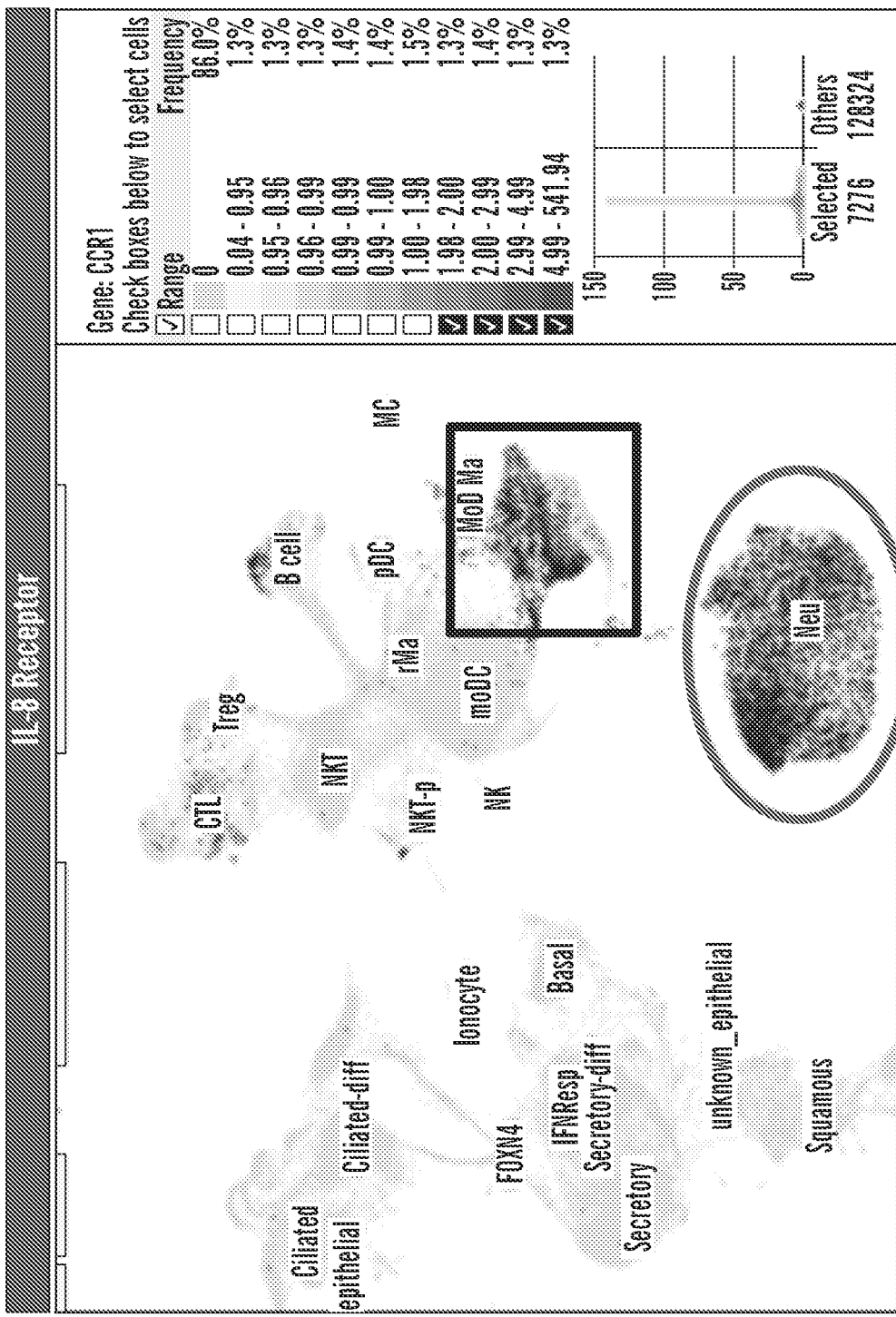
Figure 28F:
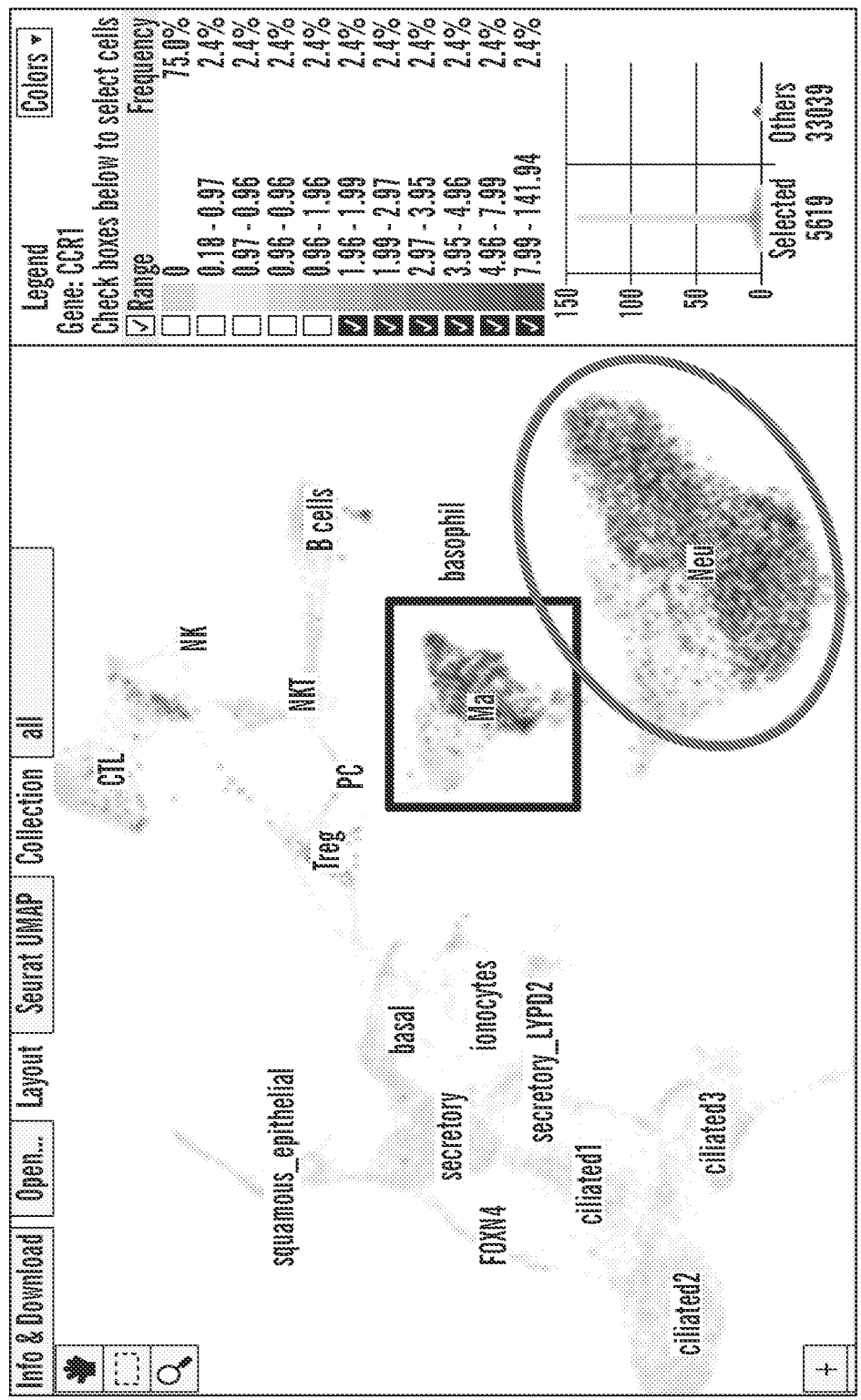
Figure 29A:
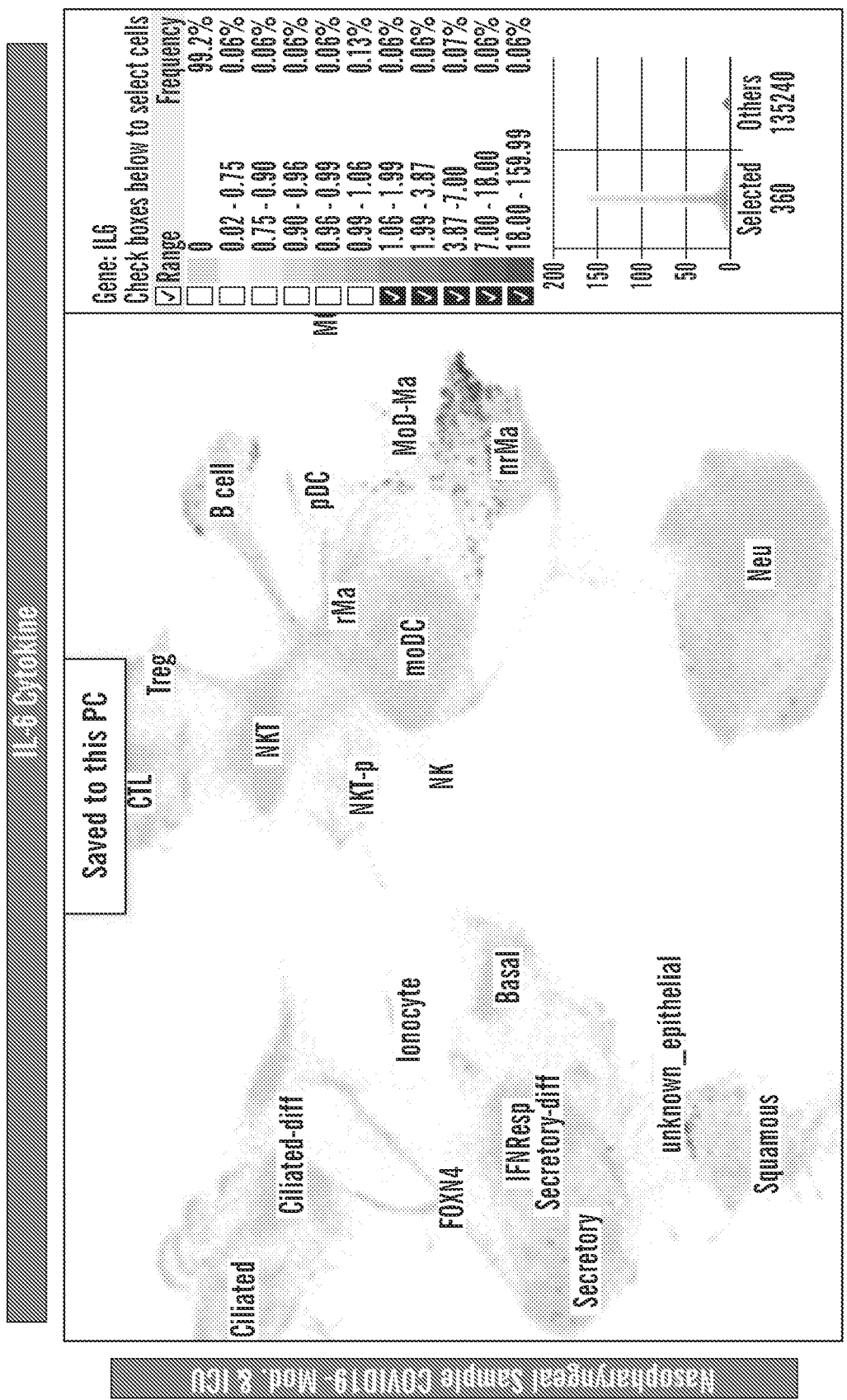
FIGS. 29A-29H depict cell-type specific expression of cytokine/receptor axes in COVID19 patients done by single cell RNA-sequencing.
Figure 29B:
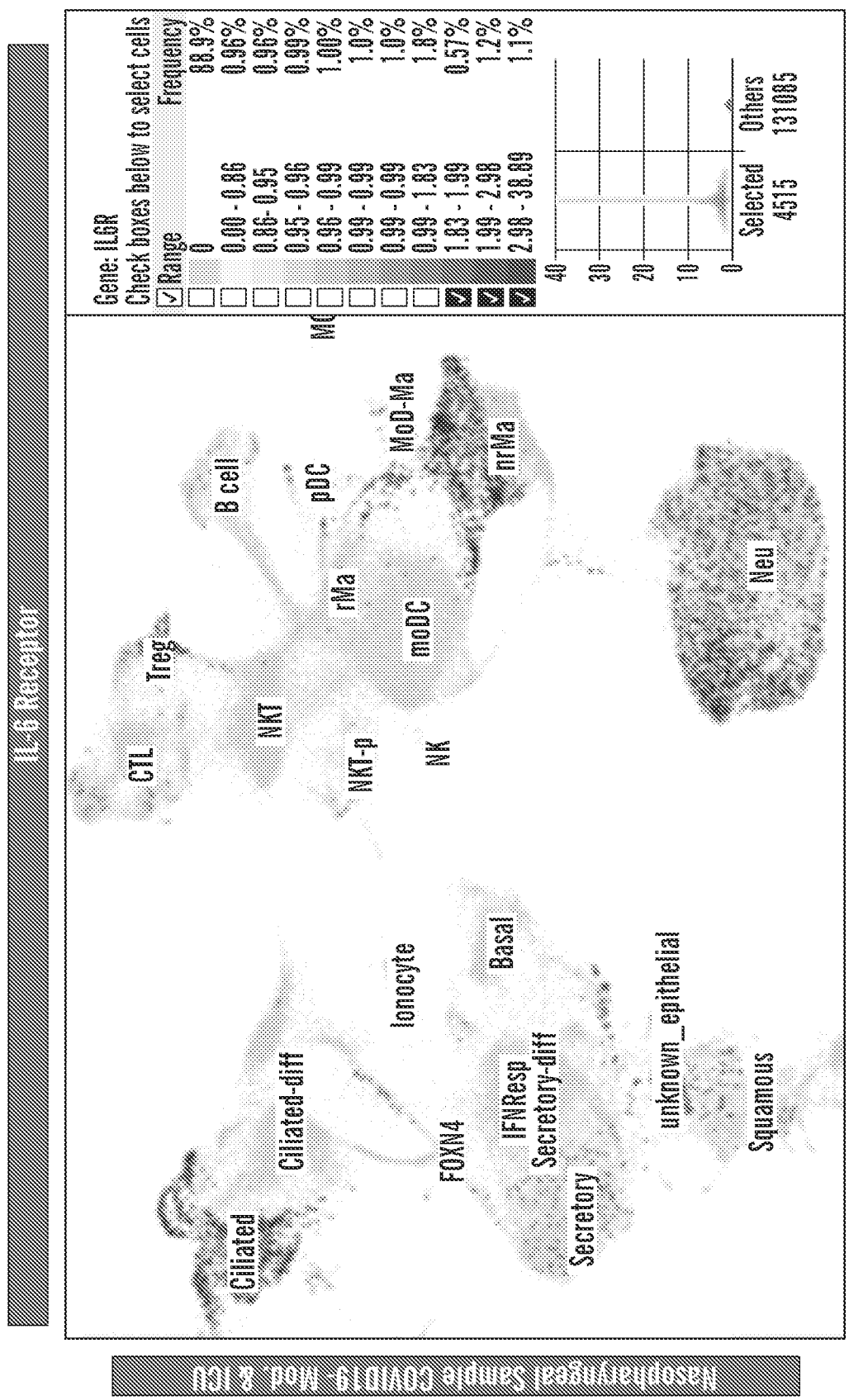
Figure 29C:
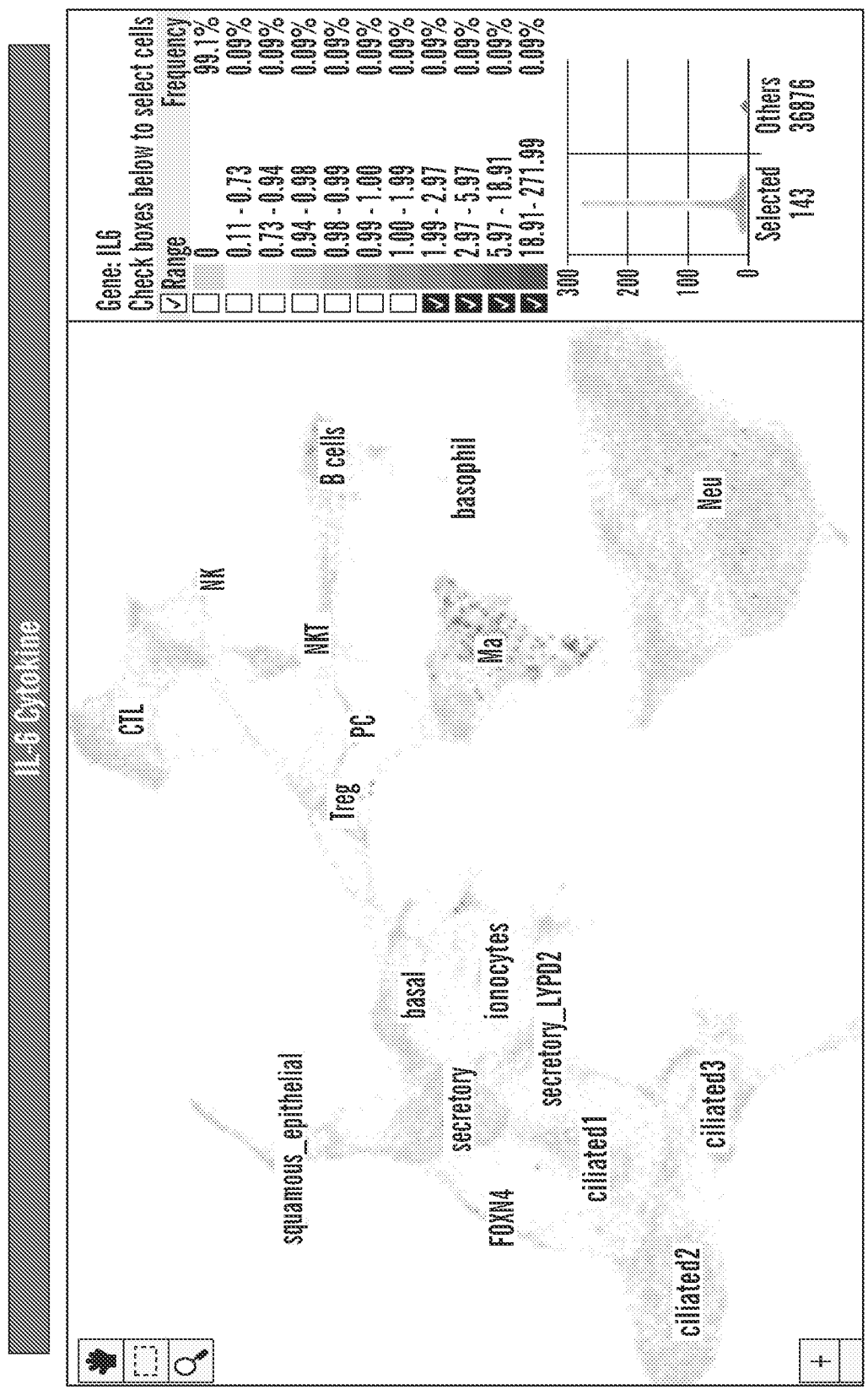
Figure 29D:
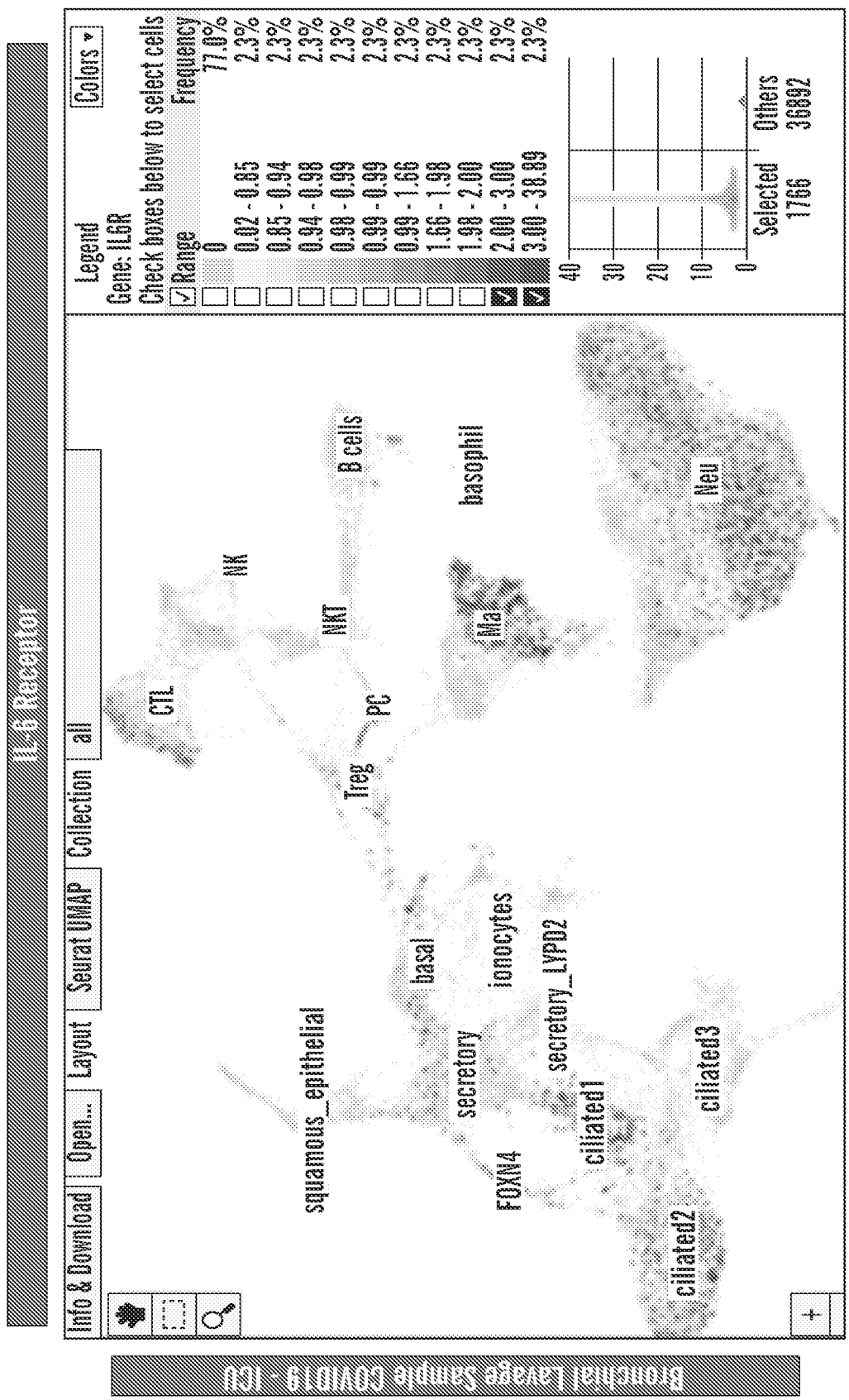
Figure 29E:
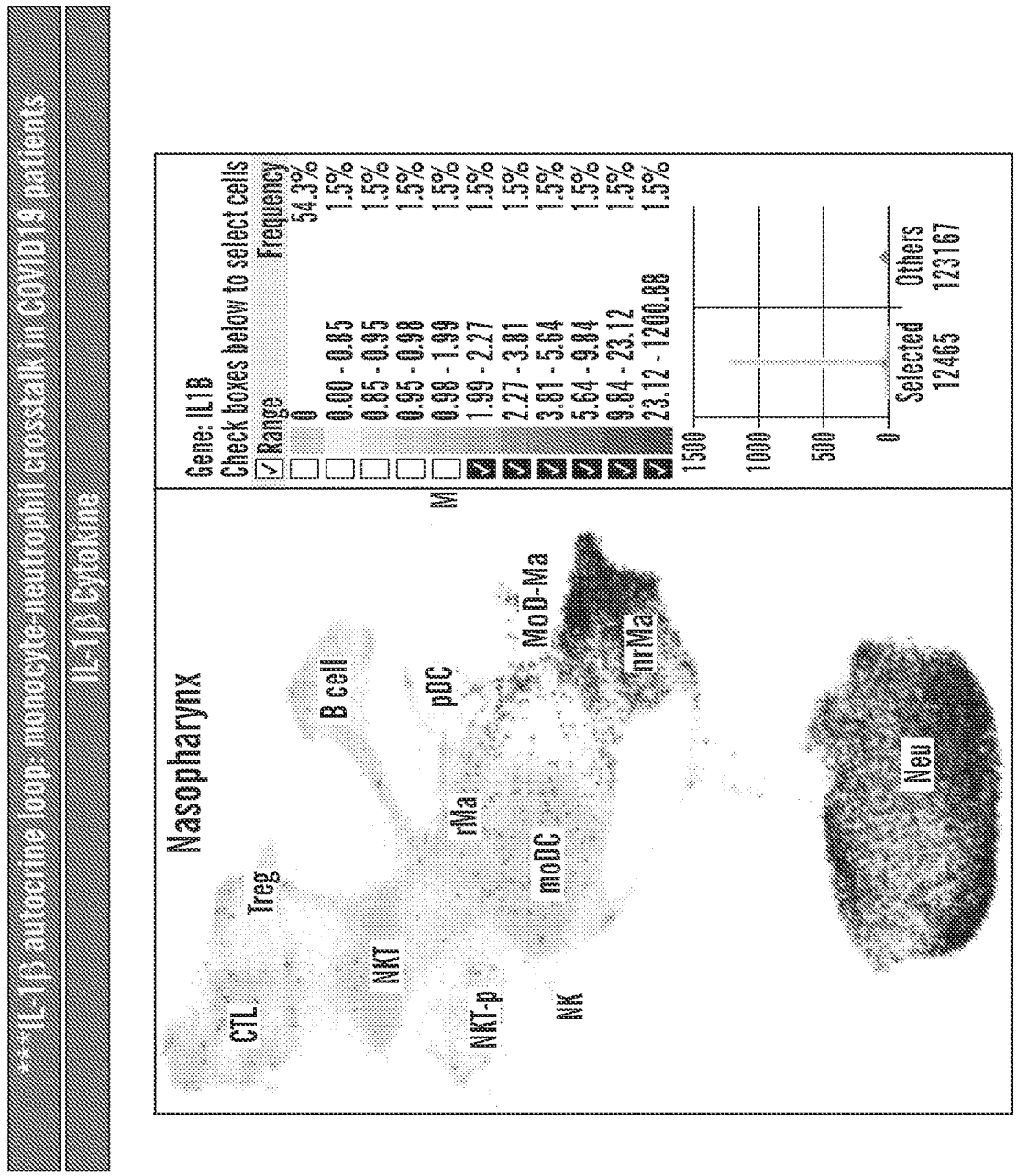
Figure 29F:
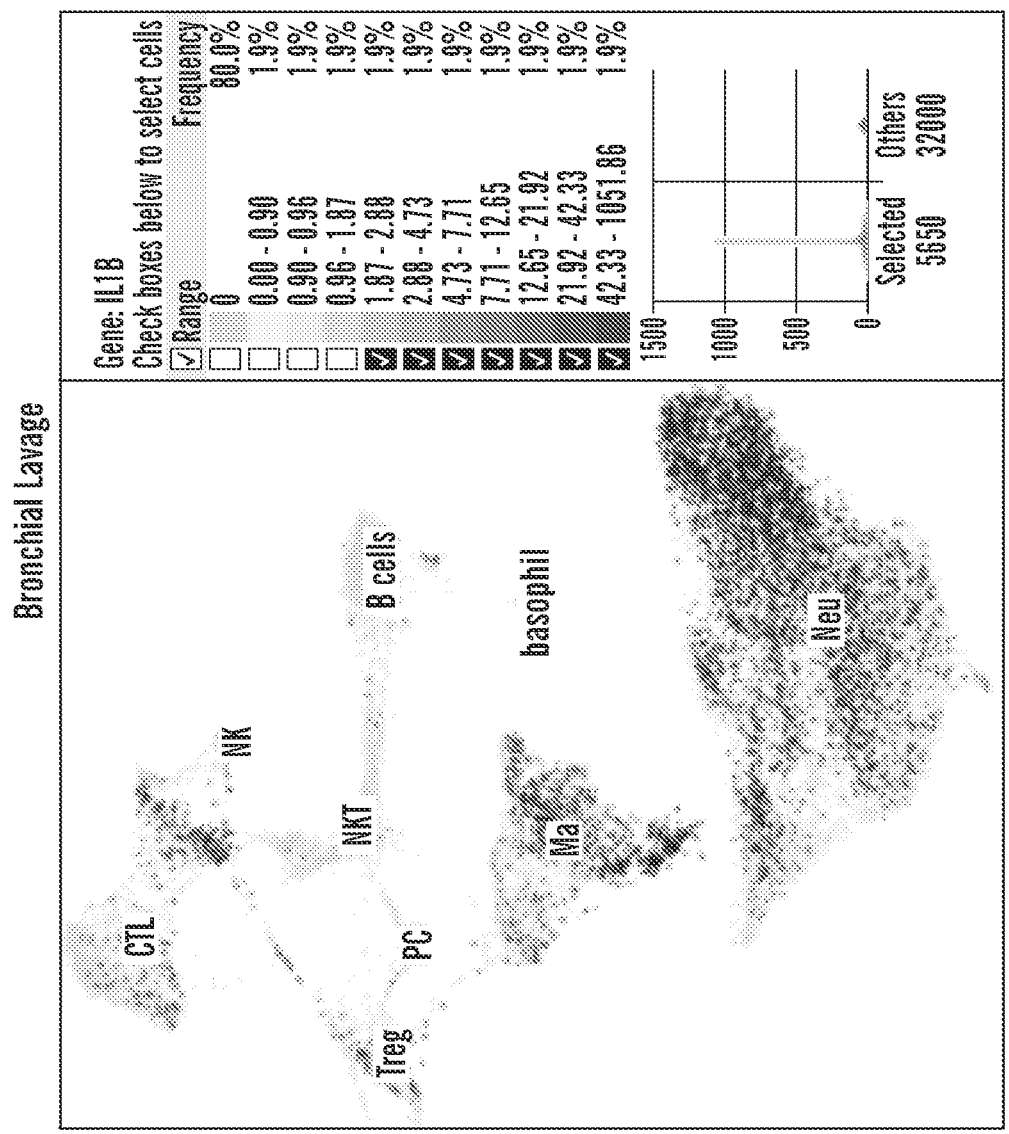
Figure 29G:
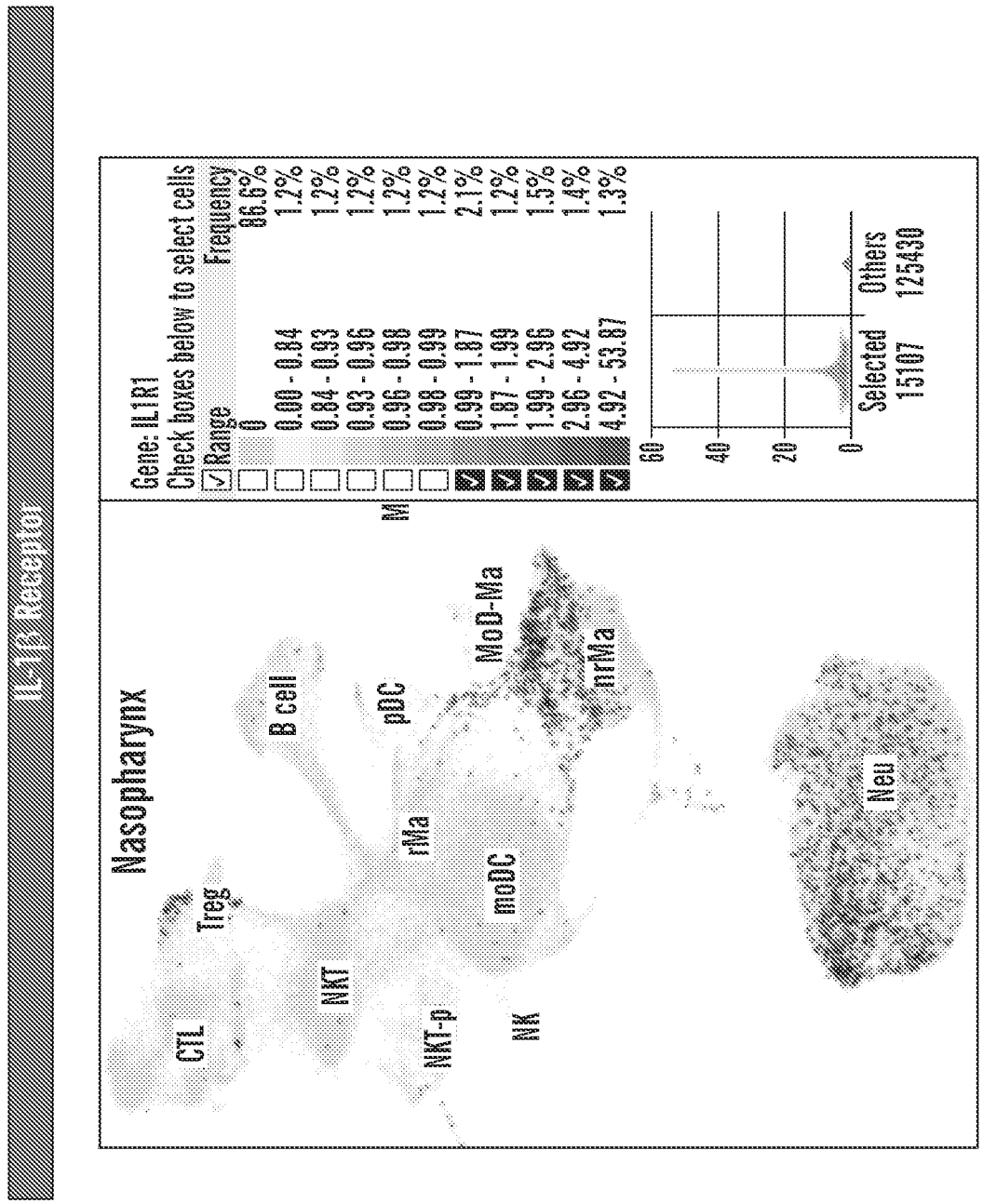
Figure 29H:
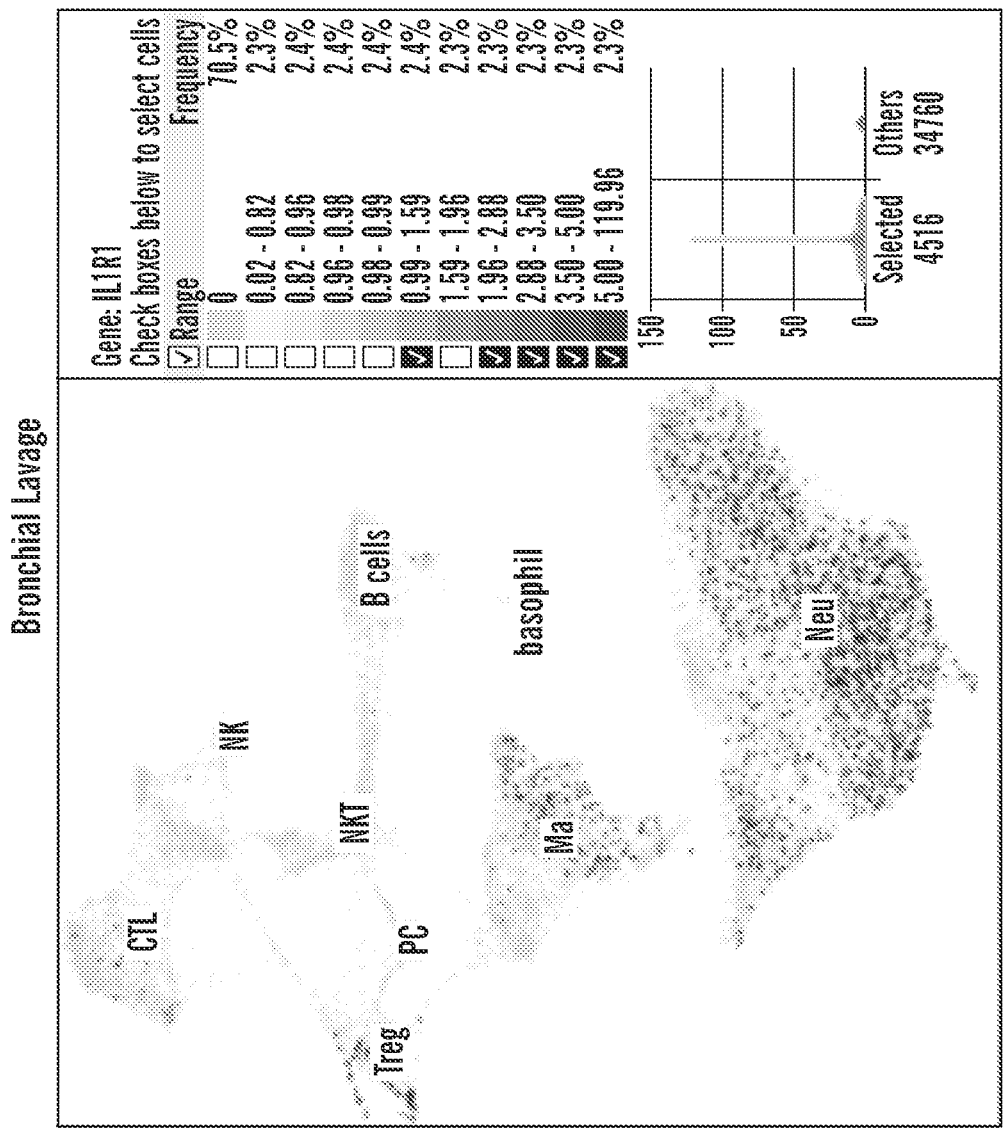
Figure 30A:
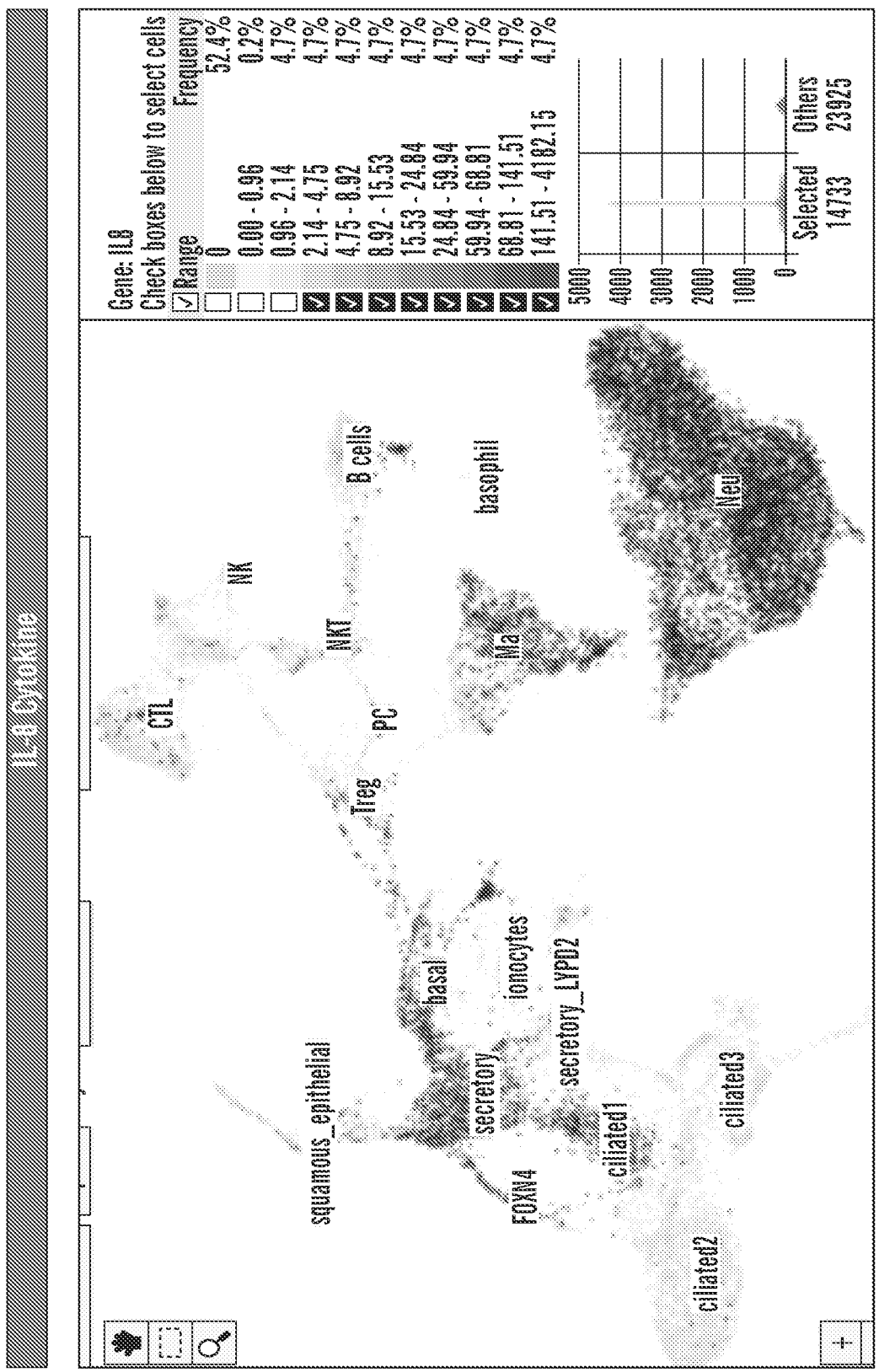
FIGS. 30A-30H depict a pathway for early activation and self-sustaining hyperinflammation other than IL-6 pathways.
Figure 30B:
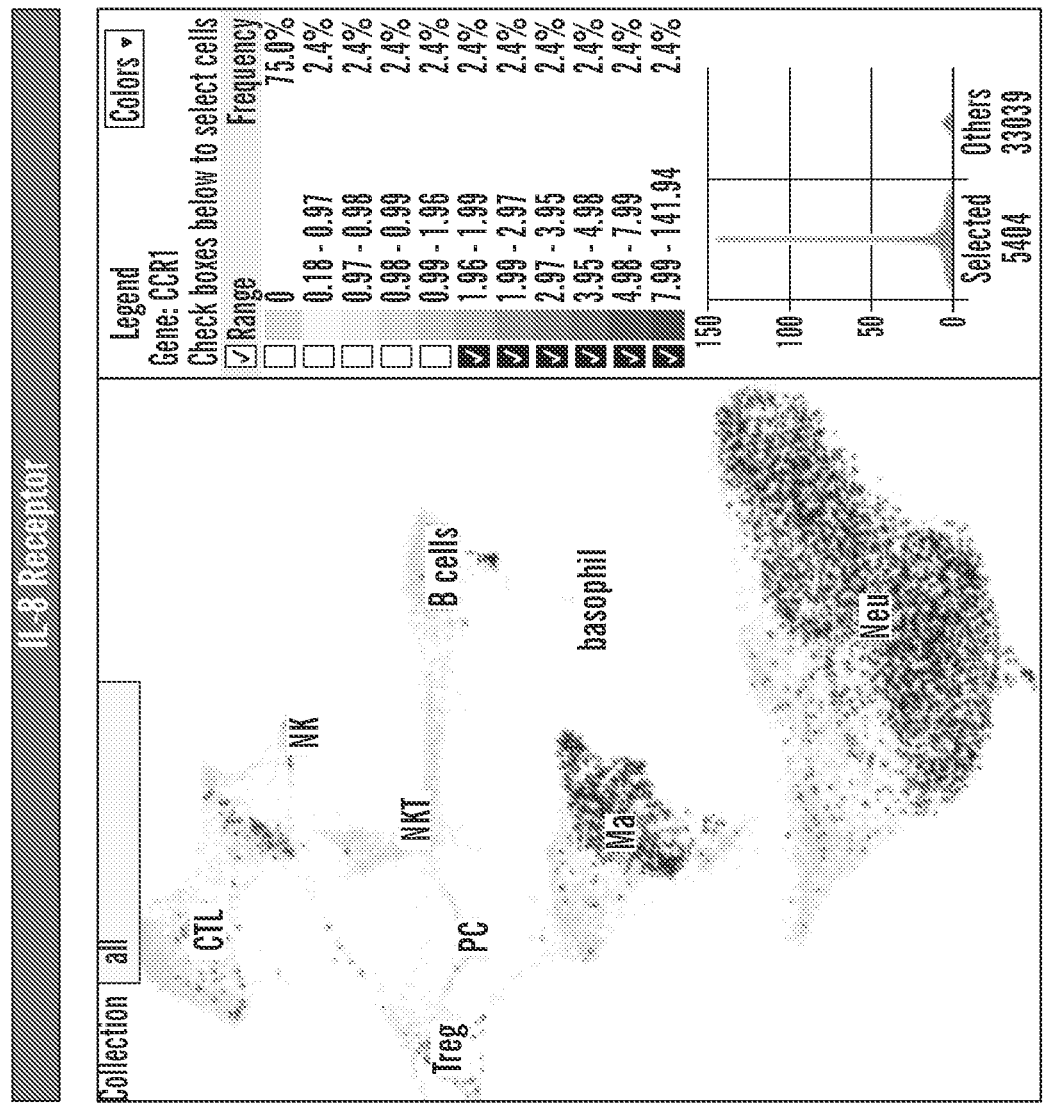
Figure 30C:
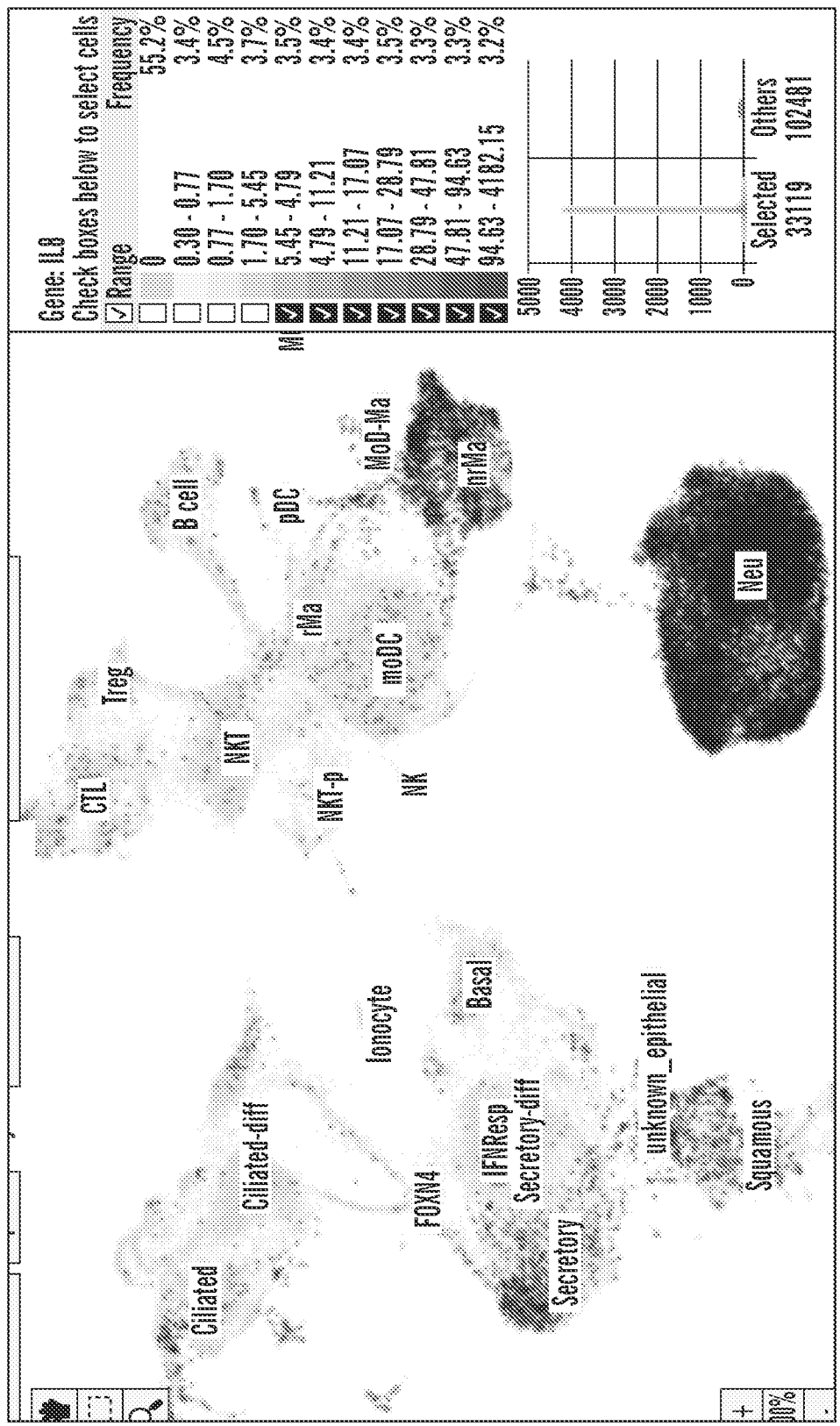
Figure 30D:
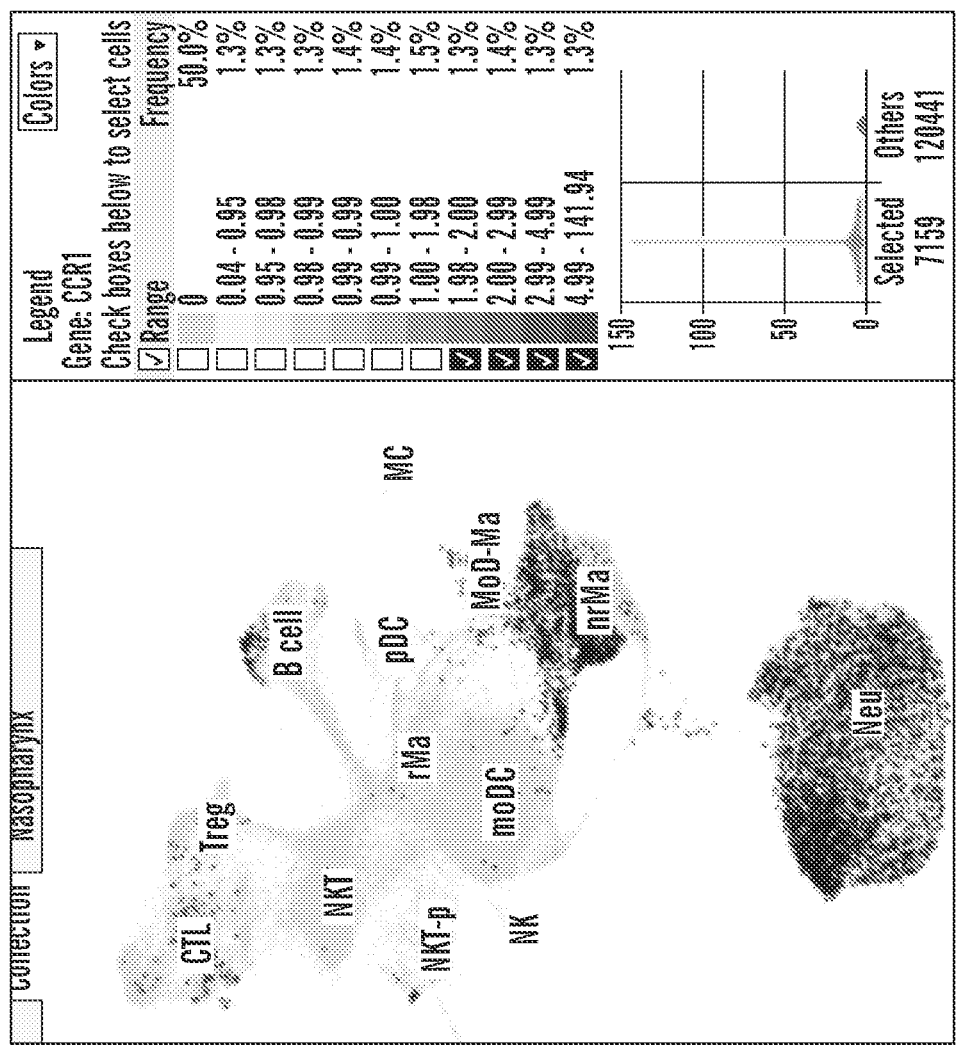
Figure 30E:
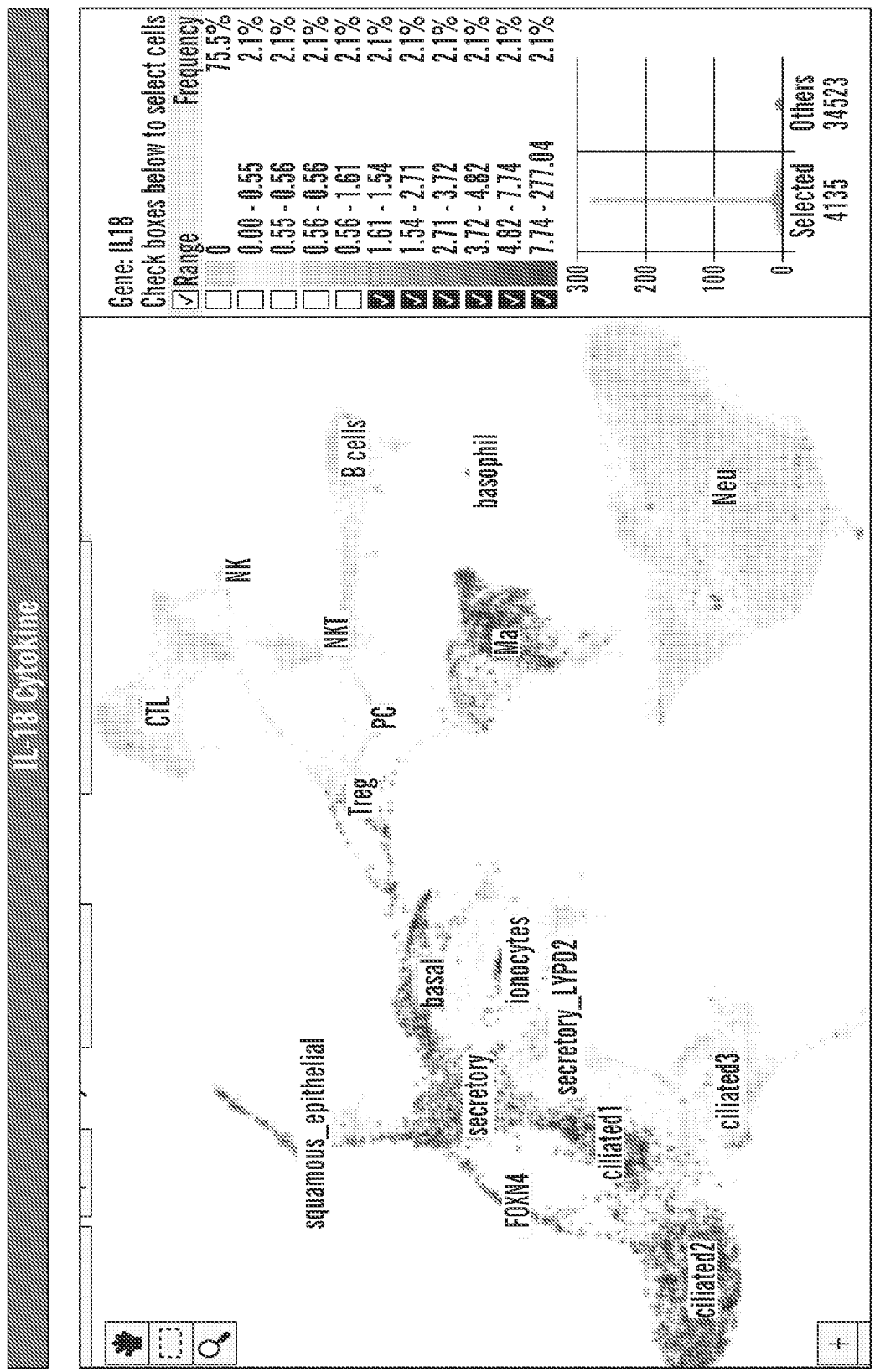
Figure 30F:
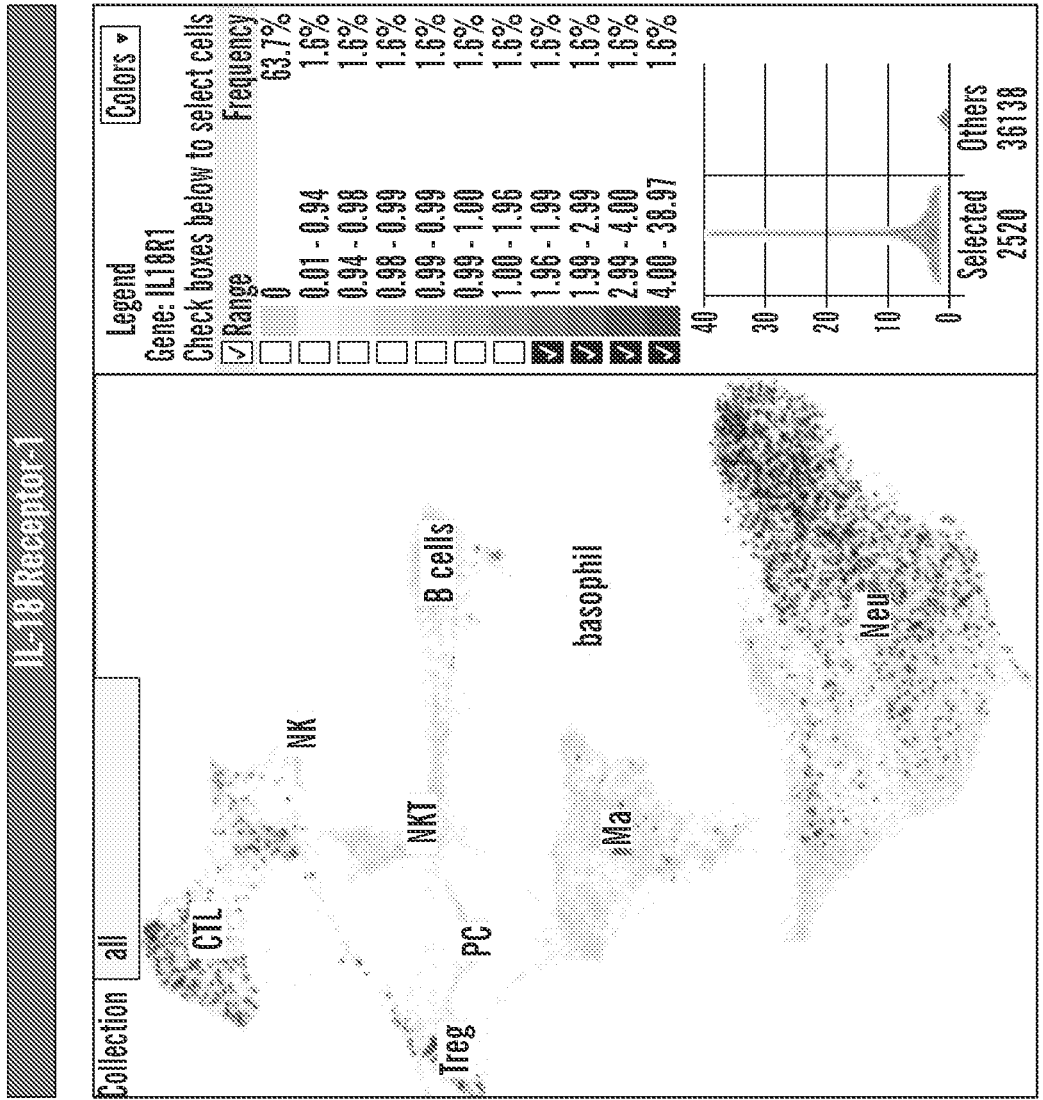
Figure 30G:
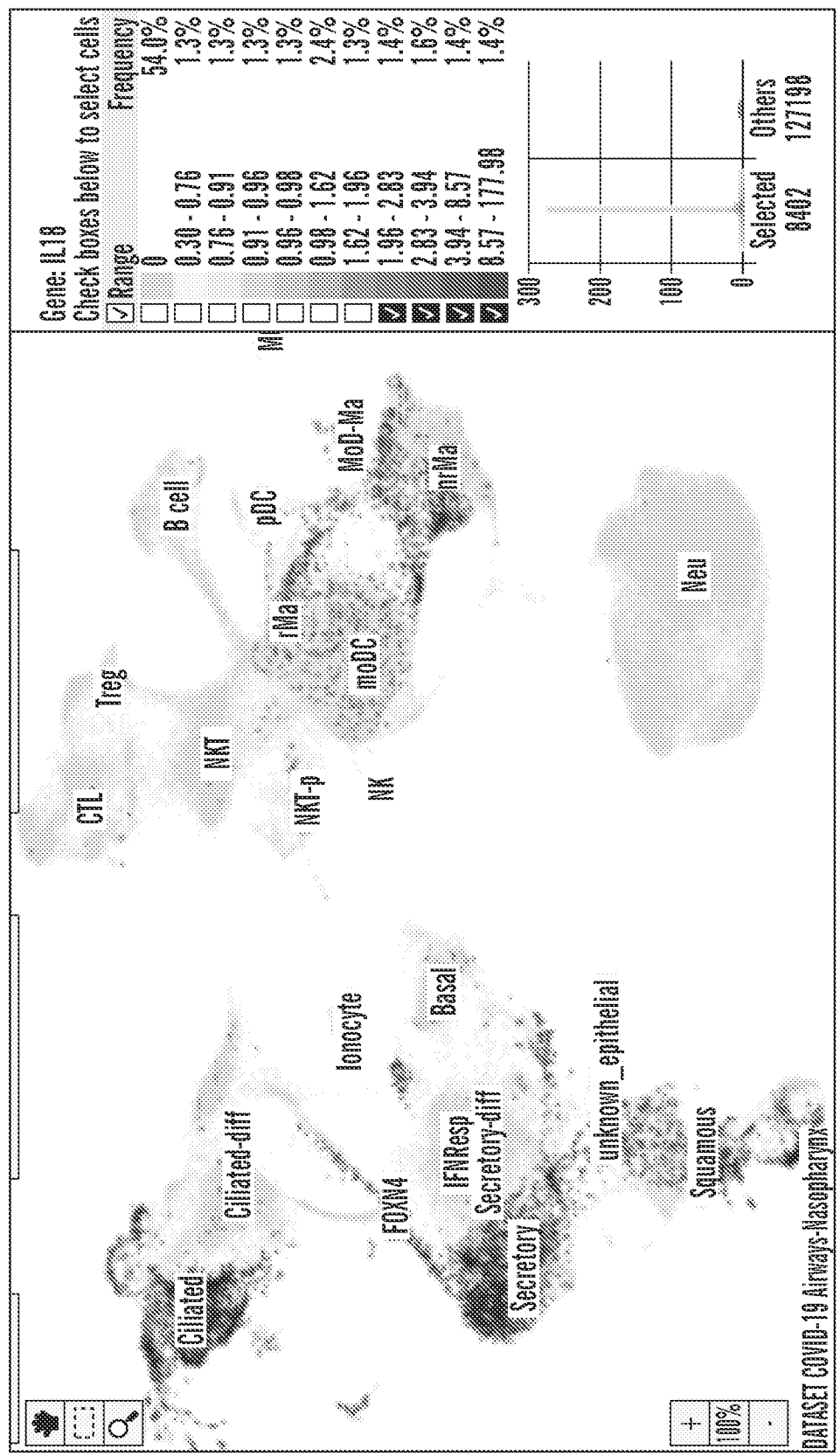
Figure 30H:
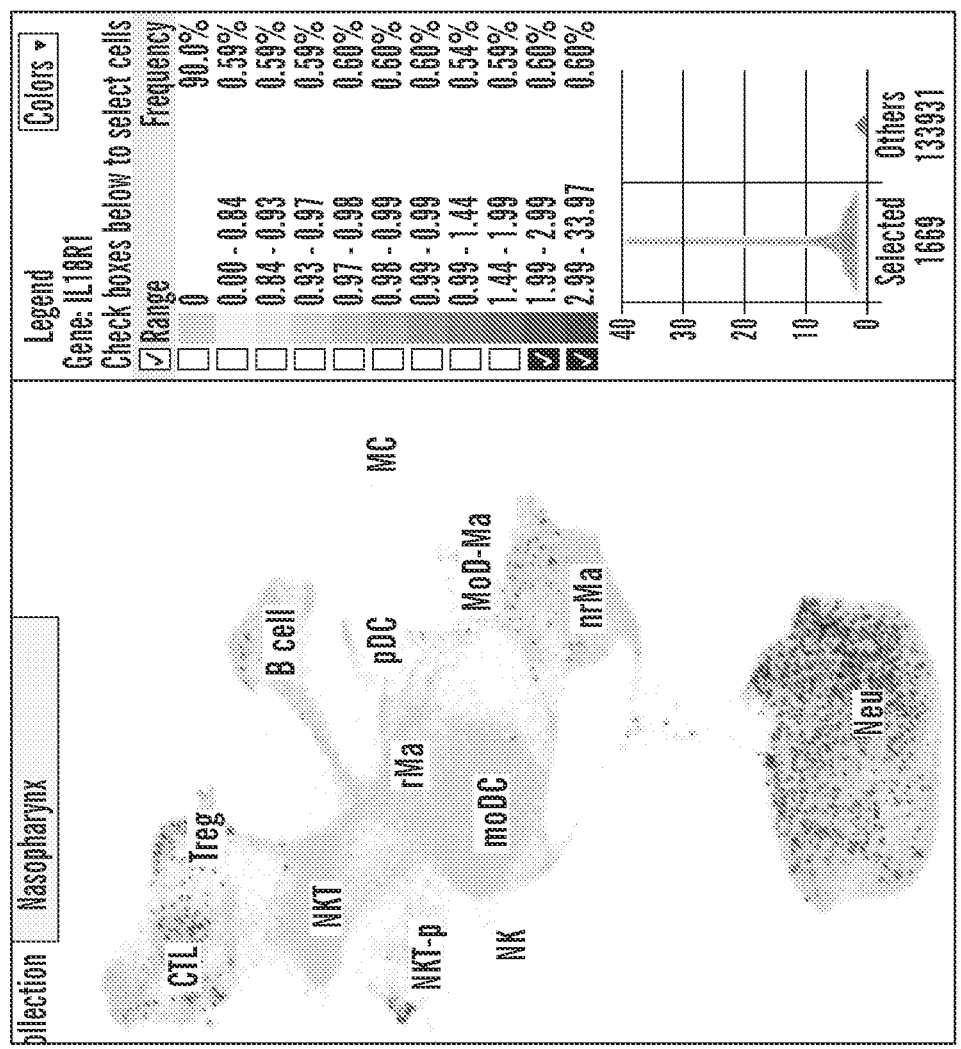

FIGS. 28A-28F depict single-cell RNA-seq database$^{R.\ Elis}$ analysis of ARDS-COVID19 patients, showing neutrophil & monocyte crosstalk via IL-8 autocrine loop and as IL-6 effectors. For example, IL-6 expression is minimal to no expression in ACE2+ respiratory epithelial cells. IL-6 from ACE2+ endothelial cells (ECs) shows the activated-ECs and primed neutrophils link. FIGS. 28A-28B depict IL-6 receptor in nasopharyngeal samples and bronchial lavage samples, indicating IL6-R+ monocytes and neutrophils: effectors of IL-6 mediated hyperinflammation. FIGS. 28C-28F depict IL-8 cytokine and IL-8 receptor in nasopharyngeal samples and bronchial lavage samples, showing that IL-8 directs epithelial to N and M autocrine loop: monocyte-neutrophil crosstalk.

FIGS. 29A-29H depict cell-type specific expression of cytokine/receptor axes in COVID19 patients done by single cell RNA-sequencing. FIGS. 29A-29D depict minimal IL-6 expression in COVID19 patient samples in both moderately ill and critically ill patient samples from the nasopharynx and bronchial lavage. Only Mo/macrophages express IL-6 but only sparsely as 99% of all cells are negative for IL-6 expression in this set of COVID19 patient samples. IL-6 Receptor (IL-6R) expression is detected in neutrophils and monocytes indicating Ns and Ms as effectors of elevated IL-6 mediated hyperinflammation in COVID19. FIGS. 29E-29H depict IL-1β/IL-1β receptor autocrine loop in nasopharynx and bronchial lavage, proposing key roles of monocyte-neutrophil crosstalk in COVID19 patients.

High IL-6 levels in COVID19 hyperinflammation: IL-6 is 'hallmark,' but only minimal to no efficacy in Phase III trials for anti-IL6-Receptor antibody inhibitors (e.g., tocizilumab or Actemra, sarilumab or Kevzara) highlights the importance of targeting N & M reciprocal interactions driven by ligand-receptor autocrine loops. Greater correlation of DEspR+ Ns and DEspR+ Ms with severity and/or poor outcomes support the need to re-focus on N & M crosstalk that can contribute to feed forward hyperinflammation.

For IL-6, minimal expression in monocytes/macrophages and no expression in neutrophils and other WBCs. For IL-6 receptor, expression predominantly in neutrophils and monocytes/macrophages indicates Ns & Ms as key effectors of IL6 in COVID19-moderately ill and critically ill (ICU). Autocrine loop (ligand+/receptor+) in monocytes/macrophages, but none in neutrophils.

FIGS. 30A-30H depict IL8+ and IL-18+ respiratory epithelia, and IL-8 and IL-18 ligand+/receptor+ on Ns and Ms, indicating early activation and self-sustaining hyperinflammation beyond IL-6. FIGS. 30A-30H depict IL-8 cytokine and IL-8 receptor. FIGS. 30E-30H depict IL-18 cytokine and IL-18 receptor-1.

Figure 31A:
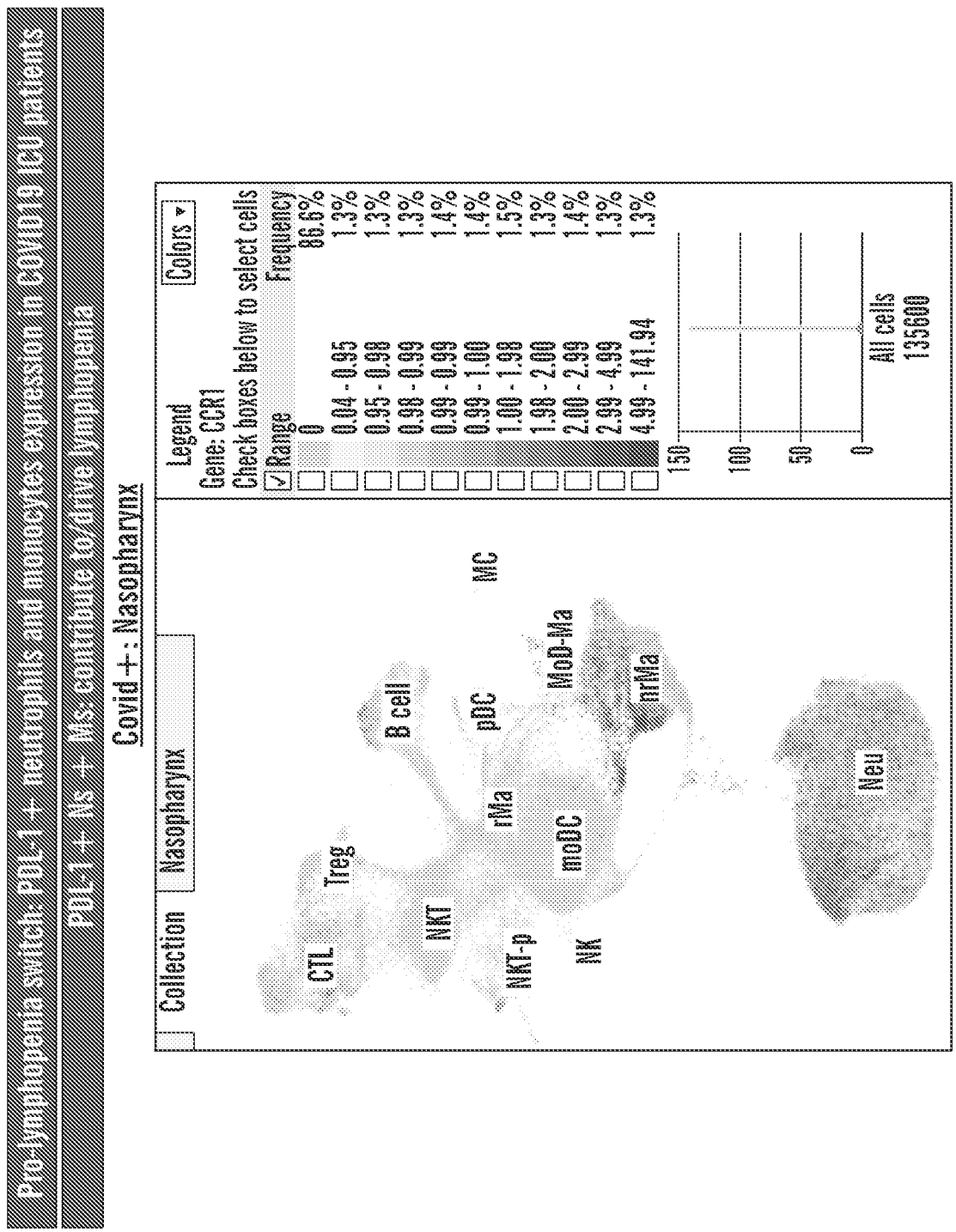
FIGS. 31A-31D show monocytes/macrophages (mps) and neutrophils express PD-L1+, suggesting a mechanism for lymphopenia and suppression of T-cell mediated anti-viral immunity. Neutrophils are also IL-10(-), showing lack of key pro-resolution cytokine.
Figure 31B:
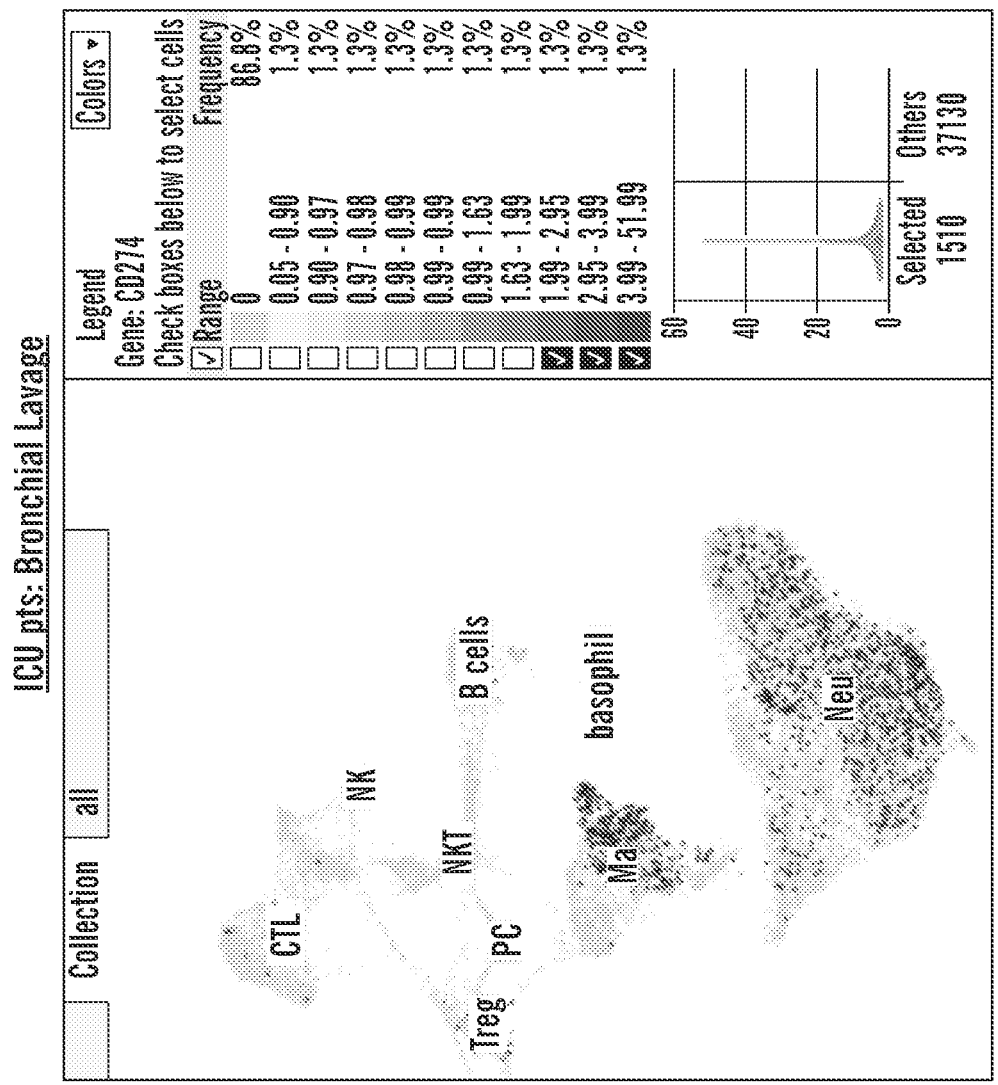

FIGS. 31A-31D show that monocytes/macrophages (mps) and neutrophils are PD-L1+, suggesting a mechanism for lymphopenia. In addition, neutrophils are IL-10(-), indicating lack of key pro-resolution cytokine. FIGS. 31A-

Figure 31C:
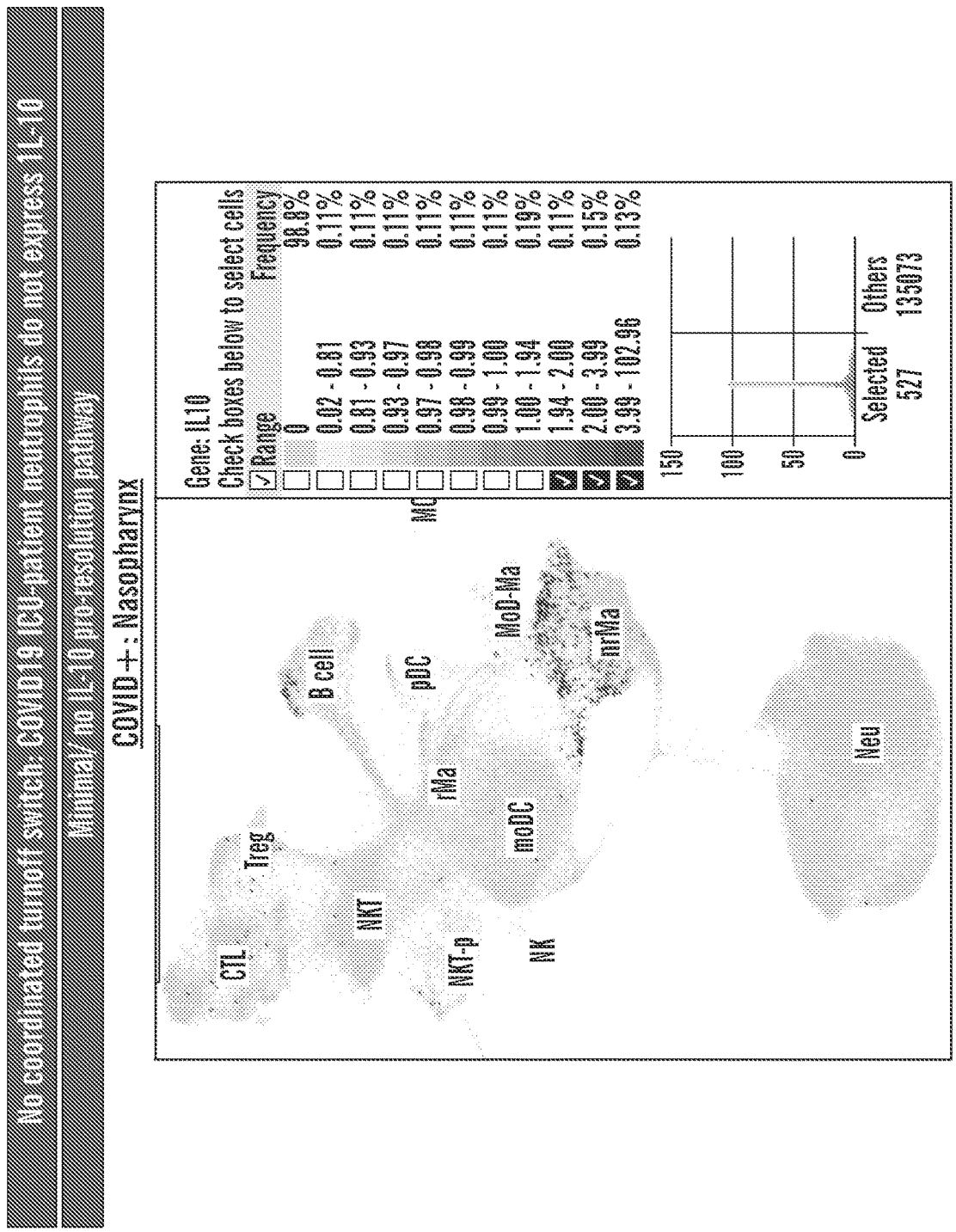
Figure 31D:
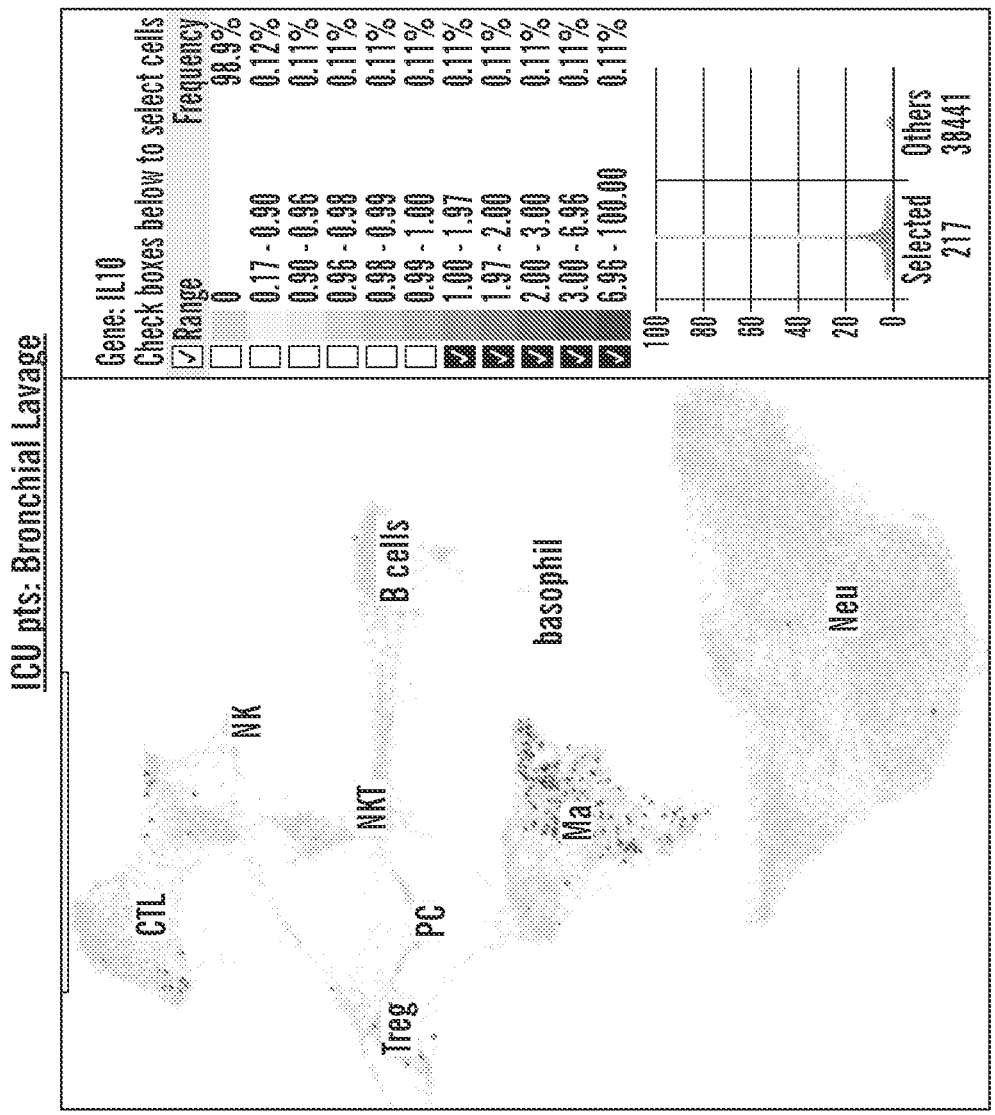

31B depict PDL-1+ neutrophils and monocytes expression in COVID19 (nasopharynx) ICU (bronchial lavage) patients, indicating that PDL-1+ Ns+Ms contribute to/drive lymphopenia. This indicates pro-lymphopenia switch. FIGS. 31C-31D show shows that neutrophils from COVID19 (nasopharynx) ICU (bronchial lavage) patients do not express IL-10, indicating minimal/no IL-10 pro-resolution pathway. This indicates no coordinated turnoff switch. The ELISA (enzyme-linked immunosorbent assay) data also show that the level of IL-10 was all below detectable limits (i.e., all negative results)(data not shown), which is concordant with the RNA-seq data showing no IL-10 expression in neutrophils in COVID 19 moderately and critically ill ICU patients.

Figure 32A:
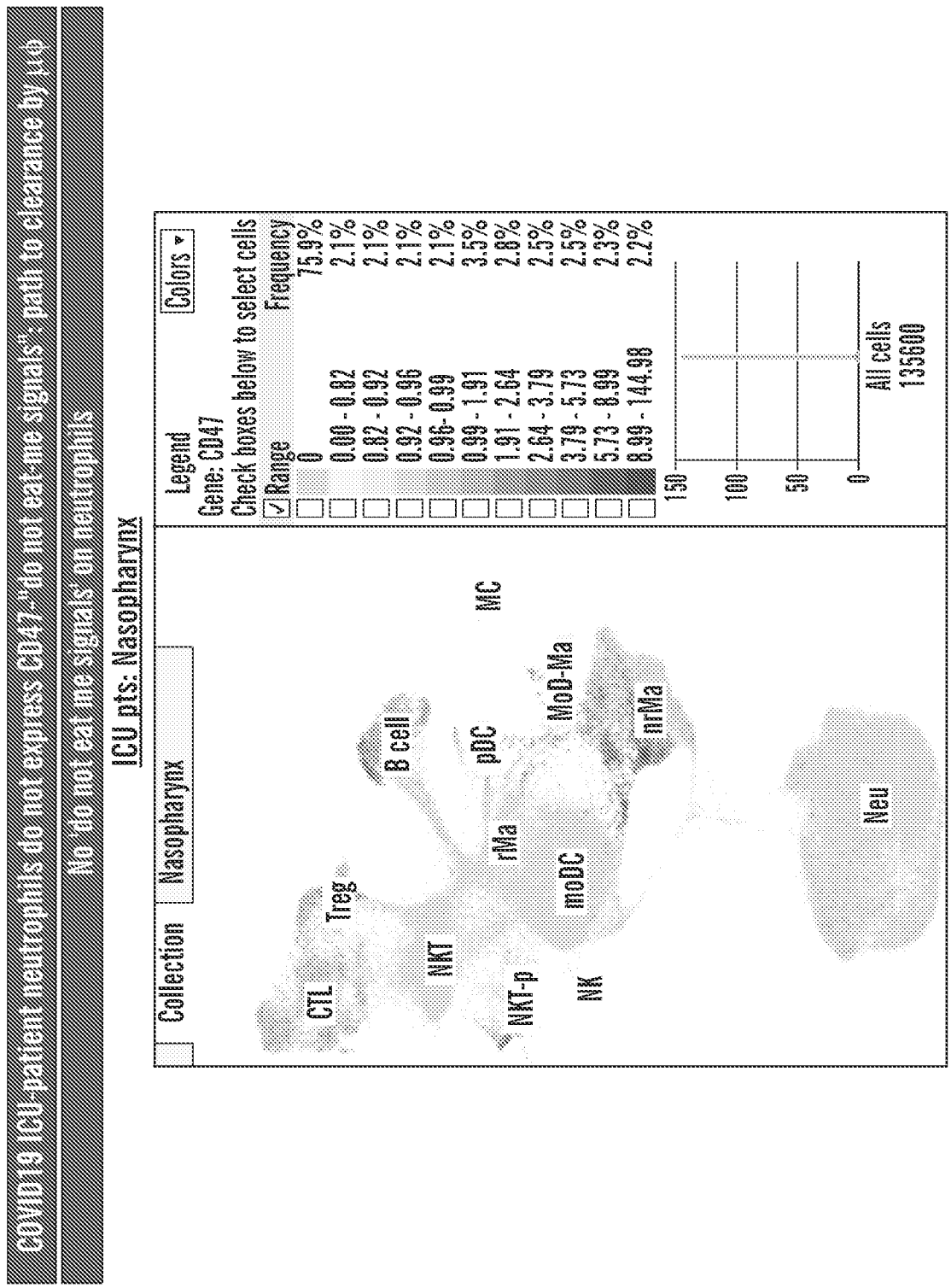
FIGS. 32A-32B show that COVID19 ICU-patient neutrophils do not express CD47-"do not eat-me signals", suggesting a normal homeostatic path to clearance by μφ. No 'do not eat me signals' on neutrophils may facilitate clearance. supporting a mechanism for required clearance of apoptosing neutrophils induced by anti-DEspR therapy.
Figure 32B:
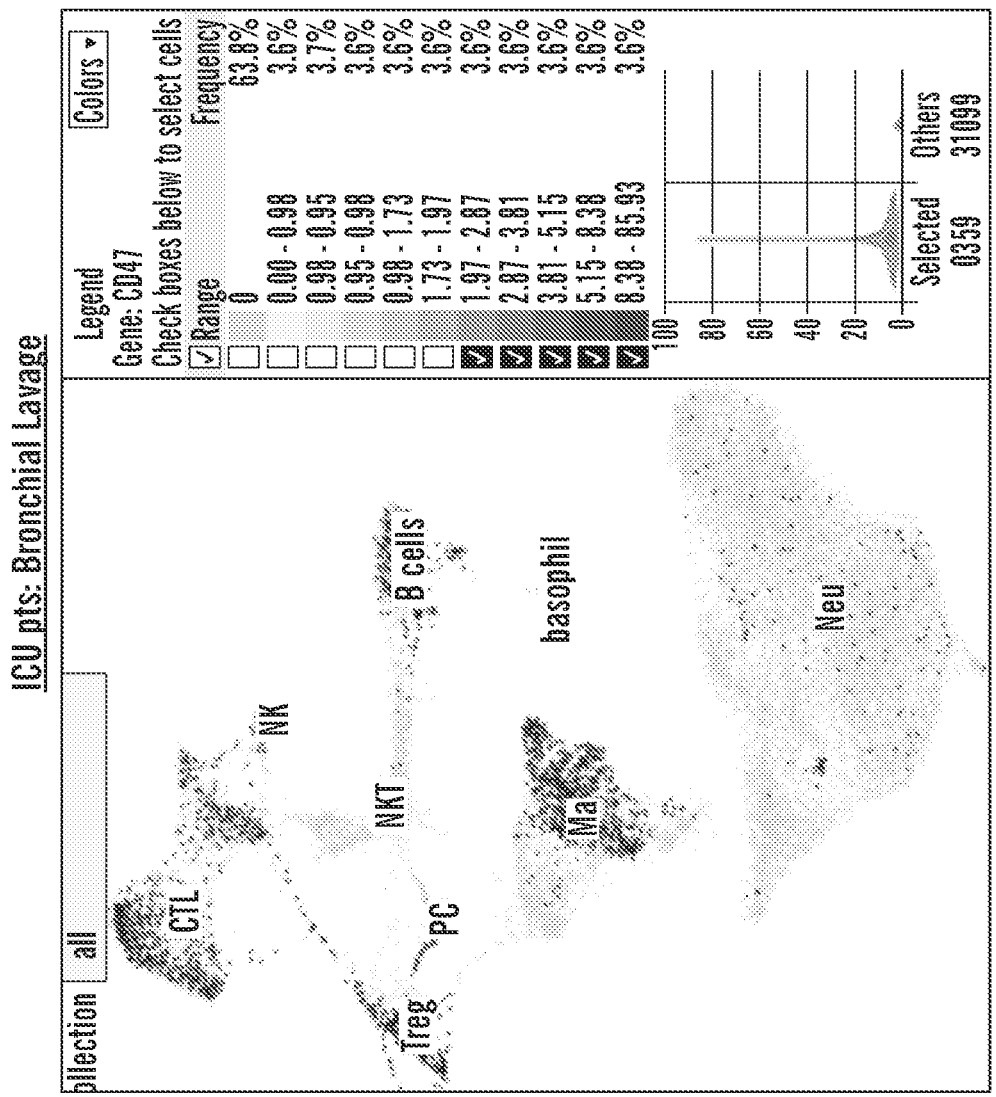

FIGS. 32A-32B show that COVID19 ICU-patient neutrophils do not express CD47-"do not eat-me signals", suggesting a normal homeostatic path to clearance by pp. No 'do not eat me signals' on neutrophils may facilitate clearance, supporting a mechanism for required clearance of apoptosing neutrophils induced by anti-DEspR therapy.

Figure 33A:
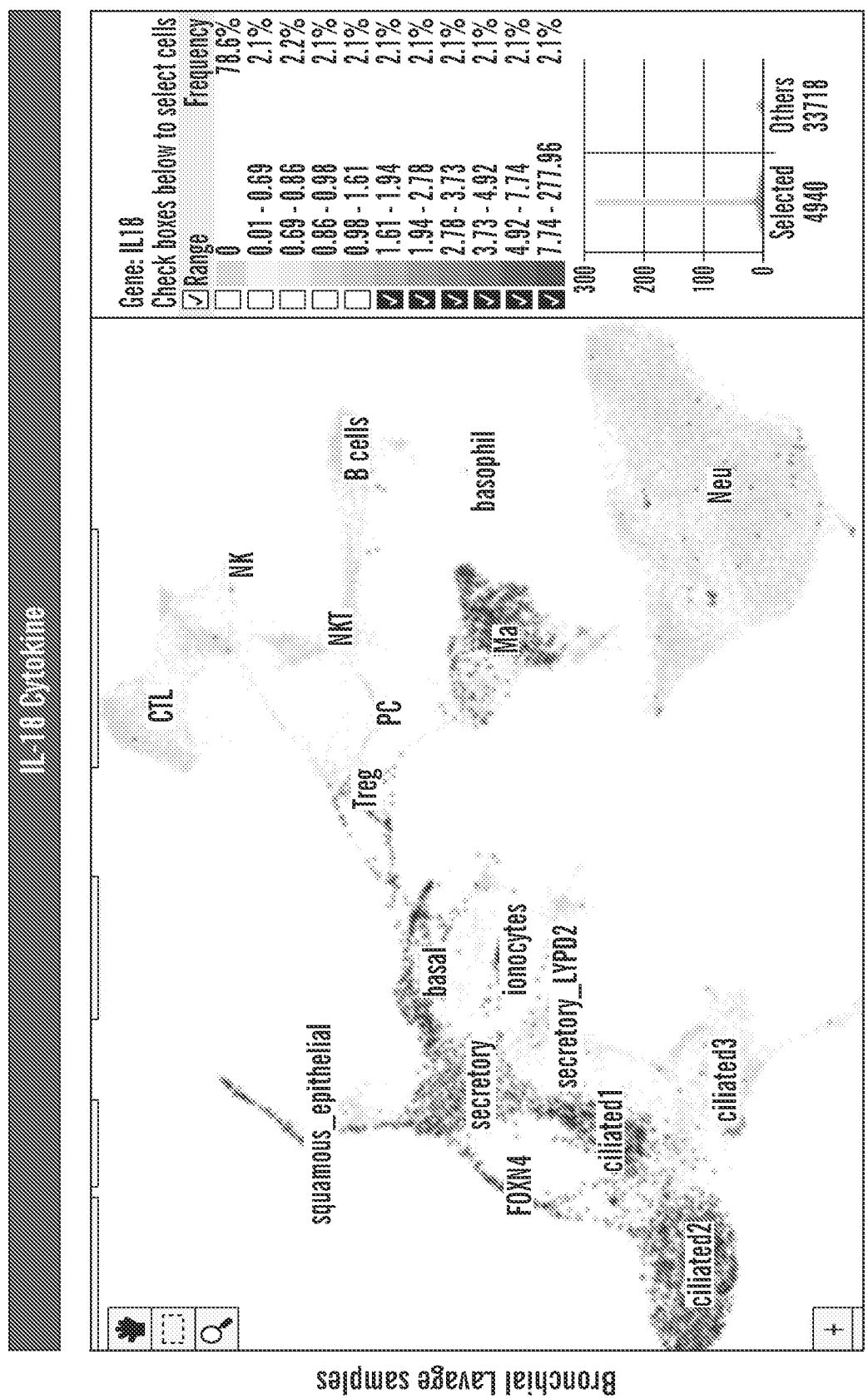
FIGS. 33A-33D show that IL-18 cytokine produced by infected respiratory epithelia activate IL-18 receptor+ Neutrophils in nasopharynx and lower respiratory tract, potentially propagated by IL-18-IL-18R monocyte-to-neutrophil paracrine loop, indicating a key role of Neutrophils.
Figure 33B:
Figure 33C:
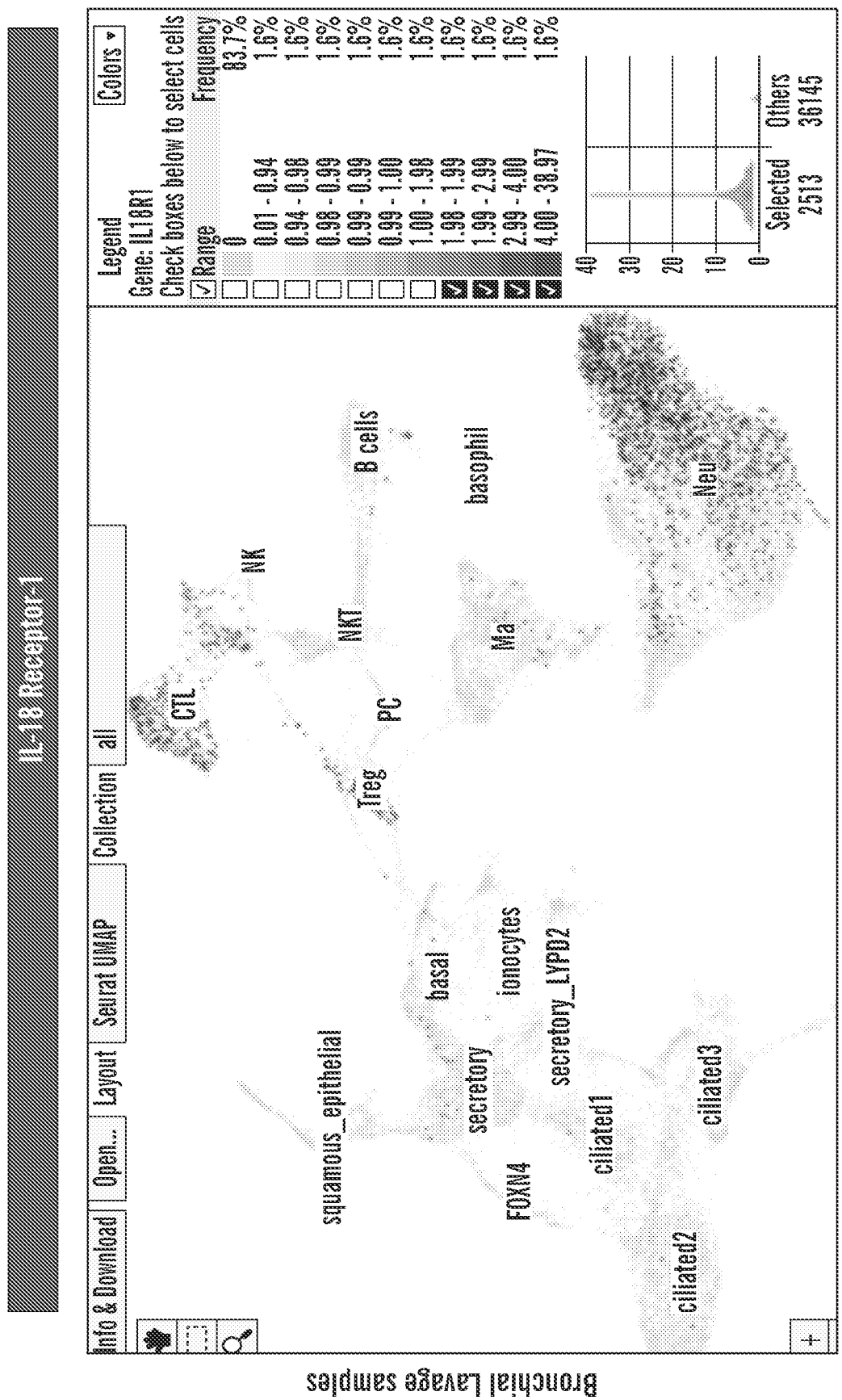
Figure 33D:
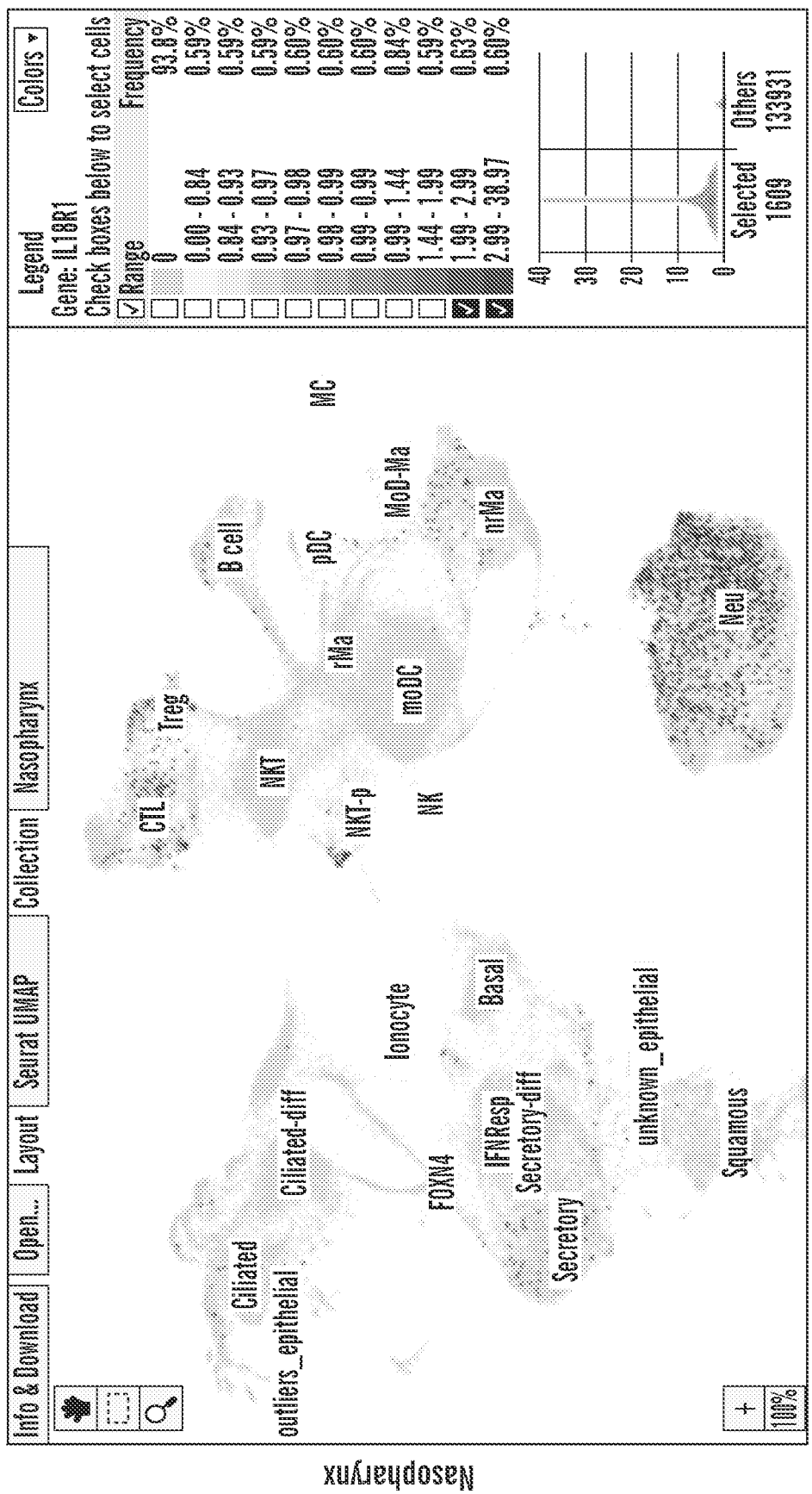

FIGS. 33A-33D show that IL-18 cytokine produced by infected respiratory epithelia activate IL-18 receptor+ Neutrophils in nasopharynx and lower respiratory tract, potentially propagated by IL-18-IL-18R monocyte-to-neutrophil paracrine loop, indicating a key role of neutrophils. FIGS. 33A-33B depict IL-18 cytokine expression in samples from the nasopharynx and bronchial lavage. FIGS. 33C-33D depict IL-18 Receptor-1 expression in samples from the nasopharynx and bronchial lavage.

IL-18/IL-18R axis in COVID19 neutrophils and monocytes: minimal to no IL6-R inhibitor efficacy in COVID19 Phase III trials suggests the need to stop other N-M reciprocal interactions: IL-8/IL-8R axis; IL-1beta/IL-1betaR axis, IL-18/IL-18R axis.

IL-18 cytokine produced by infected respiratory epithelia activates IL-18 receptor+ Neutrophils in nasopharynx and lower respiratory tract, potentially propagated by IL-18-IL-18R monocyte-to-neutrophil paracrine loop, indicating a key role of neutrophils.

Figure 34A:
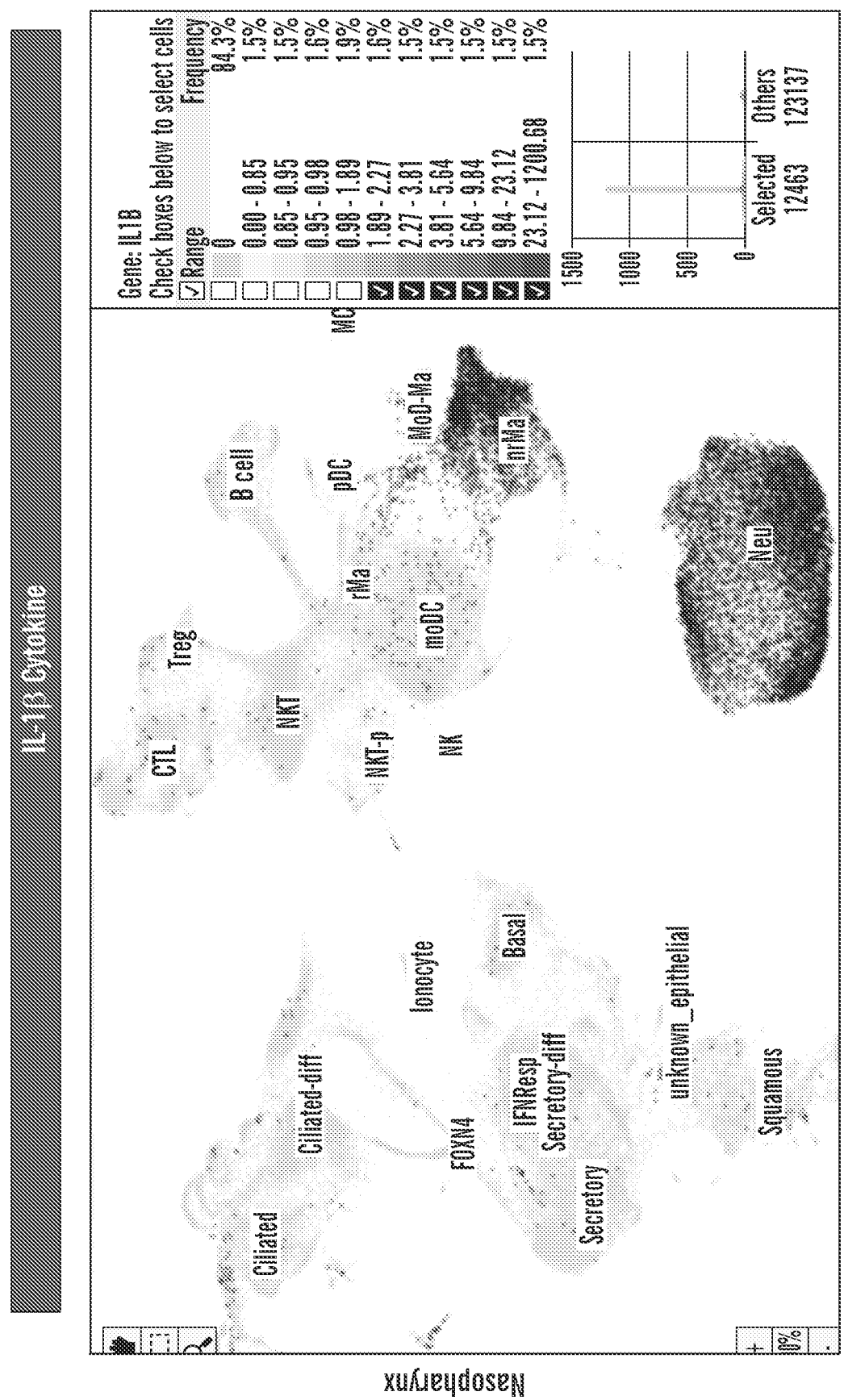
FIGS. 34A-34D show that monocyte-neutrophil crosstalk in COVID19 patients provides a pathway to sustained reciprocal coactivation, indicating the IL-1β autocrine loop.
Figure 34B:
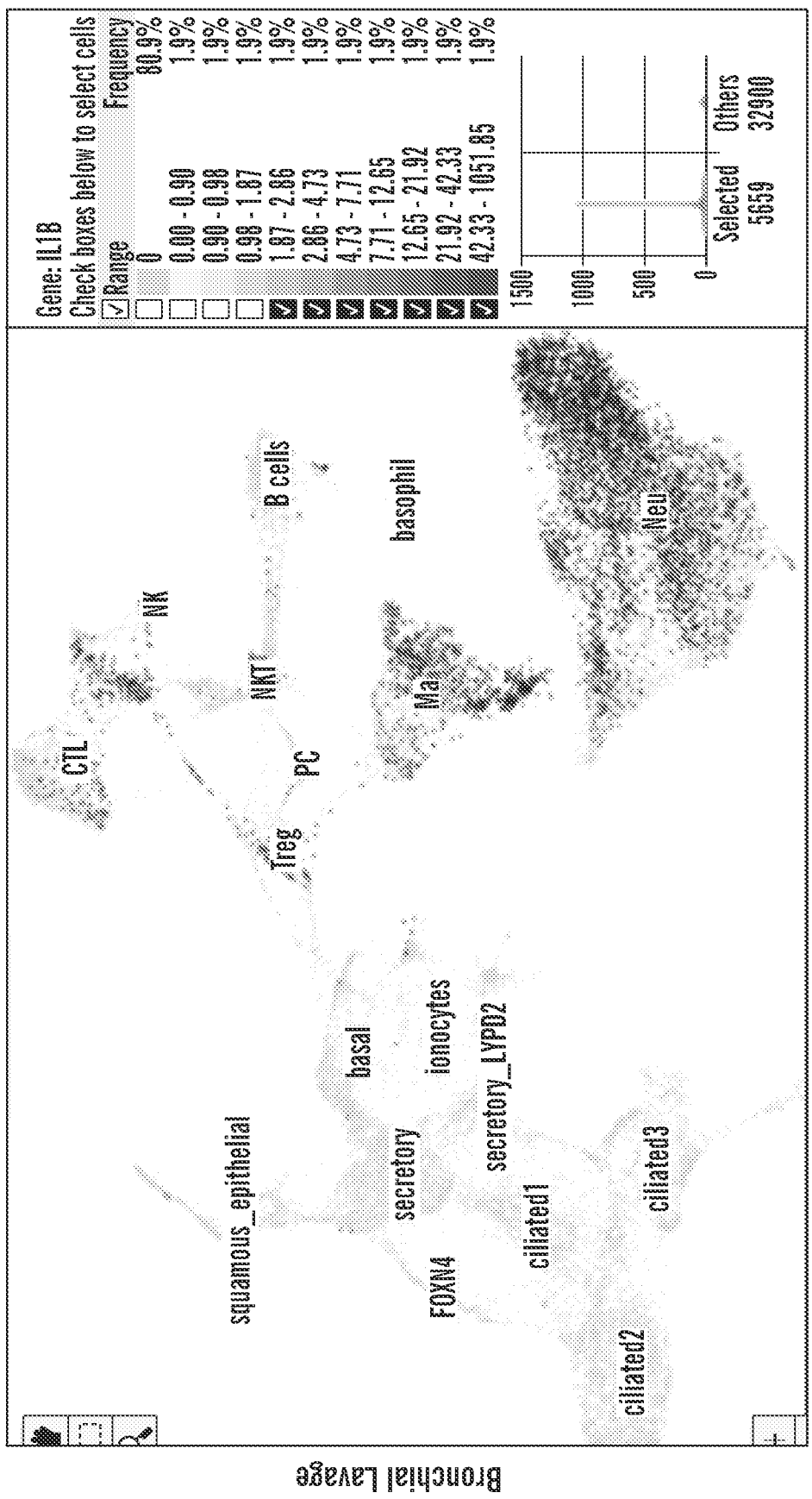
Figure 34C:
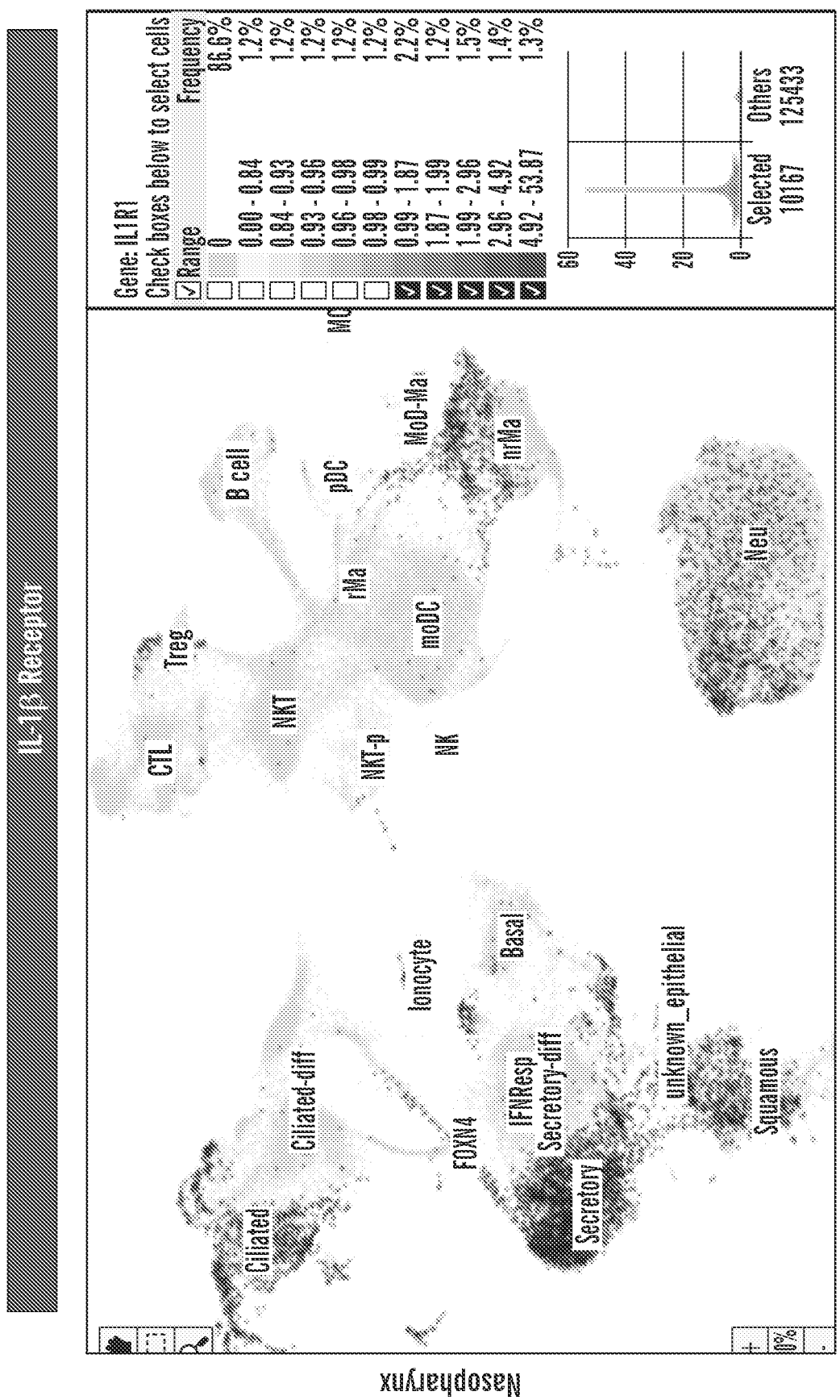
Figure 34D:
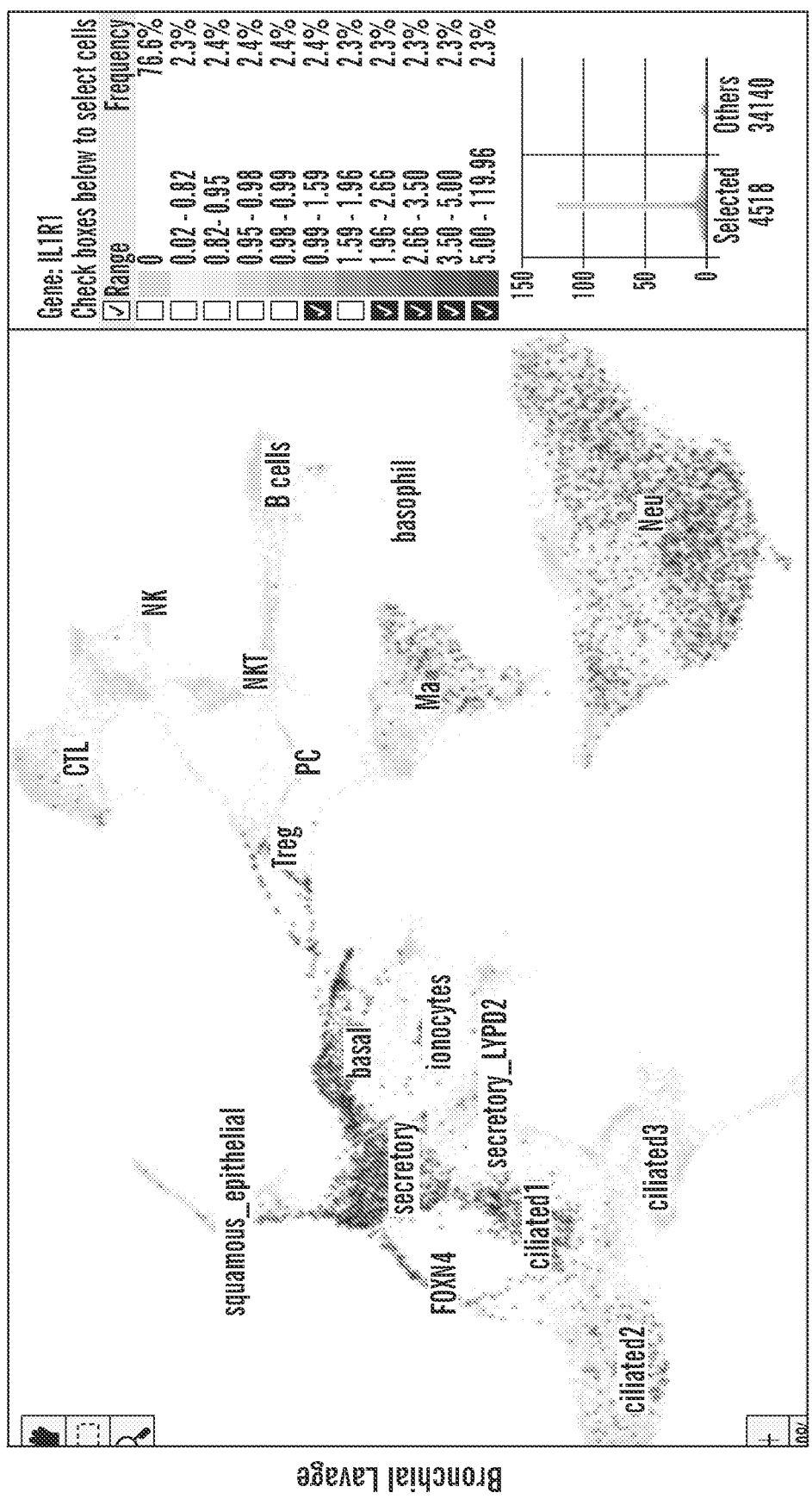

FIGS. 34A-34D show that monocyte-neutrophil crosstalk in COVID19 patients provides a pathway to sustained reciprocal coactivation, indicating the IL-1β autocrine loop. FIGS. 34A-34B depict IL-1β cytokine expression in samples from the nasopharynx and bronchial lavage. FIGS. 34C-34D depict IL-1β Receptor expression in samples from the nasopharynx and bronchial lavage.

Monocyte-neutrophil crosstalk in COVID19 patients provides a pathway to sustained reciprocal co-activation, indication IL-1 autocrine loop.

Figures 35A, 35B, 35C:
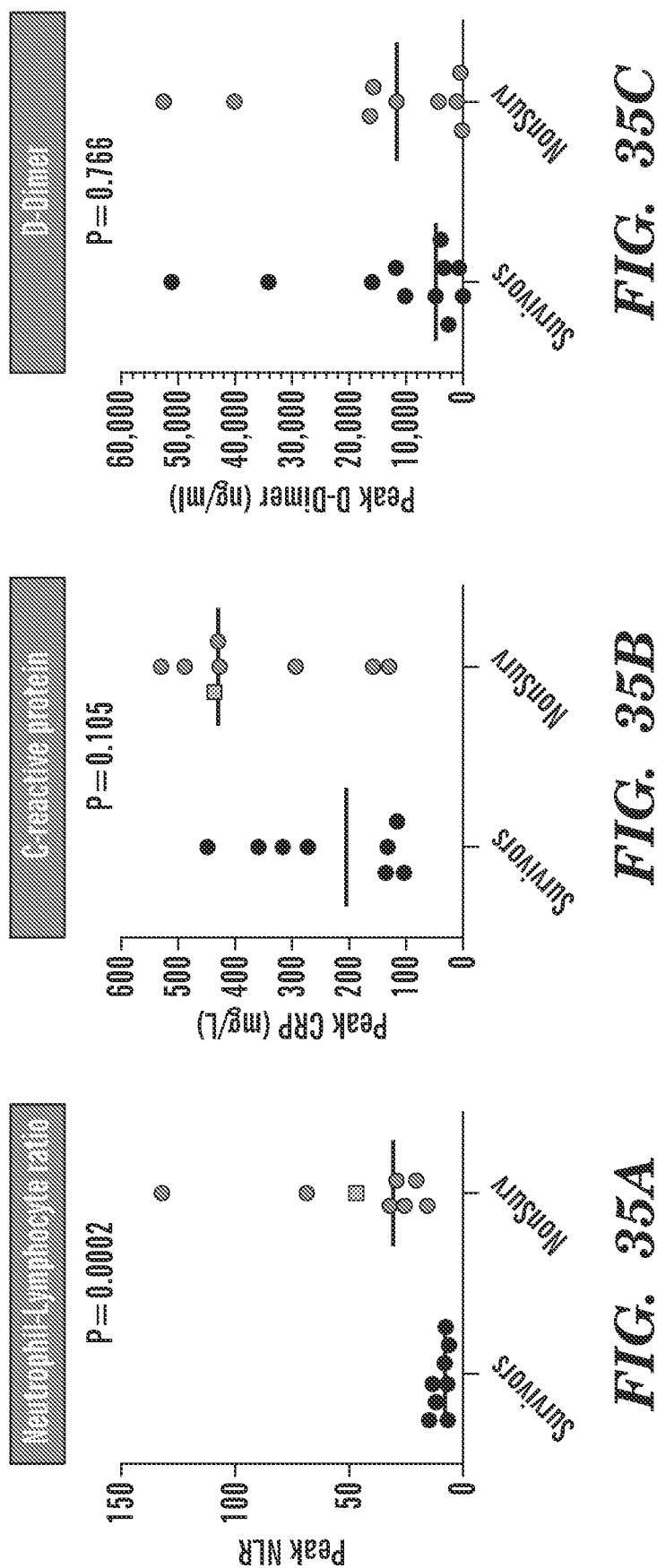
FIGS. 35A-35C show that while all elevated, Neutrophil Lymphocyte Ratio (NLR) differentiates non-survivors (p=0.0002), but not C-Reactive Protein (CRP), nor D-dimer levels in COVID19+, ARDS patients.

FIGS. 35A-35C show that while all elevated, neutrophil lymphocyte ratio (NLR) differentiates non-survivors (p=0.0002), but not C-Reactive Protein (CRP), nor D-dimer levels in patients having COVID19+ ARDS. FIG. 37A depicts a graph of Neutrophil-Lymphocyte ratio vs. outcomes in COVID19+, ARDS patients. FIG. 37B depicts a graph of C-reactive protein vs. outcomes in COVID19+, ARDS patients. FIG. 37C depicts a graph of D-Dimer vs. outcomes in COVID19+, ARDS patients.

Example 7: DNA Strands and NET-Clusters in COVID19 ARDS Patients

Figure 36:
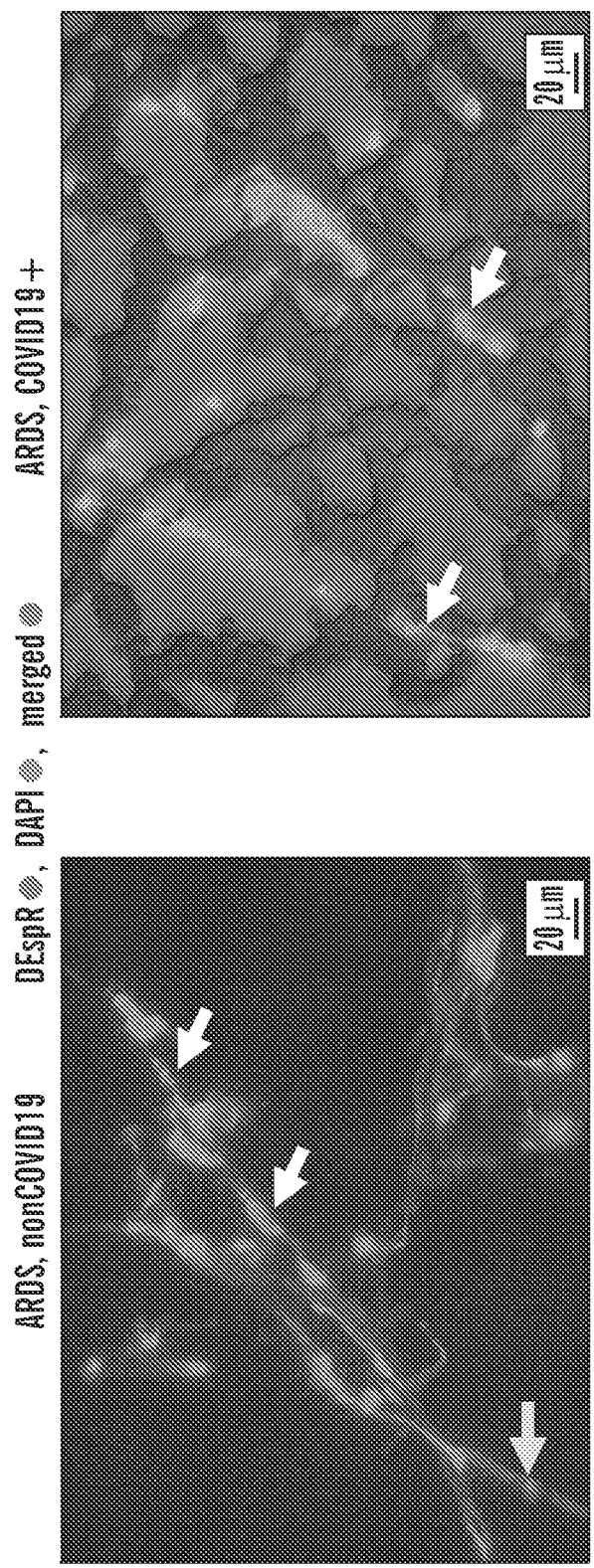
FIG. 36 shows that circulating DEspR+DAPI+ microvesicles (MVs) attached to DNA-strands are detected in ARDS and ARDS-COVID19 patients. DEspR+DAPI mvs on cfDNA strands can structurally cause low-flow ischemia per se that may underpin multi-organ dysfunction syndrome or Multi-organ Failure in ARDS. These may also act as nidus for systemic microthrombi. The left panel depicts the image of the sample from an ARDS, nonCOVID19 subject and the right panel depicts the image of the sample from an ARDS, COVID19+ subject.

FIG. 36 shows that circulating DEspR+DAPI+ microvesicles (MVs) attached to DNA-strands are detected in ARDS and ARDS-COVID19 patients. DEspR+DAPI mvs on cfDNA strands can structurally cause low-flow ischemia per se that may underpin multi-organ dysfunction syndrome or Multi-organ Failure in ARDS. These may also act as nidus for systemic microthrombi. The left panel depicts the image of the sample from an ARDS, nonCOVID19 subject and the right panel depicts the image of the sample from an ARDS, COVID19+ subject. In some embodiment, combinational therapy of anti-DEspR mAb and FDA-approved DNAse-I therapy may help alleviate low flow ischemia which can cause multi-organ dysfunction as well as QV mismatch and severe hypoxemia.

As used herein, the term "DEspR+ DNA strand(s)" refers to DEspR+DAPI+ microvesicles (MVs) attached to DNA-strands.

Figure 37:
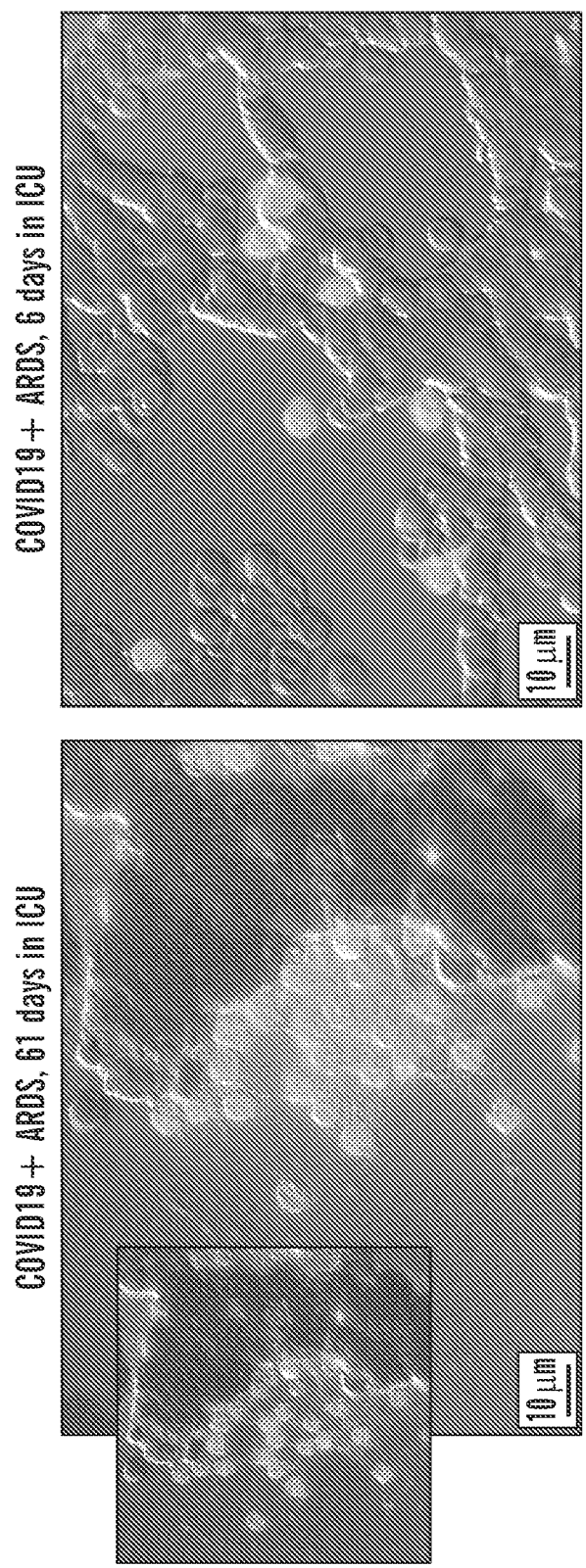
FIG. 37 depicts detection of NETosing neutrophil aggregates in COVID19+ARDS patient blood smears. The left panel depicts the image of the sample from a COVID19+ ARDS subject who was in ICU for 61 days and the right panel depicts the image of the sample from an COVID19+ ARDS subject who was in ICU for 6 days.

FIG. 37 depicts detection of NETosing neutrophil aggregates in COVID19+ ARDS patient blood smears. The left panel depicts the image of the sample from an COVID19+ ARDS subject who was in ICU for 61 days and the right panel depicts the image of the sample from an COVID19+ ARDS subject who was in ICU for 6 days.

In some embodiments, NETosing neutrophil aggregates may result in microthrombi and/or low-flow ischemia partial occlusion, or ischemic vaso-occlusion. In some embodiments, anti-DEspR mAb therapy to prevent microthrombosis without bleeding complications may provide a prophylactic therapeutic premise.

In some embodiments, DEspR+DAPI+ DNA-strands may contribute to low flow ischemia which intuitively. In some embodiments, DEspR+DAPI+ DNA-strands may induce multi-organ dysfunction and severe hypoxemia with ventilation-perfusion mismatch which has been observed in COVID19 patients.

Example 8: DEspR+ Lymphocytes and Outcomes in ARDS Patients

FIG. 38 depicts a table showing linear relationship of DEspR+ cells, neutrophils Ns, monocytes Ms, and lymphocytes Ls with outcome of ARDS. Linear regression analysis of poor outcome vs biomarkers in ARDS patients (with various underlying causes) show significant linear relationship of DEspR+ Ns, Ms, Ls with outcome of ARDS (survival vs non-survival). n=13 subjects; NLR, neutrophil/lymphocyte ratio; [total], neutrophils+early apoptosis neutrophils combined; Ls, lymphocytes; Ms, monocytes. Statistical analysis=Linear regression: outcomes: 0=survived; 0.5=survived with sequelae; 1=deceased. R: negative correlation, inverse relation of dependent variable (outcome) and explanatory variable (biomarkers). Correlation of DEspR+CD11b+ lymphocytes and outcomes in ARDS patients. DEspR+ Ls, Ms, and Ns (detected on flow cytometry or FACS analysis).

Figure 39:
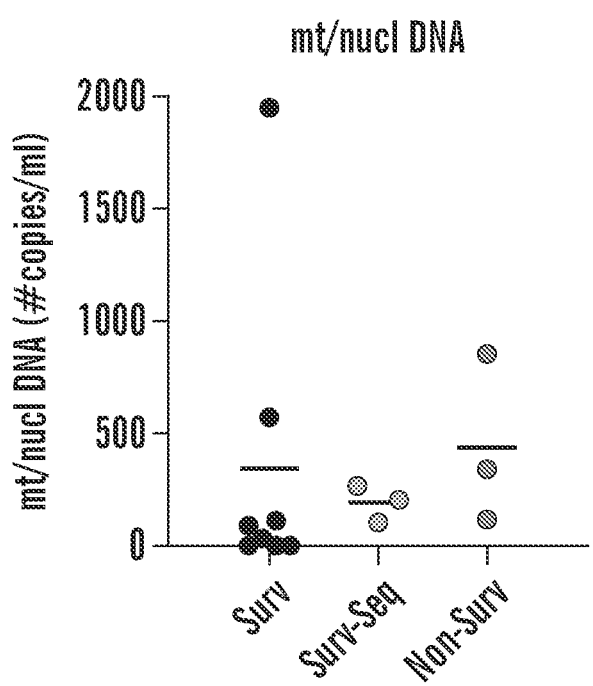
FIG. 39 depicts data showing changes in circulating cell-free mitochondrial to nuclear DNA ratio compared to reported healthy controls. Analysis of the ratio of circulating cell-free mitochondrial DNA to nuclear DNA in ARDS patients with various underlying causes by multiplex real-time quantitative PCR detects marked decrease (3-fold to 50-fold decrease) compared to reported levels in healthy controls.

FIG. 39 depicts data showing changes in circulating cell-free mitochondrial to nuclear DNA ratio compared to reported healthy controls. Analysis of the ratio of circulating cell-free mitochondrial DNA to nuclear DNA in ARDS patients with various underlying causes by multiplex real-time quantitative PCR detects marked decrease (3-fold to 50-fold decrease) compared to reported levels in healthy controls. ratio of circulating cell-free mitochondrial DNA to nuclear DNA in plasma detected by multiplex real-time quantitative PCR.

For ARDS patients, the circulating cell-free mitochondrial (mt) to nuclear (n) DNA ratio was measured using a commercially validated optimized multiplex real-time PCR kit for synchronized quantification of mtDNA and nDNA in different ARDS patient samples obtained on the same day as blood samples for flow cytometry analysis. In all ARDS samples the circulating cell free mt/nDNA ratio was <1200 copies/ml in contrast to published 'normal range reported for healthy controls of 3,000 to 50,000 more than circulating cell free nuclear DNA.

Figure 40:
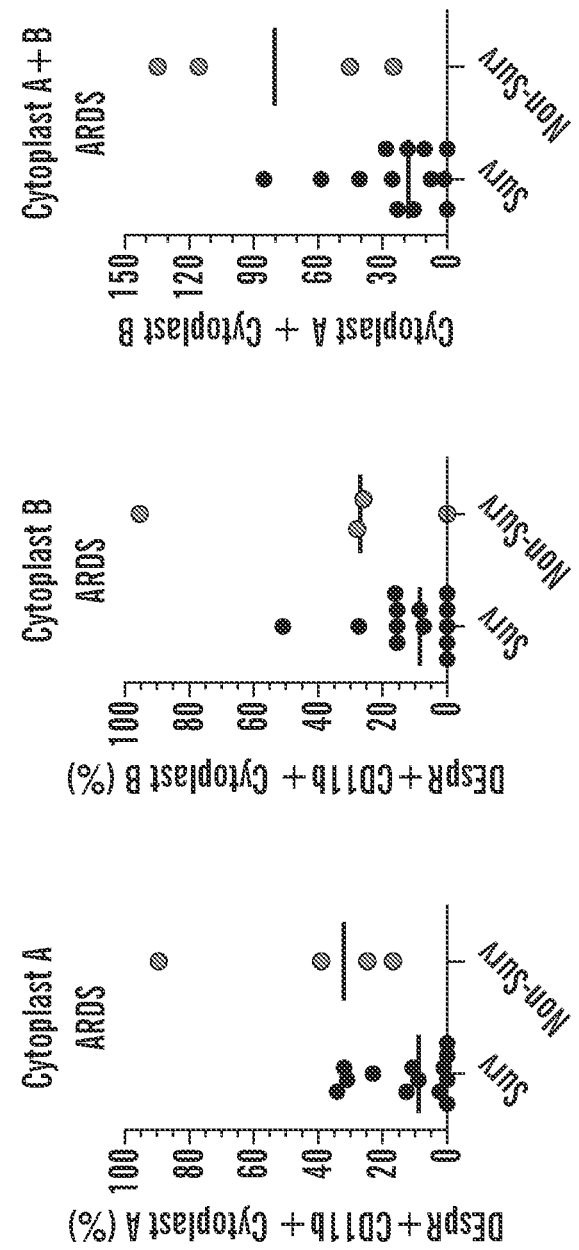
FIG. 40 depicts data showing correlation of levels of DEspR+ cytoplasts with outcomes in ARDS patients regardless of underlying etiology or precipitating event. Analysis of cytoplasts, a nuclear "cell ghost" remnants that are DEspR+CD11b+, show correlation with patient outcomes in ARDS patients with various underlying causes. Total cytoplasts show highest significant correlation.

FIG. 40 depicts data showing correlation of levels of DEspR+ cytoplasts with outcomes in ARDS patients regardless of underlying etiology or precipitating event. Analysis of cytoplasts, a nuclear "cell ghost" remnants that are DEspR+CD11b+, show correlation with patient outcomes in ARDS patients with various underlying causes. Total cytoplasts show highest significant correlation. n=17 subjects: ARDS dx with different underlying causes. Statistical analysis=Spearman Rank Order Correlation. Outcome: 0=Survived, 0.5=Survived with sequelae, 1=Deceased. Cytoplast A have similar size range but lower side scatter or granularity on flow cytometry compared to Cytoplast B. cytoplasts (detected on flow cytometry or FACS analysis).

Example 9: Anti-DEspR mAb and Brain Injury

FIGS. 41A and 41B show that anti-DEspR mAb blocks neutrophil-mediated brain injury in LPS-induced hemorrhagic encephalopathy. FIG. 41A shows that LPS administration to pre-stroke sICH rats produces global hemorrhagic encephalopathy and multi organ failure, providing a clinically relevant model of septic shock and ARDS-MOF (multiple organ failure). Brains were saline-perfused at harvest to eliminate circulating blood. FIG. 41B shows that anti-DEspR (1 mg/kg) reverses actN-mediated encephalopathy and mortality. More than 50× was increased in median overall survival (mOS). Gross hemorrhage was eliminated. Neutrophil cytotoxicity in brain (myeloperoxidase) was substantially decreased. Brain edema (albumin) was substantially reduced.

FIG. 42 shows that secondary brain injury mediated by the innate immune system drives mortality and morbidity in spontaneous ICH. sICh is the most deadly, debilitating, costly of all strokes and there are more than 2 million sICH cases annually worldwide. There is no approved therapy to reduce mortality or morbidity. In some embodiments, primary injury interventions are insufficient to significantly reduce mortality or morbidity. In some embodiments, secondary injury occurs with hematoma expansion, perihematomal edema, and neuro-toxicity. High Neutrophil to Lymphocyte ratio correlated with poor prognosis. In some embodiments, secondary injury needs to be addressed, as primary injury interventions may be insufficient. Neutrophil depletion improved outcomes in autologous blood injection ICH animal models.

Figure 43:
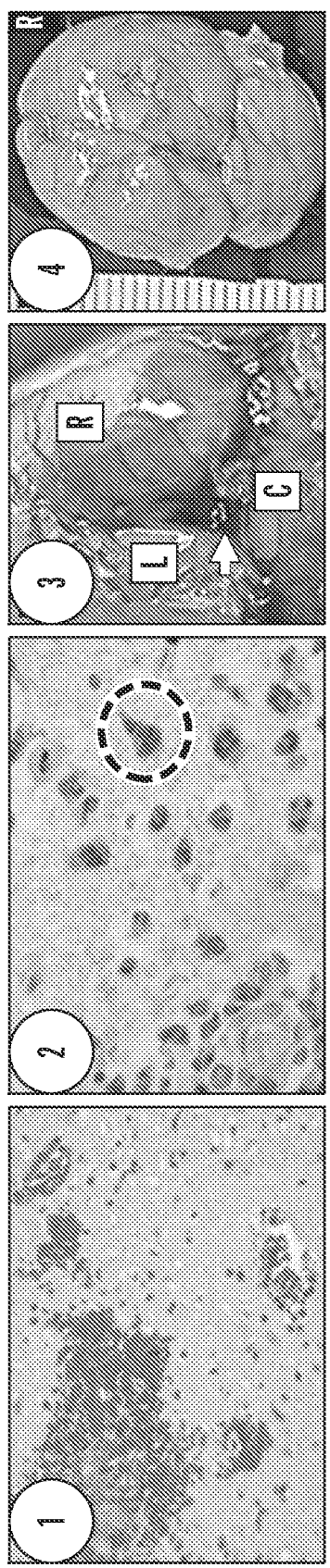
FIG. 43 shows development of a modified hypertensive DS rat model that replicates the hallmarks of human sICH.

FIG. 43 shows development of a modified hypertensive DS rat model that replicates the hallmarks of human sICH. The Dahl salt-sensitive hypertensive rat model (DS rats) is a well characterized model used in cardiovascular and hypertensive research. DS rats exhibit spontaneous hypertension which can be "accelerated" when animals are exposed to increased salt during gestation, lactation or from weaning. Such animals exhibit spontaneous ICH approximately 4.5-6 months after birth. sICH onset was evidenced by human-like neurological defects: (i) rat modified Rankin Scale (rat-mRS) score was assessed, (ii) CNS bleeds and edema were assessed by MRI. Median survival of untreated rats was <2d after initial sICH event: (1) hemorrhage and microhemorrhage with neutrophil infiltration in acute phase: (2) myeloperoxidase+ actN and NETS shown by IHC in acute phase, (3) hematomal expansion indicated by intracranial blood at end stage, and (4) perihematomal edema (brain swelling and midline shift) at end stage. DS rats became susceptible to triggers of multi-organ failure with agents such as LPS.

Figure 44:
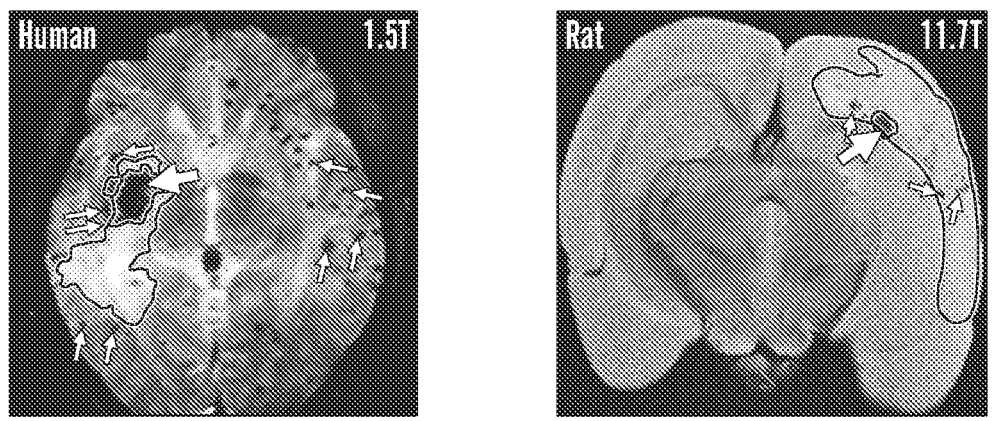
FIG. 44 shows that DS sICH rat model recapitulates clinical MRI observed in human sICH patients.

FIG. 44 shows that DS sICH rat model recapitulates clinical MRI observed in human sICH patients. Human and Rat brains.

Figure 45:
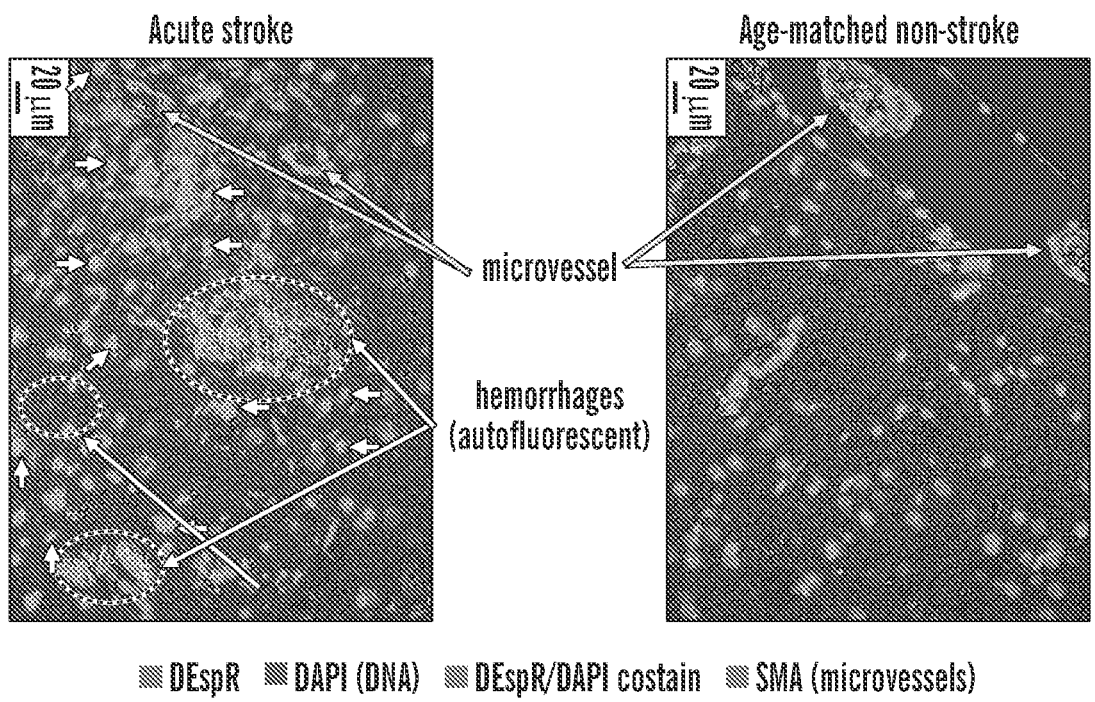
FIG. 45 shows that DEspR[+] Ns accumulate in and around brain hemorrhages in DS-sICH rats.

FIG. 45 shows that DEspR$^+$ Ns accumulate in and around brain hemorrhages in DS-sICH rats. DEspR+ Ns were seen outside vascular in acute sICH rats. No DEspR+ Ns were seen in aged matched samples without sICH.

Figure 46A:
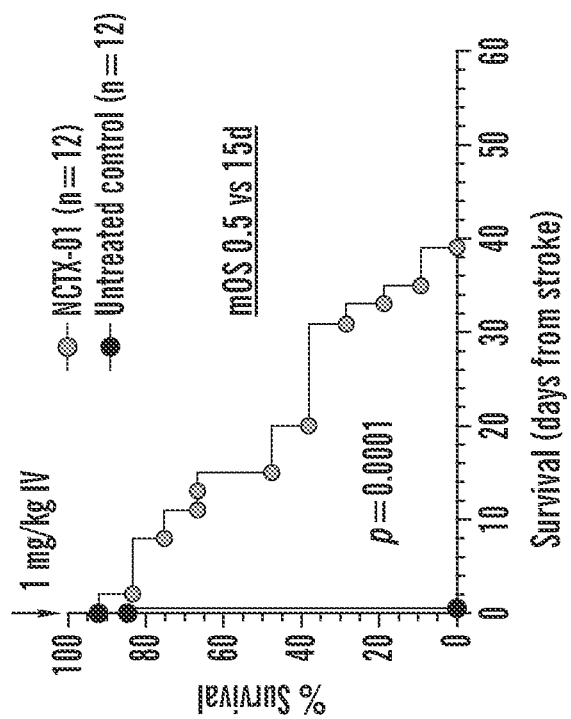
FIGS. 46A and 46B show that anti-DEspR mAbs resolve stroke deficits and prolongs survival in the sICH rat Model.
Figure 46B:
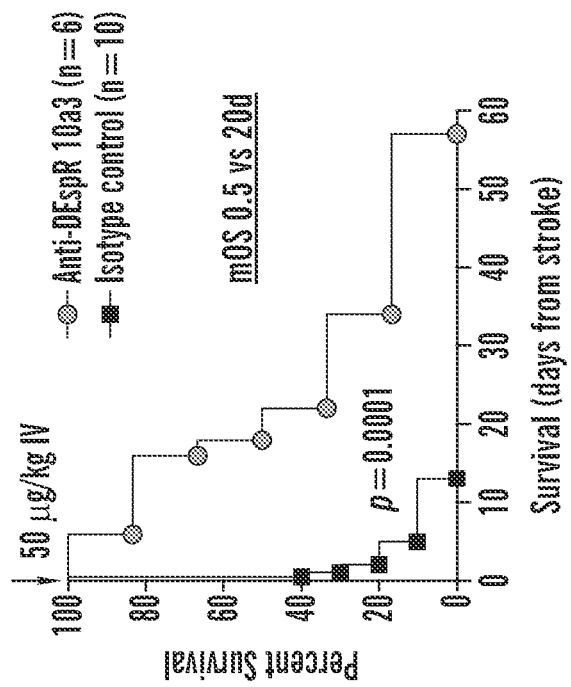

FIGS. 46A and 46B show that anti-DEspR mAbs resolve stroke deficits and prolongs survival in the sICH rat Model. In rat sICH model, single dose was administered following observed $1_{st}$ stroke. FIGS. 46A and 46B show 2 separate experiments, different mAbs tested (NCTX-01-humanized lead). FIG. 46A depicts a graph using anti-DEspR 10a3. sICH model, female rats (+hyperlipidemia) were used. Pre-treatment rat mRS scores: 1-5. All animals completely of started to resolved to normal following treatment prior to succumbing to "another" event. FIG. 46B depicts a graph using NCTX-01. sICH model, male & female rats (+hyperlipidemia) were used. Pre-treatment rat mRS scores: 3-5. All animals completely of started to resolved to normal following treatment prior to succumbing to "another" event.

Figure 47:
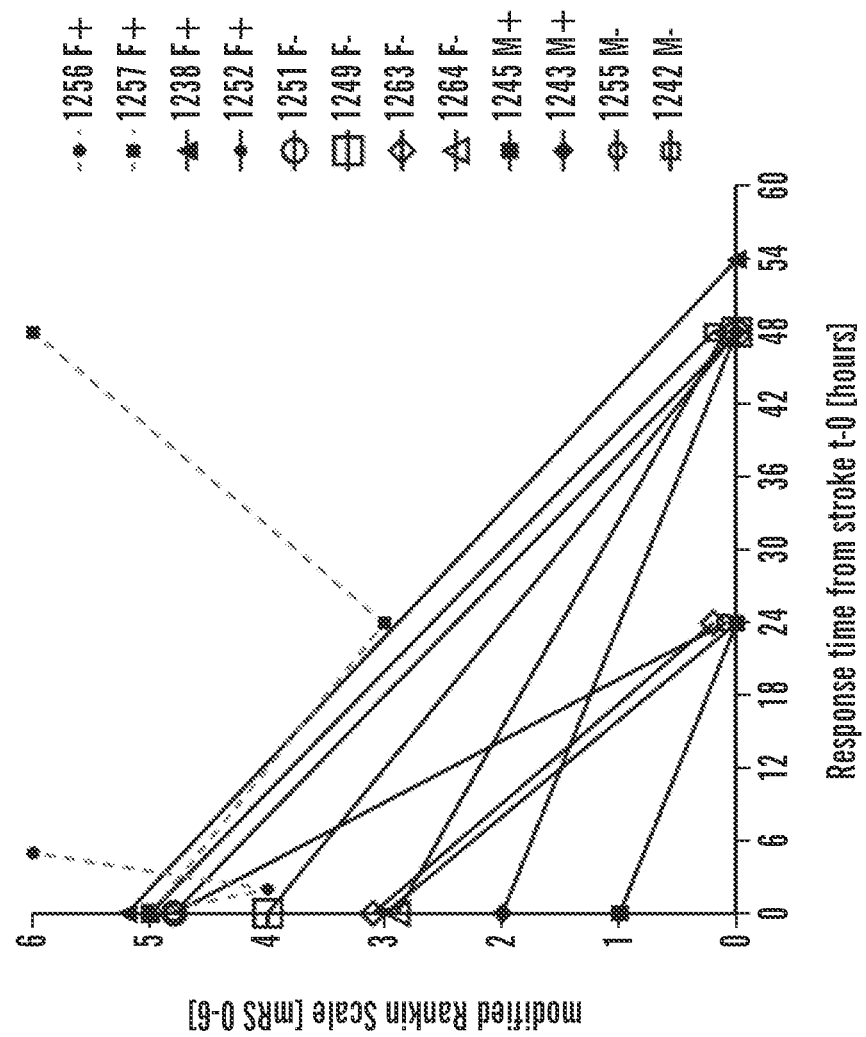
FIG. 47 shows that NCTX-01 promotes full motor recovery and prevents death during recovery in sICH rats.

FIG. 47 shows that NCTX-01 promotes full motor recovery and prevents death during recovery in sICH rats. 1 mg/kg NCTX-01 was administered after stroke was confirmed and mRS was recorded. The X-axis is mRS (stroke severity) at time of dosing (mRS=0 normal, mRS=5 full paralysis, mRS=6 dead). 10 of 12 treated rats were recovered fully (mRS=0) in 54 hr or less. All 12 untreated control animals were died<1d from time of stroke onset regardless of mRS at initial presentation.

Figure 48:
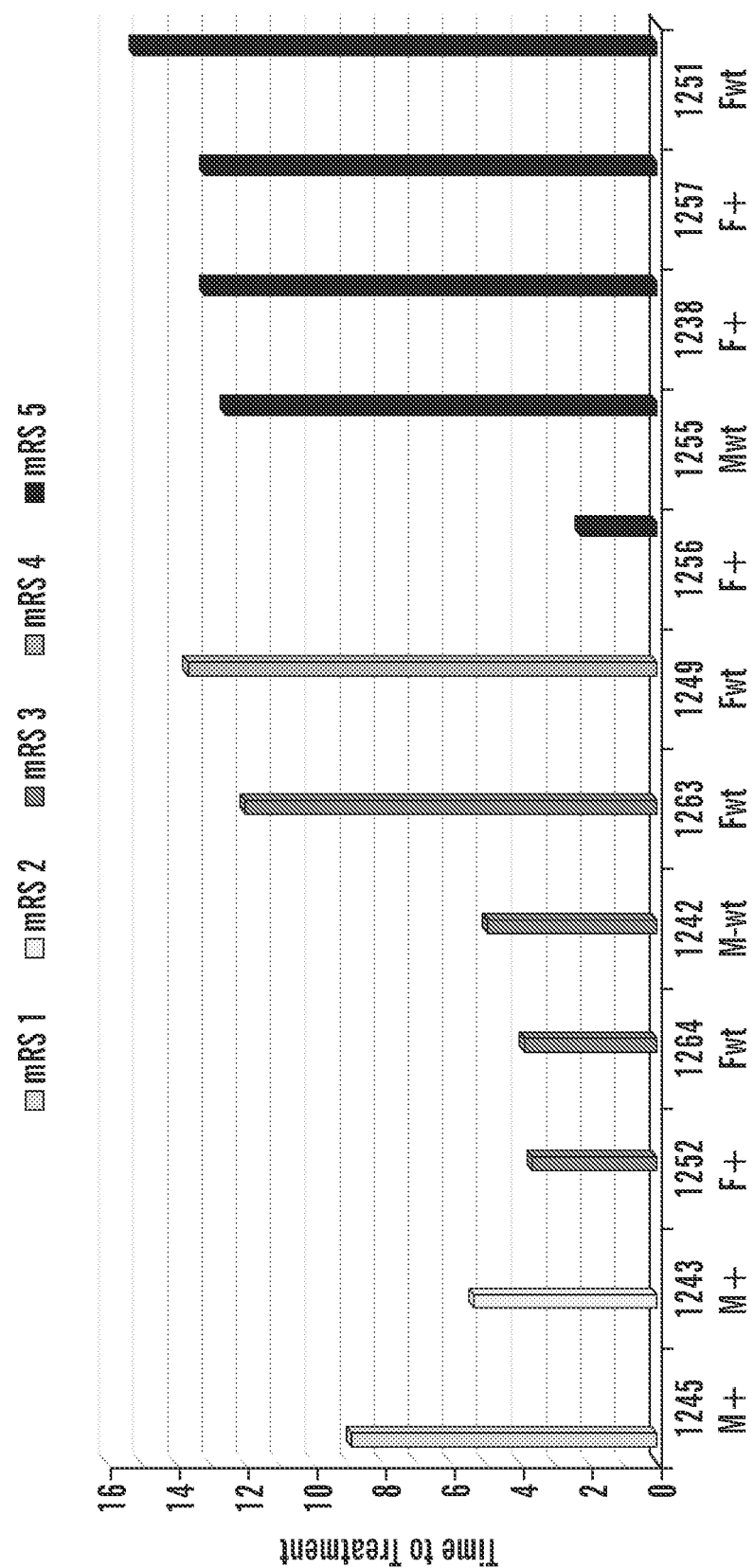
FIG. 48 shows that wide window of time to treatment provides a broad therapeutic treatment window for anti-DEspR therapy.

FIG. 48 shows that wide window of time to treatment provides a broad therapeutic treatment window for anti-DEspR therapy. Neutrophil infiltrated in human occurred immediately following event and continues for 72 hrs. The Y-axis is the time to treatment with NCTX-01 based on estimated normal last check. Each treated animal was resolved to normal (mRS=0) except 1256 and 1257 which were started to improved but regressed to death. Rats were grouped (X-axis) according to modified Rankin Scale score prior to treatment. Positive efficacy was seen across all degrees of severity regardless of time of dosing post observed initial event.

Figure 49:
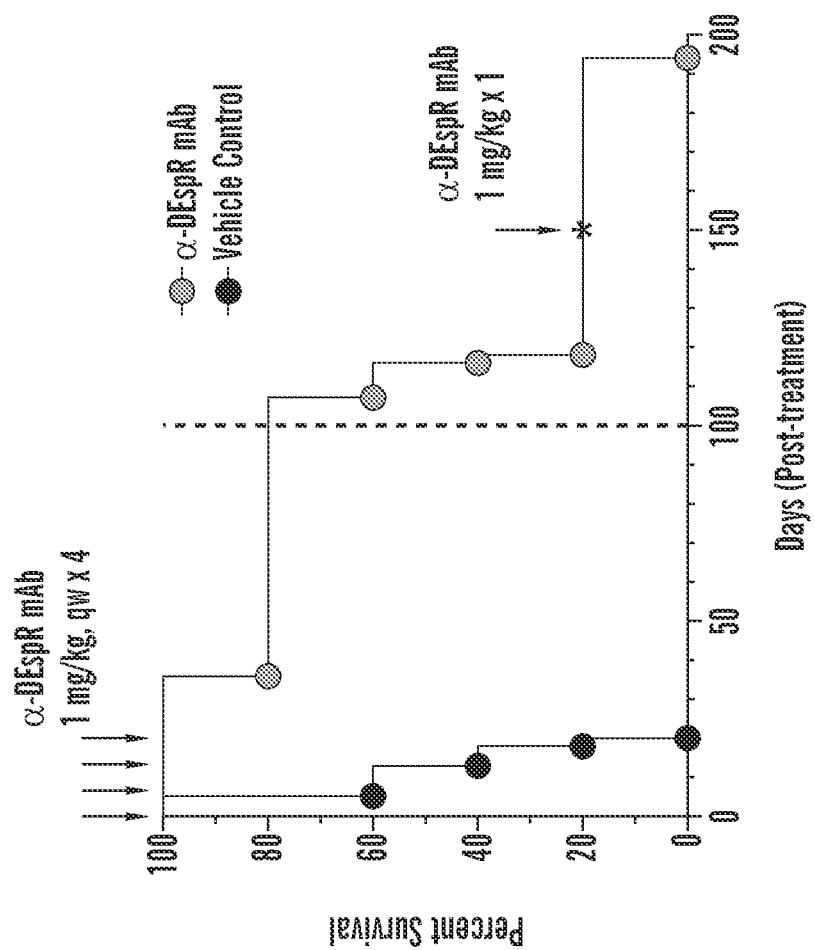
FIG. 49 shows that anti-DEspR effectively prevented stroke in a stroke prone sICH rat model.

FIG. 49 shows that anti-DEspR effectively prevented stroke in a stroke prone sICH rat model. Age matched littermates were randomly assigned to treatment and control groups after the 1st rat in the group died from stroke (sentinel/signal rat). Anti-DEspR mAb or vehicle control was administered at 1 mg/kg, qw×4 to one cohort, and the other cohort received vehicle control. Anti-DEspR mAb increased median neurologic deficit-free survival, for example, 13d (control) v 113d (treated). All non-treated rats exhibited sICH onset within 21 days from the 1st stroke rat and died within a day following event Human sICH provides rapid readouts for efficient clinical trials & Point-of-Care. In some embodiments, secondary tissue injury after primary sICH includes hematoma and perihematomal edema quantifiable by non-contrast CT or MRI. For example, a hematomal expansion occurs in 1st day after onset and perihematomal edema increases in 1st 3 days, continues until 2-3 wks. Serum markers, such as myeloperoxidase (MPO), neutrophil elastase (NE), and neutrophil/lymphocyte ratio (NLR), as assessed for rapid, quantitative assessment. Approximately, 20% of sICH patients die within 2d of admission. Majority of sICH-related mortality is within 30d of admission. Morbidity is assessed by, for example, clinical deterioration/recovery quantifiable by Modified Rankin Score (mRS) disability scale. Stroke scores increases with 2° tissue injury, but decreases with resolution. 80% of sICH survivors have debilitating sequelae: mRS 3-5. After admission, patients are monitored for deficits and imaged if progressing. No existing therapies exist. Non-invasive diagnostic marker (e.g., DEspR+ Ns in blood) is used to identify patients likely to respond.

Example 10: DEspR: Dual Endothelin1/Signal Peptide Receptor—a Stress Survival Receptor DEspR+CD11b+ rogue Neutrophils (Ns) in ARDS±COVID19
1. Pathogenic premise: early high DEspR+ rogue Ns, NETosing Ns, and their aggregates are associated with COVID19+ ARDS, and collectively:
   a. accelerate neutrophil-mediated secondary tissue injury leading to ARDS-associated multiorgan failure and lethality.
   b. facilitate systemic microthromboses and/or partial low-flow microvascular occlusion.
2. Diagnostic premise: % Rogue N levels stratifies patients for mortality risk: inform patient management and identify cohort for clinical trials.
3. Therapeutic premise: anti-DEspR+ mAb therapy has the potential to break cycles of 'rogue' neutrophil/NETosing neutrophil-mediated secondary tissue injury.

Example 11: Increased Neutrophil-Subset Associated With Severity/Mortality In ARDS And COVID19-ARDS Expresses The Dual Endothelin-1/VEGFsignal-Peptide Receptor (DEspR)

Neutrophil-mediated secondary tissue injury underlies acute respiratory distress syndrome (ARDS) and progression to multi-organ-failure (MOF) and death, processes linked to severe COVID19. This 'innocent bystander' tissue injury arises in dysregulated hyperinflammatory states from neutrophil functions and neutrophil extracellular traps (NETs) intended to kill pathogens, but injure cells instead, causing MOF. Insufficiency of prior therapeutic approaches suggest need to identify dysregulated neutrophil-subset(s) and induce subset-specific apoptosis critical for neutrophil function-shutdown and clearance. The inventors hypothesized that neutrophils expressing the pro-survival dual endothelin-1/signal peptide receptor, DEspR, are apoptosis-resistant just like DEspR+ cancer cells, hence comprise a consequential pathogenic neutrophil-subset in ARDS and COVID19-ARDS. Described herein is the correlation of circulating DEspR+CD11b+ activated neutrophils (DEspR+actNs) and NETosing-neutrophils with severity in ARDS and in COVID19-ARDS, increased DEspR+ neutrophils and monocytes in post-mortem ARDS-patient lung sections, and neutrophil DEspR/ET1 receptor/ligand autocrine loops in severe COVID19. Unlike DEspR[−] neutrophils, ARDS patient DEspR+actNs exhibit apoptosis-resistance, which decreased upon ex vivo treatment with humanized anti-DEspR-IgG4S228P antibody, hu6g8. Ex vivo live-cell imaging of non-human primate DEspR+actNs showed hu6g8 target-engagement, internalization, and induction of apoptosis. Altogether, data differentiate DEspR+actNs as a targetable neutrophil-subset associated with ARDS and COVID19-ARDS severity, and demonstrate DEspR-inhibition as a therapeutic paradigm.

Acute respiratory distress syndrome (ARDS) and progression to multi-organ failure (MOF) comprise a pathological spectrum of secondary 'bystander' tissue injury arising when one's inflammatory response to an inciting 'primary injury'—be it infectious or non-infectious—becomes dysregulated and excessive.[1] Stopping this feed-forward destructive inflammation in ARDS and MOF remains an important unmet need, as there is no FDA-approved pharmacotherapy able to reduce the high mortality in ARDS from MOF.[2] The lethality of destructive inflammation is highlighted by the COVID19 pandemic as progression to ARDS and multi-organ failure are accelerated in COVID19, and comprise the major cause of death in severe COVID-19.[3] Notably, destructive inflammation often exhibits a feed-forward progression to multi-organ failure and death even if the inciting primary injury is resolving, if not finite, such as decreasing bacterial or viral load, one-time sterile trauma. This supports the scientific rationale that effective targeted inhibitors of destructive inflammation can be agnostic of the different primary injury etiologies in ARDS—be it bacterial infection at any site, SARS CoV2, or sterile injury.

As an approach to address the pressing need for novel therapies for ARDS and COVID19-ARDS, the inventors conducted comparative analysis and identification of pathogenic commonalities in ARDS and COVID19-ARDS to identify novel therapies. A priori, this pinpoints cytokine storm inhibitors common to both ARDS and COVID10-ARDS. However, the redundancies among cytokine-mediated pathways, and the partial-only reduction in mortality by an IL-6 receptor inhibitor in severe COVID19,[4] suggest that targeted inhibition of the cellular effectors of the cytokine storm will be required. Among cytokine effector cells, neutrophils have long been implicated in ARDS and progression to multi-organ failure.[1,5] Activated neutrophils play key roles in multi-organ dysfunction and progression to failure[6] through neutrophil-mediated microvascular endothelial injury, capillary permeability,[7] and neutrophil-extracellular trap (NET)-associated endothelial and lung epithelial injury.[8,9] The central role of neutrophils is supported by the association of increased neutrophil-lymphocyte ratios (NLR) with worse ARDS prognosis[10] as well as with more severe COVID19 and poor prognosis[11].

More recently, comparative single cell RNA-sequencing (scRNA-seq) analysis of mild and critically ill COVID19-patients, and non-infected healthy controls, demonstrated molecular evidence supporting the central role of neutrophils,[12] concordant with other reports[13-15] However, inhibiting neutrophils effectively to mitigate neutrophil-driven secondary tissue injury safely and effectively has been elusive despite preclinical efficacy in animal models of acute lung injury.[5] The cumulative low translatability, due most likely to species differences in neutrophil biology and to multifactorial complexities in ARDS pathogenesis not present in preclinical models of acute lung injury, provides scientific basis for ex vivo analysis of ARDS patient whole blood samples. The ex vivo study of neutrophils within the pathobiological context of other immune cells in the circulation during progression of ARDS towards multi-organ failure or resolution is imperative in the validation of putative therapeutic targets.

Described herein is the investigation of whether DEspR+ neutrophils comprise an activated neutrophil subset with pathogenic survival advantage over other DESpR[−] activated neutrophils, and whose cumulative increase drives neutrophil-mediated secondary tissue injury in ARDS and COVID19-ARDS leading to multi-organ failure. Specifically, it was determined 1) whether DEspR+ neutrophils comprise a neutrophil-subset associated with ARDS clinical severity, mortality, and reported biomarkers of ARDS-severity, as well as, with higher levels of circulating neutrophil extracellular trap formation (NETosis), 2) whether identification of the DEspR+ neutrophil subset is reproducible in different research labs and concordant with scRNA-seq findings in severe COVID19, and 3) whether DEspR+ neutrophils can be safely inhibited to restore neutrophil apoptosis as a targetable therapeutic neutrophil subset.

DEspR+CD11b+ Human Neutrophil Subset Increased by TLR4 Activation

Figure 50A:
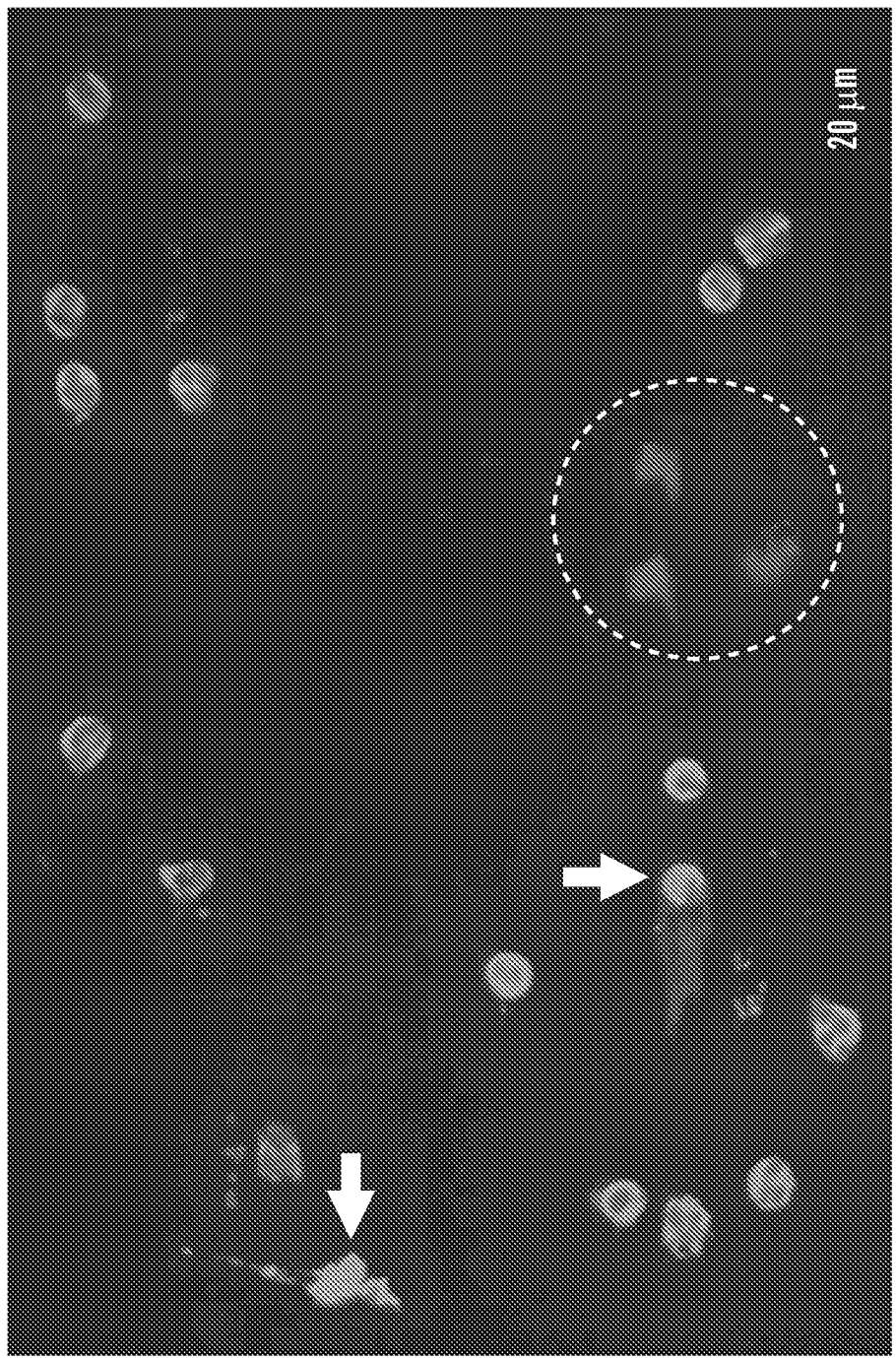
Figure 50C:
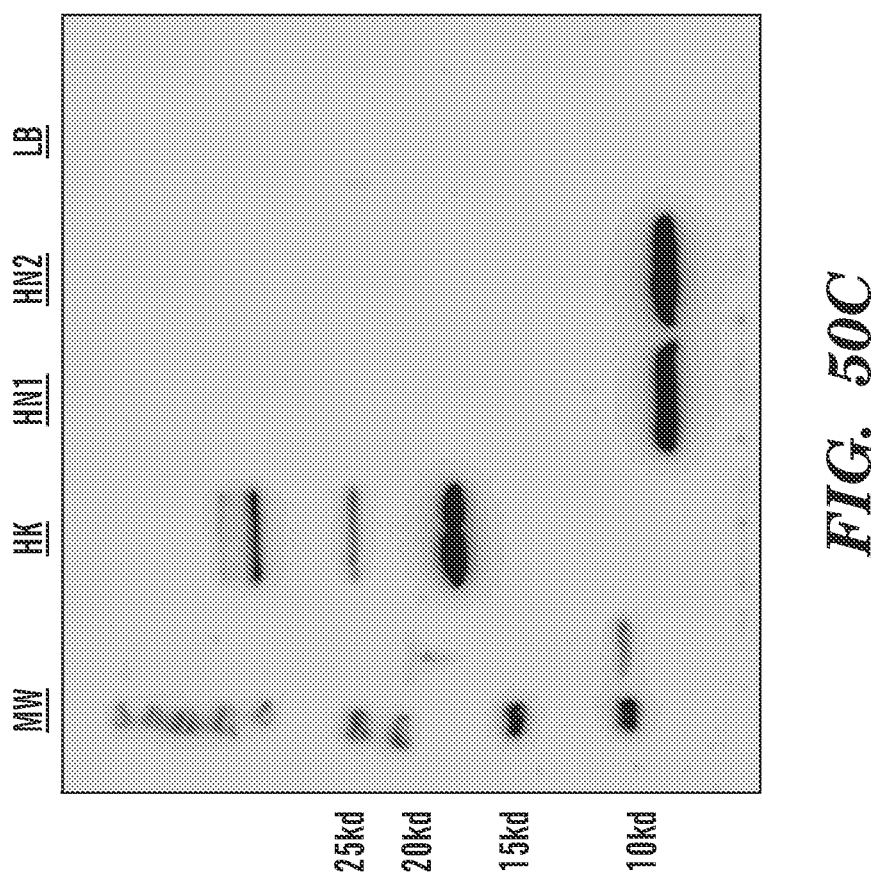
Figure 50B:
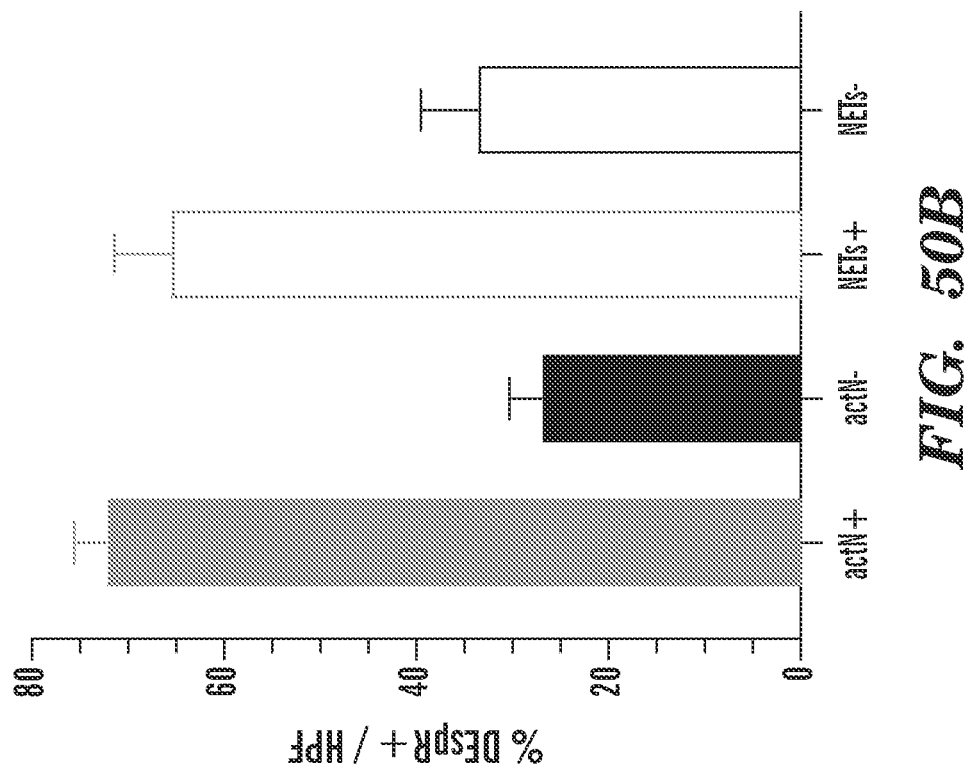
Figure 58A:
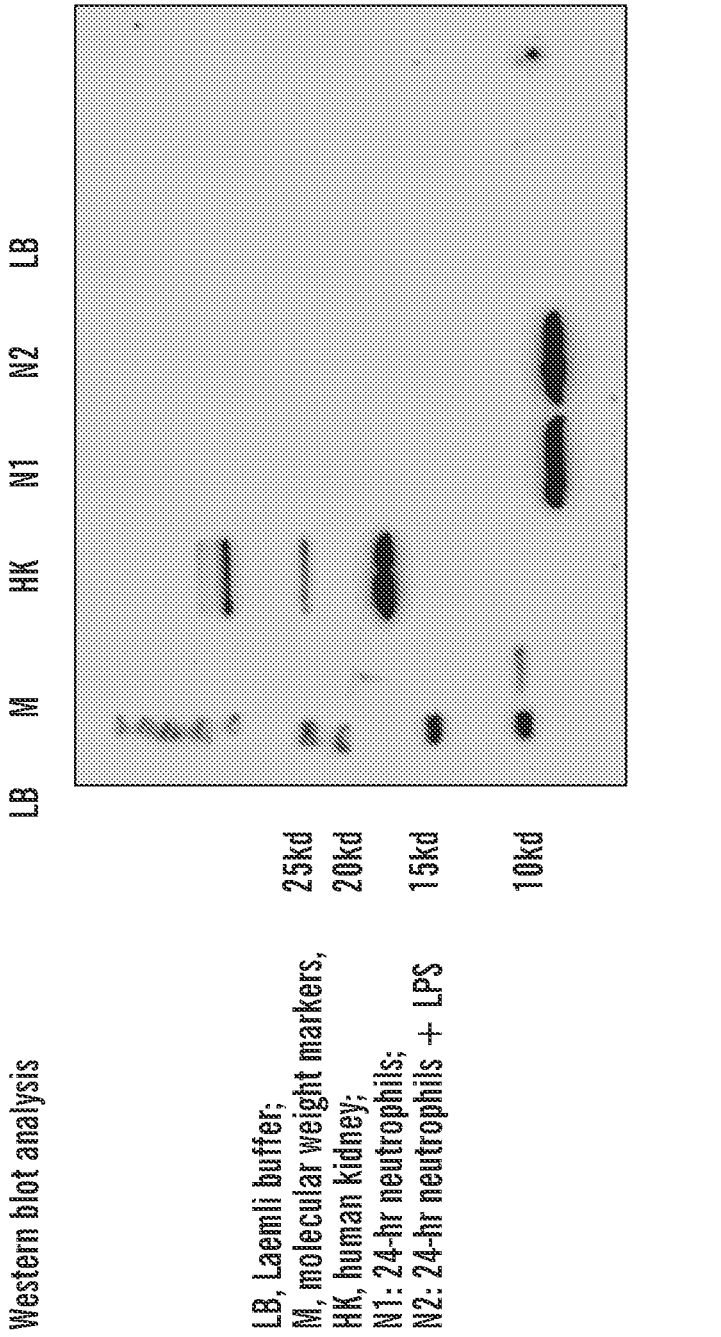
FIGS. 58A-58D depict an overview of DEspR+ expression in human neutrophils.

To determine DEspR-expression in human neutrophils as a potential therapeutic target, protein levels were analyzed by immunofluorescence, western blot and flow cytometry analyses. First, immunofluorescence staining of normal human volunteer (NHV) neutrophils that have survived ex vivo for ~24-hours was performed. A humanized anti-DEspR antibody, cross reactive to human, monkey and rodent DEspR, with a hinge-stabilized [S228P]IgG4 backbone, hu6g8, validated for detection of cancer cells expressing DEspR by immunofluorescence, western blot analysis and flow cytometry, and for in vitro and in vivo efficacy in inducing apoptosis in DEspR+ tumor cells was used.[16] Direct immunofluorescence of 24-hrs old surviving neutrophils detected DEspR expression in multiple compartments: neutrophil nuclei, cell membrane and cytoplasm (FIG. 50A), consistent with membrane-cytoplasmic-nuclear shuttling observed in cancer cells.[16] Immunofluorescence staining also detected DEspR+ neutrophils with extruded DNA and still intact cell membranes indicating DEspR+ "vital NETosis" [22,23], as well as DEspR[−] neutrophils (FIG. 50A). Notably, majority of 24-hour old neutrophils and NETosing neutrophils were DEspR+ in these ex vivo experimental conditions (FIG. 50B). Next, parallel western blot analysis of whole cell protein isolates detected the expected size DEspR protein in the NHV neutrophils, thus confirming DEspR+ expression. Western blot analysis also detected a larger DEspR protein in human kidney (FIG. 50C, FIG. 58A) due to PNGase-sensitive glycosylation, as shown previously in cancer cells.[24]

To further assess DEspR+ expression on neutrophils in preparation for ARDS patient studies, flow cytometry (FCM) analysis was performed with double-immunostaining for cell-surface co-expression of DEspR and CD11b. CD11b was selected as a marker of activated neutrophils as CD11b mediates neutrophil-complement system crosstalk, and since CD11b+ neutrophils are increased in ARDS patient peripheral blood and in broncho-alveolar fluid.[25]

Figure 50D:
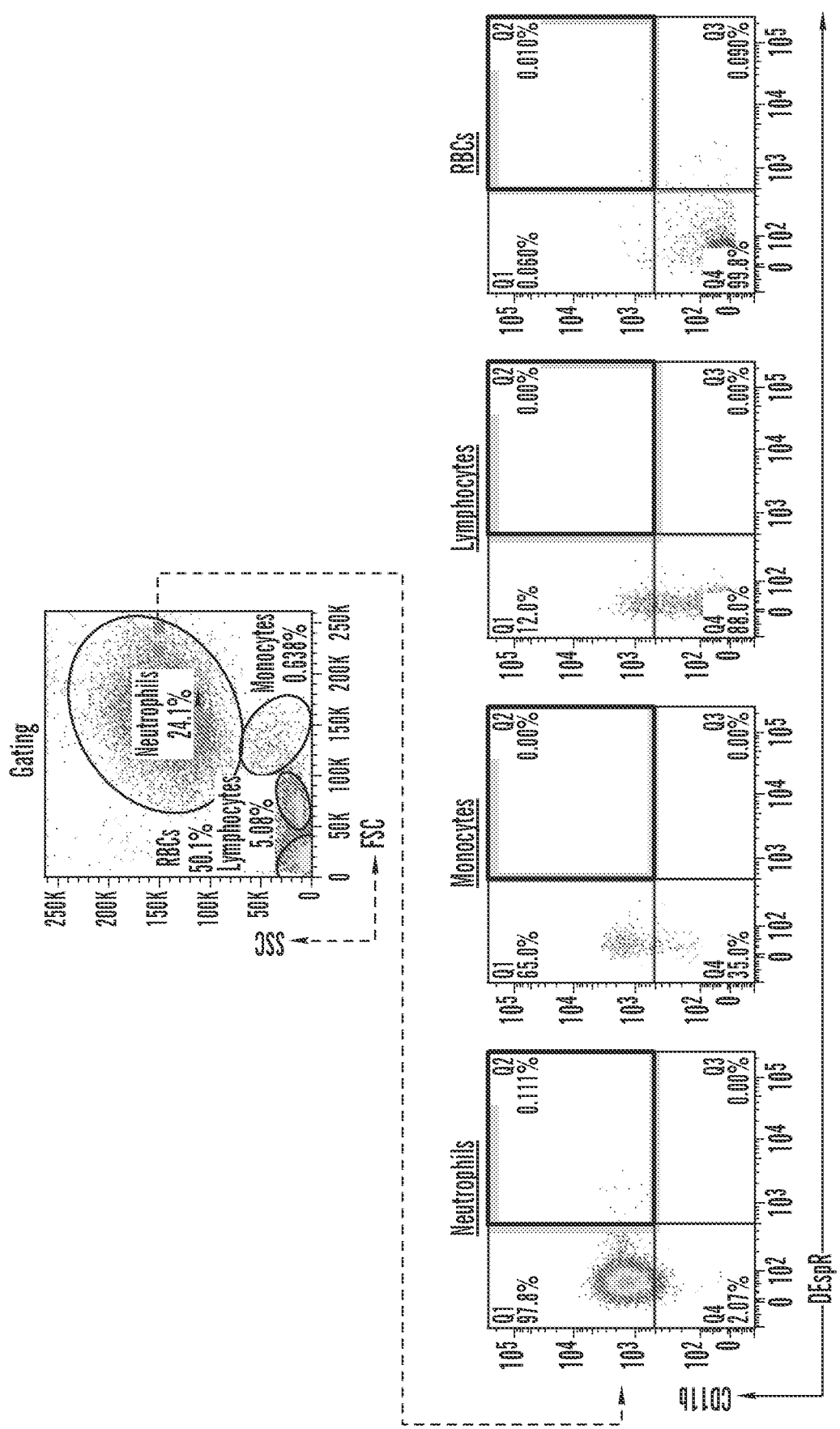
Figure 58B:
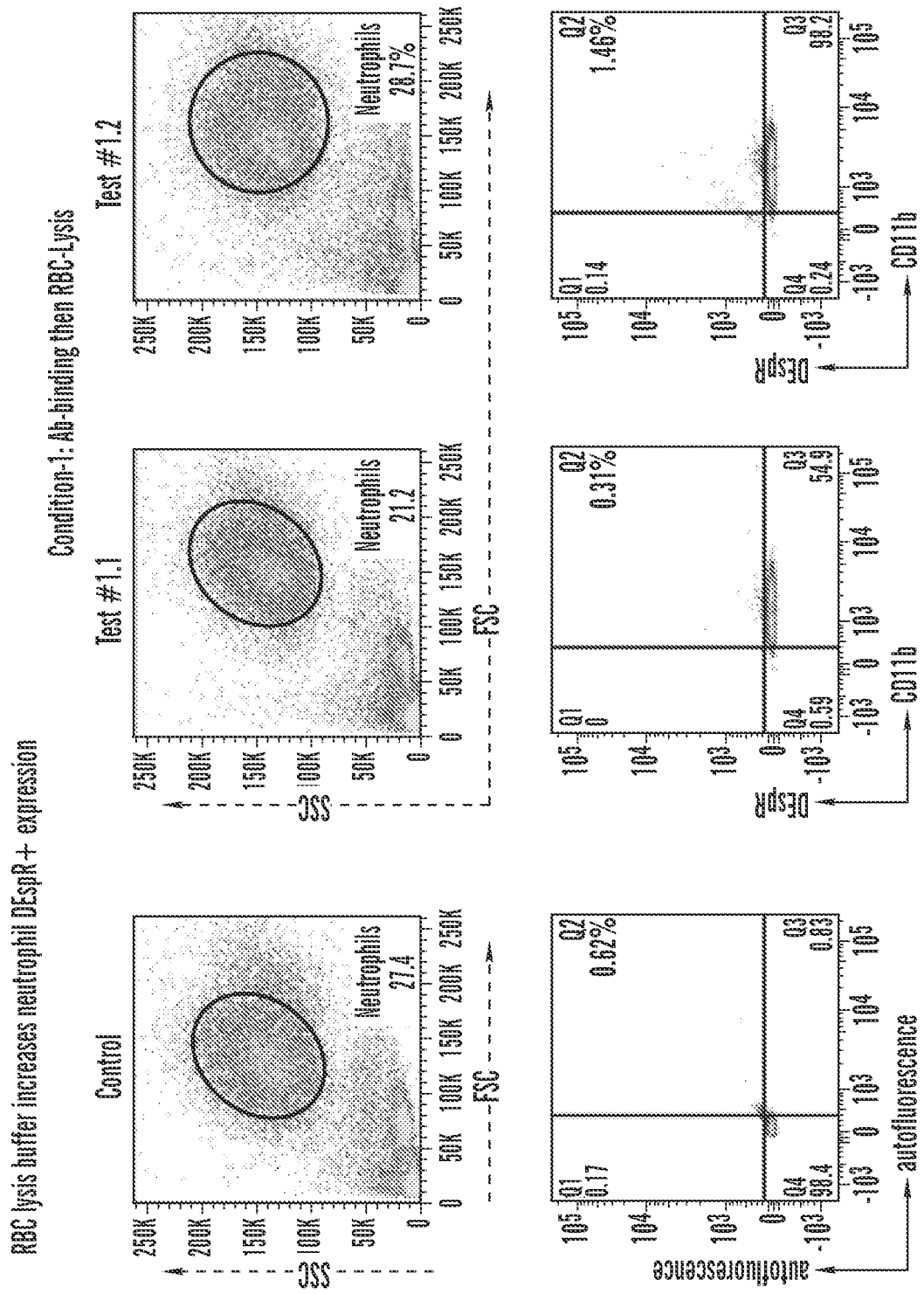

Flow cytometry analysis of normal human volunteer (NHV) EDTA-anticoagulated whole blood samples detected minimal, if any, DEspR+ expression on the cell surface of intact CD11b+ activated neutrophils (actNs), monocytes and lymphocytes in baseline conditions, and no expression on red blood cells (RBCs) (FIG. 50D). DEspR expression was increased by standard RBC-lysis step done before antibody binding (FIG. 58B), likely in response to damage associated molecular patterns (DAMPs) released during RBC hemolysis.[26] Notably, in response to cell stress expected in any ex vivo condition, DEspR expression also increased with time from blood sampling>1-hour be it at 4° C. or at 37° C. (FIG. 58C).

Having validated flow cytometry detection of DEspR+ CD11b+ neutrophils, it was next determined whether toll-like receptor 4 (TLR4)-activation increases DEspR+ expression, since TLR4-activation by DAMPs is elevated in both ARDS[27] and in COVID19-ARDS[28], and increases CD11b+ expression on neutrophils[29]. After incubation of NHV whole blood (EDTA-anticoagulation) ex vivo with an established TLR4-activator, bacterial lipopolysaccharide (LPS), flow cytometry detected increased DEspR+ expression in majority but not all CD11b+ neutrophils (FIG. 50E), identifying a specific DEspR+CD11b+ neutrophil subset (DEspR+actNs).

Figure 50G:
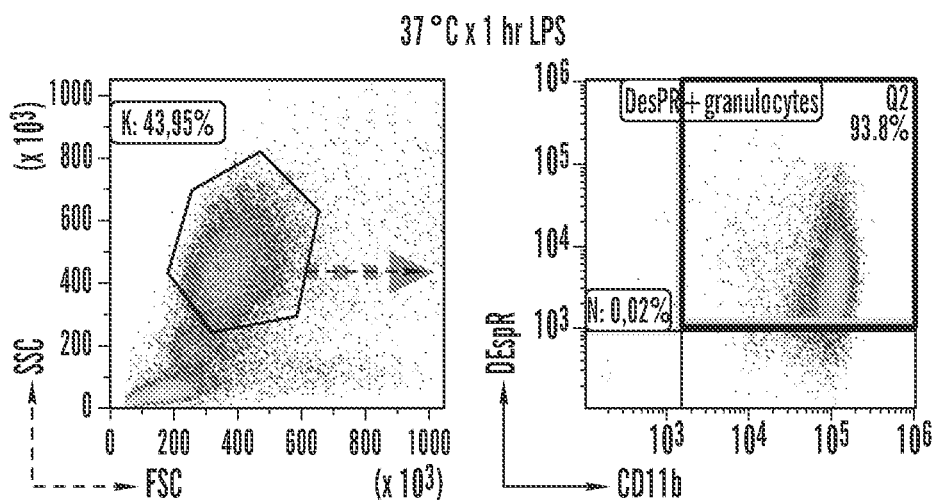
Figure 50H:
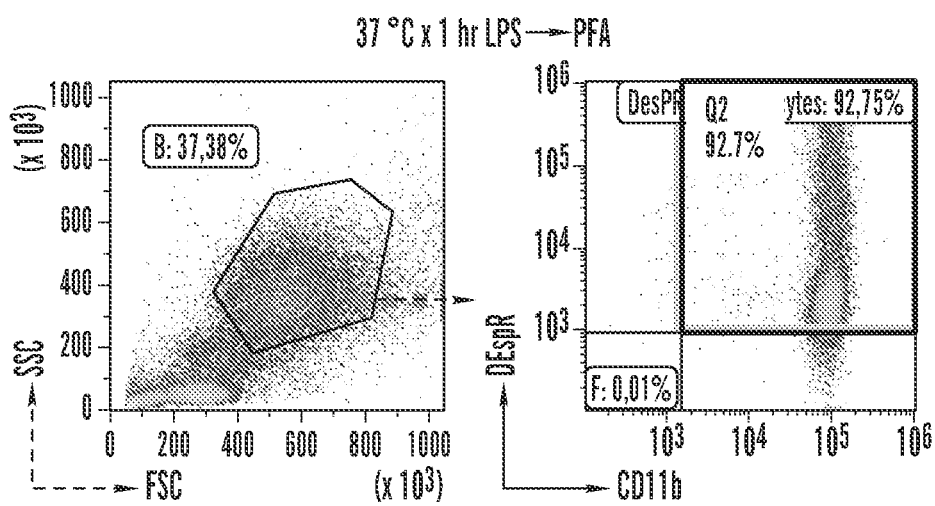

To independently test detection of DEspR+CD11b+ neutrophils in NHV blood samples, flow cytometry analysis was performed on Li-heparin anticoagulated NHV whole blood that would allow more robust LPS-activation without EDTA-chelation of $Ca^{2+}$, $Mg^{+2}$ ions. This testing detected higher DEspR+CD11b+ activated neutrophils: ~52.4% in buffer (FIG. 50F), and ~93.5% with LPS challenge (FIG. 50G). To assess potential intracellular stores, permeabilized TLR4-activated neutrophils were analyzed using light fixation (2% paraformaldehyde) only so as not to alter antigenic epitope. Flow cytometry analysis detected higher fluorescence levels of DEspR+ expression but same % of DEspR+ CD11b+ neutrophils (FIG. 50H), compared to non-PFA-permeabilized TLR4-activated neutrophils (FIG. 50G). This observation indicates the presence of intracellular DEspR, in addition to cell surface DEspR, hence higher "total" DEspR+ expression. This is supported by membrane, cytoplasmic expression detected by immunocytostaining (FIG. 50A).

Figure 58C:
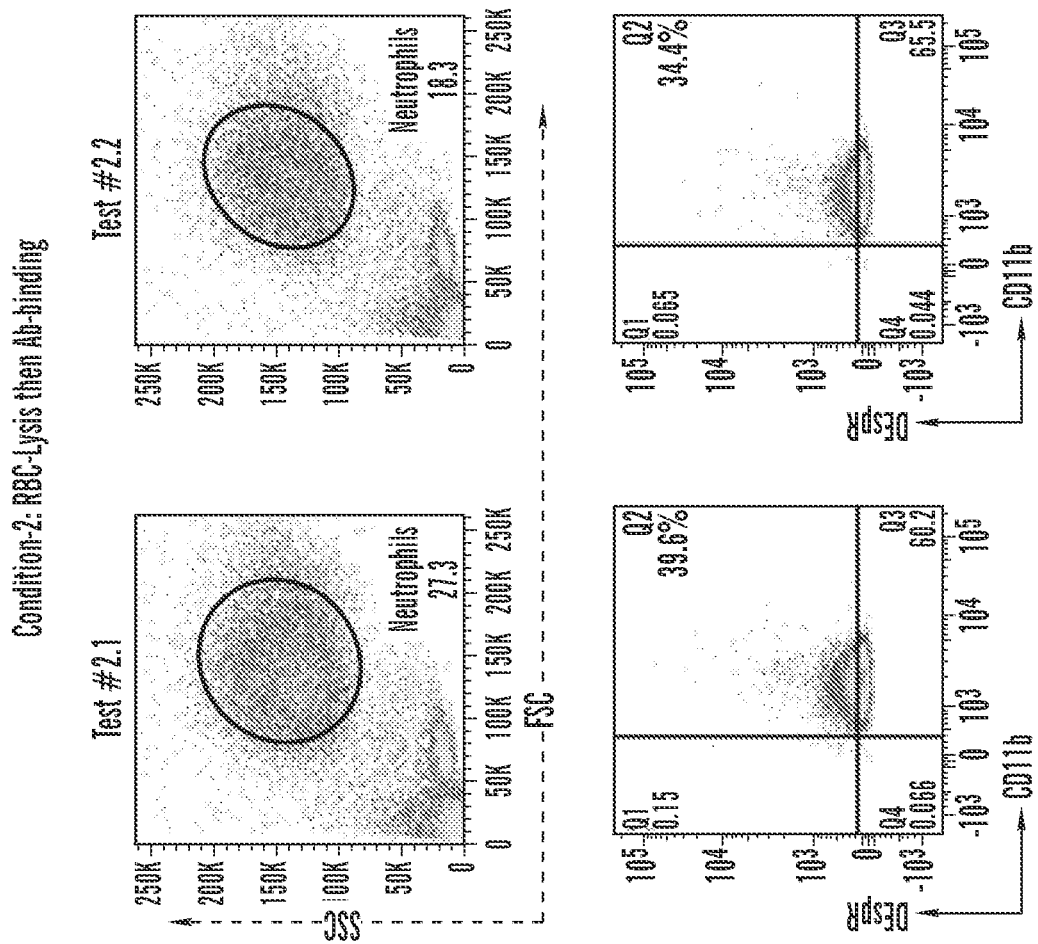
Figure 58D:
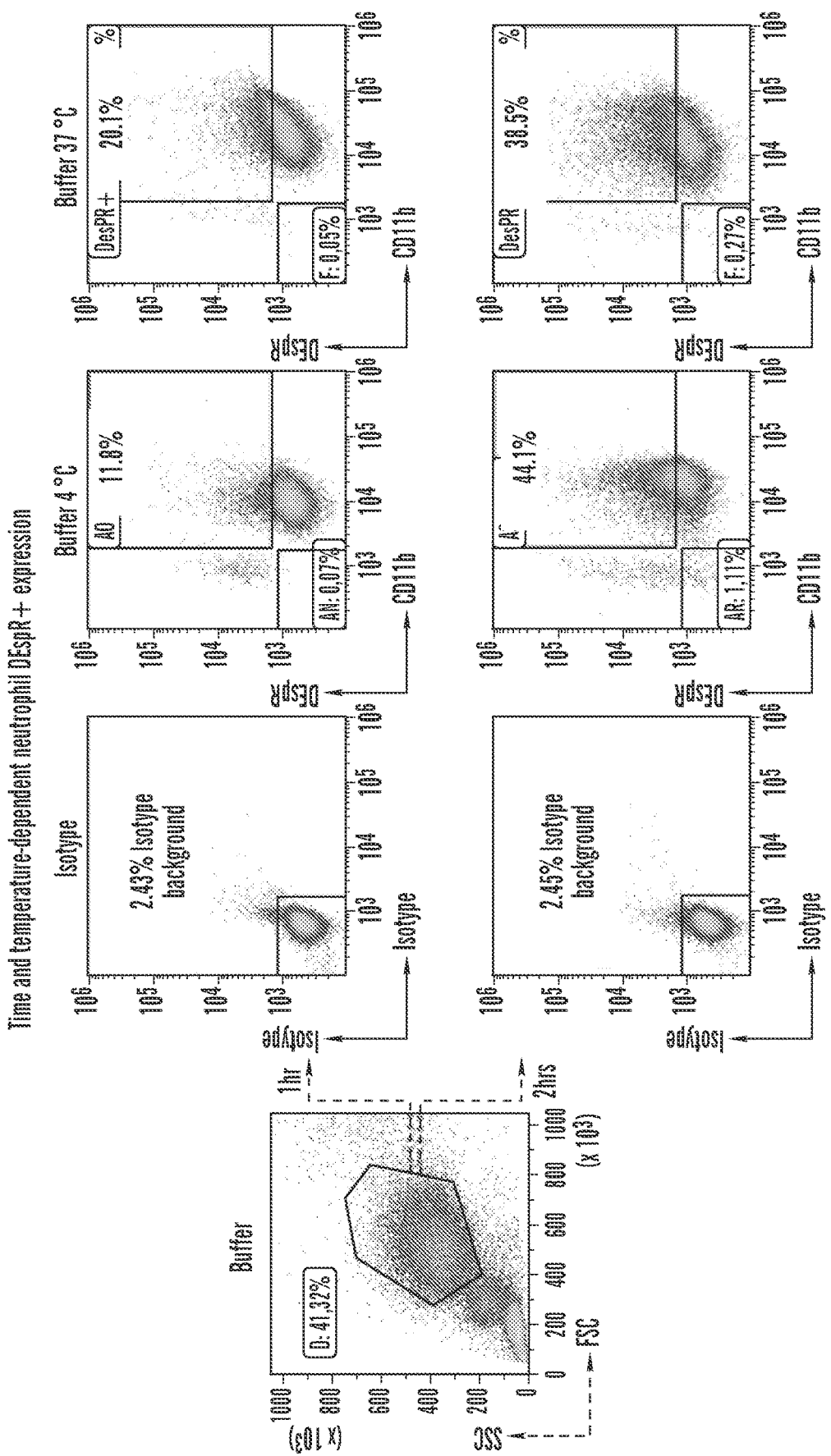

Relevant to ex vivo analysis, these observations indicate that EDTA-anticoagulated blood exhibit less susceptibility to ex vivo experimental changes with increases in time and temperature (FIG. 50E, FIG. 58C). For quantitative ex vivo ARDS patient sample analysis, only EDTA anti-coagulated whole blood processed within 1-hour from sampling therefore was used from hereon, in order to minimize confounders that increase DEspR-expression ex vivo. This avoids overestimating actual circulating levels in patient samples and false positives.

DEspR+ Neutrophils and Monocytes/Macrophages in ARDS Patient Lung Sections

Figure 51D:
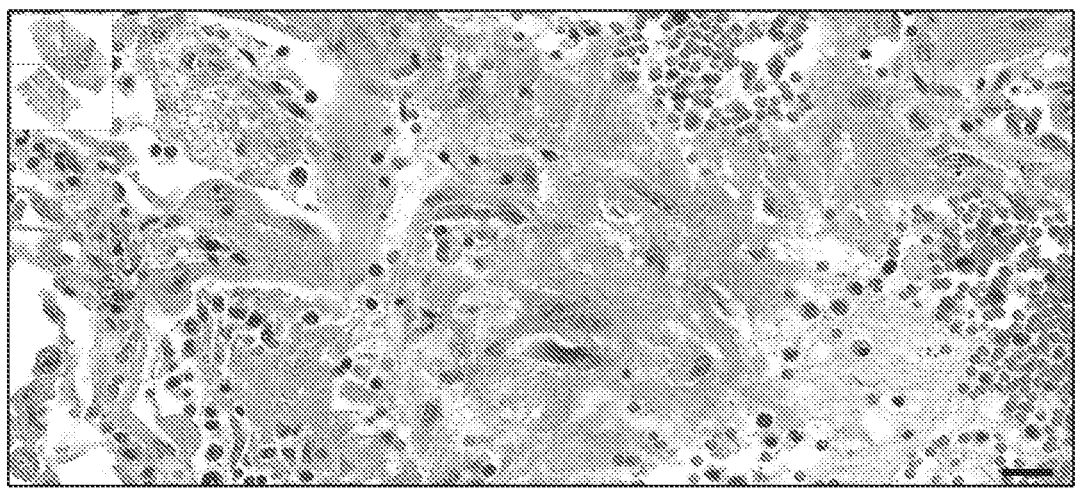
Figure 51E:
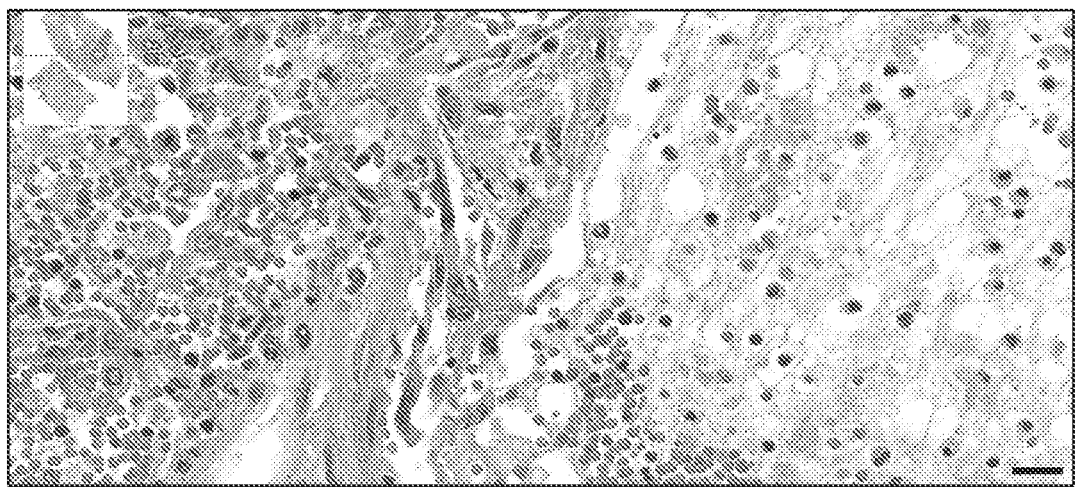
Figure 51F:
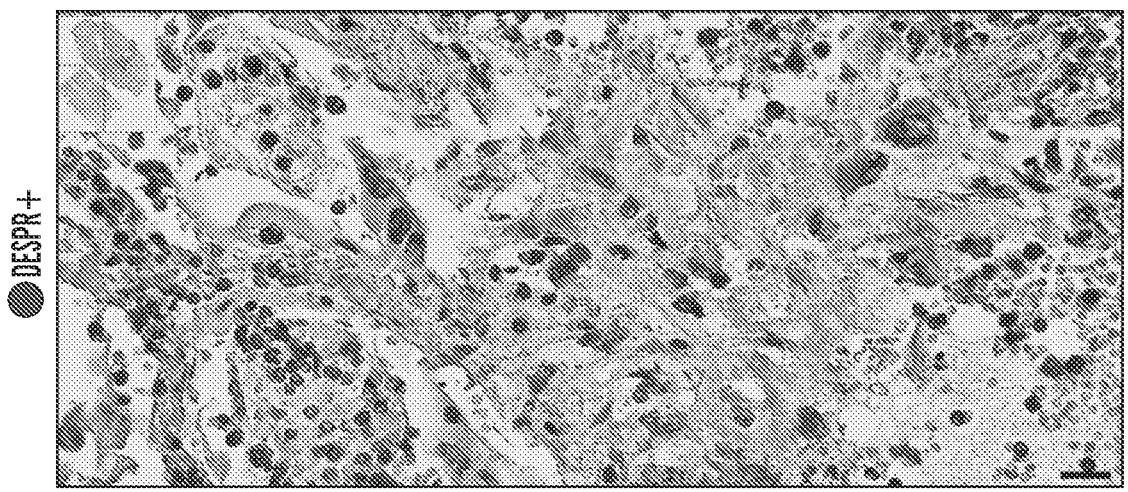
Figure 51G:
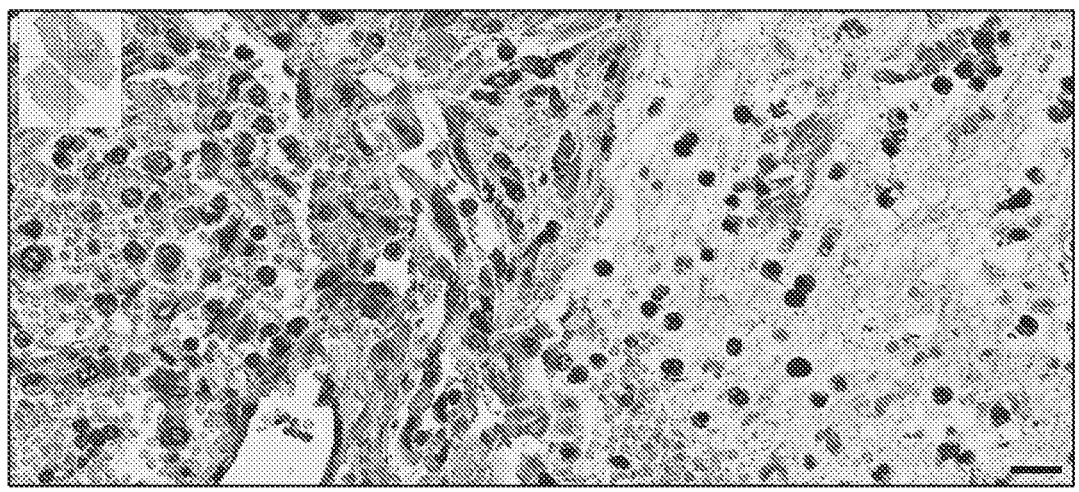
Figure 51H:
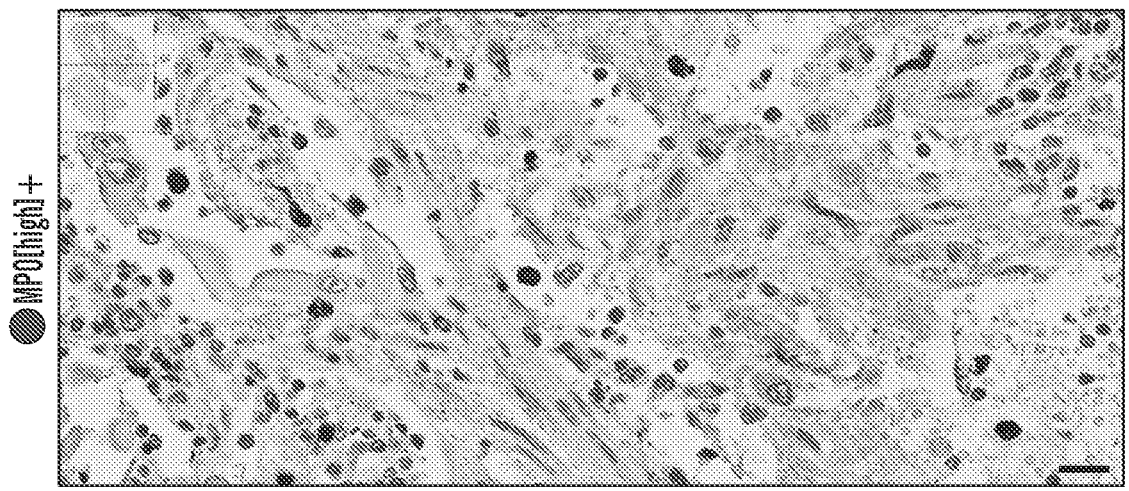
Figure 51I:
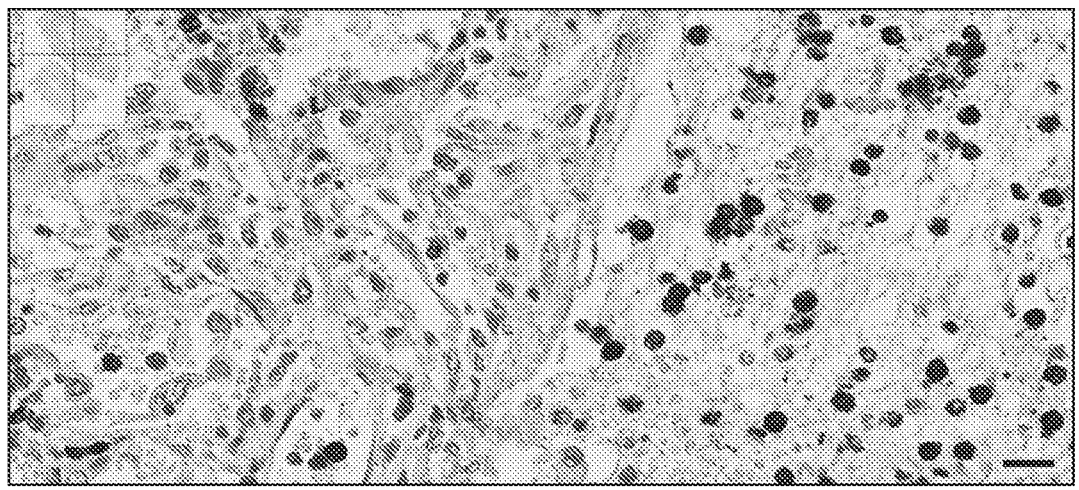
Figure 51J:
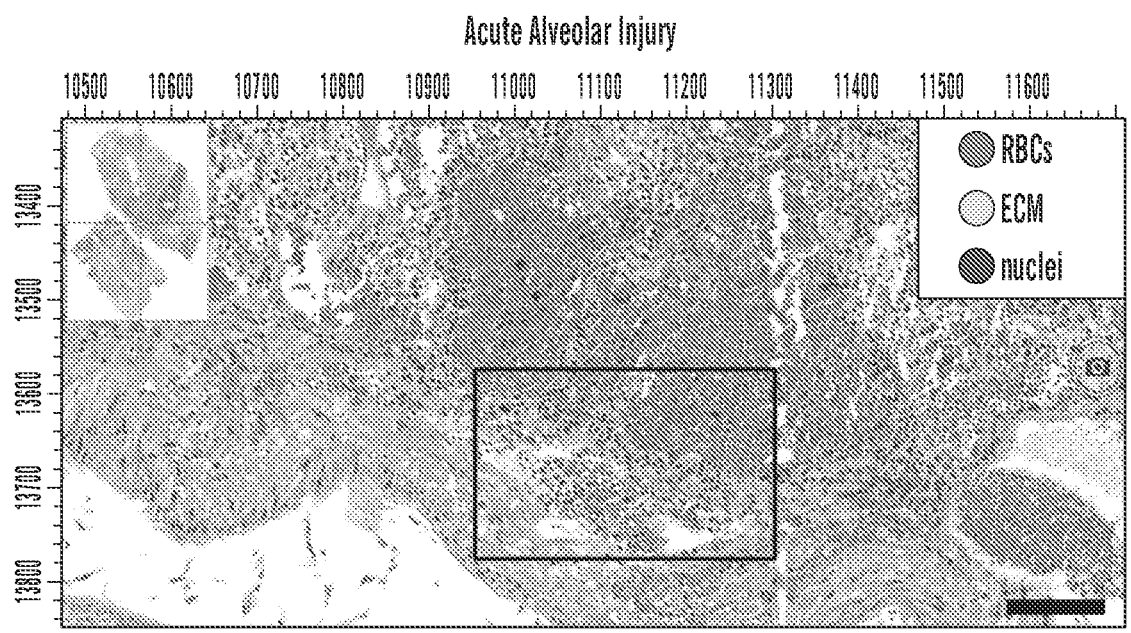
Figure 51K:
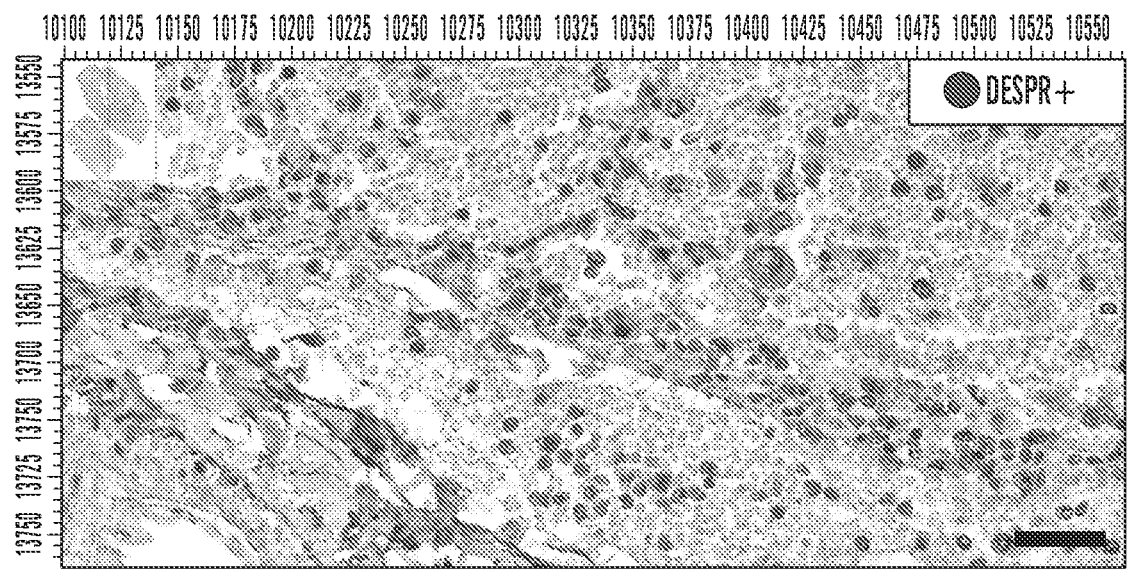

To demonstrate pathological basis to study DEspR+immune cells in ARDS patient whole blood samples, immunohistochemistry analyses of post-mortem serial lung sections from patients with ARDS (n=8) in regions of diffuse alveolar damage (FIG. 51A-51I) as well as, in areas of acute alveolar injury (FIG. 51J-51K) were performed. Using an anti-DEspR mouse-recombinant mAb of hu6g8, hu6g8-m, immunohistochemistry with DAB chromogen (IHC-DAB) was optimized and detected DEspR+ neutrophils in intra-bronchiolar exudate, along with some DEspR(−) neutrophils with characteristic polylobulated nuclei (FIG. 51B). In adjacent serial sections, IHC-DAB immunostaining conditions limited to detection of only high myeloperoxidase (MPO [high])+expression typical in neutrophils with 5× higher expression than monocytes[30,31], detected primarily MPO [high]+ neutrophils in the intrabronchiolar exudate (FIG. 51C). In areas of diffuse alveolar damage (DAD) (FIG. 51D, 51E), IHC-DAB analyses of serial sections detected intra-alveolar, intravascular and intraparenchymal DEspR+ neutrophils and monocytes (FIG. 51F-51G) and MPO[high]+ neutrophils (FIG. 51H-51I). Similarly, in lung areas of acute alveolar injury present in the same ARDS patient lung section slides (FIG. 51J), immunohistochemistry detected DEspR+ neutrophils and monocytes in the intravascular, parenchymal and intra-alveolar spaces (FIG. 51K). These observations validate measuring peripheral DEspR+ CD11b+ neutrophil- and monocyte-subset levels by flow cytometry as a window into projected pulmonary levels in ARDS or COVID19-ARDS.

DEspR Core-Expression Network Increased in COVID19 Neutrophils

To determine pathogenic basis to study DEspR+ neutrophils in COVID19-ARDS, single cell RNA-sequencing was used to analyze (scRNA-seq) a database of healthy control (n=5), mild (n=8) and severe (n=11) COVID19 patient samples. Since DEspR's ADAR1 RNA-edited transcript[16] is not discernable in scRNA-sequencing limited to 300 nucleotides from the poly-A sequence of each transcript to ascertain specificity and equivalent representation, the analysis was focused on DEspR's essential expression-network comprised of DEspR's modulators, ligands, and bioeffect marker represented in the scRNA-seq database of immune cells and epithelial cells in nasopharyngeal and broncho-lavage fluid samples from COVID19 subjects.[12]

Figure 52A:
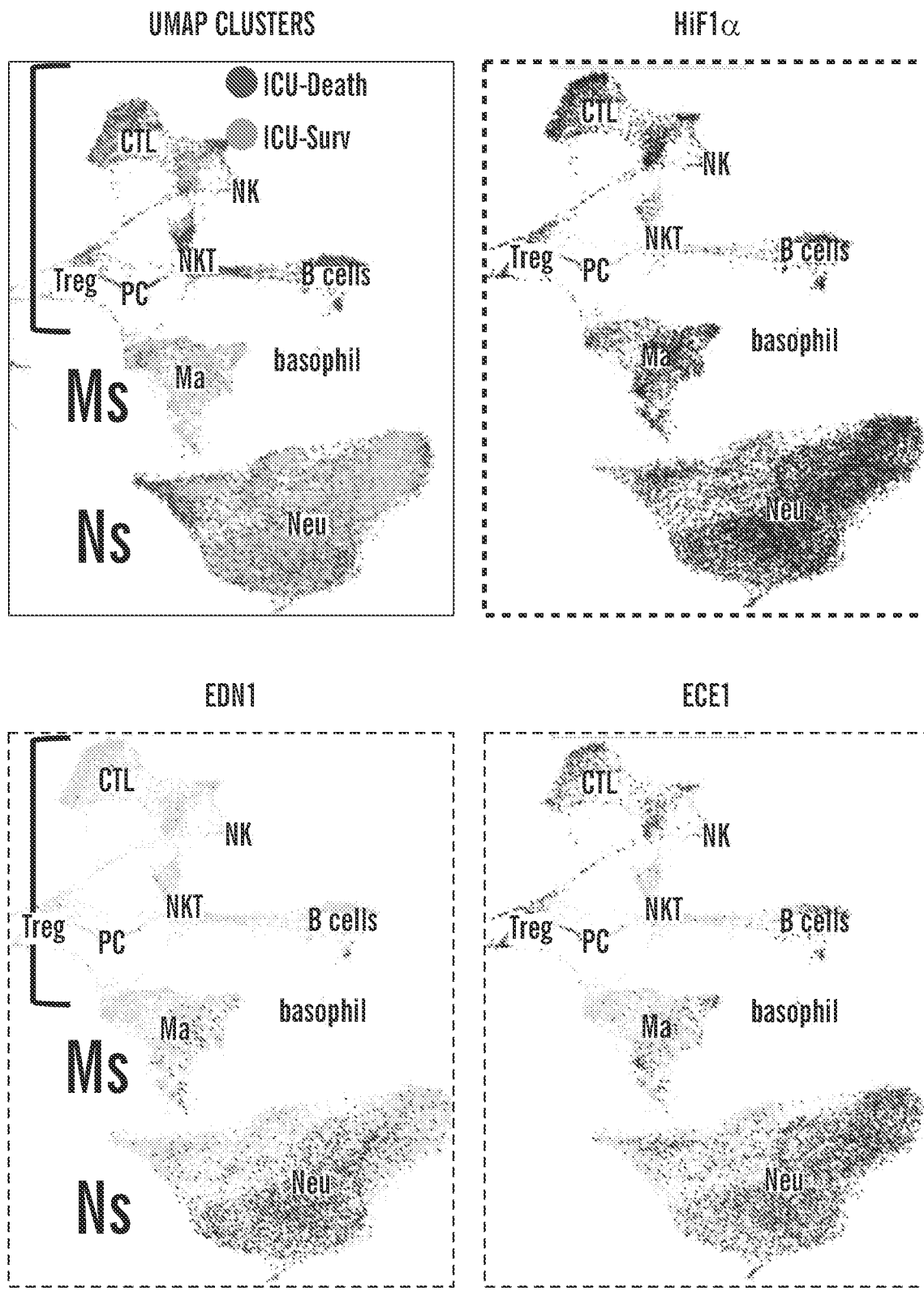
Figures 59A, 59B, 59C:
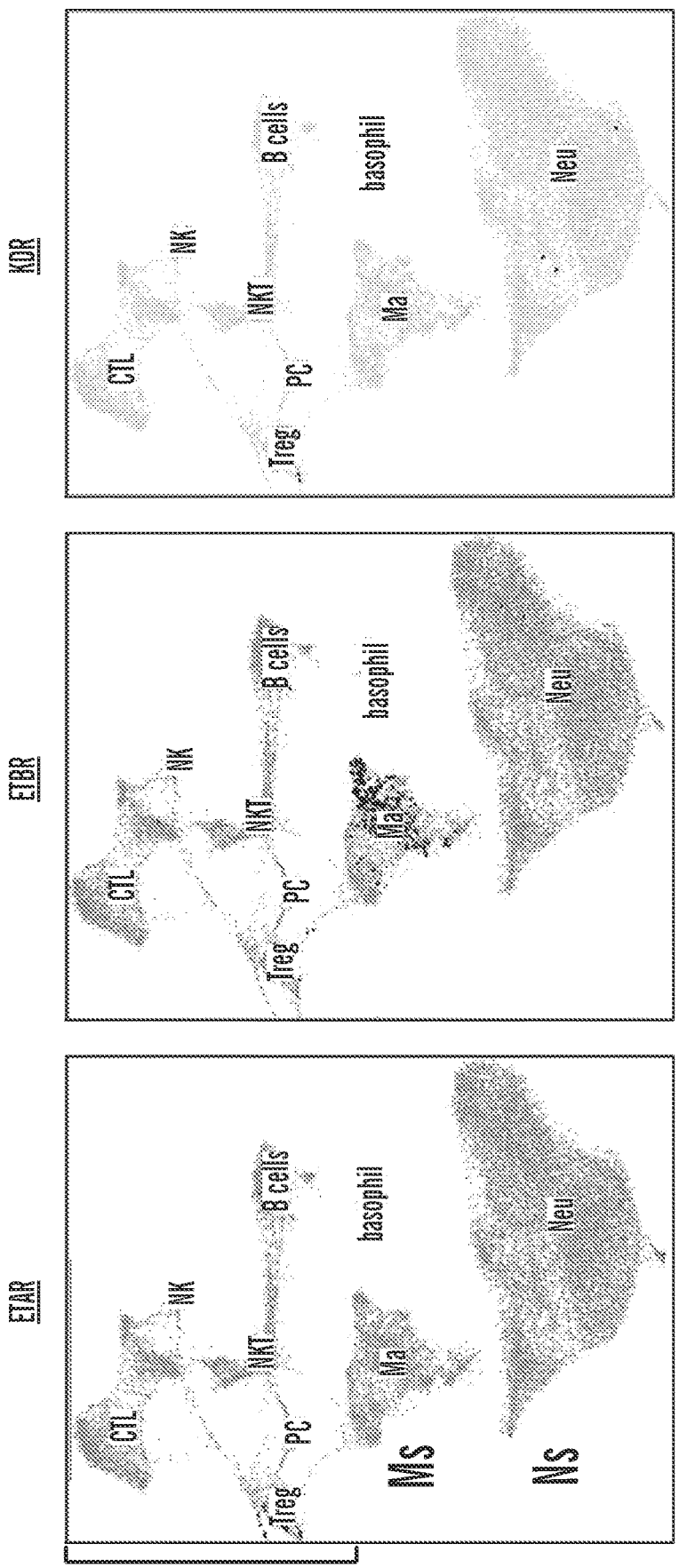
FIGS. 59A-59H depict representative UMAP visualization of RNA-seq profiles of white blood cell clusters with >2-fold increase (black dots) vs no expression (grey) obtained from broncholavage fluid and nasopharyngeal samples from two critically ill COVID19-ARDS patients.

Comparative scRNA-seq analysis showed that positive modulators of DEspR-transcription (TLR4 and Hif1-α), DEspR RNA-editing for translation (ADAR-1 RNA-editase), DEspR cell-surface mobilization (TLR4), TLR4-endogenous activators (alarmins S100A8/S100A9) and bioeffect prosurvival marker (Mcl1) are predominantly expressed in neutrophils, along with DEspR's two ligands, endothelin-1 (ET1 or EDN1), and the signal peptide in VEGFA-propeptide (spVEGF) (FIGS. 52A-52C). Interestingly, neutrophil expression of the endothelin converting enzyme (ECE1), required for release of ET1 from its propeptide (FIG. 52A-52C) indicated neutrophil self-sufficiency to produce mature ET1, and hence, a putative ET1/DEspR autocrine loop. In contrast, transcripts for other ET1 receptors: ETA-receptor (ETAR) and ETB-receptor (ETBR), VEGF-A receptors: (KDR, Flt-1), and other alarmins receptor: (AGER) were minimally, if not, detected in neutrophil scRNA-sequences (FIGS. 59A-59C).

Figure 52D:
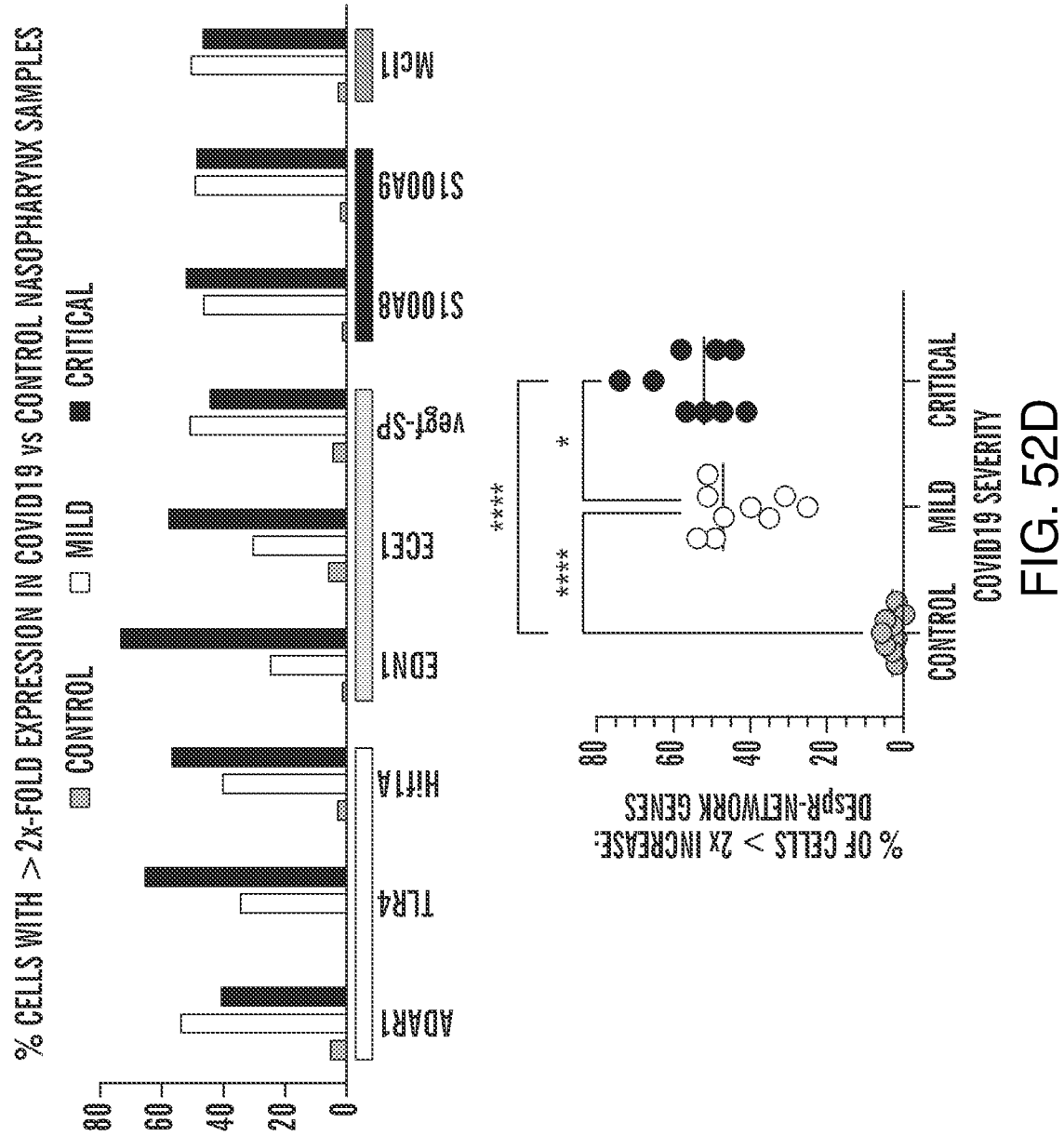
Figure 52E:
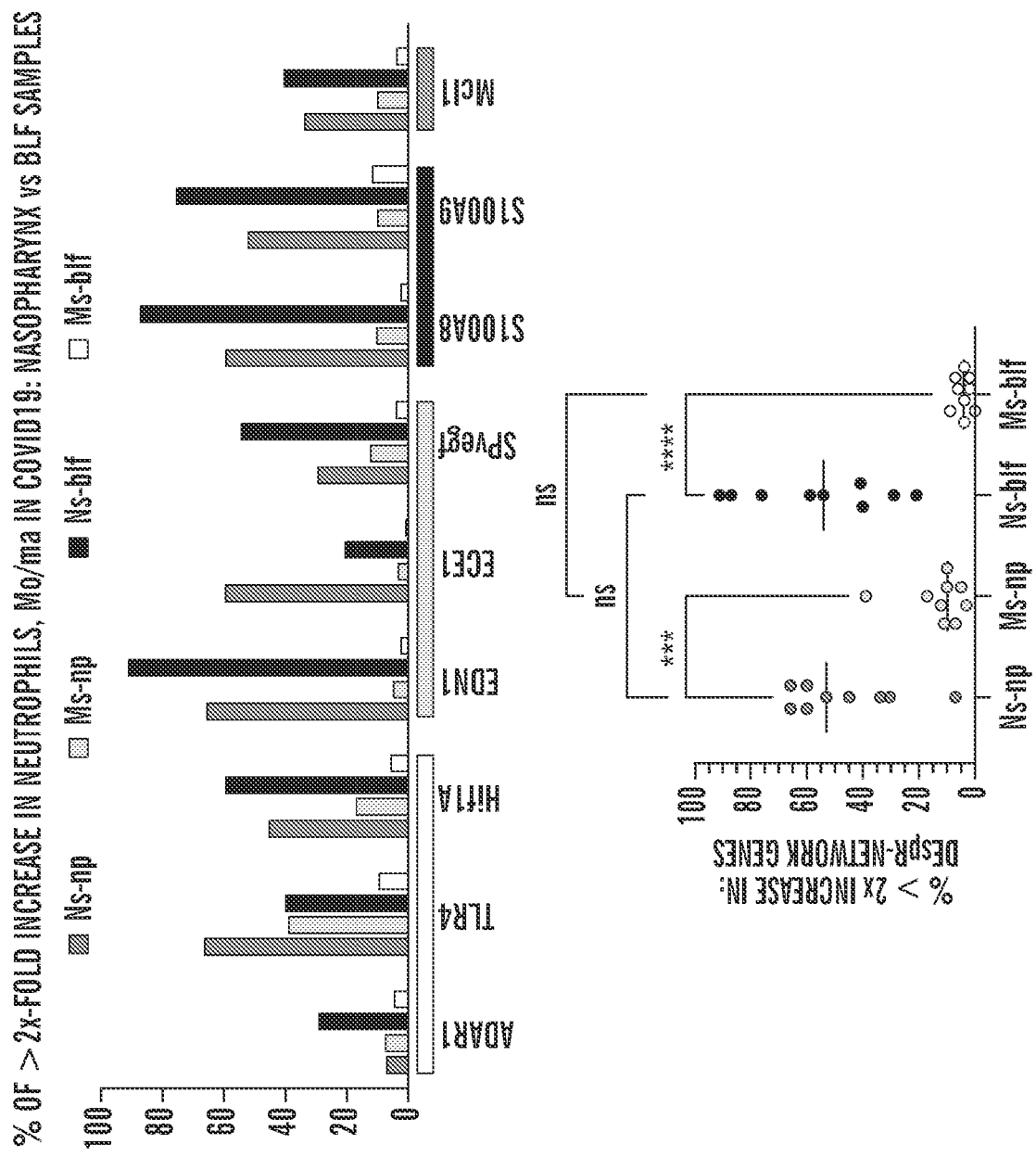
Figures 59D, 59E, 59F:
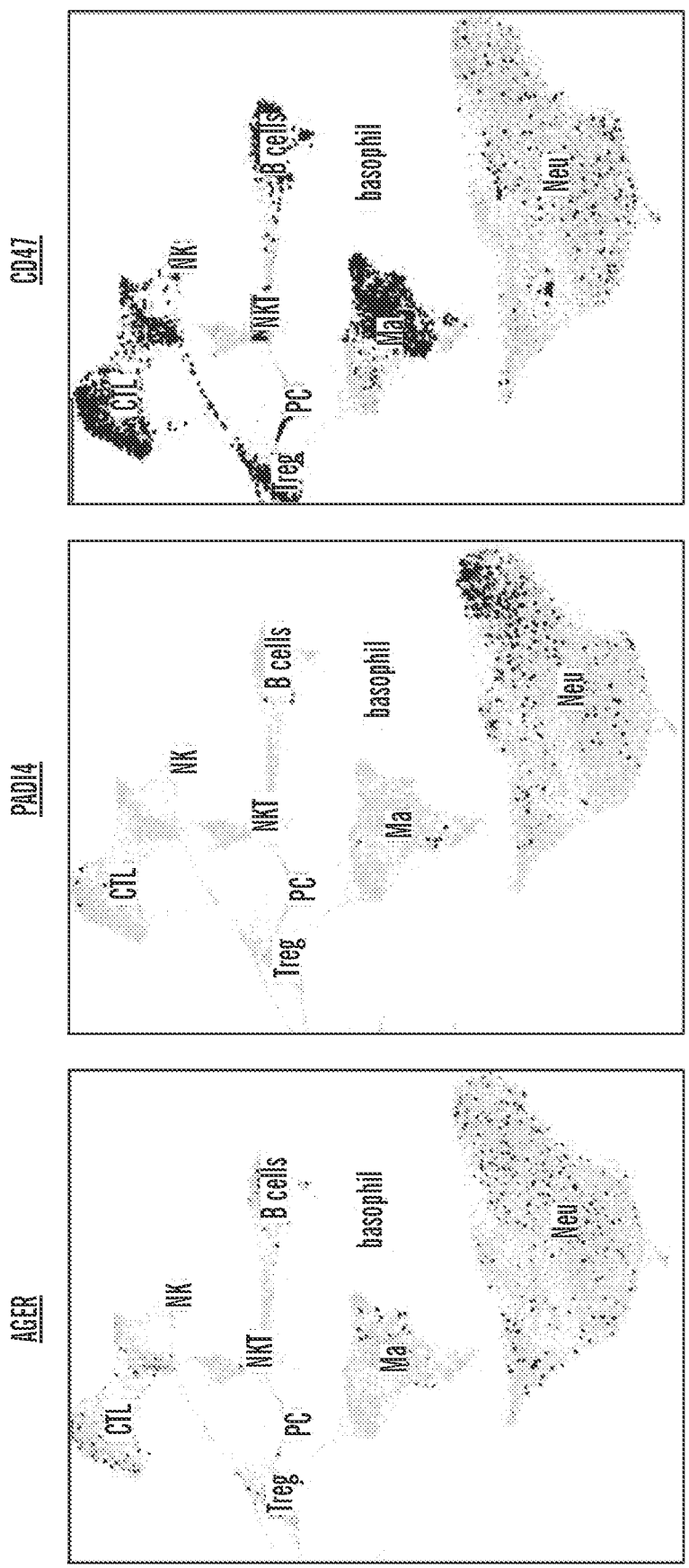
Figure 59G:
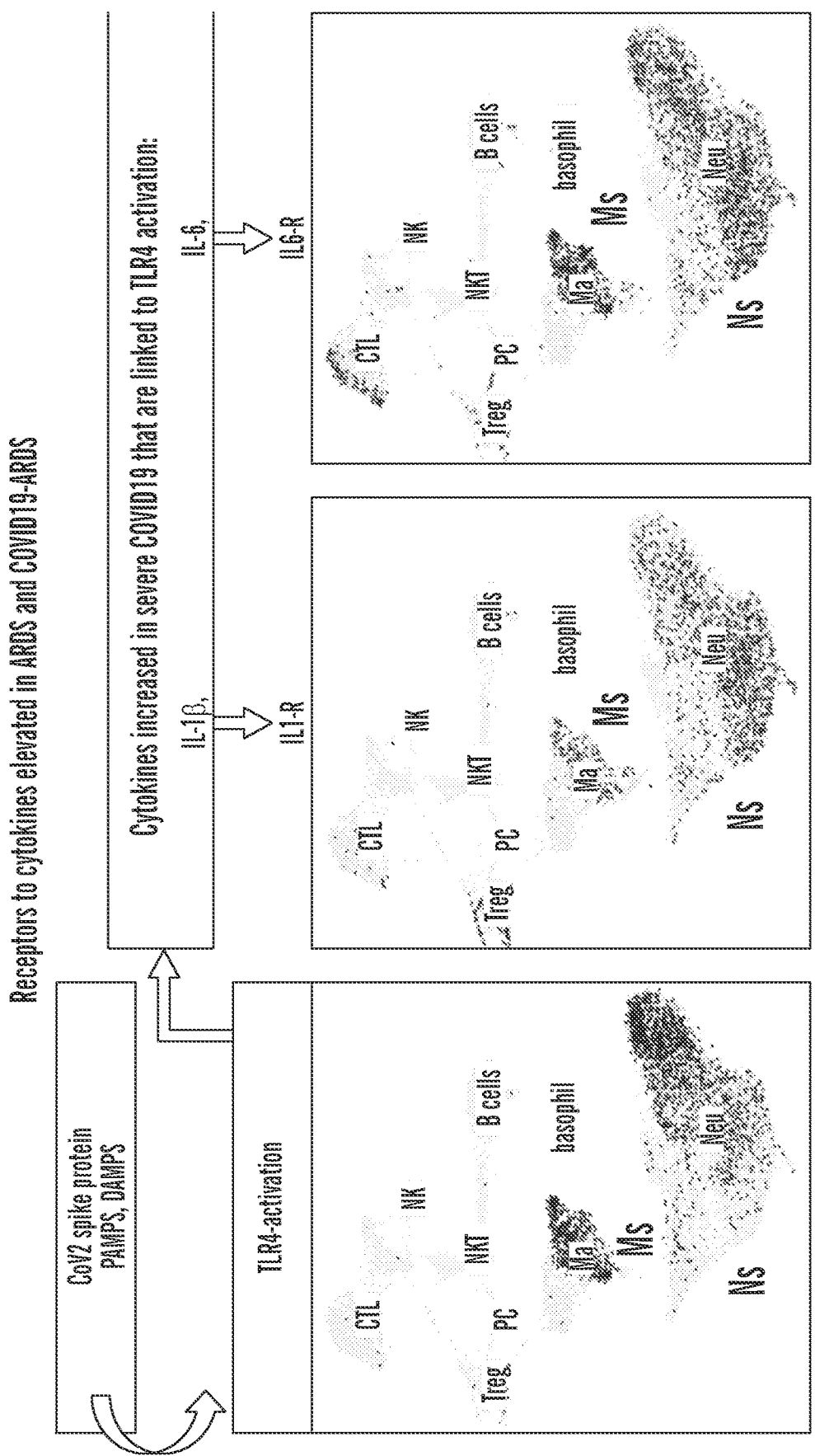
Figure 59H:
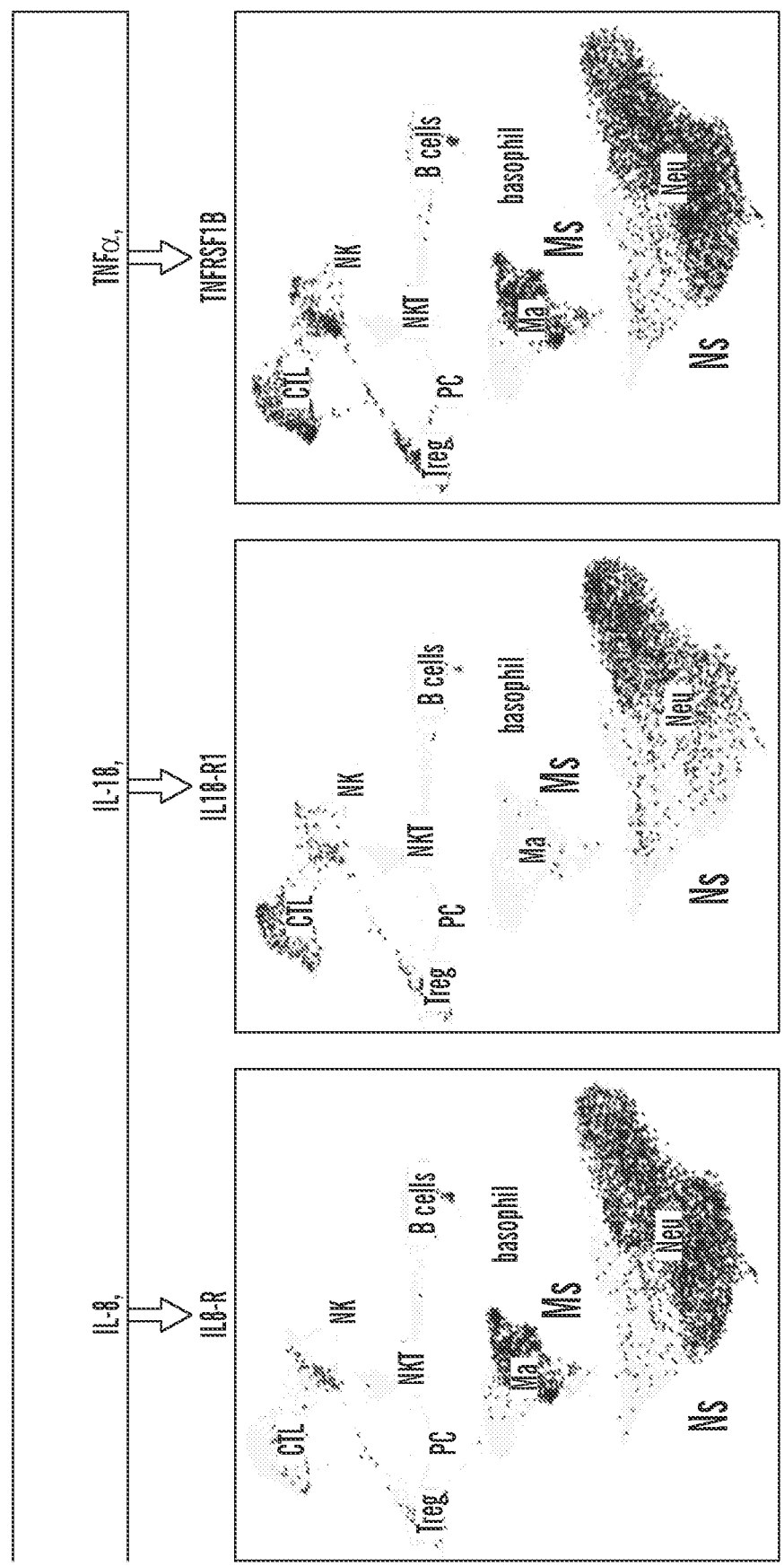

Notably, expression levels of all 9 genes representing DEspR's expression and functional network are significantly increased in COVID19 compared to healthy controls (FIG. 52D), and in neutrophils compared to monocytes-macrophages in nasopharyngeal and broncho-lavage COVID19 samples (FIG. 52E). The basis to study neutrophils is further supported by scRNA-seq documentation of increased expression of receptors to cytokines increased in ARDS32 and/or in COVID19-ARDS33, such as: IL-6, IL-8, IL-1β, IL-18, and TNF-α34 (FIG. 59G). These observations support the role of neutrophils as effectors of the "cytokine storm" leading to destructive inflammation manifesting as ARDS and/or multi-organ failure, be it COVID193 or bacterial pneumonia.[32]

Increased DEspR+CD11b+ Neutrophil-Subset in ARDS and COVID19-ARDS

To study the potential clinical relevance of the DEspR+ neutrophil-subset, a prospective pilot observational study was performed of consented patients diagnosed with ARDS based on the Berlin Definition, regardless of acute disease etiologies (sepsis, pneumonia, cardiac arrest, surgery) and comorbidities. First, DEspR-specific immunotyping was ascertained of whole blood samples from ARDS patients by validating the gating strategy for flow cytometry (FIGS. 60A-60E), DEspR-specific detection in duplicates (FIGS. 60F-60I) and reproducibility in triplicates (FIG. 53A-53F, 60J-60L). With this ascertainment, 19 ARDS patients were prospectively studied first, then 11 COVID19-ARDS patients in the ICU at Boston Medical Center.

Figures 60F, 60G:
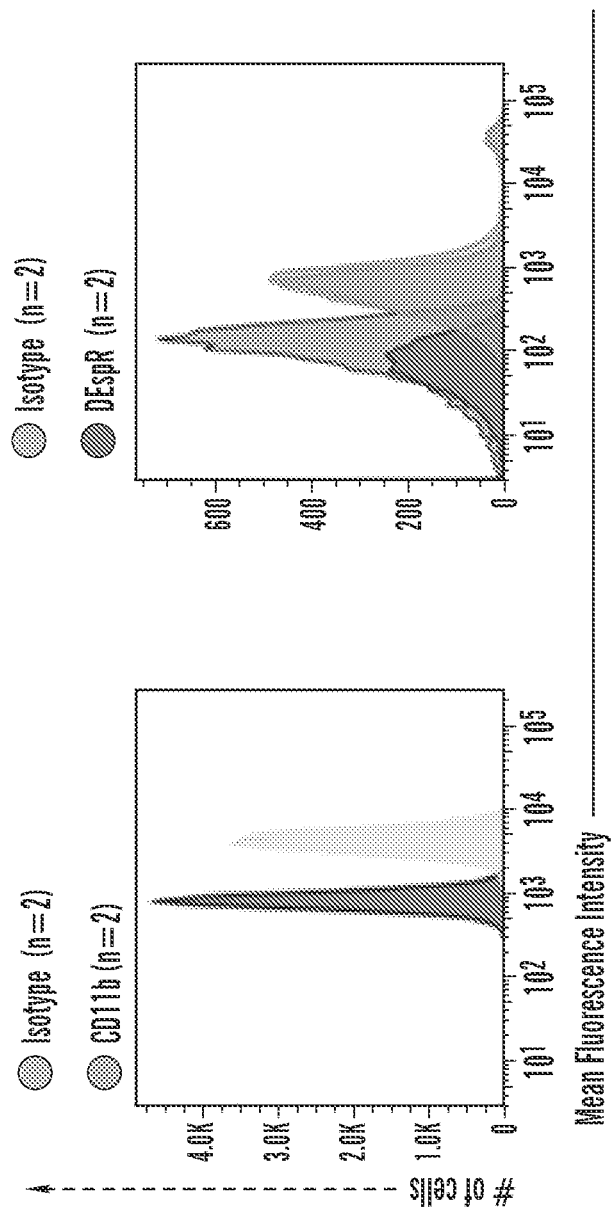
(FIG. 60F) CD11b and isotype.
(FIG. 60G) DEspR and isotype.
Figures 60H, 60I:
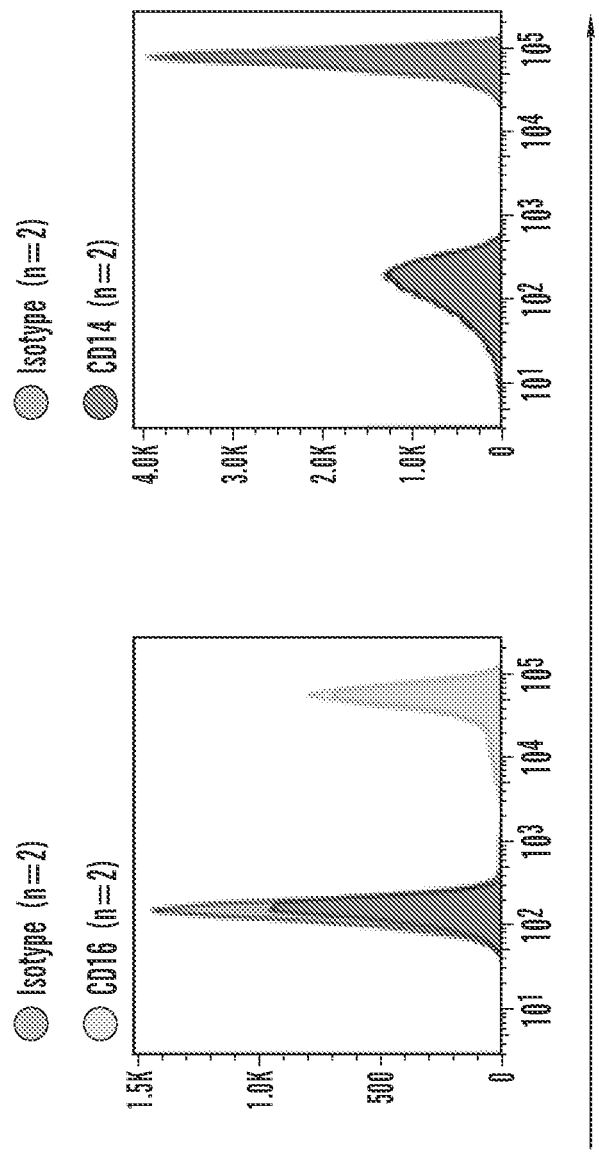
(FIG. 60H) CD16 and isotype.
(FIG. 60I) CD14 and isotype; all run in duplicates.
Figure 60J:
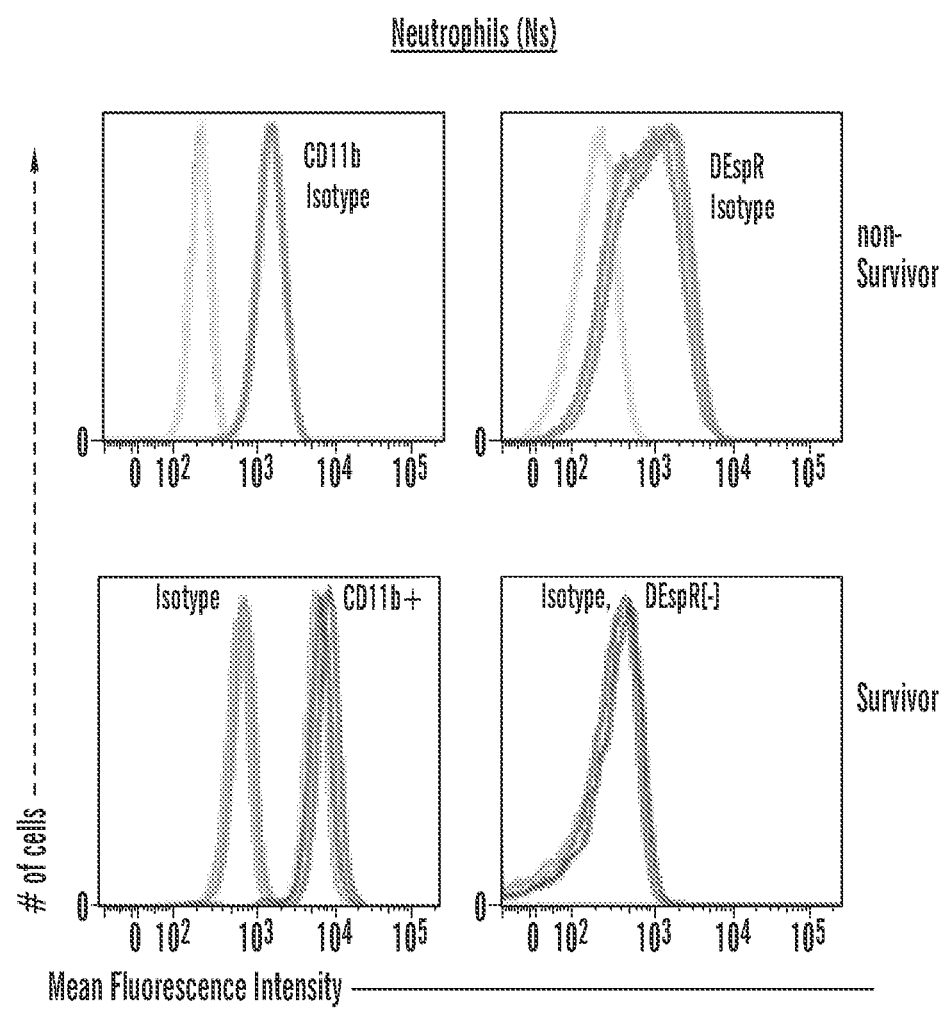
(FIGS. 60J-60L) Histograms of mean fluorescence intensity in triplicate of CD11b+ and DEspR+ neutrophils, monocytes, and lymphocytes gated by FSC and SSC as shown in FIG. 60A. Representative flow cytometry results from ARDS non-survivor and ARDS-survivor. These MFI histograms correspond to triplicate dot plots of CD11b+DEspR+ immunotyping for neutrophils, monocytes and lymphocytes.
Figure 60K:
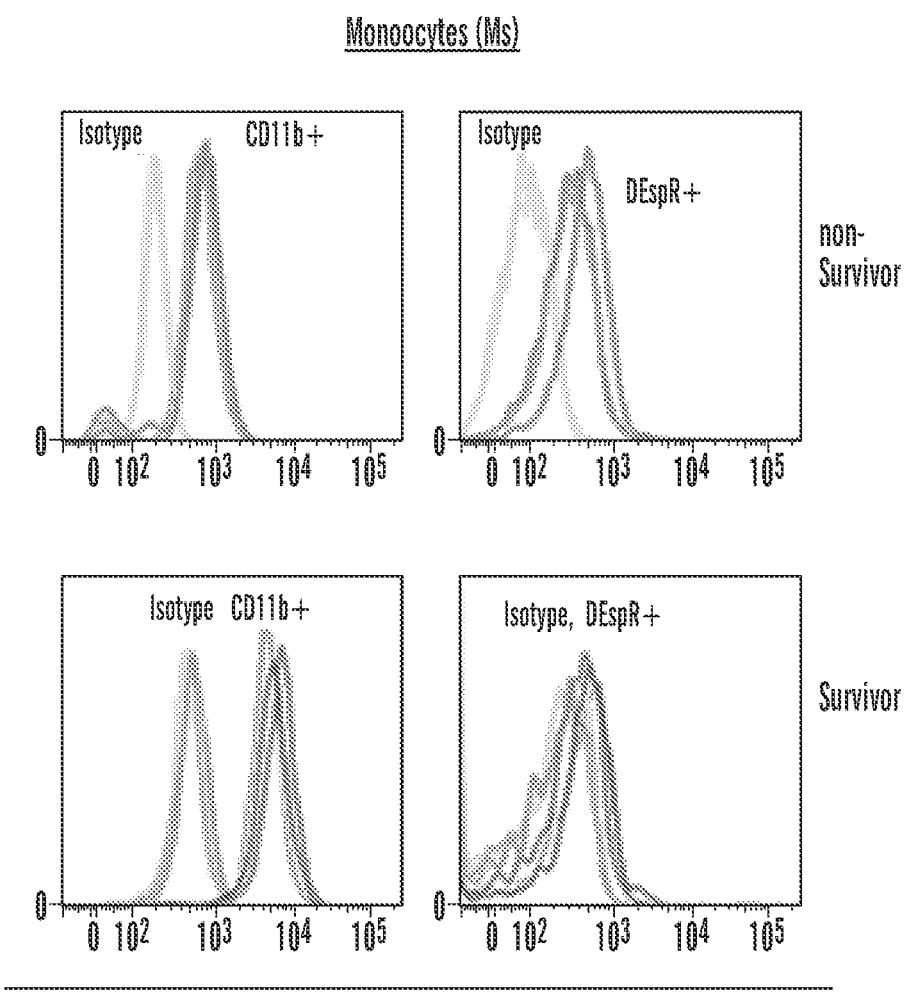
Figure 60L:
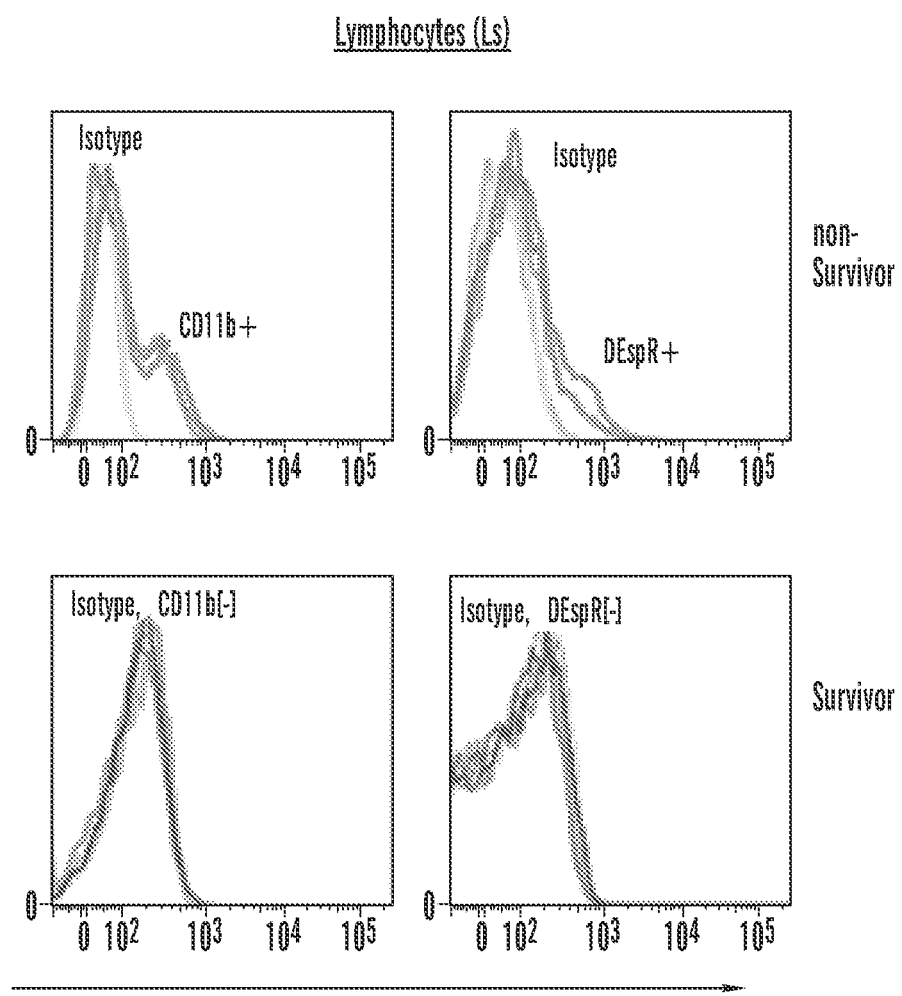

Flow cytometry (FCM) analysis comparing extremes in the clinical spectrum across subjects in the pilot study, a non-survivor with ARDS-multi-organ failure (MOF) compared with ARDS survivor discharged from the ICU in 4 days showed increased cell surface expression of DEspR on CD11b+activated neutrophils (FIGS. 53A-53B) and monocytes (FIGS. 53C-53D), and on CD11b[−]lymphocytes (FIGS. 53E-53F) in the ARDS-nonSurvivor in contrast to minimal DEspR+expression in CD11b+ neutrophils, monocytes, and lymphocytes in the ARDS-survivor (FIG. 53A-53F). Fluorescence intensity histograms corroborate DEspR-specific immunotyping and differential expression in triplicates (FIG. 60J-60L). With experimental ascertainment of DEspR-specific immunotyping, from hereon, studies were done with duplicates.

Figure 53A:
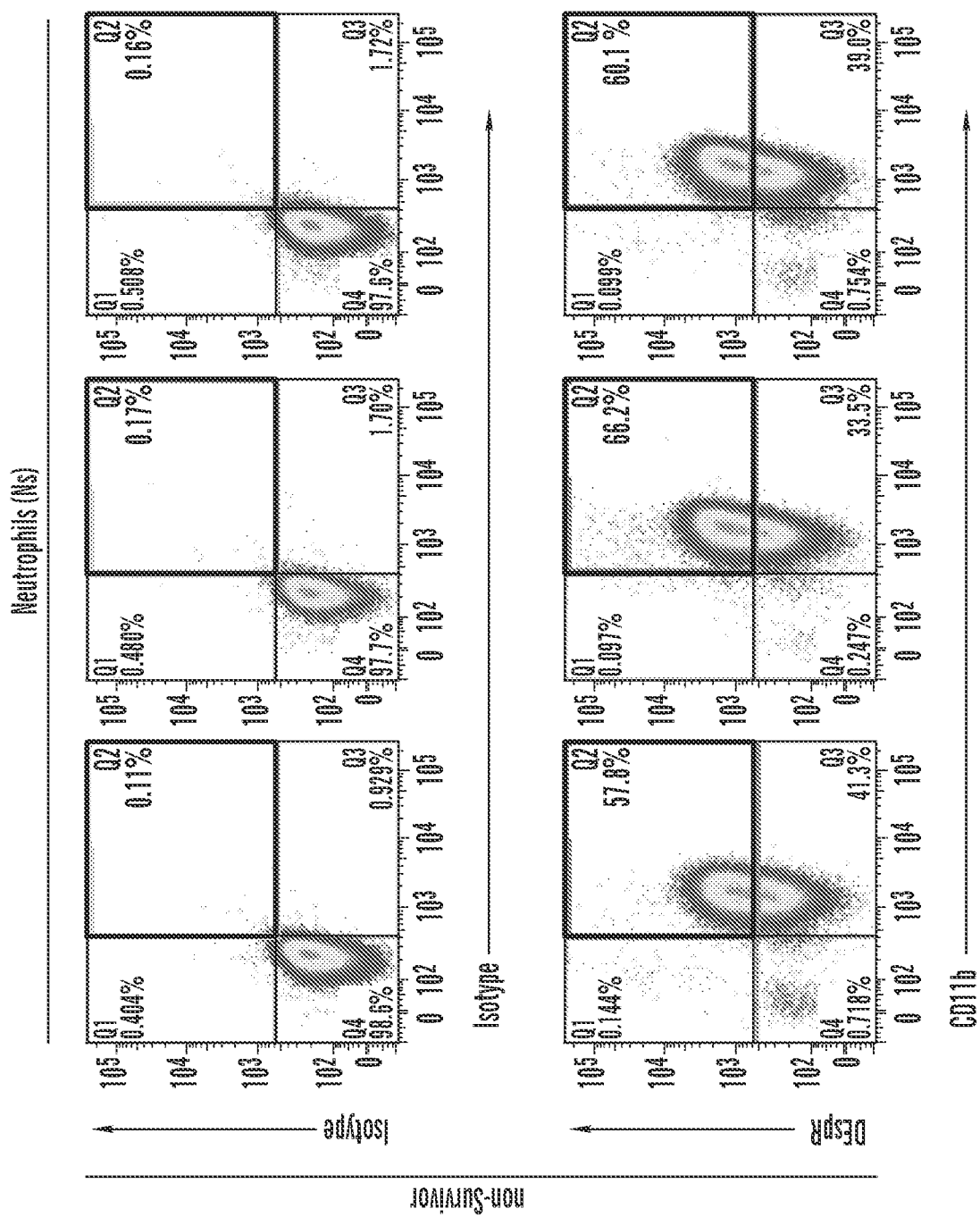
Figure 53B:
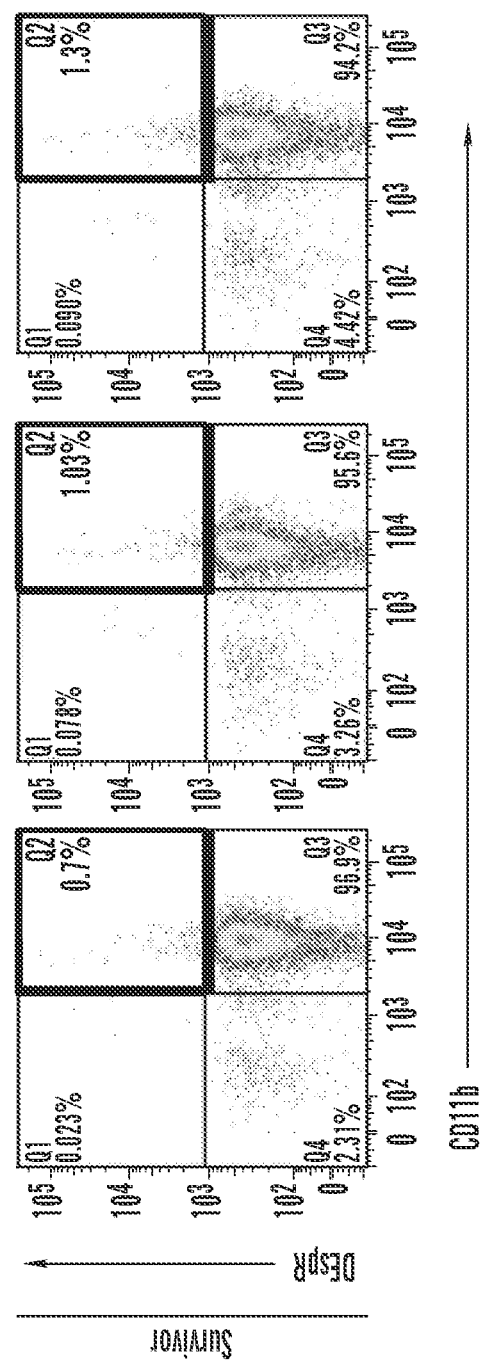
Figure 53C:
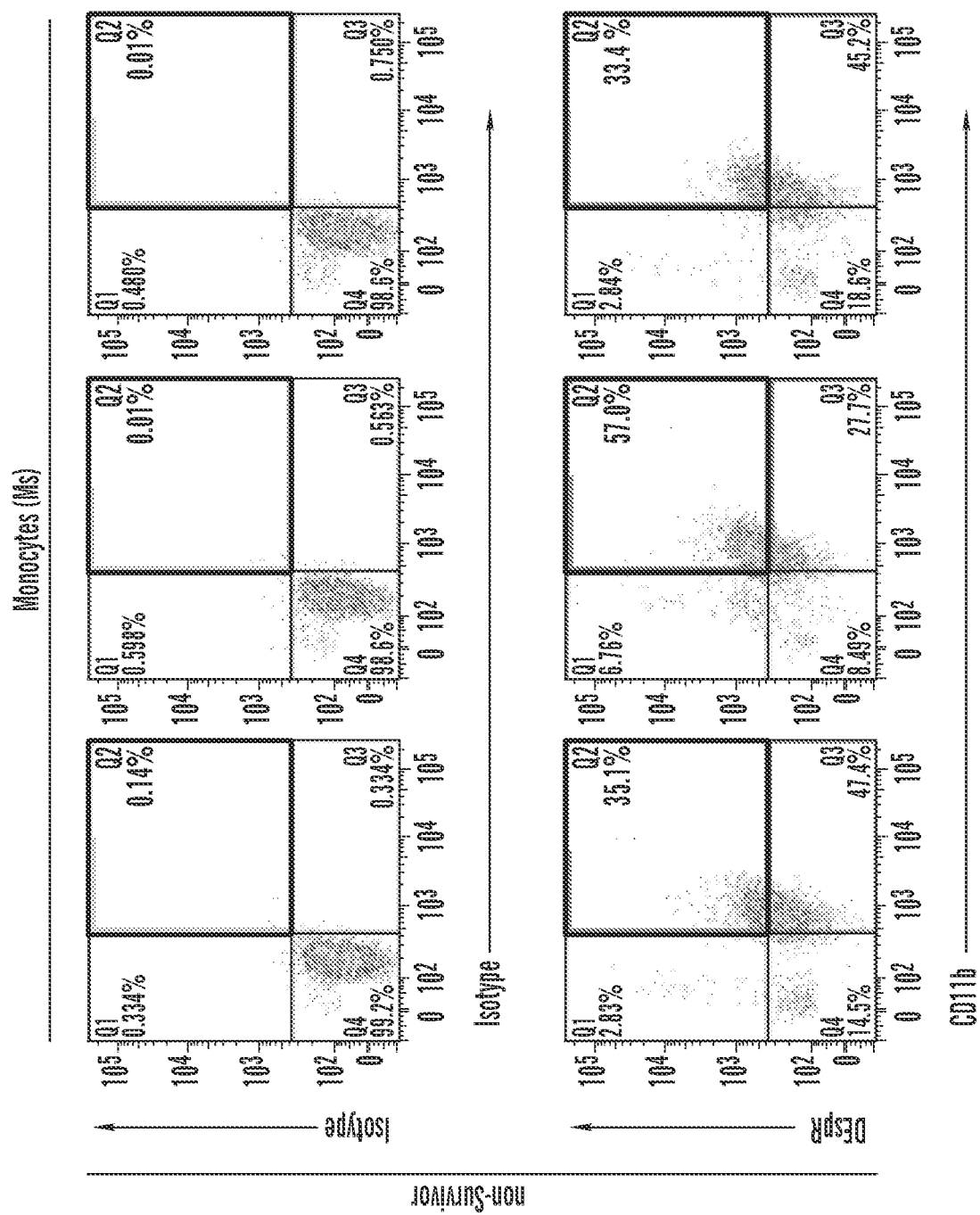
Figure 53D:
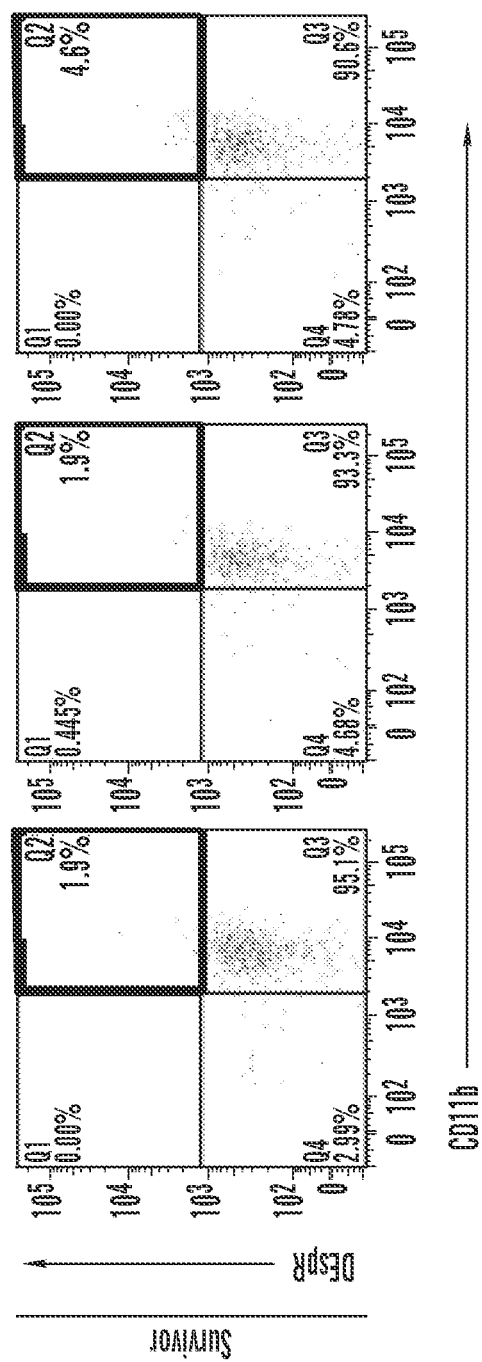
Figure 53E:
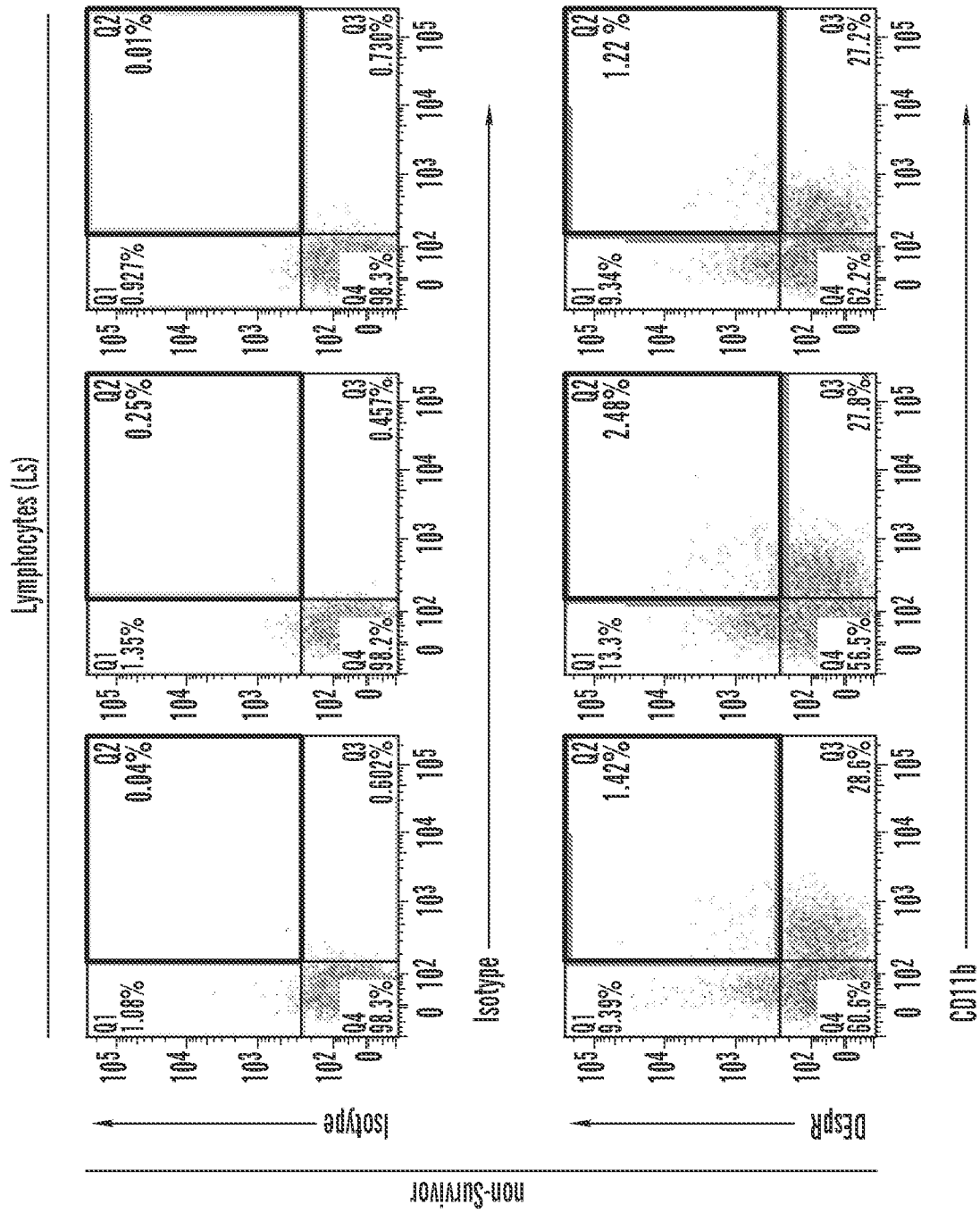
Figure 53F:
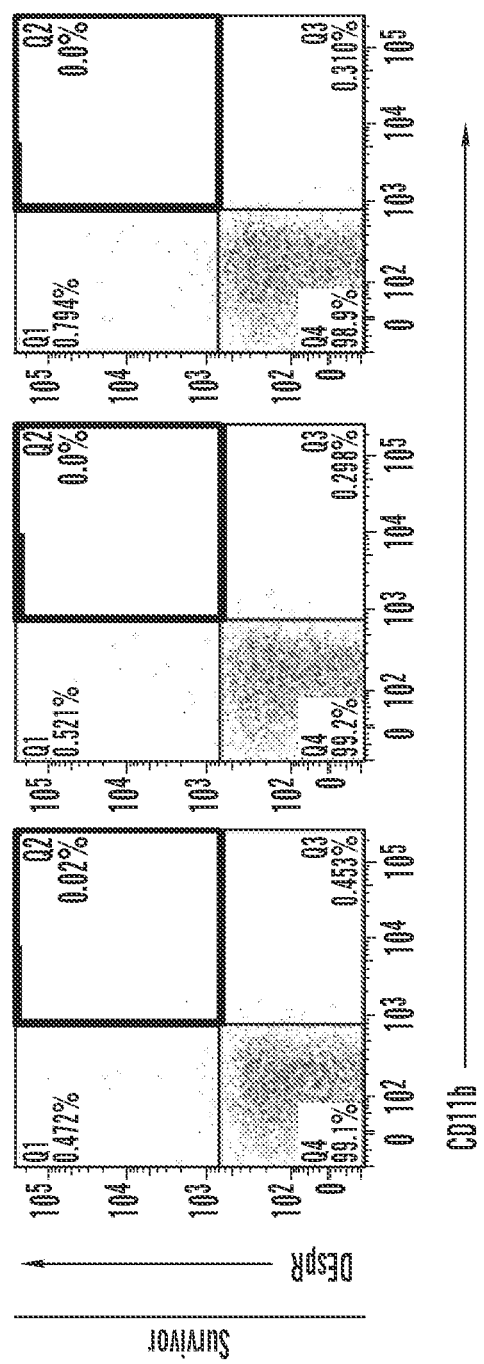
Figure 53G:
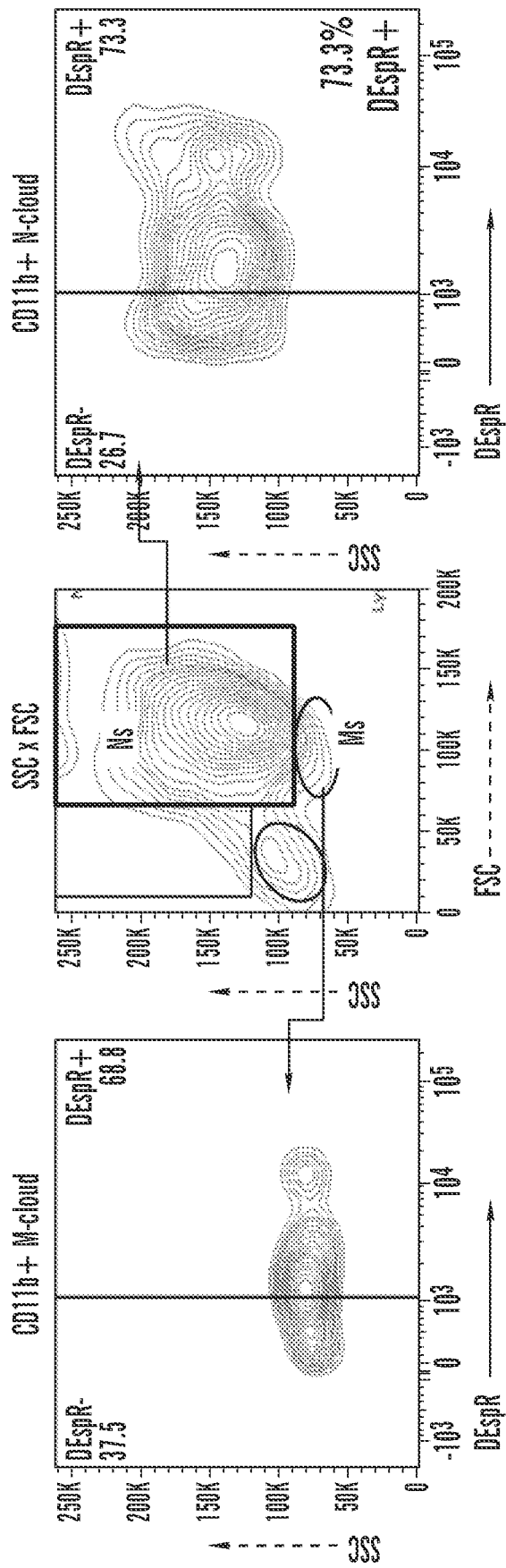
Figure 53H:
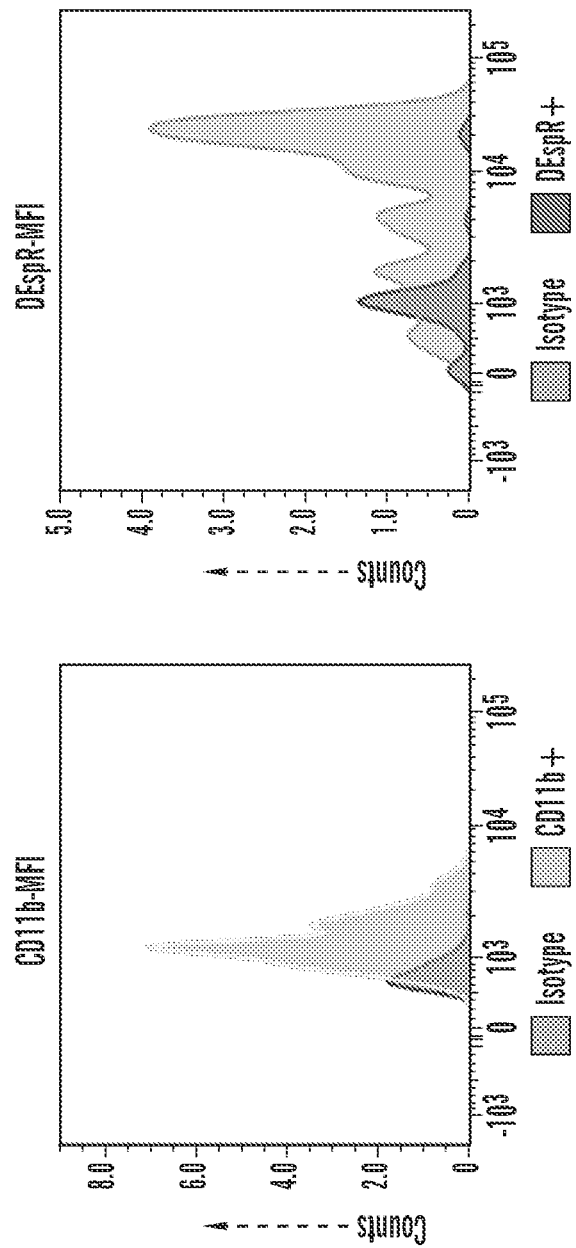
Figure 53I:
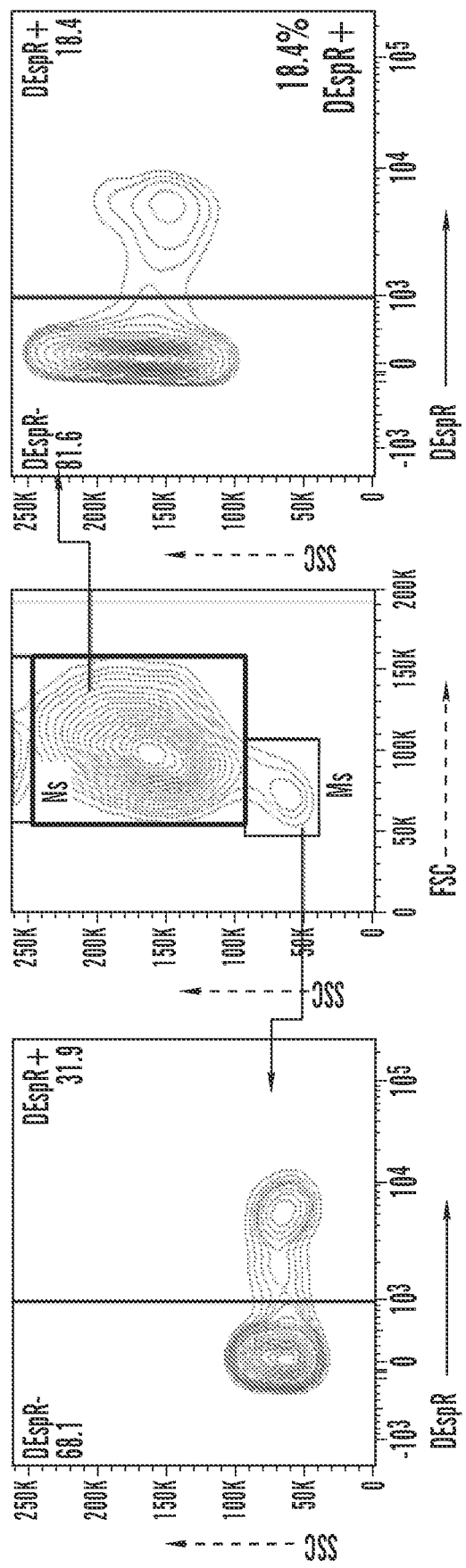

Similarly, differential DEspR+expression was also observed in COVID19-ARDS patients in the ICU requiring mechanical ventilatory support. For safety reasons, disinfected (4% paraformaldehyde or PFA) whole blood samples from COVID19-ARDS patients were studied, and FCM analysis performed within 1 hour from blood draw. FCM analysis representing extremes of the clinical severity spectrum also revealed increased total #DEspR+N-counts and monocytes (M)-counts in a patient with severe COVID19-ARDS requiring 61 days intensive care unit (ICU)-care (FIG. 53G-53H), compared with a patient with milder COVID19-ARDS discharged after 6 days in the ICU (FIG. 53I-53J).

Figure 53K:
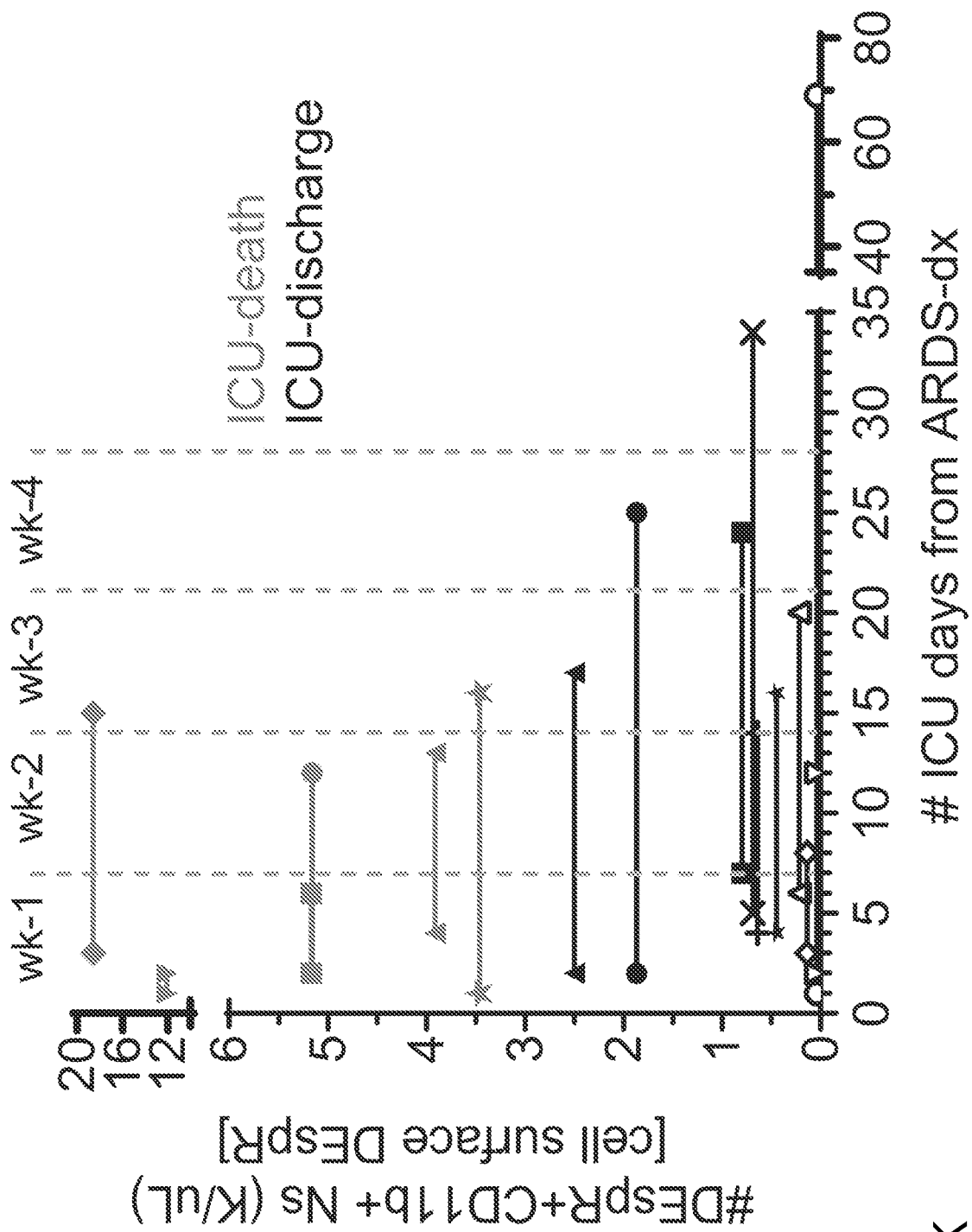
Figure 53L:
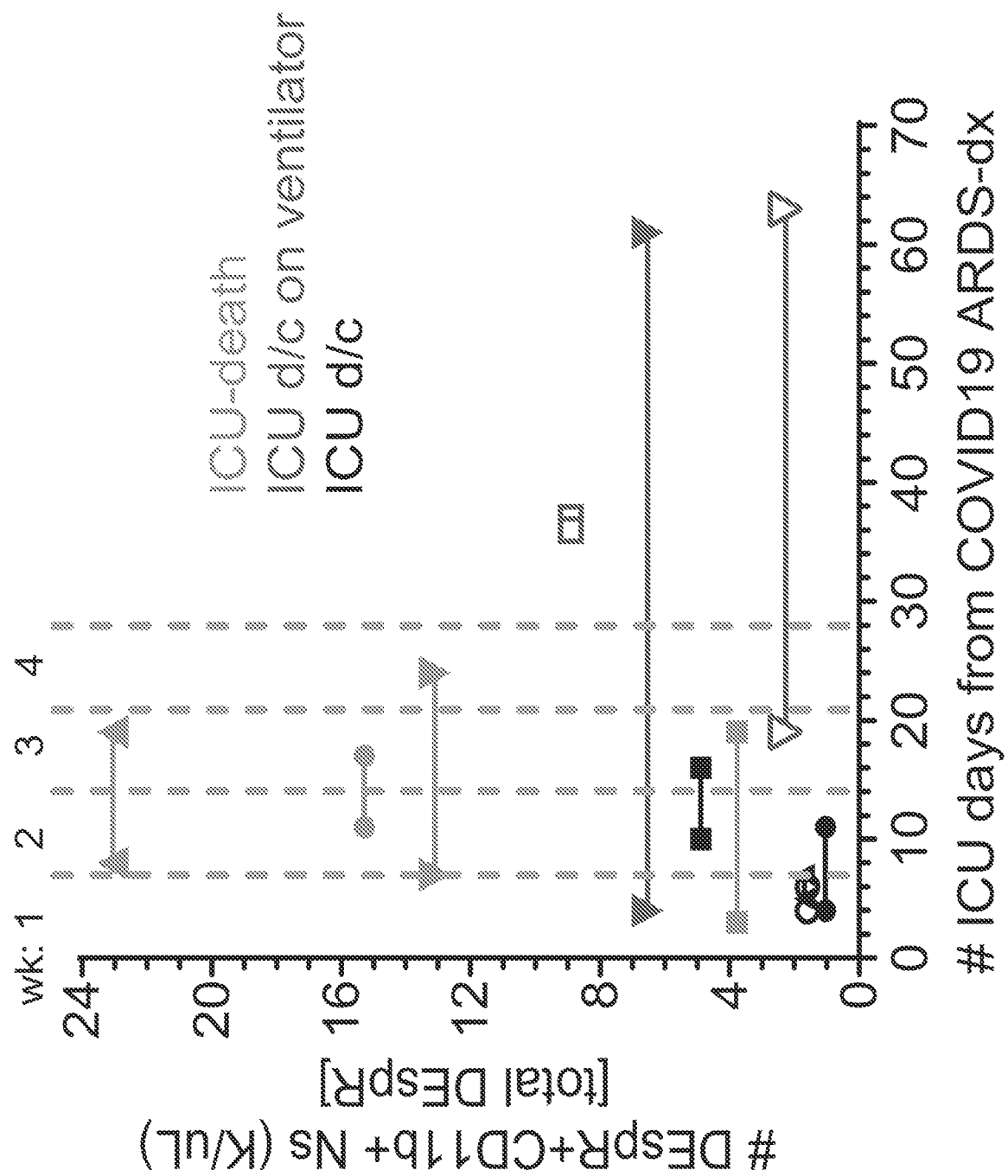

Observing marked differential levels at the polar ends of the clinical spectrum of severity, mortality outcomes were next stratified in ARDS (FIG. 53K) and COVID19-ARDS (FIG. 53L) patients by respective levels of DEspR+CD11b+ neutrophil-counts (thousand K/μL whole blood). Per level of DEspR+N-counts, the length of stay in the ICU until discharge or death was graphed, and a parallel trend of increased DEspR+N-counts with mortality was observed in the graphs. Aside from corroborating the identification of the DEspR+CD11b+ neutrophil subset, these observations provide scientific basis for quantitative analysis of emerging differential modulation between survivors and non-survivors in ARDS and COVID19-ARDS.

Association of DEspR+CD11b+ Neutrophils with ARDS Severity and Mortality

Figure 54A:
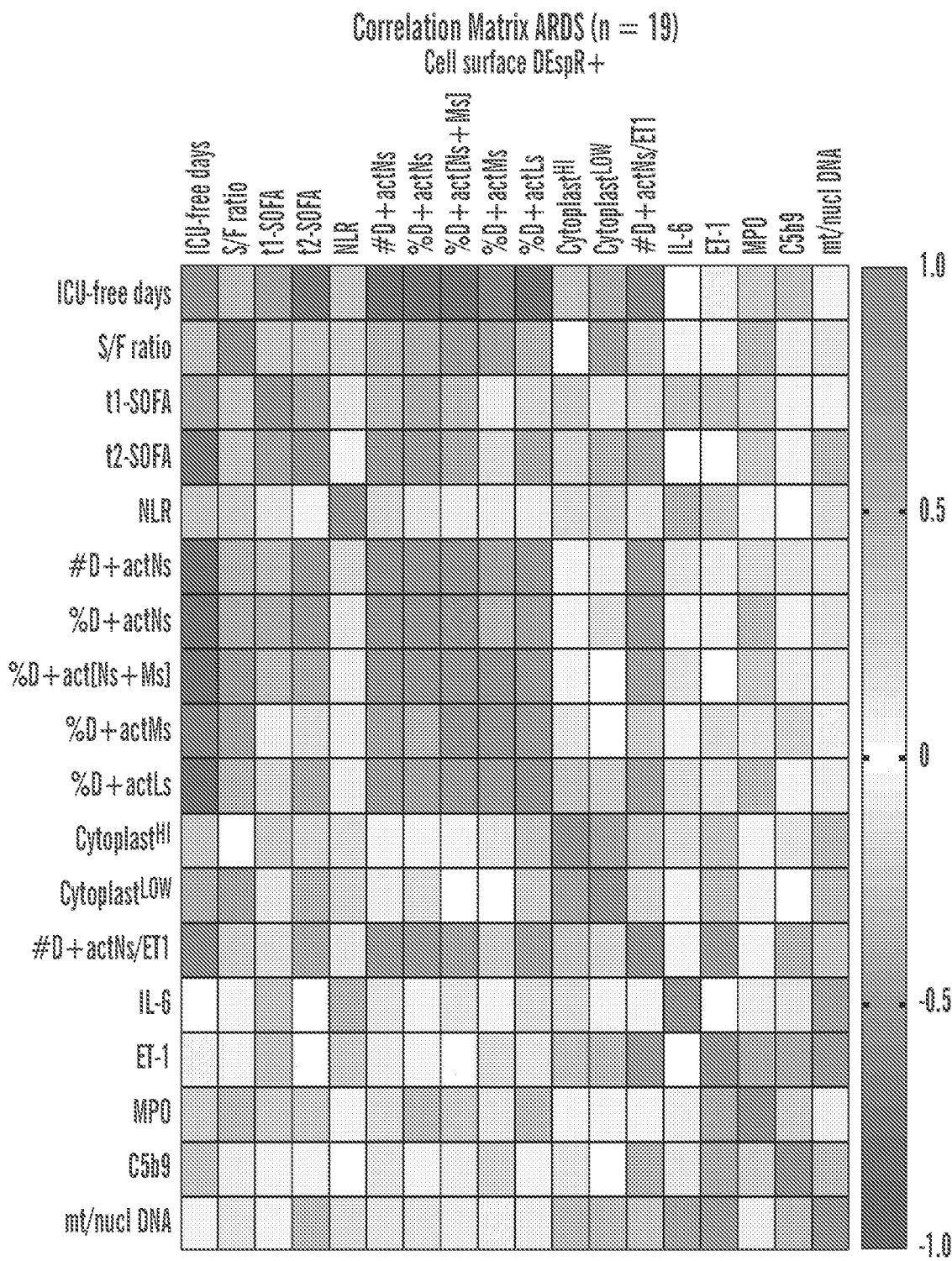
FIGS. 54A-54I depict correlation matrix analysis of DEspR+ neutrophils, clinical parameters and plasma biomarkers in ARDS and COVID19-ARDS.
Figures 54B, 54C:
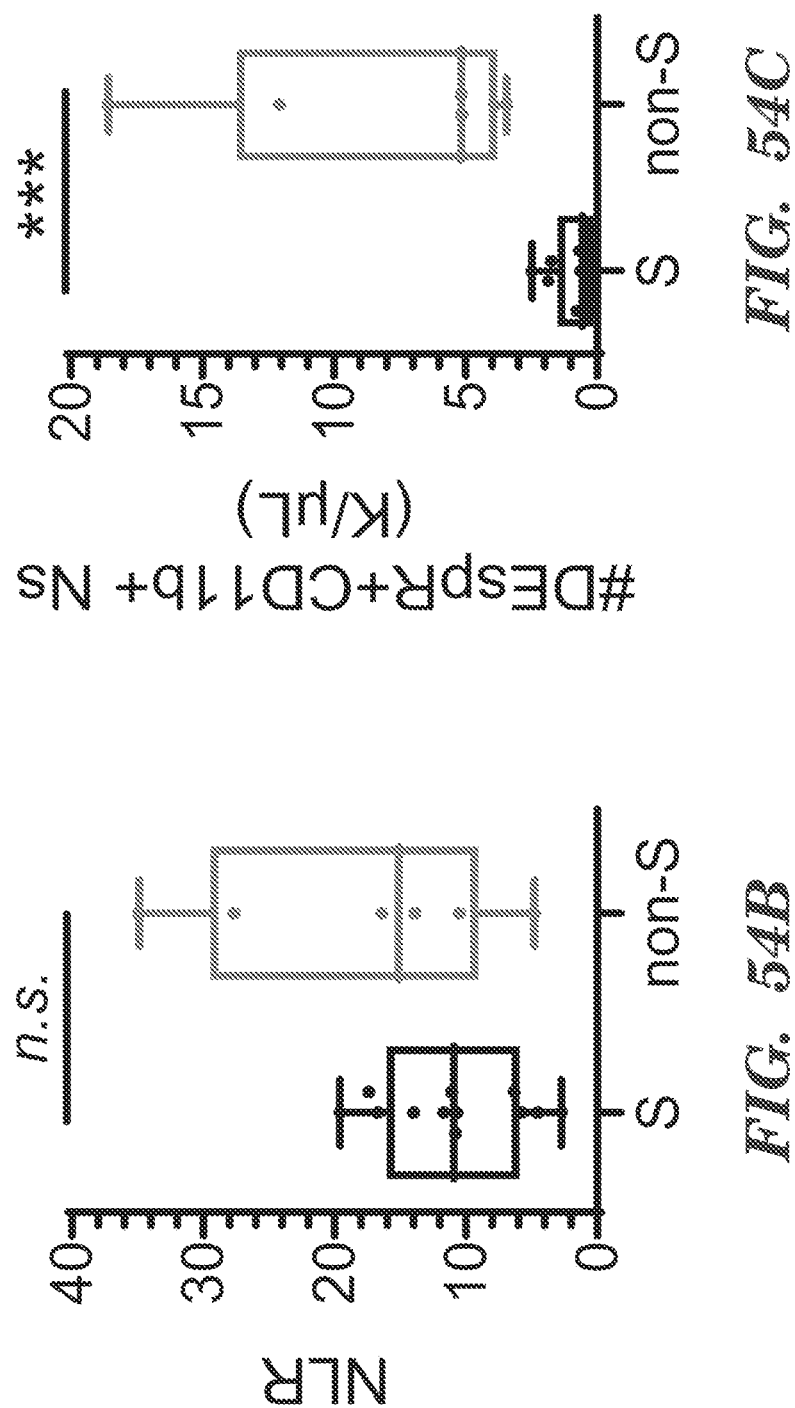

To assess clinical relevance of the DEspR+ neutrophil subset, correlation matrix analysis was performed on a panel of DEspR-based markers, clinical markers of ARDS severity, and plasma biomarkers associated with neutrophil-mediated secondary tissue injury, and endothelin-1, one of two DEspR ligands (FIG. 54A, FIGS. 56A-56B). To assess clinical severity, ICU-free days at day 28 from ARDS diagnosis, ARDS severity (PsO2/FiO2 or S/F ratio), and Sequential Organ Failure Assessment (SOFA) scores on the day of sampling for flow cytometry analysis analysis (t1-SOFA) and on day before ICU-discharge or death (t2-SOFA) were studied. Also studied were several biomarkers pertinent to ARDS pathogenic events: IL-6 (cytokine storm), soluble C5b9 (terminal complex of complement activation), myeloperoxidase or MPO (neutrophil activation), plasma mitochondrial to nuclear DNA ratio (vital NETosis-released mitochondrial DNA normalized to cell-free DNA) and DEspR+CD11b+ cytoplasts (anuclear remnants of suicidal NETosis).

In ARDS, Spearman rank correlation matrix analysis detected strong negative correlation—correlation coefficient (rS or rho)>0.6, P value<0.05, power≥0.8—between the absolute number of DEspR+CD11b+ activated neutrophils and ICU free days at day 28 (FIG. 54A, FIGS. 56A-56B). Concordantly, other DEspR-based parameters, such as % of DEspR+CD11b+ neutrophils or monocytes or lymphocytes, also showed significant negative correlation with ICU-free days at day28 (FIGS. 56A-56B). Interestingly, DEspR+CD11b+ neutrophil-counts (#) and % DEspR+CD11b+ neutrophils correlated strongly with SOFA scores at discharge from the ICU or prior to ICU-death (t2-SOFA) (FIGS. 56A-56B), suggestive of potential prognostic correlation depicted in FIG. 4F. In contrast, neutrophil-lymphocyte ratio (NLR), IL-6, MPO, nor sC5b9 levels did not correlate with ICU-free days or with t2-SOFA score (FIGS. 54A-54I, FIGS. 56A-56B), thus differentiating DEspR+expression-based markers.

Figure 54E:
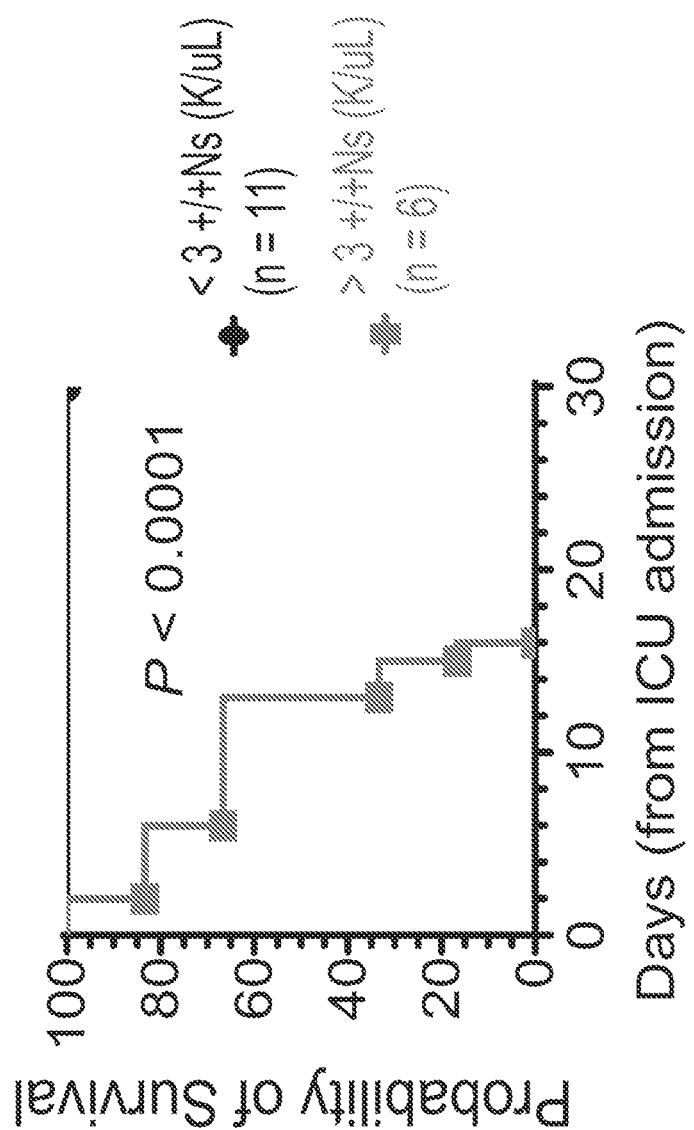
Figure 54D:
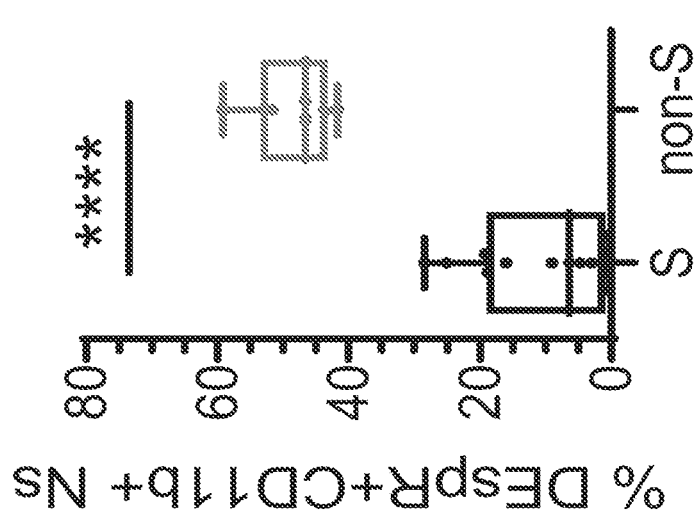

These observations are supported by analysis of difference in means between ARDS-patient survivors and non-survivors showing no significant difference for NLR (FIG. 54B), but significant differences (Mann Whitney p=0.0001) with large effect size (Hegde's g>0.8) for DEspR+CD11b+ neutrophil-counts (#) (FIG. 54C) and % DEspR+CD11b+ neutrophils (FIG. 54D). Kaplan Meier survival curve analysis with a threshold for DEspR+CD11b+ neutrophil-counts set at 3,000/μL whole blood showed significant differences in survival (P<0.0001) (FIG. 54E).

Figure 54F:
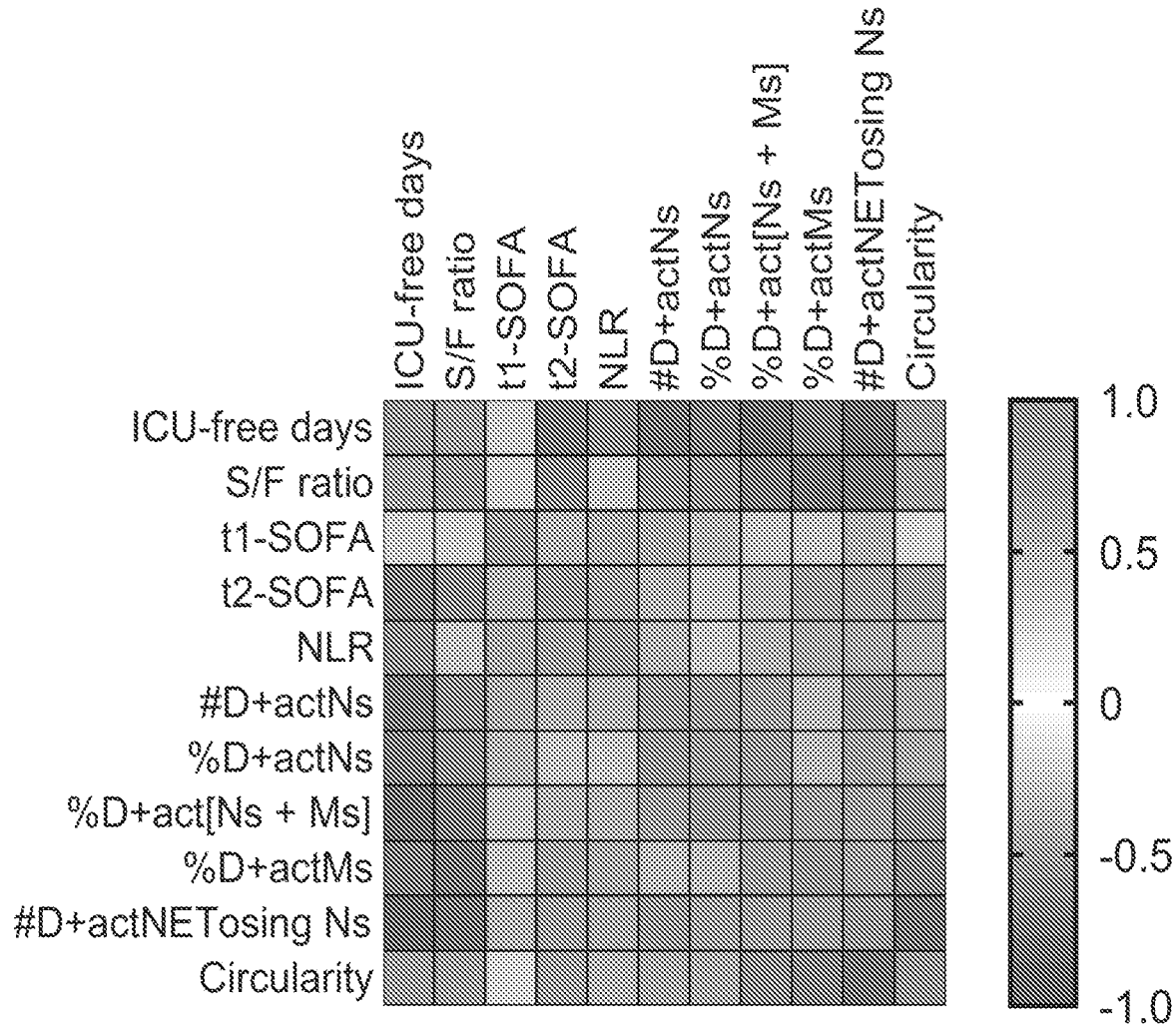

Similarly, in COVID19-ARDS pilot group, Spearman rank correlation matrix analysis also showed significant, strong, negative correlation of DEspR+CD11b+ neutrophil-counts with ICU-free days at day 28 from ARDS diagnosis, and with ARDS severity S/F ratio (FIG. 54F, FIG. 57). Interestingly, the sum of % DEspR+[monocytes and neutrophils] correlated with ICU-free days at day 28 with higher Spearman rho correlation coefficient, significance and power than either alone (FIG. 57). This observation suggests DEspR+CD11b+[neutrophil-monocyte] intravascular-interactions likely involved in systemic tissue injury in ARDS progression to multi-organ failure, as observed in acute glomerular injury.[35]

Figure 55A:
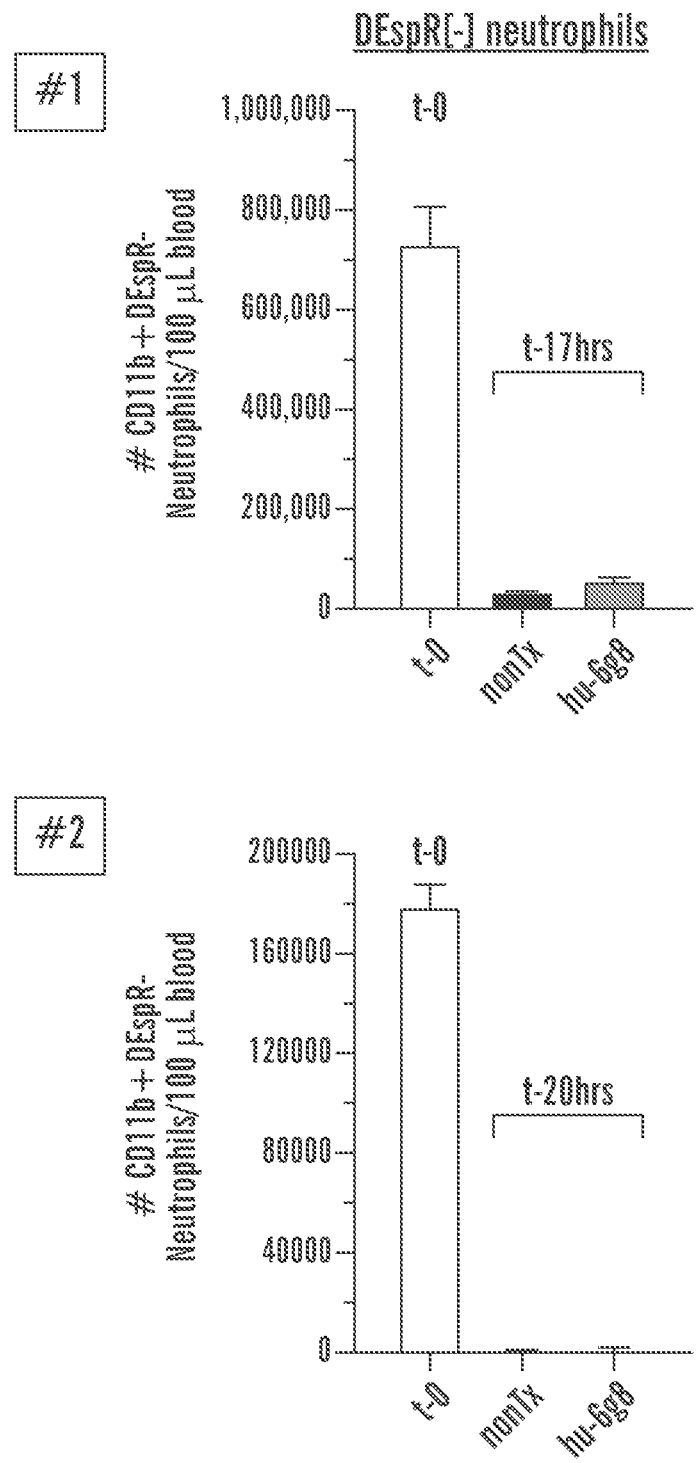
FIGS. 55A-55H depict the effects of DEspR-inhibition on neutrophil survival: ex vivo analysis of ARDS-patient and NHP neutrophils.
Figure 55B:
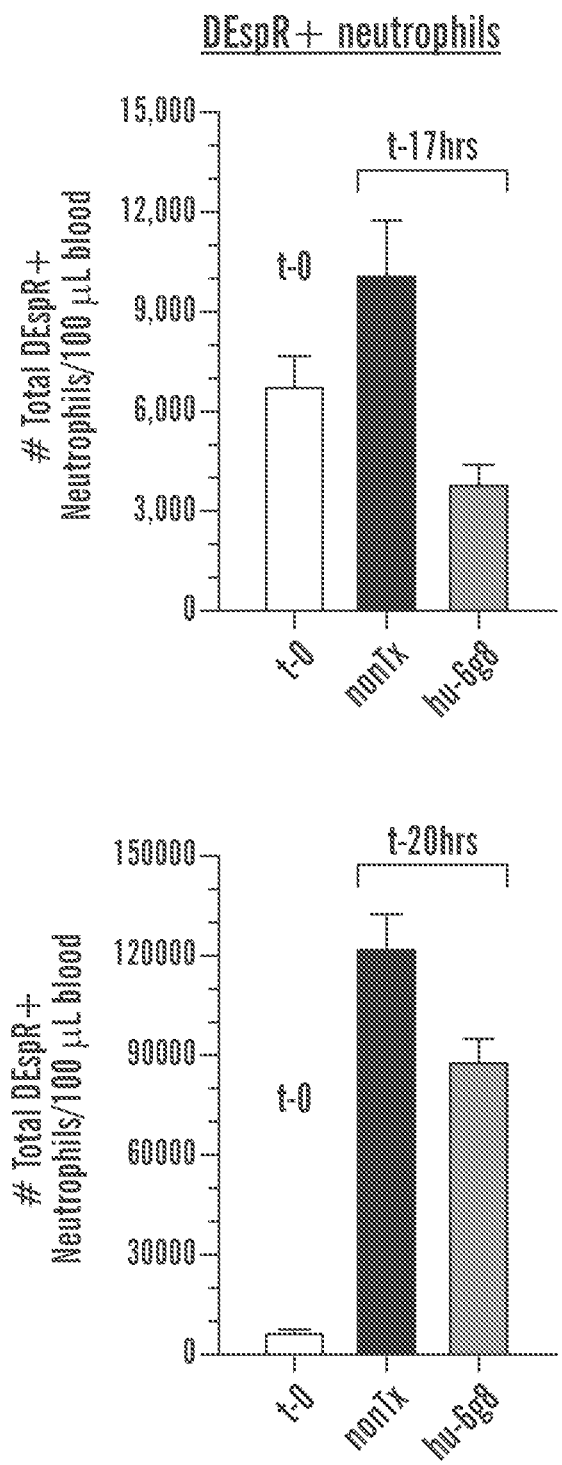
Figure 55C:
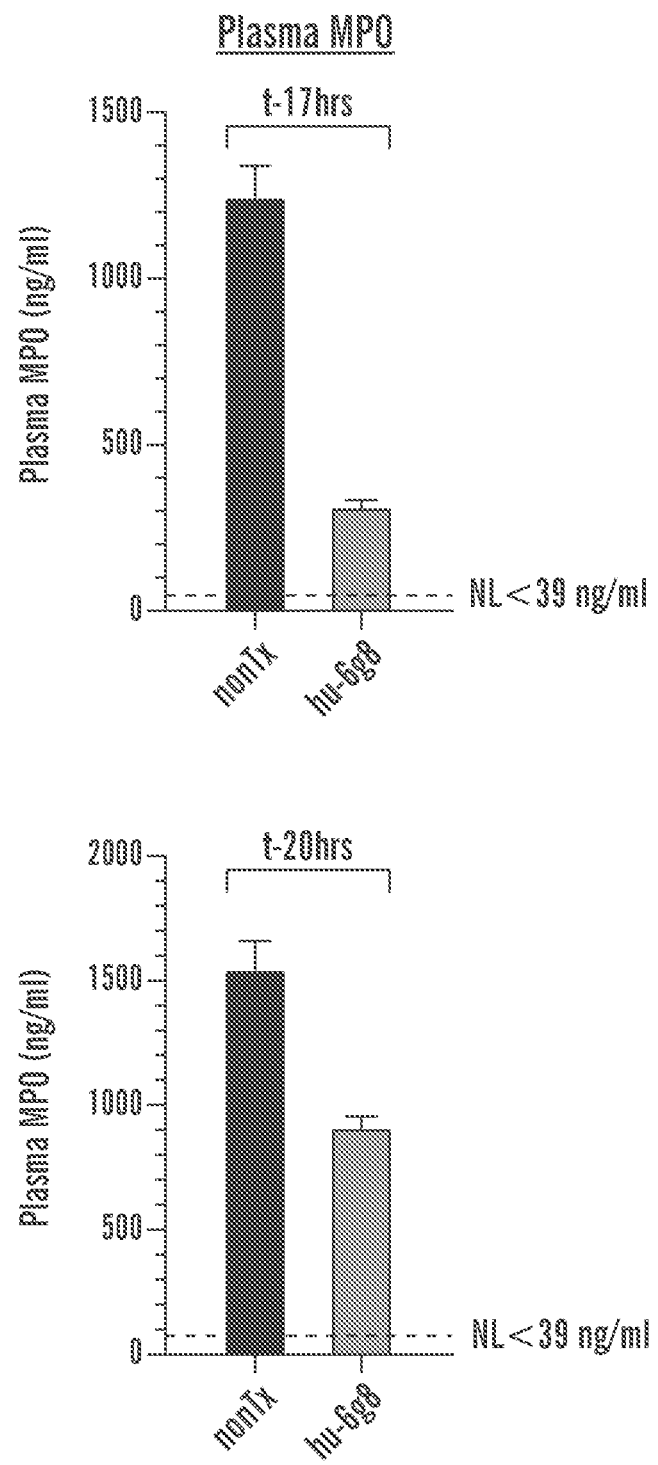
Figure 55D:
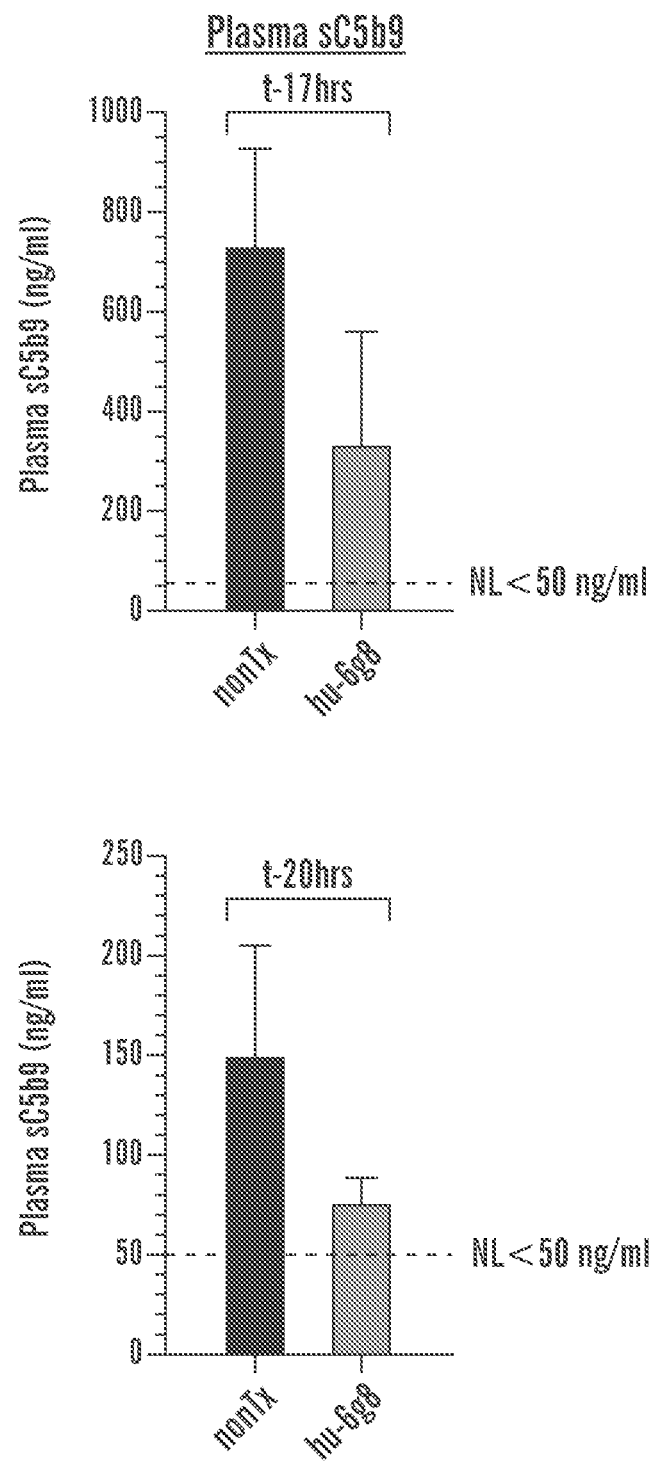
Figure 55E:
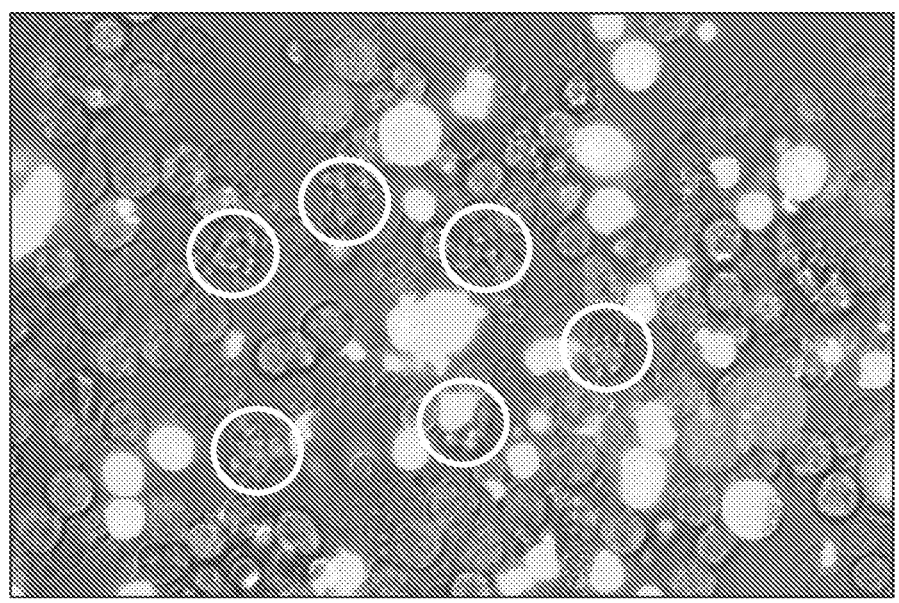
Figure 55F:
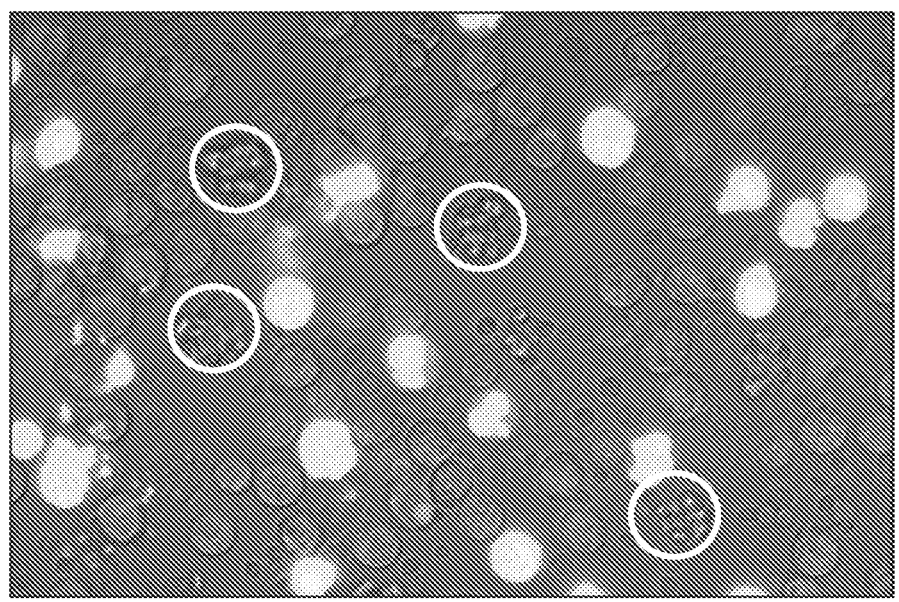
Figure 55G:
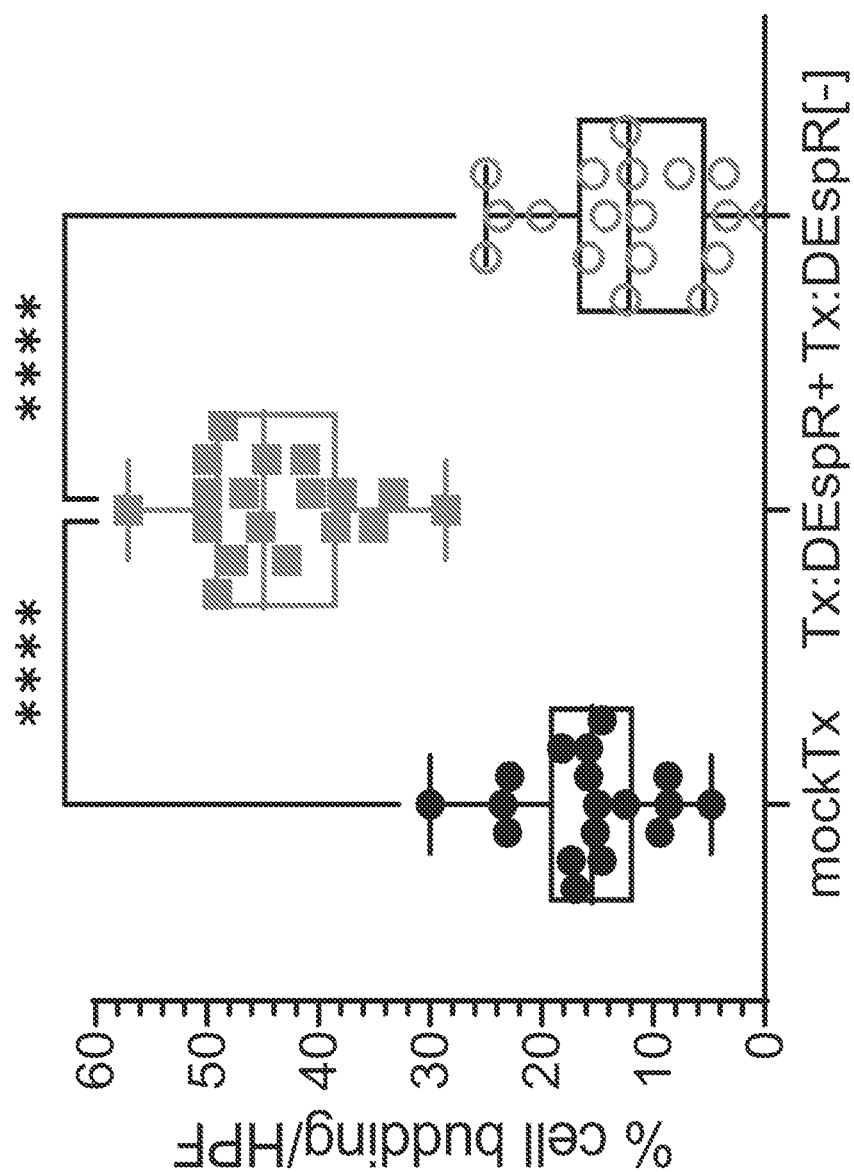
Figure 55H:
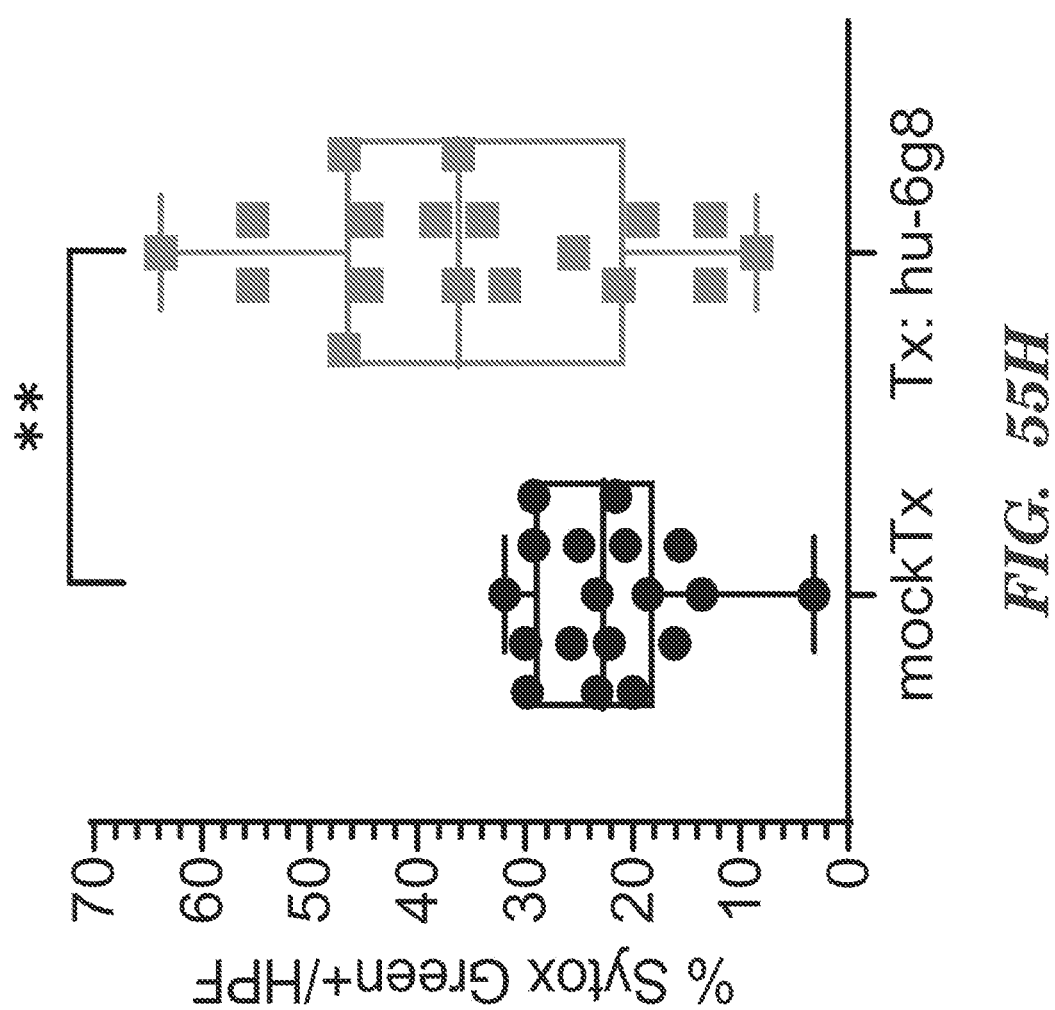

Notably, the neutrophil lymphocyte ratio (NLR) showed significant albeit less robust correlation with ICU-free days at day 28 in COVID19-ARDs. Comparative analysis of COVID19-ARDS survivors and non-survivors showed significant differences in means with large effect size for both NLR (FIG. 55G) and DEspR+CD11b+ neutrophil-counts (FIG. 55H). A retrospective analysis of COVID19-ARDS patients requiring ventilatory support at BMC corroborate significant differences in NLR (data not shown), concordant with reports that increased NLR is an independent predictor of mortality in ARDS and COVID19.[36] In contrast, C-reactive protein did not show correlation (data not shown).

Association of DEspR+ NETosing Neutrophils with Mortality and Severity in COVID19-ARDS To assess formation of neutrophil extracellular traps (NETs) increasingly implicated in severe COVID19,[37,38] immunofluorescence staining was performed to visualize and quantify NETosing neutrophils in whole blood cytology slides prepared from COVID19-ARDS patients. Using high-resolution confocal imaging of immunofluorescent-stained DEspR+CD11b+ neutrophils in patient blood smears prepared within 1 hour from blood draw, differential levels were detected of DEspR+CD11b+ NETosing neutrophils in ARDS non-survivor, compared with ARDS-survivor and ICU-patient non-ARDS survivor (data not shown). Similarly, DEspR+CD11b+ NETosing neutrophils were detected in COVID19-ARDS non-survivor (data not shown) in contrast to COVID19-ARDS survivor (data not shown). Additionally, interconnecting networks of NETosing neutrophils were detected in COVID19-ARDS non-survivors (data not shown), and DNA-strand networks with DEspR+subcellular 'beads' attached to the DNA in both ARDS and COVID19-ARDS patient cytology samples (data not shown).

In order to quantify DEspR+CD11b+ NETosing neutrophils (Ns), shape analysis was used. Semi-quantitative confocal microscopy distinguished NETosing neutrophils with low circularity index, from non-NETosing neutrophils with expected high circularity (see Supplementary Methods). Quantitative analyses of COVID19-ARDS patient samples spanning hundreds of neutrophils per slide showed significant strong negative correlation of #DEspR+NETosing neutrophils with mean circularity index per patient (Spearman rho=0.78, p=0.006, power>0.8) (data not shown). With this correlation, a circularity index<0.8 was used to identify NETosing neutrophils for quantitative analyses.

Figure 54I:
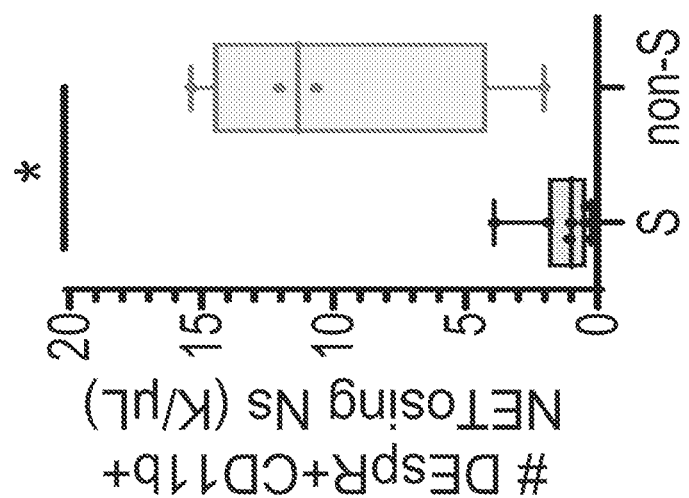
Figure 54H:
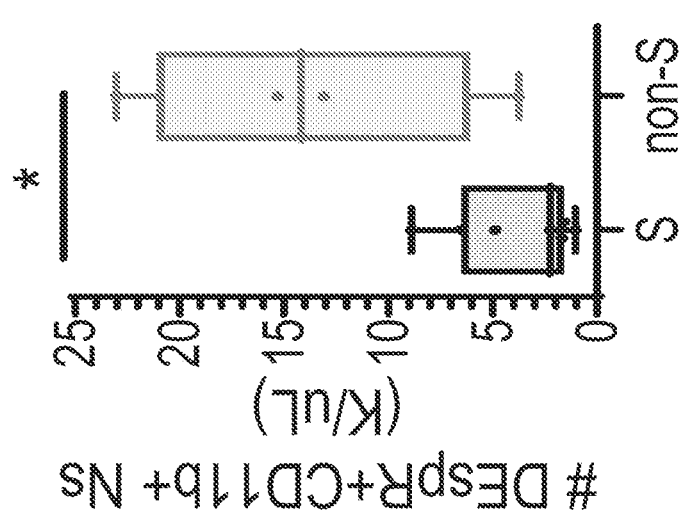
Figure 54G:
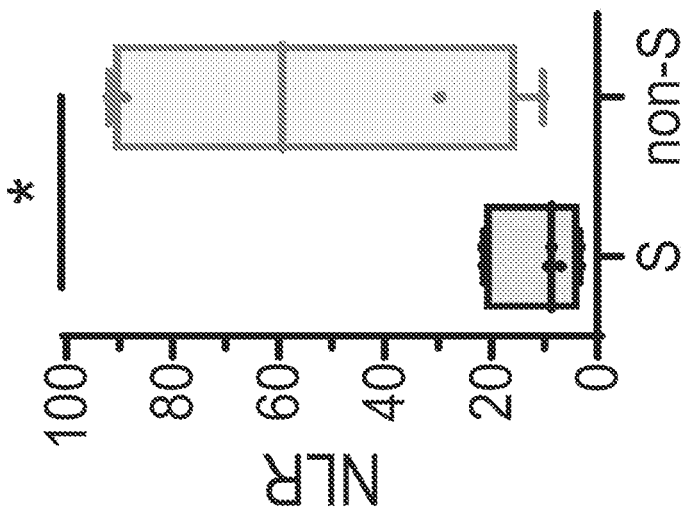

In COVID19-ARDS patients, the number (#) of DEspR+ CD11b+ NETosing neutrophils correlated strongly with three clinical measures: 1] outcome at day-28 (ICU-free days at day-28), 2] degree of hypoxemia (SpO2/FiO2 or S/F ratio), and 3] severity of multi-organ failure (SOFA score at end of ICU-stay) (FIG. 54F, FIG. 57). Significant differences in means between survivors and non-survivors was also detected (FIG. 54I). This contrasts D-dimer levels obtained during ICU which did not exhibit significant difference in means be it peak levels or average levels while patients were in the ICU (data not shown). Notably, scRNA-seq profile for PADI4 linked to suicidal NETosis is minimally expressed in neutrophils with only 1.4% of neutrophils expressing PADI4>2× fold (FIG. 59E).

Figure 61A:
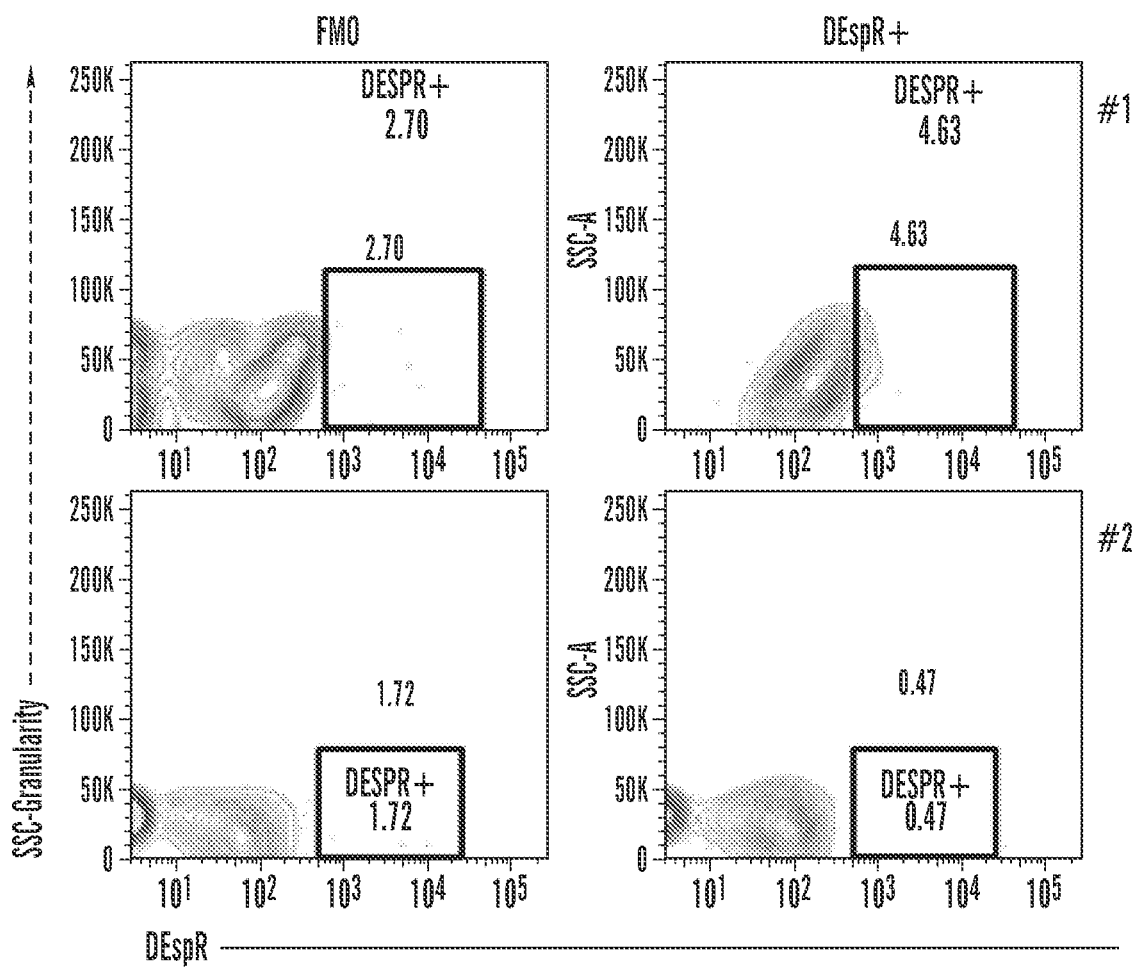
FIGS. 61A-61F depict flow cytometry (FCM) detection of DEspR+ cytoplasts in ICU-patients with sepsis-ARDS or sepsis but no ARDS, and corresponding DEspR+ expression in activated CD11b+ neutrophils. Whole blood samples (EDTA-anticoagulated) were obtained from consented healthy donors (26y, 41y, males), patients in the ICU with sepsis and ARDS, or sepsis alone. ICU-patients were all males, mean age 56y, all with acute kidney injury and on vasopressors. Samples were processed 2-3 hours from blood draw; white blood cells were isolated in 20 minutes via Inertial Microfluidic Separation validated without RBC lysis (see Methods).
Figure 61B:
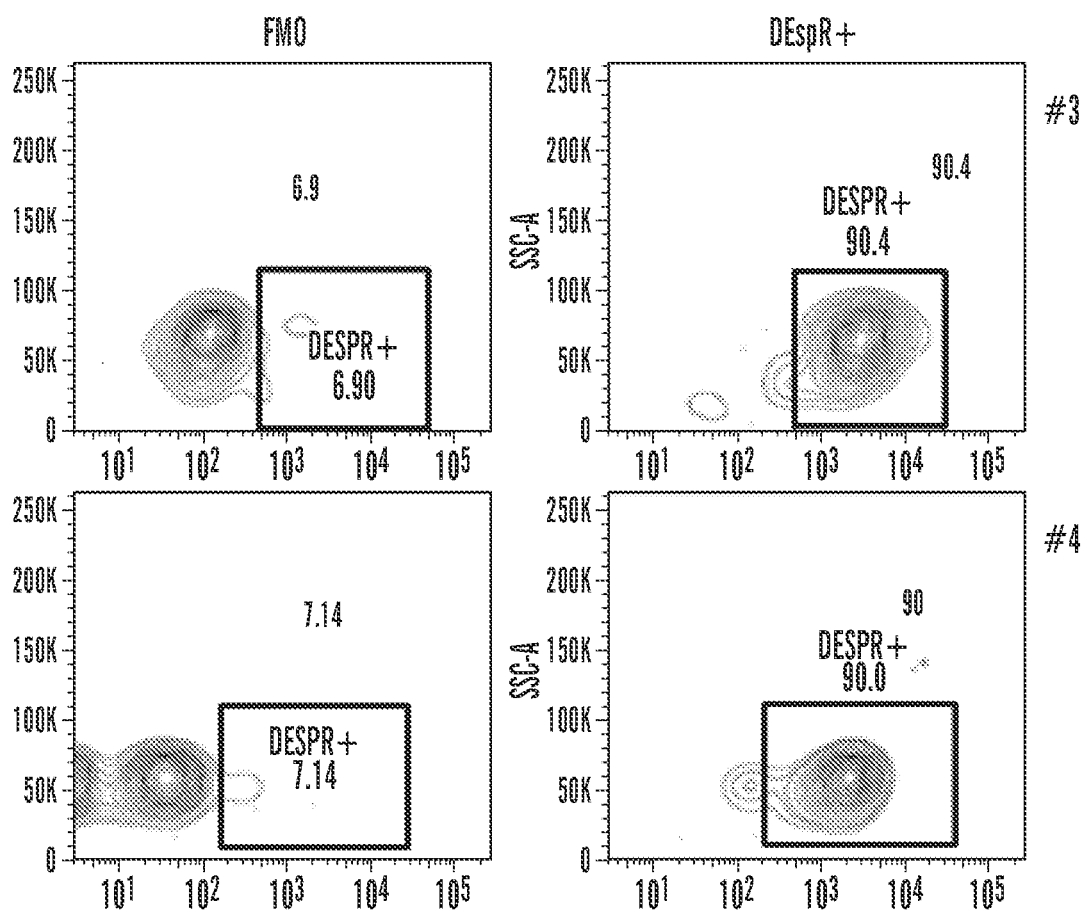
Figure 61C:
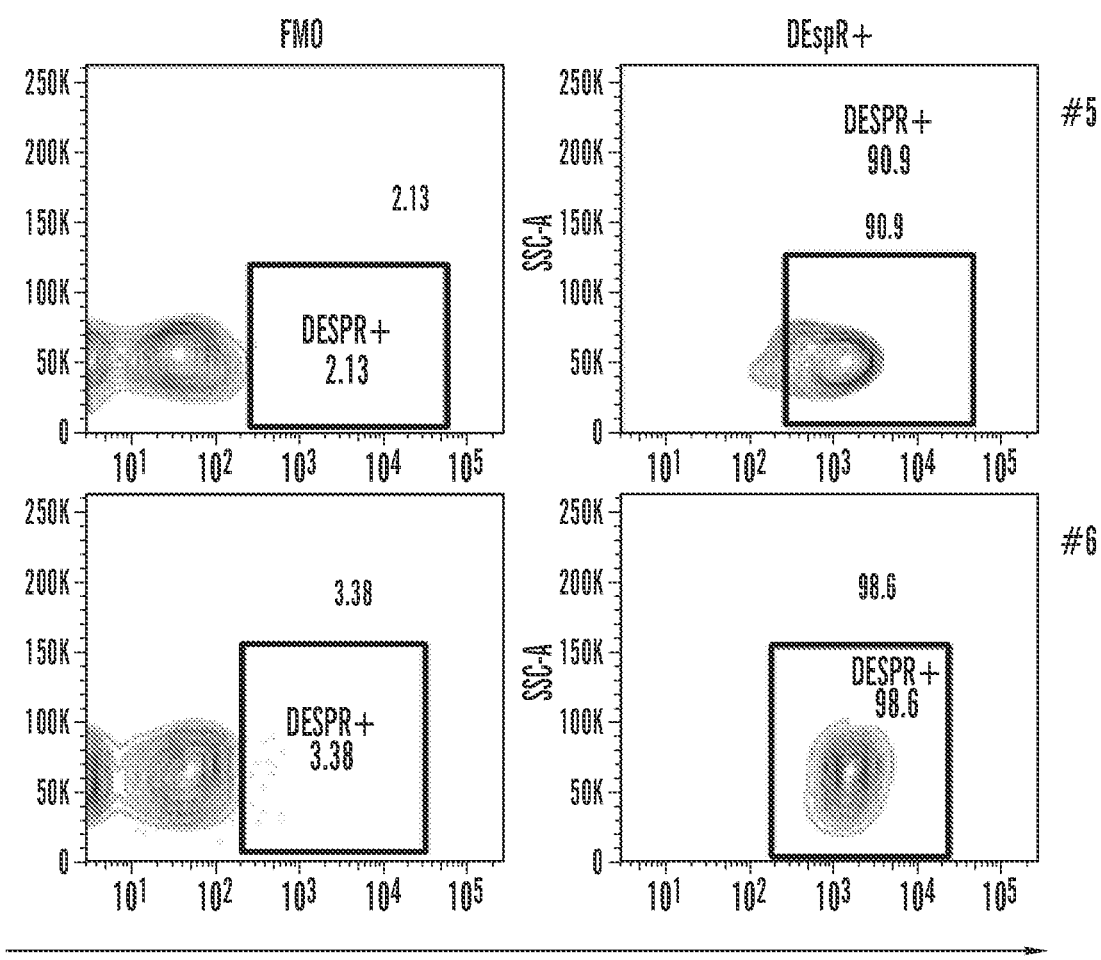
Figure 61D:
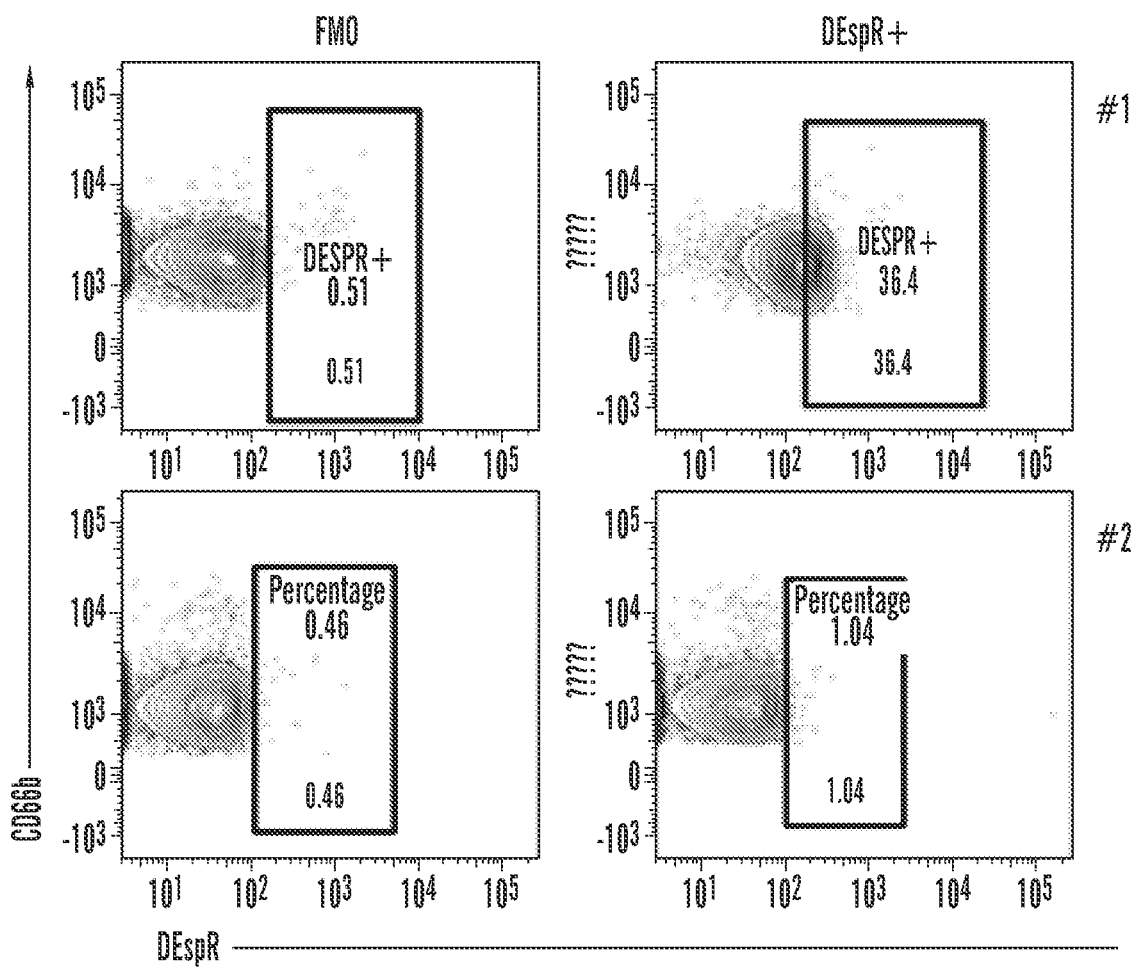
Figure 61E:
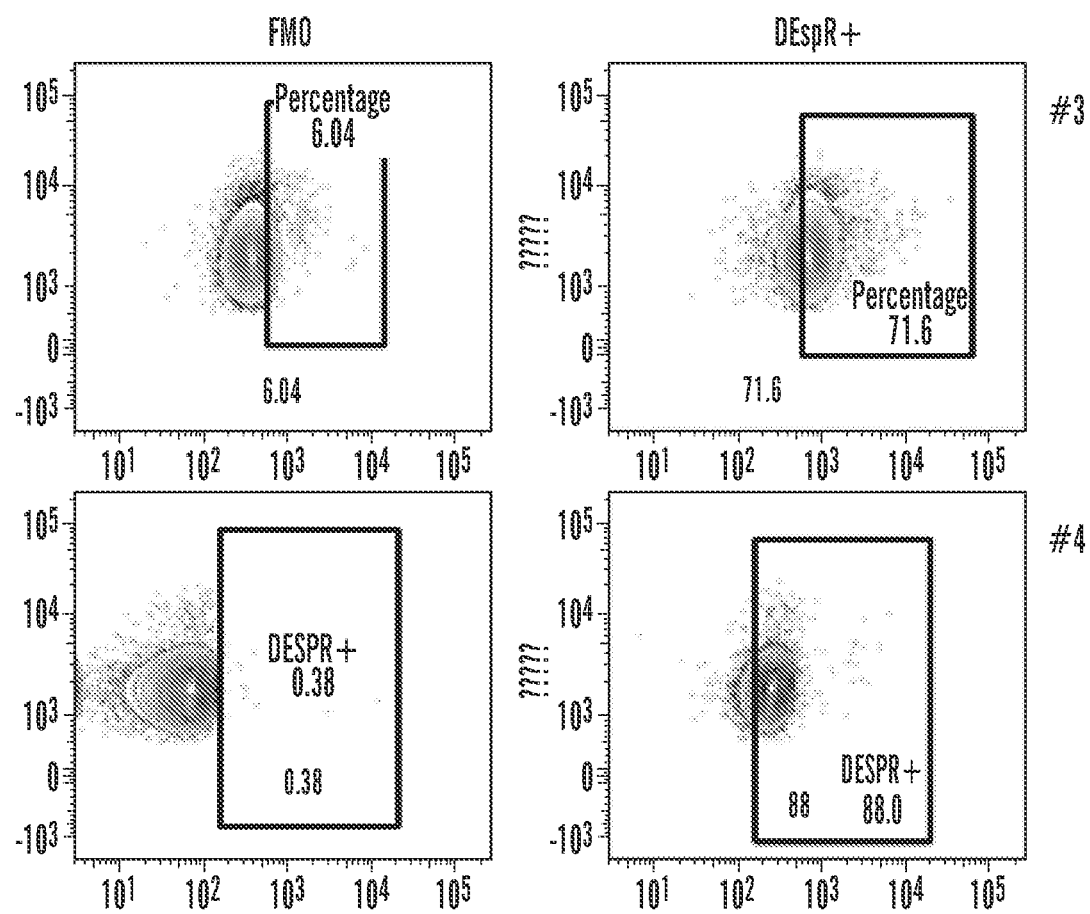
Figure 61F:
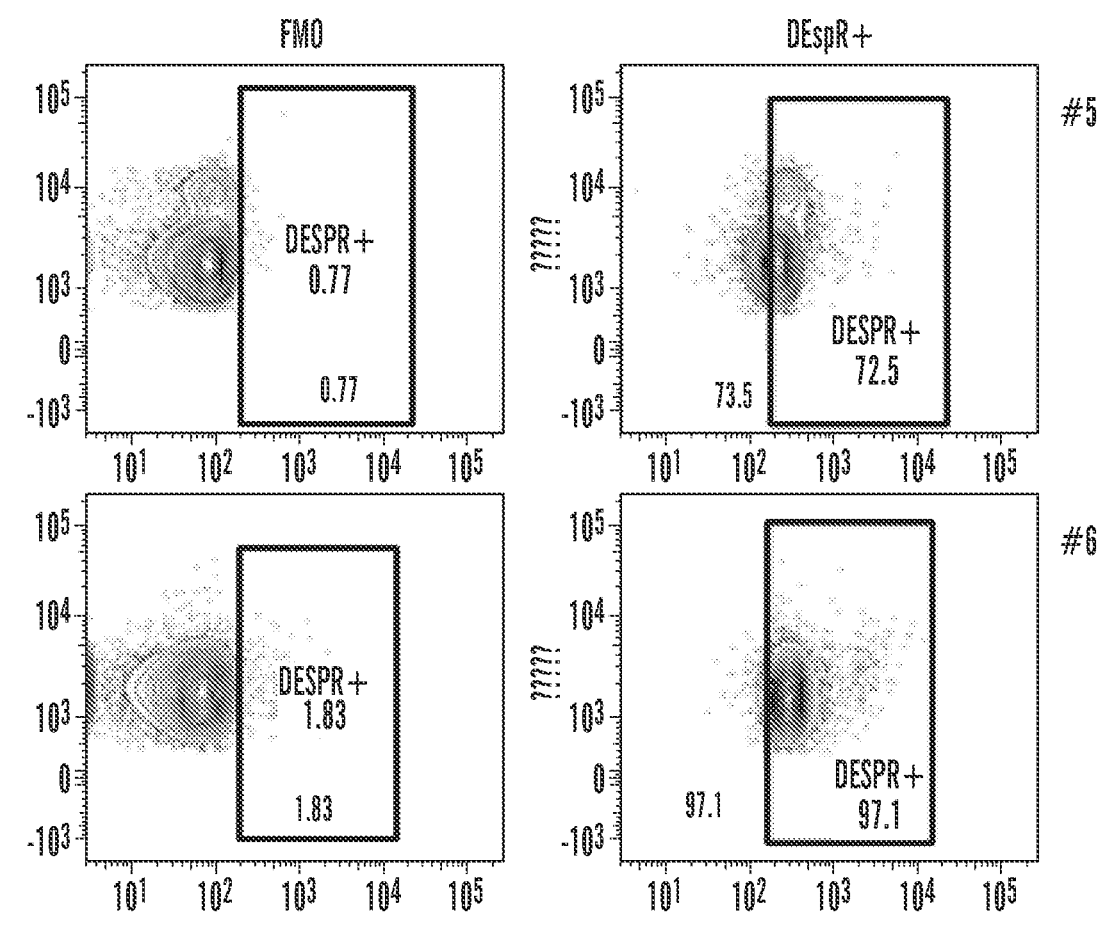

Having detected DEspR+CD11b+ cytoplasts with NETosing neutrophils on immunostained whole blood cytology slides (data not shown), levels of cytoplasts were analyzed in the circulation by flow cytometry, since cytoplasts are released during suicidal NETosis.[39] Flow cytometry analysis detected elevated DEspR+CD11b+cytoplast levels in ARDS subjects (FIG. 54A, FIG. 57) and in COVID19-ARDS (data not shown), however, no significant correlations were observed (FIG. 54A, FIG. 57). Elevated DEspR+ cytoplasts and DEspR+CD11b+ neutrophils were detected in an independent pilot study of patients with sepsis, and sepsis-ARDS in contrast to none in healthy donors (FIGS. 61A-61D) using a different methodology wherein whole blood samples were enriched for white blood cells via inertial microfluidic separation from RBCs40 (FIGS. 61E-61F).

Ex Vivo DEspR-Inhibition Induces Apoptosis in ARDS-Patient and NHP Neutrophils

To determine targetability and bioeffects of DEspR-inhibition, bioeffects of ex vivo treatment of ARDS patient whole blood with humanized anti-DEspR IgG4S228P antibody, hu6g8, for 17-20 hours overnight with rotation to prevent aggregation were analyzed. Controls comprised of patient-specific mock-treated control and baseline control (FIG. 55A). Comparative FCM-analysis showed that compared to baseline levels and after 17-20 hrs ex vivo incubation at 37° C., DEspR+ neutrophils increased in number indicating longer survival or delayed apoptosis compared with minimal number of DEspR[−] neutrophils (FIG. 55A-55B). In contrast, after DEspR-inhibition via hu6g8-treatment, ARDS patient samples showed decreased number of DEspR+ neutrophils, as well as lower myeloperoxidase (MPO) (FIG. 55C) and soluble terminal complex of complement (sC5b9) (FIG. 55D) plasma levels compared to >2-fold higher levels in respective mock-treated controls. These observations indicate induction of neutrophil apoptosis and function-shutdown of neutrophil-complement system reciprocal co-activation after 17-20 hours of DEspR-inhibition via hu6g8-treatment. Importantly, neutrophil scRNA-seq profile for CD47 is minimal, with only 0.3%-0.91% of neutrophils with >2× fold CD47 (n=19 COVID19 patients) (FIG. 59F).

To further test that DEspR-inhibition induces apoptosis in DEspR+CD11b+ neutrophils, live cell imaging was performed of non-human primate (NHP) neutrophils exposed to fluorescently labeled hu6g8-AF568 or fluorescently labeled human IgG4-AF568 isotype control for 20 minutes at 4° C. to avoid non-specific endocytosis. NHPs were selected as model system as NHP-to-human neutrophils are more similar than human-to-mouse neutrophils.[41] With this set-up, suitability of Rhesus macaque NHPs as model for study by presence of circulating DEspR+CD11b+ neutrophils is shown via detection via flow cytometry using identical conditions to ex vivo analysis of ARDS patient samples (FIGS. 62A-62H).

Figure 62A:
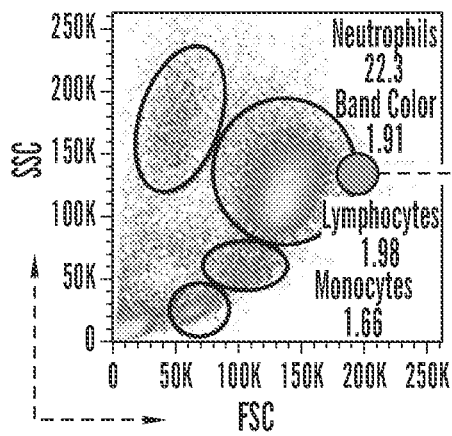
FIGS. 62A-62I depict representative flow cytometry and live-cell images of DEspR+ NHP neutrophils.
Figure 62B:
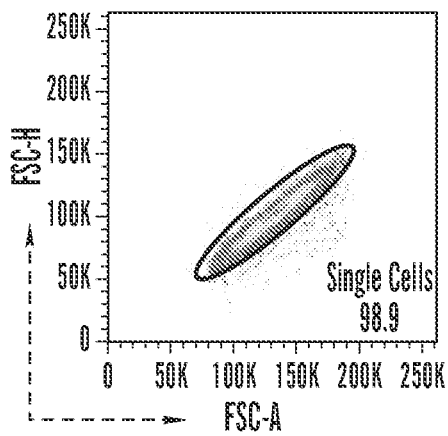
Figure 62C:
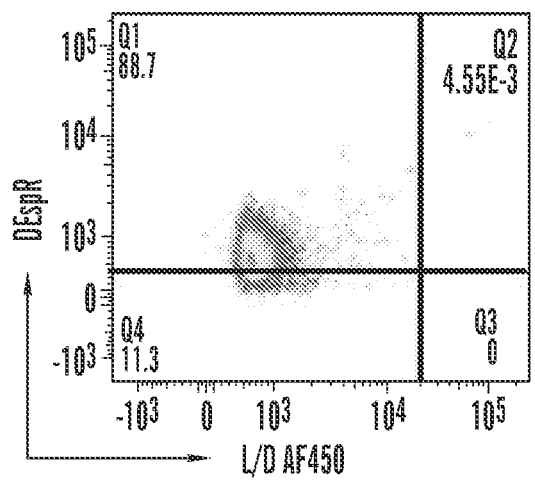
Figure 62D:
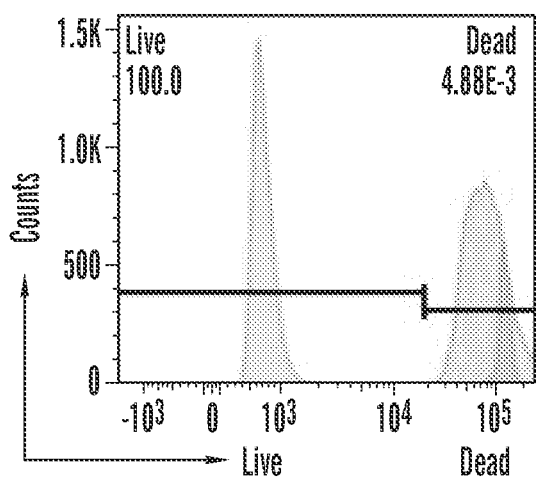
Figure 62E:
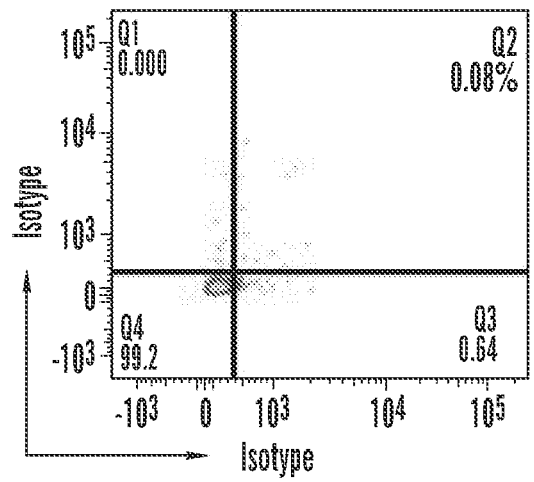
Figure 62F:
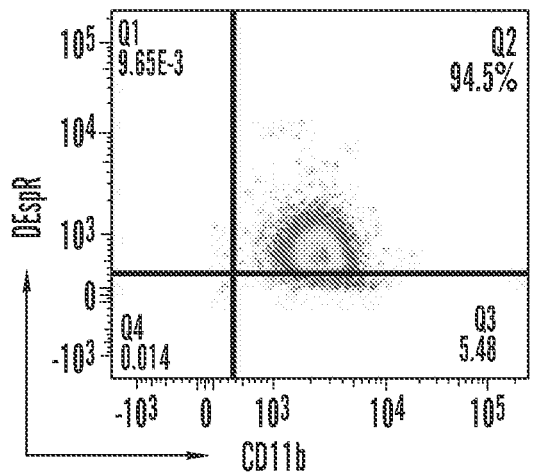
Figure 62G:
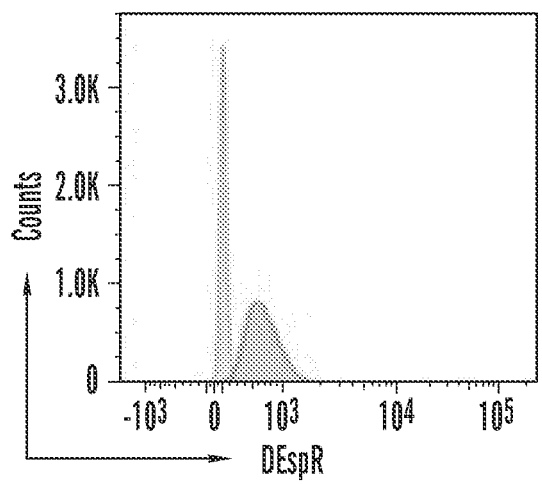
Figure 62H:
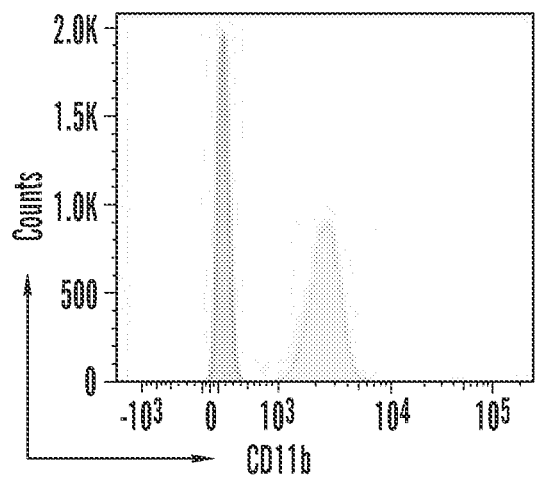
Figure 62I:
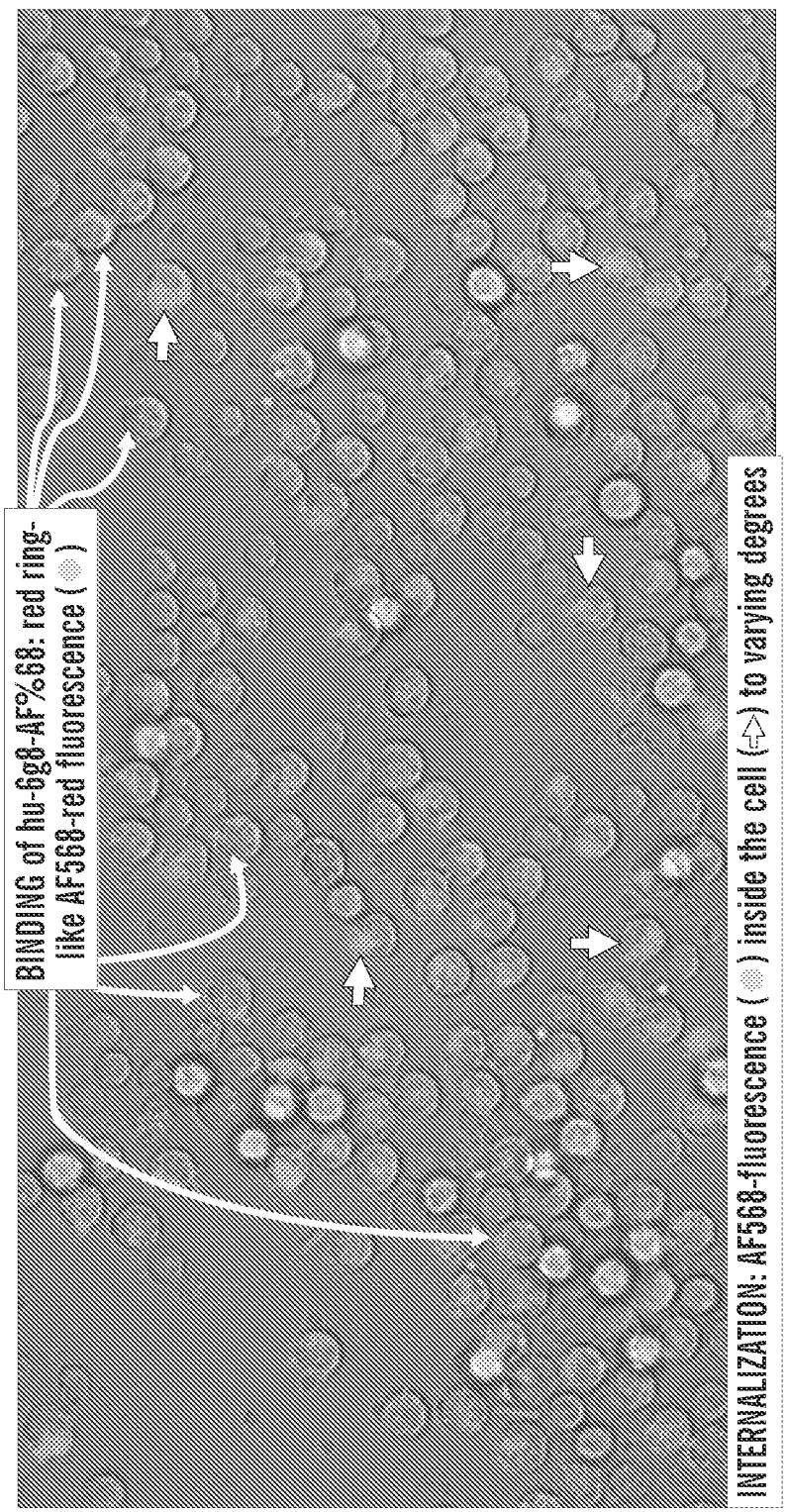

Next, was testing for target engagement, internalization, and induction of characteristic apoptosis cell-budding bioeffects by confocal live cell imaging of NHP neutrophils. NHP neutrophils were exposed to either AF568-labeled anti-DEspR hu6g8 antibody (treatment) or IgG4-isotype (mock-treatment) control for 20 minutes at 4° C. to avoid non-specific endocytosis. After removing excess unbound antibody, 24-hour live cell imaging was initiated with videorecordings. At t–45 minutes, live-cell images detected target engagement and internalization of hu6g8-AF568 antibody (FIG. 62I) but not in the isotype control. Specificities were confirmed throughout with representative t–12 hr timepoint images (FIG. 55E, FIG. 55F). Live cell imaging showed more apoptotic cell budding changes in NHP-neutrophils with internalized hu6g8. In the isotype control, apoptotic cell budding was detected concordant with neutrophil constitutive apoptosis. SytoxGreen impermeable dye uptake marked loss of cell viability. Both cell death indicators increased with time.

At the 12-hour midpoint, quantitation of apoptotic cell changes and SytoxGreen-positive non-viability were done. Representative 12-hr live cell images show hu6g8-target engagement, internalization and apoptotic cell budding in DEspR+ neutrophils (FIG. 55E) compared to minimal uptake of isotype-AF568 control by NHP neutrophils (FIG. 55F). Quantitative analysis of 18 high power fields (HPFs) with 20-50 cells/HPF representing three independent experimental fields of view showed that hu6g8 induced apoptosis in DEspR+ neutrophils significantly greater than levels seen in isotype-treated control NHP cells (FIG. 55G). Importantly, hu6g8 induced apoptosis greater than constitutive apoptosis occurring in DEspR[–] cells unaffected by hu6g8 treatment (FIG. 55H). Interestingly, loss-of-viability staining by Sytox Green occurred in neutrophils not undergoing apoptotic cell budding, and was also slightly greater in hu6g8-treated neutrophils compared with isotype mock-Tx controls (FIG. 55H), indicating that DEspR-inhibition may facilitate other programmed cell-death in neutrophils via decreased CIAP2 as observed in anti-DEspR mAb-treated pancreatic cancer stem cells.[42]

Discussion

Provided herein is data showing the correlation of DEspR+CD11b+ activated neutrophil levels with severity and mortality in both ARDS and COVID19-ARDS delineate a pathogenically relevant neutrophil-subset, DEspR+ "rogue" neutrophil-subset, that exhibits longer survival than DEspR[–] neutrophils and a predisposition to NETosis in circulation.

The subset-specific expression pattern of DEspR and its co-expression with CD11b but not in all CD11b+ activated neutrophils, are concordant with constraints arising from the need for concurrent expression of DEspR's multiple modulators: Hif1α and TLR4 for DEspR transcription, ADAR1 for RNA-editing of the DEspR transcript for translation, and activated TLR4 for mobilization to the cell surface. Among the modulators, expression of ADAR1 could be the 'gatekeeper' of DEspR+ neutrophil subsets as ADAR1 is detected in 29.2% of neutrophils, in contrast to higher levels of neutrophil expression for Hif1a (54%) in critically ill COVID19 broncho-lavage fluid and nasopharyngeal sample neutrophils. This observation is supported by increased ADAR1 localized to neutrophils in ARDS patient lung Sect. 44

Presence in pulmonary vascular lumen and in lung areas with diffuse alveolar damage (DAD) and acute alveolar injury, pathological hallmarks in ARDS, validate informativeness of flow cytometry analysis of DEspR+CD11b+ neutrophil-subset levels in whole blood samples. Notably, the cell-surface mobilization of DEspR upon TLR4-activation ties the DEspR+ neutrophil subset with neutrophil TLR4-activation upon docking of SARS-CoV2 spike protein with neutrophil TLR4 at higher affinity in silico than with the spike protein receptor, ACE245. This provides a pathogenic mechanism for direct, hence early activation of TLR4+ neutrophils without need for neutrophilic infection as observed.[12]

Additionally, direct TLR4-activation and CD11b+ induction in neutrophils by serum S100A8/A9 alarmins, the prototype DAMPS[46] found to be elevated in ARDS[47] and COVID19-ARDS[48], further ties the DEspR+CD11b+ neutrophil-subset to ARDS and COVID19-ARDS. Functionally, as alarmins and TLR4-activation provide a self-sustaining neutrophil activation loop, activated TLR4-induced DEspR upregulation provides a mechanism for delayed apoptosis. This combination of functionalities provides a putative mechanism for feed-forward progression of neutrophil-mediated secondary tissue injury as seen in severe ARDS and COVID19-ARDS, and would be concordant with the observed association of increased DEspR+CD11b+ neutrophils with severity and mortality in ARDS and COVID19-ARDS.

The detection by direct visualization of neutrophils with characteristic extruded DNA and retained cell membrane[49] in ARDS and COVID19-ARDS patient whole blood cytology slides, and detection of elevated mitochondrial to nuclear DNA ratio in plasma, together indicate neutrophils undergoing vital NETosis[50] in the circulation with extrusion of mitochondrial DNA[51]. The identification of DEspR+ expression on said NETosing neutrophils, and significant correlation of #DEspR+/CD11b+ vital NETosing neutrophils with clinical measures of severity in COVID19-ARDS, altogether implicate vital NETosis in pathogenesis of progressive multi-organ failure. The detection of NETosis derivatives on the same immuno-stained cytology slides with NETosing neutrophils, such as long DNA-strands with DEspR+ 'beads' and DEspR+CD11b+ cytoplasts, suggest a dynamic continuum of NETosis paradigms in the circulation in ARDS and COVID19-ARDS.

Intuitively, the observed DNA-strand and interconnections among NETosing neutrophils with their extruded-but still attached DNA fragments could be projected to contribute intravascular biophysical impedance to vascular flow and concomitant low-flow ischemia, thus predisposing to multiorgan dysfunction, as well as microvascular occlusion with or without micro-thromboses. These observations provide insight into why low-flow or micro-ischemic events in different organs persist despite pharmacological thromboprophylaxis or anti-thrombotic treatment.[52] Additionally, the microvascular flow impedance from DNA-strand and/or from vital-NETosing neutrophil interconnections provide pathogenic concordance with reported severe hypoxemia despite high lung compliance deduced to be due to ventilation/circulation flow mismatch.[53] More importantly, the detection of DEspR+expression on vital NETosing neutrophils provides an actionable therapeutic target to pre-empt NETosing neutrophils in the circulation.

Data showing that DEspR-inhibition leads to apoptosis in ARDS patient samples and NHP samples supports DEspR as an actionable therapeutic target to induce apoptosis in the dysregulated, apoptosis-resistant neutrophil-subset[54] implicated in progressive secondary tissue injury leading to ARDS and/or multi-organ failure[55]. Coupled with strong correlation with multiple clinical severity measures, targeted-inhibition of DEspR with endpoint induction of neutrophils apoptosis comprises a much-needed therapeutic paradigm with potential advantages. First, data showing that anti-DEspR hu6g8 induced neutrophil apoptosis and prevented terminal complex of complement sC5b9 increase, suggests function-shutdown of neutrophil-complement system reciprocal-interactions,[56] and possibly also NETs-induced complement activation.[57] Second, since neutrophil apoptosis is required for neutrophil function shutdown, clearance and neutrophil-initiation of resolution,[58] restoration of neutrophil constitutive apoptosis upon DEspR-inhibition could then be expected to promote active resolution of dysregulated hyperinflammation. While more studies are needed to elucidate mechanisms, the emerging mode-of-action of DEspR inhibition presents a valid pathway to meet therapeutic goals required to stop neutrophil-mediated tissue injury1 by inducing neutrophil apoptosis for function shutdown. Additionally, with 99.10% of neutrophils in a representative COVID19 scRNA-profile not expressing CD47 "don't eat me signal," induction of neutrophil apoptosis by anti-DEspR antibody can be expected to proceed to efferocytosis. Similarly, with 98.6% of neutrophils not expressing PADI4, anti-DEspR therapy can play a pivotal role in decreasing NETosis-mediated pathogenesis in ARDS and COVID19-ARDS. Third, non-inhibition of DEspR[−]CD11b+ activated neutrophil subsets to fight infections and initiate active resolution mechanisms elucidates an inherent safety profile.

Lastly, consideration for potential side effects, especially in the context of acute kidney injury as part of multi-organ failure in ARDS, highlights known DEspR+expression in human medullary tubular epithelial cells. In the presence of immunoglobinuria, anti-DEspR antibody passing through the glomerulus could present potential on-target tubular epithelial effects, but unlikely as antibody functionality will be altered in the increasingly acidic and hyperosmotic milieu in the kidney medullary lumen. Altogether, data identify the DEspR+CD11b+ neutrophil subset as an actionable therapeutic target whose targeted inhibition can slow progression of multi-organ failure in ARDS and COVID19-ARDS, with minimal, if any, projected side effects.

Methods

Study Design

Different tasks were compartmentalized in order to attain blinding of researchers during task-performance. The following tasks were compartmentalized: a] patient screening, b] consenting and blood sampling, c] processing of blood for flow cytometry and FlowJo analysis, d] clinical data collection, e] laboratory testing—ELISAs, etc; f] cytology slides preparation from whole blood; g] immune-fluorescence staining, h] confocal microscopy imaging and semi-quantitative measures; i] analysis of collated laboratory and clinical data. The diagnosis of ARDS was determined in real time by review of ICU diagnoses, and checked by clinicians post-hoc blinded to all experimental tasks, such as flow cytometry, cytology and ELISA results.

Study Subjects

All subjects were identified in the ICU under study protocols approved by the Institutional Review Board (IRB) of Boston University (IRB H-36744). Each subject's legal authorized representative gave written informed consent for study participation in compliance with the Declaration of Helsinki.

19 ARDS patients were enrolled in the pre-COVID19 pandemic period, and 11 COVID-19 ARDS patients admitted to the intensive care unit (ICU) at Boston Medical Center. ARDS diagnosis was based on clinical diagnosis using the Berlin Definition. COVID-19 ARDS patients were ascertained as COVID-19 positive by SARS-CoV-2 PCR testing. Additional data were obtained prospectively from 16 COVID-19 ARDS patients to examine the time-course during ICU-hospitalization and correlation of other known markers with survival: neutrophil lymphocyte ratio, C-Reactive Protein and D-Dimer. Collaborators enrolled NHVs (MM), patients with severe COVID19 in the ICU for bronchial-lavage fluid studies (RE), healthy donors and patients with sepsis-ARDS for inertial microfluidic separation (BDL, RMB, MPV) according to respective institutional guidelines.

Blood Collection

Whole blood (3 or 6 mls) was collected via pre-existing indwelling peripheral vascular lines into K2-EDTA vacutainer tubes (FisherScientific, MA) from patients hospitalized in the ICU at Boston Medical Center by the ICU-nurse. COVID-19 patient EDTA-anticoagulated blood samples were immediately fixed with one volume of 4% PFA. Both Non-COVID and COVID-19 blood samples were processed for flow cytometry analysis within 1 hour from blood collection. Platelet poor plasma was isolated and frozen at −80° C. for future testing within 2 hrs from blood draw. Cytology slides were done within 1 hour from blood draw.

Flow Cytometry Analysis of Blood Samples

At BUSM, EDTA-anticoagulated blood samples from non-COVID ARDS subjects (100 µL per tube, ×2-3 replicates) were processed for flow cytometry within 1-hour from blood sampling. Flow cytometry buffer comprised of Hank's balanced salt solution plus 2% heat-inactivated FBS as blocking agent; staining antibodies: 10 µg/ml of AF-647 labeled hu6g8 mAb, or the corresponding human IgG4-AF647 isotype IgG4, and 2.5 µg/ml anti-CD11b-AF488 or the corresponding mouse IgG1 kappa isotype control, AF-488; staining done at 4° C.×30 minutes with rotation and protected from light; after staining, cells were fixed in 2% PBS-buffered PFA pH 7.4 at 4° C., followed by RBC lysis at RT. After final wash, stained cells were resuspended in 400 µl HBSS 2% FBS, filtered and analyzed on a BD LSR-II flow cytometer. Analysis was done using FloJo Flow Cytometry Analysis Software (FloJo.com). Controls used were: both fluorescence minus one (FMO) controls, both isotype controls, compensation beads for both staining antibodies to check labeled antibody quality.

For disinfected COVID19 blood samples (2% PFA-fixed), samples were washed 3 times with 8 volumes of HBSS+2% FBS to remove residual fixative prior to processing for flow cytometry as described above. Each test sample run in duplicates.

At BWH, EDTA-anticoagulated whole blood samples were processed 2-3 hours from sampling and white blood cells were separated from RBCs via Inertial Microfluidic Separation validated previously for neutrophil characterization.40 Flow cytometry was performed immunotyping for CD45, CD66b and DEspR at room temperature×20 min, and analyzed on an LSR-Forteza.

Western Blot Analysis

Western blot analysis was done essentially as described[42] using equal amounts of total cellular protein extract (25 μg) isolated from human neutrophils. Neutrophil cell extracts were prepared by cell homogenization in 3 volumes of 1× Laemmli buffer (Bio-Rad). Human kidney protein extract was used as control. Proteins were size-separated on a 15% Tris-HCL SDS-PAGE (Bio-Rad) and transferred to PVDF membrane (Bio-Rad). The Western blot was reacted with anti-DEspR antibody (hu6g8) at 20 μg/ml for 18 hours at 4° C. with shaking. Immunoreactive proteins were detected by chemiluminescence using the ECL Western Detection kit (Thermo Scientific 34077).

Immunohistochemistry of Tissue Sections

Postmortem human lung sections were analyzed from patients with clinical diagnosis of ARDS, and pathological diagnosis of diffuse alveolar damage (DAD). Immunohistochemistry was performed at Horns Scientific, Inc using DAB (3,3'-diaminobenzidine) and hematoxylin counter stain. Chimeric anti-DEspR hu6g8 with mouse IgG2a backbone was used at 1:100 dilution (~10 μg/ml), and anti-human myeloperoxidase antibody 1:50 dilution. Primary antibodies were incubated for 16 hours at 4° C. Negative controls were run without primary antibodies, positive controls were run using DEspR+xenograft tumor Sect.[42]

scRNA-Seq Database Analysis scRNA-Seq data of two patients with critical COVID-19 disease courses (WHO stage 4), covering nasopharynx, protected specimen brush swabs of the airways, and bronchial lavage fluid were obtained from the UCSC Cell Browser generated by studies performed at Charité-Universitatsmedizin Berlin and Berlin Institute of Health. Patient cells were processed using the 10× Chromium system with v3.1 chemistry. Primary analysis was performed using Cell Ranger 3.2.0 with a hg19 reference genome, followed by removal of ambient RNA using SoupX 1.2.2. Preprocessing and primary of analysis of the scRNA-Seq data were performed using Seurat 3.1.4. For details on patient characteristics, sample processing, and data analysis, please refer to Chua et al.[12] Visualization of the expression of genes of interest was performed using the UCSC Cell browser and confirmed using Seurat 3.2.2 of original datasets. Expression values shown are normalized to the total count of unique molecular identifiers (UMIs) per cell.

Ex-Vivo LPS Treatment of Human Normal Volunteer (HNV) Neutrophils

At Fraunhofer ITEM, heparinized whole blood was stored on ice until processing and used within 1-hour after collection. Whole blood (100 μl) samples were washed with 1 ml of ice cold assay buffer, and cells were incubated in 100 μl of assay buffer containing bacterial endotoxin lipopolysaccharide LPS (100 ng/ml; *Escherichia coli* serotype 0111:B4) or assay buffer as control for 1 h at 37° C. The reaction was then stopped, cells washed, then resuspended and cells were stained with hu6g8-PE (10 μg/ml) and CD11b-FITC for 30 min on ice under constant stirring in the dark. Cells were washed to remove unbound antibodies, fixed for 10 min at 4° C., followed by RBC lysis. The cell pellet was resuspended in 250 μl flow cytometry buffer and was analyzed within 2 hours using a Beckman Coulter Navios 3L 10 C flow cytometer and data analyzed using Beckman Coulter Kaluza 2.1 Software.

At BUSM, 100 μl EDTA-anticoagulated whole blood samples (n=6) were exposed to 75-100 μg/ml LPS at 37° C.×1-hour, then subjected to FCM analysis as described above.

Plasma Level Analysis of Biomarkers by ELISA and Quantitation of Mitochondrial DNA Individual ELISA protocols were performed as per manufacturer's instructions with the following sample dilutions: For MPO ELISA (abcam cat# ab195212) plasma dilution 1:1000; for C5b-9 ELISA (MyBioSource cat# MBS2021557) plasma dilution 1:100; for IL-6 ELISA (Abcam cat# ab46027) plasma dilution 1:2; for ET-1 ELISA (abcam cat# ab133030) plasma dilution 1:2.

To compare the levels of mitochondrial to nuclear DNA in human plasma samples the NovaQUANT™ Human Mitochondrial to Nuclear DNA Ratio Kit (SIGMA-Aldrich cat#72620-1KIT) was used as per manufacturer's instructions. The kit measures the mtDNA copy number to that of nuclear DNA by Real-Time PCR of specific mitochondrial and nuclear genes. Plasma DNA was isolated from 200 uL of plasma using the Quick-cfDNA Serum & Plasma Kit (Zymo Research, cat# D4076) as per manufacturer's instruction.

Immunofluorescence Staining of NETosing Neutrophils

Cytology slides were prepared by capillary action from EDTA anticoagulated whole blood (10 μL) samples on a Superfrost Plus Microscope slide (Fisher Scientific, cat#12-550-15) within 1-hour from blood sampling. Cytology smears were air dried for 10 minutes then fixed with 100% Methanol (chilled to −20 C) for 10 min. Fixed slides were stored dry in −20° C. freezer for future immunostaining.

Immunofluorescence (IF)-staining to detect NETosing neutrophils was done as described previously.[59]

Fixed Cell Imaging of Blood Smears (NETosing Quantification)

Slides were imaged with a Nikon Ti2-E Widefield microscope equipped with a Plan Apo λ20× objective and Spectra LED light source and controlled by NIS-Elements. Briefly, an automated, JOBS routine in NIS-Elements was used to image 100 evenly spaced positions along an entire slide. At each position, focus was automatically adjusted with the Perfect Focus System (PFS) and then sequential images with the 395 (Blue), 470 (Green) and 555 (Red) nm LED light sources to detect DAPI (nuclei), Alexa Fluor 488 (CD11b) and Alexa Fluor 568 (DEspR, hu6g8), respectively. Each stack of 100 images was then processed with a General Analysis 3 algorithm in NIS-Elements to segment the nuclei, measure their circularity (Circularity=471 [area/perimeter2], area of minimum circle enclosing NETosing neutrophil, perimeter of NETosing neutrophil with all DNA-extrusions], and quantify the signal intensity of any co-localized CD11b and DEspR expression. Data were exported to a CSV file where the final scoring is completed in Excel.

Ex-Vivo Anti-DEspR Treatment of ARDS Patient Blood Samples

One ml of freshly obtained blood samples were incubated overnight at 37° C. with or without anti-DEspR mAb (hu6g8 at 100 μg/ml). After incubation half of the samples were subjected to FACS analysis as described above and the other half was processed for plasma isolation. Plasma MPO and C5b-9 levels were determined with corresponding ELISA kits as described above.

Quantitation of apoptotic cell changes and viability after anti-DEspR treatment of non-human primate (NHP) DEspR+CD11b+ neutrophils by live cell imaging Briefly, whole blood from Rhesus macaque NHP provided by Biomere (Biomere Biomedical Research Models, Inc., Worcester Mass.) was analyzed by flow cytometry to determine the number of DEspR+CD11b+activated neutrophils. White blood cells (WBCs) were then obtained, washed and resuspended in Hank's Balanced Salt Solution (HBSS)+2%

Fetal Bovine Serum (FBS). WBCs were counted, divided into aliquots and incubated with 10 µg/ml Alexa Fluor 568-conjugated hu6g8 antibody or Alexa Fluor 568-conjugated IgG4 isotype antibody for 20 minutes at 4° C. Cells were washed to remove unbound antibody, then concentrated at to approximately 108 cells/mL, then loaded into imaging device. Live cell imaging was performed using a microfluidic chip with three parallel conjoined microfluidic channels, and a confocal microscope (Ti2-E microscope equipped with Nikon A1R HD25 point scanner and 60× Plan Apo λ Oil objective) housed within a temperature and CO2-controlled incubator. Images were then acquired every minute for the first 9 hours, and then every 5 minutes for 15 hours thereafter, for a total of 24 hours observation time. At 15 minutes into imaging, Sytox Green (Thermo-Fisher) was added into the imaging media for each chip at a final concentration of 1:6000.

Statistical Analysis

For demographics, statistical comparisons of clinical parameters between the non-COVID and COVID-19 ARDS subjects we used the Fisher Exact test (GraphPad Prism v9.0.1) comparing corresponding proportions, except for age, S/F ratio and SOFA score which were done by using a two-tailed Mann Whitney (GraphPad Prism v9.0.1). For survivor vs non-survivor group comparisons, we used the two-tailed Mann Whitney test (GraphPad Prism v9.0.1) with effect size calculated via Hedge's g with 4% correction. Correlations were calculated by using the Spearman Rank Order correlation test (GraphPad Prism v9.0.1) and power calculations determined by using SigmaPlot 11.0 software. All data sets conformed to the assumptions of each specific statistical test. $P<0.05$ was considered statistically significant, sufficient power 0.8.

REFERENCES

1. Vassallo, A., Wood, A. J., Subburayalu, J., Summers, C., & Chilvers, E. R. The counter-intuitive role of the neutrophil in the acute respiratory distress syndrome. Br. Med. Bull. 131(1), 43-55 (2019).
2. Matthay, M. A. et al. Acute respiratory distress syndrome. Nat. Rev. Dis. Primers. 14(5), 18 (2019).
3. de la Rica, R., Borges, M., & Gonzalez-Freire, M. COVID-19: In the Eye of the Cytokine Storm. Front. Immunol. 11, 558898 (2020).
4. Horby, P. W. & Landray M. J. Randomised Evaluation of 13 COVID-19 Therapy (RECOVERY) trial. 2021. Tocilizumab in patients admitted to hospital with COVID-19 (RECOVERY): preliminary results of a randomised, controlled, open-label, platform trial. Preprint at https://doi.org/10.1101/2021.02.11.21249258 (2021).
5. Potey, P. M., Rossi, A. G., Lucas, C. D., & Dorward, D. A. Neutrophils in the initiation and resolution of acute pulmonary inflammation: understanding biological function and therapeutic potential. The Journal of pathology 247(5), 672-685 (2019).
6. Brown, K. A. et al. Neutrophils in development of multiple organ failure in sepsis. Lancet 368, 157-169 (2006).
7. Opal, S. M. Immunologic alterations and the pathogenesis of organ failure in the ICU. Semin. Resp. Crit. Care Med. 32, 569-580 (2011).
8. Xu, J. et al. Extracellular histones are major mediators of death in sepsis. Nat. Med. 15, 1318-1321 (2009).
9. Yang, H. et al. New insights into neutrophil extracellular traps: mechanisms of formation and role in inflammation. Front. Immunol. 7, 302 (2016).
10. Wang, Y. et al. Neutrophil-to-lymphocyte ratio as a prognostic marker in acute respiratory distress syndrome patients: a retrospective study. J. Thorac. Dis. 10, 273-282 (2018).
11. Jimeno, S. et al. Prognostic implications of neutrophil-lymphocyte ratio in COVID-19. Eur. J. Clin. Invest. 51(1), e13404 (2021).
12. Chua, R. L. et al. COVID-19 severity correlates with airway epithelium-immune cell interactions identified by single-cell analysis. Nat. Biotechnol. 38(8), 970-979 (2020).
13. Silvin, A. et al. Elevated Calprotectin and Abnormal Myeloid Cell Subsets Discriminate Severe from Mild COVID-19. Cell 182(6), 1401-1418 (2020).
14. Guo, Q. et al. Induction of alarmin S100A8/A9 mediates activation of aberrant neutrophils in the pathogenesis of COVID-19. Cell Host Microbe. 29(2), 222-235 (2021)
15. Schulte-Schrepping, J. et al. Severe COVID-19 Is Marked by a Dysregulated Myeloid Cell Compartment. Cell 182(6), 1419-1440 (2020).
16. Gromisch, C. M. et al. Humanized anti-DEspR IgG4S228P antibody increases overall survival in a pancreatic cancer stem cell-xenograft peritoneal carcinomatosis ratnu/nu model. BMC Cancer 21, 407 (2021).
17. Moulding, D. A., Quayle, J. A., Hart, C. A., & Edwards, S. W. Mcl-1 expression in human neutrophils: regulation by cytokines and correlation with cell survival. Blood 92(7), 2495-2502 (1998).
18. Filep, J. G. & El Kebir, D. Neutrophil apoptosis: a target for enhancing the resolution of inflammation. J. Cell Biochem. 108(5), 1039-1046 (2009).
19. Herrera, V. L. et al. Embryonic lethality in Dear gene deficient mice: new player in angiogenesis. Physiol. Genomics 23, 257-268 (2005).
20. Druml, W. et al. Endothelin-1 in adult respiratory distress syndrome. Am. Rev. Respir. Dis. 148(5), 1169-1173 (1993).
21. Zouki, C. et al. Endothelin-1 enhances neutrophil adhesion to human coronary artery endothelial cells: role of ET(A) receptors and platelet-activating factor. Br. J. Pharmacol. 127(4), 969-979 (1999).
22. Jorch, S. & Kubes, P. An emerging role for neutrophil extracellular traps in noninfectious disease. Nat Med 23, 279-287 (2017).
23. Vassallo, A., Wood, A. J., Subburayalu, J., Summers, C., & Chilvers, E. R. The counter-intuitive role of the neutrophil in the acute respiratory distress syndrome. British Medical Bulletin 131(1), 43-55 (2019).
24. Herrera, V. L. et al. Confirmation of translatability and functionality certifies the dual endothelin1/VEGFsp receptor (DEspR) protein. BMC Mol. Biol. 17, 15 (2016).
25. Juss, J. K. et al. Acute Respiratory Distress Syndrome Neutrophils Have a Distinct Phenotype and Are Resistant to Phosphoinositide 3-Kinase Inhibition. Am. J. Respir. Crit. Care Med. 194(8), 961-973 (2016).
26. Mendonga, R., Silveira, A. A. A. & Conran, N. Red cell DAMPs and inflammation. Inflamm. Res. 65, 665-678 (2016).
27. Xiang, M. & Fan, J. Pattern Recognition Receptor-Dependent Mechanisms of Acute Lung Injury. Mol. Med. 16, 69-82 (2010).
28. Aboudounya, M. M. & Heads, R. J. COVID-19 and Toll-Like Receptor 4 (TLR4): SARS-CoV-2 May Bind and Activate TLR4 to Increase ACE2 Expression, Facilitating Entry and Causing Hyperinflammation. Mediators Inflamm. 2021, U.S. Pat. No. 8,874,339 (2021).

29. Zhou, X. et al. LPS activation of Toll-like receptor 4 signals CD11b/CD18 expression in neutrophils. Am. J. Physiol. Lung Cell Mol. Physiol. 288(4), L655-L662 (2005).
30. Odobasic, D., Kitching, A. R. & Holdsworth, S. R. Neutrophil-Mediated Regulation of Innate and Adaptive Immunity: The Role of Myeloperoxidase. J. Immunol. Res. 2016, U.S. Pat. No. 2,349,817 (2016).
31. van der Veen, B. S., de Winther, M. P. & Heeringa, P. Myeloperoxidase: molecular mechanisms of action and their relevance to human health and disease. Antioxid Redox Signal. 11(11), 2899-2937 (2009).
32. Bordon, J. et al. Understanding the roles of cytokines and neutrophil activity and neutrophil apoptosis in the protective versus deleterious inflammatory response in pneumonia. Int. J. Infect. Dis. 17(2), e76-83 (2013).
33. Hojyo, S. et al. How COVID-19 induces cytokine storm with high mortality. Inflamm. Regener. 40, 37 (2020).
34. Butt, Y., Kurdowska, A. & Allen, T. C. Acute Lung Injury: A Clinical and Molecular Review. Arch. Pathol. Lab. Med. 140(4), 345-350 (2016).
35. Finsterbusch, M. et al. Patrolling monocytes promote intravascular neutrophil activation and glomerular injury in the acutely inflamed glomerulus. Proc. Natl. Acad. Sci. U.S.A. 113(35), E5172-E5181 (2016).
36. Liu, Y. et al. Neutrophil-to-lymphocyte ratio as an independent risk factor for mortality in hospitalized patients with COVID-19. The Journal of infection 81(1), e6-e12 (2020).
37. Arcanjo, A. et al. The emerging role of neutrophil extracellular traps in severe acute respiratory syndrome coronavirus 2 (COVID-19). Sci. Rep. 10(1), 19630 (2020).
38. Veras, F. P. et al. SARS-CoV-2-triggered neutrophil extracellular traps mediate COVID-19 pathology. J. Exp. Med. 217(12), e20201129 (2020).
39. Krishnamoorthy, N. et al. Neutrophil cytoplasts induce TH17 differentiation and skew inflammation toward neutrophilia in severe asthma. Sci. Immunol. 3(26), eaao4747 (2018).
40. Jundi, B. et al. Leukocyte function assessed via serial microlitre sampling of peripheral blood from sepsis patients correlates with disease severity. Nat. Biomed. Eng. 3, 961-973 (2019).
41. Bjornson-Hooper, Z. B. et al. A comprehensive atlas of immunological differences between humans, mice and non-human primates. bioRxiv (2019)
42. Herrera, V. L. et al. DEspR roles in tumor vasculoangiogenesis, invasiveness, CSC-survival and anoikis resistance: a 'common receptor coordinator' paradigm. PLoS One 9(1), e85821 (2014).
43. Grégoire, M. et al. Impaired efferocytosis and neutrophil extracellular trap clearance by macrophages in ARDS. Eur. Respir. J. 52(2), 1702590 (2018).
44. Wu, Y. et al. Adenosine deaminase that acts on RNA 1 p150 in alveolar macrophage is involved in LPS-induced lung injury. Shock. 31(4), 410-415 (2009).
45. Choudhury, A. & S. Mukherjee, S. In silico studies on the comparative characterization of the interactions of SARS CoV-2 spike glycoprotein with ACE-2 receptor homologs and human TLRs. J. Med. Virol. 92(10), 2105-2113 (2020).
46. Wang, S. et al. S100A8/A9 in Inflammation. Front. Immunol. 9, 1298 (2018).
47. Kuipers, M. T. et al. High levels of S100A8/A9 proteins aggravate ventilator-induced lung injury via TLR4 signaling. PLoS One. 8(7), e68694 (2013).
48. Chen, L. et al. Elevated serum levels of S100A8/A9 and HMGB1 at hospital admission are correlated with inferior clinical outcomes in COVID-19 patients. Cell Mol Immunol 17, 992-994 (2020)
49. Yipp, B. G., & Kubes, P. NETosis: how vital is it? Blood 122(16), 2784-2794 (2013).
50. Yipp, B. G. & Kubes, P. NETosis: how vital is it? Blood. 122(16), 2784-2794 (2013).
51. Yousefi, S. et al. Untangling "NETosis" from NETs. Eur J Immunol. 49(2), 221-227 (2019).
52. Klok, F. A. et al. Confirmation of the high cumulative incidence of thrombotic complications in critically ill ICU patients with COVID-19: An updated analysis. Thromb. Res. 191, 148-150 (2020).
53. Gattinoni, L. et al. COVID-19 pneumonia: different respiratory treatments for different phenotypes? Intensive Care Med. 46, 1099-1102 (2020).
54. Fox, S., Leitch, A. E., Duffin, R., Haslett, C., & Rossi, A. G. Neutrophil apoptosis: relevance to the innate immune response and inflammatory disease. J. Innate Immun. 2(3), 216-227 (2010).
55. Brown, K. A. et al. Neutrophils in development of multiple organ failure in sepsis. Lancet 368, 157-169 (2006).
56. Camous, L. et al. Complement alternative pathway acts as a positive feedback amplification of neutrophil activation. Blood. 117(4), 1340-1349 (2011).
57. Skendros, P. et al. Complement and tissue factor-enriched neutrophil extracellular traps are key drivers in COVID-19 immunothrombosis. J. Clin. Invest. 130(11), 6151-6157 (2020).
58. El Kebir, D. & Filep, J. G. Modulation of Neutrophil Apoptosis and the Resolution of Inflammation through β2 Integrins. Front. Immunol. 4, 60 (2013).
59. Hamaguchi, S. et al. Identification of neutrophil extracellular traps in the blood of patients with systemic inflammatory response syndrome. J. Int. Med. Res. 41(1), 162-168 (2013).

What is claimed herein is:

1. A method of treating a coronavirus infection in a subject,
the method comprising administering a therapeutically effective amount of a Dual Endothelin/VEGF signal peptide Receptor (DEspR) inhibitor to the subject;
wherein the DEspR inhibitor is an anti-DEspR antibody reagent or antigen-binding fragment thereof, capable of specifically binding DEspR.

2. The method of claim 1, wherein the subject is determined to have an elevated level of DEspR+CD11b+ cells as compared to a non-infected subject.

3. The method of claim 2, wherein the DEspR+CD11b+ cells are DEspR+CD11b+ neutrophils, DEspR+CD11b+ monocytes, DEspR+CD11b+ lymphocytes, DEspR+CD11b+ cytoplasts, or DEspR+ DNA strands, or a combination of any of the foregoing.

4. The method of claim 1, wherein the administering is effective to treat COVID19 disease manifestations and complications beyond the coronavirus infectivity status in the subject.

5. The method of claim 1, wherein the coronavirus is SARS CoV2 causing COVID-19.

6. The method of claim 1, wherein the subject is further determined to have i) an elevated DEspR+ neutrophil to lymphocyte ratio (d+NLR); ii) an elevated ratio of DEspR+ neutrophils to COVID19-associated (a) hyperinflammation cytokines or cytokine storm biomarkers, (b) oxidative stress biomarkers, (c) endothelial dysfunction biomarkers, or (d) a combination of any of (a), (b), and (c); or iii) a combination of i) or ii).

7. The method of claim 6, wherein the hyperinflammation cytokines or cytokine storm biomarkers comprise IL-6, IL-8, IL-1β, or IL-18, or a combination thereof.

8. The method of claim 6, wherein the oxidative stress biomarkers comprise myeloperoxidase (MPO).

9. The method of claim 6, wherein the endothelial dysfunction biomarkers comprise endothelin-1 (ET1).

10. The method of claim 1, wherein the anti-DEspR antibody reagent or fragment thereof comprises 6 complementary determining regions selected from:

a) SEQ ID NOs: 1-3 and 9-11,
b) SEQ ID NOs: 1-3 and 17-19,
c) SEQ ID NOs: 5-7 and 13-15,
d) SEQ ID NOs: 21-23 and 25-27, and
e) SEQ ID NOs: 29-31 and 33-35.

11. The method of claim 1, wherein the subject has or is diagnosed as having acute respiratory distress syndrome (ARDS).

12. A method of treating a subject having a coronavirus infection in a subject in need thereof, the method comprising administering a Dual Endothelin/VEGF signal peptide Receptor (DEspR) inhibitor to a subject determined to have:
i) an elevated level or rising level of DEspR+CD11b+ cells, or
ii) an elevated level of non-resolving neutrophil-monocyte inflammatory amplification that blocks initiation of next step anti-viral adaptive immunity, anti-viral cellular immunity, resolution, or a combination thereof, measured as:
(1) DEspR+CD11b+ cells,
(2) a level of hyperinflammation-response marked by elevated ratio DEspR+CD11b+ neutrophils to plasma cytokine storm biomarkers,
(3) a level of hyperinflammation-response marked by elevated ratio DEspR+CD11b+ neutrophils to plasma oxidative stress biomarkers,
(4) a level of hyperinflammation-response marked by elevated ratio DEspR+CD11b+ neutrophils to endothelial dysfunction biomarkers, or
(5) a combination of any of (1), (2), (3), or (4);
in a sample obtained from the subject,
wherein an elevated level is elevated as compared to the level in a control subject not having a coronavirus infection; and
wherein the DEspR inhibitor is an anti-DEspR antibody reagent or antigen-binding fragment thereof.

13. The method of claim 12, wherein the DEspR+CD11b+ cells are DEspR+CD11b+ neutrophils, DEspR+CD11b+ monocytes, DEspR+CD11b+ lymphocytes, DEspR+CD11b+ cytoplasts, or a combination thereof.

14. The method of claim 12, wherein the level of DEspR+ CD11b+ cells is detected by measuring a level of DEspR+ CD11b+ aggregates or DEspR+ DNA strands in a blood sample.

15. The method of claim 12, wherein an elevated or rising level of DEspR+CD11b+ cells in the subject indicates the subject will require intensive care.

16. The method of claim 12, wherein the subject has or is diagnosed as having acute respiratory distress syndrome (ARDS).

17. A method of treating organ-dysfunction or multi-organ dysfunction or multi-organ failure associated with a coronavirus infection in a subject in need thereof, the method comprising administering a therapeutically effective amount of a Dual Endothelin/VEGF signal peptide Receptor (DEspR) inhibitor to the subject;
   wherein the DEspR inhibitor is an anti-DEspR antibody reagent or antigen-binding fragment thereof.

18. The method of claim 17, subject is a subject determined to have elevated or rising levels of DEspR+CD11b+ cells, elevated hyperinflammation DEspR+ neutrophil-IL6/MPO/ET1 ratios, or a combination thereof, as compared to a control subject.

19. The method of claim 17, wherein the DEspR+CD11b+ cells are DEspR+CD11b+ neutrophils, DEspR+CD11b+ monocytes, DEspR+CD11b+ lymphocytes, DEspR+CD11b+ cytoplasts, or a combination thereof.

20. The method of claim 17, wherein the organ-dysfunction or multi-organ dysfunction or multi-organ failure associated with the coronavirus infection arises from microcirculatory dysfunction, microvascular inclusion, low flow ischemia, thromboses, systemic microthromboses, microcirculatory vascular aggregation, or a combination thereof.

21. The method of claim 17, wherein the organ-dysfunction or multi-organ dysfunction or multi-organ failure associated with the coronavirus infection is derived from COVID19-induced cytokine storm, low flow organ ischemia from DEspR+CD11b+ aggregates leading to characteristic COVID19-hypoxemia, renal dysfunction, cardiac ischemia, neurological dysfunction from low flow ischemia or delayed cerebral ischemia or neuroinflammation, liver dysfunction/failure, hematological coagulopathy or microthromboses, or a combination thereof.

22. The method of claim 21, wherein the neurological dysfunction is characterized by loss of consciousness, seizures, confusion, or a combination thereof.

23. The method of claim 17, wherein the organ-dysfunction or multi-organ dysfunction or multi-organ failure associated with the coronavirus infection is selected from the group consisting of systemic inflammatory response syndrome (SIRS); acute lung injury (ALI); acute respiratory distress syndrome (ARDS); multi-organ failure or multi-organ dysfunction syndrome (MODS); acute kidney injury (AKI); liver failure, ischemic stroke; delayed cerebral ischemia, and/or encephalopathy.

24. The method of claim 17, wherein the organ-dysfunction or multi-organ dysfunction or multi-organ failure associated with the coronavirus infection is ARDS.

25. The method of claim 17, wherein the subject has or is diagnosed as having acute respiratory distress syndrome (ARDS).

26. A method of combinational therapy for a subject having a coronavirus infection, the method comprising administering to the subject a therapeutic agent or a therapy in combination with a Dual Endothelin/VEGF signal peptide Receptor (DEspR) inhibitor, wherein the therapeutic agent or the therapy alleviates a sign or a symptom associated with the coronavirus infection in the subject; and
   wherein the DEspR inhibitor is an anti-DEspR antibody reagent or antigen-binding fragment thereof.

27. The method of claim 26, wherein the therapy is an application of a respiratory ventilation or an alternative delivery system for supplemental oxygen.

28. The method of claim 26, wherein the subject has or is diagnosed as having acute respiratory distress syndrome (ARDS).

* * * * *

SEQUENCE LISTING

<160> NUMBER OF SEQ ID NOS: 39

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

```
Gly Tyr Gly Val Asn
1               5

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Met Ile Trp Asp Asp Gly Ser Thr Asp Tyr Asn Ser Ala Leu Lys Ser
1               5                   10                  15

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Pro Val Val His Phe Tyr Ala Met Asp Tyr
1               5                   10

<210> SEQ ID NO 4
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gly Ser Gln Val Gln Leu Gln Glu Ser Gly Pro Gly Leu Val Ala Pro
1               5                   10                  15

Ser Gln Ser Leu Ser Ile Thr Cys Thr Val Ser Gly Phe Ser Leu Thr
                20                  25                  30

Gly Tyr Gly Val Asn Trp Val Arg Gln Pro Pro Gly Lys Gly Leu Glu
            35                  40                  45

Trp Leu Gly Met Ile Trp Asp Asp Gly Ser Thr Asp Tyr Asn Ser Ala
    50                  55                  60

Leu Lys Ser Arg Leu Ile Ile Thr Lys Asp Asn Ser Arg Ser Gln Val
65                  70                  75                  80

Phe Leu Lys Met Asn Ser Leu Gln Thr Asp Thr Ala Arg Tyr Tyr
                85                  90                  95

Cys Ala Arg Asp Pro Val Val His Phe Tyr Ala Met Asp Tyr Trp Gly
                100                 105                 110

Gln Gly Thr Ser Val Thr Val Ser Ser Ala Lys Thr Thr Pro Pro Ser
            115                 120                 125

Val Tyr Gly Gly Gly Gly Ser
        130                 135

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 5

Arg Tyr Trp Met Ser
1               5

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Glu Ile Asn Pro Asp Ser Ser Thr Ile Asn Tyr Thr Pro Ser Leu Lys
1               5                   10                  15

Asp

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

His Gly Arg Gly Met Asp Tyr
1               5

<210> SEQ ID NO 8
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gly Ser Glu Val Gln Leu Gln Glu Ser Gly Gly Leu Val Gln Pro
1               5                   10                  15

Gly Gly Ser Leu Lys Leu Ser Cys Ala Ala Ser Gly Phe Asp Phe Ser
                20                  25                  30

Arg Tyr Trp Met Ser Trp Val Arg Gln Ala Pro Gly Lys Gly Leu Glu
            35                  40                  45

Trp Ile Gly Glu Ile Asn Pro Asp Ser Ser Thr Ile Asn Tyr Thr Pro
        50                  55                  60

Ser Leu Lys Asp Lys Phe Ile Ile Ser Arg Asp Thr Ala Lys Lys Thr
65                  70                  75                  80

Leu Tyr Leu Gln Met Ser Lys Val Arg Ser Glu Asp Thr Ala Leu Tyr
                85                  90                  95

Tyr Cys Ala Arg His Gly Arg Gly Met Asp Tyr Trp Ser Gln Gly Thr
            100                 105                 110

Ser Val Thr Val Ser Ser Ala Lys Thr Thr Pro Pro Ser Val Tyr Gly
        115                 120                 125

Gly Gly Gly Ser
    130

<210> SEQ ID NO 9
<211> LENGTH: 11
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 9

Lys Ala Ser Gln Asn Val Asp Ser Asn Val Ala
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Ala Ser Tyr Arg Tyr Ser
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln Gln Tyr His Ser Tyr Pro
1               5

<210> SEQ ID NO 12
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gly Gly Gly Gly Ser Asp Ile Val Leu Thr Gln Thr Asn Gln Ile Met
1               5                   10                  15

Ser Ala Ser Val Gly Asp Arg Val Ser Val Thr Cys Lys Ala Ser Gln
                20                  25                  30

Asn Val Asp Ser Asn Val Ala Trp Tyr Gln Gln Lys Pro Gly His Ser
            35                  40                  45

Pro Lys Ala Leu Ile Tyr Ser Ala Ser Tyr Arg Tyr Ser Arg Val Pro
    50                  55                  60

Asp Arg Ile Thr Gly Ser Gly Ser Gly Thr Asp Phe Thr Leu Thr Ile
65                  70                  75                  80

Thr Asn Val Gln Ser Lys Asp Leu Ala Asp Tyr Phe Cys Gln Gln Tyr
                85                  90                  95

His Ser Tyr Pro Leu Leu Ala Phe Gly Ala Gly Thr Lys Leu Glu Leu
            100                 105                 110

Lys Arg Ala Asp Ala Ala Pro Thr Val Ser Leu Glu
        115                 120

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Ala Ser Gln Ser Val Ser Asn Asp Val Ala
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Tyr Ala Ser Asn Arg Tyr Thr
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Gln Asp Tyr Ser Ser Pro Phe Thr
1               5

<210> SEQ ID NO 16
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gly Gly Gly Ser Asp Ile Val Leu Thr Gln Thr His Lys Phe Leu Leu
1               5                   10                  15

Val Ser Ala Gly Asp Arg Ile Thr Ile Thr Cys Lys Ala Ser Gln Ser
            20                  25                  30

Val Ser Asn Asp Val Ala Trp Tyr Gln Gln Lys Pro Gly Gln Ser Pro
        35                  40                  45

Lys Leu Leu Ile Tyr Tyr Ala Ser Asn Arg Tyr Thr Gly Val Pro Asp
    50                  55                  60

Arg Phe Thr Gly Ser Gly Tyr Gly Thr Asp Phe Thr Phe Thr Ile Ser
65                  70                  75                  80

Thr Val Gln Ala Asp Asp Leu Ala Val Tyr Phe Cys Gln Gln Asp Tyr
                85                  90                  95

Ser Ser Pro Phe Thr Phe Gly Gly Gly Thr Lys Leu Glu Ile Lys Arg
            100                 105                 110

Ala Asp Ala Ala Pro Thr Val Ser Leu Glu
        115                 120

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Ala Ser Ser Ser Val Ser Phe Met His
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Thr Ser Asn Leu Ala Ser
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Gln Arg Ser Ser Tyr Pro
1               5

<210> SEQ ID NO 20
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gly Gly Gly Gly Ser Asp Ile Val Ile Thr Gln Ser Asn Ala Ile Met
1               5                   10                  15

Ser Ala Ser Pro Gly Glu Lys Val Thr Ile Thr Cys Ser Ala Ser Ser
            20                  25                  30

Ser Val Ser Phe Met His Trp Phe Gln Gln Lys Pro Gly Thr Ser Pro
        35                  40                  45

Lys Leu Trp Ile Tyr Ser Thr Ser Asn Leu Ala Ser Gly Val Pro Ala
    50                  55                  60

Arg Phe Ser Gly Ser Gly Ser Gly Thr Ser Tyr Ser Leu Thr Ile Ser
65                  70                  75                  80

Arg Met Glu Ala Glu Asp Ala Ala Thr Tyr Tyr Cys Gln Gln Arg Ser
                85                  90                  95

Ser Tyr Pro Leu Thr Phe Gly Ala Gly Thr Lys Leu Glu Leu Lys Arg
            100                 105                 110

Ala Asp Ala Ala Pro Thr Val Ser Leu Glu
        115                 120

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Tyr Ala Val Ser

```
<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Val Ile Trp Gly Asp Gly Ser Thr Asp Tyr His Ser Ala Leu Ile Ser
1               5                   10                  15

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Thr Gly Thr Gly Phe Ala Tyr
1               5

<210> SEQ ID NO 24
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Lys Ser Tyr
            20                  25                  30

Ala Val Ser Trp Val Arg Gln Pro Pro Gly Lys Gly Leu Glu Trp Leu
        35                  40                  45

Gly Val Ile Trp Gly Asp Gly Ser Thr Asp Tyr His Ser Ala Leu Ile
    50                  55                  60

Ser Arg Leu Ser Ile Ser Lys Asp Asn Ser Lys Ser Gln Phe Phe Leu
65                  70                  75                  80

Arg Leu Asn Ser Leu Gln Thr Asp Asp Thr Ala Thr Tyr Tyr Cys Ala
                85                  90                  95

Arg Gly Thr Gly Thr Gly Phe Ala Tyr Trp Gly Gln Gly Thr Leu Val
            100                 105                 110

Thr Val Ser Ala
        115

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Ser Ser Gln Ser Leu Val His Ser Asn Gly Asn Thr Tyr Leu His
1               5                   10                  15
```

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Lys Val Ser Asn Arg Phe Ser
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Gln Cys Thr His Ile Pro Trp Thr
1               5

<210> SEQ ID NO 28
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Ser Gln Cys
                85                  90                  95

Thr His Ile Pro Trp Thr Phe Gly Gly Gly Thr Asn Leu Glu Ile Lys
            100                 105                 110

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Phe Ser Leu Thr Ser Tyr Asp Ile Ser
1               5                   10

<210> SEQ ID NO 30
<211> LENGTH: 16
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 30

Val Ile Trp Thr Gly Gly Gly Thr Asn Tyr Asn Ser Ala Phe Met Ser
1               5                   10                  15

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asp Arg Asp Tyr Asp Gly Trp Tyr Phe Asp Val
1               5                   10

<210> SEQ ID NO 32
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Asp Ile Ser Trp Ile Arg Gln Pro Pro Gly Lys Gly Leu Glu Trp Leu
        35                  40                  45

Gly Val Ile Trp Thr Gly Gly Gly Thr Asn Tyr Asn Ser Ala Phe Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Ile Tyr Tyr Cys Val
                85                  90                  95

Arg Asp Arg Asp Tyr Asp Gly Trp Tyr Phe Asp Val Trp Gly Ala Gly
            100                 105                 110

Thr Thr Val Thr Val Ser Ser
        115

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Ser Ser Gln Ser Ile Val His Ser Asn Gly Asn Thr Tyr Leu Glu
1               5                   10                  15

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 34

Lys Val Ser Asn Arg Phe Ser
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Phe Gln Gly Ser His Val Pro Tyr Thr
1               5

<210> SEQ ID NO 36
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 37
<211> LENGTH: 85
<212> TYPE: PRT
<213> ORGANISM: Homo sapiens

<400> SEQUENCE: 37

Met Thr Met Phe Lys Gly Ser Asn Glu Met Lys Ser Arg Trp Asn Trp
1               5                   10                  15

Gly Ser Ile Thr Cys Ile Ile Cys Phe Thr Cys Val Gly Ser Gln Leu
            20                  25                  30

Ser Met Ser Ser Ser Lys Ala Ser Asn Phe Ser Gly Pro Leu Gln Leu
        35                  40                  45

Tyr Gln Arg Glu Leu Glu Ile Phe Ile Val Leu Thr Asp Val Pro Asn
    50                  55                  60

Tyr Arg Leu Ile Lys Glu Asn Ser His Leu His Thr Ile Val Asp
65                  70                  75                  80

Gln Gly Arg Thr Val
                85

```
<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Gly Gly Gly Ser
1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 39

His His His His His His
1               5
```